US011161906B2

(12) United States Patent
Lowman et al.

(10) Patent No.: US 11,161,906 B2
(45) Date of Patent: Nov. 2, 2021

(54) MULTISPECIFIC ANTIBODIES, MULTISPECIFIC ACTIVATABLE ANTIBODIES AND METHODS OF USING THE SAME

(71) Applicant: CytomX Therapeutics, Inc., South San Francisco, CA (US)

(72) Inventors: Henry Bernard Lowman, El Granada, CA (US); James William West, Bend, OR (US); Sherry Lynn La Porte, San Francisco, CA (US); Bryan Allen Irving, Woodside, CA (US); Daniel Robert Hostetter, Palo Alto, CA (US); Chihunt Wong, El Cerrito, CA (US)

(73) Assignee: CYTOMX THERAPEUTICS, INC., South San Francisco, CA (US)

( * ) Notice: Subject to any disclaimer, the term of this patent is extended or adjusted under 35 U.S.C. 154(b) by 0 days.

(21) Appl. No.: 14/340,872

(22) Filed: Jul. 25, 2014

(65) Prior Publication Data
US 2015/0079088 A1  Mar. 19, 2015

Related U.S. Application Data

(60) Provisional application No. 61/858,402, filed on Jul. 25, 2013.

(51) Int. Cl.
C07K 16/28 (2006.01)

(52) U.S. Cl.
CPC ...... *C07K 16/2863* (2013.01); *C07K 16/2803* (2013.01); *C07K 16/2809* (2013.01); *C07K 16/2818* (2013.01); *C07K 16/2896* (2013.01); *C07K 2317/31* (2013.01); *C07K 2317/50* (2013.01); *C07K 2317/622* (2013.01); *C07K 2317/64* (2013.01); *C07K 2317/73* (2013.01); *C07K 2317/92* (2013.01)

(58) Field of Classification Search
CPC .......... C07K 2317/92; C07K 2317/622; C07K 2317/50; C07K 2317/31
USPC .......................................... 424/133.1, 135.1
See application file for complete search history.

(56) References Cited

U.S. PATENT DOCUMENTS

| | | | |
|---|---|---|---|
| 3,773,919 A | 11/1973 | Bostwell et al. | |
| 4,485,045 A | 11/1984 | Regen | |
| 4,522,811 A | 6/1985 | Eppstein et al. | |
| 4,544,545 A | 10/1985 | Ryan et al. | |
| 5,013,556 A | 5/1991 | Woodle et al. | |
| 5,030,719 A | 7/1991 | Umemoto et al. | |
| 5,151,510 A | 9/1992 | Stec et al. | |
| 5,733,743 A | 3/1998 | Johnson et al. | |
| 5,968,509 A | 10/1999 | Gorman et al. | |
| 7,381,803 B1 | 6/2008 | Weiner et al. | |
| 7,465,790 B2 | 12/2008 | Waldmann et al. | |
| 7,951,918 B2 | 5/2011 | Glaser et al. | |
| 7,994,289 B2 | 8/2011 | Waldmann et al. | |
| 8,513,390 B2 | 8/2013 | Stagliano et al. | |
| 8,518,404 B2 | 8/2013 | Daugherty et al. | |
| 8,529,898 B2* | 9/2013 | Daugherty ......... | C07K 16/2818 424/134.1 |
| 8,541,203 B2 | 9/2013 | Daugherty et al. | |
| 8,563,269 B2 | 10/2013 | Stagliano et al. | |
| 8,809,504 B2 | 8/2014 | Lauerman | |
| 8,846,042 B2 | 9/2014 | Zhou | |
| 9,120,853 B2 | 9/2015 | Lowman et al. | |
| 9,169,321 B2 | 10/2015 | Daugherty et al. | |
| 9,181,349 B2 | 11/2015 | Baurin et al. | |
| 9,249,217 B2 | 2/2016 | Bigner et al. | |
| 9,453,078 B2 | 9/2016 | Stagliano et al. | |
| 9,540,440 B2 | 1/2017 | Lowman et al. | |
| 9,545,442 B2 | 1/2017 | Lowman et al. | |
| 9,562,073 B2* | 2/2017 | Moore ...................... | C07K 7/06 |
| 9,889,211 B2 | 2/2018 | Lowman et al. | |
| 10,138,272 B2* | 11/2018 | Moore ...................... | C07K 7/06 |
| 10,179,817 B2* | 1/2019 | Sagert ................... | C07K 16/30 |
| 10,533,053 B2 | 1/2020 | Lowman et al. | |
| 10,669,337 B2 | 6/2020 | Irving et al. | |
| 10,709,799 B2 | 7/2020 | Lowman et al. | |
| 2004/0109855 A1 | 6/2004 | Waldmann et al. | |
| 2006/0269547 A1 | 11/2006 | Bolt et al. | |
| 2009/0304719 A1 | 12/2009 | Daugherty et al. | |
| 2010/0189651 A1* | 7/2010 | Stagliano et al. | |
| 2010/0189727 A1 | 7/2010 | Rodeck et al. | |
| 2012/0149061 A1* | 6/2012 | Stagliano et al. | |
| 2012/0207756 A1* | 8/2012 | Stagliano ............... | C07K 16/22 424/134.1 |

(Continued)

FOREIGN PATENT DOCUMENTS

EP    1 523 503 B1    4/2009
EP    1324771 B1    6/2011

(Continued)

OTHER PUBLICATIONS

Song et al. (Biochem Biophys Res Comm 268:390-394 (2000)).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Amgen vs Sanofi and Regeneron Case: 17-1480 Document: 176 Filed: Feb. 6, 2018.*
Viricel et al (Chem Sci. Apr. 14, 2019; 10(14): 4048-4053).*
Geiger et al. (Nat Commun 11, 3196 (2020), //doi.org/10.1038/S41467-020-16838-w.*

(Continued)

*Primary Examiner* — Lynn A Bristol
(74) *Attorney, Agent, or Firm* — Rothwell, Figg, Ernst & Manbeck, P.C.

(57) ABSTRACT

The invention relates generally to multispecific antibodies and to multispecific activatable antibodies that specifically bind to two or more different antigens or epitopes, as well as to methods of making and using these multispecific antibodies and/or multispecific activatable antibodies in a variety of therapeutic, diagnostic and prophylactic indications.

45 Claims, 26 Drawing Sheets

Specification includes a Sequence Listing.

(56) References Cited

U.S. PATENT DOCUMENTS

| | | | |
|---|---|---|---|
| 2012/0237512 A1* | 9/2012 | Daugherty | C07K 16/2818 424/134.1 |
| 2012/0237977 A1* | 9/2012 | Daugherty et al. | |
| 2012/0244154 A1* | 9/2012 | Daugherty | C07K 16/2818 424/134.1 |
| 2013/0060011 A1 | 3/2013 | Bruenker et al. | |
| 2013/0129730 A1 | 5/2013 | Kufer et al. | |
| 2013/0150558 A1 | 6/2013 | Williams et al. | |
| 2013/0309230 A1 | 11/2013 | Stagliano et al. | |
| 2013/0315906 A1* | 11/2013 | Lowman et al. | |
| 2014/0010810 A1* | 1/2014 | West et al. | |
| 2014/0024810 A1 | 1/2014 | Stagliano et al. | |
| 2014/0045195 A1* | 2/2014 | Daugherty et al. | |
| 2014/0154253 A1 | 6/2014 | Ng et al. | |
| 2014/0255313 A1* | 9/2014 | Vasiljeva | C07K 16/2863 424/9.6 |
| 2014/0363430 A1* | 12/2014 | West et al. | |
| 2015/0005477 A1* | 1/2015 | Lowman et al. | |
| 2015/0079088 A1* | 3/2015 | Lowman | C07K 16/2809 424/135.1 |
| 2015/0118254 A1* | 4/2015 | Lowman et al. | |
| 2016/0122425 A1 | 5/2016 | Daugherty et al. | |
| 2016/0193332 A1* | 7/2016 | Lowman et al. | |
| 2016/0194399 A1* | 7/2016 | Irving et al. | |
| 2016/0200826 A1* | 7/2016 | West et al. | |
| 2016/0220537 A1* | 8/2016 | Garner | A61K 45/06 |
| 2016/0228546 A1* | 8/2016 | Stagliano et al. | |
| 2017/0081397 A1 | 3/2017 | Stagliano et al. | |
| 2017/0196996 A1 | 7/2017 | Lowman et al. | |
| 2018/0333507 A1 | 11/2018 | Lowman et al. | |
| 2019/0135943 A1 | 5/2019 | Boustany et al. | |

FOREIGN PATENT DOCUMENTS

| | | |
|---|---|---|
| EP | 2155788 B1 | 6/2012 |
| EP | 2155783 B1 | 7/2012 |
| WO | WO 1991/001752 A1 | 2/1991 |
| WO | WO 1991/009966 A1 | 7/1991 |
| WO | WO 1992/006193 A1 | 4/1992 |
| WO | WO 1992/022653 A1 | 12/1992 |
| WO | WO 1994/11026 A2 | 5/1994 |
| WO | WO 1994/028027 A1 | 12/1994 |
| WO | WO 1995/016037 | 6/1995 |
| WO | WO 1997/044362 A1 | 11/1997 |
| WO | WO 2001/91798 A2 | 12/2001 |
| WO | WO 2002/030460 A2 | 4/2002 |
| WO | WO 2004/00963 8 A1 | 1/2004 |
| WO | WO 2004/003019 * | 6/2004 |
| WO | WO 2004/106380 A2 | 12/2004 |
| WO | WO 2005/040220 A1 | 5/2005 |
| WO | WO 2005/047461 | 5/2005 |
| WO | WO 2006/107786 A2 | 10/2006 |
| WO | WO 2007/024705 A2 | 3/2007 |
| WO | WO 2007/027935 | 3/2007 |
| WO | WO 2007/033230 A2 | 3/2007 |
| WO | WO 2007/042261 A2 | 4/2007 |
| WO | WO 2007/105027 A1 | 9/2007 |
| WO | WO 2007/109254 A2 | 9/2007 |
| WO | WO 2007/146968 A2 | 12/2007 |
| WO | WO 2007/147001 A2 | 12/2007 |
| WO | WO 2008/119565 A2 | 10/2008 |
| WO | WO 2008/119566 A2 | 10/2008 |
| WO | WO 2008/119567 | 10/2008 |
| WO | WO 2009/014726 | 1/2009 |
| WO | WO 2009/018386 A1 | 2/2009 |
| WO | WO 2009/025846 | 2/2009 |
| WO | WO 2010/037836 A2 | 4/2010 |
| WO | WO 2010/037838 | 4/2010 |
| WO | WO 2010/042904 A2 | 4/2010 |
| WO | WO 2010/081173 | 7/2010 |
| WO | WO 2010/093395 A1 | 8/2010 |
| WO | WO 2010/096838 | 8/2010 |
| WO | WO 2010/109924 A1 | 9/2010 |
| WO | WO 2010/127284 A2 | 11/2010 |
| WO | WO 2010/129609 | 11/2010 |
| WO | WO 2011/028811 A2 | 3/2011 |
| WO | WO 2011/109789 A2 | 9/2011 |
| WO | WO 2012/025525 A1 | 3/2012 |
| WO | WO 2012/135345 A1 | 10/2012 |
| WO | WO 2012/158818 A2 | 11/2012 |
| WO | WO 2012/162067 A2 | 11/2012 |
| WO | WO 2013/026835 A1 | 2/2013 |
| WO | WO 2013/026839 A1 | 2/2013 |
| WO | WO 2013/092001 A1 | 6/2013 |
| WO | WO 2013/128194 | 9/2013 |
| WO | WO 2013/163631 | 10/2013 |
| WO | WO 2013/192546 | 12/2013 |
| WO | WO 2013/192550 | 12/2013 |
| WO | WO 2014/047231 A1 | 3/2014 |
| WO | WO 2014/107599 | 7/2014 |
| WO | WO 2015/001085 A1 | 1/2015 |
| WO | WO 2016/014974 A2 | 1/2016 |
| WO | WO 2016/071355 A1 | 5/2016 |
| WO | WO 2016/118629 A1 | 7/2016 |
| WO | WO 2017/157305 A1 | 9/2017 |
| WO | WO 2019/075405 A1 | 4/2019 |
| WO | WO 2019/213444 A1 | 11/2019 |

OTHER PUBLICATIONS

Erster et al. (J Control Release. Aug. 10, 2012; 161(3): 804-812).*
Han et al. (Mol Ther. Jan. 4, 2017; 25(1): 274-284).*
Ibragimova and Eade (Biophysical Journal, Oct. 1999, vol. 77, pp. 2191-2198).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Boersma, Y.L. et al., "Bispecific designed ankyrin repeat proteins (DARPins) targeting epidermal growth factor receptor inhibit A431 cell proliferation and receptor recycling", J. Biol. Chem., (2011), vol. 286, p. 41273-41285.
Chan, A. et al., "Therapeutic antibodies for autoimmunity and inflammation", Nature Reviews/ Immunology, (2010), vol. 10, p. 301-316.
Cochlovius B. et al., "Cure of Burkitt's lymphoma in severe combined immunodeficiency mice by T cells, tetravalent CD3×CD19 tandem diabody, and CD28 costimulation", Cancer Research, (2000), vol. 60, p. 4336-4341.
Deng, R. et al., Subcutaneous bioavailability of therapeutic antibodies as a function of FcRn binding affinity in mice, mAbs (2012), 4:1, p. 101-109.
Donaldson J. et al., "Design and development of masked therapeutic antibodies to limit off-target effects: application to anti-EGFR antibodies", Cancer Biology & Therapy, (Nov. 2009); 8(22):2147-2152.
Dong et al., A stable IgG-like bispecific antibody targeting the epidermal growth factor receptor and the type I insulin-like growth factor receptor demonstrates superior anti-tumor activity, mAbs, (2011), 3(3):273-88.
Epstein et al., "Biological activity of liposome-encapsulated murine interferon gamma is mediated by a cell membrane receptor", Proc. Natl. Acad. Sci. USA, (1985), 82: 3688-3692.
Fitzgerald J. et al., "Rational engineering of antibody therapeutics targeting multiple oncogene pathways", mAbs, (2011), 3(3):299-309.
Jackman J. et al., "Development of a two-part strategy to identify a therapeutic human bispecific antibody that inhibits IgE receptor signaling", J. Biol. Chem., (2010), 285, 20850-20859.
Junttila T. et al., "Antitumor efficacy of a bispecific antibody that targets HER2 and activates T cells", Cancer Research, (Oct. 1, 2014 ); 74(19):5561-5571.
Kroesen, B. et al. "Bispecific antibodies for treatment of cancer in experimental animal models and man", Advanced Drug Delivery Reviews, (1998), vol. 31, p. 105-129.
La Rocca et al., "Zymographic detection and clinical correlations of MMP-2 and MMP-9 in breast cancer sera", British Journal of Cancer, (2004), 90(7): 1414-1421.
Linke, R. et al., "Catumaxomab: clinical development and future directions", mAbs, (2010), vol. 2, p. 129-136.

(56) References Cited

OTHER PUBLICATIONS

Liu, M. et al., "Heteroantibody duplexes target cells for lysis by cytotoxic T lymphocytes", Proc. Natl. Acad. Sci. USA, vol. 82, (1985), p. 8648-8652.
Lund, J. et al., "Multiple binding sites on the CH2 domain of IgG for mouse Fc gamma R11", Molecular Immunology, (1992), vol. 29, p. 53-59.
Lutterbuese R. et al., "T cell-engaging BiTE antibodies specific for EGFR potently eliminate KRAS- and BRAF-mutated colorectal cancer cells", Proc Natl Acad Sci USA, (Jul. 13, 2010), 107(28):12605-12610.
Marvin, J. et al., "Recombinant approaches to IgG-like bispecific antibodies", Acta Pharmacologica Sinica, (2005), vol. 26, p. 649-658.
Nisonoff, A. et al., "Quantitative estimation of the hybridization of rabbit antibodies", Nature, (1962), vol. 194, p. 355-359.
Olafsen T., "Fc engineering: serum half-life modulation through FcRn binding", Methods Mol. Biol., (2012), vol. 907, p. 537-556.
Orcutt, K. et al., "A modular IgG-scFv bispecific antibody topology", Protein Engineering, Design & Selection, (2010), vol. 23, No. 4, p. 221-228.
Petkova, S. et al., "Enhanced half-life of genetically engineered human IgG1 antibodies in a humanized FcRn mouse model: potential application in humorally mediated autoimmune disease", International Immunology, (2006), vol. 18, p. 1759-1769.
Reusch U. et al., "Anti-CD3 x anti-epidermal growth factor receptor (EGFR) bispecific antibody redirects T-cell cytolytic activity to EGFR-positive cancers in vitro and in an animal model", Clinical Cancer Research, (Jan. 1, 2006), AACR, vol. 12, No. 1, p. 183-190.
Riethmuller, G., "Symmetry breaking: bispecific antibodies, the beginnings, and 50 years on", Cancer Immunity, (2012), vol. 12, p. 12-18.
Spangler, J. et al., "Triepitopic antibody fusions inhibit cetuximab-resistant BRAF and KRAS mutant tumors via EGFR signal repression", J. Mol. Biol., (2012), vol. 422, p. 532-544.
Stevenson et al., "A chimeric antibody with dual Fc regions (bisFabFc) prepared by manipulations at the IgG hinge", Anti-Cancer Drug Design, (1989), 3: 219-230.
Wu, C. et al., "Simultaneous targeting of multiple disease mediators by a dual-variable-domain immunoglobulin", Nature Biotechnology, (2007), vol. 25, p. 1290-1297.
Baeuerle, P.A. and Reinhardt, C., "Bispecific T-Cell Engaging Antibodies for Cancer Therapy", *Anti-Cancer Research*, vol. 69, No. 12, p. 4941-4944, (2009).
Bostrom, J. et al. "Variants of the Antibody Herceptin That Interact with HER2 and VEGF at the Antigen Binding Site", Science, 2009, vol. 323, p. 1610-1614.
Caron et al. "Engineered Humanized Dimeric Forms of IgG Are More Effective Antibodies", J. Exp Med., 1992, vol. 176, p. 1191-1195.
Chichili G. et al. "A CD3×CD123 bispecific DART for redirecting host T cells to myelogenous leukemia: Preclinical activity and safety in nonhuman primates", Science Translational Medicine, 2015, vol. 7, Issue 289, 14 pages.
Desnoyers, L.R. et al. "Tumor-Specific Activation of an EGFR-Targeting Probody Enhances Therapeutic Index", Science Translation Medicine, 2013, vol. 5, Issue 207, 10 pages.
Grosschedl et al. "Cell-type specificity of immunoglobulin gene expression is regulated by at least three DNA sequence elements" Cell, 1985, vol. 41, p. 885-897.
Irving, "Probodies Empower a New Generation of Antibody Immunotherapies," presented at Keystone Symposia on Molecular and Cellular Biology, Feb. 2015, 25 pages.
Malmqvist, M. "Biospecific interaction analysis using biosensor technology", Nature, 1993, vol. 361, p. 186-187.
Okayama et al. "A cDNA cloning vector that permits expression of cDNA inserts in mammalian cells", Molecular and Cellular Biology, 1983, vol. 3, No. 2, p. 280-289.
Shopes B. "A Genetically Engineered Human IgG Mutant with Enhanced Cytolytic Activity", Journal of Immunology, 1992, vol. 148, No. 1, p. 2918-2922.
Sun LL et al. "Anti-CD20/CD3 T cell-dependent bispecific antibody for the treatment of B cell malignancies" Science Translational Medicine 2015, vol. 7, Issue 287, 11 pages.
F. Hoffmann-La Roche Ag, Notice of Opposition to EP 2 155 788 on Mar. 22, 2013, 39 pages.
Affimed Therapeutics, Notice of Opposition to EP 2 155 783 on Apr. 29, 2014, 10 pages.
Chugai Seiyaku, Notice of Opposition to EP 2 155 783 on Apr. 29, 2014, 19 pages.
Robert W. Bahr. Deputy Commissioner for Patent Examination Policy, U.S. Patent and Trademark Office. Memorandum of Feb. 22, 2018, 2 pages (Year: 2018).
"D4" Submission filed with Affimed Notice of Opposition to EP 2 155 783 on Apr. 29, 2014, p. 1-5.
"D05" Submission associated with EP 2 155 783, filed sometime prior to Apr. 29, 2014, p. 1-5.
"D17" Summary: Methods used for the sequencing of SP34 filed F. Hoffmann-La Roche Ag letter dated Mar. 22, 2013, p. 1-4.
Guilmeau et al., "Heterogeneity of Jagged1 expression in human and mouse intestinal tumors: implications for targeting Notch signaling", Oncogene (2010) 29:992-1002,.
Kiewe, P. "Ertumaxomab: a trifunctional antibody for breast cancer treatment", Expert Opinion on Investigational Drugs, vol. 17, p. 1553-1558 (2008).
Sebastian et al., "Treatment of non-small cell lung cancer patients with the trifunctional monoclonal antibody catumaxomab (anti-EpCAM x anti-CD3): a phase I study", Cancer Immunol. Immunother (2007) 56:1637-1644.
Watanabe et al., "In vitro and in vivo antitumor effects of recombinant bispecific antibodies based on humanized anti-EGFR antibody", Oncology Reports (2011) 26:949-955.
Bagshawe, K.D. (2006) "Antibody-directed enzyme prodrug therapy (ADEPT) for cancer" *Expert Rev Anticancer Ther*, 6(10):1421-1431.
Bluemel, C. et al. (2010) "Epitope distance to the target cell membrane and antigen size determine the potency of T cell-mediated lysis by BiTE anibodies specific for a large melanoma surface antigen" *Cancer Immunol Immunother*, 59:1197-1209.
Dimasi, N. et al. (2009) "The Design and Characterization of Oligospecific Antibodies for Simultaneous Targeting of Multiple Disease Mediators" *J Mol Biol*, 393:672-692.
Malcolm, S.L et al. (2012) "A humanised mouse model of cytokine release: Comparison of CD3-specific antibody fragments" *J Immunol Meth*, 384:33-42.
Pace, C.S. et al. (Aug. 2013) "Bispecific antibodies directed to CD4 domain 2 and HIV envelope exhibit exceptional breadth and picomolar potency against HIV-1" *PNAS*, 110(33):13540-13545.
Polu, K.R. and H.B. Lowman (2014) "Probody therapeutics for targeting antibodies to diseased tissue" *Expert Opin Biol Ther*, 14(8):1049-1053.
Bedouelle, H. et al. (Jan. 2006) "Diversity and junction residues as hotspots of binding energy in an antibody neutralizing the dengue virus" *FEBS J*, 273(1):34-46.
Conrad, M.L. et al. (2007) "TCR and CD3 Antibody Cross-Reactivity in 44 Species" *Cytometry Part A*, 71A:925-933.
Croasdale, R. et al. (2012) "Development of tetravalent IgG1 dual targeting IGF-1R-EGFR antibodies with potent tumor inhibition" *Archives of Biochemistry and Biophysics*, 526(2)206-218.
Dong, J. et al. (Feb. 1, 2011) "Stable IgG-like Bispecific Antibodies Directed toward the Type I Insulin-like Growth Factor Receptor Demonstrate Enhanced Ligand Blockade and Anti-tumor Activity" *JBC*, 286(6):4703-4717, with Supplemental pp. 1-6.
Dufner, P. et al. (2006) "Harnessing phage and ribosome display for antibody optimisation" *Trends in Biotechnol*, 24(11):523-529.
Jäger, L. (Ed.) *Klinicheskaja immunologija i allergologija*. [*Clinical Immunology and Allergology*]. vol. 2. 2nd Edition, M.: Medicina, 1990; pp. 484-485 (Russian, translated from German).
Vajdos, F.F. et al. (Jul. 5, 2002) "Comprehensive Function Maps of the Antigen-binding Site of an Anti-ErbB2 Antibody Obtained with Shotgun Scanning Mutagenesis" *J Mol Biol*, 320(2):415-428.

(56) References Cited

OTHER PUBLICATIONS

Singer, M. and Berg, P. (1998) "Geny and Genomy" M.: Mir, vol. 1, pp. 123-125 (Russian).
Chatenoud, L. (2005) "CD3-specific antibodies restore self-tolerance: mechanisms and clinical applications" Curr Opin Immunol, 17:632-637.
Wu, Z. and Cheung, N.V. (2018) "T cell engaging bispecific antibody (T-BsAb): From technology to therapeutics" Pharmacology and Therapeutics, 182:161-175.
In re Goldenberg, Appeal No. 2016-002936, U.S. Appl. No. 13/402,480 (non-precedential) (now granted as U.S. Pat. No. 9,745,374) (P.T.A.B. Feb. 14, 2017)—9 pgs.
In re Ambati, Appeal No. 2017-011580, U.S. Appl. No. 11/357,288 (non-precedential) (now granted as U.S. Pat. No. 10,344,095) (P.T.A.B. Jan. 29, 2019)—8 pgs.
Grant of Patent dated Nov. 13, 2020 in corresponding Korean Application No. 10-2016-7005101, 3 pgs.
Office Action issued Sep. 28, 2020, in corresponding European Application No. 18 163 581.4, 3 pgs.

\* cited by examiner

FIGURE 1
*From Chan and Carter, Nat. Rev. Immunol. 2010*
Antigen-Binding Building Blocks:
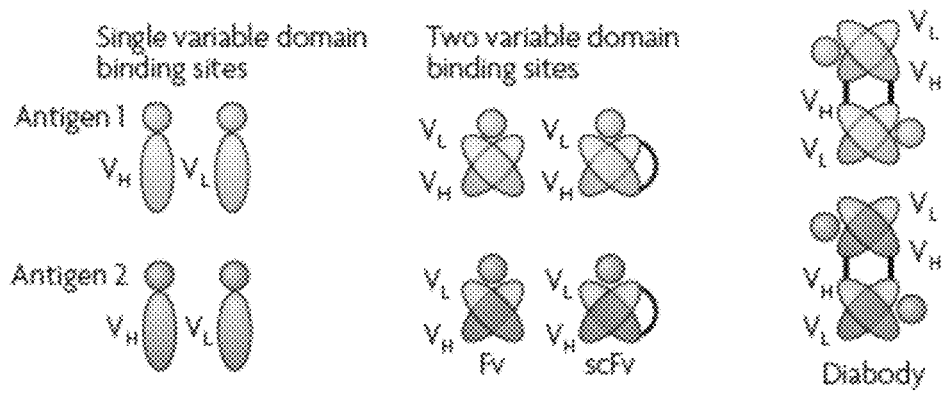
Bispecific Antibody Fragments:
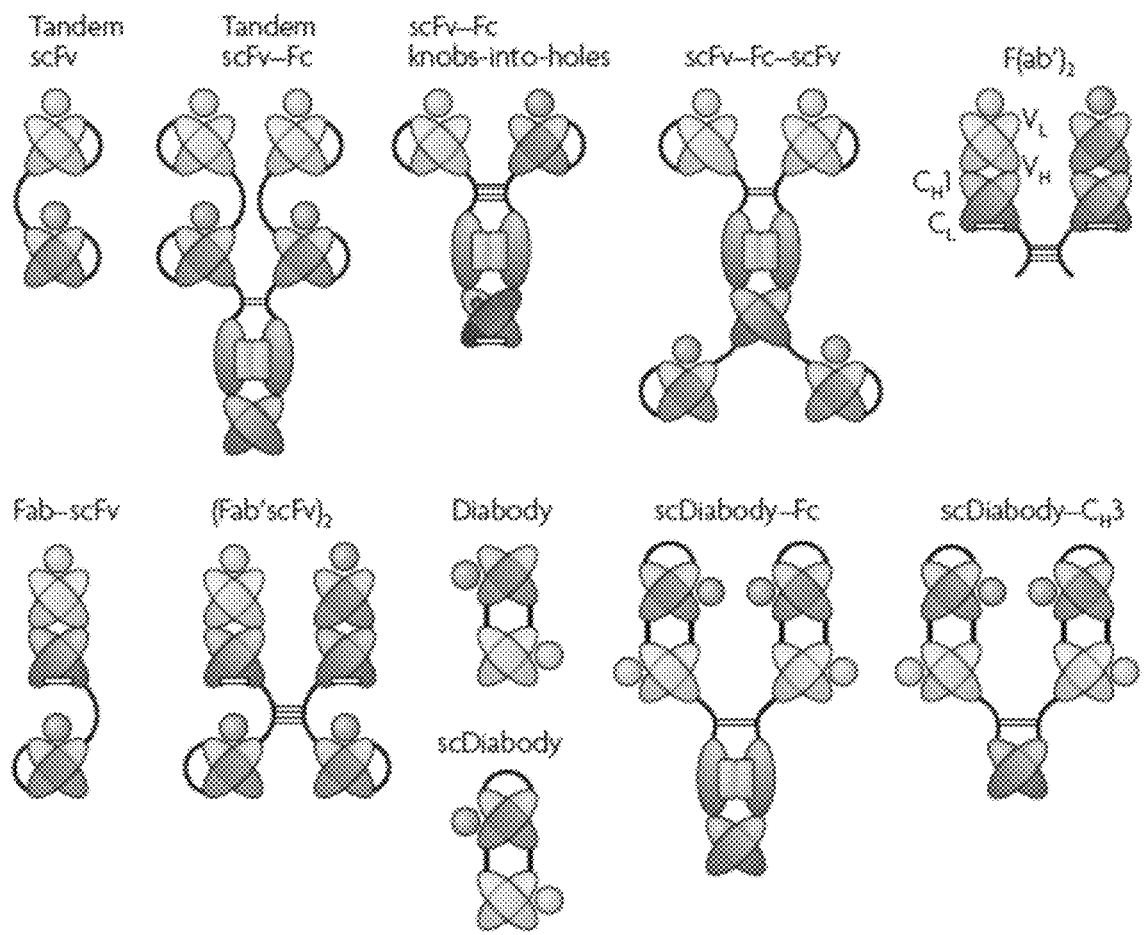

FIGURE 1, cont'd
IgG-Based Bispecific Antibodies
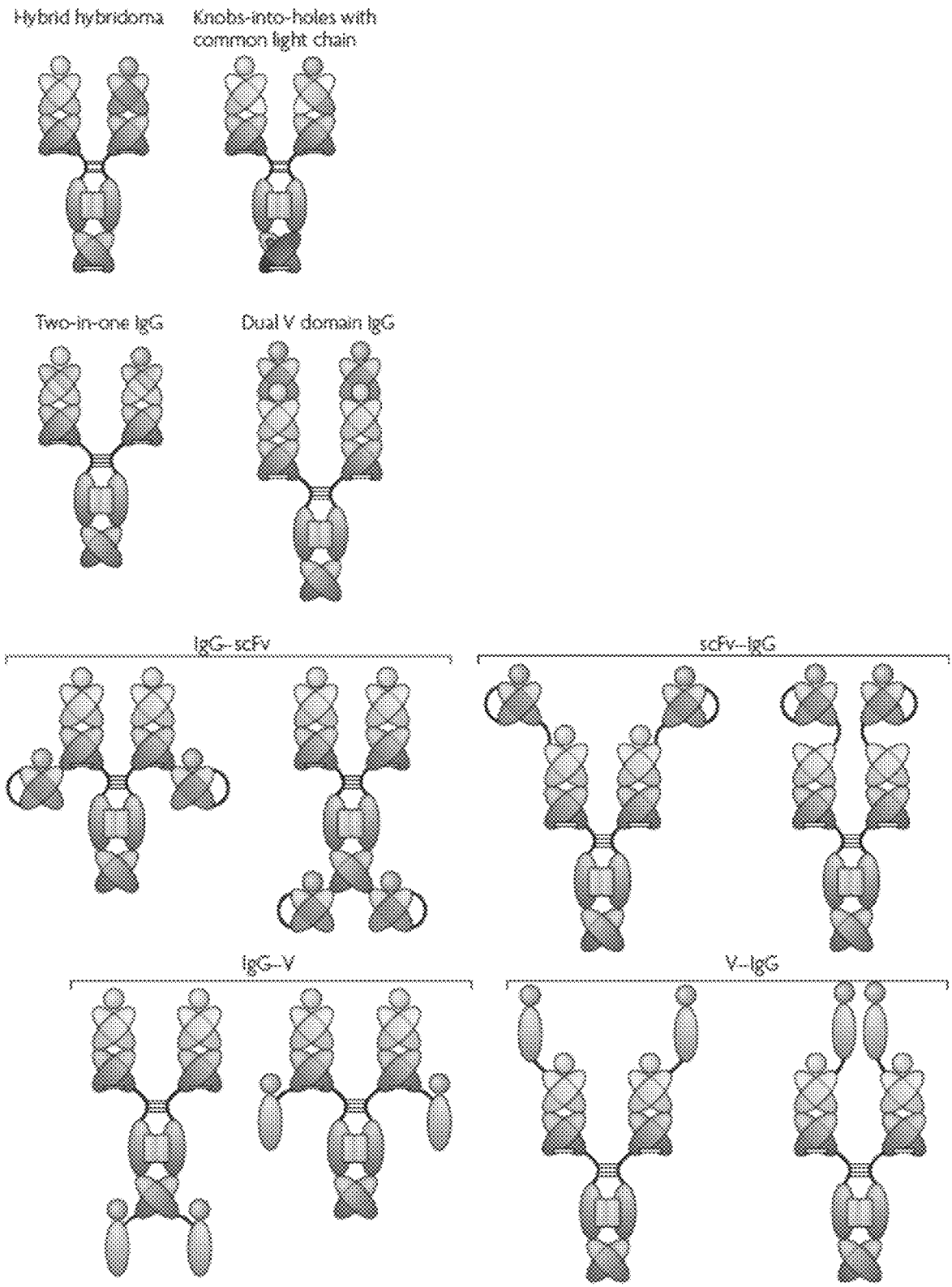

Multispecific activatable antibody arrays:

| Lane | Name | % Monomer |
|---|---|---|
| 1 | 4D11v2 OKT3 | 70.1% |
| 2 | C225v5 OKT3 | 68.0% |
| 3 | 3954-1204-C225v5-OKT3 | 67.9% |
| 4 | 4D11v2 CTLA4 | 100% |
| 5 | C225v5 CTLA4 | 100% |
| 6 | 3954-1204-C225v5 CTLA4 | 100% |
| 7 | 3954-1204-C225v5 CTLA4 | 100% |
| 8 | 3954-1204-C225v5 OKT3 | 66.0% |
| 9 | Antibody | |
| 10 | Antibody | |
| 11 | Activatable Antibody | |

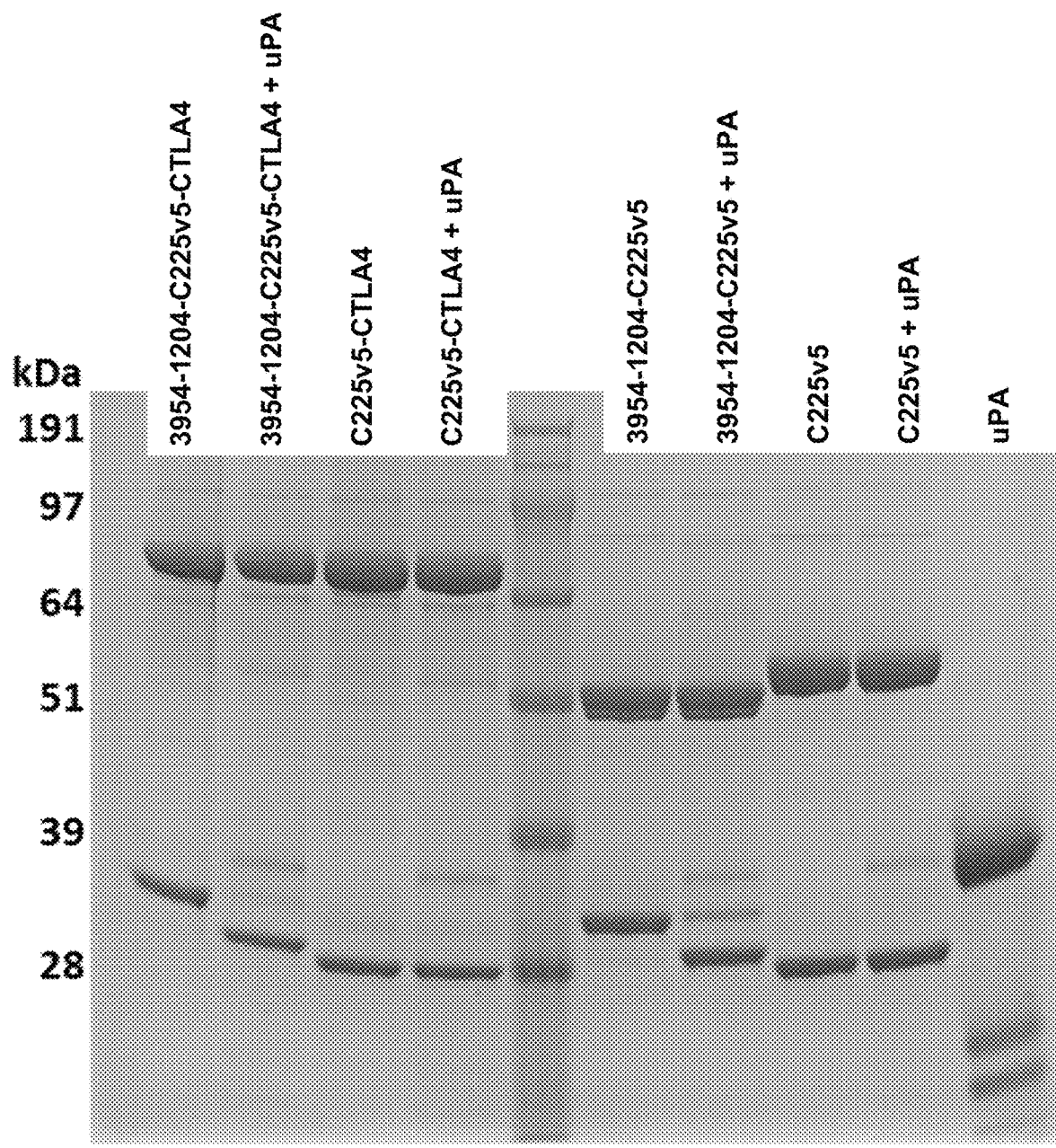
FIGURE 14, cont'd

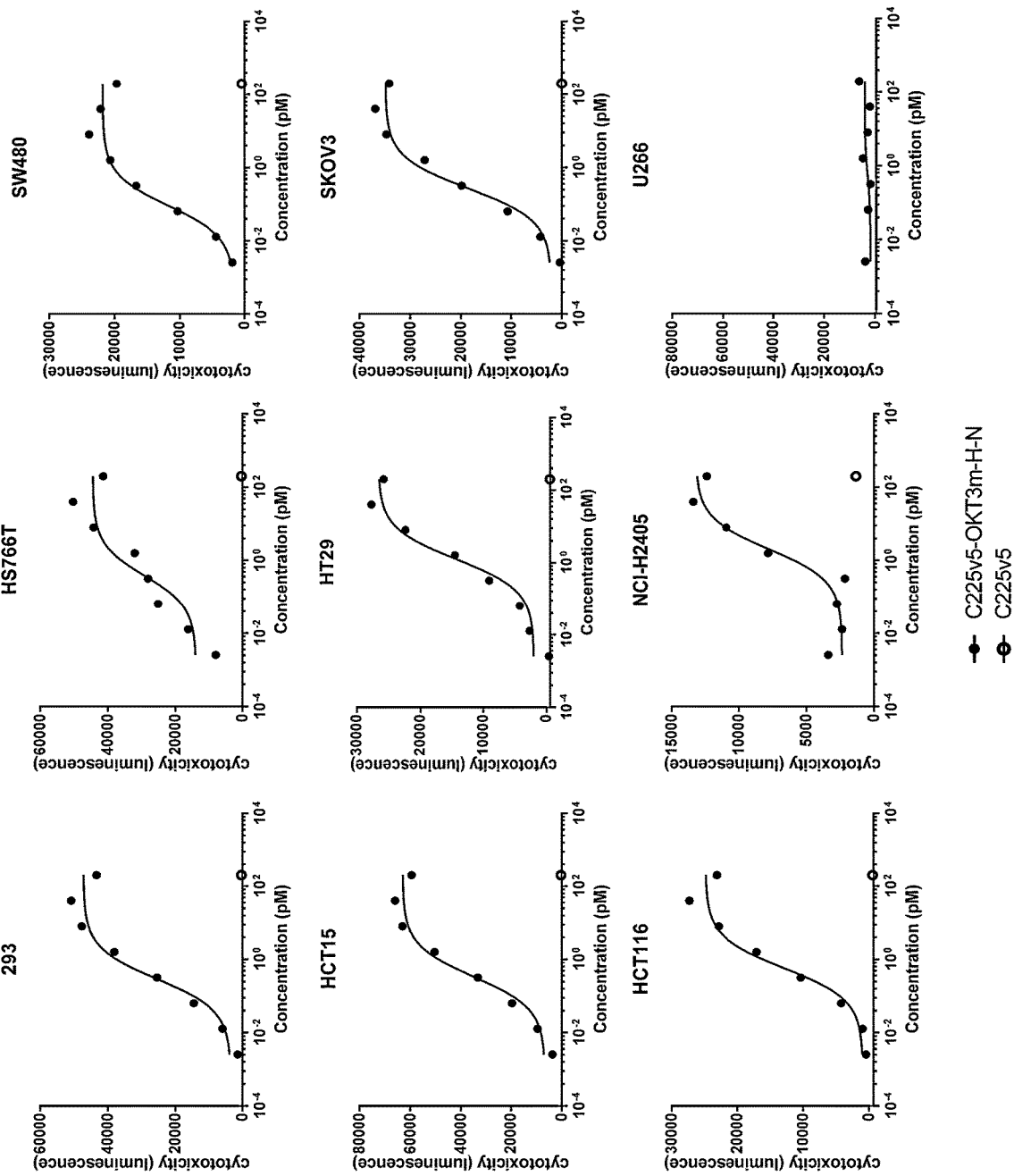

SEQUENCE LISTING

```
<160> NUMBER OF SEQ ID NOS: 339

<210> SEQ ID NO 1
<211> LENGTH: 34
<212> TYPE: DNA
<213> ORGANISM: Artificial Sequence
<220> FEATURE:
<223> OTHER INFORMATION: Primer CTRevNot

<400> SEQUENCE: 1
tcgagcggcc gctcaactag ctgaagagac agtg                               34

<210> SEQ ID NO 2
<211> LENGTH: 44
<212> TYPE: DNA
<213> ORGANISM: Artificial Sequence
<220> FEATURE:
<223> OTHER INFORMATION: Primer CTForOL

<400> SEQUENCE: 2
gccctctaga ctcgatctag ctagctgaag agacagtgac cagg                    44

<210> SEQ ID NO 3
<211> LENGTH: 27
<212> TYPE: DNA
<213> ORGANISM: Artificial Sequence
<220> FEATURE:
<223> OTHER INFORMATION: Primer HCForNhe

<400> SEQUENCE: 3
ctcagctagc accagggccc atcggtc                                       27

<210> SEQ ID NO 4
<211> LENGTH: 32
<212> TYPE: DNA
```

<213> ORGANISM: Artificial Sequence
<220> FEATURE:
<223> OTHER INFORMATION: Primer HCRevOL

<400> SEQUENCE: 4
ctttacccgg agacagggag aggctcttct gc              32

<210> SEQ ID NO 5
<211> LENGTH: 35
<212> TYPE: DNA
<213> ORGANISM: Artificial Sequence
<220> FEATURE:
<223> OTHER INFORMATION: Primer OKREVNot

<400> SEQUENCE: 5
ctcgagcggc cgctcaacga ttaatttcca gtttg           35

<210> SEQ ID NO 6
<211> LENGTH: 5
<212> TYPE: PRT
<213> ORGANISM: Artificial Sequence
<220> FEATURE:
<223> OTHER INFORMATION: anti-Jagged VH CDR1

<400> SEQUENCE: 6

Ser Tyr Ala Met Ser
1               5

<210> SEQ ID NO 7
<211> LENGTH: 17
<212> TYPE: PRT
<213> ORGANISM: Artificial Sequence
<220> FEATURE:
<223> OTHER INFORMATION: anti-Jagged VH CDR2

<400> SEQUENCE: 7

Ser Ile Asp Pro Glu Gly Arg Gln Thr Tyr Tyr Ala Asp Ser Val Lys
1               5                   10                  15

Gly

<210> SEQ ID NO 8
<211> LENGTH: 10
<212> TYPE: PRT
<213> ORGANISM: Artificial Sequence
<220> FEATURE:
<223> OTHER INFORMATION: anti-Jagged VH CDR3

<400> SEQUENCE: 8

Asp Ile Gly Gly Arg Ser Ala Phe Asp Tyr
1               5                   10

<210> SEQ ID NO 9
<211> LENGTH: 9
<212> TYPE: PRT
<213> ORGANISM: Artificial Sequence
<220> FEATURE:
<223> OTHER INFORMATION: anti-Jagged VL CDR1

<400> SEQUENCE: 9

Arg Ala Ser Gln Ser Ile Ser Ser Tyr
1               5

<210> SEQ ID NO 10
<211> LENGTH: 7
<212> TYPE: PRT
<213> ORGANISM: Artificial Sequence

```
<220> FEATURE:
<223> OTHER INFORMATION: anti-Jagged VL CDR2

<400> SEQUENCE: 10

Ala Ala Ser Ser Leu Gln Ser
1               5

<210> SEQ ID NO 11
<211> LENGTH: 9
<212> TYPE: PRT
<213> ORGANISM: Artificial Sequence
<220> FEATURE:
<223> OTHER INFORMATION: anti-Jagged VL CDR3

<400> SEQUENCE: 11

Gln Gln Thr Val Val Ala Pro Pro Leu
1               5

<210> SEQ ID NO 12
<211> LENGTH: 5
<212> TYPE: PRT
<213> ORGANISM: Artificial Sequence
<220> FEATURE:
<223> OTHER INFORMATION: anti-EGFR VH CDR1

<400> SEQUENCE: 12

Asn Tyr Gly Val His
1               5

<210> SEQ ID NO 13
<211> LENGTH: 16
<212> TYPE: PRT
<213> ORGANISM: Artificial Sequence
<220> FEATURE:
<223> OTHER INFORMATION: anti-EGFR VH CDR2

<400> SEQUENCE: 13

Val Ile Trp Ser Gly Gly Asn Thr Asp Tyr Asn Thr Pro Phe Thr Ser
1               5                   10                  15

<210> SEQ ID NO 14
<211> LENGTH: 11
<212> TYPE: PRT
<213> ORGANISM: Artificial Sequence
<220> FEATURE:
<223> OTHER INFORMATION: anti-EGFR VH CDR3

<400> SEQUENCE: 14

Ala Leu Thr Tyr Tyr Asp Tyr Glu Phe Ala Tyr
1               5                   10

<210> SEQ ID NO 15
<211> LENGTH: 11
<212> TYPE: PRT
<213> ORGANISM: Artificial Sequence
<220> FEATURE:
<223> OTHER INFORMATION: anti-EGFR VL CDR1

<400> SEQUENCE: 15

Arg Ala Ser Gln Ser Ile Gly Thr Asn Ile His
1               5                   10

<210> SEQ ID NO 16
<211> LENGTH: 8
<212> TYPE: PRT
<213> ORGANISM: Artificial Sequence
<220> FEATURE:
```

```
<223> OTHER INFORMATION: anti-EGFR VL CDR2

<400> SEQUENCE: 16

Lys Tyr Ala Ser Glu Ser Ile Ser
1               5

<210> SEQ ID NO 17
<211> LENGTH: 9
<212> TYPE: PRT
<213> ORGANISM: Artificial Sequence
<220> FEATURE:
<223> OTHER INFORMATION: anti-EGFR VL CDR3

<400> SEQUENCE: 17

Gln Gln Asn Asn Asn Trp Pro Thr Thr
1               5

<210> SEQ ID NO 18
<211> LENGTH: 5
<212> TYPE: PRT
<213> ORGANISM: Artificial Sequence
<220> FEATURE:
<223> OTHER INFORMATION: linking peptide
<220> FEATURE:
<221> NAME/KEY: REPEAT
<222> LOCATION: (1)..(5)
<223> OTHER INFORMATION: May be repeated

<400> SEQUENCE: 18

Gly Ser Gly Gly Ser
1               5

<210> SEQ ID NO 19
<211> LENGTH: 4
<212> TYPE: PRT
<213> ORGANISM: Artificial Sequence
<220> FEATURE:
<223> OTHER INFORMATION: linking peptide
<220> FEATURE:
<221> NAME/KEY: REPEAT
<222> LOCATION: (1)..(4)
<223> OTHER INFORMATION: May be repeated

<400> SEQUENCE: 19

Gly Gly Gly Ser
1

<210> SEQ ID NO 20
<211> LENGTH: 4
<212> TYPE: PRT
<213> ORGANISM: Artificial Sequence
<220> FEATURE:
<223> OTHER INFORMATION: linking peptide

<400> SEQUENCE: 20

Gly Gly Ser Gly
1

<210> SEQ ID NO 21
<211> LENGTH: 5
<212> TYPE: PRT
<213> ORGANISM: Artificial Sequence
<220> FEATURE:
<223> OTHER INFORMATION: linking peptide

<400> SEQUENCE: 21

Gly Gly Ser Gly Gly
1               5
```

```
<210> SEQ ID NO 22
<211> LENGTH: 5
<212> TYPE: PRT
<213> ORGANISM: Artificial Sequence
<220> FEATURE:
<223> OTHER INFORMATION: linking peptide

<400> SEQUENCE: 22

Gly Ser Gly Ser Gly
1               5

<210> SEQ ID NO 23
<211> LENGTH: 5
<212> TYPE: PRT
<213> ORGANISM: Artificial Sequence
<220> FEATURE:
<223> OTHER INFORMATION: linking peptide

<400> SEQUENCE: 23

Gly Ser Gly Gly Gly
1               5

<210> SEQ ID NO 24
<211> LENGTH: 5
<212> TYPE: PRT
<213> ORGANISM: Artificial Sequence
<220> FEATURE:
<223> OTHER INFORMATION: linking peptide

<400> SEQUENCE: 24

Gly Gly Gly Ser Gly
1               5

<210> SEQ ID NO 25
<211> LENGTH: 5
<212> TYPE: PRT
<213> ORGANISM: Artificial Sequence
<220> FEATURE:
<223> OTHER INFORMATION: linking peptide

<400> SEQUENCE: 25

Gly Ser Ser Ser Gly
1               5

<210> SEQ ID NO 26
<211> LENGTH: 8
<212> TYPE: PRT
<213> ORGANISM: Artificial Sequence
<220> FEATURE:
<223> OTHER INFORMATION: cleavable moiety

<400> SEQUENCE: 26

Leu Ser Gly Arg Ser Asp Asn His
1               5

<210> SEQ ID NO 27
<211> LENGTH: 8
<212> TYPE: PRT
<213> ORGANISM: Artificial Sequence
<220> FEATURE:
<223> OTHER INFORMATION: cleavable moiety

<400> SEQUENCE: 27

Thr Gly Arg Gly Pro Ser Trp Val
1               5
```

```
<210> SEQ ID NO 28
<211> LENGTH: 8
<212> TYPE: PRT
<213> ORGANISM: Artificial Sequence
<220> FEATURE:
<223> OTHER INFORMATION: cleavable moiety

<400> SEQUENCE: 28

Ser Ala Arg Gly Pro Ser Arg Trp
1               5

<210> SEQ ID NO 29
<211> LENGTH: 8
<212> TYPE: PRT
<213> ORGANISM: Artificial Sequence
<220> FEATURE:
<223> OTHER INFORMATION: cleavable moiety

<400> SEQUENCE: 29

Thr Ala Arg Gly Pro Ser Phe Lys
1               5

<210> SEQ ID NO 30
<211> LENGTH: 8
<212> TYPE: PRT
<213> ORGANISM: Artificial Sequence
<220> FEATURE:
<223> OTHER INFORMATION: cleavable moiety

<400> SEQUENCE: 30

Gly Gly Trp His Thr Gly Arg Asn
1               5

<210> SEQ ID NO 31
<211> LENGTH: 8
<212> TYPE: PRT
<213> ORGANISM: Artificial Sequence
<220> FEATURE:
<223> OTHER INFORMATION: cleavable moiety

<400> SEQUENCE: 31

His Thr Gly Arg Ser Gly Ala Leu
1               5

<210> SEQ ID NO 32
<211> LENGTH: 8
<212> TYPE: PRT
<213> ORGANISM: Artificial Sequence
<220> FEATURE:
<223> OTHER INFORMATION: cleavable moiety

<400> SEQUENCE: 32

Pro Leu Thr Gly Arg Ser Gly Gly
1               5

<210> SEQ ID NO 33
<211> LENGTH: 8
<212> TYPE: PRT
<213> ORGANISM: Artificial Sequence
<220> FEATURE:
<223> OTHER INFORMATION: cleavable moiety

<400> SEQUENCE: 33

Ala Ala Arg Gly Pro Ala Ile His
1               5
```

```
<210> SEQ ID NO 34
<211> LENGTH: 8
<212> TYPE: PRT
<213> ORGANISM: Artificial Sequence
<220> FEATURE:
<223> OTHER INFORMATION: cleavable moiety

<400> SEQUENCE: 34

Arg Gly Pro Ala Phe Asn Pro Met
1               5

<210> SEQ ID NO 35
<211> LENGTH: 8
<212> TYPE: PRT
<213> ORGANISM: Artificial Sequence
<220> FEATURE:
<223> OTHER INFORMATION: cleavable moiety

<400> SEQUENCE: 35

Ser Ser Arg Gly Pro Ala Tyr Leu
1               5

<210> SEQ ID NO 36
<211> LENGTH: 8
<212> TYPE: PRT
<213> ORGANISM: Artificial Sequence
<220> FEATURE:
<223> OTHER INFORMATION: cleavable moiety

<400> SEQUENCE: 36

Arg Gly Pro Ala Thr Pro Ile Met
1               5

<210> SEQ ID NO 37
<211> LENGTH: 4
<212> TYPE: PRT
<213> ORGANISM: Artificial Sequence
<220> FEATURE:
<223> OTHER INFORMATION: cleavable moiety

<400> SEQUENCE: 37

Arg Gly Pro Ala
1

<210> SEQ ID NO 38
<211> LENGTH: 10
<212> TYPE: PRT
<213> ORGANISM: Artificial Sequence
<220> FEATURE:
<223> OTHER INFORMATION: cleavable moiety

<400> SEQUENCE: 38

Gly Gly Gln Pro Ser Gly Met Trp Gly Trp
1               5                   10

<210> SEQ ID NO 39
<211> LENGTH: 10
<212> TYPE: PRT
<213> ORGANISM: Artificial Sequence
<220> FEATURE:
<223> OTHER INFORMATION: cleavable moiety

<400> SEQUENCE: 39

Phe Pro Arg Pro Leu Gly Ile Thr Gly Leu
1               5                   10

<210> SEQ ID NO 40
```

```
<211> LENGTH: 10
<212> TYPE: PRT
<213> ORGANISM: Artificial Sequence
<220> FEATURE:
<223> OTHER INFORMATION: cleavable moiety

<400> SEQUENCE: 40

Val His Met Pro Leu Gly Phe Leu Gly Pro
1               5                   10

<210> SEQ ID NO 41
<211> LENGTH: 8
<212> TYPE: PRT
<213> ORGANISM: Artificial Sequence
<220> FEATURE:
<223> OTHER INFORMATION: cleavable moiety

<400> SEQUENCE: 41

Ser Pro Leu Thr Gly Arg Ser Gly
1               5

<210> SEQ ID NO 42
<211> LENGTH: 8
<212> TYPE: PRT
<213> ORGANISM: Artificial Sequence
<220> FEATURE:
<223> OTHER INFORMATION: cleavable moiety

<400> SEQUENCE: 42

Ser Ala Gly Phe Ser Leu Pro Ala
1               5

<210> SEQ ID NO 43
<211> LENGTH: 9
<212> TYPE: PRT
<213> ORGANISM: Artificial Sequence
<220> FEATURE:
<223> OTHER INFORMATION: cleavable moiety

<400> SEQUENCE: 43

Leu Ala Pro Leu Gly Leu Gln Arg Arg
1               5

<210> SEQ ID NO 44
<211> LENGTH: 8
<212> TYPE: PRT
<213> ORGANISM: Artificial Sequence
<220> FEATURE:
<223> OTHER INFORMATION: cleavable moiety

<400> SEQUENCE: 44

Ser Gly Gly Pro Leu Gly Val Arg
1               5

<210> SEQ ID NO 45
<211> LENGTH: 4
<212> TYPE: PRT
<213> ORGANISM: Artificial Sequence
<220> FEATURE:
<223> OTHER INFORMATION: cleavable moiety

<400> SEQUENCE: 45

Pro Leu Gly Leu
1

<210> SEQ ID NO 46
<211> LENGTH: 6
```

```
<212> TYPE: PRT
<213> ORGANISM: Artificial Sequence
<220> FEATURE:
<223> OTHER INFORMATION: spacer peptide

<400> SEQUENCE: 46

Gln Gly Gln Ser Gly Gln
1               5

<210> SEQ ID NO 47
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 47

Pro Arg Phe Lys Ile Ile Gly Gly
1               5

<210> SEQ ID NO 48
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 48

Pro Arg Phe Arg Ile Ile Gly Gly
1               5

<210> SEQ ID NO 49
<211> LENGTH: 9
<212> TYPE: PRT
<213> ORGANISM: Artificial Sequence
<220> FEATURE:
<223> OTHER INFORMATION: cleavable linker sequence

<400> SEQUENCE: 49

Ser Ser Arg His Arg Arg Ala Leu Asp
1               5

<210> SEQ ID NO 50
<211> LENGTH: 14
<212> TYPE: PRT
<213> ORGANISM: Artificial Sequence
<220> FEATURE:
<223> OTHER INFORMATION: cleavable linker sequence

<400> SEQUENCE: 50

Arg Lys Ser Ser Ile Ile Ile Arg Met Arg Asp Val Val Leu
1               5                   10

<210> SEQ ID NO 51
<211> LENGTH: 15
<212> TYPE: PRT
<213> ORGANISM: Artificial Sequence
<220> FEATURE:
<223> OTHER INFORMATION: cleavable linker sequence

<400> SEQUENCE: 51

Ser Ser Ser Phe Asp Lys Gly Lys Tyr Lys Lys Gly Asp Asp Ala
1               5                   10                  15

<210> SEQ ID NO 52
<211> LENGTH: 15
<212> TYPE: PRT
```

```
<213> ORGANISM: Artificial Sequence
<220> FEATURE:
<223> OTHER INFORMATION: cleavable linker sequence

<400> SEQUENCE: 52

Ser Ser Ser Phe Asp Lys Gly Lys Tyr Lys Arg Gly Asp Asp Ala
1               5                   10                  15

<210> SEQ ID NO 53
<211> LENGTH: 4
<212> TYPE: PRT
<213> ORGANISM: Artificial Sequence
<220> FEATURE:
<223> OTHER INFORMATION: cleavable linker sequence

<400> SEQUENCE: 53

Ile Glu Gly Arg
1

<210> SEQ ID NO 54
<211> LENGTH: 4
<212> TYPE: PRT
<213> ORGANISM: Artificial Sequence
<220> FEATURE:
<223> OTHER INFORMATION: cleavable linker sequence

<400> SEQUENCE: 54

Ile Asp Gly Arg
1

<210> SEQ ID NO 55
<211> LENGTH: 7
<212> TYPE: PRT
<213> ORGANISM: Artificial Sequence
<220> FEATURE:
<223> OTHER INFORMATION: cleavable linker sequence

<400> SEQUENCE: 55

Gly Gly Ser Ile Asp Gly Arg
1               5

<210> SEQ ID NO 56
<211> LENGTH: 6
<212> TYPE: PRT
<213> ORGANISM: Artificial Sequence
<220> FEATURE:
<223> OTHER INFORMATION: cleavable linker sequence

<400> SEQUENCE: 56

Pro Leu Gly Leu Trp Ala
1               5

<210> SEQ ID NO 57
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 57

Gly Pro Gln Gly Ile Ala Gly Gln
1               5

<210> SEQ ID NO 58
<211> LENGTH: 8
<212> TYPE: PRT
<213> ORGANISM: Artificial Sequence
```

```
<220> FEATURE:
<223> OTHER INFORMATION: cleavable linker sequence

<400> SEQUENCE: 58

Gly Pro Gln Gly Leu Leu Gly Ala
1               5

<210> SEQ ID NO 59
<211> LENGTH: 5
<212> TYPE: PRT
<213> ORGANISM: Artificial Sequence
<220> FEATURE:
<223> OTHER INFORMATION: cleavable linker sequence

<400> SEQUENCE: 59

Gly Ile Ala Gly Gln
1               5

<210> SEQ ID NO 60
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 60

Gly Pro Leu Gly Ile Ala Gly Ile
1               5

<210> SEQ ID NO 61
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 61

Gly Pro Glu Gly Leu Arg Val Gly
1               5

<210> SEQ ID NO 62
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 62

Tyr Gly Ala Gly Leu Gly Val Val
1               5

<210> SEQ ID NO 63
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 63

Ala Gly Leu Gly Val Val Glu Arg
1               5

<210> SEQ ID NO 64
<211> LENGTH: 8
<212> TYPE: PRT
<213> ORGANISM: Artificial Sequence
<220> FEATURE:
```

```
<223> OTHER INFORMATION: cleavable linker sequence

<400> SEQUENCE: 64

Ala Gly Leu Gly Ile Ser Ser Thr
1               5

<210> SEQ ID NO 65
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 65

Glu Pro Gln Ala Leu Ala Met Ser
1               5

<210> SEQ ID NO 66
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 66

Gln Ala Leu Ala Met Ser Ala Ile
1               5

<210> SEQ ID NO 67
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 67

Ala Ala Tyr His Leu Val Ser Gln
1               5

<210> SEQ ID NO 68
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 68

Met Asp Ala Phe Leu Glu Ser Ser
1               5

<210> SEQ ID NO 69
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 69

Glu Ser Leu Pro Val Val Ala Val
1               5

<210> SEQ ID NO 70
<211> LENGTH: 8
<212> TYPE: PRT
<213> ORGANISM: Artificial Sequence
<220> FEATURE:
<223> OTHER INFORMATION: cleavable linker sequence
```

-continued

<400> SEQUENCE: 70

Ser Ala Pro Ala Val Glu Ser Glu
1               5

<210> SEQ ID NO 71
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 71

Asp Val Ala Gln Phe Val Leu Thr
1               5

<210> SEQ ID NO 72
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 72

Val Ala Gln Phe Val Leu Thr Glu
1               5

<210> SEQ ID NO 73
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 73

Ala Gln Phe Val Leu Thr Glu Gly
1               5

<210> SEQ ID NO 74
<211> LENGTH: 8
<212> TYPE: PRT
<213> ORGANISM: Artificial Sequence
<220> FEATURE:
<223> OTHER INFORMATION: cleavable linker sequence

<400> SEQUENCE: 74

Pro Val Gln Pro Ile Gly Pro Gln
1               5

<210> SEQ ID NO 75
<211> LENGTH: 6
<212> TYPE: PRT
<213> ORGANISM: Artificial Sequence
<220> FEATURE:
<223> OTHER INFORMATION: masking moiety

<400> SEQUENCE: 75

Cys Ile Ser Pro Arg Gly
1               5

<210> SEQ ID NO 76
<211> LENGTH: 8
<212> TYPE: PRT
<213> ORGANISM: Artificial Sequence
<220> FEATURE:
<223> OTHER INFORMATION: masking moiety

```
<400> SEQUENCE: 76

Cys Ile Ser Pro Arg Gly Cys Gly
1               5

<210> SEQ ID NO 77
<211> LENGTH: 15
<212> TYPE: PRT
<213> ORGANISM: Artificial Sequence
<220> FEATURE:
<223> OTHER INFORMATION: masking moiety

<400> SEQUENCE: 77

Cys Ile Ser Pro Arg Gly Cys Pro Asp Gly Pro Tyr Val Met Tyr
1               5                   10                  15

<210> SEQ ID NO 78
<211> LENGTH: 14
<212> TYPE: PRT
<213> ORGANISM: Artificial Sequence
<220> FEATURE:
<223> OTHER INFORMATION: masking moiety

<400> SEQUENCE: 78

Cys Ile Ser Pro Arg Gly Cys Pro Asp Gly Pro Tyr Val Met
1               5                   10

<210> SEQ ID NO 79
<211> LENGTH: 15
<212> TYPE: PRT
<213> ORGANISM: Artificial Sequence
<220> FEATURE:
<223> OTHER INFORMATION: masking moiety

<400> SEQUENCE: 79

Cys Ile Ser Pro Arg Gly Cys Glu Pro Gly Thr Tyr Val Pro Thr
1               5                   10                  15

<210> SEQ ID NO 80
<211> LENGTH: 15
<212> TYPE: PRT
<213> ORGANISM: Artificial Sequence
<220> FEATURE:
<223> OTHER INFORMATION: masking moiety

<400> SEQUENCE: 80

Cys Ile Ser Pro Arg Gly Cys Pro Gly Gln Ile Trp His Pro Pro
1               5                   10                  15

<210> SEQ ID NO 81
<211> LENGTH: 15
<212> TYPE: PRT
<213> ORGANISM: Artificial Sequence
<220> FEATURE:
<223> OTHER INFORMATION: masking moiety

<400> SEQUENCE: 81

Gly Ser His Cys Leu Ile Pro Ile Asn Met Gly Ala Pro Ser Cys
1               5                   10                  15

<210> SEQ ID NO 82
<211> LENGTH: 32
<212> TYPE: PRT
<213> ORGANISM: Artificial Sequence
<220> FEATURE:
<223> OTHER INFORMATION: masking moiety

<400> SEQUENCE: 82
```

```
Cys Ile Ser Pro Arg Gly Cys Gly Gly Ser Ser Ala Ser Gln Ser Gly
1               5                   10                  15

Gln Gly Ser His Cys Leu Ile Pro Ile Asn Met Gly Ala Pro Ser Cys
            20                  25                  30
```

<210> SEQ ID NO 83
<211> LENGTH: 19
<212> TYPE: PRT
<213> ORGANISM: Artificial Sequence
<220> FEATURE:
<223> OTHER INFORMATION: masking moiety

<400> SEQUENCE: 83

```
Cys Asn His His Tyr Phe Tyr Thr Cys Gly Cys Ile Ser Pro Arg Gly
1               5                   10                  15

Cys Pro Gly
```

<210> SEQ ID NO 84
<211> LENGTH: 19
<212> TYPE: PRT
<213> ORGANISM: Artificial Sequence
<220> FEATURE:
<223> OTHER INFORMATION: masking moiety

<400> SEQUENCE: 84

```
Ala Asp His Val Phe Trp Gly Ser Tyr Gly Cys Ile Ser Pro Arg Gly
1               5                   10                  15

Cys Pro Gly
```

<210> SEQ ID NO 85
<211> LENGTH: 19
<212> TYPE: PRT
<213> ORGANISM: Artificial Sequence
<220> FEATURE:
<223> OTHER INFORMATION: masking moiety

<400> SEQUENCE: 85

```
Cys His His Val Tyr Trp Gly His Cys Gly Cys Ile Ser Pro Arg Gly
1               5                   10                  15

Cys Pro Gly
```

<210> SEQ ID NO 86
<211> LENGTH: 19
<212> TYPE: PRT
<213> ORGANISM: Artificial Sequence
<220> FEATURE:
<223> OTHER INFORMATION: masking moiety

<400> SEQUENCE: 86

```
Cys Pro His Phe Thr Thr Thr Ser Cys Gly Cys Ile Ser Pro Arg Gly
1               5                   10                  15

Cys Pro Gly
```

<210> SEQ ID NO 87
<211> LENGTH: 19
<212> TYPE: PRT
<213> ORGANISM: Artificial Sequence
<220> FEATURE:
<223> OTHER INFORMATION: masking moiety

<400> SEQUENCE: 87

```
Cys Asn His His Tyr His Tyr Tyr Cys Gly Cys Ile Ser Pro Arg Gly
1               5                   10                  15
```

```
Cys Pro Gly

<210> SEQ ID NO 88
<211> LENGTH: 19
<212> TYPE: PRT
<213> ORGANISM: Artificial Sequence
<220> FEATURE:
<223> OTHER INFORMATION: masking moiety

<400> SEQUENCE: 88

Cys Pro His Val Ser Phe Gly Ser Cys Gly Cys Ile Ser Pro Arg Gly
1               5                   10                  15

Cys Pro Gly

<210> SEQ ID NO 89
<211> LENGTH: 19
<212> TYPE: PRT
<213> ORGANISM: Artificial Sequence
<220> FEATURE:
<223> OTHER INFORMATION: masking moiety

<400> SEQUENCE: 89

Cys Pro Tyr Tyr Thr Leu Ser Tyr Cys Gly Cys Ile Ser Pro Arg Gly
1               5                   10                  15

Cys Pro Gly

<210> SEQ ID NO 90
<211> LENGTH: 19
<212> TYPE: PRT
<213> ORGANISM: Artificial Sequence
<220> FEATURE:
<223> OTHER INFORMATION: masking moiety

<400> SEQUENCE: 90

Cys Asn His Val Tyr Phe Gly Thr Cys Gly Cys Ile Ser Pro Arg Gly
1               5                   10                  15

Cys Pro Gly

<210> SEQ ID NO 91
<211> LENGTH: 19
<212> TYPE: PRT
<213> ORGANISM: Artificial Sequence
<220> FEATURE:
<223> OTHER INFORMATION: masking moiety

<400> SEQUENCE: 91

Cys Asn His Phe Thr Leu Thr Thr Cys Gly Cys Ile Ser Pro Arg Gly
1               5                   10                  15

Cys Pro Gly

<210> SEQ ID NO 92
<211> LENGTH: 19
<212> TYPE: PRT
<213> ORGANISM: Artificial Sequence
<220> FEATURE:
<223> OTHER INFORMATION: masking moiety

<400> SEQUENCE: 92

Cys His His Phe Thr Leu Thr Thr Cys Gly Cys Ile Ser Pro Arg Gly
1               5                   10                  15

Cys Pro Gly
```

```
<210> SEQ ID NO 93
<211> LENGTH: 18
<212> TYPE: PRT
<213> ORGANISM: Artificial Sequence
<220> FEATURE:
<223> OTHER INFORMATION: masking moiety

<400> SEQUENCE: 93

Tyr Asn Pro Cys Ala Thr Pro Met Cys Cys Ile Ser Pro Arg Gly Cys
1               5                   10                  15
Pro Gly

<210> SEQ ID NO 94
<211> LENGTH: 18
<212> TYPE: PRT
<213> ORGANISM: Artificial Sequence
<220> FEATURE:
<223> OTHER INFORMATION: masking moiety

<400> SEQUENCE: 94

Cys Asn His His Tyr Phe Tyr Thr Cys Gly Cys Ile Ser Pro Arg Gly
1               5                   10                  15
Cys Gly

<210> SEQ ID NO 95
<211> LENGTH: 18
<212> TYPE: PRT
<213> ORGANISM: Artificial Sequence
<220> FEATURE:
<223> OTHER INFORMATION: masking moiety

<400> SEQUENCE: 95

Cys Asn His His Tyr His Tyr Tyr Cys Gly Cys Ile Ser Pro Arg Gly
1               5                   10                  15
Cys Gly

<210> SEQ ID NO 96
<211> LENGTH: 18
<212> TYPE: PRT
<213> ORGANISM: Artificial Sequence
<220> FEATURE:
<223> OTHER INFORMATION: masking moiety

<400> SEQUENCE: 96

Cys Asn His Val Tyr Phe Gly Thr Cys Gly Cys Ile Ser Pro Arg Gly
1               5                   10                  15
Cys Gly

<210> SEQ ID NO 97
<211> LENGTH: 18
<212> TYPE: PRT
<213> ORGANISM: Artificial Sequence
<220> FEATURE:
<223> OTHER INFORMATION: masking moiety

<400> SEQUENCE: 97

Cys His His Val Tyr Trp Gly His Cys Gly Cys Ile Ser Pro Arg Gly
1               5                   10                  15
Cys Gly

<210> SEQ ID NO 98
<211> LENGTH: 18
<212> TYPE: PRT
<213> ORGANISM: Artificial Sequence
```

<220> FEATURE:
<223> OTHER INFORMATION: masking moiety

<400> SEQUENCE: 98

Cys Pro His Phe Thr Thr Thr Ser Cys Gly Cys Ile Ser Pro Arg Gly
1               5                   10                  15

Cys Gly

<210> SEQ ID NO 99
<211> LENGTH: 18
<212> TYPE: PRT
<213> ORGANISM: Artificial Sequence
<220> FEATURE:
<223> OTHER INFORMATION: masking moiety

<400> SEQUENCE: 99

Cys Asn His Phe Thr Leu Thr Thr Cys Gly Cys Ile Ser Pro Arg Gly
1               5                   10                  15

Cys Gly

<210> SEQ ID NO 100
<211> LENGTH: 18
<212> TYPE: PRT
<213> ORGANISM: Artificial Sequence
<220> FEATURE:
<223> OTHER INFORMATION: masking moiety

<400> SEQUENCE: 100

Cys His His Phe Thr Leu Thr Thr Cys Gly Cys Ile Ser Pro Arg Gly
1               5                   10                  15

Cys Gly

<210> SEQ ID NO 101
<211> LENGTH: 18
<212> TYPE: PRT
<213> ORGANISM: Artificial Sequence
<220> FEATURE:
<223> OTHER INFORMATION: masking moiety

<400> SEQUENCE: 101

Cys Pro Tyr Tyr Thr Leu Ser Tyr Cys Gly Cys Ile Ser Pro Arg Gly
1               5                   10                  15

Cys Gly

<210> SEQ ID NO 102
<211> LENGTH: 18
<212> TYPE: PRT
<213> ORGANISM: Artificial Sequence
<220> FEATURE:
<223> OTHER INFORMATION: masking moiety

<400> SEQUENCE: 102

Cys Pro His Val Ser Phe Gly Ser Cys Gly Cys Ile Ser Pro Arg Gly
1               5                   10                  15

Cys Gly

<210> SEQ ID NO 103
<211> LENGTH: 18
<212> TYPE: PRT
<213> ORGANISM: Artificial Sequence
<220> FEATURE:
<223> OTHER INFORMATION: masking moiety

<400> SEQUENCE: 103

```
Ala Asp His Val Phe Trp Gly Ser Tyr Gly Cys Ile Ser Pro Arg Gly
1               5                   10                  15

Cys Gly

<210> SEQ ID NO 104
<211> LENGTH: 17
<212> TYPE: PRT
<213> ORGANISM: Artificial Sequence
<220> FEATURE:
<223> OTHER INFORMATION: masking moiety

<400> SEQUENCE: 104

Tyr Asn Pro Cys Ala Thr Pro Met Cys Cys Ile Ser Pro Arg Gly Cys
1               5                   10                  15

Gly

<210> SEQ ID NO 105
<211> LENGTH: 18
<212> TYPE: PRT
<213> ORGANISM: Artificial Sequence
<220> FEATURE:
<223> OTHER INFORMATION: masking moiety

<400> SEQUENCE: 105

Cys His His Val Tyr Trp Gly His Cys Gly Cys Ile Ser Pro Arg Gly
1               5                   10                  15

Cys Gly

<210> SEQ ID NO 106
<211> LENGTH: 18
<212> TYPE: PRT
<213> ORGANISM: Artificial Sequence
<220> FEATURE:
<223> OTHER INFORMATION: masking moiety
<220> FEATURE:
<221> NAME/KEY: MISC_FEATURE
<222> LOCATION: (2)..(2)
<223> OTHER INFORMATION: Xaa may be Asn or Pro
<220> FEATURE:
<221> NAME/KEY: MISC_FEATURE
<222> LOCATION: (4)..(4)
<223> OTHER INFORMATION: Xaa may be His, Val or Phe
<220> FEATURE:
<221> NAME/KEY: MISC_FEATURE
<222> LOCATION: (5)..(5)
<223> OTHER INFORMATION: Xaa may be Tyr or Thr
<220> FEATURE:
<221> NAME/KEY: MISC_FEATURE
<222> LOCATION: (6)..(6)
<223> OTHER INFORMATION: Xaa may be Phe, Trp, Thr or Leu
<220> FEATURE:
<221> NAME/KEY: MISC_FEATURE
<222> LOCATION: (7)..(7)
<223> OTHER INFORMATION: Xaa may be Tyr, Gly, Thr or Ser
<220> FEATURE:
<221> NAME/KEY: MISC_FEATURE
<222> LOCATION: (8)..(8)
<223> OTHER INFORMATION: Xaa may be Thr, Ser, Tyr or His

<400> SEQUENCE: 106

Cys Xaa His Xaa Xaa Xaa Xaa Xaa Cys Gly Cys Ile Ser Pro Arg Gly
1               5                   10                  15

Cys Gly

<210> SEQ ID NO 107
<211> LENGTH: 15
<212> TYPE: PRT
```

<213> ORGANISM: Artificial Sequence
<220> FEATURE:
<223> OTHER INFORMATION: masking moiety

<400> SEQUENCE: 107

Cys Ile Ser Pro Arg Gly Cys Gly Gln Pro Ile Pro Ser Val Lys
1               5                   10                  15

<210> SEQ ID NO 108
<211> LENGTH: 15
<212> TYPE: PRT
<213> ORGANISM: Artificial Sequence
<220> FEATURE:
<223> OTHER INFORMATION: masking moiety

<400> SEQUENCE: 108

Cys Ile Ser Pro Arg Gly Cys Thr Gln Pro Tyr His Val Ser Arg
1               5                   10                  15

<210> SEQ ID NO 109
<211> LENGTH: 15
<212> TYPE: PRT
<213> ORGANISM: Artificial Sequence
<220> FEATURE:
<223> OTHER INFORMATION: masking moiety

<400> SEQUENCE: 109

Cys Ile Ser Pro Arg Gly Cys Asn Ala Val Ser Gly Leu Gly Ser
1               5                   10                  15

<210> SEQ ID NO 110
<211> LENGTH: 26
<212> TYPE: PRT
<213> ORGANISM: Artificial Sequence
<220> FEATURE:
<223> OTHER INFORMATION: masking moiety

<400> SEQUENCE: 110

Gln Gly Gln Ser Gly Gln Gly Gln Gln Trp Cys Asn Ile Trp Ile
1               5                   10                  15

Asn Gly Gly Asp Cys Arg Gly Trp Asn Gly
            20                  25

<210> SEQ ID NO 111
<211> LENGTH: 15
<212> TYPE: PRT
<213> ORGANISM: Artificial Sequence
<220> FEATURE:
<223> OTHER INFORMATION: masking moiety

<400> SEQUENCE: 111

Pro Trp Cys Met Gln Arg Gln Asp Phe Leu Arg Cys Pro Gln Pro
1               5                   10                  15

<210> SEQ ID NO 112
<211> LENGTH: 15
<212> TYPE: PRT
<213> ORGANISM: Artificial Sequence
<220> FEATURE:
<223> OTHER INFORMATION: masking moiety

<400> SEQUENCE: 112

Gln Leu Gly Leu Pro Ala Tyr Met Cys Thr Phe Glu Cys Leu Arg
1               5                   10                  15

<210> SEQ ID NO 113

<211> LENGTH: 15
<212> TYPE: PRT
<213> ORGANISM: Artificial Sequence
<220> FEATURE:
<223> OTHER INFORMATION: masking moiety

<400> SEQUENCE: 113

Cys Asn Leu Trp Val Ser Gly Gly Asp Cys Gly Gly Leu Gln Gly
1 5 10 15

<210> SEQ ID NO 114
<211> LENGTH: 15
<212> TYPE: PRT
<213> ORGANISM: Artificial Sequence
<220> FEATURE:
<223> OTHER INFORMATION: masking moiety

<400> SEQUENCE: 114

Ser Cys Ser Leu Trp Thr Ser Gly Ser Cys Leu Pro His Ser Pro
1 5 10 15

<210> SEQ ID NO 115
<211> LENGTH: 15
<212> TYPE: PRT
<213> ORGANISM: Artificial Sequence
<220> FEATURE:
<223> OTHER INFORMATION: masking moiety

<400> SEQUENCE: 115

Tyr Cys Leu Gln Leu Pro His Tyr Met Gln Ala Met Cys Gly Arg
1 5 10 15

<210> SEQ ID NO 116
<211> LENGTH: 15
<212> TYPE: PRT
<213> ORGANISM: Artificial Sequence
<220> FEATURE:
<223> OTHER INFORMATION: masking moiety

<400> SEQUENCE: 116

Cys Phe Leu Tyr Ser Cys Thr Asp Val Ser Tyr Trp Asn Asn Thr
1 5 10 15

<210> SEQ ID NO 117
<211> LENGTH: 15
<212> TYPE: PRT
<213> ORGANISM: Artificial Sequence
<220> FEATURE:
<223> OTHER INFORMATION: masking moiety

<400> SEQUENCE: 117

Pro Trp Cys Met Gln Arg Gln Asp Tyr Leu Arg Cys Pro Gln Pro
1 5 10 15

<210> SEQ ID NO 118
<211> LENGTH: 15
<212> TYPE: PRT
<213> ORGANISM: Artificial Sequence
<220> FEATURE:
<223> OTHER INFORMATION: masking moiety

<400> SEQUENCE: 118

Cys Asn Leu Trp Ile Ser Gly Gly Asp Cys Arg Gly Leu Ala Gly
1 5 10 15

<210> SEQ ID NO 119
<211> LENGTH: 15

<212> TYPE: PRT
<213> ORGANISM: Artificial Sequence
<220> FEATURE:
<223> OTHER INFORMATION: masking moiety

<400> SEQUENCE: 119

Cys Asn Leu Trp Val Ser Gly Gly Asp Cys Arg Gly Val Gln Gly
1 5 10 15

<210> SEQ ID NO 120
<211> LENGTH: 15
<212> TYPE: PRT
<213> ORGANISM: Artificial Sequence
<220> FEATURE:
<223> OTHER INFORMATION: masking moiety

<400> SEQUENCE: 120

Cys Asn Leu Trp Val Ser Gly Gly Asp Cys Arg Gly Leu Arg Gly
1 5 10 15

<210> SEQ ID NO 121
<211> LENGTH: 15
<212> TYPE: PRT
<213> ORGANISM: Artificial Sequence
<220> FEATURE:
<223> OTHER INFORMATION: masking moiety

<400> SEQUENCE: 121

Cys Asn Leu Trp Ile Ser Gly Gly Asp Cys Arg Gly Leu Pro Gly
1 5 10 15

<210> SEQ ID NO 122
<211> LENGTH: 15
<212> TYPE: PRT
<213> ORGANISM: Artificial Sequence
<220> FEATURE:
<223> OTHER INFORMATION: masking moiety

<400> SEQUENCE: 122

Cys Asn Leu Trp Val Ser Gly Gly Asp Cys Arg Asp Ala Pro Trp
1 5 10 15

<210> SEQ ID NO 123
<211> LENGTH: 15
<212> TYPE: PRT
<213> ORGANISM: Artificial Sequence
<220> FEATURE:
<223> OTHER INFORMATION: masking moiety

<400> SEQUENCE: 123

Cys Asn Leu Trp Val Ser Gly Gly Asp Cys Arg Asp Leu Leu Gly
1 5 10 15

<210> SEQ ID NO 124
<211> LENGTH: 15
<212> TYPE: PRT
<213> ORGANISM: Artificial Sequence
<220> FEATURE:
<223> OTHER INFORMATION: masking moiety

<400> SEQUENCE: 124

Cys Asn Leu Trp Val Ser Gly Gly Asp Cys Arg Gly Leu Gln Gly
1 5 10 15

<210> SEQ ID NO 125
<211> LENGTH: 15
<212> TYPE: PRT

```
<213> ORGANISM: Artificial Sequence
<220> FEATURE:
<223> OTHER INFORMATION: masking moiety

<400> SEQUENCE: 125

Cys Asn Leu Trp Leu His Gly Gly Asp Cys Arg Gly Trp Gln Gly
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: masking moiety

<400> SEQUENCE: 126

Cys Asn Ile Trp Leu Val Gly Gly Asp Cys Arg Gly Trp Gln Gly
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: masking moiety

<400> SEQUENCE: 127

Cys Thr Thr Trp Phe Cys Gly Gly Asp Cys Gly Val Met Arg Gly
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: masking moiety

<400> SEQUENCE: 128

Cys Asn Ile Trp Gly Pro Ser Val Asp Cys Gly Ala Leu Leu Gly
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: masking moiety

<400> SEQUENCE: 129

Cys Asn Ile Trp Val Asn Gly Gly Asp Cys Arg Ser Phe Glu Gly
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: masking moiety

<400> SEQUENCE: 130

Tyr Cys Leu Asn Leu Pro Arg Tyr Met Gln Asp Met Cys Trp Ala
1               5                   10                  15

<210> SEQ ID NO 131
<211> LENGTH: 15
<212> TYPE: PRT
<213> ORGANISM: Artificial Sequence
```

<220> FEATURE:
<223> OTHER INFORMATION: masking moiety

<400> SEQUENCE: 131

Tyr Cys Leu Ala Leu Pro His Tyr Met Gln Ala Asp Cys Ala Arg
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: masking moiety

<400> SEQUENCE: 132

Cys Phe Leu Tyr Ser Cys Gly Asp Val Ser Tyr Trp Gly Ser Ala
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: masking moiety

<400> SEQUENCE: 133

Cys Tyr Leu Tyr Ser Cys Thr Asp Ser Ala Phe Trp Asn Asn Arg
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: masking moiety

<400> SEQUENCE: 134

Cys Tyr Leu Tyr Ser Cys Asn Asp Val Ser Tyr Trp Ser Asn Thr
1               5                   10                  15

<210> SEQ ID NO 135
<211> LENGTH: 12
<212> TYPE: PRT
<213> ORGANISM: Artificial Sequence
<220> FEATURE:
<223> OTHER INFORMATION: masking moiety

<400> SEQUENCE: 135

Cys Phe Leu Tyr Ser Cys Thr Asp Val Ser Tyr Trp
1               5                   10

<210> SEQ ID NO 136
<211> LENGTH: 15
<212> TYPE: PRT
<213> ORGANISM: Artificial Sequence
<220> FEATURE:
<223> OTHER INFORMATION: masking moiety

<400> SEQUENCE: 136

Cys Phe Leu Tyr Ser Cys Thr Asp Val Ala Tyr Trp Asn Ser Ala
1               5                   10                  15

<210> SEQ ID NO 137
<211> LENGTH: 15
<212> TYPE: PRT
<213> ORGANISM: Artificial Sequence
<220> FEATURE:

<223> OTHER INFORMATION: masking moiety

<400> SEQUENCE: 137

Cys Phe Leu Tyr Ser Cys Thr Asp Val Ser Tyr Trp Gly Asp Thr
1               5                   10                  15

<210> SEQ ID NO 138
<211> LENGTH: 15
<212> TYPE: PRT
<213> ORGANISM: Artificial Sequence
<220> FEATURE:
<223> OTHER INFORMATION: masking moiety

<400> SEQUENCE: 138

Cys Phe Leu Tyr Ser Cys Thr Asp Val Ser Tyr Trp Gly Asn Ser
1               5                   10                  15

<210> SEQ ID NO 139
<211> LENGTH: 15
<212> TYPE: PRT
<213> ORGANISM: Artificial Sequence
<220> FEATURE:
<223> OTHER INFORMATION: masking moiety

<400> SEQUENCE: 139

Cys Phe Leu Tyr Ser Cys Thr Asp Val Ala Tyr Trp Asn Asn Thr
1               5                   10                  15

<210> SEQ ID NO 140
<211> LENGTH: 18
<212> TYPE: PRT
<213> ORGANISM: Artificial Sequence
<220> FEATURE:
<223> OTHER INFORMATION: masking moiety

<400> SEQUENCE: 140

Cys Phe Leu Tyr Ser Cys Gly Asp Val Ser Tyr Trp Gly Asn Pro Gly
1               5                   10                  15

Leu Ser

<210> SEQ ID NO 141
<211> LENGTH: 15
<212> TYPE: PRT
<213> ORGANISM: Artificial Sequence
<220> FEATURE:
<223> OTHER INFORMATION: masking moiety

<400> SEQUENCE: 141

Cys Phe Leu Tyr Ser Cys Thr Asp Val Ala Tyr Trp Ser Gly Leu
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: masking moiety

<400> SEQUENCE: 142

Cys Tyr Leu Tyr Ser Cys Thr Asp Gly Ser Tyr Trp Asn Ser Thr
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: masking moiety

<400> SEQUENCE: 143

Cys Phe Leu Tyr Ser Cys Ser Asp Val Ser Tyr Trp Gly Asn Ile
1               5                   10                  15

<210> SEQ ID NO 144
<211> LENGTH: 12
<212> TYPE: PRT
<213> ORGANISM: Artificial Sequence
<220> FEATURE:
<223> OTHER INFORMATION: masking moiety

<400> SEQUENCE: 144

Cys Phe Leu Tyr Ser Cys Thr Asp Val Ala Tyr Trp
1               5                   10

<210> SEQ ID NO 145
<211> LENGTH: 15
<212> TYPE: PRT
<213> ORGANISM: Artificial Sequence
<220> FEATURE:
<223> OTHER INFORMATION: masking moiety

<400> SEQUENCE: 145

Cys Phe Leu Tyr Ser Cys Thr Asp Val Ser Tyr Trp Gly Ser Thr
1               5                   10                  15

<210> SEQ ID NO 146
<211> LENGTH: 15
<212> TYPE: PRT
<213> ORGANISM: Artificial Sequence
<220> FEATURE:
<223> OTHER INFORMATION: masking moiety

<400> SEQUENCE: 146

Cys Phe Leu Tyr Ser Cys Thr Asp Val Ala Tyr Trp Gly Asp Thr
1               5                   10                  15

<210> SEQ ID NO 147
<211> LENGTH: 20
<212> TYPE: PRT
<213> ORGANISM: Artificial Sequence
<220> FEATURE:
<223> OTHER INFORMATION: masking moiety

<400> SEQUENCE: 147

Gly Cys Asn Ile Trp Leu Asn Gly Gly Asp Cys Arg Gly Trp Val Asp
1               5                   10                  15

Pro Leu Gln Gly
            20

<210> SEQ ID NO 148
<211> LENGTH: 20
<212> TYPE: PRT
<213> ORGANISM: Artificial Sequence
<220> FEATURE:
<223> OTHER INFORMATION: masking moiety

<400> SEQUENCE: 148

Gly Cys Asn Ile Trp Leu Val Gly Gly Asp Cys Arg Gly Trp Ile Gly
1               5                   10                  15

Asp Thr Asn Gly
            20

```
<210> SEQ ID NO 149
<211> LENGTH: 20
<212> TYPE: PRT
<213> ORGANISM: Artificial Sequence
<220> FEATURE:
<223> OTHER INFORMATION: masking moiety

<400> SEQUENCE: 149

Gly Cys Asn Ile Trp Leu Val Gly Gly Asp Cys Arg Gly Trp Ile Glu
1               5                   10                  15

Asp Ser Asn Gly
            20

<210> SEQ ID NO 150
<211> LENGTH: 20
<212> TYPE: PRT
<213> ORGANISM: Artificial Sequence
<220> FEATURE:
<223> OTHER INFORMATION: masking moiety

<400> SEQUENCE: 150

Gly Cys Asn Ile Trp Ala Asn Gly Gly Asp Cys Arg Gly Trp Ile Asp
1               5                   10                  15

Asn Ile Asp Gly
            20

<210> SEQ ID NO 151
<211> LENGTH: 20
<212> TYPE: PRT
<213> ORGANISM: Artificial Sequence
<220> FEATURE:
<223> OTHER INFORMATION: masking moiety

<400> SEQUENCE: 151

Gly Cys Asn Ile Trp Leu Val Gly Gly Asp Cys Arg Gly Trp Leu Gly
1               5                   10                  15

Glu Ala Val Gly
            20

<210> SEQ ID NO 152
<211> LENGTH: 20
<212> TYPE: PRT
<213> ORGANISM: Artificial Sequence
<220> FEATURE:
<223> OTHER INFORMATION: masking moiety

<400> SEQUENCE: 152

Gly Cys Asn Ile Trp Leu Val Gly Gly Asp Cys Arg Gly Trp Leu Glu
1               5                   10                  15

Glu Ala Val Gly
            20

<210> SEQ ID NO 153
<211> LENGTH: 20
<212> TYPE: PRT
<213> ORGANISM: Artificial Sequence
<220> FEATURE:
<223> OTHER INFORMATION: masking moiety

<400> SEQUENCE: 153

Gly Gly Pro Ala Leu Cys Asn Ile Trp Leu Asn Gly Gly Asp Cys Arg
1               5                   10                  15

Gly Trp Ser Gly
            20
```

```
<210> SEQ ID NO 154
<211> LENGTH: 20
<212> TYPE: PRT
<213> ORGANISM: Artificial Sequence
<220> FEATURE:
<223> OTHER INFORMATION: masking moiety

<400> SEQUENCE: 154

Gly Ala Pro Val Phe Cys Asn Ile Trp Leu Asn Gly Gly Asp Cys Arg
1               5                   10                  15

Gly Trp Met Gly
            20

<210> SEQ ID NO 155
<211> LENGTH: 20
<212> TYPE: PRT
<213> ORGANISM: Artificial Sequence
<220> FEATURE:
<223> OTHER INFORMATION: masking moiety

<400> SEQUENCE: 155

Gly Gln Gln Gln Trp Cys Asn Ile Trp Ile Asn Gly Gly Asp Cys Arg
1               5                   10                  15

Gly Trp Asn Gly
            20

<210> SEQ ID NO 156
<211> LENGTH: 20
<212> TYPE: PRT
<213> ORGANISM: Artificial Sequence
<220> FEATURE:
<223> OTHER INFORMATION: masking moiety

<400> SEQUENCE: 156

Gly Lys Ser Glu Phe Cys Asn Ile Trp Leu Asn Gly Gly Asp Cys Arg
1               5                   10                  15

Gly Trp Ile Gly
            20

<210> SEQ ID NO 157
<211> LENGTH: 20
<212> TYPE: PRT
<213> ORGANISM: Artificial Sequence
<220> FEATURE:
<223> OTHER INFORMATION: masking moiety

<400> SEQUENCE: 157

Gly Thr Pro Gly Gly Cys Asn Ile Trp Ala Asn Gly Gly Asp Cys Arg
1               5                   10                  15

Gly Trp Glu Gly
            20

<210> SEQ ID NO 158
<211> LENGTH: 20
<212> TYPE: PRT
<213> ORGANISM: Artificial Sequence
<220> FEATURE:
<223> OTHER INFORMATION: masking moiety

<400> SEQUENCE: 158

Gly Ala Ser Gln Tyr Cys Asn Leu Trp Ile Asn Gly Gly Asp Cys Arg
1               5                   10                  15

Gly Trp Arg Gly
```

```
<210> SEQ ID NO 159
<211> LENGTH: 18
<212> TYPE: PRT
<213> ORGANISM: Artificial Sequence
<220> FEATURE:
<223> OTHER INFORMATION: masking moiety

<400> SEQUENCE: 159

Gly Cys Asn Ile Trp Leu Val Gly Gly Asp Cys Arg Pro Trp Val Glu
1               5                   10                  15

Gly Gly

<210> SEQ ID NO 160
<211> LENGTH: 18
<212> TYPE: PRT
<213> ORGANISM: Artificial Sequence
<220> FEATURE:
<223> OTHER INFORMATION: masking moiety

<400> SEQUENCE: 160

Gly Cys Asn Ile Trp Ala Val Gly Gly Asp Cys Arg Pro Phe Val Asp
1               5                   10                  15

Gly Gly

<210> SEQ ID NO 161
<211> LENGTH: 18
<212> TYPE: PRT
<213> ORGANISM: Artificial Sequence
<220> FEATURE:
<223> OTHER INFORMATION: masking moiety

<400> SEQUENCE: 161

Gly Cys Asn Ile Trp Leu Asn Gly Gly Asp Cys Arg Ala Trp Val Asp
1               5                   10                  15

Thr Gly

<210> SEQ ID NO 162
<211> LENGTH: 18
<212> TYPE: PRT
<213> ORGANISM: Artificial Sequence
<220> FEATURE:
<223> OTHER INFORMATION: masking moiety

<400> SEQUENCE: 162

Gly Cys Asn Ile Trp Ile Val Gly Gly Asp Cys Arg Pro Phe Ile Asn
1               5                   10                  15

Asp Gly

<210> SEQ ID NO 163
<211> LENGTH: 18
<212> TYPE: PRT
<213> ORGANISM: Artificial Sequence
<220> FEATURE:
<223> OTHER INFORMATION: masking moiety

<400> SEQUENCE: 163

Gly Cys Asn Ile Trp Leu Asn Gly Gly Asp Cys Arg Pro Val Val Phe
1               5                   10                  15

Gly Gly

<210> SEQ ID NO 164
```

```
<211> LENGTH: 18
<212> TYPE: PRT
<213> ORGANISM: Artificial Sequence
<220> FEATURE:
<223> OTHER INFORMATION: masking moiety

<400> SEQUENCE: 164

Gly Cys Asn Ile Trp Leu Ser Gly Gly Asp Cys Arg Met Phe Met Asn
1               5                   10                  15

Glu Gly

<210> SEQ ID NO 165
<211> LENGTH: 18
<212> TYPE: PRT
<213> ORGANISM: Artificial Sequence
<220> FEATURE:
<223> OTHER INFORMATION: masking moiety

<400> SEQUENCE: 165

Gly Cys Asn Ile Trp Val Asn Gly Gly Asp Cys Arg Ser Phe Val Tyr
1               5                   10                  15

Ser Gly

<210> SEQ ID NO 166
<211> LENGTH: 18
<212> TYPE: PRT
<213> ORGANISM: Artificial Sequence
<220> FEATURE:
<223> OTHER INFORMATION: masking moiety

<400> SEQUENCE: 166

Gly Cys Asn Ile Trp Leu Asn Gly Gly Asp Cys Arg Gly Trp Glu Ala
1               5                   10                  15

Ser Gly

<210> SEQ ID NO 167
<211> LENGTH: 18
<212> TYPE: PRT
<213> ORGANISM: Artificial Sequence
<220> FEATURE:
<223> OTHER INFORMATION: masking moiety

<400> SEQUENCE: 167

Gly Cys Asn Ile Trp Ala His Gly Gly Asp Cys Arg Gly Phe Ile Glu
1               5                   10                  15

Pro Gly

<210> SEQ ID NO 168
<211> LENGTH: 18
<212> TYPE: PRT
<213> ORGANISM: Artificial Sequence
<220> FEATURE:
<223> OTHER INFORMATION: masking moiety

<400> SEQUENCE: 168

Gly Cys Asn Ile Trp Leu Asn Gly Gly Asp Cys Arg Thr Phe Val Ala
1               5                   10                  15

Ser Gly

<210> SEQ ID NO 169
<211> LENGTH: 18
<212> TYPE: PRT
<213> ORGANISM: Artificial Sequence
<220> FEATURE:
```

<223> OTHER INFORMATION: masking moiety

<400> SEQUENCE: 169

Gly Cys Asn Ile Trp Ala His Gly Gly Asp Cys Arg Gly Phe Ile Glu
1               5                   10                  15

Pro Gly

<210> SEQ ID NO 170
<211> LENGTH: 18
<212> TYPE: PRT
<213> ORGANISM: Artificial Sequence
<220> FEATURE:
<223> OTHER INFORMATION: masking moiety

<400> SEQUENCE: 170

Gly Phe Leu Glu Asn Cys Asn Ile Trp Leu Asn Gly Gly Asp Cys Arg
1               5                   10                  15

Thr Gly

<210> SEQ ID NO 171
<211> LENGTH: 18
<212> TYPE: PRT
<213> ORGANISM: Artificial Sequence
<220> FEATURE:
<223> OTHER INFORMATION: masking moiety

<400> SEQUENCE: 171

Gly Ile Tyr Glu Asn Cys Asn Ile Trp Leu Asn Gly Gly Asp Cys Arg
1               5                   10                  15

Met Gly

<210> SEQ ID NO 172
<211> LENGTH: 18
<212> TYPE: PRT
<213> ORGANISM: Artificial Sequence
<220> FEATURE:
<223> OTHER INFORMATION: masking moiety

<400> SEQUENCE: 172

Gly Ile Pro Asp Asn Cys Asn Ile Trp Ile Asn Gly Gly Asp Cys Arg
1               5                   10                  15

Tyr Gly

<210> SEQ ID NO 173
<211> LENGTH: 19
<212> TYPE: PRT
<213> ORGANISM: Artificial Sequence
<220> FEATURE:
<223> OTHER INFORMATION: masking moiety

<400> SEQUENCE: 173

Arg Glu Cys Gly Arg Cys Gly Asp Ile Pro Phe Pro Ala His Trp Val
1               5                   10                  15

Pro Arg Thr

<210> SEQ ID NO 174
<211> LENGTH: 21
<212> TYPE: PRT
<213> ORGANISM: Artificial Sequence
<220> FEATURE:
<223> OTHER INFORMATION: masking moiety

<400> SEQUENCE: 174

Gln Gly Gln Ser Gly Gln Tyr Gly Ser Cys Ser Trp Asn Tyr Val His
1               5                   10                  15

Ile Phe Met Asp Cys
            20

<210> SEQ ID NO 175
<211> LENGTH: 21
<212> TYPE: PRT
<213> ORGANISM: Artificial Sequence
<220> FEATURE:
<223> OTHER INFORMATION: masking moiety

<400> SEQUENCE: 175

Gln Gly Gln Ser Gly Gln Gly Asp Phe Asp Ile Pro Phe Pro Ala His
1               5                   10                  15

Trp Val Pro Ile Thr
            20

<210> SEQ ID NO 176
<211> LENGTH: 24
<212> TYPE: PRT
<213> ORGANISM: Artificial Sequence
<220> FEATURE:
<223> OTHER INFORMATION: masking moiety

<400> SEQUENCE: 176

Gln Gly Gln Ser Gly Gln Met Gly Val Pro Ala Gly Cys Val Trp Asn
1               5                   10                  15

Tyr Ala His Ile Phe Met Asp Cys
            20

<210> SEQ ID NO 177
<211> LENGTH: 15
<212> TYPE: PRT
<213> ORGANISM: Artificial Sequence
<220> FEATURE:
<223> OTHER INFORMATION: masking moiety

<400> SEQUENCE: 177

Tyr Arg Ser Cys Asn Trp Asn Tyr Val Ser Ile Phe Leu Asp Cys
1               5                   10                  15

<210> SEQ ID NO 178
<211> LENGTH: 16
<212> TYPE: PRT
<213> ORGANISM: Artificial Sequence
<220> FEATURE:
<223> OTHER INFORMATION: masking moiety

<400> SEQUENCE: 178

Pro Gly Ala Phe Asp Ile Pro Phe Pro Ala His Trp Val Pro Asn Thr
1               5                   10                  15

<210> SEQ ID NO 179
<211> LENGTH: 15
<212> TYPE: PRT
<213> ORGANISM: Artificial Sequence
<220> FEATURE:
<223> OTHER INFORMATION: masking moiety

<400> SEQUENCE: 179

Glu Ser Ser Cys Val Trp Asn Tyr Val His Ile Tyr Met Asp Cys
1               5                   10                  15

<210> SEQ ID NO 180

```
<211> LENGTH: 15
<212> TYPE: PRT
<213> ORGANISM: Artificial Sequence
<220> FEATURE:
<223> OTHER INFORMATION: masking moiety

<400> SEQUENCE: 180

Tyr Pro Gly Cys Lys Trp Asn Tyr Asp Arg Ile Phe Leu Asp Cys
1               5                   10                  15

<210> SEQ ID NO 181
<211> LENGTH: 15
<212> TYPE: PRT
<213> ORGANISM: Artificial Sequence
<220> FEATURE:
<223> OTHER INFORMATION: masking moiety

<400> SEQUENCE: 181

Tyr Arg Thr Cys Ser Trp Asn Tyr Val Gly Ile Phe Leu Asp Cys
1               5                   10                  15

<210> SEQ ID NO 182
<211> LENGTH: 15
<212> TYPE: PRT
<213> ORGANISM: Artificial Sequence
<220> FEATURE:
<223> OTHER INFORMATION: masking moiety

<400> SEQUENCE: 182

Tyr Gly Ser Cys Ser Trp Asn Tyr Val His Ile Phe Met Asp Cys
1               5                   10                  15

<210> SEQ ID NO 183
<211> LENGTH: 15
<212> TYPE: PRT
<213> ORGANISM: Artificial Sequence
<220> FEATURE:
<223> OTHER INFORMATION: masking moiety

<400> SEQUENCE: 183

Tyr Gly Ser Cys Ser Trp Asn Tyr Val His Ile Phe Leu Asp Cys
1               5                   10                  15

<210> SEQ ID NO 184
<211> LENGTH: 15
<212> TYPE: PRT
<213> ORGANISM: Artificial Sequence
<220> FEATURE:
<223> OTHER INFORMATION: masking moiety

<400> SEQUENCE: 184

Tyr Gly Ser Cys Asn Trp Asn Tyr Val His Ile Phe Leu Asp Cys
1               5                   10                  15

<210> SEQ ID NO 185
<211> LENGTH: 15
<212> TYPE: PRT
<213> ORGANISM: Artificial Sequence
<220> FEATURE:
<223> OTHER INFORMATION: masking moiety

<400> SEQUENCE: 185

Tyr Thr Ser Cys Asn Trp Asn Tyr Val His Ile Phe Met Asp Cys
1               5                   10                  15

<210> SEQ ID NO 186
<211> LENGTH: 15
```

```
<212> TYPE: PRT
<213> ORGANISM: Artificial Sequence
<220> FEATURE:
<223> OTHER INFORMATION: masking moiety

<400> SEQUENCE: 186

Tyr Pro Gly Cys Lys Trp Asn Tyr Asp Arg Ile Phe Leu Asp Cys
1               5                   10                  15

<210> SEQ ID NO 187
<211> LENGTH: 15
<212> TYPE: PRT
<213> ORGANISM: Artificial Sequence
<220> FEATURE:
<223> OTHER INFORMATION: masking moiety

<400> SEQUENCE: 187

Trp Arg Ser Cys Asn Trp Asn Tyr Ala His Ile Phe Leu Asp Cys
1               5                   10                  15

<210> SEQ ID NO 188
<211> LENGTH: 15
<212> TYPE: PRT
<213> ORGANISM: Artificial Sequence
<220> FEATURE:
<223> OTHER INFORMATION: masking moiety

<400> SEQUENCE: 188

Trp Ser Asn Cys His Trp Asn Tyr Val His Ile Phe Leu Asp Cys
1               5                   10                  15

<210> SEQ ID NO 189
<211> LENGTH: 15
<212> TYPE: PRT
<213> ORGANISM: Artificial Sequence
<220> FEATURE:
<223> OTHER INFORMATION: masking moiety

<400> SEQUENCE: 189

Asp Arg Ser Cys Thr Trp Asn Tyr Val Arg Ile Ser Tyr Asp Cys
1               5                   10                  15

<210> SEQ ID NO 190
<211> LENGTH: 15
<212> TYPE: PRT
<213> ORGANISM: Artificial Sequence
<220> FEATURE:
<223> OTHER INFORMATION: masking moiety

<400> SEQUENCE: 190

Ser Gly Ser Cys Lys Trp Asp Tyr Val His Ile Phe Leu Asp Cys
1               5                   10                  15

<210> SEQ ID NO 191
<211> LENGTH: 15
<212> TYPE: PRT
<213> ORGANISM: Artificial Sequence
<220> FEATURE:
<223> OTHER INFORMATION: masking moiety

<400> SEQUENCE: 191

Ser Arg Ser Cys Ile Trp Asn Tyr Ala His Ile His Leu Asp Cys
1               5                   10                  15

<210> SEQ ID NO 192
<211> LENGTH: 15
<212> TYPE: PRT
```

```
<213> ORGANISM: Artificial Sequence
<220> FEATURE:
<223> OTHER INFORMATION: masking moiety

<400> SEQUENCE: 192

Ser Met Ser Cys Tyr Trp Gln Tyr Glu Arg Ile Phe Leu Asp Cys
1               5                   10                  15

<210> SEQ ID NO 193
<211> LENGTH: 15
<212> TYPE: PRT
<213> ORGANISM: Artificial Sequence
<220> FEATURE:
<223> OTHER INFORMATION: masking moiety

<400> SEQUENCE: 193

Tyr Arg Ser Cys Asn Trp Asn Tyr Val Ser Ile Phe Leu Asp Cys
1               5                   10                  15

<210> SEQ ID NO 194
<211> LENGTH: 15
<212> TYPE: PRT
<213> ORGANISM: Artificial Sequence
<220> FEATURE:
<223> OTHER INFORMATION: masking moiety

<400> SEQUENCE: 194

Tyr Gly Ser Cys Ser Trp Asn Tyr Val His Ile Phe Met Asp Cys
1               5                   10                  15

<210> SEQ ID NO 195
<211> LENGTH: 15
<212> TYPE: PRT
<213> ORGANISM: Artificial Sequence
<220> FEATURE:
<223> OTHER INFORMATION: masking moiety

<400> SEQUENCE: 195

Ser Gly Ser Cys Lys Trp Asp Tyr Val His Ile Phe Leu Asp Cys
1               5                   10                  15

<210> SEQ ID NO 196
<211> LENGTH: 15
<212> TYPE: PRT
<213> ORGANISM: Artificial Sequence
<220> FEATURE:
<223> OTHER INFORMATION: masking moiety

<400> SEQUENCE: 196

Tyr Lys Ser Cys His Trp Asp Tyr Val His Ile Phe Leu Asp Cys
1               5                   10                  15

<210> SEQ ID NO 197
<211> LENGTH: 15
<212> TYPE: PRT
<213> ORGANISM: Artificial Sequence
<220> FEATURE:
<223> OTHER INFORMATION: masking moiety

<400> SEQUENCE: 197

Tyr Gly Ser Cys Thr Trp Asn Tyr Val His Ile Phe Met Glu Cys
1               5                   10                  15

<210> SEQ ID NO 198
<211> LENGTH: 15
<212> TYPE: PRT
<213> ORGANISM: Artificial Sequence

<220> FEATURE:
<223> OTHER INFORMATION: masking moiety

<400> SEQUENCE: 198

Phe Ser Ser Cys Asn Trp Asn Tyr Val His Ile Phe Leu Asp Cys
1               5                   10                  15

<210> SEQ ID NO 199
<211> LENGTH: 15
<212> TYPE: PRT
<213> ORGANISM: Artificial Sequence
<220> FEATURE:
<223> OTHER INFORMATION: masking moiety

<400> SEQUENCE: 199

Trp Arg Ser Cys Asn Trp Asn Tyr Ala His Ile Phe Leu Asp Cys
1               5                   10                  15

<210> SEQ ID NO 200
<211> LENGTH: 15
<212> TYPE: PRT
<213> ORGANISM: Artificial Sequence
<220> FEATURE:
<223> OTHER INFORMATION: masking moiety

<400> SEQUENCE: 200

Tyr Gly Ser Cys Gln Trp Asn Tyr Val His Ile Phe Leu Asp Cys
1               5                   10                  15

<210> SEQ ID NO 201
<211> LENGTH: 15
<212> TYPE: PRT
<213> ORGANISM: Artificial Sequence
<220> FEATURE:
<223> OTHER INFORMATION: masking moiety

<400> SEQUENCE: 201

Tyr Arg Ser Cys Asn Trp Asn Tyr Val His Ile Phe Leu Asp Cys
1               5                   10                  15

<210> SEQ ID NO 202
<211> LENGTH: 15
<212> TYPE: PRT
<213> ORGANISM: Artificial Sequence
<220> FEATURE:
<223> OTHER INFORMATION: masking moiety

<400> SEQUENCE: 202

Asn Met Ser Cys His Trp Asp Tyr Val His Ile Phe Leu Asp Cys
1               5                   10                  15

<210> SEQ ID NO 203
<211> LENGTH: 15
<212> TYPE: PRT
<213> ORGANISM: Artificial Sequence
<220> FEATURE:
<223> OTHER INFORMATION: masking moiety

<400> SEQUENCE: 203

Phe Gly Pro Cys Thr Trp Asn Tyr Ala Arg Ile Ser Trp Asp Cys
1               5                   10                  15

<210> SEQ ID NO 204
<211> LENGTH: 15
<212> TYPE: PRT
<213> ORGANISM: Artificial Sequence
<220> FEATURE:

```
<223> OTHER INFORMATION: masking moiety
<220> FEATURE:
<221> NAME/KEY: misc_feature
<222> LOCATION: (1)..(2)
<223> OTHER INFORMATION: Xaa may be any amino acid
<220> FEATURE:
<221> NAME/KEY: misc_feature
<222> LOCATION: (5)..(5)
<223> OTHER INFORMATION: Xaa may be any amino acid
<220> FEATURE:
<221> NAME/KEY: misc_feature
<222> LOCATION: (7)..(7)
<223> OTHER INFORMATION: Xaa may be any amino acid
<220> FEATURE:
<221> NAME/KEY: misc_feature
<222> LOCATION: (13)..(13)
<223> OTHER INFORMATION: Xaa may be any amino acid

<400> SEQUENCE: 204

Xaa Xaa Ser Cys Xaa Trp Xaa Tyr Val His Ile Phe Xaa Asp Cys
 1               5                  10                  15

<210> SEQ ID NO 205
<211> LENGTH: 18
<212> TYPE: PRT
<213> ORGANISM: Artificial Sequence
<220> FEATURE:
<223> OTHER INFORMATION: masking moiety

<400> SEQUENCE: 205

Met Gly Val Pro Ala Gly Cys Val Trp Asn Tyr Ala His Ile Phe Met
 1               5                  10                  15

Asp Cys

<210> SEQ ID NO 206
<211> LENGTH: 18
<212> TYPE: PRT
<213> ORGANISM: Artificial Sequence
<220> FEATURE:
<223> OTHER INFORMATION: masking moiety

<400> SEQUENCE: 206

Arg Asp Thr Gly Gly Gln Cys Arg Trp Asp Tyr Val His Ile Phe Met
 1               5                  10                  15

Asp Cys

<210> SEQ ID NO 207
<211> LENGTH: 18
<212> TYPE: PRT
<213> ORGANISM: Artificial

```
<210> SEQ ID NO 209
<211> LENGTH: 18
<212> TYPE: PRT
<213> ORGANISM: Artificial Sequence
<220> FEATURE:
<223> OTHER INFORMATION: masking moiety

<400> SEQUENCE: 209

Asp Gly Gly Pro Ala Gly Cys Ser Trp Asn Tyr Val His Ile Phe Met
1               5                   10                  15

Glu Cys

<210> SEQ ID NO 210
<211> LENGTH: 18
<212> TYPE: PRT
<213> ORGANISM: Artificial Sequence
<220> FEATURE:
<223> OTHER INFORMATION: masking moiety

<400> SEQUENCE: 210

Ala Val Gly Pro Ala Gly Cys Trp Trp Asn Tyr Val His Ile Phe Met
1               5                   10                  15

Glu Cys

<210> SEQ ID NO 211
<211> LENGTH: 18
<212> TYPE: PRT
<213> ORGANISM: Artificial Sequence
<220> FEATURE:
<223> OTHER INFORMATION: masking moiety

<400> SEQUENCE: 211

Cys Thr Trp Asn Tyr Val His Ile Phe Met Asp Cys Gly Glu Gly Glu
1               5                   10                  15

Gly Pro

<210> SEQ ID NO 212
<211> LENGTH: 18
<212> TYPE: PRT
<213> ORGANISM: Artificial Sequence
<220> FEATURE:
<223> OTHER INFORMATION: masking moiety

<400> SEQUENCE: 212

Gly Gly Val Pro Glu Gly Cys Thr Trp Asn Tyr Ala His Ile Phe Met
1               5                   10                  15

Glu Cys

<210> SEQ ID NO 213
<211> LENGTH: 18
<212> TYPE: PRT
<213> ORGANISM: Artificial Sequence
<220> FEATURE:
<223> OTHER INFORMATION: masking moiety

<400> SEQUENCE: 213

Ala Glu Val Pro Ala Gly Cys Trp Trp Asn Tyr Val His Ile Phe Met
1               5                   10                  15

Glu Cys
```

<210> SEQ ID NO 214
<211> LENGTH: 18
<212> TYPE: PRT
<213> ORGANISM: Artificial Sequence
<220> FEATURE:
<223> OTHER INFORMATION: masking moiety

<400> SEQUENCE: 214

Ala Gly Val Pro Ala Gly Cys Thr Trp Asn Tyr Val His Ile Phe Met
1               5                   10                  15

Glu Cys

<210> SEQ ID NO 215
<211> LENGTH: 18
<212> TYPE: PRT
<213> ORGANISM: Artificial Sequence
<220> FEATURE:
<223> OTHER INFORMATION: masking moiety

<400> SEQUENCE: 215

Ser Gly Ala Ser Gly Gly Cys Lys Trp Asn Tyr Val His Ile Phe Met
1               5                   10                  15

Asp Cys

<210> SEQ ID NO 216
<211> LENGTH: 18
<212> TYPE: PRT
<213> ORGANISM: Artificial Sequence
<220> FEATURE:
<223> OTHER INFORMATION: masking moiety

<400> SEQUENCE: 216

Met Gly Val Pro Ala Gly Cys Val Trp Asn Tyr Ala His Ile Phe Met
1               5                   10                  15

Asp Cys

<210> SEQ ID NO 217
<211> LENGTH: 18
<212> TYPE: PRT
<213> ORGANISM: Artificial Sequence
<220> FEATURE:
<223> OTHER INFORMATION: masking moiety

<400> SEQUENCE: 217

Thr Pro Gly Cys Arg Trp Asn Tyr Val His Ile Phe Met Glu Cys Glu
1               5                   10                  15

Ala Leu

<210> SEQ ID NO 218
<211> LENGTH: 18
<212> TYPE: PRT
<213> ORGANISM: Artificial Sequence
<220> FEATURE:
<223> OTHER INFORMATION: masking moiety

<400> SEQUENCE: 218

Val Gly Val Pro Asn Gly Cys Val Trp Asn Tyr Ala His Ile Phe Met
1               5                   10                  15

Glu Cys

<210> SEQ ID NO 219
<211> LENGTH: 16
<212> TYPE: PRT

```
<213> ORGANISM: Artificial Sequence
<220> FEATURE:
<223> OTHER INFORMATION: masking moiety

<400> SEQUENCE: 219

Pro Gly Ala Phe Asp Ile Pro Phe Pro Ala His Trp Val Pro Asn Thr
1               5                   10                  15

<210> SEQ ID NO 220
<211> LENGTH: 16
<212> TYPE: PRT
<213> ORGANISM: Artificial Sequence
<220> FEATURE:
<223> OTHER INFORMATION: masking moiety

<400> SEQUENCE: 220

Arg Gly Ala Cys Asp Ile Pro Phe Pro Ala His Trp Ile Pro Asn Thr
1               5                   10                  15

<210> SEQ ID NO 221
<211> LENGTH: 16
<212> TYPE: PRT
<213> ORGANISM: Artificial Sequence
<220> FEATURE:
<223> OTHER INFORMATION: masking moiety

<400> SEQUENCE: 221

Gln Gly Asp Phe Asp Ile Pro Phe Pro Ala His Trp Val Pro Ile Thr
1               5                   10                  15

<210> SEQ ID NO 222
<211> LENGTH: 16
<212> TYPE: PRT
<213> ORGANISM: Artificial Sequence
<220> FEATURE:
<223> OTHER INFORMATION: masking moiety
<220> FEATURE:
<221> NAME/KEY: misc_feature
<222> LOCATION: (1)..(1)
<223> OTHER INFORMATION: Xaa may be any amino acid

<400> SEQUENCE: 222

Xaa Gly Ala Phe Asp Ile Pro Phe Pro Ala His Trp Val Pro Asn Thr
1               5                   10                  15

<210> SEQ ID NO 223
<211> LENGTH: 19
<212> TYPE: PRT
<213> ORGANISM: Artificial Sequence
<220> FEATURE:
<223> OTHER INFORMATION: masking moiety

<400> SEQUENCE: 223

Arg Gly Asp Gly Asn Asp Ser Asp Ile Pro Phe Pro Ala His Trp Val
1               5                   10                  15

Pro Arg Thr

<210> SEQ ID NO 224
<211> LENGTH: 19
<212> TYPE: PRT
<213> ORGANISM: Artificial Sequence
<220> FEATURE:
<223> OTHER INFORMATION: masking moiety

<400> SEQUENCE: 224

Ser Gly Val Gly Arg Asp Arg Asp Ile Pro Phe Pro Ala His Trp Val
1               5                   10                  15
```

Pro Arg Thr

<210> SEQ ID NO 225
<211> LENGTH: 19
<212> TYPE: PRT
<213> ORGANISM: Artificial Sequence
<220> FEATURE:
<223> OTHER INFORMATION: masking moiety

<400> SEQUENCE: 225

Trp Ala Gly Gly Asn Asp Cys Asp Ile Pro Phe Pro Ala His Trp Ile
1               5                   10                  15

Pro Asn Thr

<210> SEQ ID NO 226
<211> LENGTH: 19
<212> TYPE: PRT
<213> ORGANISM: Artificial Sequence
<220> FEATURE:
<223> OTHER INFORMATION: masking moiety

<400> SEQUENCE: 226

Trp Gly Asp Gly Met Asp Val Asp Ile Pro Phe Pro Ala His Trp Val
1               5                   10                  15

Pro Val Thr

<210> SEQ ID NO 227
<211> LENGTH: 19
<212> TYPE: PRT
<213> ORGANISM: Artificial Sequence
<220> FEATURE:
<223> OTHER INFORMATION: masking moiety

<400> SEQUENCE: 227

Ala Gly Ser Gly Asn Asp Ser Asp Ile Pro Phe Pro Ala His Trp Val
1               5                   10                  15

Pro Arg Thr

<210> SEQ ID NO 228
<211> LENGTH: 19
<212> TYPE: PRT
<213> ORGANISM: Artificial Sequence
<220> FEATURE:
<223> OTHER INFORMATION: masking moiety

<400> SEQUENCE: 228

Glu Ser Arg Ser Gly Tyr Ala Asp Ile Pro Phe Pro Ala His Trp Val
1               5                   10                  15

Pro Arg Thr

<210> SEQ ID NO 229
<211> LENGTH: 819
<212> TYPE: DNA
<213> ORGANISM: Artificial Sequence
<220> FEATURE:
<223> OTHER INFORMATION: Anti-human CTLA-4 scFv Antibody

<400> SEQUENCE: 229
ggaggtggat ctggaggtgg cggttcaggc tctggcggag gctcaggtgg tggaggatca      60
ggcggaggtg aaattgtgtt gacacagtct ccaggcaccc tgtctttgtc tccaggggaa     120
agagccaccc tctcctgcag ggccagtcag agtgttagca gcagctactt agcctggtac     180

-continued

```
cagcagaaac ctggccaggc tcccaggctc ctcatctatg gtgcatccag cagggccact    240
ggcatcccag acaggttcag tggcagtggg tctgggacag acttcactct caccatcagc    300
agactggagc ctgaagattt tgcagtgtat tactgtcagc agtatggtag ctcaccgctc    360
actttcggcg gagggaccaa ggtggaaatc aaacgttccg agggtcgac cataacttcg     420 tataatgtat actatacgaa gttatcctcg agcggtaccc aggtgcagct ggtgcagact    480 ggggaggcg tggtccagcc tgggaggtcc ctgagactct cctgtgcagc ctctggatcc     540 accttagca gctatgccat gagctgggtc cgccaggctc agggaaggg gctggagtgg      600 gtctcagcta ttagtggtag tggtggtagc acatactacg cagactccgt gaagggccgg    660
ttcaccatct ccagagacaa ttccaagaac acgctgtatc tgcaaatgaa cagcctgaga    720
gccgaggaca cggccgtata ttactgtgcg acaaactccc tttactggta cttcgatctc    780
tggggccgtg gcaccctggt cactgtctct tcagctagc                            819
```

<210> SEQ ID NO 230
<211> LENGTH: 273
<212> TYPE: PRT
<213> ORGANISM: Artificial Sequence
<220> FEATURE:
<223> OTHER INFORMATION: Anti-human CTLA-4 scFv Antibody

<400> SEQUENCE: 230

```
Gly Gly Gly Ser Gly Gly Gly Ser Gly Ser Gly Gly Gly Ser Gly
 1               5                   10                  15

Gly Gly Gly Ser Gly Gly Gly Glu Ile Val Leu Thr Gln Ser Pro Gly
            20                  25                  30

Thr Leu Ser Leu Ser Pro Gly Glu Arg Ala Thr Leu Ser Cys Arg Ala
        35                  40                  45

Ser Gln Ser Val Ser Ser Ser Tyr Leu Ala Trp Tyr Gln Gln Lys Pro
    50                  55                  60

Gly Gln Ala Pro Arg Leu Leu Ile Tyr Gly Ala Ser Ser Arg Ala Thr
65                  70                  75                  80

Gly Ile Pro Asp Arg Phe Ser Gly Ser Gly Ser Gly Thr Asp Phe Thr
                85                  90                  95

Leu Thr Ile Ser Arg Leu Glu Pro Glu Asp Phe Ala Val Tyr Tyr Cys
            100                 105                 110

Gln Gln Tyr Gly Ser Ser Pro Leu Thr Phe Gly Gly Gly Thr Lys Val
        115                 120                 125

Glu Ile Lys Arg Ser Gly Gly Ser Thr Ile Thr Ser Tyr Asn Val Tyr
    130                 135                 140

Tyr Thr Lys Leu Ser Ser Ser Gly Thr Gln Val Gln Leu Val Gln Thr
145                 150                 155                 160

Gly Gly Gly Val Val Gln Pro Gly Arg Ser Leu Arg Leu Ser Cys Ala
                165                 170                 175

Ala Ser Gly Ser Thr Phe Ser Ser Tyr Ala Met Ser Trp Val Arg Gln
            180                 185                 190

Ala Pro Gly Lys Gly Leu Glu Trp Val Ser Ala Ile Ser Gly Ser Gly
        195                 200                 205

Gly Ser Thr Tyr Tyr Ala Asp Ser Val Lys Gly Arg Phe Thr Ile Ser
    210                 215                 220

Arg Asp Asn Ser Lys Asn Thr Leu Tyr Leu Gln Met Asn Ser Leu Arg
225                 230                 235                 240

Ala Glu Asp Thr Ala Val Tyr Tyr Cys Ala Thr Asn Ser Leu Tyr Trp
                245                 250                 255
```

Tyr Phe Asp Leu Trp Gly Arg Gly Thr Leu Val Thr Val Ser Ser Ala
                260                 265                 270

Ser

<210> SEQ ID NO 231
<211> LENGTH: 792
<212> TYPE: DNA
<213> ORGANISM: Artificial Sequence
<220> FEATURE:
<223> OTHER INFORMATION: Anti-human CD3 epsilon OKT3 scFv Antibody

<400> SEQUENCE: 231

```
ggaggtggat ctggaggtgg cggttcaggc tctggcggag gctcaggtgg tgaggatca    60 ggcggaggtc aggttcagct gcagcagagc ggtgcagaac tggcacgtcc gggtgcaagc   120
gttaaaatga gctgtaaagc aagcggttat acctttaccc gttataccat gcattgggtt   180
aaacagcgtc cgggtcaggg tctggaatgg attggttata tcaatccgag ccgtggttat   240
accaactaca accagaaatt caaagataaa gcaaccctga ccaccgataa agcagcagc    300 accgcctata tgcagctgag cagcctgacc tcagaggata gcgcagttta ttactgtgca   360
cgctattatg atgatcacta ttgcctggat tattggggtc agggcaccac cctgaccgtt   420
agcagcggtg gtggtggtag tggtggcggt ggttcaggcg gtggcggtag ccagattgtt   480
ctgacccaga gtccggcaat tatgagcgca agtccgggtg aaaaagttac catgacctgt   540
agcgccagca gcagcgttag ctatatgaat tggtatcagc agaaaagcgg caccagcccg   600
aaacgttgga tttatgatac cagcaaactg gcaagcggtg ttccggcaca ttttcgtggt   660
agcggtagcg gcacctcata tagcctgacc attagcggta tggaagcaga agatgcagca   720
acctattatt gtcagcagtg gtcaagcaat ccgtttacct ttggtagtgg caccaaactg   780
gaaattaatc gt                                                       792
```

<210> SEQ ID NO 232
<211> LENGTH: 264
<212> TYPE: PRT
<213> ORGANISM: Artificial Sequence
<220> FEATURE:
<223> OTHER INFORMATION: Anti-human CD3 epsilon OKT3 scFv Antibody

<400> SEQUENCE: 232

Gly Gly Gly Ser Gly Gly Gly Gly Ser Ser Gly Gly Gly Ser Gly
1               5                   10                  15

Gly Gly Gly Ser Gly Gly Gly Gln Val Gln Leu Gln Gln Ser Gly Ala
            20                  25                  30

Glu Leu Ala Arg Pro Gly Ala Ser Val Lys Met Ser Cys Lys Ala Ser
        35                  40                  45

Gly Tyr Thr Phe Thr Arg Tyr Thr Met His Trp Val Lys Gln Arg Pro
    50                  55                  60

Gly Gln Gly Leu Glu Trp Ile Gly Tyr Ile Asn Pro Ser Arg Gly Tyr
65                  70                  75                  80

Thr Asn Tyr Asn Gln Lys Phe Lys Asp Lys Ala Thr Leu Thr Thr Asp
                85                  90                  95

Lys Ser Ser Ser Thr Ala Tyr Met Gln Leu Ser Ser Leu Thr Ser Glu
            100                 105                 110

Asp Ser Ala Val Tyr Tyr Cys Ala Arg Tyr Tyr Asp Asp His Tyr Cys
        115                 120                 125

Leu Asp Tyr Trp Gly Gln Gly Thr Thr Leu Thr Val Ser Ser Gly Gly

```
                130              135                 140
Gly Gly Ser Gly Gly Gly Ser Gly Gly Gly Ser Gln Ile Val
145             150                 155                 160

Leu Thr Gln Ser Pro Ala Ile Met Ser Ala Ser Pro Gly Glu Lys Val
                165                 170                 175

Thr Met Thr Cys Ser Ala Ser Ser Ser Val Ser Tyr Met Asn Trp Tyr
                180                 185                 190

Gln Gln Lys Ser Gly Thr Ser Pro Lys Arg Trp Ile Tyr Asp Thr Ser
                195                 200                 205

Lys Leu Ala Ser Gly Val Pro Ala His Phe Arg Gly Ser Gly Ser Gly
                210                 215                 220

Thr Ser Tyr Ser Leu Thr Ile Ser Gly Met Glu Ala Glu Asp Ala Ala
225             230                 235                 240

Thr Tyr Tyr Cys Gln Gln Trp Ser Ser Asn Pro Phe Thr Phe Gly Ser
                245                 250                 255

Gly Thr Lys Leu Glu Ile Asn Arg
            260

<210> SEQ ID NO 233
<211> LENGTH: 1347
<212> TYPE: DNA
<213> ORGANISM: Artificial Sequence
<220> FEATURE:
<223> OTHER INFORMATION: Anti-human Jagged 4D11v2 Antibody Heavy Chain

<400> SEQUENCE: 233
gaggtgcacc tgttggagtc tggggggaggc ttggtacagc ctggggggtc cctgagactc      60
tcctgtgcag cctctggatt cacctttagc agctatgcca tgagctgggt ccgccaggct    120
ccagggaagg gctggagtg gtgtcaagt attgacccgg aaggtcggca gacatattac     180
gcagactccg tgaagggccg gttcaccatc tccagagaca attccaagaa cacgctgtat    240
ctgcaaatga acagcctgag agccgaggac acggccgtat attactgtgc gaaagacatc    300
ggcggcaggt cggcctttga ctactggggc cagggaaccc tggtcaccgt ctcctcagct    360
agcaccaagg gcccatcggt cttccccctg gcaccctcct ccaagagcac ctctgggggc    420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
```
aagagcctct ccctgtctcc gggtaaa                                           1347

<210> SEQ ID NO 234
<211> LENGTH: 449
<212> TYPE: PRT
<213> ORGANISM: Artificial Sequence
<220> FEATURE:
<223> OTHER INFORMATION: Anti-human Jagged 4D11v2 Antibody Heavy Chain

<400> SEQUENCE: 234

```
Glu Val His Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350
```

```
Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 235
<211> LENGTH: 642
<212> TYPE: DNA
<213> ORGANISM: Artificial Sequence
<220> FEATURE:
<223> OTHER INFORMATION: Anti-human Jagged 4D11v2 Antibody Light Chain
<220> FEATURE:
<221> NAME/KEY: misc_feature
<222> LOCATION: (545)..(545)
<223> OTHER INFORMATION: n may be any nucleotide

<400> SEQUENCE: 235
gacatccaga tgacccagtc tccatcctcc ctgtctgcat ctgtaggaga cagagtcacc      60
atcacttgcc gggcaagtca gagcattagc agctatttaa attggtatca gcagaaacca    120
gggaaagccc ctaagctcct gatctatgcg gcatccagtt tgcaaagtgg ggtcccatca    180
aggttcagtg gcagtggatc tgggacagat ttcactctca ccatcagcag tctgcaacct    240
gaagattttg caacttacta ctgtcaacag acggttgtgg cgcctccgtt attcggccaa    300
gggaccaagg tggaaatcaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag cacactgacg    540
ctgancaaag cagactacga gaaacacaaa gtctacgcct gcgaagtcac ccatcagggc    600
ctgagctcgc ccgtcacaaa gagcttcaac aggggagagt gt                       642

<210> SEQ ID NO 236
<211> LENGTH: 214
<212> TYPE: PRT
<213> ORGANISM: Artificial Sequence
<220> FEATURE:
<223> OTHER INFORMATION: Anti-human Jagged 4D11v2 Antibody Light Chain
<220> FEATURE:
<221> NAME/KEY: misc_feature
<222> LOCATION: (182)..(182)
<223> OTHER INFORMATION: Xaa may be any amino acid

<400> SEQUENCE: 236

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45
```

```
Tyr Ala Ala Ser Ser Leu Gln Ser Gly Val Pro Ser Arg Phe Ser Gly
         50                   55                   60

Ser Gly Ser Gly Thr Asp Phe Thr Leu Thr Ile Ser Ser Leu Gln Pro
 65                  70                   75                   80

Glu Asp Phe Ala Thr Tyr Tyr Cys Gln Gln Thr Val Val Ala Pro Pro
                 85                   90                   95

Leu Phe Gly Gln Gly Thr Lys Val Glu Ile Lys Arg Thr Val Ala Ala
             100                 105                 110

Pro Ser Val Phe Ile Phe Pro Pro Ser Asp Glu Gln Leu Lys Ser Gly
             115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Xaa Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```

<210> SEQ ID NO 237
<211> LENGTH: 1347
<212> TYPE: DNA
<213> ORGANISM: Artificial Sequence
<220> FEATURE:
<223> OTHER INFORMATION: Anti-human Jagged 4D11 Antibody Heavy Chain

<400> SEQUENCE: 237

```
gaggtgcagc tgttggagtc tggggggaggc ttggtacagc ctggggggtc cctgagactc      60
tcctgtgcag cctctggatt caccttttagc agctatgcca tgagctgggt ccgccaggct    120
ccagggaagg gctggagtg gtgtcaagt attgacccgg aaggtcggca gacatattac      180
gcagactccg tgaagggccg gttcaccatc tccagagaca attccaagaa cacgctgtat    240
ctgcaaatga acagcctgag agccgaggac acggccgtat attactgtgc gaaagacatc    300
ggcggcaggt cggccttgga ctactgggggc cagggaaccc tggtcaccgt ctcctcagct    360
agcaccaagg gcccatcggt cttccccctg gcaccctcct ccaagagcac ctctggggggc    420 acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
```

```
accaagaacc aggtcagcct gacctgcctg gtcaaaggct ctatcccag cgacatcgcc      1140 gtggagtggg agagcaatgg gcagccggag aacaactaca agaccacgcc tcccgtgctg      1200
gactccgacg gctccttctt cctctacagc aagctcaccg tggacaagag caggtggcag      1260 cagggaacg tcttctcatg ctccgtgatg catgaggctc tgcacaacca ctacacgcag      1320
aagagcctct ccctgtctcc gggtaaa                                        1347
```

<210> SEQ ID NO 238
<211> LENGTH: 449
<212> TYPE: PRT
<213> ORGANISM: Artificial Sequence
<220> FEATURE:
<223> OTHER INFORMATION: Anti-human Jagged 4D11 Antibody Heavy Chain

<400> SEQUENCE: 238

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320
```

```
Tyr Lys Cys Lys Val Ser Asn Lys Ala Leu Pro Ala Pro Ile Glu Lys
            325                 330                 335

Thr Ile Ser Lys Ala Lys Gly Gln Pro Arg Glu Pro Gln Val Tyr Thr
        340                 345                 350

Leu Pro Pro Ser Arg Glu Glu Met Thr Lys Asn Gln Val Ser Leu Thr
    355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
            405                 410                 415

Ser Arg Trp Gln Gln Gly Asn Val Phe Ser Cys Ser Val Met His Glu
        420                 425                 430

Ala Leu His Asn His Tyr Thr Gln Lys Ser Leu Ser Leu Ser Pro Gly
    435                 440                 445

Lys

<210> SEQ ID NO 239
<211> LENGTH: 774
<212> TYPE: DNA
<213> ORGANISM: Artificial Sequence
<220> FEATURE:
<223> OTHER INFORMATION: Anti-Jagged Activatable Antibody 5342-1204-
      4D11v2 Light Chain

<400> SEQUENCE: 239
caaggccagt ctggccagtg caatatttgg ctcgtaggtg gtgattgcag gggctggcag    60
gggggctcga gcgtggcag cggtggctct ggtggtctga gcggccgttc cgataatcat   120
ggcggcggtt ctgacatcca gatgacccag tctccatcct ccctgtctgc atctgtagga   180
gacagagtca ccatcacttg ccgggcaagt cagagcatta gcagctattt aaattggtat   240
cagcagaaac cagggaaagc ccctaagctc ctgatctatg cggcatccag tttgcaaagt   300
ggggtcccat caaggttcag tggcagtgga tctgggacag atttcactct caccatcagc   360
agtctgcaac tgaagatttt gcaacttac tactgtcaac agacggttgt ggcgcctccg   420
ttattcggcc aagggaccaa ggtggaaatc aaacgtacgg tggctgcacc atctgtcttc   480
atcttcccgc catctgatga gcagttgaaa tctggaactg cctctgttgt gtgcctgctg   540
aataacttct atcccagaga ggccaaagta cagtggaagg tggataacgc cctccaatcg   600
ggtaactccc aggagagtgt cacagagcag gacagcaagg acagcaccta cagcctcagc   660
agcaccctga cgctgagcaa agcagactac gagaaacaca agtctacgc ctgcgaagtc   720 acccatcagg gcctgagctc gcccgtcaca aagagcttca caggggagag tgt          774

<210> SEQ ID NO 240
<211> LENGTH: 258
<212> TYPE: PRT
<213> ORGANISM: Artificial Sequence
<220> FEATURE:
<223> OTHER INFORMATION: Anti-Jagged Activatable Antibody 5342-1204-
      4D11v2 Light Chain
<220> FEATURE:
<221> NAME/KEY: misc_feature
<222> LOCATION: (226)..(226)
<223> OTHER INFORMATION: Xaa may be any amino acid

<400> SEQUENCE: 240
```

Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Gly Gly
            20              25              30

Leu Ser Gly Arg Ser Asp Asn His Gly Gly Gly Ser Asp Ile Gln Met
            35              40                  45

Thr Gln Ser Pro Ser Ser Leu Ser Ala Ser Val Gly Asp Arg Val Thr
    50              55              60

Ile Thr Cys Arg Ala Ser Gln Ser Ile Ser Ser Tyr Leu Asn Trp Tyr
65              70              75                  80

Gln Gln Lys Pro Gly Lys Ala Pro Lys Leu Leu Ile Tyr Ala Ala Ser
                85              90                  95

Ser Leu Gln Ser Gly Val Pro Ser Arg Phe Ser Gly Ser Gly Ser Gly
            100             105             110

Thr Asp Phe Thr Leu Thr Ile Ser Ser Leu Gln Pro Glu Asp Phe Ala
            115             120             125

Thr Tyr Tyr Cys Gln Gln Thr Val Val Ala Pro Pro Leu Phe Gly Gln
            130             135             140

Gly Thr Lys Val Glu Ile Lys Arg Thr Val Ala Ala Pro Ser Val Phe
145             150             155             160

Ile Phe Pro Pro Ser Asp Glu Gln Leu Lys Ser Gly Thr Ala Ser Val
                165             170             175

Val Cys Leu Leu Asn Asn Phe Tyr Pro Arg Glu Ala Lys Val Gln Trp
            180             185             190

Lys Val Asp Asn Ala Leu Gln Ser Gly Asn Ser Gln Glu Ser Val Thr
            195             200             205

Glu Gln Asp Ser Lys Asp Ser Thr Tyr Ser Leu Ser Ser Thr Leu Thr
210             215             220

Leu Xaa Lys Ala Asp Tyr Glu Lys His Lys Val Tyr Ala Cys Glu Val
225             230             235             240

Thr His Gln Gly Leu Ser Ser Pro Val Thr Lys Ser Phe Asn Arg Gly
            245             250             255

Glu Cys

<210> SEQ ID NO 241
<211> LENGTH: 2139
<212> TYPE: DNA
<213> ORGANISM: Artificial Sequence
<220> FEATURE:
<223> OTHER INFORMATION: Anti-Jagged 4D11v2 - anti-CD3 OKT3
      Multispecific Antibody Heavy Chain

<400> SEQUENCE: 241
gaggtgcacc tgttggagtc tgggggaggc ttggtacagc ctgggggtc cctgagactc    60 tcctgtgcag cctctggatt cacctttagc agctatgcca tgagctgggt ccgccaggct   120
ccagggaagg gctggagtg gtgtcaagt attgacccgg aaggtcggca gacatattac    180
gcagactccg tgaagggccg gttcaccatc tccagagaca attccaagaa cacgctgtat   240
ctgcaaatga acagcctgag agccgaggac acggccgtat attactgtgc gaaagacatc   300
ggcggcaggt cggcctttga ctactggggc caggaaccc tggtcaccgt ctcctcagct   360
agcaccaagg gcccatcggt cttccccctg gcaccctcct ccaagagcac ctctgggggc   420
acagcggccc tgggctgcct ggtcaaggac tacttccccg aaccggtgac ggtgtcgtgg   480
aactcaggcg ccctgaccag cggcgtgcac accttcccgg ctgtcctaca gtcctcagga   540

```
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gaccccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggaggagatg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaagga ggtggatctg gaggtggcgg ttcaggctct   1380
ggcggaggct caggtggtgg aggatcaggc ggaggtcagg ttcagctgca gcagagcggt   1440
gcagaactgg cacgtccggg tgcaagcgtt aaaatgagct gtaaagcaag cggttatacc   1500
tttacccgtt ataccatgca ttgggttaaa cagcgtccgg tcagggtct ggaatggatt   1560
ggttatatca atccgagccg tggttatacc aactacaacc agaaattcaa agataaagca   1620
accctgacca ccgataaaag cagcagcacc gcctatatgc agctgagcag cctgacctca   1680
gaggatagcg cagtttatta ctgtgcacgc tattatgatg atcactattg cctggattat   1740
tggggtcagg gcaccaccct gaccgttagc agcggtggtg gtggtagtgg tggcggtggt   1800
tcaggcggtg gcggtagcca gattgttctg acccagagtc cggcaattat gagcgcaagt   1860
ccgggtgaaa aagttaccat gacctgtagc gccagcagca cgttagcta tatgaattgg   1920
tatcagcaga aaagcggcac cagcccgaaa cgttggattt atgataccag caaactggca   1980
agcggtgttc cggcacattt tcgtggtagc ggtagcggca cctcatatag cctgaccatt   2040
agcggtatgg aagcagaaga tgcagcaacc tattattgtc agcagtggtc aagcaatccg   2100
tttacctttg gtagtggcac caaactggaa attaatcgt                          2139
```

<210> SEQ ID NO 242
<211> LENGTH: 713
<212> TYPE: PRT
<213> ORGANISM: Artificial Sequence
<220> FEATURE:
<223> OTHER INFORMATION: Anti-Jagged 4D11v2 - anti-CD3 OKT3
      Multispecific Antibody Heavy Chain

<400> SEQUENCE: 242

Glu Val His Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                 85                  90                  95

Ala Lys Asp Ile Gly Gly Arg Ser Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Ser Gly Gly Gly Gly Ser Gly Gly Gly Gly Gly Ser
    450                 455                 460

Gly Gly Gly Gly Ser Gly Gly Gly Gln Val Gln Leu Gln Gln Ser Gly
465                 470                 475                 480

Ala Glu Leu Ala Arg Pro Gly Ala Ser Val Lys Met Ser Cys Lys Ala
                485                 490                 495
```

```
Ser Gly Tyr Thr Phe Thr Arg Tyr Thr Met His Trp Val Lys Gln Arg
            500                 505                 510

Pro Gly Gln Gly Leu Glu Trp Ile Gly Tyr Ile Asn Pro Ser Arg Gly
        515                 520                 525

Tyr Thr Asn Tyr Asn Gln Lys Phe Lys Asp Lys Ala Thr Leu Thr Thr
    530                 535                 540

Asp Lys Ser Ser Ser Thr Ala Tyr Met Gln Leu Ser Ser Leu Thr Ser
545                 550                 555                 560

Glu Asp Ser Ala Val Tyr Tyr Cys Ala Arg Tyr Tyr Asp Asp His Tyr
                565                 570                 575

Cys Leu Asp Tyr Trp Gly Gln Gly Thr Thr Leu Thr Val Ser Ser Gly
            580                 585                 590

Gly Gly Gly Ser Gly Gly Gly Gly Ser Gly Gly Gly Gly Ser Gln Ile
        595                 600                 605

Val Leu Thr Gln Ser Pro Ala Ile Met Ser Ala Ser Pro Gly Glu Lys
    610                 615                 620

Val Thr Met Thr Cys Ser Ala Ser Ser Ser Val Ser Tyr Met Asn Trp
625                 630                 635                 640

Tyr Gln Gln Lys Ser Gly Thr Ser Pro Lys Arg Trp Ile Tyr Asp Thr
                645                 650                 655

Ser Lys Leu Ala Ser Gly Val Pro Ala His Phe Arg Gly Ser Gly Ser
            660                 665                 670

Gly Thr Ser Tyr Ser Leu Thr Ile Ser Gly Met Glu Ala Glu Asp Ala
        675                 680                 685

Ala Thr Tyr Tyr Cys Gln Gln Trp Ser Ser Asn Pro Phe Thr Phe Gly
    690                 695                 700

Ser Gly Thr Lys Leu Glu Ile Asn Arg
705                 710

<210> SEQ ID NO 243
<211> LENGTH: 1434
<212> TYPE: DNA
<213> ORGANISM: Artificial Sequence
<220> FEATURE:
<223> OTHER INFORMATION: Anti-Jagged 4D11v2 - anti-CD3 OKT3
      Multispecific Antibody Light Chain
<220> FEATURE:
<221> NAME/KEY: misc_feature
<222> LOCATION: (545)..(545)
<223> OTHER INFORMATION: n may be any nucleotide

<400> SEQUENCE: 243
gacatccaga tgacccagtc tccatcctcc ctgtctgcat ctgtaggaga cagagtcacc      60
atcacttgcc gggcaagtca gagcattagc agctatttaa attggtatca gcagaaacca     120
gggaaagccc ctaagctcct gatctatgcg gcatccagtt tgcaaagtgg ggtcccatca     180
aggttcagtg gcagtggatc tgggacagat ttcactctca ccatcagcag tctgcaacct     240
gaagattttg caacttacta ctgtcaacag acggttgtgg cgcctccgtt attcggccaa     300
gggaccaagg tggaaatcaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgancaaag cagactacga gaaacacaaa gtctacgcct gcgaagtcac ccatcagggc     600
ctgagctcgc ccgtcacaaa gagcttcaac aggggagagt gtggaggtgg atctggaggt     660
```

```
ggcggttcag gctctggcgg aggctcaggt ggtggaggat caggcggagg tcaggttcag    720
ctgcagcaga gcggtgcaga actggcacgt ccgggtgcaa gcgttaaaat gagctgtaaa    780
gcaagcggtt ataccttac ccgttatacc atgcattggg ttaaacagcg tccgggtcag     840
ggtctggaat ggattggtta tatcaatccg agccgtggtt ataccaacta caaccagaaa    900
ttcaaagata aagcaaccct gaccaccgat aaaagcagca gcaccgccta tatgcagctg    960
agcagcctga cctcagagga tagcgcagtt tattactgtg cacgctatta tgatgatcac   1020
tattgcctgg attattgggg tcagggcacc accctgaccg ttagcagcgg tggtggtggt   1080
agtggtggcg gtggttcagg cggtggcggt agccagattg ttctgaccca gagtccggca   1140
attatgagcg caagtccggg tgaaaaagtt accatgacct gtagcgccag cagcagcgtt   1200
agctatatga attggtatca gcagaaaagc ggcaccagcc cgaaacgttg gatttatgat   1260
accagcaaac tggcaagcgg tgttccggca catttcgtg gtagcggtag cggcacctca   1320
tatagcctga ccattagcgg tatggaagca gaagatgcag caacctatta ttgtcagcag   1380
tggtcaagca atccgtttac ctttggtagt ggcaccaaac tggaaattaa tcgt          1434
```

<210> SEQ ID NO 244
<211> LENGTH: 478
<212> TYPE: PRT
<213> ORGANISM: Artificial Sequence
<220> FEATURE:
<223> OTHER INFORMATION: Anti-Jagged 4D11v2 - anti-CD3 OKT3
      Multispecific Antibody Light Chain
<220> FEATURE:
<221> NAME/KEY: misc_feature
<222> LOCATION: (182)..(182)
<223> OTHER INFORMATION: Xaa may be any amino acid

<400> SEQUENCE: 244

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Val Val Ala Pro Pro
                85                  90                  95

Leu Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Xaa Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

Phe Asn Arg Gly Glu Cys Gly Gly Ser Gly Gly Gly Ser Gly
                210                 215                 220

Ser Gly Gly Gly Ser Gly Gly Gly Ser Gly Gly Gln Val Gln
225                 230                 235                 240

Leu Gln Gln Ser Gly Ala Glu Leu Ala Arg Pro Gly Ala Ser Val Lys
                245                 250                 255

Met Ser Cys Lys Ala Ser Gly Tyr Thr Phe Thr Arg Tyr Thr Met His
                260                 265                 270

Trp Val Lys Gln Arg Pro Gly Gln Gly Leu Glu Trp Ile Gly Tyr Ile
                275                 280                 285

Asn Pro Ser Arg Gly Tyr Thr Asn Tyr Asn Gln Lys Phe Lys Asp Lys
                290                 295                 300

Ala Thr Leu Thr Thr Asp Lys Ser Ser Ser Thr Ala Tyr Met Gln Leu
305                 310                 315                 320

Ser Ser Leu Thr Ser Glu Asp Ser Ala Val Tyr Tyr Cys Ala Arg Tyr
                325                 330                 335

Tyr Asp Asp His Tyr Cys Leu Asp Tyr Trp Gly Gln Gly Thr Thr Leu
                340                 345                 350

Thr Val Ser Ser Gly Gly Gly Gly Ser Gly Gly Gly Gly Ser Gly Gly
                355                 360                 365

Gly Gly Ser Gln Ile Val Leu Thr Gln Ser Pro Ala Ile Met Ser Ala
370                 375                 380

Ser Pro Gly Glu Lys Val Thr Met Thr Cys Ser Ala Ser Ser Ser Val
385                 390                 395                 400

Ser Tyr Met Asn Trp Tyr Gln Gln Lys Ser Gly Thr Ser Pro Lys Arg
                405                 410                 415

Trp Ile Tyr Asp Thr Ser Lys Leu Ala Ser Gly Val Pro Ala His Phe
                420                 425                 430

Arg Gly Ser Gly Ser Gly Thr Ser Tyr Ser Leu Thr Ile Ser Gly Met
                435                 440                 445

Glu Ala Glu Asp Ala Ala Thr Tyr Tyr Cys Gln Gln Trp Ser Ser Asn
    450                 455                 460

Pro Phe Thr Phe Gly Ser Gly Thr Lys Leu Glu Ile Asn Arg
465                 470                 475

<210> SEQ ID NO 245
<211> LENGTH: 1566
<212> TYPE: DNA
<213> ORGANISM: Artificial Sequence
<220> FEATURE:
<223> OTHER INFORMATION: Anti-Jagged-anti-CD3 Multispecific Activatable
      Antibody 5342-1204-4D11v2-CD3 OKT3 Light Chain
<220> FEATURE:
<221> NAME/KEY: misc_feature
<222> LOCATION: (677)..(677)
<223> OTHER INFORMATION: n may be any nucleotide

<400> SEQUENCE: 245
caaggccagt ctggccagtg caatatttgg ctcgtaggtg gtgattgcag gggctggcag     60
gggggctcga gcggtggcag cggtggctct ggtggtctga gcggccgttc cgataatcat    120
ggcggcggtt ctgacatcca gatgacccag tctccatcct ccctgtctgc atctgtagga    180
gacagagtca ccatcacttg ccgggcaagt cagagcatta gcagctattt aaattggtat    240
cagcagaaac cagggaaagc ccctaagctc ctgatctatg cggcatccag tttgcaaagt    300
ggggtcccat caaggttcag tggcagtgga tctgggacag atttcactct caccatcagc    360

```
agtctgcaac ctgaagattt tgcaacttac tactgtcaac agacggttgt ggcgcctccg    420
ttattcggcc aagggaccaa ggtggaaatc aaacgtacgg tggctgcacc atctgtcttc    480
atcttcccgc atctgatga gcagttgaaa tctggaactg cctctgttgt gtgcctgctg    540
aataacttct atcccagaga ggccaaagta cagtggaagg tggataacgc cctccaatcg    600
ggtaactccc aggagagtgt cacagagcag acagcaagg acagcaccta cagcctcagc    660
agcaccctga cgctgancaa agcagactac gagaaacaca agtctacgc ctgcgaagtc    720 acccatcagg gcctgagctc gcccgtcaca aagagcttca cagggggaga gtgtggaggt    780
ggatctggag gtggcggttc aggctctggc ggaggctcag gtggtggagg atcaggcgga    840
ggtcaggttc agctgcagca gagcggtgca gaactggcac gtccgggtgc aagcgttaaa    900
atgagctgta aagcaagcgg ttatacctt accgttata ccatgcattg ggttaaacag    960
cgtccgggtc agggtctgga atggattggt tatatcaatc cgagccgtgg ttataccaac   1020
tacaaccaga aattcaaaga taaagcaacc ctgaccaccg ataaaagcag cagcaccgcc   1080
tatatgcagc tgagcagcct gacctcagag gatagcgcag tttattactg tgcacgctat   1140
tatgatgatc actattgcct ggattattgg ggtcagggca ccaccctgac cgttagcagc   1200
ggtggtggtg gtagtggtgg cggtggttca ggcggtggcg gtagccagat tgttctgacc   1260
cagagtccgg caattatgag cgcaagtccg ggtgaaaaag ttaccatgac ctgtagcgcc   1320
agcagcagcg ttagctatat gaattggtat cagcagaaaa gcggcaccag cccgaaacgt   1380
tggatttatg ataccagcaa actggcaagc ggtgttccgg cacattttcg tggtagcggt   1440
agcggcacct catatagcct gaccattagc ggtatggaag cagaagatgc agcaacctat   1500
tattgtcagc agtggtcaag caatccgttt accttggta gtggcaccaa actggaaatt   1560
aatcgt                                                              1566
```

<210> SEQ ID NO 246
<211> LENGTH: 522
<212> TYPE: PRT
<213> ORGANISM: Artificial Sequence
<220> FEATURE:
<223> OTHER INFORMATION: Anti-Jagged-anti-CD3 Multispecific Activatable
      Antibody 5342-1204-4D11v2-CD3 OKT3 Light Chain
<220> FEATURE:
<221> NAME/KEY: misc_feature
<222> LOCATION: (226)..(226)
<223> OTHER INFORMATION: Xaa may be any amino acid

<400> SEQUENCE: 246

Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Gly Gly Ser Gly Gly
            20                  25                  30

Leu Ser Gly Arg Ser Asp Asn His Gly Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Ser Ile Ser Ser Tyr Leu Asn Trp Tyr
65                  70                  75                  80

Gln Gln Lys Pro Gly Lys Ala Pro Lys Leu Leu Ile Tyr Ala Ala Ser
                85                  90                  95

Ser Leu Gln Ser Gly Val Pro Ser Arg Phe Ser Gly Ser Gly Ser Gly
            100                 105                 110

Thr Asp Phe Thr Leu Thr Ile Ser Ser Leu Gln Pro Glu Asp Phe Ala

```
            115                 120                 125
Thr Tyr Tyr Cys Gln Gln Thr Val Val Ala Pro Pro Leu Phe Gly Gln
            130                 135                 140
Gly Thr Lys Val Glu Ile Lys Arg Thr Val Ala Ala Pro Ser Val Phe
145                 150                 155                 160
Ile Phe Pro Pro Ser Asp Glu Gln Leu Lys Ser Gly Thr Ala Ser Val
            165                 170                 175
Val Cys Leu Leu Asn Asn Phe Tyr Pro Arg Glu Ala Lys Val Gln Trp
            180                 185                 190
Lys Val Asp Asn Ala Leu Gln Ser Gly Asn Ser Gln Glu Ser Val Thr
            195                 200                 205
Glu Gln Asp Ser Lys Asp Ser Thr Tyr Ser Leu Ser Ser Thr Leu Thr
            210                 215                 220
Leu Xaa Lys Ala Asp Tyr Glu Lys His Lys Val Tyr Ala Cys Glu Val
225                 230                 235                 240
Thr His Gln Gly Leu Ser Ser Pro Val Thr Lys Ser Phe Asn Arg Gly
            245                 250                 255
Glu Cys Gly Gly Gly Ser Gly Gly Gly Ser Gly Ser Gly Gly Gly
            260                 265                 270
Ser Gly Gly Gly Ser Gly Gly Gly Gln Val Gln Leu Gln Gln Ser
            275                 280                 285
Gly Ala Glu Leu Ala Arg Pro Gly Ala Ser Val Lys Met Ser Cys Lys
            290                 295                 300
Ala Ser Gly Tyr Thr Phe Thr Arg Tyr Thr Met His Trp Val Lys Gln
305                 310                 315                 320
Arg Pro Gly Gln Gly Leu Glu Trp Ile Gly Tyr Ile Asn Pro Ser Arg
            325                 330                 335
Gly Tyr Thr Asn Tyr Asn Gln Lys Phe Lys Asp Lys Ala Thr Leu Thr
            340                 345                 350
Thr Asp Lys Ser Ser Ser Thr Ala Tyr Met Gln Leu Ser Ser Leu Thr
            355                 360                 365
Ser Glu Asp Ser Ala Val Tyr Tyr Cys Ala Arg Tyr Tyr Asp Asp His
            370                 375                 380
Tyr Cys Leu Asp Tyr Trp Gly Gln Gly Thr Thr Leu Thr Val Ser Ser
385                 390                 395                 400
Gly Gly Gly Gly Ser Gly Gly Gly Ser Gly Gly Gly Gly Ser Gln
            405                 410                 415
Ile Val Leu Thr Gln Ser Pro Ala Ile Met Ser Ala Ser Pro Gly Glu
            420                 425                 430
Lys Val Thr Met Thr Cys Ser Ala Ser Ser Ser Val Ser Tyr Met Asn
            435                 440                 445
Trp Tyr Gln Gln Lys Ser Gly Thr Ser Pro Lys Arg Trp Ile Tyr Asp
            450                 455                 460
Thr Ser Lys Leu Ala Ser Gly Val Pro Ala His Phe Arg Gly Ser Gly
465                 470                 475                 480
Ser Gly Thr Ser Tyr Ser Leu Thr Ile Ser Gly Met Glu Ala Glu Asp
            485                 490                 495
Ala Ala Thr Tyr Tyr Cys Gln Gln Trp Ser Ser Asn Pro Phe Thr Phe
            500                 505                 510
Gly Ser Gly Thr Lys Leu Glu Ile Asn Arg
            515                 520

<210> SEQ ID NO 247
```

<211> LENGTH: 2162
<212> TYPE: DNA
<213> ORGANISM: Artificial Sequence
<220> FEATURE:
<223> OTHER INFORMATION: Anti-Jagged 4D11v2-anti-CTLA-4 Multispecific
      Antibody Heavy Chain

<400> SEQUENCE: 247

| | | | | |
|---|---|---|---|---|
| gaggtgcacc | tgttggagtc | tgggggaggc | ttggtacagc | ctggggggtc | cctgagactc | 60 |
| tcctgtgcag | cctctggatt | cacctttagc | agctatgcca | tgagctgggt | ccgccaggct | 120 |
| ccagggaagg | gctggagtg | gtgtcaagt | attgacccgg | aaggtcggca | gacatattac | 180 |
| gcagactccg | tgaagggccg | gttcaccatc | tccagagaca | attccaagaa | cacgctgtat | 240 |
| ctgcaaatga | acagcctgag | agccgaggac | acggccgtat | attactgtgc | gaaagacatc | 300 |
| ggcggcaggt | cggcctttga | ctactggggc | caggaaccc | tggtcaccgt | ctcctcagct | 360 |
| agcaccaagg | gcccatcggt | cttccccctg | gcaccctcct | ccaagagcac | ctctgggggc | 420 |
| acagcggccc | tgggctgcct | ggtcaaggac | tacttcccg | aaccggtgac | ggtgtcgtgg | 480 |
| aactcaggcg | ccctgaccag | cggcgtgcac | accttcccgg | ctgtcctaca | gtcctcagga | 540 |
| ctctactccc | tcagcagcgt | ggtgaccgtg | ccctccagca | gcttgggcac | ccagacctac | 600 |
| atctgcaacg | tgaatcacaa | gcccagcaac | accaaggtgg | acaagaaagt | tgagcccaaa | 660 |
| tcttgtgaca | aaactcacac | atgcccaccg | tgcccagcac | ctgaactcct | ggggggaccg | 720 |
| tcagtcttcc | tcttcccccc | aaaacccaag | gacaccctca | tgatctcccg | gacccctgag | 780 |
| gtcacatgcg | tggtggtgga | cgtgagccac | gaagaccctg | aggtcaagtt | caactggtac | 840 |
| gtggacggcg | tggaggtgca | taatgccaag | acaaagccgc | gggaggagca | gtacaacagc | 900 |
| acgtaccgtg | tggtcagcgt | cctcaccgtc | ctgcaccagg | actggctgaa | tggcaaggag | 960 |
| tacaagtgca | aggtctccaa | caaagccctc | ccagcccca | tcgagaaaac | catctccaaa | 1020 |
| gccaaagggc | agccccgaga | accacaggtg | tacaccctgc | ccccatcccg | ggaggagatg | 1080 |
| accaagaacc | aggtcagcct | gacctgcctg | gtcaaaggct | tctatcccag | cgacatcgcc | 1140 |
| gtggagtggg | agagcaatgg | gcagccggag | aacaactaca | agaccacgcc | tcccgtgctg | 1200 |
| gactccgacg | gctccttctt | cctctacagc | aagctcaccg | tggacaagag | caggtggcag | 1260 |
| caggggaacg | tcttctcatg | ctccgtgatg | catgaggctc | tgcacaacca | ctacacgcag | 1320 |
| aagagcctct | ccctgtctcc | gggtaaagga | ggtggatctg | gaggtggcgg | ttcaggctct | 1380 |
| ggcggaggct | caggtggtgg | aggatcaggc | ggaggtgaaa | ttgtgttgac | acagtctcca | 1440 |
| ggcaccctgt | ctttgtctcc | aggggaaaga | gccaccctct | cctgcagggc | cagtcagagt | 1500 |
| gttagcagca | gctacttagc | ctggtaccag | cagaaacctg | gccaggctcc | caggctcctc | 1560 |
| atctatggtg | catccagcag | ggccactggc | atcccagaca | ggttcagtgg | cagtgggtct | 1620 |
| gggacagact | tcactctcac | catcagcaga | ctggagcctg | aagattttgc | agtgtattac | 1680 |
| tgtcagcagt | atggtagctc | accgctcact | ttcggcggag | ggaccaaggt | ggaaatcaaa | 1740 |
| cgttccggag | ggtcgaccat | aacttcgtat | aatgtatact | atacgaagtt | atcctcgagc | 1800 |
| ggtacccagg | tgcagctggt | gcagactggg | ggaggcgtgg | tccagcctgg | gaggtccctg | 1860 |
| agactctcct | gtgcagcctc | tggatccacc | tttagcagct | atgccatgag | ctgggtccgc | 1920 |
| caggctccag | ggaaggggct | ggagtgggtc | tcagctatta | gtggtagtgg | tggtagcaca | 1980 |
| tactacgcag | actccgtgaa | gggccggttc | accatctcca | gagacaattc | caagaacacg | 2040 |
| ctgtatctgc | aaatgaacag | cctgagagcc | gaggacacgg | ccgtatatta | ctgtgcgaca | 2100 |

```
aactcccttt actggtactt cgatctctgg ggccgtggca ccctggtcac tgtctcttca    2160
gc                                                                   2162
```

<210> SEQ ID NO 248
<211> LENGTH: 722
<212> TYPE: PRT
<213> ORGANISM: Artificial Sequence
<220> FEATURE:
<223> OTHER INFORMATION: Anti-Jagged 4D11v2-anti-CTLA-4 Multispecific
      Antibody Heavy Chain

<400> SEQUENCE: 248

```
Glu Val His Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ser Ile Asp Pro Glu Gly Arg Gln Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Ile Gly Gly Arg Ser Ala Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
```

-continued

```
              340                 345                 350
Leu Pro Pro Ser Arg Glu Glu Met Thr Lys Asn Gln Val Ser Leu Thr
            355                 360                 365
Cys Leu Val Lys Gly Phe Tyr Pro Ser Asp Ile Ala Val Glu Trp Glu
        370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys Gly Gly Gly Ser Gly Gly Gly Gly Ser Gly Gly Gly Gly Gly Ser
450                 455                 460
Gly Gly Gly Gly Ser Gly Gly Gly Glu Ile Val Leu Thr Gln Ser Pro
465                 470                 475                 480
Gly Thr Leu Ser Leu Ser Pro Gly Glu Arg Ala Thr Leu Ser Cys Arg
                485                 490                 495
Ala Ser Gln Ser Val Ser Ser Tyr Leu Ala Trp Tyr Gln Gln Lys
            500                 505                 510
Pro Gly Gln Ala Pro Arg Leu Leu Ile Tyr Gly Ala Ser Ser Arg Ala
        515                 520                 525
Thr Gly Ile Pro Asp Arg Phe Ser Gly Ser Gly Ser Gly Thr Asp Phe
    530                 535                 540
Thr Leu Thr Ile Ser Arg Leu Glu Pro Glu Asp Phe Ala Val Tyr Tyr
545                 550                 555                 560
Cys Gln Gln Tyr Gly Ser Ser Pro Leu Thr Phe Gly Gly Gly Thr Lys
                565                 570                 575
Val Glu Ile Lys Arg Ser Gly Gly Ser Thr Ile Thr Ser Tyr Asn Val
            580                 585                 590
Tyr Tyr Thr Lys Leu Ser Ser Ser Gly Thr Gln Val Gln Leu Val Gln
        595                 600                 605
Thr Gly Gly Gly Val Val Gln Pro Gly Arg Ser Leu Arg Leu Ser Cys
    610                 615                 620
Ala Ala Ser Gly Ser Thr Phe Ser Ser Tyr Ala Met Ser Trp Val Arg
625                 630                 635                 640
Gln Ala Pro Gly Lys Gly Leu Glu Trp Val Ser Ala Ile Ser Gly Ser
                645                 650                 655
Gly Gly Ser Thr Tyr Tyr Ala Asp Ser Val Lys Gly Arg Phe Thr Ile
            660                 665                 670
Ser Arg Asp Asn Ser Lys Asn Thr Leu Tyr Leu Gln Met Asn Ser Leu
        675                 680                 685
Arg Ala Glu Asp Thr Ala Val Tyr Tyr Cys Ala Thr Asn Ser Leu Tyr
    690                 695                 700
Trp Tyr Phe Asp Leu Trp Gly Arg Gly Thr Leu Val Thr Val Ser Ser
705                 710                 715                 720
Ala Ser
```

<210> SEQ ID NO 249
<211> LENGTH: 1461
<212> TYPE: DNA
<213> ORGANISM: Artificial Sequence
<220> FEATURE:

<223> OTHER INFORMATION: Anti-Jagged 4D11v2-anti-CTLA-4 Multispecific
      Antibody Light Chain
<220> FEATURE:
<221> NAME/KEY: misc_feature
<222> LOCATION: (545)..(545)
<223> OTHER INFORMATION: n may be any nucleotide

<400> SEQUENCE: 249

```
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgcg gcatccagtt tgcaaagtgg ggtcccatca   180
aggttcagtg gcagtggatc tgggacagat tcactctca ccatcagcag tctgcaacct    240
gaagattttg caacttacta ctgtcaacag acggttgtgg cgcctccgtt attcggccaa   300
gggaccaagg tggaaatcaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgancaaag cagactacga aaacacaaa gtctacgcct gcgaagtcac ccatcagggc    600
ctgagctcgc ccgtcacaaa gagcttcaac aggggagagt gtggaggtgg atctggaggt   660
ggcggttcag gctctggcgg aggctcaggt ggtggaggat caggcggagg tgaaattgtg   720
ttgacacagt ctccaggcac cctgtctttg tctccagggg aaagagccac cctctcctgc   780
agggccagtc agagtgttag cagcagctac ttagcctggt accagcagaa acctggccag   840
gctcccaggc tcctcatcta tggtgcatcc agcagggcca ctggcatccc agacaggttc   900
agtggcagtg ggtctgggac agacttcact ctcaccatca gcagactgga gcctgaagat   960
tttgcagtgt attactgtca gcagtatggt agctcaccgc tcactttcgg cggagggacc  1020
aaggtggaaa tcaaacgttc ggagggtcg accataactt cgtataatgt atactatacg   1080
aagttatcct cgagcggtac ccaggtgcag ctggtgcaga ctggggagg cgtggtccag   1140
cctgggaggt ccctgagact ctcctgtgca gcctctggat ccacctttag cagctatgcc   1200
atgagctggg tccgccaggc tccagggaag gggctggagt gggtctcagc tattagtggt   1260
agtggtggta gcacatacta cgcagactcc gtgaagggcc ggttcaccat ctccagagac   1320
aattccaaga cacgctgta tctgcaaatg aacagcctga gagccgagga cacggccgta   1380
tattactgtg cgacaaactc cctttactgg tacttcgatc tctggggccg tggcaccctg   1440
gtcactgtct cttcagctag c                                            1461
```

<210> SEQ ID NO 250
<211> LENGTH: 487
<212> TYPE: PRT
<213> ORGANISM: Artificial Sequence
<220> FEATURE:
<223> OTHER INFORMATION: Anti-Jagged 4D11v2-anti-CTLA-4 Multispecific
      Antibody Light Chain
<220> FEATURE:
<221> NAME/KEY: misc_feature
<222> LOCATION: (182)..(182)
<223> OTHER INFORMATION: Xaa may be any amino acid

<400> SEQUENCE: 250

```
Asp Ile Gln Met Thr Gln Ser Pro Ser Ser Leu Ser Ala Ser Val Gly
1               5                   10                  15
Asp Arg Val Thr Ile Thr Cys Arg Ala Ser Gln Ser Ile Ser Ser Tyr
            20                  25                  30
```

-continued

```
Leu Asn Trp Tyr Gln Gln Lys Pro Gly Lys Ala Pro Lys Leu Leu Ile
         35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Val Val Ala Pro Pro
                     85                  90                  95

Leu Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
                115                 120                 125

Thr Ala Ser Val Val Cys Leu Leu Asn Asn Phe Tyr Pro Arg Glu Ala
         130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Xaa Lys Ala Asp Tyr Glu Lys His Lys Val Tyr
                180                 185                 190

Ala Cys Glu Val Thr His Gln Gly Leu Ser Ser Pro Val Thr Lys Ser
         195                 200                 205

Phe Asn Arg Gly Glu Cys Gly Gly Gly Ser Gly Gly Gly Gly Ser Gly
         210                 215                 220

Ser Gly Gly Gly Ser Gly Gly Gly Ser Gly Gly Gly Glu Ile Val
225                 230                 235                 240

Leu Thr Gln Ser Pro Gly Thr Leu Ser Leu Ser Pro Gly Glu Arg Ala
                245                 250                 255

Thr Leu Ser Cys Arg Ala Ser Gln Ser Val Ser Ser Ser Tyr Leu Ala
         260                 265                 270

Trp Tyr Gln Gln Lys Pro Gly Gln Ala Pro Arg Leu Leu Ile Tyr Gly
         275                 280                 285

Ala Ser Ser Arg Ala Thr Gly Ile Pro Asp Arg Phe Ser Gly Ser Gly
         290                 295                 300

Ser Gly Thr Asp Phe Thr Leu Thr Ile Ser Arg Leu Glu Pro Glu Asp
305                 310                 315                 320

Phe Ala Val Tyr Tyr Cys Gln Gln Tyr Gly Ser Ser Pro Leu Thr Phe
                325                 330                 335

Gly Gly Gly Thr Lys Val Glu Ile Lys Arg Ser Gly Gly Ser Thr Ile
                340                 345                 350

Thr Ser Tyr Asn Val Tyr Tyr Thr Lys Leu Ser Ser Ser Gly Thr Gln
         355                 360                 365

Val Gln Leu Val Gln Thr Gly Gly Gly Val Val Gln Pro Gly Arg Ser
         370                 375                 380

Leu Arg Leu Ser Cys Ala Ala Ser Gly Ser Thr Phe Ser Ser Tyr Ala
385                 390                 395                 400

Met Ser Trp Val Arg Gln Ala Pro Gly Lys Gly Leu Glu Trp Val Ser
                405                 410                 415

Ala Ile Ser Gly Ser Gly Gly Ser Thr Tyr Tyr Ala Asp Ser Val Lys
         420                 425                 430

Gly Arg Phe Thr Ile Ser Arg Asp Asn Ser Lys Asn Thr Leu Tyr Leu
         435                 440                 445
```

Gln Met Asn Ser Leu Arg Ala Glu Asp Thr Ala Val Tyr Tyr Cys Ala
    450                 455                 460

Thr Asn Ser Leu Tyr Trp Tyr Phe Asp Leu Trp Gly Arg Gly Thr Leu
465                 470                 475                 480

Val Thr Val Ser Ser Ala Ser
                485

<210> SEQ ID NO 251
<211> LENGTH: 1593
<212> TYPE: DNA
<213> ORGANISM: Artificial Sequence
<220> FEATURE:
<223> OTHER INFORMATION: Anti-Jagged-anti-CTLA-4 Multispecific
      Activatable Antibody 5342-1204-4D11v2-CTLA-4 Light Chain
<220> FEATURE:
<221> NAME/KEY: misc_feature
<222> LOCATION: (677)..(677)
<223> OTHER INFORMATION: n may be any nucleotide

<400> SEQUENCE: 251

| | | | | | |
|---|---|---|---|---|---|
| caaggccagt | ctggccagtg | caatatttgg | ctcgtaggtg | gtgattgcag | gggctggcag | 60 |
| gggggctcga | gcggtggcag | cggtggctct | ggtggtctga | gcggccgttc | cgataatcat | 120 |
| ggcggcggtt | ctgacatcca | gatgacccag | tctccatcct | ccctgtctgc | atctgtagga | 180 |
| gacagagtca | ccatcacttg | ccgggcaagt | cagagcatta | gcagctattt | aaattggtat | 240 |
| cagcagaaac | cagggaaagc | ccctaagctc | ctgatctatg | cggcatccag | tttgcaaagt | 300 |
| ggggtcccat | caaggttcag | tggcagtgga | tctgggacag | atttcactct | caccatcagc | 360 |
| agtctgcaac | ctgaagattt | tgcaacttac | tactgtcaac | agacggttgt | ggcgcctccg | 420 |
| ttattcggcc | aagggaccaa | ggtggaaatc | aaacgtacgg | tggctgcacc | atctgtcttc | 480 |
| atcttcccgc | catctgatga | gcagttgaaa | tctggaactg | cctctgttgt | gtgcctgctg | 540 |
| aataacttct | atcccagaga | ggccaaagta | cagtggaagg | tggataacgc | cctccaatcg | 600 |
| ggtaactccc | aggagagtgt | cacagagcag | gacagcaagg | acagcaccta | cagcctcagc | 660 |
| agcaccctga | cgctgancaa | agcagactac | gagaaacaca | aagtctacgc | ctgcgaagtc | 720 |
| acccatcagg | gcctgagctc | gcccgtcaca | aagagcttca | acaggggaga | gtgtggaggt | 780 |
| ggatctggag | gtggcggttc | aggctctggc | ggaggctcag | gtggtggagg | atcaggcgga | 840 |
| ggtgaaattg | tgttgacaca | gtctccaggc | accctgtctt | tgtctccagg | ggaaagagcc | 900 |
| accctctcct | gcagggccag | tcagagtgtt | agcagcagct | acttagcctg | gtaccagcag | 960 |
| aaacctggcc | aggctcccag | gctcctcatc | tatggtgcat | ccagcagggc | cactggcatc | 1020 |
| ccagacaggt | tcagtggcag | tgggtctggg | acagacttca | ctctcaccat | cagcagactg | 1080 |
| gagcctgaag | attttgcagt | gtattactgt | cagcagtatg | gtagctcacc | gctcactttc | 1140 |
| ggcggaggga | ccaaggtgga | aatcaaacgt | tccggagggt | cgaccataac | ttcgtataat | 1200 |
| gtatactata | cgaagttatc | ctcgagcggt | acccaggtgc | agctggtgca | gactggggga | 1260 |
| ggcgtggtcc | agcctgggag | gtccctgaga | ctctcctgtg | cagcctctgg | atccacctt | 1320 |
| agcagctatg | ccatgagctg | ggtccgccag | gctccaggga | aggggctgga | gtgggtctca | 1380 |
| gctattagtg | gtagtggtgg | tagcacatac | tacgcagact | ccgtgaaggg | ccggttcacc | 1440 |
| atctccagag | acaattccaa | gaacacgctg | tatctgcaaa | tgaacagcct | gagagccgag | 1500 |
| gacacggccg | tatattactg | tgcgacaaac | tcccttact | ggtacttcga | tctctgggc | 1560 |
| cgtggcaccc | tggtcactgt | ctcttcagct | agc | | | 1593 |

<210> SEQ ID NO 252
<211> LENGTH: 531
<212> TYPE: PRT
<213> ORGANISM: Artificial Sequence
<220> FEATURE:
<223> OTHER INFORMATION: Anti-Jagged-anti-CTLA-4 Multispecific
      Activatable Antibody 5342-1204-4D11v2-CTLA-4 Light Chain
<220> FEATURE:
<221> NAME/KEY: misc_feature
<222> LOCATION: (226)..(226)
<223> OTHER INFORMATION: Xaa may be any amino acid

<400> SEQUENCE: 252

Gln Gly Gln Ser Gly Gln Cys Asn Ile Trp Leu Val Gly Gly Asp Cys
1               5                   10                  15

Arg Gly Trp Gln Gly Gly Ser Ser Gly Gly Ser Gly Gly Ser Gly Gly
            20                  25                  30

Leu Ser Gly Arg Ser Asp Asn His Gly Gly Gly Ser Asp Ile Gln Met
        35                  40                  45

Thr Gln Ser Pro Ser Ser Leu Ser Ala Ser Val Gly Asp Arg Val Thr
    50                  55                  60

Ile Thr Cys Arg Ala Ser Gln Ser Ile Ser Ser Tyr Leu Asn Trp Tyr
65                  70                  75                  80

Gln Gln Lys Pro Gly Lys Ala Pro Lys Leu Ile Tyr Ala Ala Ser Ser
                85                  90                  95

Ser Leu Gln Ser Gly Val Pro Ser Arg Phe Ser Gly Ser Gly Ser Gly
            100                 105                 110

Thr Asp Phe Thr Leu Thr Ile Ser Ser Leu Gln Pro Glu Asp Phe Ala
        115                 120                 125

Thr Tyr Tyr Cys Gln Gln Thr Val Val Ala Pro Pro Leu Phe Gly Gln
    130                 135                 140

Gly Thr Lys Val Glu Ile Lys Arg Thr Val Ala Ala Pro Ser Val Phe
145                 150                 155                 160

Ile Phe Pro Pro Ser Asp Glu Gln Leu Lys Ser Gly Thr Ala Ser Val
                165                 170                 175

Val Cys Leu Leu Asn Asn Phe Tyr Pro Arg Glu Ala Lys Val Gln Trp
            180                 185                 190

Lys Val Asp Asn Ala Leu Gln Ser Gly Asn Ser Gln Glu Ser Val Thr
        195                 200                 205

Glu Gln Asp Ser Lys Asp Ser Thr Tyr Ser Leu Ser Ser Thr Leu Thr
    210                 215                 220

Leu Xaa Lys Ala Asp Tyr Glu Lys His Lys Val Tyr Ala Cys Glu Val
225                 230                 235                 240

Thr His Gln Gly Leu Ser Ser Pro Val Thr Lys Ser Phe Asn Arg Gly
                245                 250                 255

Glu Cys Gly Gly Gly Ser Gly Gly Ser Gly Gly Ser Gly Gly Gly Gly
            260                 265                 270

Ser Gly Gly Gly Gly Ser Gly Gly Glu Ile Val Leu Thr Gln Ser
        275                 280                 285

Pro Gly Thr Leu Ser Leu Ser Pro Gly Glu Arg Ala Thr Leu Ser Cys
    290                 295                 300

Arg Ala Ser Gln Ser Val Ser Ser Ser Tyr Leu Ala Trp Tyr Gln Gln
305                 310                 315                 320

Lys Pro Gly Gln Ala Pro Arg Leu Leu Ile Tyr Gly Ala Ser Ser Arg
                325                 330                 335

Ala Thr Gly Ile Pro Asp Arg Phe Ser Gly Ser Gly Ser Gly Thr Asp
            340                 345                 350

```
        Phe Thr Leu Thr Ile Ser Arg Leu Glu Pro Glu Asp Phe Ala Val Tyr
                355                 360                 365

Tyr Cys Gln Gln Tyr Gly Ser Ser Pro Leu Thr Phe Gly Gly Gly Thr
            370                 375                 380

Lys Val Glu Ile Lys Arg Ser Gly Gly Ser Thr Ile Thr Ser Tyr Asn
        385                 390                 395                 400

Val Tyr Tyr Thr Lys Leu Ser Ser Ser Gly Thr Gln Val Gln Leu Val
                    405                 410                 415

Gln Thr Gly Gly Gly Val Val Gln Pro Gly Arg Ser Leu Arg Leu Ser
                    420                 425                 430

Cys Ala Ala Ser Gly Ser Thr Phe Ser Ser Tyr Ala Met Ser Trp Val
                        435                 440                 445

Arg Gln Ala Pro Gly Lys Gly Leu Glu Trp Val Ser Ala Ile Ser Gly
            450                 455                 460

Ser Gly Gly Ser Thr Tyr Tyr Ala Asp Ser Val Lys Gly Arg Phe Thr
        465                 470                 475                 480

Ile Ser Arg Asp Asn Ser Lys Asn Thr Leu Tyr Leu Gln Met Asn Ser
                        485                 490                 495

Leu Arg Ala Glu Asp Thr Ala Val Tyr Tyr Cys Ala Thr Asn Ser Leu
                    500                 505                 510

Tyr Trp Tyr Phe Asp Leu Trp Gly Arg Gly Thr Leu Val Thr Val Ser
                515                 520                 525

Ser Ala Ser
            530

<210> SEQ ID NO 253
<211> LENGTH: 1350
<212> TYPE: DNA
<213> ORGANISM: Artificial Sequence
<220> FEATURE:
<223> OTHER INFORMATION: Anti-EGFR C225v5 Antibody Heavy Chain

<400> SEQUENCE: 253
caggtgcagc tgaaacagag cggcccgggc ctggtgcagc cgagccagag cctgagcatt       60
acctgcaccg tgagcggctt tagcctgacc aactatggcg tgcattgggt gcgccagagc      120
ccgggcaaag cctggaatg gctgggcgtg atttggagcg gcggcaacac cgattataac      180
accccgttta ccagccgcct gagcattaac aaagataaca gcaaaagcca ggtgtttttt      240
aaaatgaaca gcctgcaaag ccaggatacc gcgatttatt attgcgcgcg cgcgctgacc      300
tattatgatt atgaatttgc gtattggggc cagggcaccc tggtgaccgt gagcgcggct      360
agcaccaagg gcccatcggt cttccccctg gcaccctcct ccaagagcac ctctgggggc      420
acagcggccc tgggctgcct ggtcaaggac tacttccccg aaccggtgac ggtgtcgtgg      480
aactcaggcg ccctgaccag cggcgtgcac accttcccgg ctgtcctaca gtcctcagga      540
ctctactccc tcagcagcgt ggtgaccgtg ccctccagca gcttgggcac ccagacctac      600
atctgcaacg tgaatcacaa gcccagcaac accaaggtgg acaagaaagt tgagcccaaa      660
tcttgtgaca aaactcacac atgcccaccg tgcccagcac ctgaactcct ggggggaccg      720
tcagtcttcc tcttccccc aaaacccaag gacaccctca tgatctcccg gacccctgag      780
gtcacatgcg tggtggtgga cgtgagccac gaagaccctg aggtcaagtt caactggtac      840
gtggacggcg tggaggtgca taatgccaag acaaagccgc gggaggagca gtacaacagc      900
acgtaccgtg tggtcagcgt cctcaccgtc ctgcaccagg actggctgaa tggcaaggag      960
```

-continued

```
tacaagtgca aggtctccaa caaagccctc ccagccccca tcgagaaaac catctccaaa    1020
gccaaagggc agccccgaga accacaggtg tacaccctgc ccccatcccg ggatgaactg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                     1350

<210> SEQ ID NO 254
<211> LENGTH: 449
<212> TYPE: PRT
<213> ORGANISM: Artificial Sequence
<220> FEATURE:
<223> OTHER INFORMATION: Anti-EGFR C225v5 Antibody Heavy Chain

<400> SEQUENCE: 254
```

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 255
<211> LENGTH: 642
<212> TYPE: DNA
<213> ORGANISM: Artificial Sequence
<220> FEATURE:
<223> OTHER INFORMATION: Anti-EGFR C225v5 Antibody Light Chain

<400> SEQUENCE: 255
cagatcttgc tgacccagag cccggtgatt ctgagcgtga gcccgggcga acgtgtgagc    60
tttagctgcc gcgcgagcca gagcattggc accaacattc attggtatca gcagcgcacc   120
aacggcagcc cgcgcctgct gattaaatat gcgagcgaaa gcattagcgg cattccgagc   180
cgctttagcg gcagcggcag cggcaccgat tttaccctga gcattaacag cgtggaaagc   240
gaagatattg cggattatta ttgccagcag aacaacaact ggccgaccac ctttggcgcg   300
ggcaccaaac tggaactgaa acgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                     642

<210> SEQ ID NO 256
<211> LENGTH: 214
<212> TYPE: PRT
<213> ORGANISM: Artificial Sequence
<220> FEATURE:
<223> OTHER INFORMATION: Anti-EGFR C225v5 Antibody Light Chain

<400> SEQUENCE: 256

Gln Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

```
Ile His Trp Tyr Gln Gln Arg Thr Asn Gly Ser Pro Arg Leu Leu Ile
             35                  40                  45
Lys Tyr Ala Ser Glu Ser Ile Ser Gly Ile Pro Ser Arg Phe Ser Gly
 50                  55                  60
Ser Gly Ser Gly Thr Asp Phe Thr Leu Ser Ile Asn Ser Val Glu Ser
 65                  70                  75                  80
Glu Asp Ile Ala Asp Tyr Tyr Cys Gln Gln Asn Asn Asn Trp Pro Thr
                 85                  90                  95
Thr Phe Gly Ala Gly Thr Lys Leu Glu Leu Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 257
<211> LENGTH: 1347
<212> TYPE: DNA
<213> ORGANISM: Artificial Sequence
<220> FEATURE:
<223> OTHER INFORMATION: Anti-EGFR C225v5 Antibody Heavy Chain

<400> SEQUENCE: 257
caggtgcagc tgaaacagag cggcccgggc ctggtgcagc cgagccagag cctgagcatt    60
acctgcaccg tgagcggctt tagcctgacc aactatggcg tgcattgggt gcgccagagc   120
ccgggcaaag cctggaatgg ctgggcgtg atttggagcg gcggcaacac cgattataac   180
accccgttta ccagccgcct gagcattaac aaagataaca gcaaaagcca ggtgtttttt   240
aaaatgaaca gcctgcaaag caacgatacc gcgatttatt attgcgcgcg cgcgctgacc   300
tattatgatt atgaatttgc gtattggggc cagggcaccc tggtgaccgt gagcgcggct   360
agcaccaagg gcccatcggt cttccccctg gcaccctcct ccaagagcac ctctgggggc   420
acagcggccc tgggctgcct ggtcaaggac tacttccccg aaccggtgac ggtgtcgtgg   480
aactcaggcg ccctgaccag cggcgtgcac accttcccgg ctgtcctaca gtcctcagga   540
ctctactccc tcagcagcgt ggtgaccgtg ccctccagca gcttgggcac ccagacctac   600
atctgcaacg tgaatcacaa gcccagcaac accaaggtgg acaagcgcgt tgagcccaaa   660
tcttgtgaca aaactcacac atgcccaccg tgcccagcac ctgaactcct ggggggaccg   720
tcagtcttcc tcttcccccc aaaacccaag gacaccctca tgatctcccg gacccctgag   780
gtcacatgcg tggtggtgga cgtgagccac gaagaccctg aggtcaagtt caactggtac   840
gtggacggcg tggaggtgca taatgccaag acaaagccgc gggaggagca gtacaacagc   900
acgtaccgtg tggtcagcgt cctcaccgtc ctgcaccagg actggctgaa tggcaaggag   960
tacaagtgca aggtctccaa caaagccctc ccagccccca tcgagaaaac catctccaaa  1020
```

-continued

```
gccaagggc agccccgaga accacaggtg tacaccctgc ccccatcccg ggatgaactg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaa                                        1347
```

<210> SEQ ID NO 258
<211> LENGTH: 449
<212> TYPE: PRT
<213> ORGANISM: Artificial Sequence
<220> FEATURE:
<223> OTHER INFORMATION: Anti-EGFR C225v5 Antibody Heavy Chain

<400> SEQUENCE: 258

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 259
<211> LENGTH: 648
<212> TYPE: DNA
<213> ORGANISM: Artificial Sequence
<220> FEATURE:
<223> OTHER INFORMATION: Anti-EGFR C225v5 Antibody Light Chain

<400> SEQUENCE: 259
ggcggtaccc agatcttgct gacccagagc ccggtgattc tgagcgtgag cccgggcgaa     60
cgtgtgagct ttagctgccg cgcgagccag agcattggca ccaacattca ttggtatcag    120
cagcgcacca acggcagccc gcgcctgctg attaaatatg cgagcgaaag cattagcggc    180
attccgagcc gctttagcgg cagcggcagc ggcaccgatt ttaccctgag cattaacagc    240
gtggaaagcg aagatattgc ggattattat tgccagcaga caacaactg gccgaccacc    300 tttggcgcgg gcaccaaact ggaactgaaa cgtacggtgg ctgcaccatc tgtcttcatc    360
ttcccgccat ctgatgagca gttgaaatct ggaactgcct ctgttgtgtg cctgctgaat    420
aacttctatc ccagagaggc caaagtacag tggaaggtgg ataacgccct ccaatcgggt    480
aactcccagg agagtgtcac agagcaggac agcaaggaca gcacctacag cctcagcagc    540
accctgacgc tgagcaaagc agactacgag aaacacaaag tctacgcctg cgaagtcacc    600
catcagggcc tgagctcgcc cgtcacaaag agcttcaaca ggggagcg              648

<210> SEQ ID NO 260
<211> LENGTH: 214
<212> TYPE: PRT
<213> ORGANISM: Artificial Sequence
<220> FEATURE:
<223> OTHER INFORMATION: Anti-EGFR C225v5 Antibody Light Chain

<400> SEQUENCE: 260

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
```

35                  40                  45
Lys Tyr Ala Ser Glu Ser Ile Ser Gly Ile Pro Ser Arg Phe Ser Gly
     50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 261
<211> LENGTH: 1350
<212> TYPE: DNA
<213> ORGANISM: Artificial Sequence
<220> FEATURE:
<223> OTHER INFORMATION: Anti-EGFR C225v4 Antibody Heavy Chain

<400> SEQUENCE: 261
caggtgcagc tgaaacagag cggcccgggc ctggtgcagc cgagccagag cctgagcatt      60
acctgcaccg tgagcggctt tagcctgacc aactatggcg tgcattgggt gcgccagagc     120
ccgggcaaag cctggaatg gctgggcgtg atttggagcg gcggcaacac cgattataac      180
accccgttta ccagccgcct gagcattaac aaagataaca gcaaaagcca ggtgtttttt     240
aaaatgaaca gcctgcaaag caacgatacc gcgatttatt attgcgcgcg cgcgctgacc     300
tattatgatt atgaatttgc gtattgggggc cagggcaccc tggtgaccgt gagcgcggct    360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttccccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacaacagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020

-continued

```
gccaaagggc agccccgaga accacaggtg tacaccctgc ccccatcccg ggatgaactg    1080
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                     1350
```

<210> SEQ ID NO 262
<211> LENGTH: 449
<212> TYPE: PRT
<213> ORGANISM: Artificial Sequence
<220> FEATURE:
<223> OTHER INFORMATION: Anti-EGFR C225v4 Antibody Heavy Chain

<400> SEQUENCE: 262

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Asn Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300
```

```
Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
        370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 263
<211> LENGTH: 645
<212> TYPE: DNA
<213> ORGANISM: Artificial Sequence
<220> FEATURE:
<223> OTHER INFORMATION: Anti-EGFR C225v4 Antibody Light Chain

<400> SEQUENCE: 263
cagatcttgc tgacccagag cccggtgatt ctgagcgtga gcccgggcga acgtgtgagc      60
tttagctgcc gcgcgagcca gagcattggc accaacattc attggtatca gcagcgcacc    120
aacggcagcc cgcgcctgct gattaaatat gcgagcgaaa gcattagcgg cattccgagc    180
cgctttagcg gcagcggcag cggcaccgat tttaccctga gcattaacag cgtggaaagc    240
gaagatattg cggattatta ttgccagcag aacaacaact ggccgaccac ctttggcgcg    300
ggcaccaaac tggaactgaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg gataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gttag                    645

<210> SEQ ID NO 264
<211> LENGTH: 214
<212> TYPE: PRT
<213> ORGANISM: Artificial Sequence
<220> FEATURE:
<223> OTHER INFORMATION: Anti-EGFR C225v4 Antibody Light Chain

<400> SEQUENCE: 264

Gln Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45
```

```
Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 265
<211> LENGTH: 1350
<212> TYPE: DNA
<213> ORGANISM: Artificial Sequence
<220> FEATURE:
<223> OTHER INFORMATION: Anti-EGFR C225v6 Antibody Heavy Chain

<400> SEQUENCE: 265

```
caggtgcagc tgaaacagag cggcccgggc ctggtgcagc cgagccagag cctgagcatt      60
acctgcaccg tgagcggctt tagcctgacc aactatggcg tgcattgggt gcgccagagc     120
ccgggcaaag cctggaatg gctgggcgtg atttggagcg gcggcaacac cgattataac     180
accccgttta ccagccgcct gagcattaac aaagataaca gcaaaagcca ggtgtttttt     240
aaaatgaaca gcctgcaaag ccaggatacc gcgatttatt attgcgcgcg cgcgctgacc     300
tattatgatt atgaatttgc gtattggggc cagggcaccc tggtgaccgt gagcgcggct     360
agcaccaagg gcccatcggt cttccccctg gcaccctcct ccaagagcac ctctgggggc     420
acagcggccc tgggctgcct ggtcaaggac tacttccccg aaccggtgac ggtgtcgtgg     480
aactcaggcg ccctgaccag cggcgtgcac accttcccgg ctgtcctaca gtcctcagga     540
ctctactccc tcagcagcgt ggtgaccgtg ccctccagca gcttgggcac ccagacctac     600
atctgcaacg tgaatcacaa gcccagcaac accaaggtgg acaagaaagt tgagcccaaa     660
tcttgtgaca aaactcacac atgcccaccg tgcccagcac ctgaactcct ggggggaccg     720
tcagtcttcc tcttcccccc aaaacccaag gacaccctca tgatctcccg gacccctgag     780
gtcacatgcg tggtggtgga cgtgagccac gaagaccctg aggtcaagtt caactggtac     840
gtggacggcg tggaggtgca taatgccaag acaaagccgc gggaggagca gtacgccagc     900
acgtaccgtg tggtcagcgt cctcaccgtc ctgcaccagg actggctgaa tggcaaggag     960
tacaagtgca aggtctccaa caaagccctc ccagccccca tcgagaaaac catctccaaa    1020
gccaaagggc agccccgaga accacaggtg tacaccctgc ccccatcccg ggatgaactg    1080
```

```
accaagaacc aggtcagcct gacctgcctg gtcaaaggct tctatcccag cgacatcgcc    1140
gtggagtggg agagcaatgg gcagccggag aacaactaca agaccacgcc tcccgtgctg    1200
gactccgacg gctccttctt cctctacagc aagctcaccg tggacaagag caggtggcag    1260
caggggaacg tcttctcatg ctccgtgatg catgaggctc tgcacaacca ctacacgcag    1320
aagagcctct ccctgtctcc gggtaaatga                                     1350
```

<210> SEQ ID NO 266
<211> LENGTH: 449
<212> TYPE: PRT
<213> ORGANISM: Artificial Sequence
<220> FEATURE:
<223> OTHER INFORMATION: Anti-EGFR C225v6 Antibody Heavy Chain

<400> SEQUENCE: 266

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Ala Ser Thr Tyr Arg Val
    290                 295                 300

Val Ser Val Leu Thr Val Leu His Gln Asp Trp Leu Asn Gly Lys Glu
```

```
                305                 310                 315                 320
Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
            370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
            435                 440                 445

Lys
```

```
<210> SEQ ID NO 267
<211> LENGTH: 645
<212> TYPE: DNA
<213> ORGANISM: Artificial Sequence
<220> FEATURE:
<223> OTHER INFORMATION: Anti-EGFR C225v6 Antibody Light Chain

<400> SEQUENCE: 267
cagatcttgc tgacccagag cccggtgatt ctgagcgtga gcccgggcga acgtgtgagc      60
tttagctgcc gcgcgagcca gagcattggc accaacattc attggtatca gcagcgcacc     120
aacggcagcc cgcgcctgct gattaaatat gcgagcgaaa gcattagcgg cattccgagc     180
cgctttagcg gcagcggcag cggcaccgat tttaccctga gcattaacag cgtggaaagc     240
gaagatattg cggattatta ttgccagcag aacaacaact ggccgaccac ctttggcgcg     300
ggcaccaaac tggaactgaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                     645
```

```
<210> SEQ ID NO 268
<211> LENGTH: 214
<212> TYPE: PRT
<213> ORGANISM: Artificial Sequence
<220> FEATURE:
<223> OTHER INFORMATION: Anti-EGFR C225v6 Antibody Light Chain

<400> SEQUENCE: 268

Gln Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
                20                  25                  30

Ile His Trp Tyr Gln Gln Arg Thr Asn Gly Ser Pro Arg Leu Leu Ile
            35                  40                  45
```

```
Lys Tyr Ala Ser Glu Ser Ile Ser Gly Ile Pro Ser Arg Phe Ser Gly
 50                  55                  60

Ser Gly Ser Gly Thr Asp Phe Thr Leu Ser Ile Asn Ser Val Glu Ser
 65                  70                  75                  80

Glu Asp Ile Ala Asp Tyr Tyr Cys Gln Gln Asn Asn Asn Trp Pro Thr
                 85                  90                  95

Thr Phe Gly Ala Gly Thr Lys Leu Glu Leu Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
210
```

<210> SEQ ID NO 269
<211> LENGTH: 786
<212> TYPE: DNA
<213> ORGANISM: Artificial Sequence
<220> FEATURE:
<223> OTHER INFORMATION: Anti-EGFR Activatable Antibody 3954-1204-C225v5
      Light Chain

<400> SEQUENCE: 269

```
caaggccagt ctggccagtg catctcacct cgtggttgtc cggacggccc atacgtcatg      60
tacggctcga gcggtggcag cggtggctct ggtggatccg gtctgagcgg ccgttccgat     120
aatcatggca gtagcggtac ccagatcttg ctgacccaga gccggtgat tctgagcgtg      180 agcccgggcg aacgtgtgag ctttagctgc cgcgcgagcc agagcattgg caccaacatt     240
cattggtatc agcagcgcac caacggcagc ccgcgcctgc tgattaaata tgcgagcgaa     300
agcattagcg gcattccgag ccgctttagc ggcagcggca gcggcaccga ttttaccctg     360
agcattaaca gcgtggaaag cgaagatatt gcggattatt attgccagca gaacaacaac     420
tggccgacca ccttggcgc gggcaccaaa ctggaactga acgtacggt ggctgcacca      480 tctgtcttca tcttcccgcc atctgatgag cagttgaaat ctggaactgc ctctgttgtg     540
tgcctgctga ataacttcta tcccagagag gccaaagtac agtggaaggt ggataacgcc     600
ctccaatcgg gtaactccca ggagagtgtc acagagcagg acagcaagga cagcacctac     660
agcctcagca gcaccctgac gctgagcaaa gcagactacg agaaacacaa agtctacgcc     720
tgcgaagtca cccatcaggg cctgagctcg cccgtcacaa agagcttcaa caggggagag     780
tgttag                                                                786
```

<210> SEQ ID NO 270
<211> LENGTH: 261
<212> TYPE: PRT
<213> ORGANISM: Artificial Sequence
<220> FEATURE:
<223> OTHER INFORMATION: Anti-EGFR Activatable Antibody 3954-1204-C225v5

Light Chain

<400> SEQUENCE: 270

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly
            20                  25                  30

Ser Gly Leu Ser Gly Arg Ser Asp Asn His Gly Ser Ser Gly Thr Gln
            35                  40                  45

Ile Leu Leu Thr Gln Ser Pro Val Ile Leu Ser Val Ser Pro Gly Glu
50                  55                  60

Arg Val Ser Phe Ser Cys Arg Ala Ser Gln Ser Ile Gly Thr Asn Ile
65                  70                  75                  80

His Trp Tyr Gln Gln Arg Thr Asn Gly Ser Pro Arg Leu Leu Ile Lys
                85                  90                  95

Tyr Ala Ser Glu Ser Ile Ser Gly Ile Pro Ser Arg Phe Ser Gly Ser
            100                 105                 110

Gly Ser Gly Thr Asp Phe Thr Leu Ser Ile Asn Ser Val Glu Ser Glu
            115                 120                 125

Asp Ile Ala Asp Tyr Tyr Cys Gln Gln Asn Asn Asn Trp Pro Thr Thr
130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
            195                 200                 205

Ser Val Thr Glu Gln Asp Ser Lys Asp Ser Thr Tyr Ser Leu Ser Ser
210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 271
<211> LENGTH: 2139
<212> TYPE: DNA
<213> ORGANISM: Artificial Sequence
<220> FEATURE:
<223> OTHER INFORMATION: Anti-EGFR C225v5 - Anti-CD3 OKT3 Multispecific
      Antibody Heavy Chain

<400> SEQUENCE: 271
caggtgcagc tgaaacagag cggcccgggc ctggtgcagc cgagccagag cctgagcatt      60
acctgcaccg tgagcggctt tagcctgacc aactatggcg tgcattgggt gcgccagagc    120
ccgggcaaag cctggaatg gctgggcgtg atttggagcg gcggcaacac cgattataac     180
accccgttta ccagccgcct gagcattaac aaagataaca gcaaaagcca ggtgtttttt    240
aaaatgaaca gcctgcaaag ccaggatacc gcgatttatt attgcgcgcg cgcgctgacc    300
tattatgatt atgaatttgc gtattggggc cagggcaccc tggtgaccgt gagcgcggct    360
agcaccaagg gcccatcggt cttccccctg gcaccctcct ccaagagcac ctctgggggc    420

```
acagcggccc tgggctgcct ggtcaaggac tacttcccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc ccccatcccg ggatgaactg   1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg   1200
gactccgacg gctccttctt cctctacagc aagctcaccg tggacaagag caggtggcag   1260
caggggaacg tcttctcatg ctccgtgatg catgaggctc tgcacaacca ctacacgcag   1320
aagagcctct ccctgtctcc gggtaaagga ggtggatctg aggtggcgg ttcaggctct   1380 ggcggaggct caggtggtgg aggatcaggc ggaggtcagg ttcagctgca gcagagcggt   1440
gcagaactgg cacgtccggg tgcaagcgtt aaaatgagct gtaaagcaag cggttatacc   1500
tttacccgtt ataccatgca ttgggttaaa cagcgtccgg gtcagggtct ggaatggatt   1560
ggttatatca atccgagccg tggttatacc aactacaacc agaaattcaa agataaagca   1620
accctgacca ccgataaaag cagcagcacc gcctatatgc agctgagcag cctgacctca   1680
gaggatagcg cagtttatta ctgtgcacgc tattatgatg atcactattg cctggattat   1740
tggggtcagg gcaccaccct gaccgttagc agcggtggtg gtggtagtgg tggcggtggt   1800
tcaggcggtg gcggtagcca gattgttctg acccagagtc cggcaattat gagcgcaagt   1860
ccgggtgaaa aagttaccat gacctgtagc gccagcagca gcgttagcta tatgaattgg   1920
tatcagcaga aaagcggcac cagcccgaaa cgttggattt atgataccag caaactggca   1980
agcggtgttc cggcacattt tcgtggtagc ggtagcggca cctcatatag cctgaccatt   2040
agcggtatgg aagcagaaga tgcagcaacc tattattgtc agcagtggtc aagcaatccg   2100
tttacctttg gtagtggcac caaactggaa attaatcgt                         2139
```

<210> SEQ ID NO 272
<211> LENGTH: 713
<212> TYPE: PRT
<213> ORGANISM: Artificial Sequence
<220> FEATURE:
<223> OTHER INFORMATION: Anti-EGFR C225v5 - Anti-CD3 OKT3 Multispecific
      Antibody Heavy Chain

<400> SEQUENCE: 272

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

```
Gly Val Ile Trp Ser Gly Gly Asn Thr Asp Tyr Asn Thr Pro Phe Thr
 50              55                  60

Ser Arg Leu Ser Ile Asn Lys Asp Asn Ser Lys Ser Gln Val Phe Phe
 65              70                  75                  80

Lys Met Asn Ser Leu Gln Ser Gln Asp Thr Ala Ile Tyr Tyr Cys Ala
                 85                  90                  95

Arg Ala Leu Thr Tyr Tyr Asp Tyr Glu Phe Ala Tyr Trp Gly Gln Gly
                100                 105                 110

Thr Leu Val Thr Val Ser Ala Ala Ser Thr Lys Gly Pro Ser Val Phe
                115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
                195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
                275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Asp Glu Leu Thr Lys Asn Gln Val Ser Leu Thr
                355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys Gly Gly Gly Ser Gly Gly Gly Ser Gly Ser Gly Gly Gly Ser
                450                 455                 460

Gly Gly Gly Gly Ser Gly Gly Gly Gln Val Gln Leu Gln Gln Ser Gly
```

```
                465                 470                 475                 480
Ala Glu Leu Ala Arg Pro Gly Ala Ser Val Lys Met Ser Cys Lys Ala
                485                 490                 495

Ser Gly Tyr Thr Phe Thr Arg Tyr Thr Met His Trp Val Lys Gln Arg
                500                 505                 510

Pro Gly Gln Gly Leu Glu Trp Ile Gly Tyr Ile Asn Pro Ser Arg Gly
                515                 520                 525

Tyr Thr Asn Tyr Asn Gln Lys Phe Lys Asp Lys Ala Thr Leu Thr Thr
                530                 535                 540

Asp Lys Ser Ser Ser Thr Ala Tyr Met Gln Leu Ser Ser Leu Thr Ser
545                 550                 555                 560

Glu Asp Ser Ala Val Tyr Tyr Cys Ala Arg Tyr Tyr Asp Asp His Tyr
                565                 570                 575

Cys Leu Asp Tyr Trp Gly Gln Gly Thr Thr Leu Thr Val Ser Ser Gly
                580                 585                 590

Gly Gly Gly Ser Gly Gly Gly Gly Ser Gly Gly Gly Gly Ser Gln Ile
                595                 600                 605

Val Leu Thr Gln Ser Pro Ala Ile Met Ser Ala Ser Pro Gly Glu Lys
                610                 615                 620

Val Thr Met Thr Cys Ser Ala Ser Ser Val Ser Tyr Met Asn Trp
625                 630                 635                 640

Tyr Gln Gln Lys Ser Gly Thr Ser Pro Lys Arg Trp Ile Tyr Asp Thr
                645                 650                 655

Ser Lys Leu Ala Ser Gly Val Pro Ala His Phe Arg Gly Ser Gly Ser
                660                 665                 670

Gly Thr Ser Tyr Ser Leu Thr Ile Ser Gly Met Glu Ala Glu Asp Ala
                675                 680                 685

Ala Thr Tyr Tyr Cys Gln Gln Trp Ser Ser Asn Pro Phe Thr Phe Gly
                690                 695                 700

Ser Gly Thr Lys Leu Glu Ile Asn Arg
705                 710
```

<210> SEQ ID NO 273
<211> LENGTH: 1434
<212> TYPE: DNA
<213> ORGANISM: Artificial Sequence
<220> FEATURE:
<223> OTHER INFORMATION: Anti-EGFR C225v5 - Anti-CD3 OKT3 Multispecific
      Antibody Light Chain

<400> SEQUENCE: 273
cagatcttgc tgacccagag cccggtgatt ctgagcgtga gcccgggcga acgtgtgagc      60
tttagctgcc gcgcgagcca gagcattggc accaacattc attggtatca gcagcgcacc     120
aacggcagcc cgcgcctgct gattaaatat gcgagcgaaa gcattagcgg cattccgagc     180
cgctttagcg gcagcggcag cggcaccgat tttaccctga gcattaacag cgtggaaagc     240
gaagatattg cggattatta ttgccagcag aacaacaact ggccgaccac ctttggcgcg     300
ggcaccaaac tggaactgaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gtggaggtgg atctggaggt     660

```
ggcggttcag gctctggcgg aggctcaggt ggtggaggat caggcggagg tcaggttcag    720
ctgcagcaga gcggtgcaga actggcacgt ccgggtgcaa gcgttaaaat gagctgtaaa    780
gcaagcggtt ataccttac ccgttatacc atgcattggg ttaaacagcg tccgggtcag     840
ggtctggaat ggattggtta tatcaatccg agccgtggtt ataccaacta caaccagaaa    900
ttcaaagata aagcaaccct gaccaccgat aaaagcagca gcaccgccta tatgcagctg    960
agcagcctga cctcagagga tagcgcagtt tattactgtg cacgctatta tgatgatcac   1020
tattgcctgg attattgggg tcagggcacc accctgaccg ttagcagcgg tggtggtggt   1080
agtggtggcg gtggttcagg cggtggcggt agccagattg ttctgaccca gagtccggca   1140
attatgagcg caagtccggg tgaaaaagtt accatgacct gtagcgccag cagcagcgtt   1200
agctatatga attggtatca gcagaaaagc ggcaccagcc cgaaacgttg gatttatgat   1260
accagcaaac tggcaagcgg tgttccggca catttcgtg gtagcggtag cggcacctca    1320
tatagcctga ccattagcgg tatggaagca gaagatgcag caacctatta ttgtcagcag   1380
tggtcaagca atccgtttac ctttggtagt ggcaccaaac tggaaattaa tcgt         1434
```

<210> SEQ ID NO 274
<211> LENGTH: 478
<212> TYPE: PRT
<213> ORGANISM: Artificial Sequence
<220> FEATURE:
<223> OTHER INFORMATION: Anti-EGFR C225v5 - Anti-CD3 OKT3 Multispecific
      Antibody Light Chain

<400> SEQUENCE: 274

```
Gln Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys Gly Gly Gly Ser Gly Gly Gly Gly Ser Gly
    210                 215                 220
```

```
Ser Gly Gly Gly Ser Gly Gly Gly Ser Gly Gly Gln Val Gln
225                 230                 235                 240

Leu Gln Gln Ser Gly Ala Glu Leu Ala Arg Pro Gly Ala Ser Val Lys
                245                 250                 255

Met Ser Cys Lys Ala Ser Gly Tyr Thr Phe Thr Arg Tyr Thr Met His
            260                 265                 270

Trp Val Lys Gln Arg Pro Gly Gln Gly Leu Glu Trp Ile Gly Tyr Ile
        275                 280                 285

Asn Pro Ser Arg Gly Tyr Thr Asn Tyr Asn Gln Lys Phe Lys Asp Lys
    290                 295                 300

Ala Thr Leu Thr Thr Asp Lys Ser Ser Ser Thr Ala Tyr Met Gln Leu
305                 310                 315                 320

Ser Ser Leu Thr Ser Glu Asp Ser Ala Val Tyr Tyr Cys Ala Arg Tyr
                325                 330                 335

Tyr Asp Asp His Tyr Cys Leu Asp Tyr Trp Gly Gln Gly Thr Thr Leu
            340                 345                 350

Thr Val Ser Ser Gly Gly Gly Gly Ser Gly Gly Gly Gly Ser Gly Gly
        355                 360                 365

Gly Gly Ser Gln Ile Val Leu Thr Gln Ser Pro Ala Ile Met Ser Ala
370                 375                 380

Ser Pro Gly Glu Lys Val Thr Met Thr Cys Ser Ala Ser Ser Ser Val
385                 390                 395                 400

Ser Tyr Met Asn Trp Tyr Gln Gln Lys Ser Gly Thr Ser Pro Lys Arg
                405                 410                 415

Trp Ile Tyr Asp Thr Ser Lys Leu Ala Ser Gly Val Pro Ala His Phe
            420                 425                 430

Arg Gly Ser Gly Ser Gly Thr Ser Tyr Ser Leu Thr Ile Ser Gly Met
        435                 440                 445

Glu Ala Glu Asp Ala Ala Thr Tyr Tyr Cys Gln Gln Trp Ser Ser Asn
    450                 455                 460

Pro Phe Thr Phe Gly Ser Gly Thr Lys Leu Glu Ile Asn Arg
465                 470                 475
```

<210> SEQ ID NO 275
<211> LENGTH: 1575
<212> TYPE: DNA
<213> ORGANISM: Artificial Sequence
<220> FEATURE:
<223> OTHER INFORMATION: Anti-EGFR - anti-CD3 Multispecific Activatable Antibody 3954-1204-C225v5-OKT3 Light Chain

<400> SEQUENCE: 275

```
caaggccagt ctggccagtg catctcacct cgtggttgtc cggacggccc atacgtcatg      60
tacggctcga gcggtggcag cggtggctct ggtggatccg gtctgagcgg ccgttccgat     120
aatcatggca gtagcggtac ccagatcttg ctgacccaga gcccggtgat tctgagcgtg     180
agcccgggcg aacgtgtgag ctttagctgc cgcgcgagcc agagcattgg caccaacatt     240
cattggtatc agcagcgcac caacggcagc ccgcgcctgc tgattaaata tgcgagcgaa     300
agcattagcg gcattccgag ccgctttagc ggcagcggca cggcaccga ttttaccctg      360 agcattaaca gcgtggaaag cgaagatatt gcggattatt attgccagca gaacaacaac     420
tggccgacca cctttggcgc gggcaccaaa ctggaactga acgtacggt ggctgcacca      480 tctgtcttca tcttcccgcc atctgatgag cagttgaaat ctggaactgc ctctgttgtg     540
tgcctgctga ataacttcta tcccagagag gccaaagtac agtggaaggt ggataacgcc     600
```

```
ctccaatcgg gtaactccca ggagagtgtc acagagcagg acagcaagga cagcacctac    660
agcctcagca gcaccctgac gctgagcaaa gcagactacg agaaacacaa agtctacgcc    720
tgcgaagtca cccatcaggg cctgagctcg cccgtcacaa agagcttcaa caggggagag    780
tgtggaggtg gatctggagg tggcggttca ggctctggcg gaggctcagg tggtggagga    840
tcaggcggag gtcaggttca gctgcagcag agcggtgcag aactggcacg tccgggtgca    900
agcgttaaaa tgagctgtaa agcaagcggt tatacctttta cccgttatac catgcattgg    960
gttaaacagc gtccgggtca gggtctggaa tggattggtt atatcaatcc gagccgtggt   1020
tataccaact acaaccagaa attcaaagat aaagcaaccc tgaccaccga taaaagcagc   1080
agcaccgcct atatgcagct gagcagcctg acctcagagg atagcgcagt ttattactgt   1140
gcacgctatt atgatgatca ctattgcctg gattattggg gtcagggcac cacccctgacc   1200 gttagcagcg tggtggtgg tagtggtggc ggtggttcag gcggtggcgg tagccagatt   1260
gttctgaccc agagtccggc aattatgagc gcaagtccgg gtgaaaaagt taccatgacc   1320
tgtagcgcca gcagcagcgt tagctatatg aattggtatc agcagaaaag cggcaccagc   1380
ccgaaacgtt ggatttatga taccagcaaa ctggcaagcg gtgttccggc acattttcgt   1440
ggtagcggta gcggcaccctc atatagcctg accattagcg gtatggaagc agaagatgca   1500
gcaacctatt attgtcagca gtggtcaagc aatccgttta cctttggtag tggcaccaaa   1560
ctggaaatta atcgt                                                    1575
```

<210> SEQ ID NO 276
<211> LENGTH: 525
<212> TYPE: PRT
<213> ORGANISM: Artificial Sequence
<220> FEATURE:
<223> OTHER INFORMATION: Anti-EGFR - anti-CD3 Multispecific Activatable
      Antibody 3954-1204-C225v5-OKT3 Light Chain

<400> SEQUENCE: 276

```
Gln Gly Gln Ser Gly Gln Cys Ile Ser Pro Arg Gly Cys Pro Asp Gly
 1               5                  10                  15

Pro Tyr Val Met Tyr Gly Ser Ser Gly Gly Ser Gly Gly Ser Gly Gly
             20                  25                  30

Ser Gly Leu Ser Gly Arg Ser Asp Asn His Gly Ser Ser Gly Thr Gln
         35                  40                  45

Ile Leu Leu Thr Gln Ser Pro Val Ile Leu Ser Val Ser Pro Gly Glu
     50                  55                  60

Arg Val Ser Phe Ser Cys Arg Ala Ser Gln Ser Ile Gly Thr Asn Ile
 65                  70                  75                  80

His Trp Tyr Gln Gln Arg Thr Asn Gly Ser Pro Arg Leu Leu Ile Lys
                 85                  90                  95

Tyr Ala Ser Glu Ser Ile Ser Gly Ile Pro Ser Arg Phe Ser Gly Ser
            100                 105                 110

Gly Ser Gly Thr Asp Phe Thr Leu Ser Ile Asn Ser Val Glu Ser Glu
        115                 120                 125

Asp Ile Ala Asp Tyr Tyr Cys Gln Gln Asn Asn Asn Trp Pro Thr Thr
    130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
                165                 170                 175
```

```
Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
        210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys Gly Gly Gly Ser Gly Gly Gly Gly Ser Gly Ser
            260                 265                 270

Gly Gly Gly Ser Gly Gly Gly Ser Gly Gly Gln Val Gln Leu
        275                 280                 285

Gln Gln Ser Gly Ala Glu Leu Ala Arg Pro Gly Ala Ser Val Lys Met
        290                 295                 300

Ser Cys Lys Ala Ser Gly Tyr Thr Phe Thr Arg Tyr Thr Met His Trp
305                 310                 315                 320

Val Lys Gln Arg Pro Gly Gln Gly Leu Glu Trp Ile Gly Tyr Ile Asn
                325                 330                 335

Pro Ser Arg Gly Tyr Thr Asn Tyr Asn Gln Lys Phe Lys Asp Lys Ala
            340                 345                 350

Thr Leu Thr Thr Asp Lys Ser Ser Ser Thr Ala Tyr Met Gln Leu Ser
        355                 360                 365

Ser Leu Thr Ser Glu Asp Ser Ala Val Tyr Tyr Cys Ala Arg Tyr Tyr
        370                 375                 380

Asp Asp His Tyr Cys Leu Asp Tyr Trp Gly Gln Gly Thr Thr Leu Thr
385                 390                 395                 400

Val Ser Ser Gly Gly Gly Gly Ser Gly Gly Gly Ser Gly Gly Gly
                405                 410                 415

Gly Ser Gln Ile Val Leu Thr Gln Ser Pro Ala Ile Met Ser Ala Ser
            420                 425                 430

Pro Gly Glu Lys Val Thr Met Thr Cys Ser Ala Ser Ser Ser Val Ser
        435                 440                 445

Tyr Met Asn Trp Tyr Gln Gln Lys Ser Gly Thr Ser Pro Lys Arg Trp
        450                 455                 460

Ile Tyr Asp Thr Ser Lys Leu Ala Ser Gly Val Pro Ala His Phe Arg
465                 470                 475                 480

Gly Ser Gly Ser Gly Thr Ser Tyr Ser Leu Thr Ile Ser Gly Met Glu
                485                 490                 495

Ala Glu Asp Ala Ala Thr Tyr Tyr Cys Gln Gln Trp Ser Ser Asn Pro
            500                 505                 510

Phe Thr Phe Gly Ser Gly Thr Lys Leu Glu Ile Asn Arg
        515                 520                 525

<210> SEQ ID NO 277
<211> LENGTH: 2166
<212> TYPE: DNA
<213> ORGANISM: Artificial Sequence
<220> FEATURE:
<223> OTHER INFORMATION: Anti-EGFR C225v5-Anti-CTLA-4 Multispecific
      Antibody Heavy Chain

<400> SEQUENCE: 277
caggtgcagc tgaaacagag cggcccgggc ctggtgcagc cgagccagag cctgagcatt      60
```

```
acctgcaccg tgagcggctt tagcctgacc aactatggcg tgcattgggt gcgccagagc      120
ccgggcaaag gcctggaatg gctgggcgtg atttggagcg gcggcaacac cgattataac      180
accccgttta ccagccgcct gagcattaac aaagataaca gcaaaagcca ggtgttttttt     240 aaaatgaaca gcctgcaaag ccaggatacc gcgatttatt attgcgcgcg cgcgctgacc      300
tattatgatt atgaatttgc gtattggggc cagggcaccc tggtgaccgt gagcgcggct      360
agcaccaagg gcccatcggt cttccccctg gcaccctcct ccaagagcac ctctgggggc      420
acagcggccc tgggctgcct ggtcaaggac tacttccccg aaccggtgac ggtgtcgtgg      480
aactcaggcg ccctgaccag cggcgtgcac accttcccgg ctgtcctaca gtcctcagga      540
ctctactccc tcagcagcgt ggtgaccgtg ccctccagca gcttgggcac ccagacctac      600
atctgcaacg tgaatcacaa gcccagcaac accaaggtgg acaagaaagt tgagcccaaa      660
tcttgtgaca aaactcacac atgcccaccg tgcccagcac ctgaactcct ggggggaccg      720
tcagtcttcc tcttcccccc aaaacccaag gacaccctca tgatctcccg gacccctgag      780
gtcacatgcg tggtggtgga cgtgagccac gaagaccctg aggtcaagtt caactggtac      840
gtggacggcg tggaggtgca taatgccaag acaaagccgc gggaggagca gtacaacagc      900
acgtaccgtg tggtcagcgt cctcaccgtc ctgcaccagg actggctgaa tggcaaggag      960
tacaagtgca aggtctccaa caaagccctc ccagccccca tcgagaaaac catctccaaa     1020
gccaaagggc agccccgaga accacaggtg tacaccctgc ccccatcccg ggatgaactg     1080
accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctacagc aagctcaccg tggacaagag caggtggcag     1260
caggggaacg tcttctcatg ctccgtgatg catgaggctc tgcacaacca ctacacgcag     1320
aagagcctct ccctgtctcc gggtaaagga ggtggatctg aggtggcgg ttcaggctct     1380 ggcggaggct caggtggtgg aggatcaggc ggaggtgaaa ttgtgttgac acagtctcca     1440
ggcaccctgt ctttgtctcc aggggaaaga gccaccctct cctgcagggc cagtcagagt     1500
gttagcagca gctacttagc ctggtaccag cagaaacctg gccaggctcc caggctcctc     1560
atctatggtg catccagcag ggccactggc atcccagaca ggttcagtgg cagtgggtct     1620
gggacagact tcactctcac catcagcaga ctggagcctg aagattttgc agtgtattac     1680
tgtcagcagt atggtagctc accgctcact ttcggcggag ggaccaaggt ggaaatcaaa     1740
cgttccggag gtcgaccat aacttcgtat aatgtatact atacgaagtt atcctcgagc     1800
ggtacccagg tgcagctggt gcagactggg ggaggcgtgg tccagcctgg gaggtccctg     1860
agactctcct gtgcagcctc tggatccacc tttagcagct atgccatgag ctgggtccgc     1920
caggctccag ggaaggggct ggagtgggtc tcagctatta gtggtagtgg tggtagcaca     1980
tactacgcag actccgtgaa gggccggttc accatctcca gagacaattc caagaacacg     2040
ctgtatctgc aaatgaacag cctgagagcc gaggacacgg ccgtatatta ctgtgcgaca     2100
aactcccttt actggtactt cgatctctgg ggccgtggca ccctggtcac tgtctcttca     2160
gctagc                                                                2166
```

<210> SEQ ID NO 278
<211> LENGTH: 722
<212> TYPE: PRT
<213> ORGANISM: Artificial Sequence
<220> FEATURE:
<223> OTHER INFORMATION: Anti-EGFR C225v5-Anti-CTLA-4 Multispecific Antibody Heavy Chain

<400> SEQUENCE: 278

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys Gly Gly Gly Ser Gly Gly Gly Ser Gly Ser Gly Gly Gly Gly Ser
    450                 455                 460
Gly Gly Gly Gly Ser Gly Gly Glu Ile Val Leu Thr Gln Ser Pro
465                 470                 475                 480
Gly Thr Leu Ser Leu Ser Pro Gly Glu Arg Ala Thr Leu Ser Cys Arg
                485                 490                 495
Ala Ser Gln Ser Val Ser Ser Ser Tyr Leu Ala Trp Tyr Gln Gln Lys
            500                 505                 510
Pro Gly Gln Ala Pro Arg Leu Leu Ile Tyr Gly Ala Ser Ser Arg Ala
        515                 520                 525
Thr Gly Ile Pro Asp Arg Phe Ser Gly Ser Gly Ser Gly Thr Asp Phe
    530                 535                 540
Thr Leu Thr Ile Ser Arg Leu Glu Pro Glu Asp Phe Ala Val Tyr Tyr
545                 550                 555                 560
Cys Gln Gln Tyr Gly Ser Ser Pro Leu Thr Phe Gly Gly Gly Thr Lys
                565                 570                 575
Val Glu Ile Lys Arg Ser Gly Gly Ser Thr Ile Thr Ser Tyr Asn Val
            580                 585                 590
Tyr Tyr Thr Lys Leu Ser Ser Ser Gly Thr Gln Val Gln Leu Val Gln
        595                 600                 605
Thr Gly Gly Gly Val Val Gln Pro Gly Arg Ser Leu Arg Leu Ser Cys
    610                 615                 620
Ala Ala Ser Gly Ser Thr Phe Ser Ser Tyr Ala Met Ser Trp Val Arg
625                 630                 635                 640
Gln Ala Pro Gly Lys Gly Leu Glu Trp Val Ser Ala Ile Ser Gly Ser
                645                 650                 655
Gly Gly Ser Thr Tyr Tyr Ala Asp Ser Val Lys Gly Arg Phe Thr Ile
            660                 665                 670
Ser Arg Asp Asn Ser Lys Asn Thr Leu Tyr Leu Gln Met Asn Ser Leu
        675                 680                 685
Arg Ala Glu Asp Thr Ala Val Tyr Tyr Cys Ala Thr Asn Ser Leu Tyr
    690                 695                 700
Trp Tyr Phe Asp Leu Trp Gly Arg Gly Thr Leu Val Thr Val Ser Ser
705                 710                 715                 720
Ala Ser

<210> SEQ ID NO 279
<211> LENGTH: 1461
<212> TYPE: DNA
<213> ORGANISM: Artificial Sequence
<220> FEATURE:
<223> OTHER INFORMATION: Anti-EGFR C225v5-Anti-CTLA-4 Multispecific
      Antibody Light Chain

<400> SEQUENCE: 279
cagatcttgc tgacccagag cccggtgatt ctgagcgtga gcccgggcga acgtgtgagc      60
tttagctgcc gcgcgagcca gagcattggc accaacattc attggtatca gcagcgcacc     120
aacggcagcc cgcgcctgct gattaaatat gcgagcgaaa gcattagcgg cattccgagc     180
```

```
cgctttagcg gcagcggcag cggcaccgat tttaccctga gcattaacag cgtggaaagc    240
gaagatattg cggattatta ttgccagcag aacaacaact ggccgaccac ctttggcgcg    300
ggcaccaaac tggaactgaa acgtacggtg gctgcaccat ctgtcttcat cttcccgcca    360
tctgatgagc agttgaaatc tggaactgcc tctgttgtgt gcctgctgaa taacttctat    420
cccagagagg ccaaagtaca gtggaaggtg ataacgccc tccaatcggg taactcccag    480
gagagtgtca cagagcagga cagcaaggac agcacctaca gcctcagcag caccctgacg    540
ctgagcaaag cagactacga gaaacacaaa gtctacgcct gcgaagtcac ccatcagggc    600
ctgagctcgc ccgtcacaaa gagcttcaac aggggagagt gtggaggtgg atctggaggt    660
ggcggttcag gctctggcgg aggctcaggt ggtggaggat caggcggagg tgaaattgtg    720
ttgacacagt ctccaggcac cctgtctttg tctccagggg aaagagccac cctctcctgc    780
agggccagtc agagtgttag cagcagctac ttagcctggt accagcagaa acctggccag    840
gctcccaggc tcctcatcta tggtgcatcc agcagggcca ctggcatccc agacaggttc    900
agtggcagtg ggtctgggac agacttcact ctcaccatca gcagactgga gcctgaagat    960
tttgcagtgt attactgtca gcagtatggt agctcaccgc tcactttcgg cggagggacc   1020
aaggtggaaa tcaaacgttc cggagggtcg accataactt cgtataatgt atactatacg   1080
aagttatcct cgagcggtac ccaggtgcag ctggtgcaga ctgggggagg cgtggtccag   1140
cctgggaggt ccctgagact ctcctgtgca gcctctggat ccacctttag cagctatgcc   1200
atgagctggg tccgccaggc tccagggaag gggctggagt gggtctcagc tattagtggt   1260
agtggtggta gcacatacta cgcagactcc gtgaagggcc ggttcaccat ctccagagac   1320
aattccaaga acacgctgta tctgcaaatg aacagcctga gagccgagga cacggccgta   1380
tattactgtg cgacaaactc cctttactgg tacttcgatc tctggggccg tggcaccctg   1440
gtcactgtct cttcagctag c                                              1461
```

<210> SEQ ID NO 280
<211> LENGTH: 487
<212> TYPE: PRT
<213> ORGANISM: Artificial Sequence
<220> FEATURE:
<223> OTHER INFORMATION: Anti-EGFR C225v5-Anti-CTLA-4 Multispecific
      Antibody Light Chain

<400> SEQUENCE: 280

```
Gln Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125
```

Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Gly Gly Gly Ser Gly Gly Gly Ser Gly
    210                 215                 220
Ser Gly Gly Gly Ser Gly Gly Gly Ser Gly Gly Gly Glu Ile Val
225                 230                 235                 240
Leu Thr Gln Ser Pro Gly Thr Leu Ser Leu Ser Pro Gly Glu Arg Ala
                245                 250                 255
Thr Leu Ser Cys Arg Ala Ser Gln Ser Val Ser Ser Ser Tyr Leu Ala
            260                 265                 270
Trp Tyr Gln Gln Lys Pro Gly Gln Ala Pro Arg Leu Leu Ile Tyr Gly
        275                 280                 285
Ala Ser Ser Arg Ala Thr Gly Ile Pro Asp Arg Phe Ser Gly Ser Gly
    290                 295                 300
Ser Gly Thr Asp Phe Thr Leu Thr Ile Ser Arg Leu Glu Pro Glu Asp
305                 310                 315                 320
Phe Ala Val Tyr Tyr Cys Gln Gln Tyr Gly Ser Ser Pro Leu Thr Phe
                325                 330                 335
Gly Gly Gly Thr Lys Val Glu Ile Lys Arg Ser Gly Gly Ser Thr Ile
            340                 345                 350
Thr Ser Tyr Asn Val Tyr Tyr Thr Lys Leu Ser Ser Ser Gly Thr Gln
        355                 360                 365
Val Gln Leu Val Gln Thr Gly Gly Val Val Gln Pro Gly Arg Ser
    370                 375                 380
Leu Arg Leu Ser Cys Ala Ala Ser Gly Ser Thr Phe Ser Ser Tyr Ala
385                 390                 395                 400
Met Ser Trp Val Arg Gln Ala Pro Gly Lys Gly Leu Glu Trp Val Ser
                405                 410                 415
Ala Ile Ser Gly Ser Gly Gly Ser Thr Tyr Tyr Ala Asp Ser Val Lys
            420                 425                 430
Gly Arg Phe Thr Ile Ser Arg Asp Asn Ser Lys Asn Thr Leu Tyr Leu
        435                 440                 445
Gln Met Asn Ser Leu Arg Ala Glu Asp Thr Ala Val Tyr Tyr Cys Ala
    450                 455                 460
Thr Asn Ser Leu Tyr Trp Tyr Phe Asp Leu Trp Gly Arg Gly Thr Leu
465                 470                 475                 480
Val Thr Val Ser Ser Ala Ser
                485

<210> SEQ ID NO 281
<211> LENGTH: 1602
<212> TYPE: DNA
<213> ORGANISM: Artificial Sequence
<220> FEATURE:
<223> OTHER INFORMATION: Anti-EGFR - Anti-CTLA-4 Multispecific
      Activatable Antibody 3954-1204-C225v5-CTLA-4 Light Chain

<400> SEQUENCE: 281

```
caaggccagt ctggccagtg catctcacct cgtggttgtc cggacggccc atacgtcatg    60
tacggctcga gcggtggcag cggtggctct ggtggatccg gtctgagcgg ccgttccgat   120
aatcatggca gtagcggtac ccagatcttg ctgacccaga gcccggtgat tctgagcgtg   180
agcccgggcg aacgtgtgag ctttagctgc cgcgcgagcc agagcattgg caccaacatt   240
cattggtatc agcagcgcac caacggcagc ccgcgcctgc tgattaaata tgcgagcgaa   300
agcattagcg gcattccgag ccgctttagc ggcagcggca cggcaccga ttttaccctg   360 agcattaaca gcgtggaaag cgaagatatt gcggattatt attgccagca gaacaacaac   420
tggccgacca cctttggcgc gggcaccaaa ctggaactga acgtacggt ggctgcacca   480 tctgtcttca tcttcccgcc atctgatgag cagttgaaat ctggaactgc ctctgttgtg   540
tgcctgctga ataacttcta tcccagagag gccaaagtac agtggaaggt ggataacgcc   600
ctccaatcgg gtaactccca ggagagtgtc acagagcagg acagcaagga cagcacctac   660
agcctcagca gcaccctgac gctgagcaaa gcagactacg agaaacacaa agtctacgcc   720
tgcgaagtca cccatcaggg cctgagctcg cccgtcacaa agagcttcaa caggggagag   780
tgtggaggtg gatctggagg tggcggttca ggctctggcg gaggctcagg tggtggagga   840
tcaggcggag gtgaaattgt gttgacacag tctccaggca ccctgtcttt gtctccaggg   900
gaaagagcca ccctctcctg cagggccagt cagagtgtta gcagcagcta cttagcctgg   960
taccagcaga aacctggcca ggctcccagg ctcctcatct atggtgcatc cagcagggcc  1020
actggcatcc cagacaggtt cagtggcagt gggtctggga cagacttcac tctcaccatc  1080
agcagactgg agcctgaaga ttttgcagtg tattactgtc agcagtatgg tagctcaccg  1140
ctcactttcg gcggagggac caaggtggaa atcaaacgtt ccggagggtc gaccataact  1200
tcgtataatg tatactatac gaagttatcc tcgagcggta cccaggtgca gctggtgcag  1260 actggggag cgtggtcca gcctgggagg tccctgagac tctcctgtgc agcctctgga  1320 tccacctta gcagctatgc catgagctgg gtccgccagg ctccagggaa ggggctggag  1380
tgggtctcag ctattagtgg tagtggtggt agcacatact acgcagactc cgtgaagggc  1440
cggttcacca tctccagaga caattccaag aacacgctgt atctgcaaat gaacagcctg  1500
agagccgagg acacggccgt atattactgt gcgacaaact ccctttactg gtacttcgat  1560
ctctggggcc gtggcaccct ggtcactgtc tcttcagcta gc                     1602
```

<210> SEQ ID NO 282
<211> LENGTH: 534
<212> TYPE: PRT
<213> ORGANISM: Artificial Sequence
<220> FEATURE:
<223> OTHER INFORMATION: Anti-EGFR - Anti-CTLA-4 Multispecific
      Activatable Antibody 3954-1204-C225v5-CTLA-4 Light Chain

<400> SEQUENCE: 282

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Leu Ser Gly Arg Ser Asp Asn His Gly Ser Ser Gly Thr Gln
        35                  40                  45

Ile Leu Leu Thr Gln Ser Pro Val Ile Leu Ser Val Ser Pro Gly Glu
    50                  55                  60

Arg Val Ser Phe Ser Cys Arg Ala Ser Gln Ser Ile Gly Thr Asn Ile

```
                65                  70                  75                  80
His Trp Tyr Gln Gln Arg Thr Asn Gly Ser Pro Arg Leu Leu Ile Lys
                    85                  90                  95

Tyr Ala Ser Glu Ser Ile Ser Gly Ile Pro Ser Arg Phe Ser Gly Ser
                100                 105                 110

Gly Ser Gly Thr Asp Phe Thr Leu Ser Ile Asn Ser Val Glu Ser Glu
                115                 120                 125

Asp Ile Ala Asp Tyr Tyr Cys Gln Gln Asn Asn Asn Trp Pro Thr Thr
130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
                180                 185                 190

Val Gln Trp Lys Val Asp Asn Ala Leu Gln Ser Gly Asn Ser Gln Glu
                195                 200                 205

Ser Val Thr Glu Gln Asp Ser Lys Asp Ser Thr Tyr Ser Leu Ser Ser
210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys Gly Gly Gly Ser Gly Gly Gly Ser Gly Ser
                260                 265                 270

Gly Gly Gly Ser Gly Gly Gly Ser Gly Gly Gly Glu Ile Val Leu
                275                 280                 285

Thr Gln Ser Pro Gly Thr Leu Ser Leu Ser Pro Gly Glu Arg Ala Thr
                290                 295                 300

Leu Ser Cys Arg Ala Ser Gln Ser Val Ser Ser Ser Tyr Leu Ala Trp
305                 310                 315                 320

Tyr Gln Gln Lys Pro Gly Gln Ala Pro Arg Leu Leu Ile Tyr Gly Ala
                325                 330                 335

Ser Ser Arg Ala Thr Gly Ile Pro Asp Arg Phe Ser Gly Ser Gly Ser
                340                 345                 350

Gly Thr Asp Phe Thr Leu Thr Ile Ser Arg Leu Glu Pro Glu Asp Phe
                355                 360                 365

Ala Val Tyr Tyr Cys Gln Gln Tyr Gly Ser Ser Pro Leu Thr Phe Gly
                370                 375                 380

Gly Gly Thr Lys Val Glu Ile Lys Arg Ser Gly Gly Ser Thr Ile Thr
385                 390                 395                 400

Ser Tyr Asn Val Tyr Tyr Thr Lys Leu Ser Ser Ser Gly Thr Gln Val
                405                 410                 415

Gln Leu Val Gln Thr Gly Gly Val Val Gln Pro Gly Arg Ser Leu
                420                 425                 430

Arg Leu Ser Cys Ala Ala Ser Gly Ser Thr Phe Ser Ser Tyr Ala Met
                435                 440                 445

Ser Trp Val Arg Gln Ala Pro Gly Lys Gly Leu Glu Trp Val Ser Ala
                450                 455                 460

Ile Ser Gly Ser Gly Gly Ser Thr Tyr Tyr Ala Asp Ser Val Lys Gly
465                 470                 475                 480

Arg Phe Thr Ile Ser Arg Asp Asn Ser Lys Asn Thr Leu Tyr Leu Gln
                485                 490                 495
```

```
Met Asn Ser Leu Arg Ala Glu Asp Thr Ala Val Tyr Tyr Cys Ala Thr
                500                 505                 510

Asn Ser Leu Tyr Trp Tyr Phe Asp Leu Trp Gly Arg Gly Thr Leu Val
        515                 520                 525

Thr Val Ser Ser Ala Ser
    530

<210> SEQ ID NO 283
<211> LENGTH: 18
<212> TYPE: DNA
<213> ORGANISM: Artificial Sequence
<220> FEATURE:
<223> OTHER INFORMATION: spacer peptide coding sequence

<400> SEQUENCE: 283
caaggccagt ctggccag                                                       18

<210> SEQ ID NO 284
<211> LENGTH: 45
<212> TYPE: DNA
<213> ORGANISM: Artificial Sequence
<220> FEATURE:
<223> OTHER INFORMATION: masking peptide coding sequence

<400> SEQUENCE: 284
tgcatctcac ctcgtggttg tccggacggc ccatacgtca tgtac                         45

<210> SEQ ID NO 285
<211> LENGTH: 39
<212> TYPE: DNA
<213> ORGANISM: Artificial Sequence
<220> FEATURE:
<223> OTHER INFORMATION: linker peptide coding sequence

<400> SEQUENCE: 285
ggctcgagcg gtggcagcgg tggctctggt ggatccggt                                39

<210> SEQ ID NO 286
<211> LENGTH: 24
<212> TYPE: DNA
<213> ORGANISM: Artificial Sequence
<220> FEATURE:
<223> OTHER INFORMATION: 1204 Substrate coding sequence

<400> SEQUENCE: 286
ctgagcggcc gttccgataa tcat                                                24

<210> SEQ ID NO 287
<211> LENGTH: 15
<212> TYPE: DNA
<213> ORGANISM: Artificial Sequence
<220> FEATURE:
<223> OTHER INFORMATION: linker peptide coding sequence

<400> SEQUENCE: 287
ggcagtagcg gtacc                                                          15

<210> SEQ ID NO 288
<211> LENGTH: 13
<212> TYPE: PRT
<213> ORGANISM: Artificial Sequence
<220> FEATURE:
<223> OTHER INFORMATION: linker peptide

<400> SEQUENCE: 288
```

```
Gly Ser Ser Gly Gly Ser Gly Gly Ser Gly
1               5                   10

<210> SEQ ID NO 289
<211> LENGTH: 5
<212> TYPE: PRT
<213> ORGANISM: Artificial Sequence
<220> FEATURE:
<223> OTHER INFORMATION: linker peptide

<400> SEQUENCE: 289

Gly Ser Ser Gly Thr
1               5

<210> SEQ ID NO 290
<211> LENGTH: 264
<212> TYPE: PRT
<213> ORGANISM: Artificial Sequence
<220> FEATURE:
<223> OTHER INFORMATION: Antibody OKT3m scFv with long linker

<400> SEQUENCE: 290

Gly Gly Gly Ser Gly Gly Gly Ser Gly Ser Gly Gly Ser Gly
1               5                   10                  15

Gly Gly Gly Ser Gly Gly Gly Gln Val Gln Leu Gln Gln Ser Gly Ala
                20                  25                  30

Glu Leu Ala Arg Pro Gly Ala Ser Val Lys Met Ser Cys Lys Ala Ser
            35                  40                  45

Gly Tyr Thr Phe Thr Arg Tyr Thr Met His Trp Val Lys Gln Arg Pro
    50                  55                  60

Gly Gln Gly Leu Glu Trp Ile Gly Tyr Ile Asn Pro Ser Arg Gly Tyr
65                  70                  75                  80

Thr Asn Tyr Asn Gln Lys Phe Lys Asp Lys Ala Thr Leu Thr Thr Asp
                85                  90                  95

Lys Ser Ser Ser Thr Ala Tyr Met Gln Leu Ser Ser Leu Thr Ser Glu
            100                 105                 110

Asp Ser Ala Val Tyr Tyr Cys Ala Arg Tyr Tyr Asp Asp His Tyr Ser
        115                 120                 125

Leu Asp Tyr Trp Gly Gln Gly Thr Thr Leu Thr Val Ser Ser Gly Gly
    130                 135                 140

Gly Gly Ser Gly Gly Gly Gly Ser Gly Gly Gly Ser Gln Ile Val
145                 150                 155                 160

Leu Thr Gln Ser Pro Ala Ile Met Ser Ala Ser Pro Gly Glu Lys Val
                165                 170                 175

Thr Met Thr Cys Ser Ala Ser Ser Ser Val Ser Tyr Met Asn Trp Tyr
            180                 185                 190

Gln Gln Lys Ser Gly Thr Ser Pro Lys Arg Trp Ile Tyr Asp Thr Ser
        195                 200                 205

Lys Leu Ala Ser Gly Val Pro Ala His Phe Arg Gly Ser Gly Ser Gly
    210                 215                 220

Thr Ser Tyr Ser Leu Thr Ile Ser Gly Met Glu Ala Glu Asp Ala Ala
225                 230                 235                 240

Thr Tyr Tyr Cys Gln Gln Trp Ser Ser Asn Pro Phe Thr Phe Gly Ser
                245                 250                 255

Gly Thr Lys Leu Glu Ile Asn Arg
            260
```

<210> SEQ ID NO 291
<211> LENGTH: 795
<212> TYPE: DNA
<213> ORGANISM: Artificial Sequence
<220> FEATURE:
<223> OTHER INFORMATION: Antibody OKT3m scFv with long linker

<400> SEQUENCE: 291

```
ggaggtggat ctggaggtgg cggttcaggc tctggcggag gctcaggtgg tggaggatca    60
ggcggaggtc aggttcagct gcagcagagc ggtgcagaac tggcacgtcc gggtgcaagc   120
gttaaaatga gctgtaaagc aagcggttat acctttaccc gttataccat gcattgggtt   180
aaacagcgtc cgggtcaggg tctggaatgg attggttata tcaatccgag ccgtggttat   240
accaactaca accagaaatt caaagataaa gcaaccctga ccaccgataa aagcagcagc   300
accgcctata tgcagctgag cagcctgacc tcagaggata cgcagtttta ttactgtgca   360
cgctattatg atgatcacta tagcctggat tattggggtc agggcaccac cctgaccgtt   420
agcagcggtg gtggtggtag tggtggcggt ggttcaggcg gtggcggtag ccagattgtt   480
ctgacccaga gtccggcaat tatgagcgca agtccgggtg aaaaagttac catgacctgt   540
agcgccagca gcagcgttag ctatatgaat tggtatcagc agaaaagcgg caccagcccg   600
aaacgttgga tttatgatac cagcaaactg gcaagcggtg ttccggcaca ttttcgtggt   660
agcggtagcg gcacctcata tagcctgacc attagcggta tggaagcaga agatgcagca   720
acctattatt gtcagcagtg gtcaagcaat ccgtttacct ttggtagtgg caccaaactg   780
gaaattaatc gttga                                                    795
```

<210> SEQ ID NO 292
<211> LENGTH: 246
<212> TYPE: PRT
<213> ORGANISM: Artificial Sequence
<220> FEATURE:
<223> OTHER INFORMATION: Antibody OKT3m scFv with short linker

<400> SEQUENCE: 292

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
                20                  25                  30

Thr Met His Trp Val Lys Gln Arg Pro Gly Gln Gly Leu Glu Trp Ile
            35                  40                  45

Gly Tyr Ile Asn Pro Ser Arg Gly Tyr Thr Asn Tyr Asn Gln Lys Phe
        50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
                100                 105                 110

Thr Thr Leu Thr Val Ser Ser Gly Gly Gly Ser Gly Gly Gly Gly
            115                 120                 125

Ser Gly Gly Gly Gly Ser Gln Ile Val Leu Thr Gln Ser Pro Ala Ile
        130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175
```

```
Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
        195                 200                 205

Ser Gly Met Glu Ala Glu Asp Ala Ala Thr Tyr Tyr Cys Gln Gln Trp
    210                 215                 220

Ser Ser Asn Pro Phe Thr Phe Gly Ser Gly Thr Lys Leu Glu Ile Asn
225             230                 235                 240

Arg Gly Gly Gly Gly Ser
            245
```

<210> SEQ ID NO 293
<211> LENGTH: 738
<212> TYPE: DNA
<213> ORGANISM: Artificial Sequence
<220> FEATURE:
<223> OTHER INFORMATION: Antibody OKT3m scFv with short linker

<400> SEQUENCE: 293

```
caggttcagc tgcagcagag cggtgcagaa ctggcacgtc cgggtgcaag cgttaaaatg    60
agctgtaaag caagcggtta cctttacc cgttatacca tgcattgggt taaacagcgt   120
ccgggtcagg gtctggaatg gattggttat atcaatccga gccgtggtta taccaactac   180
aaccagaaat tcaaagataa agcaaccctg accaccgata aaagcagcag caccgcctat   240
atgcagctga gcagcctgac ctcagaggat agcgcagttt attactgtgc acgctattat   300
gatgatcact atagcctgga ttattggggt cagggcacca ccctgaccgt tagcagcggt   360
ggtggtggta gtggtggcgg tggttcaggc ggtggcggta gccagattgt tctgacccag   420
agtccggcaa ttatgagcgc aagtccgggt gaaaaagtta ccatgacctg tagcgccagc   480
agcagcgtta gctatatgaa ttggtatcag cagaaaagcg gcaccagccc gaaacgttgg   540
atttatgata ccagcaaact ggcaagcggt gttccggcac attttcgtgg tagcggtagc   600
ggcacctcat atagcctgac cattagcggt atggaagcag aagatgcagc aacctattat   660
tgtcagcagt ggtcaagcaa tccgttacc tttggtagtg gcaccaaact ggaaattaat   720
cgtggaggtg gtggatcc                                                 738
```

<210> SEQ ID NO 294
<211> LENGTH: 695
<212> TYPE: PRT
<213> ORGANISM: Artificial Sequence
<220> FEATURE:
<223> OTHER INFORMATION: Multispecific antibody C225v5-OKT3m-H-N heavy
      chain

<400> SEQUENCE: 294

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
```

-continued

```
                85                  90                  95
Ala Arg Tyr Tyr Asp Asp His Tyr Ser Leu Asp Tyr Trp Gly Gln Gly
            100                 105                 110

Thr Thr Leu Thr Val Ser Ser Gly Gly Gly Ser Gly Gly Gly Gly
            115                 120                 125

Ser Gly Gly Gly Ser Gln Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190

Ala His Phe Arg Gly Ser Gly Ser Gly Thr Ser Tyr Ser Leu Thr Ile
            195                 200                 205

Ser Gly Met Glu Ala Glu Asp Ala Ala Thr Tyr Tyr Cys Gln Gln Trp
    210                 215                 220

Ser Ser Asn Pro Phe Thr Phe Gly Ser Gly Thr Lys Leu Glu Ile Asn
225                 230                 235                 240

Arg Gly Gly Gly Ser Gln Val Gln Leu Lys Gln Ser Gly Pro Gly
                245                 250                 255

Leu Val Gln Pro Ser Gln Ser Leu Ser Ile Thr Cys Thr Val Ser Gly
            260                 265                 270

Phe Ser Leu Thr Asn Tyr Gly Val His Trp Val Arg Gln Ser Pro Gly
            275                 280                 285

Lys Gly Leu Glu Trp Leu Gly Val Ile Trp Ser Gly Gly Asn Thr Asp
    290                 295                 300

Tyr Asn Thr Pro Phe Thr Ser Arg Leu Ser Ile Asn Lys Asp Asn Ser
305                 310                 315                 320

Lys Ser Gln Val Phe Phe Lys Met Asn Ser Leu Gln Ser Gln Asp Thr
                325                 330                 335

Ala Ile Tyr Tyr Cys Ala Arg Ala Leu Thr Tyr Tyr Asp Tyr Glu Phe
            340                 345                 350

Ala Tyr Trp Gly Gln Gly Thr Leu Val Thr Val Ser Ala Ala Ser Thr
            355                 360                 365

Lys Gly Pro Ser Val Phe Pro Leu Ala Pro Ser Ser Lys Ser Thr Ser
    370                 375                 380

Gly Gly Thr Ala Ala Leu Gly Cys Leu Val Lys Asp Tyr Phe Pro Glu
385                 390                 395                 400

Pro Val Thr Val Ser Trp Asn Ser Gly Ala Leu Thr Ser Gly Val His
                405                 410                 415

Thr Phe Pro Ala Val Leu Gln Ser Gly Leu Tyr Ser Leu Ser Ser
            420                 425                 430

Val Val Thr Val Pro Ser Ser Leu Gly Thr Gln Thr Tyr Ile Cys
            435                 440                 445

Asn Val Asn His Lys Pro Ser Asn Thr Lys Val Asp Lys Lys Val Glu
    450                 455                 460

Pro Lys Ser Cys Asp Lys Thr His Thr Cys Pro Pro Cys Pro Ala Pro
465                 470                 475                 480

Glu Leu Leu Gly Gly Pro Ser Val Phe Leu Phe Pro Lys Pro Lys
                485                 490                 495

Asp Thr Leu Met Ile Ser Arg Thr Pro Glu Val Thr Cys Val Val Val
            500                 505                 510
```

```
Asp Val Ser His Glu Asp Pro Glu Val Lys Phe Asn Trp Tyr Val Asp
        515                 520                 525
Gly Val Glu Val His Asn Ala Lys Thr Lys Pro Arg Glu Glu Gln Tyr
    530                 535                 540
Asn Ser Thr Tyr Arg Val Val Ser Val Leu Thr Val Leu His Gln Asp
545                 550                 555                 560
Trp Leu Asn Gly Lys Glu Tyr Lys Cys Lys Val Ser Asn Lys Ala Leu
                565                 570                 575
Pro Ala Pro Ile Glu Lys Thr Ile Ser Lys Ala Lys Gly Gln Pro Arg
            580                 585                 590
Glu Pro Gln Val Tyr Thr Leu Pro Pro Ser Arg Glu Met Thr Lys
        595                 600                 605
Asn Gln Val Ser Leu Thr Cys Leu Val Lys Gly Phe Tyr Pro Ser Asp
        610                 615                 620
Ile Ala Val Glu Trp Glu Ser Asn Gly Gln Pro Glu Asn Asn Tyr Lys
625                 630                 635                 640
Thr Thr Pro Pro Val Leu Asp Ser Asp Gly Ser Phe Phe Leu Tyr Ser
                645                 650                 655
Lys Leu Thr Val Asp Lys Ser Arg Trp Gln Gln Gly Asn Val Phe Ser
            660                 665                 670
Cys Ser Val Met His Glu Ala Leu His Asn His Tyr Thr Gln Lys Ser
        675                 680                 685
Leu Ser Leu Ser Pro Gly Lys
        690             695

<210> SEQ ID NO 295
<211> LENGTH: 2088
<212> TYPE: DNA
<213> ORGANISM: Artificial Sequence
<220> FEATURE:
<223> OTHER INFORMATION: Multispecific antibody C225v5-OKT3m-H-N heavy
      chain

<400> SEQUENCE: 295
caggttcagc tgcagcagag cggtgcagaa ctggcacgtc cgggtgcaag cgttaaaatg      60
agctgtaaag caagcggtta cctttacc cgttatacca tgcattgggt taaacagcgt     120
ccgggtcagg gtctggaatg gattggttat atcaatccga ccgtggttac taccaactac     180
aaccagaaat caaagataa agcaaccctg accaccgata aaagcagcag caccgcctat     240
atgcagctga gcagcctgac ctcagaggat agcgcagttt attactgtgc acgctattat     300
gatgatcact atagcctgga ttattgggt cagggcacca ccctgaccgt tagcagcggt     360
ggtggtggta gtggtggcgg tggttcaggc ggtggcggta gccagattgt tctgacccag     420
agtccggcaa ttatgagcgc aagtccgggt gaaaaagtta ccatgacctg tagcgccagc     480
agcagcgtta gctatatgaa ttggtatcag cagaaaagcg gcaccagccc gaaacgttgg     540
atttatgata ccagcaaact ggcaagcggt gttccggcac attttcgtgg tagcggtagc     600
ggcacctcat atagcctgac cattagcggt atggaagcag aagatgcagc aacctattat     660
tgtcagcagt ggtcaagcaa tccgtttacc tttggtagtg caccaaaact ggaaattaat     720
cgtggaggtg gtggatccca ggtgcagctg aaacagagcg gcccgggcct ggtgcagccg     780
agccagagcc tgagcattac ctgcaccgtg agcggcttta gcctgaccaa ctatggcgtg     840
cattgggtgc gccagagccc gggcaaaggc ctggaatggc tgggcgtgat ttggagcggc     900
ggcaacaccg attataacac cccgtttacc agccgcctga gcattaacaa agataacagc     960
```

```
aaaagccagg tgttttttaa aatgaacagc ctgcaaagcc aggataccgc gatttattat    1020
tgcgcgcgcg cgctgaccta ttatgattat gaatttgcgt attggggcca gggcaccctg    1080
gtgaccgtga gcgcggctag caccaagggc ccatcggtct tccccctggc accctcctcc    1140
aagagcacct ctgggggcac agcggccctg ggctgcctgg tcaaggacta cttccccgaa    1200
ccggtgacgg tgtcgtggaa ctcaggcgcc ctgaccagcg gcgtgcacac cttcccggct    1260
gtcctacagt cctcaggact ctactccctc agcagcgtgg tgaccgtgcc ctccagcagc    1320
ttgggcaccc agacctacat ctgcaacgtg aatcacaagc ccagcaacac caaggtggac    1380
aagaaagttg agcccaaatc ttgtgacaaa actcacacat gcccaccgtg cccagcacct    1440
gaactcctgg ggggaccgtc agtcttcctc ttccccccaa acccaaggac accctcatg     1500
atctcccgga cccctgaggt cacatgcgtg gtggtggacg tgagccacga agaccctgag    1560
gtcaagttca actggtacgt ggacggcgtg gaggtgcata atgccaagac aaagccgcgg    1620
gaggagcagt acaacagcac gtaccgtgtg gtcagcgtcc tcaccgtcct gcaccaggac    1680
tggctgaatg gcaaggagta caagtgcaag gtctccaaca aagccctccc agcccccatc    1740
gagaaaacca tctccaaagc caagggcag ccccgagaac cacaggtgta caccctgccc     1800
ccatcccggg aggagatgac caagaaccag gtcagcctga cctgcctggt caaaggcttc    1860
tatcccagcg acatcgccgt ggagtgggag agcaatgggc agccggagaa caactacaag    1920
accacgcctc ccgtgctgga ctccgacggc tccttcttcc tctacagcaa gctcaccgtg    1980
gacaagagca ggtggcagca ggggaacgtc ttctcatgct ccgtgatgca tgaggctctg    2040
cacaaccact acacgcagaa gagcctctcc ctgtctccgg gtaaatga                 2088
```

```
<210> SEQ ID NO 296
<211> LENGTH: 713
<212> TYPE: PRT
<213> ORGANISM: Artificial Sequence
<220> FEATURE:
<223> OTHER INFORMATION: Multispecific antibody C225v5-OKT3m-H-C heavy
      chain

<400> SEQUENCE: 296

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160
```

```
Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys Gly Gly Gly Ser Gly Gly Gly Ser Gly Gly Gly Gly Ser
    450                 455                 460

Gly Gly Gly Ser Gly Gly Gln Val Gln Leu Gln Gln Ser Gly
465                 470                 475                 480

Ala Glu Leu Ala Arg Pro Gly Ala Ser Val Lys Met Ser Cys Lys Ala
                485                 490                 495

Ser Gly Tyr Thr Phe Thr Arg Tyr Thr Met His Trp Val Lys Gln Arg
            500                 505                 510

Pro Gly Gln Gly Leu Glu Trp Ile Gly Tyr Ile Asn Pro Ser Arg Gly
        515                 520                 525

Tyr Thr Asn Tyr Asn Gln Lys Phe Lys Asp Lys Ala Thr Leu Thr Thr
    530                 535                 540

Asp Lys Ser Ser Ser Thr Ala Tyr Met Gln Leu Ser Ser Leu Thr Ser
545                 550                 555                 560

Glu Asp Ser Ala Val Tyr Tyr Cys Ala Arg Tyr Tyr Asp Asp His Tyr
                565                 570                 575
```

```
Ser Leu Asp Tyr Trp Gly Gln Gly Thr Thr Leu Thr Val Ser Ser Gly
            580                 585                 590

Gly Gly Gly Ser Gly Gly Gly Ser Gly Gly Gly Ser Gln Ile
        595                 600                 605

Val Leu Thr Gln Ser Pro Ala Ile Met Ser Ala Ser Pro Gly Glu Lys
            610                 615                 620

Val Thr Met Thr Cys Ser Ala Ser Ser Val Ser Tyr Met Asn Trp
625                 630                 635                 640

Tyr Gln Gln Lys Ser Gly Thr Ser Pro Lys Arg Trp Ile Tyr Asp Thr
                645                 650                 655

Ser Lys Leu Ala Ser Gly Val Pro Ala His Phe Arg Gly Ser Gly Ser
            660                 665                 670

Gly Thr Ser Tyr Ser Leu Thr Ile Ser Gly Met Glu Ala Glu Asp Ala
        675                 680                 685

Ala Thr Tyr Tyr Cys Gln Gln Trp Ser Ser Asn Pro Phe Thr Phe Gly
        690                 695                 700

Ser Gly Thr Lys Leu Glu Ile Asn Arg
705                 710
```

<210> SEQ ID NO 297
<211> LENGTH: 2142
<212> TYPE: DNA
<213> ORGANISM: Artificial Sequence
<220> FEATURE:
<223> OTHER INFORMATION: Multispecific antibody C225v5-OKT3m-H-C heavy chain

<400> SEQUENCE: 297

```
caggtgcagc tgaaacagag cggcccgggc ctggtgcagc cgagccagag cctgagcatt      60
acctgcaccg tgagcggctt tagcctgacc aactatggcg tgcattgggt gcgccagagc     120
ccgggcaaag cctggaatg gctgggcgtg atttggagcg gcggcaacac cgattataac      180
accccgttta ccagccgcct gagcattaac aaagataaca gcaaaagcca ggtgtttttt    240
aaaatgaaca gcctgcaaag ccaggatacc gcgatttatt attgcgcgcg cgcgctgacc    300
tattatgatt atgaatttgc gtattggggc cagggcaccc tggtgaccgt gagcgcggct    360
agcaccaagg gcccatcggt cttccccctg gcaccctcct ccaagagcac ctctggggc     420
acagcggccc tgggctgcct ggtcaaggac tacttccccg aaccggtgac ggtgtcgtgg    480
aactcaggcg ccctgaccag cggcgtgcac accttcccgg ctgtcctaca gtcctcagga    540
ctctactccc tcagcagcgt ggtgaccgtg ccctccagca gcttgggcac ccagacctac    600
atctgcaacg tgaatcacaa gcccagcaac accaaggtgg acaagaaagt tgagcccaaa    660
tcttgtgaca aaactcacac atgcccaccg tgcccagcac ctgaactcct ggggggaccg    720
tcagtcttcc tcttcccccc aaaacccaag gacaccctca tgatctcccg gacccctgag    780
gtcacatgcg tggtggtgga cgtgagccac gaagaccctg aggtcaagtt caactggtac    840
gtggacggcg tggaggtgca taatgccaag acaaagccgc gggaggagca gtacaacagc    900
acgtaccgtg tggtcagcgt cctcaccgtc ctgcaccagg actggctgaa tggcaaggag    960
tacaagtgca aggtctccaa caaagccctc ccagccccca tcgagaaaac catctccaaa   1020
gccaaagggc agccccgaga accacaggtg tacaccctgc cccatcccg ggaggagatg    1080
accaagaacc aggtcagcct gacctgcctg gtcaaaggct tctatcccag cgacatcgcc   1140
gtggagtggg agagcaatgg gcagccggag aacaactaca agaccacgcc tcccgtgctg    1200
gactccgacg gctccttctt cctctacagc aagctcaccg tggacaagag caggtggcag    1260
```

-continued

```
cagggaacg tcttctcatg ctccgtgatg catgaggctc tgcacaacca ctacacgcag    1320
aagagcctct ccctgtctcc gggtaaagga ggtggatctg gaggtggcgg ttcaggctct    1380
ggcggaggct caggtggtgg aggatcaggc ggaggtcagg ttcagctgca gcagagcggt    1440
gcagaactgg cacgtccggg tgcaagcgtt aaaatgagct gtaaagcaag cggttatacc    1500
tttacccgtt ataccatgca ttgggttaaa cagcgtccgg tcagggtct ggaatggatt    1560
ggttatatca atccgagccg tggttatacc aactacaacc agaaattcaa agataaagca    1620
accctgacca ccgataaaag cagcagcacc gcctatatgc agctgagcag cctgacctca    1680
gaggatagcg cagtttatta ctgtgcacgc tattatgatg atcactatag cctggattat    1740
tggggtcagg gcaccaccct gaccgttagc agcggtggtg gtggtagtgg tggcggtggt    1800
tcaggcggtg gcggtagcca gattgttctg acccagagtc cggcaattat gagcgcaagt    1860
ccgggtgaaa aagttaccat gacctgtagc gccagcagca gcgttagcta tatgaattgg    1920
tatcagcaga aaagcggcac cagcccgaaa cgttggattt atgataccag caaactggca    1980
agcggtgttc cggcacattt tcgtggtagc ggtagcggca cctcatatag cctgaccatt    2040
agcggtatgg aagcagaaga tgcagcaacc tattattgtc agcagtggtc aagcaatccg    2100
tttacctttg gtagtggcac caaactggaa attaatcgtt ga                       2142
```

<210> SEQ ID NO 298
<211> LENGTH: 478
<212> TYPE: PRT
<213> ORGANISM: Artificial Sequence
<220> FEATURE:
<223> OTHER INFORMATION: Multispecific antibody C225v5-OKT3m-L-C light chain

<400> SEQUENCE: 298

```
Asp Ile Leu Leu Thr Gln Ser Pro Val Ile Leu Ser Val Ser Pro Gly
1               5                   10                  15
Glu Arg Val Ser Phe Ser Cys Arg Ala Ser Gln Ser Ile Gly Thr Asn
            20                  25                  30
Ile His Trp Tyr Gln Gln Arg Thr Asn Gly Ser Pro Arg Leu Leu Ile
        35                  40                  45
Lys Tyr Ala Ser Glu Ser Ile Ser Gly Ile Pro Ser Arg Phe Ser Gly
    50                  55                  60
Ser Gly Ser Gly Thr Asp Phe Thr Leu Ser Ile Asn Ser Val Glu Ser
65                  70                  75                  80
Glu Asp Ile Ala Asp Tyr Tyr Cys Gln Gln Asn Asn Asn Trp Pro Thr
                85                  90                  95
Thr Phe Gly Ala Gly Thr Lys Leu Glu Leu Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
```

```
                195                 200                 205
Phe Asn Arg Gly Glu Cys Gly Gly Ser Gly Gly Gly Ser Gly
    210                 215                 220
Ser Gly Gly Gly Ser Gly Gly Gly Ser Gly Gly Gln Val Gln
225                 230                 235                 240
Leu Gln Gln Ser Gly Ala Glu Leu Ala Arg Pro Gly Ala Ser Val Lys
                245                 250                 255
Met Ser Cys Lys Ala Ser Gly Tyr Thr Phe Thr Arg Tyr Thr Met His
            260                 265                 270
Trp Val Lys Gln Arg Pro Gly Gln Gly Leu Glu Trp Ile Gly Tyr Ile
        275                 280                 285
Asn Pro Ser Arg Gly Tyr Thr Asn Tyr Asn Gln Lys Phe Lys Asp Lys
    290                 295                 300
Ala Thr Leu Thr Thr Asp Lys Ser Ser Ser Thr Ala Tyr Met Gln Leu
305                 310                 315                 320
Ser Ser Leu Thr Ser Glu Asp Ser Ala Val Tyr Tyr Cys Ala Arg Tyr
                325                 330                 335
Tyr Asp Asp His Tyr Ser Leu Asp Tyr Trp Gly Gln Gly Thr Thr Leu
            340                 345                 350
Thr Val Ser Ser Gly Gly Gly Gly Ser Gly Gly Gly Gly Ser Gly Gly
        355                 360                 365
Gly Gly Ser Gln Ile Val Leu Thr Gln Ser Pro Ala Ile Met Ser Ala
    370                 375                 380
Ser Pro Gly Glu Lys Val Thr Met Thr Cys Ser Ala Ser Ser Ser Val
385                 390                 395                 400
Ser Tyr Met Asn Trp Tyr Gln Gln Lys Ser Gly Thr Ser Pro Lys Arg
                405                 410                 415
Trp Ile Tyr Asp Thr Ser Lys Leu Ala Ser Gly Val Pro Ala His Phe
            420                 425                 430
Arg Gly Ser Gly Ser Gly Thr Ser Tyr Ser Leu Thr Ile Ser Gly Met
        435                 440                 445
Glu Ala Glu Asp Ala Ala Thr Tyr Tyr Cys Gln Gln Trp Ser Ser Asn
    450                 455                 460
Pro Phe Thr Phe Gly Ser Gly Thr Lys Leu Glu Ile Asn Arg
465                 470                 475

<210> SEQ ID NO 299
<211> LENGTH: 1437
<212> TYPE: DNA
<213> ORGANISM: Artificial Sequence
<220> FEATURE:
<223> OTHER INFORMATION: Multispecific antibody C225v5-OKT3m-L-C light
      chain

<400> SEQUENCE: 299
gacatcttgc tgacccagag cccggtgatt ctgagcgtga gcccgggcga acgtgtgagc      60
tttagctgcc gcgcgagcca gagcattggc accaacattc attggtatca gcagcgcacc     120
aacggcagcc cgcgcctgct gattaaatat gcgagcgaaa gcattagcgg cattccgagc     180
cgctttagcg gcagcggcag cggcaccgat tttaccctga gcattaacag cgtggaaagc     240
gaagatattg cggattatta ttgccagcag aacaacaact ggccgaccac ctttggcgcg     300
ggcaccaaac tggaactgaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
```

```
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gtggaggtgg atctggaggt      660
ggcggttcag gctctggcgg aggctcaggt ggtggaggat caggcggagg tcaggttcag      720
ctgcagcaga gcggtgcaga actggcacgt ccgggtgcaa gcgttaaaat gagctgtaaa      780
gcaagcggtt atacctttac ccgttatacc atgcattggg ttaaacagcg tccgggtcag      840
ggtctggaat ggattggtta tatcaatccg agccgtggtt ataccaacta caaccagaaa      900
ttcaaagata aagcaaccct gaccaccgat aaaagcagca gcaccgccta tatgcagctg      960
agcagcctga cctcagagga tagcgcagtt tattactgtg cacgctatta tgatgatcac     1020
tatagcctgg attattgggg tcagggcacc accctgaccg ttagcagcgg tggtggtggt     1080
agtggtggcg gtggttcagg cggtggcggt agccagattg ttctgaccca gagtccggca     1140
attatgagcg caagtccggg tgaaaaagtt accatgacct gtagcgccag cagcagcgtt     1200
agctatatga attggtatca gcagaaaagc ggcaccagcc cgaaacgttg gatttatgat     1260
accagcaaac tggcaagcgg tgttccggca catttccgtg gtagcggtag cggcaccctca     1320 tatagcctga ccattagcgg tatggaagca gaagatgcag caacctatta ttgtcagcag     1380
tggtcaagca atccgtttac ctttggtagt ggcaccaaac tggaaattaa tcgttag       1437
```

```
<210> SEQ ID NO 300
<211> LENGTH: 695
<212> TYPE: PRT
<213> ORGANISM: Artificial Sequence
<220> FEATURE:
<223> OTHER INFORMATION: Multispecific antibody C225v5 N297Q - OKT3m-H-N
      heavy chain

<400> SEQUENCE: 300

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

Thr Thr Leu Thr Val Ser Ser Gly Gly Gly Gly Ser Gly Gly Gly Gly
        115                 120                 125

Ser Gly Gly Gly Gly Ser Gln Ile Val Leu Thr Gln Ser Pro Ala Ile
    130                 135                 140

Met Ser Ala Ser Pro Gly Glu Lys Val Thr Met Thr Cys Ser Ala Ser
145                 150                 155                 160

Ser Ser Val Ser Tyr Met Asn Trp Tyr Gln Gln Lys Ser Gly Thr Ser
                165                 170                 175

Pro Lys Arg Trp Ile Tyr Asp Thr Ser Lys Leu Ala Ser Gly Val Pro
            180                 185                 190
```

-continued

```
Ala His Phe Arg Gly Ser Gly Ser Gly Thr Ser Tyr Ser Leu Thr Ile
        195                 200                 205

Ser Gly Met Glu Ala Glu Asp Ala Ala Thr Tyr Tyr Cys Gln Gln Trp
210                 215                 220

Ser Ser Asn Pro Phe Thr Phe Gly Ser Gly Thr Lys Leu Glu Ile Asn
225                 230                 235                 240

Arg Gly Gly Gly Ser Gln Val Gln Leu Lys Gln Ser Gly Pro Gly
                245                 250                 255

Leu Val Gln Pro Ser Gln Ser Leu Ser Ile Thr Cys Thr Val Ser Gly
            260                 265                 270

Phe Ser Leu Thr Asn Tyr Gly Val His Trp Val Arg Gln Ser Pro Gly
            275                 280                 285

Lys Gly Leu Glu Trp Leu Gly Val Ile Trp Ser Gly Gly Asn Thr Asp
        290                 295                 300

Tyr Asn Thr Pro Phe Thr Ser Arg Leu Ser Ile Asn Lys Asp Asn Ser
305                 310                 315                 320

Lys Ser Gln Val Phe Phe Lys Met Asn Ser Leu Gln Ser Gln Asp Thr
                325                 330                 335

Ala Ile Tyr Tyr Cys Ala Arg Ala Leu Thr Tyr Tyr Asp Tyr Glu Phe
            340                 345                 350

Ala Tyr Trp Gly Gln Gly Thr Leu Val Thr Val Ser Ala Ala Ser Thr
            355                 360                 365

Lys Gly Pro Ser Val Phe Pro Leu Ala Pro Ser Ser Lys Ser Thr Ser
        370                 375                 380

Gly Gly Thr Ala Ala Leu Gly Cys Leu Val Lys Asp Tyr Phe Pro Glu
385                 390                 395                 400

Pro Val Thr Val Ser Trp Asn Ser Gly Ala Leu Thr Ser Gly Val His
                405                 410                 415

Thr Phe Pro Ala Val Leu Gln Ser Ser Gly Leu Tyr Ser Leu Ser Ser
            420                 425                 430

Val Val Thr Val Pro Ser Ser Ser Leu Gly Thr Gln Thr Tyr Ile Cys
            435                 440                 445

Asn Val Asn His Lys Pro Ser Asn Thr Lys Val Asp Lys Lys Val Glu
        450                 455                 460

Pro Lys Ser Cys Asp Lys Thr His Thr Cys Pro Pro Cys Pro Ala Pro
465                 470                 475                 480

Glu Leu Leu Gly Gly Pro Ser Val Phe Leu Phe Pro Pro Lys Pro Lys
                485                 490                 495

Asp Thr Leu Met Ile Ser Arg Thr Pro Glu Val Thr Cys Val Val Val
            500                 505                 510

Asp Val Ser His Glu Asp Pro Glu Val Lys Phe Asn Trp Tyr Val Asp
            515                 520                 525

Gly Val Glu Val His Asn Ala Lys Thr Lys Pro Arg Glu Glu Gln Tyr
        530                 535                 540

Gln Ser Thr Tyr Arg Val Val Ser Val Leu Thr Val Leu His Gln Asp
545                 550                 555                 560

Trp Leu Asn Gly Lys Glu Tyr Lys Cys Lys Val Ser Asn Lys Ala Leu
                565                 570                 575

Pro Ala Pro Ile Glu Lys Thr Ile Ser Lys Ala Lys Gly Gln Pro Arg
            580                 585                 590

Glu Pro Gln Val Tyr Thr Leu Pro Pro Ser Arg Glu Glu Met Thr Lys
            595                 600                 605
```

| | | | | | | | | | | | | |
|---|---|---|---|---|---|---|---|---|---|---|---|---|
| Asn | Gln | Val | Ser | Leu | Thr | Cys | Leu | Val | Lys | Gly | Phe | Tyr | Pro | Ser | Asp |
| 610 | | | | | 615 | | | | | 620 | | | | | |
| Ile | Ala | Val | Glu | Trp | Glu | Ser | Asn | Gly | Gln | Pro | Glu | Asn | Asn | Tyr | Lys |
| 625 | | | | | 630 | | | | | 635 | | | | | 640 |
| Thr | Thr | Pro | Pro | Val | Leu | Asp | Ser | Asp | Gly | Ser | Phe | Phe | Leu | Tyr | Ser |
| | | | | 645 | | | | | 650 | | | | | 655 | |
| Lys | Leu | Thr | Val | Asp | Lys | Ser | Arg | Trp | Gln | Gln | Gly | Asn | Val | Phe | Ser |
| | | | 660 | | | | | 665 | | | | | 670 | | |
| Cys | Ser | Val | Met | His | Glu | Ala | Leu | His | Asn | His | Tyr | Thr | Gln | Lys | Ser |
| | | | 675 | | | | | 680 | | | | | 685 | | |
| Leu | Ser | Leu | Ser | Pro | Gly | Lys |
| | | 690 | | | | 695 |

<210> SEQ ID NO 301
<211> LENGTH: 2088
<212> TYPE: DNA
<213> ORGANISM: Artificial Sequence
<220> FEATURE:
<223> OTHER INFORMATION: Multispecific antibody C225v5 N297Q - OKT3m-H-N
    heavy chain

<400> SEQUENCE: 301

```
caggttcagc tgcagcagag cggtgcagaa ctggcacgtc cgggtgcaag cgttaaaatg      60
agctgtaaag caagcggtta tacctttacc cgttatacca tgcattgggt taaacagcgt     120
ccgggtcagg gtctggaatg gattggttat atcaatccga ccgtggttta ccaactac      180
aaccagaaat caaagataa agcaaccctg accaccgata aaagcagcag caccgccta      240
atgcagctga gcagcctgac ctcagaggat agcgcagttt attactgtgc acgtattat     300
gatgatcact atagcctgga ttattgggt cagggcacca ccctgaccgt tagcagcggt     360
ggtggtggta gtggtggcgg tggttcaggc ggtggcggta gccagattgt tctgacccag     420
agtccggcaa ttatgagcgc aagtccgggt gaaaaagtta ccatgacctg tagcgccagc     480
agcagcgtta gctatatgaa ttggtatcag cagaaaagcg gcaccagccc gaaacgttgg     540
atttatgata ccagcaaact ggcaagcggt gttccggcac attttcgtgg tagcggtagc     600
ggcacctcat atagcctgac cattagcggt atggaagcag aagatgcagc aacctatta     660
tgtcagcagt ggtcaagcaa tccgtttacc tttggtagtg caccaaact ggaaattaat     720
cgtggaggtg gtggatccca ggtgcagctg aaacagagcg gcccgggcct ggtgcagccg     780
agccagagcc tgagcattac ctgcaccgtg agcggcttta gcctgaccaa ctatggcgtg     840
cattgggtgc gccagagccc gggcaaaggc ctggaatggc tgggcgtgat ttggagcggc     900
ggcaacaccg attataacac cccgtttacc agccgcctga gcattaacaa agataacagc     960
aaaagccagg tgttttttaa aatgaacagc ctgcaaagcc aggataccgc gatttattat    1020
tgcgcgcgcg cgctgaccta ttatgattat gaatttgcgt attggggcca gggcacccctg   1080
gtgaccgtga gcgcggctag caccaagggc ccatcggtct tccccctggc acctcctcc    1140
aagagcacct ctgggggcac agcggccctg ggctgcctgg tcaaggacta cttccccgaa    1200
ccggtgacgg tgtcgtggaa ctcaggcgcc ctgaccagcg gcgtgcacac cttcccggct    1260
gtcctacagt cctcaggact ctactccctc agcagcgtgg tgaccgtgcc ctccagcagc   1320
ttgggcaccc agacctacat ctgcaacgtg aatcacaagc ccagcaacac caaggtggac    1380
aagaaagttg agcccaaatc ttgtgacaaa actcacacat gcccaccgtg cccagcacct    1440
gaactcctgg ggggaccgtc agtcttcctc ttccccccaa aacccaagga caccctcatg    1500
```

-continued

```
atctcccgga cccctgaggt cacatgcgtg gtggtggacg tgagccacga agaccctgag   1560
gtcaagttca actggtacgt ggacggcgtg gaggtgcata atgccaagac aaagccgcgg   1620
gaggagcagt accagagcac gtaccgtgtg gtcagcgtcc tcaccgtcct gcaccaggac   1680
tggctgaatg gcaaggagta caagtgcaag gtctccaaca aagccctccc agcccccatc   1740
gagaaaacca tctccaaagc caagggcag ccccgagaac acaggtgta caccctgccc    1800 ccatcccggg aggagatgac caagaaccag gtcagcctga cctgcctggt caaaggcttc   1860
tatcccagcg acatcgccgt ggagtgggag agcaatgggc agccggagaa caactacaag   1920
accacgcctc ccgtgctgga ctccgacggc tccttcttcc tctacagcaa gctcaccgtg   1980
gacaagagca ggtggcagca ggggaacgtc ttctcatgct ccgtgatgca tgaggctctg   2040
cacaaccact acacgcagaa gagcctctcc ctgtctccgg gtaaatga              2088
```

```
<210> SEQ ID NO 302
<211> LENGTH: 713
<212> TYPE: PRT
<213> ORGANISM: Artificial Sequence
<220> FEATURE:
<223> OTHER INFORMATION: Multispecific antibody C225v5 N297Q - OKT3m-H-C
      heavy chain

<400> SEQUENCE: 302
```

```
Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255
```

```
Arg Thr Pro Glu Val Thr Cys Val Val Asp Val Ser His Glu Asp
            260                 265                 270
Pro Glu Val Lys Phe Asn Trp Tyr Val Asp Gly Val Glu Val His Asn
        275                 280                 285
Ala Lys Thr Lys Pro Arg Glu Glu Gln Tyr Gln Ser Thr Tyr Arg Val
    290                 295                 300
Val Ser Val Leu Thr Val Leu His Gln Asp Trp Leu Asn Gly Lys Glu
305                 310                 315                 320
Tyr Lys Cys Lys Val Ser Asn Lys Ala Leu Pro Ala Pro Ile Glu Lys
                325                 330                 335
Thr Ile Ser Lys Ala Lys Gly Gln Pro Arg Glu Pro Gln Val Tyr Thr
            340                 345                 350
Leu Pro Pro Ser Arg Glu Glu Met Thr Lys Asn Gln Val Ser Leu Thr
        355                 360                 365
Cys Leu Val Lys Gly Phe Tyr Pro Ser Asp Ile Ala Val Glu Trp Glu
    370                 375                 380
Ser Asn Gly Gln Pro Glu Asn Asn Tyr Lys Thr Thr Pro Pro Val Leu
385                 390                 395                 400
Asp Ser Asp Gly Ser Phe Phe Leu Tyr Ser Lys Leu Thr Val Asp Lys
                405                 410                 415
Ser Arg Trp Gln Gln Gly Asn Val Phe Ser Cys Ser Val Met His Glu
            420                 425                 430
Ala Leu His Asn His Tyr Thr Gln Lys Ser Leu Ser Leu Ser Pro Gly
        435                 440                 445
Lys Gly Gly Gly Ser Gly Gly Gly Ser Gly Gly Gly Ser
    450                 455                 460
Gly Gly Gly Gly Ser Gly Gly Gly Gln Val Gln Leu Gln Gln Ser Gly
465                 470                 475                 480
Ala Glu Leu Ala Arg Pro Gly Ala Ser Val Lys Met Ser Cys Lys Ala
                485                 490                 495
Ser Gly Tyr Thr Phe Thr Arg Tyr Thr Met His Trp Val Lys Gln Arg
            500                 505                 510
Pro Gly Gln Gly Leu Glu Trp Ile Gly Tyr Ile Asn Pro Ser Arg Gly
        515                 520                 525
Tyr Thr Asn Tyr Asn Gln Lys Phe Lys Asp Lys Ala Thr Leu Thr Thr
    530                 535                 540
Asp Lys Ser Ser Ser Thr Ala Tyr Met Gln Leu Ser Ser Leu Thr Ser
545                 550                 555                 560
Glu Asp Ser Ala Val Tyr Tyr Cys Ala Arg Tyr Tyr Asp Asp His Tyr
                565                 570                 575
Ser Leu Asp Tyr Trp Gly Gln Gly Thr Thr Leu Thr Val Ser Ser Gly
            580                 585                 590
Gly Gly Ser Gly Gly Gly Gly Ser Gly Gly Gly Ser Gln Ile
        595                 600                 605
Val Leu Thr Gln Ser Pro Ala Ile Met Ser Ala Ser Pro Gly Glu Lys
    610                 615                 620
Val Thr Met Thr Cys Ser Ala Ser Ser Val Ser Tyr Met Asn Trp
625                 630                 635                 640
Tyr Gln Gln Lys Ser Gly Thr Ser Pro Lys Arg Trp Ile Tyr Asp Thr
                645                 650                 655
Ser Lys Leu Ala Ser Gly Val Pro Ala His Phe Arg Gly Ser Gly Ser
            660                 665                 670
Gly Thr Ser Tyr Ser Leu Thr Ile Ser Gly Met Glu Ala Glu Asp Ala
```

|     | 675 |     |     |     | 680 |     |     |     | 685 |     |     |     |
| --- | --- | --- | --- | --- | --- | --- | --- | --- | --- | --- | --- | --- |
| Ala | Thr | Tyr | Tyr | Cys | Gln | Gln | Trp | Ser | Ser | Asn | Pro | Phe | Thr | Phe | Gly |
|     | 690 |     |     |     | 695 |     |     |     | 700 |     |     |     |

Ser Gly Thr Lys Leu Glu Ile Asn Arg
705             710

<210> SEQ ID NO 303
<211> LENGTH: 2142
<212> TYPE: DNA
<213> ORGANISM: Artificial Sequence
<220> FEATURE:
<223> OTHER INFORMATION: Multispecific antibody C225v5 N297Q - OKT3m-H-C heavy chain
<400> SEQUENCE: 303

```
caggtgcagc tgaaacagag cggcccgggc ctggtgcagc cgagccagag cctgagcatt        60
acctgcaccg tgagcggctt tagcctgacc aactatggcg tgcattgggt gcgccagagc       120
ccgggcaaag ccctggaatg gctgggcgtg atttggagcg gcggcaacac cgattataac       180
accccgttta ccagccgcct gagcattaac aaagataaca gcaaaagcca ggtgtttttt       240
aaaatgaaca ccctgcaaag ccaggatacc gcgatttatt attgcgcgcg cgcgctgacc       300
tattatgatt atgaatttgc gtattggggc cagggcaccc tggtgaccgt gagcgcggct       360
agcaccaagg gcccatcggt cttccccctg gcaccctcct ccaagagcac ctctgggggc       420
acagcggccc tgggctgcct ggtcaaggac tacttccccg aaccggtgac ggtgtcgtgg       480
aactcaggcg ccctgaccag cggcgtgcac accttcccgg ctgtcctaca gtcctcagga       540
ctctactccc tcagcagcgt ggtgaccgtg ccctccagca gcttgggcac ccagacctac       600
atctgcaacg tgaatcacaa gcccagcaac accaaggtgg acaagaaagt tgagcccaaa       660
tcttgtgaca aaactcacac atgcccaccg tgcccagcac ctgaactcct ggggggaccg       720
tcagtcttcc tcttcccccc aaaacccaag gacaccctca tgatctcccg gacccctgag       780
gtcacatgcg tggtggtgga cgtgagccac gaagaccctg aggtcaagtt caactggtac       840
gtggacggcg tggaggtgca taatgccaag acaaagccgc gggaggagca gtaccagagc       900
acgtaccgtg tggtcagcgt cctcaccgtc ctgcaccagg actggctgaa tggcaaggag       960
tacaagtgca aggtctccaa caaagccctc ccagccccca tcgagaaaac catctccaaa      1020
gccaaagggc agccccgaga accacaggtg tacaccctgc ccccatcccg ggaggagatg      1080
accaagaacc aggtcagcct gacctgcctg gtcaaaggct tctatccag cgacatcgcc      1140
gtggagtggg agagcaatgg gcagccggag aacaactaca agaccacgcc tcccgtgctg      1200
gactccgacg gctccttctt cctctacagc aagctcaccg tggacaagag caggtggcag      1260
caggggaacg tcttctcatg ctccgtgatg catgaggctc tgcacaacca ctacacgcag      1320
aagagcctct ccctgtctcc gggtaaagga ggtggatctg gaggtggcgg ttcaggctct      1380
ggcggaggct caggtggtgg aggatcaggc ggaggtcagg ttcagctgca gcagagcggt      1440
gcagaactgg cacgtccggg tgcaagcgtt aaaatgagct gtaaagcaag cggttatacc      1500
tttacccgtt ataccatgca ttgggttaaa cagcgtccgg tcagggtct ggaatggatt      1560
ggttatatca atccgagccg tggttatacc aactacaacc agaaattcaa agataaagca      1620
accctgacca ccgataaaag cagcagcacc gcctatatgc agctgagcag cctgacctca      1680
gaggatagcg cagtttatta ctgtgcacgc tattatgatg atcactatag cctggattat      1740
tggggtcagg gcaccaccct gaccgttagc agcggtggtg gtggtagtgg tggcggtggt      1800
```

```
tcaggcggtg gcggtagcca gattgttctg acccagagtc cggcaattat gagcgcaagt    1860
ccgggtgaaa agttaccat gacctgtagc gccagcagca gcgttagcta tatgaattgg    1920
tatcagcaga aaagcggcac cagcccgaaa cgttggattt atgataccag caaactggca    1980
agcggtgttc cggcacattt tcgtggtagc ggtagcggca cctcatatag cctgaccatt    2040
agcggtatgg aagcagaaga tgcagcaacc tattattgtc agcagtggtc aagcaatccg    2100 tttaccttg gtagtggcac caaactggaa attaatcgtt ga                      2142
```

<210> SEQ ID NO 304
<211> LENGTH: 261
<212> TYPE: PRT
<213> ORGANISM: Artificial Sequence
<220> FEATURE:
<223> OTHER INFORMATION: Activatable antibody 3954-1204-C225v5 light
      chain

<400> SEQUENCE: 304

Gln Gly Gln Ser Gly Gln Cys Ile Ser Pro Arg Gly Cys Pro Asp Gly
1               5                   10                  15

Pro Tyr Val Met Tyr Gly Ser Ser Gly Gly Ser Gly Gly Ser Gly Gly
            20                  25                  30

Ser Gly Leu Ser Gly Arg Ser Asp Asn His Gly Ser Ser Gly Thr Gln
        35                  40                  45

Ile Leu Leu Thr Gln Ser Pro Val Ile Leu Ser Val Ser Pro Gly Glu
    50                  55                  60

Arg Val Ser Phe Ser Cys Arg Ala Ser Gln Ser Ile Gly Thr Asn Ile
65                  70                  75                  80

His Trp Tyr Gln Gln Arg Thr Asn Gly Ser Pro Arg Leu Leu Ile Lys
                85                  90                  95

Tyr Ala Ser Glu Ser Ile Ser Gly Ile Pro Ser Arg Phe Ser Gly Ser
            100                 105                 110

Gly Ser Gly Thr Asp Phe Thr Leu Ser Ile Asn Ser Val Glu Ser Glu
        115                 120                 125

Asp Ile Ala Asp Tyr Tyr Cys Gln Gln Asn Asn Asn Trp Pro Thr Thr
    130                 135                 140

Phe Gly Ala Gly Thr Lys Leu Glu Leu Lys Arg Thr Val Ala Ala Pro
145                 150                 155                 160

Ser Val Phe Ile Phe Pro Pro Ser Asp Glu Gln Leu Lys Ser Gly Thr
                165                 170                 175

Ala Ser Val Val Cys Leu Leu Asn Asn Phe Tyr Pro Arg Glu Ala Lys
            180                 185                 190

Val Gln Trp Lys Val Asp Asn Ala Leu Gln Ser Gly Asn Ser Gln Glu
        195                 200                 205

Ser Val Thr Glu Gln Asp Ser Lys Asp Ser Thr Tyr Ser Leu Ser Ser
    210                 215                 220

Thr Leu Thr Leu Ser Lys Ala Asp Tyr Glu Lys His Lys Val Tyr Ala
225                 230                 235                 240

Cys Glu Val Thr His Gln Gly Leu Ser Ser Pro Val Thr Lys Ser Phe
                245                 250                 255

Asn Arg Gly Glu Cys
            260

<210> SEQ ID NO 305
<211> LENGTH: 1578
<212> TYPE: DNA
<213> ORGANISM: Artificial Sequence
<220> FEATURE:
<223> OTHER INFORMATION: Activatable antibody 3954-1204-C225v5 light chain

<400> SEQUENCE: 305

```
caaggccagt ctggccagtg catctcacct cgtggttgtc cggacggccc atacgtcatg      60
tacggctcga gcggtggcag cggtggctct ggtggatccg gtctgagcgg ccgttccgat     120
aatcatggca gtagcggtac ccagatcttg ctgacccaga gcccggtgat tctgagcgtg     180
agcccgggcg aacgtgtgag ctttagctgc cgcgcgagcc agagcattgg caccaacatt     240
cattggtatc agcagcgcac caacggcagc ccgcgcctgc tgattaaata tgcgagcgaa     300
agcattagcg gcattccgag ccgctttagc ggcagcggca gcggcaccga ttttaccctg     360
agcattaaca gcgtggaaag cgaagatatt gcggattatt attgccagca gaacaacaac     420
tggccgacca cctttggcgc gggcaccaaa ctggaactga acgtacggt ggctgcacca     480
tctgtcttca tcttcccgcc atctgatgag cagttgaaat ctggaactgc ctctgttgtg     540
tgcctgctga taacttcta tcccagagag gccaaagtac agtggaaggt ggataacgcc     600
ctccaatcgg gtaactccca ggagagtgtc acagagcagg acagcaagga cagcacctac     660
agcctcagca gcaccctgac gctgagcaaa gcagactacg agaaacacaa agtctacgcc     720
tgcgaagtca cccatcaggg cctgagctcg cccgtcacaa agagcttcaa caggggagag     780
tgtggaggtg gatctggagg tggcggttca ggctctggcg gaggctcagg tggtggagga     840
tcaggcggag gtcaggttca gctgcagcag agcggtgcag aactggcacg tccgggtgca     900
agcgttaaaa tgagctgtaa agcaagcggt taccctta cccgttatac catgcattgg     960
gttaaacagc gtccgggtca gggtctggaa tggattggtt atatcaatcc gagccgtggt    1020
tataccaact acaaccagaa attcaaagat aaagcaaccc tgaccaccga taaaagcagc    1080
agcaccgcct atatgcagct gagcagcctg acctcagagg atagcgcagt ttattactgt    1140
gcacgctatt atgatgatca ctatagcctg gattattggg gtcagggcac caccctgacc    1200
gttagcagcg gtggtggtgg tagtggtggc ggtggttcag gcggtggcgg tagccagatt    1260
gttctgaccc agagtccggc aattatgagc gcaagtccgg gtgaaaaagt taccatgacc    1320
tgtagcgcca gcagcagcgt tagctatatg aattggtatc agcagaaaag cggcaccagc    1380
ccgaaacgtt ggatttatga taccagcaaa ctggcaagcg gtgttccggc acattttcgt    1440
ggtagcggta gcggcacctc atatagcctg accattagcg gtatggaagc agaagatgca    1500
gcaacctatt attgtcagca gtggtcaagc aatccgttta cctttggtag tggcaccaaa    1560
ctggaaatta atcgttag                                                  1578
```

<210> SEQ ID NO 306
<211> LENGTH: 241
<212> TYPE: PRT
<213> ORGANISM: Artificial Sequence
<220> FEATURE:
<223> OTHER INFORMATION: Antibody OKT3m scFv

<400> SEQUENCE: 306

```
Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45
```

```
Gly Tyr Ile Asn Pro Ser Arg Gly Tyr Thr Asn Tyr Asn Gln Lys Phe
         50                  55                  60
Lys Asp Lys Ala Thr Leu Thr Thr Asp Lys Ser Ser Thr Ala Tyr
 65                  70                  75                  80
Met Gln Leu Ser Ser Leu Thr Ser Glu Asp Ser Ala Val Tyr Tyr Cys
                 85                  90                  95
Ala Arg Tyr Tyr Asp Asp His Tyr Ser Leu Asp Tyr Trp Gly Gln Gly
             100                 105                 110
Thr Thr Leu Thr Val Ser Ser Gly Gly Gly Ser Gly Gly Gly
         115                 120                 125
Ser Gly Gly Gly Gly Ser Gln Ile Val Leu Thr Gln Ser Pro Ala Ile
    130                 135                 140
Met Ser Ala Ser Pro Gly Glu Lys Val Thr Met Thr Cys Ser Ala Ser
145                 150                 155                 160
Ser Ser Val Ser Tyr Met Asn Trp Tyr Gln Gln Lys Ser Gly Thr Ser
                165                 170                 175
Pro Lys Arg Trp Ile Tyr Asp Thr Ser Lys Leu Ala Ser Gly Val Pro
            180                 185                 190
Ala His Phe Arg Gly Ser Gly Ser Gly Thr Ser Tyr Ser Leu Thr Ile
        195                 200                 205
Ser Gly Met Glu Ala Glu Asp Ala Ala Thr Tyr Tyr Cys Gln Gln Trp
    210                 215                 220
Ser Ser Asn Pro Phe Thr Phe Gly Ser Gly Thr Lys Leu Glu Ile Asn
225                 230                 235                 240
Arg

<210> SEQ ID NO 307
<211> LENGTH: 723
<212> TYPE: DNA
<213> ORGANISM: Artificial Sequence
<220> FEATURE:
<223> OTHER INFORMATION: Antibody OKT3m scFv

<400> SEQUENCE: 307
caggttcagc tgcagcagag cggtgcagaa ctggcacgtc cgggtgcaag cgttaaaatg    60
agctgtaaag caagcggtta tacctttacc cgttatacca tgcattgggt taaacagcgt   120
ccgggtcagg gtctggaatg gattggttat atcaatccga ccgtggttta ccaactac    180
aaccagaaat caaagataa agcaaccctg accaccgata aaagcagcag caccgcctat   240
atgcagctga gcagcctgac ctcagaggat agcgcagttt attactgtgc acgctattat   300
gatgatcact atagcctgga ttattggggt cagggcacca ccctgaccgt tagcagcggt   360
ggtggtggta gtggtggcgg tggttcaggc ggtggcggta gccagattgt tctgacccag   420
agtccggcaa ttatgagcgc aagtccgggt gaaaaagtta ccatgacctg tagcgccagc   480
agcagcgtta gctatatgaa ttggtatcag cagaaaagcg gcaccagccc gaaacgttgg   540
atttatgata ccagcaaaact ggcaagcggt gttccggcac attttcgtgg tagcggtagc   600
ggcacctcat atagcctgac cattagcggt atggaagcag aagatgcagc aacctattat   660
tgtcagcagt ggtcaagcaa tccgtttacc tttggtagtg gcaccaaact ggaaattaat   720
cgt                                                                 723

<210> SEQ ID NO 308
<211> LENGTH: 107
<212> TYPE: PRT
<213> ORGANISM: Artificial Sequence
```

<220> FEATURE:
<223> OTHER INFORMATION: Antibody OKT3m scFv LV

<400> SEQUENCE: 308

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

Asn Trp Tyr Gln Gln Lys Ser Gly Thr Ser Pro Lys Arg Trp Ile Tyr
        35                  40                  45

Asp Thr Ser Lys Leu Ala Ser Gly Val Pro Ala His Phe Arg Gly Ser
    50                  55                  60

Gly Ser Gly Thr Ser Tyr Ser Leu Thr Ile Ser Gly Met Glu Ala Glu
65                  70                  75                  80

Asp Ala Ala Thr Tyr Tyr Cys Gln Gln Trp Ser Ser Asn Pro Phe Thr
                85                  90                  95

Phe Gly Ser Gly Thr Lys Leu Glu Ile Asn Arg
            100                 105

<210> SEQ ID NO 309
<211> LENGTH: 321
<212> TYPE: DNA
<213> ORGANISM: Artificial Sequence
<220> FEATURE:
<223> OTHER INFORMATION: Antibody OKT3m scFv LV

<400> SEQUENCE: 309
cagattgttc tgacccagag tccggcaatt atgagcgcaa gtccgggtga aaaagttacc      60
atgacctgta gcgccagcag cagcgttagc tatatgaatt ggtatcagca␣gaaaagcggc     120 accagcccga␣aacgttggat␣ttatgatacc␣agcaaactgg␣caagcggtgt␣tccggcacat     180 tttcgtggta␣gcggtagcgg␣cacctcatat␣agcctgacca␣ttagcggtat␣ggaagcagaa     240 gatgcagcaa␣cctattattg␣tcagcagtgg␣tcaagcaatc␣cgtttacctt␣tggtagtggc     300 accaaactgg␣aaattaatcg␣t                                               321

<210> SEQ ID NO 310
<211> LENGTH: 119
<212> TYPE: PRT
<213> ORGANISM: Artificial Sequence
<220> FEATURE:
<223> OTHER INFORMATION: Antibody OKT3m scFv Hv

<400> SEQUENCE: 310

Gln Val Gln Leu Gln Gln Ser Gly Ala Glu Leu Ala Arg Pro Gly Ala
1               5                   10                  15

Ser Val Lys Met Ser Cys Lys Ala Ser Gly Tyr Thr Phe Thr Arg Tyr
            20                  25                  30

Thr Met His Trp Val Lys Gln Arg Pro Gly Gln Gly Leu Glu Trp Ile
        35                  40                  45

Gly Tyr Ile Asn Pro Ser Arg Gly Tyr Thr Asn Tyr Asn Gln Lys Phe
    50                  55                  60

Lys Asp Lys Ala Thr Leu Thr Thr Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Tyr Tyr Asp Asp His Tyr Ser Leu Asp Tyr Trp Gly Gln Gly
            100                 105                 110

<210> SEQ ID NO 311
<211> LENGTH: 357
<212> TYPE: DNA
<213> ORGANISM: Artificial Sequence
<220> FEATURE:
<223> OTHER INFORMATION: Antibody OKT3m scFv Hv

<400> SEQUENCE: 311

```
caggttcagc tgcagcagag cggtgcagaa ctggcacgtc cgggtgcaag cgttaaaatg      60
agctgtaaag caagcggtta tacctttacc cgttatacca tgcattgggt taaacagcgt     120
ccgggtcagg gtctggaatg gattggttat atcaatccga gccgtggtta taccaactac     180
aaccagaaat tcaaagataa agcaaccctg accaccgata aagcagcag caccgcctat     240
atgcagctga gcagcctgac ctcagaggat agcgcagttt attactgtgc acgctattat     300
gatgatcact atagcctgga ttattggggt cagggcacca ccctgaccgt tagcagc       357
```

<210> SEQ ID NO 312
<211> LENGTH: 8
<212> TYPE: PRT
<213> ORGANISM: Artificial Sequence
<220> FEATURE:
<223> OTHER INFORMATION: cleavable moiety

<400> SEQUENCE: 312

Arg Pro Ser Pro Met Trp Ala Tyr
1               5

<210> SEQ ID NO 313
<211> LENGTH: 645
<212> TYPE: DNA
<213> ORGANISM: Artificial Sequence
<220> FEATURE:
<223> OTHER INFORMATION: C225v5 LIGHT CHAIN

<400> SEQUENCE: 313

```
cagatcttgc tgacccagag cccggtgatt ctgagcgtga gcccgggcga acgtgtgagc      60
tttagctgcc gcgcgagcca gagcattggc accaacattc attggtatca gcagcgcacc     120
aacggcagcc cgcgcctgct gattaaatat gcgagcgaaa gcattagcgg cattccgagc     180
cgctttagcg gcagcggcag cggcaccgat tttaccctga gcattaacag cgtggaaagc     240
gaagatattg cggattatta ttgccagcag aacaacaact ggccgaccac ctttggcgcg     300
ggcaccaaac tggaactgaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gttag                    645
```

<210> SEQ ID NO 314
<211> LENGTH: 214
<212> TYPE: PRT
<213> ORGANISM: Artificial Sequence
<220> FEATURE:
<223> OTHER INFORMATION: Multispecific activatable antibody
      3954-1204-C225v5-OKT3m-H-N

<400> SEQUENCE: 314

```
Asp Ile Leu Leu Thr Gln Ser Pro Val Ile Leu Ser Val Ser Pro Gly
1               5                   10                  15
Glu Arg Val Ser Phe Ser Cys Arg Ala Ser Gln Ser Ile Gly Thr Asn
            20                  25                  30
Ile His Trp Tyr Gln Gln Arg Thr Asn Gly Ser Pro Arg Leu Leu Ile
        35                  40                  45
Lys Tyr Ala Ser Glu Ser Ile Ser Gly Ile Pro Ser Arg Phe Ser Gly
    50                  55                  60
Ser Gly Ser Gly Thr Asp Phe Thr Leu Ser Ile Asn Ser Val Glu Ser
65                  70                  75                  80
Glu Asp Ile Ala Asp Tyr Tyr Cys Gln Gln Asn Asn Asn Trp Pro Thr
                85                  90                  95
Thr Phe Gly Ala Gly Thr Lys Leu Glu Leu Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210
```

<210> SEQ ID NO 315
<211> LENGTH: 1437
<212> TYPE: DNA
<213> ORGANISM: Artificial Sequence
<220> FEATURE:
<223> OTHER INFORMATION: Multispecific activatable antibody
      3954-1204-C225v5-OKT3m-H-N

<400> SEQUENCE: 315

```
gacatcttgc tgacccagag cccggtgatt ctgagcgtga gcccgggcga acgtgtgagc      60
tttagctgcc gcgcgagcca gagcattggc accaacattc attggtatca gcagcgcacc     120
aacggcagcc cgcgcctgct gattaaatat gcgagcgaaa gcattagcgg cattccgagc     180
cgctttagcg gcagcggcag cggcaccgat tttaccctga gcattaacag cgtggaaagc     240
gaagatattg cggattatta ttgccagcag aacaacaact ggccgaccac ctttggcgcg     300
ggcaccaaac tggaactgaa acgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg     540
ctgagcaaag cagactacga gaaacacaaa gtctacgcct gcgaagtcac ccatcagggc     600
ctgagctcgc ccgtcacaaa gagcttcaac aggggagagt gttgaggtgg atctggaggt     660
ggcggttcag gctctggcgg aggctcaggt ggtggaggat caggcggagg tcaggttcag     720
```

```
ctgcagcaga gcggtgcaga actggcacgt ccgggtgcaa gcgttaaaat gagctgtaaa    780
gcaagcggtt ataccttac ccgttatacc atgcattggg ttaaacagcg tccgggtcag    840
ggtctggaat ggattggtta tatcaatccg agccgtggtt ataccaacta caaccagaaa    900
ttcaaagata aagcaaccct gaccaccgat aaaagcagca gcaccgccta tatgcagctg    960
agcagcctga cctcagagga tagcgcagtt tattactgtg cacgctatta tgatgatcac   1020
tatagcctgg attattgggg tcagggcacc accctgaccg ttagcagcgg tggtggtggt   1080
agtggtggcg gtggttcagg cggtggcggt agccagattg ttctgaccca gagtccggca   1140
attatgagcg caagtccggg tgaaaaagtt accatgacct gtagcgccag cagcagcgtt   1200
agctatatga attggtatca gcagaaaagc ggcaccagcc cgaaacgttg gatttatgat   1260
accagcaaac tggcaagcgg tgttccggca cattttcgtg gtagcggtag cggcacctca   1320
tatagcctga ccattagcgg tatggaagca gaagatgcag caacctatta ttgtcagcag   1380
tggtcaagca atccgtttac ctttggtagt ggcaccaaac tggaaattaa tcgttag      1437
```

<210> SEQ ID NO 316
<211> LENGTH: 8
<212> TYPE: PRT
<213> ORGANISM: Artificial Sequence
<220> FEATURE:
<223> OTHER INFORMATION: cleavable moiety

<400> SEQUENCE: 316

Ile Ser Ser Gly Leu Leu Ser Ser
1               5

<210> SEQ ID NO 317
<211> LENGTH: 8
<212> TYPE: PRT
<213> ORGANISM: Artificial Sequence
<220> FEATURE:
<223> OTHER INFORMATION: cleavable moiety

<400> SEQUENCE: 317

Gln Asn Gln Ala Leu Arg Met Ala
1               5

<210> SEQ ID NO 318
<211> LENGTH: 8
<212> TYPE: PRT
<213> ORGANISM: Artificial Sequence
<220> FEATURE:
<223> OTHER INFORMATION: cleavable moiety

<400> SEQUENCE: 318

Ala Gln Asn Leu Leu Gly Met Val
1               5

<210> SEQ ID NO 319
<211> LENGTH: 8
<212> TYPE: PRT
<213> ORGANISM: Artificial Sequence
<220> FEATURE:
<223> OTHER INFORMATION: cleavable moiety

<400> SEQUENCE: 319

Ser Thr Phe Pro Phe Gly Met Phe
1               5

<210> SEQ ID NO 320
<211> LENGTH: 8

```
<212> TYPE: PRT
<213> ORGANISM: Artificial Sequence
<220> FEATURE:
<223> OTHER INFORMATION: cleavable moiety

<400> SEQUENCE: 320

Pro Val Gly Tyr Thr Ser Ser Leu
1               5

<210> SEQ ID NO 321
<211> LENGTH: 8
<212> TYPE: PRT
<213> ORGANISM: Artificial Sequence
<220> FEATURE:
<223> OTHER INFORMATION: cleavable moiety

<400> SEQUENCE: 321

Asp Trp Leu Tyr Trp Pro Gly Ile
1               5

<210> SEQ ID NO 322
<211> LENGTH: 8
<212> TYPE: PRT
<213> ORGANISM: Artificial Sequence
<220> FEATURE:
<223> OTHER INFORMATION: cleavable moiety

<400> SEQUENCE: 322

Met Ile Ala Pro Val Ala Tyr Arg
1               5

<210> SEQ ID NO 323
<211> LENGTH: 8
<212> TYPE: PRT
<213> ORGANISM: Artificial Sequence
<220> FEATURE:
<223> OTHER INFORMATION: cleavable moiety

<400> SEQUENCE: 323

Trp Ala Thr Pro Arg Pro Met Arg
1               5

<210> SEQ ID NO 324
<211> LENGTH: 8
<212> TYPE: PRT
<213> ORGANISM: Artificial Sequence
<220> FEATURE:
<223> OTHER INFORMATION: cleavable moiety

<400> SEQUENCE: 324

Phe Arg Leu Leu Asp Trp Gln Trp
1               5

<210> SEQ ID NO 325
<211> LENGTH: 8
<212> TYPE: PRT
<213> ORGANISM: Artificial Sequence
<220> FEATURE:
<223> OTHER INFORMATION: cleavable moiety

<400> SEQUENCE: 325

Leu Lys Ala Ala Pro Arg Trp Ala
1               5

<210> SEQ ID NO 326
<211> LENGTH: 8
<212> TYPE: PRT
```

```
<213> ORGANISM: Artificial Sequence
<220> FEATURE:
<223> OTHER INFORMATION: cleavable moiety

<400> SEQUENCE: 326

Gly Pro Ser His Leu Val Leu Thr
1               5

<210> SEQ ID NO 327
<211> LENGTH: 8
<212> TYPE: PRT
<213> ORGANISM: Artificial Sequence
<220> FEATURE:
<223> OTHER INFORMATION: cleavable moiety

<400> SEQUENCE: 327

Leu Pro Gly Gly Leu Ser Pro Trp
1               5

<210> SEQ ID NO 328
<211> LENGTH: 8
<212> TYPE: PRT
<213> ORGANISM: Artificial Sequence
<220> FEATURE:
<223> OTHER INFORMATION: cleavable moiety

<400> SEQUENCE: 328

Met Gly Leu Phe Ser Glu Ala Gly
1               5

<210> SEQ ID NO 329
<211> LENGTH: 8
<212> TYPE: PRT
<213> ORGANISM: Artificial Sequence
<220> FEATURE:
<223> OTHER INFORMATION: cleavable moiety

<400> SEQUENCE: 329

Ser Pro Leu Pro Leu Arg Val Pro
1               5

<210> SEQ ID NO 330
<211> LENGTH: 8
<212> TYPE: PRT
<213> ORGANISM: Artificial Sequence
<220> FEATURE:
<223> OTHER INFORMATION: cleavable moiety

<400> SEQUENCE: 330

Arg Met His Leu Arg Ser Leu Gly
1               5

<210> SEQ ID NO 331
<211> LENGTH: 8
<212> TYPE: PRT
<213> ORGANISM: Artificial Sequence
<220> FEATURE:
<223> OTHER INFORMATION: cleavable moiety

<400> SEQUENCE: 331

Leu Ala Ala Pro Leu Gly Leu Leu
1               5

<210> SEQ ID NO 332
<211> LENGTH: 8
<212> TYPE: PRT
<213> ORGANISM: Artificial Sequence
```

```
<220> FEATURE:
<223> OTHER INFORMATION: cleavable moiety

<400> SEQUENCE: 332

Ala Val Gly Leu Leu Ala Pro Pro
1               5

<210> SEQ ID NO 333
<211> LENGTH: 8
<212> TYPE: PRT
<213> ORGANISM: Artificial Sequence
<220> FEATURE:
<223> OTHER INFORMATION: cleavable moiety

<400> SEQUENCE: 333

Leu Leu Ala Pro Ser His Arg Ala
1               5

<210> SEQ ID NO 334
<211> LENGTH: 8
<212> TYPE: PRT
<213> ORGANISM: Artificial Sequence
<220> FEATURE:
<223> OTHER INFORMATION: cleavable moiety

<400> SEQUENCE: 334

Pro Ala Gly Leu Trp Leu Asp Pro
1               5

<210> SEQ ID NO 335
<211> LENGTH: 7
<212> TYPE: PRT
<213> ORGANISM: Artificial Sequence
<220> FEATURE:
<223> OTHER INFORMATION: cleavable moiety

<400> SEQUENCE: 335

Ile Ser Ser Gly Leu Ser Ser
1               5

<210> SEQ ID NO 336
<211> LENGTH: 449
<212> TYPE: PRT
<213> ORGANISM: Artificial Sequence
<220> FEATURE:
<223> OTHER INFORMATION: Antibody C225v5 N297Q heavy chain

<400> SEQUENCE: 336

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Gln Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala Ala Ser Thr Lys Gly Pro Ser Val Phe
```

|     |     |     |     | 115 |     |     |     |     | 120 |     |     |     |     | 125 |     |     |     |
|-----|-----|-----|-----|-----|-----|-----|-----|-----|-----|-----|-----|-----|-----|-----|-----|-----|-----|

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
                180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
            210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Gln Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
            435                 440                 445

Lys

<210> SEQ ID NO 337
<211> LENGTH: 1350
<212> TYPE: DNA
<213> ORGANISM: Artificial Sequence
<220> FEATURE:
<223> OTHER INFORMATION: Antibody C225v5 N297Q heavy chain

<400> SEQUENCE: 337
caggtgcagc tgaaacagag cggcccgggc ctggtgcagc cgagccagag cctgagcatt    60
acctgcaccg tgagcggctt tagcctgacc aactatggcg tgcattgggt gcgccagagc   120
ccgggcaaag gcctggaatg gctgggcgtg atttggagcg gcggcaacac cgattataac   180

```
acccogttta ccagccgcct gagcattaac aaagataaca gcaaaagcca ggtgttttt      240 aaaatgaaca gcctgcaaag ccaggatacc gcgatttatt attgcgcgcg cgcgctgacc      300
tattatgatt atgaatttgc gtattggggc cagggcaccc tggtgaccgt gagcgcggct      360
agcaccaagg gcccatcggt cttccccctg gcaccctcct ccaagagcac ctctgggggc      420
acagcggccc tgggctgcct ggtcaaggac tacttccccg aaccggtgac ggtgtcgtgg      480
aactcaggcg ccctgaccag cggcgtgcac accttcccgg ctgtcctaca gtcctcagga      540
ctctactccc tcagcagcgt ggtgaccgtg ccctccagca gcttgggcac ccagacctac      600
atctgcaacg tgaatcacaa gcccagcaac accaaggtgg acaagaaagt tgagcccaaa      660
tcttgtgaca aaactcacac atgcccaccg tgcccagcac ctgaactcct ggggggaccg      720
tcagtcttcc tcttcccccc aaaacccaag gacaccctca tgatctcccg gacccctgag      780
gtcacatgcg tggtggtgga cgtgagccac gaagaccctg aggtcaagtt caactggtac      840
gtggacggcg tggaggtgca taatgccaag acaaagccgc gggaggagca gtaccagagc      900
acgtaccgtg tggtcagcgt cctcaccgtc ctgcaccagg actggctgaa tggcaaggag      960
tacaagtgca aggtctccaa caaagccctc ccagccccca tcgagaaaac catctccaaa     1020
gccaaagggc agccccgaga accacaggtg tacaccctgc cccatcccg ggaggagatg      1080 accaagaacc aggtcagcct gacctgcctg gtcaaaggct tctatcccag cgacatcgcc     1140
gtggagtggg agagcaatgg gcagccggag aacaactaca agaccacgcc tcccgtgctg     1200
gactccgacg gctccttctt cctctacagc aagctcaccg tggacaagag caggtggcag     1260
caggggaacg tcttctcatg ctccgtgatg catgaggctc tgcacaacca ctacacgcag     1320
aagagcctct ccctgtctcc gggtaaatga                                      1350
```

<210> SEQ ID NO 338
<211> LENGTH: 21
<212> TYPE: PRT
<213> ORGANISM: Artificial Sequence
<220> FEATURE:
<223> OTHER INFORMATION: masking moiety

<400> SEQUENCE: 338

Gln Gly Gln Ser Gly Gln Cys Asn Ile Trp Leu Val Gly Gly Asp Cys
1               5                   10                  15
Arg Gly Trp Gln Gly
            20

<210> SEQ ID NO 339
<211> LENGTH: 7
<212> TYPE: PRT
<213> ORGANISM: Artificial Sequence
<220> FEATURE:
<223> OTHER INFORMATION: masking moiety

<400> SEQUENCE: 339

Cys Ile Ser Pro Arg Gly Cys
1               5

MULTISPECIFIC ANTIBODIES, MULTISPECIFIC ACTIVATABLE ANTIBODIES AND METHODS OF USING THE SAME

RELATED APPLICATIONS

This application claims the benefit of U.S. Provisional Application No. 61/858,402, filed Jul. 25, 2013, the contents of which are incorporated herein by reference in their entirety.

INCORPORATION OF SEQUENCE LISTING

The contents of the text file named "CYTM_025_001US_SeqList_ST25.txt", which was created on Oct. 17, 2014 and is 284 KB in size, are hereby incorporated by reference in their entirety.

FIELD OF THE INVENTION

The invention relates generally to multispecific antibodies and to multispecific activatable antibodies that specifically bind to two or more different targets or epitopes, as well as to methods of making and using these multispecific antibodies and/or multispecific activatable antibodies in a variety of therapeutic, diagnostic and prophylactic indications.

BACKGROUND OF THE INVENTION

Monoclonal antibodies have emerged as molecules for therapeutic intervention in a variety of disorders. However, targeting or neutralizing a single protein is not always sufficient for effective treatment of certain disorders, which limits the therapeutic use of monospecific monoclonal antibodies. Moreover, antibody-based therapies have proven effective treatments for some diseases but in some cases, toxicities due to broad target expression have limited their therapeutic effectiveness. In addition, antibody-based therapies have exhibited other limitations such as rapid clearance from the circulation following administration.

Accordingly, there exists a need for antibodies and therapeutics that enable targeting of multiple targets and/or multiple epitopes with a single molecule and also provide for increased selectivity for the intended targets and for a reduction of adverse effects upon administration.

SUMMARY OF THE INVENTION

The present disclosure provides multispecific antibodies and multispecific activatable antibodies. The multispecific antibodies provided herein are antibodies that recognize two or more different antigens or epitopes. The multispecific activatable antibodies provided herein are multispecific antibodies that include at least one masking moiety (MM) linked to at least one antigen- or epitope-binding domain of the multispecific antibody such that coupling of the MM reduces the ability of the antigen- or epitope-binding domain to bind its target. In some embodiments, the MM is coupled to the antigen- or epitope-binding domain of the multispecific antibody via a cleavable moiety (CM) that functions as a substrate for a protease. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

In some embodiments, the multispecific antibodies and/or multispecific activatable antibodies are designed to engage immune effector cells, also referred to herein as immune-effector engaging multispecific antibodies and/or immune-effector engaging multispecific activatable antibodies. In some embodiments, the multispecific antibodies and/or multispecific activatable antibodies are designed to engage leukocytes, also referred to herein as leukocyte engaging multispecific antibodies and/or leukocyte engaging multispecific activatable antibodies. In some embodiments, the multispecific antibodies and/or multispecific activatable antibodies are designed to engage T cells, also referred to herein as T-cell engaging multispecific antibodies and/or T-cell engaging multispecific activatable antibodies. In some embodiments, the multispecific antibodies and/or multispecific activatable antibodies engage a surface antigen on a leukocyte, such as on a T cell, on a natural killer (NK) cell, on a myeloid mononuclear cell, on a macrophage, and/or on another immune effector cell. In some embodiments, the immune effector cell is a leukocyte. In some embodiments, the immune effector cell is a T cell. In some embodiments, the immune effector cell is a NK cell. In some embodiments, the immune effector cell is a mononuclear cell, such as a myeloid mononuclear cell. In some embodiments, the multispecific antibodies and/or multispecific activatable antibodies are designed to bind or otherwise interact with more than one target and/or more than one epitope, also referred to herein as multi-antigen targeting antibodies and/or multi-antigen targeting activatable antibodies. As used herein, the terms "target" and "antigen" are used interchangeably.

In some embodiments, the immune effector cell engaging multispecific antibodies include a targeting antibody or antigen-binding fragment thereof and an immune effector cell engaging antibody or antigen-binding portion thereof. In some embodiments, the immune effector cell engaging multispecific antibodies include a cancer targeting antibody or antigen-binding fragment thereof and an immune effector cell engaging antibody or antigen-binding portion thereof. In some embodiments, the immune effector cell engaging multispecific antibodies include a cancer targeting IgG antibody or antigen-binding fragment thereof and an immune effector cell engaging scFv. In some embodiments, the immune effector cell is a leukocyte. In some embodiments, the immune effector cell is a T cell. In some embodiments, the immune effector cell is a NK cell. In some embodiments, the immune effector cell is a myeloid mononuclear cell.

In some embodiments, the T-cell engaging multispecific antibodies include a targeting antibody or antigen-binding fragment thereof and a T-cell engaging antibody or antigen-binding portion thereof. In some embodiments, the T-cell engaging multispecific antibodies include a cancer targeting antibody or antigen-binding fragment thereof and a T-cell engaging antibody or antigen-binding portion thereof. In some embodiments, the T-cell engaging multispecific antibodies include a cancer targeting IgG antibody or antigen-binding fragment thereof and a T-cell engaging scFv. In some embodiments, the T-cell engaging multispecific antibody includes an anti-CD3 epsilon (CD3ε, also referred to herein as CD3e and CD3) scFv and a targeting antibody or antigen-binding fragment thereof. In some embodiments, the T-cell engaging multispecific antibody includes an anti-CD3ε scFv and a cancer targeting antibody or antigen-binding fragment thereof. In some embodiments, the T-cell engaging multispecific antibody includes an anti-CD3ε scFv and a cancer targeting IgG antibody or antigen-binding fragment thereof. In some embodiments, the T-cell engaging multispecific antibody includes an anti-CD3 epsilon (CD3ε)

scFv that is derived from OKT3. In some embodiments, the T-cell engaging multispecific antibody includes an anti-CTLA-4 scFv.

In some embodiments, immune effector cell engaging multispecific activatable antibodies of the disclosure include a targeting antibody or antigen-binding fragment thereof and an immune effector cell engaging antibody or antigen-binding portion thereof, where at least one of the targeting antibody or antigen-binding fragment thereof and/or the immune effector cell engaging antibody or antigen-binding portion thereof is masked. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the immune effector cell engaging antibody or antigen binding fragment thereof includes a first antibody or antigen-binding fragment thereof (AB1) that binds a first, immune effector cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the non-immune effector cell engaging antibody is a cancer targeting antibody. In some embodiments the non-immune cell effector antibody is an IgG. In some embodiments the immune effector cell engaging antibody is a scFv. In some embodiments the targeting antibody (e.g., non-immune cell effector antibody) is an IgG and the immune effector cell engaging antibody is a scFv. In some embodiments, the immune effector cell is a leukocyte. In some embodiments, the immune effector cell is a T cell. In some embodiments, the immune effector cell is a NK cell. In some embodiments, the immune effector cell is a myeloid mononuclear cell.

In some embodiments, T-cell engaging multispecific activatable antibodies of the disclosure include a targeting antibody or antigen-binding fragment thereof and a T-cell engaging antibody or antigen-binding portion thereof, where at least one of the targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibodies include a cancer targeting antibody or antigen-binding fragment thereof and a T-cell engaging antibody or antigen-binding portion thereof, where at least one of the cancer targeting antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibodies include a cancer targeting IgG antibody or antigen-binding fragment thereof and a T-cell engaging scFv, where at least one of the cancer targeting IgG antibody or antigen-binding fragment thereof and/or the T-cell engaging antibody or antigen-binding portion thereof is masked. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the T-cell engaging antibody or antigen binding fragment thereof includes a first antibody or antigen-binding fragment thereof (AB1) that binds a first, T-cell engaging target, where the AB1 is attached to a masking moiety (MM1) such that coupling of the MM1 reduces the ability of the AB1 to bind the first target, and the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments of an immune effector cell engaging multispecific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA. In some embodiments, the antigen is a stimulatory receptor present on the surface of a T cell or NK cell; examples of such stimulatory receptors include, but are not limited to, CD3, CD27, CD28, CD137 (also referred to as 4-1BB), GITR, HVEM, ICOS, NKG2D, and OX40. In some embodiments, the antigen is an inhibitory receptor present on the surface of a T-cell; examples of such inhibitory receptors include, but are not limited to, BTLA, CTLA-4, LAG3, PD-1, TIGIT, TIM3, and NK-expressed KIRs. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9.

One embodiment of the disclosure is a multispecific activatable antibody that is activatable in a cancer microenvironment and that includes an antibody, for example a IgG or scFv, directed to a tumor target and an agonist antibody, for example an IgG or scFv, directed to a co-stimulatory receptor expressed on the surface of an activated T cell or NK cell, wherein at least one of the cancer target antibody and/or agonist antibody is masked. Examples of co-stimulatory receptors include, but are not limited to, CD27, CD137, GITR, HVEM, NKG2D, and OX40. In this embodiment, the multispecific activatable antibody, once activated by tumor-associated proteases, would effectively crosslink and activate the T cell or NK cell expressed co-stimulatory receptors in a tumor-dependent manner to enhance the activity of T cells that are responding to any tumor antigen via their endogenous T cell antigen or NK-activating receptors. The activation-dependent nature of these T cell or NK cell costimulatory receptors would focus the activity of the activated multispecific activatable antibody to tumor-specific T cells, without activating all T cells independent of their antigen specificity. In one embodiment, at least the co-stimulatory receptor antibody of the multispecific activatable antibody is masked to prevent activation of autoreactive T cells that may be present in tissues that also express the antigen recognized by the tumor target-directed antibody in the multispecific activatable antibody, but whose activity is restricted by lack of co-receptor engagement.

One embodiment of the disclosure is a multispecific activatable antibody that is activatable in a disease characterized by T cell overstimulation, such as, but not limited to, an autoimmune disease or inflammatory disease microenvironment. Such a multispecific activatable antibody includes an antibody, for example a IgG or scFv, directed to a target comprising a surface antigen expressed in a tissue targeted by a T cell in autoimmune or inflammatory disease and an antibody, for example a IgG or scFv, directed to an inhibitory receptor expressed on the surface of a T cell or NK cell, wherein at least one of the disease tissue target antibody and/or T cell inhibitory receptor antibody is masked. Examples of inhibitory receptors include, but are not limited to, BTLA, CTLA-4, LAG3, PD-1, TIGIT, TIM3, and NK-expressed KIRs. Examples of a tissue antigen targeted by T cells in autoimmune disease include, but are not limited to, a surface antigen expressed on myelin or nerve cells in multiple sclerosis or a surface antigen expressed on pancreatic islet cells in Type 1 diabetes. In this embodiment, the multispecific activatable antibody when localized in the tissue under autoimmune attack or inflammation is activated and co-engages the T cell or NK cell inhibitory receptor to suppress the activity of autoreactive T cells responding to any disease tissue-targeted antigens via their endogenous TCR or activating receptors. In one embodiment, at least one or multiple antibodies are masked to prevent suppression of desired T cell responses in non-disease tissues where the target antigen may also be expressed.

In some embodiments, the T-cell engaging multispecific activatable antibody includes an anti-CD3 epsilon (CD3ε, also referred to herein as CD3e and CD3) scFv and a targeting antibody or antigen-binding fragment thereof, where at least one of the anti-CD3ε scFv and/or the targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an anti-CD3ε scFv and a cancer targeting antibody or antigen-binding fragment thereof, where at least one of the anti-CD3ε scFv and/or the cancer targeting antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CD3ε scFv and a cancer targeting IgG antibody or antigen-binding fragment thereof, where at least one of the anti-CD3ε scFv and/or the cancer targeting IgG antibody or antigen-binding portion thereof is masked. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the CD3ε scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody IgG or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CD3 epsilon (CD3ε) scFv that is derived from OKT3, where at least one of the targeting antibody or antigen-binding fragment thereof and/or the OKT3 scFv or OKT3-derived scFv is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an OKT3 scFv or OKT3-derived scFv and a cancer targeting antibody or antigen-binding fragment thereof, where at least one of the OKT3 scFv or OKT3-derived scFv and/or the cancer targeting antibody or antigen-binding portion thereof is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an OKT3 scFv or OKT3-derived scFv and a cancer targeting IgG antibody or antigen-binding fragment thereof, where at least one of the OKT3 scFv or OKT3-derived scFv and/or the cancer targeting IgG antibody or antigen-binding portion thereof is masked. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε. In some embodiments, the cancer targeting IgG antibody or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target. In some embodiments, the OKT3 scFv or OKT3-derived scFv includes a first antibody or antigen-binding fragment thereof (AB1) that binds CD3ε, where the AB1 is attached to a masking moiety (MM1) such that coupling of the MM1 reduces the ability of the AB1 to bind CD3ε, and the cancer targeting antibody IgG or antigen-binding fragment thereof includes a second antibody or fragment thereof that includes a second antibody or antigen-binding fragment thereof (AB2) that binds a second, cancer-related target, where the AB2 is attached to a masking moiety (MM2) such that coupling of the MM2 reduces the ability of the AB2 to bind the second, cancer-related target.

In some embodiments, the T-cell engaging multispecific activatable antibody includes an anti-CTLA-4 scFv, where at least one of the targeting antibody or antigen-binding fragment thereof and/or the anti-CTLA-4 scFv is masked. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4. In some embodiments, the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4, and the targeting antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the T-cell engaging multispecific activatable antibody includes an anti-CTLA-4 scFv and a targeting IgG antibody or antigen-binding fragment thereof, where at least one of the anti-CTLA-4 scFv and/or the targeting IgG antibody or antigen-binding portion thereof is masked. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4. In some embodiments, the targeting IgG antibody or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the anti-CTLA-4 scFv includes a first antibody or antigen-binding fragment thereof (AB1) that binds CTLA-4, where the AB1 is attached to a masking moiety (MM1) such that coupling of the MM1 reduces the ability of the AB1 to bind CTLA-4, and the targeting antibody IgG or antigen-binding fragment thereof includes a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target.

In some embodiments, the multi-antigen targeting antibodies and/or multi-antigen targeting activatable antibodies include at least a first antibody or antigen-binding fragment thereof that binds a first target and/or first epitope and a second antibody or antigen-binding fragment thereof that binds a second target and/or a second epitope. In some embodiments, the multi-antigen targeting antibodies and/or multi-antigen targeting activatable antibodies bind two or more different targets. In some embodiments, the multi-antigen targeting antibodies and/or multi-antigen targeting activatable antibodies bind two or more different epitopes on the same target. In some embodiments, the multi-antigen targeting antibodies and/or multi-antigen targeting activatable antibodies bind a combination of two or more different targets and two or more different epitopes on the same target.

Various embodiments of multispecific activatable antibodies of the disclosure are shown in FIGS. 3A, and 5-9. In some embodiments, a multispecific activatable antibody comprising an IgG has the IgG variable domains masked. In some embodiments, a multispecific activatable antibody comprising a scFv has the scFv domains masked. In some embodiments, a multispecific activatable antibody has both IgG variable domains and scFv domains, where at least one of the IgG variable domains is coupled to a masking moiety. In some embodiments, a multispecific activatable antibody has both IgG variable domains and scFv domains, where at least one of the scFv domains is coupled to a masking moiety. In some embodiments, a multispecific activatable antibody has both IgG variable domains and scFv domains, where at least one of the IgG variable domains is coupled to a masking moiety and at least one of the scFv domains is coupled to a masking moiety. In some embodiments, a multispecific activatable antibody has both IgG variable domains and scFv domains, where each of the IgG variable domains and the scFv domains is coupled to its own masking moiety. In some embodiments, one antibody domain of a multispecific activatable antibody has specificity for a target antigen and another antibody domain has specificity for a T-cell surface antigen. In some embodiments, one antibody domain of a multispecific activatable antibody has specificity for a target antigen and another antibody domain has specificity for another target antigen. In some embodiments, one antibody domain of a multispecific activatable antibody has specificity for an epitope of a target antigen and another antibody domain has specificity for another epitope of the target antigen.

In a multispecific activatable antibody, a scFv can be fused to the carboxyl terminus of the heavy chain of an IgG activatable antibody, to the carboxyl terminus of the light chain of an IgG activatable antibody, or to the carboxyl termini of both the heavy and light chains of an IgG activatable antibody. In a multispecific activatable antibody, a scFv can be fused to the amino terminus of the heavy chain of an IgG activatable antibody, to the amino terminus of the light chain of an IgG activatable antibody, or to the amino termini of both the heavy and light chains of an IgG activatable antibody. In a multispecific activatable antibody, a scFv can be fused to any combination of one or more carboxyl termini and one or more amino termini of an IgG activatable antibody. In some embodiments, a masking moiety (MM) linked to a cleavable moiety (CM) is attached to and masks an antigen binding domain of the IgG. In some embodiments, a masking moiety (MM) linked to a cleavable moiety (CM) is attached to and masks an antigen binding domain of at least one scFv. In some embodiments, a masking moiety (MM) linked to a cleavable moiety (CM) is attached to and masks an antigen binding domain of an IgG and a masking moiety (MM) linked to a cleavable moiety (CM) is attached to and masks an antigen binding domain of at least one scFv.

The disclosure provides examples of multispecific activatable antibody structures which include, but are not limited to, the following: (VL-CL)$_2$:(VH-CH1-CH2-CH3-L4-VH*-L3-VL*-L2-CM-L1-MM)$_2$; (VL-CL)$_2$:(VH-CH1-CH2-CH3-L4-VL*-L3-VH*-L2-CM-L1-MM)$_2$; (MM-L1-CM-L2-VL-CL)$_2$:(VH-CH1-CH2-CH3-L4-VH*-L3-VL*)$_2$; (MM-L1-CM-L2-VL-CL)$_2$:(VH-CH1-CH2-CH3-L4-VL*-L3-VH*)$_2$; (VL-CL)$_2$:(MM-L1-CM-L2-VL*-L3-VH*-L4-VH-CH1-CH2-CH3)$_2$; (VL-CL)$_2$:(MM-L1-CM-L2-VH*-L3-VL*-L4-VH-CH1-CH2-CH3)$_2$; (MM-L1-CM-L2-VL-CL)$_2$:(VL*-L3-VH*-L4-VH-CH1-CH2-CH3)$_2$; (MM-L1-CM-L2-VL-CL)$_2$:(VH*-L3-VL*-L4-VH-CH1-

CH2-CH3)$_2$; (VL-CL-L4-VH*-L3-VL*-L2-CM-L1-MM)$_2$: (VH-CH1-CH2-CH3)$_2$; (VL-CL-L4-VL*-L3-VH*-L2-CM-L1-MM)$_2$: (VH-CH1-CH2-CH3)$_2$; (MM-L1-CM-L2-VL*-L3-VH*-L4-VL-CL)$_2$:(VH-CH1-CH2-CH3)$_2$; (MM-L1-CM-L2-VH*-L3-VL*-L4-VL-CL)$_2$:(VH-CH1-CH2-CH3)$_2$; (VL-CL-L4-VH*-L3-VL*-L2-CM-L1-MM)$_2$: (MM-L1-CM-L2-VL*-L3-VH*-L4-VH-CH1-CH2-CH3)$_2$; (VL-CL-L4-VH*-L3-VL*-L2-CM-L1-MM)$_2$: (MM-L1-CM-L2-VH*-L3-VL*-L4-VH-CH1-CH2-CH3)$_2$; (VL-CL-L4-VL*-L3-VH*-L2-CM-L1-MM)$_2$: (MM-L1-CM-L2-VL*-L3-VH*-L4-VH-CH1-CH2-CH3)$_2$; (VL-CL-L4-VL*-L3-VH*-L2-CM-L1-MM)$_2$: (MM-L1-CM-L2-VH*-L3-VL*-L4-VH-CH1-CH2-CH3)$_2$; (VL-CL-L4-VH*-L3-VL*)$_2$: (MM-L1-CM-L2-VL*-L3-VH*-L4-VH-CH1-CH2-CH3)$_2$; (VL-CL-L4-VH*-L3-VL*)$_2$: (MM-L1-CM-L2-VH*-L3-VL*-L4-VH-CH1-CH2-CH3)$_2$; (VL-CL-L4-VL*-L3-VH*)$_2$: (MM-L1-CM-L2-VL*-L3-VH*-L4-VH-CH1-CH2-CH3)$_2$; (VL-CL-L4-VL*-L3-VH*)$_2$: (MM-L1-CM-L2-VH*-L3-VL*-L4-VH-CH1-CH2-CH3)$_2$; (VL-CL-L4-VH*-L3-VL*-L2-CM-L1-MM)$_2$: (VL*-L3-VH*-L4-VH-CH1-CH2-CH3)$_2$; (VL-CL-L4-VH*-L3-VL*-L2-CM-L1-MM)$_2$: (VH*-L3-VL*-L4-VH-CH1-CH2-CH3)$_2$; (VL-CL-L4-VL*-L3-VH*-L2-CM-L1-MM)$_2$: (VL*-L3-VH*-L4-VH-CH1-CH2-CH3)$_2$; or (VL-CL-L4-VL*-L3-VH*-L2-CM-L1-MM)$_2$: (VH*-L3-VL*-L4-VH-CH1-CH2-CH3)$_2$, wherein: VL and VH represent the light and heavy variable domains of the first specificity, contained in the IgG; VL* and VH* represent the variable domains of the second specificity, contained in the scFv; L1 is a linker peptide connecting the masking moiety (MM) and the cleavable moiety (CM); L2 is a linker peptide connecting the cleavable moiety (CM), and the antibody; L3 is a linker peptide connecting the variable domains of the scFv; L4 is a linker peptide connecting the antibody of the first specificity to the antibody of the second specificity; CL is the light-chain constant domain; and CH1, CH2, CH3 are the heavy chain constant domains. The first and second specificities may be toward any antigen or epitope.

In some embodiments of a T-cell engaging multispecific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory (also referred to herein as activating) or inhibitory receptor present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137 (also referred to as TNFRSF9), CTLA-4, GITR, HVEM, ICOS, LAG3, NKG2D, OX40, PD-1, TIGIT, TIM3, or VISTA. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9. In some embodiments of a multi-antigen targeting activatable antibody, one antigen is selected from the group of targets listed in Table 1, and another antigen is selected from the group of targets listed in Table 1.

In some embodiments, the targeting antibody is an anti-EGFR antibody. In some embodiments, the targeting antibody is C225v5, which is specific for binding to EGFR. In some embodiments, the targeting antibody is C225, which is specific for binding to EGFR. In some embodiments, the targeting antibody is C225v4, which is specific for binding to EGFR. In some embodiments, the targeting antibody is C225v6, which is specific for binding to EGFR. In some embodiments, the targeting antibody is an anti-Jagged antibody. In some embodiments, the targeting antibody is 4D11, which is specific for binding to human and mouse Jagged 1 and Jagged 2. In some embodiments, the targeting antibody is 4D11v2, which is specific for binding to human and mouse Jagged 1 and Jagged 2.

In some embodiments, the targeting antibody can be in the form an activatable antibody. In some embodiments, the scFv(s) can be in the form of a Pro-scFv (see, e.g., WO 2009/025846, WO 2010/081173).

In some embodiments, the scFv is specific for binding CD3ε, and is or is derived from an antibody or fragment thereof that binds CD3ε, e.g., CH2527, FN18, H2C, OKT3, 2C11, UCHT1, or V9. In some embodiments, the scFv is specific for binding CTLA-4 (also referred to herein as CTLA and CTLA4).

In some embodiments, the anti-CD3ε scFv includes a sequence selected from the group consisting of those sequences shown in Table 7 and/or in Example 5. In some embodiments, the anti-CD3ε scFv includes an amino acid sequence that is at least 90%, 91%, 92%, 93%, 94%, 95%, 96%, 97%, 98%, 99% or more identical to an amino acid sequence selected from the group consisting of those sequences shown in Table 7 and/or in Example 5.

In some embodiments, the scFv is specific for binding one or more T-cells, one or more NK-cells and/or one or more macrophages. In some embodiments, the scFv is specific for binding a target selected from the group consisting of B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA.

In some embodiments, the multispecific antibodies, multispecific activatable antibodies, conjugated multispecific antibodies and/or conjugated multispecific activatable antibodies provided herein include at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 that sequence includes at least the amino acid sequence SYAMS (SEQ ID NO: 6); a VH CD2 sequence that includes at least the amino acid sequence SIDPEGRQTYYADSVKG (SEQ ID NO: 7); a VH CDR3 sequence that includes at least the amino acid sequence DIGGRSAFDY (SEQ ID NO: 8), and combinations thereof.

In some embodiments, the multispecific antibodies, multispecific activatable antibodies, conjugated multispecific antibodies and/or conjugated multispecific activatable antibodies provided herein include at least a first antibody or antigen binding fragment thereof (AB1) that specifically binds a Jagged target, e.g., Jagged 1 and/or Jagged 2, and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes at least the amino acid sequence RASQSISSY (SEQ ID NO: 9); a VL CDR2 sequence that includes at least the amino acid sequence AASSLQS (SEQ ID NO: 10); a VL CDR3 sequence that includes at least the amino acid sequence QQTVVAPPL (SEQ ID NO: 11), and combinations thereof.

In some embodiments, the multispecific antibodies, multispecific activatable antibodies, conjugated multispecific antibodies and/or conjugated multispecific activatable antibodies provided herein include at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes a sequence that is at least 90%, 91%, 92%, 93%, 94%, 95%, 96%, 97%, 98%, 99% or more identical to the amino acid sequence SYAMS (SEQ ID NO: 6); a VH CD2 sequence that includes a sequence that is at least 90%, 91%, 92%, 93%, 94%, 95%, 96%, 97%, 98%, 99% or more identical to the amino acid sequence SIDPEGRQTYYADSVKG (SEQ ID NO: 7); a VH CDR3 sequence that includes a sequence that is at least 90%, 91%, 92%, 93%, 94%, 95%, 96%, 97%, 98%, 99% or more identical to the amino acid sequence DIGGRSAFDY (SEQ ID NO: 8), and combinations thereof.

In some embodiments, the multispecific antibodies, multispecific activatable antibodies, conjugated multispecific antibodies and/or conjugated multispecific activatable antibodies provided herein include at least a first antibody or antigen binding fragment thereof (AB1) that specifically binds a Jagged target, e.g., Jagged 1 and/or Jagged 2, and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes a sequence that is at least 90%, 91%, 92%, 93%, 94%, 95%, 96%, 97%, 98%, 99% or more identical to the amino acid sequence RASQSISSY (SEQ ID NO: 9); a VL CDR2 sequence that includes a sequence that is at least 90%, 91%, 92%, 93%, 94%, 95%, 96%, 97%, 98%, 99% or more identical to the amino acid sequence AASSLQS (SEQ ID NO: 10); and a VL CDR3 sequence that includes a sequence that is at least 90%, 91%, 92%, 93%, 94%, 95%, 96%, 97%, 98%, 99% or more identical to the amino acid sequence QQTVVAPPL (SEQ ID NO: 11), and combinations thereof.

In some embodiments, the multispecific antibodies, multispecific activatable antibodies, conjugated multispecific antibodies and/or conjugated multispecific activatable antibodies provided herein include at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes at least the amino acid sequence SYAMS (SEQ ID NO: 6); the VH CD2 sequence includes at least the amino acid sequence SIDPEGRQTYYADSVKG (SEQ ID NO: 7); the VH CDR3 sequence includes at least the amino acid sequence DIGGRSAFDY (SEQ ID NO: 8); the VL CDR1 sequence includes at least the amino acid sequence RASQSISSY (SEQ ID NO: 9); the VL CDR2 sequence includes at least the amino acid sequence AASSLQS (SEQ ID NO: 10); and the VL CDR3 sequence includes at least the amino acid sequence QQTVVAPPL (SEQ ID NO: 11).

In some embodiments, the multispecific antibodies, multispecific activatable antibodies, conjugated multispecific antibodies and/or conjugated multispecific activatable antibodies provided herein include at least a first antibody or antigen binding fragment thereof (AB1) that specifically binds a Jagged target, e.g., Jagged 1 and/or Jagged 2, and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes a sequence that is at least 90%, 91%, 92%, 93%, 94%, 95%, 96%, 97%, 98%, 99% or more identical to the amino acid sequence SYAMS (SEQ ID NO: 6); the VH CD2 sequence includes a sequence that is at least 90%, 91%, 92%, 93%, 94%, 95%, 96%, 97%, 98%, 99% or more identical to the amino acid sequence SIDPEGRQTYYADSVKG (SEQ ID NO: 7); the VH CDR3 sequence includes a sequence that is at least 90%, 91%, 92%, 93%, 94%, 95%, 96%, 97%, 98%, 99% or more identical to the amino acid sequence DIGGRSAFDY (SEQ ID NO: 8); the VL CDR1 sequence includes a sequence that is at least 90%, 91%, 92%, 93%, 94%, 95%, 96%, 97%, 98%, 99% or more identical to the amino acid sequence RASQSISSY (SEQ ID NO: 9); the VL CDR2 sequence includes a sequence that is at least 90%, 91%, 92%, 93%, 94%, 95%, 96%, 97%, 98%, 99% or more identical to the amino acid sequence AASSLQS (SEQ ID NO: 10); and the VL CDR3 sequence includes a sequence that is at least 90%, 91%, 92%, 93%, 94%, 95%, 96%, 97%, 98%, 99% or more identical to the amino acid sequence QQTVVAPPL (SEQ ID NO: 11).

In some embodiments, the multispecific antibodies, multispecific activatable antibodies, conjugated multispecific antibodies and/or conjugated multispecific activatable antibodies provided herein include at least a first antibody or antigen binding fragment thereof (AB1) that specifically binds Epidermal Growth Factor Receptor (EGFR) and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes at least the amino acid sequence NYGVH (SEQ ID NO: 12); a VH CD2 sequence that includes at least the amino acid sequence VIWSGGNTDYNTPFTS (SEQ ID NO: 13); a VH CDR3 sequence that includes at least the amino acid sequence ALTYYDYEFAY (SEQ ID NO: 14); and combinations thereof.

In some embodiments, the multispecific antibodies, multispecific activatable antibodies, conjugated multispecific antibodies and/or conjugated multispecific activatable antibodies provided herein include at least a first antibody or antigen binding fragment thereof (AB1) that specifically binds EGFR and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes at least the amino acid sequence RASQSIGTNIH (SEQ ID NO: 15); a VL CDR2 sequence that includes at least the amino acid sequence KYASESIS (SEQ ID NO: 16); and a VL CDR3 sequence that includes at least the amino acid sequence QQNNNWPTT (SEQ ID NO: 17), and combinations thereof.

In some embodiments, the multispecific antibodies, multispecific activatable antibodies, conjugated multispecific antibodies and/or conjugated multispecific activatable antibodies provided herein include at least a first antibody or antigen binding fragment thereof (AB1) that specifically binds EGFR and that contains a combination of a VH CDR1 sequence, a VH CDR2 sequence, and a VH CDR3 sequence, wherein at least one of the VH CDR1 sequence, the VH CDR2 sequence, and the VH CDR3 sequence is selected from a VH CDR1 sequence that includes a sequence that is at least 90%, 91%, 92%, 93%, 94%, 95%, 96%, 97%, 98%, 99% or more identical to the amino acid sequence NYGVH (SEQ ID NO: 12); a VH CD2 sequence that includes a sequence that is at least 90%, 91%, 92%, 93%, 94%, 95%, 96%, 97%, 98%, 99% or more identical to the amino acid sequence VIWSGGNTDYNTPFTS (SEQ ID NO: 13); a VH CDR3 sequence that includes a sequence that is at least 90%, 91%, 92%, 93%, 94%, 95%, 96%, 97%, 98%, 99% or more identical to the amino acid sequence ALTYYDYEFAY (SEQ ID NO: 14); and combinations thereof.

In some embodiments, the multispecific antibodies, multispecific activatable antibodies, conjugated multispecific antibodies and/or conjugated multispecific activatable antibodies provided herein include at least a first antibody or antigen binding fragment thereof (AB1) that specifically binds EGFR and that contains a combination of a VL CDR1 sequence, a VL CDR2 sequence, and a VL CDR3 sequence, wherein at least one of the VL CDR1 sequence, the VL CDR2 sequence, and the VL CDR3 sequence is selected from a VL CDR1 sequence that includes a sequence that is at least 90%, 91%, 92%, 93%, 94%, 95%, 96%, 97%, 98%, 99% or more identical to the amino acid sequence RASQSIGTNIH (SEQ ID NO: 15); a VL CDR2 sequence that includes a sequence that is at least 90%, 91%, 92%, 93%, 94%, 95%, 96%, 97%, 98%, 99% or more identical to the amino acid sequence KYASESIS (SEQ ID NO: 16); and a VL CDR3 sequence that includes a sequence that is at least 90%, 91%, 92%, 93%, 94%, 95%, 96%, 97%, 98%, 99% or more identical to the amino acid sequence QQNNNWPTT (SEQ ID NO: 17), and combinations thereof.

In some embodiments, the multispecific antibodies, multispecific activatable antibodies, conjugated multispecific antibodies and/or conjugated multispecific activatable antibodies provided herein include at least a first antibody or antigen binding fragment thereof (AB1) that specifically binds EGFR and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes at least the amino acid sequence NYGVH (SEQ ID NO: 12); the VH CD2 sequence includes at least the amino acid sequence VIWSGGNTDYNTPFTS (SEQ ID NO: 13); the VH CDR3 sequence includes at least the amino acid sequence ALTYYDYEFAY (SEQ ID NO: 14); the VL CDR1 sequence includes at least the amino acid sequence RASQSIGTNIH (SEQ ID NO: 15); the VL CDR2 sequence includes at least the amino acid sequence KYASESIS (SEQ ID NO: 16); and the VL CDR3 sequence includes at least the amino acid sequence QQNNNWPTT (SEQ ID NO: 17).

In some embodiments, the multispecific antibodies, multispecific activatable antibodies, conjugated multispecific antibodies and/or conjugated multispecific activatable antibodies provided herein include at least a first antibody or antigen binding fragment thereof (AB1) that specifically binds EGFR and that contains a combination of a VH CDR1 sequence, a VH CDR2 sequence, a VH CDR3 sequence, a VL CDR1 sequence, a VL CDR2 sequence, and a VL CDR3 sequence, wherein the VH CDR1 sequence includes a sequence that is at least 90%, 91%, 92%, 93%, 94%, 95%, 96%, 97%, 98%, 99% or more identical to the amino acid sequence NYGVH (SEQ ID NO: 12); the VH CD2 sequence includes a sequence that is at least 90%, 91%, 92%, 93%, 94%, 95%, 96%, 97%, 98%, 99% or more identical to the amino acid sequence VIWSGGNTDYNTPFTS (SEQ ID NO: 13); the VH CDR3 sequence includes a sequence that is at least 90%, 91%, 92%, 93%, 94%, 95%, 96%, 97%, 98%, 99% or more identical to the amino acid sequence ALTYYDYEFAY (SEQ ID NO: 14); the VL CDR1 sequence includes a sequence that is at least 90%, 91%, 92%, 93%, 94%, 95%, 96%, 97%, 98%, 99% or more identical to the amino acid sequence RASQSIGTNIH (SEQ ID NO: 15); the VL CDR2 sequence includes a sequence that is at least 90%, 91%, 92%, 93%, 94%, 95%, 96%, 97%, 98%, 99% or more identical to the amino acid sequence KYASESIS (SEQ ID NO: 16); and the VL CDR3 sequence includes a sequence that is at least 90%, 91%, 92%, 93%, 94%, 95%, 96%, 97%, 98%, 99% or more identical to the amino acid sequence QQNNNWPTT (SEQ ID NO: 17).

In some embodiments, the multispecific antibodies, multispecific activatable antibodies, conjugated multispecific antibodies and/or conjugated multispecific activatable antibodies provided herein include at least a heavy chain amino acid sequence selected from the group consisting of those sequences shown in Table 7 and/or in Example 5, including Table 11 therein. In some embodiments, the multispecific antibodies, multispecific activatable antibodies, conjugated multispecific antibodies and/or conjugated multispecific activatable antibodies provided herein include at least a light chain amino acid sequence selected from the group consisting of those sequences shown in Table 7 and/or in Example 5, including Table 11 therein. In some embodiments, the multispecific antibodies, multispecific activatable antibodies, conjugated multispecific antibodies and/or conjugated multispecific activatable antibodies provided herein include at least a heavy chain amino acid sequence selected from the group consisting of those sequences shown in Table 7 and/or in Example 5, including Table 11 therein, and a light chain amino acid sequence selected from the group consisting of those sequences shown in Table 7 and/or in Example 5, including Table 11 therein.

In some embodiments, the multispecific antibodies, multispecific activatable antibodies, conjugated multispecific antibodies and/or conjugated multispecific activatable antibodies provided herein include at least a heavy chain amino acid sequence that is at least 90%, 91%, 92%, 93%, 94%, 95%, 96%, 97%, 98%, 99% or more identical to an amino acid sequence selected from the group consisting of those sequences shown in Table 7 and/or in Example 5, including Table 11 therein. In some embodiments, the multispecific antibodies, multispecific activatable antibodies, conjugated multispecific antibodies and/or conjugated multispecific activatable antibodies provided herein include at least a light chain amino acid sequence that is at least 90%, 91%, 92%, 93%, 94%, 95%, 96%, 97%, 98%, 99% or more identical to an amino acid sequence selected from the group consisting of those sequences shown in Table 7 and/or in Example 5, including Table 11 therein. In some embodiments, the multispecific antibodies, multispecific activatable antibodies, conjugated multispecific antibodies and/or conjugated multispecific activatable antibodies provided herein include at least a heavy chain amino acid sequence that is at least 90%, 91%, 92%, 93%, 94%, 95%, 96%, 97%, 98%, 99% or more identical to an amino acid sequence selected from the group consisting of those sequences shown in Table 7 and/or in Example 5, including Table 11 therein, and a light chain amino acid sequence that is at least 90%, 91%, 92%, 93%, 94%, 95%, 96%, 97%, 98%, 99% or more identical to an amino acid sequence selected from the group consisting of those sequences shown in Table 7 and/or in Example 5, including Table 11 therein.

In some embodiments, the multispecific antibody and/or multispecific activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the multispecific via a linker. In some embodiments, the linker is a non-cleavable linker. In some embodiments, the agent is a microtubule inhibitor. In some embodiments, the agent is a nucleic acid damaging agent, such as a DNA alkylator or DNA intercalator, or other DNA damaging agent. In some embodiments, the linker is a cleavable linker. In some embodiments, the agent is an agent selected from the group listed in Table 4. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some embodiments, the multispecific antibody and/or multispecific activatable antibody also includes a detectable moiety. In some embodiments, the detectable moiety is a diagnostic agent.

In some embodiments, the multispecific antibody and/or multispecific activatable antibody naturally contains one or more disulfide bonds. In some embodiments, the multispecific antibody and/or multispecific activatable antibody can be engineered to include one or more disulfide bonds.

The disclosure also provides an isolated nucleic acid molecule encoding a multispecific antibody and/or multispecific activatable antibody described herein, as well as vectors that include these isolated nucleic acid sequences. The disclosure provides methods of producing a multispecific antibody by culturing a cell under conditions that lead to expression of the antibody, wherein the cell comprises such a nucleic acid molecule. In some embodiments, the cell comprises such a vector.

The disclosure also provides multispecific activatable antibodies and/or multispecific activatable antibody compositions that include at least a first antibody or antigen-binding fragment thereof (AB1) that specifically binds a first target or first epitope and a second antibody or antigen-biding fragment thereof (AB2) that binds a second target or a second epitope, where at least AB1 is coupled or otherwise attached to a masking moiety (MM1), such that coupling of the MM1 reduces the ability of AB1 to bind its target. In some embodiments, the MM1 is coupled to AB1 via a first cleavable moiety (CM1) sequence that includes a substrate for a protease, for example, a protease that is co-localized with the target of AB1 at a treatment site or a diagnostic site in a subject. The multispecific activatable antibodies provided herein are stable in circulation, activated at intended sites of therapy and/or diagnosis but not in normal, i.e., healthy tissue, and, when activated, exhibit binding to the target of AB1 that is at least comparable to the corresponding, unmodified multispecific antibody.

In some embodiments, the multispecific activatable antibody comprises a linking peptide between the MM1 and the CM1.

In some embodiments, the multispecific activatable antibody comprises a linking peptide between the CM1 and the AB1.

In some embodiments, the activatable antibody comprises a first linking peptide (LP1) and a second linking peptide (LP2), and at least a portion of the multispecific activatable antibody has the structural arrangement from N-terminus to C-terminus as follows in the uncleaved state: MM1-LP1-CM1-LP2-AB1 or AB1-LP2-CM1-LP1-MM1. In some embodiments, the two linking peptides need not be identical to each other.

In some embodiments, at least one of LP1 or LP2 includes an amino acid sequence selected from the group consisting of $(GS)_n$, $(GGS)_n$, $(GSGGS)_n$ (SEQ ID NO: 18) and $(GGGS)_n$ (SEQ ID NO: 19), where n is an integer of at least one. In some embodiments, at least one of LP1 or LP2 includes an amino acid sequence selected from the group consisting of GGSG (SEQ ID NO: 20), GGSGG (SEQ ID NO: 21), GSGSG (SEQ ID NO: 22), GSGGG (SEQ ID NO: 23), GGGSG (SEQ ID NO: 24), and GSSSG (SEQ ID NO: 25).

In some embodiments, the multispecific activatable antibody includes at least a first antibody or antigen-binding fragment thereof (AB1) that specifically binds a first target or first epitope and a second antibody or antigen-binding fragment thereof (AB2) that specifically binds a second target or second epitope. In some embodiments, each of the AB in the multispecific activatable antibody is independently selected from the group consisting of a monoclonal antibody, domain antibody, single chain, Fab fragment, a F(ab')$_2$ fragment, a scFv, a scAb, a dAb, a single domain heavy chain antibody, and a single domain light chain antibody. In some embodiments, each of the AB in the multispecific activatable antibody is a rodent (e.g., mouse or rat), chimeric, humanized or fully human monoclonal antibody.

In some embodiments, each of the AB in the multispecific activatable antibody has an equilibrium dissociation constant of about 100 nM or less for binding to its corresponding target or epitope.

In some embodiments, MM1 has an equilibrium dissociation constant for binding to its corresponding AB that is greater than the equilibrium dissociation constant of the AB to its corresponding target or epitope.

In some embodiments, MM1 has an equilibrium dissociation constant for binding to its corresponding AB that is no more than the equilibrium dissociation constant of the AB to its corresponding target or epitope.

In some embodiments, MM1 does not interfere or compete with its corresponding AB for binding to the corresponding target or epitope when the multispecific activatable antibody is in a cleaved state.

In some embodiments, MM1 is a polypeptide of about 2 to 40 amino acids in length. In some embodiments, each of the MM in the multispecific activatable antibody is a polypeptide of no more than 40 amino acids in length.

In some embodiments, MM1 has a polypeptide sequence that is different from that of target of the corresponding AB.

In some embodiments, MM1 has a polypeptide sequence that is no more than 50% identical to any natural binding partner of the corresponding AB. In some embodiments, MM1 has a polypeptide sequence that is no more than 25% identical to any natural binding partner of the corresponding AB. In some embodiments, MM1 has a polypeptide sequence that is no more than 10% identical to any natural binding partner of the corresponding AB.

In some embodiments, the coupling of MM1 reduces the ability of the corresponding AB to bind its target or epitope such that the dissociation constant ($K_d$) of the AB when coupled to the MM1 towards its corresponding target or epitope is at least 20 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 40 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 100 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 1000 times greater than the $K_d$ of the AB when not coupled to the MM1 towards its corresponding target or epitope.

In some embodiments, the coupling of MM1 reduces the ability of the corresponding AB to bind its target or epitope such that the dissociation constant ($K_d$) of the AB when coupled to the MM1 towards its corresponding target or epitope is at least 10,000 times greater than the $K_d$ of the AB when not coupled to the MM1 towards its corresponding target or epitope.

In some embodiments, MM1 is an amino acid sequence selected from a MM shown in the Examples provided herein.

In some embodiments, the multispecific activatable antibody includes at least a second masking moiety (MM2) that inhibits the binding of the AB2 to its target when the multispecific activatable antibody is in an uncleaved state, and a second cleavable moiety (CM2) coupled to the AB2, wherein the CM2 is a polypeptide that functions as a substrate for a second protease. In some embodiments, CM2 is a polypeptide of no more than 15 amino acids long. In some embodiments, the second protease is co-localized with the second target or epitope in a tissue, and wherein the second protease cleaves the CM2 in the multispecific activatable antibody when the multispecific activatable antibody is exposed to the second protease. In some embodiments, the first protease and the second protease are co-localized with the first target or epitope and the second target or epitope in a tissue. In some embodiments, the first protease and the second protease are the same protease. In some embodiments, CM1 and CM2 are different substrates for the same protease. In some embodiments, the protease is selected from the group consisting of those shown in Table 3. In some embodiments, the first protease and the second protease are different proteases. In some embodiments, the first protease and the second protease are different proteases selected from the group consisting of those shown in Table 3.

In some embodiments, each of the MM in the multispecific activatable antibody, e.g., MM1 and at least MM2, has an equilibrium dissociation constant for binding to its corresponding AB that is greater than the equilibrium dissociation constant of the AB to its corresponding target or epitope.

In some embodiments, each of the MM in the multispecific activatable antibody has an equilibrium dissociation constant for binding to its corresponding AB that is no more than the equilibrium dissociation constant of the AB to its corresponding target or epitope.

In some embodiments, each of the MM in the multispecific activatable antibody does not interfere or compete with its corresponding AB for binding to the corresponding target or epitope when the multispecific activatable antibody is in a cleaved state.

In some embodiments, each of the MM in the multispecific activatable antibody is a polypeptide of about 2 to 40 amino acids in length. In some embodiments, each of the MM in the multispecific activatable antibody is a polypeptide of no more than 40 amino acids in length.

In some embodiments, each of the MM in the multispecific activatable antibody has a polypeptide sequence that is different from that of target of the corresponding AB.

In some embodiments, each of the MM in the multispecific activatable antibody has a polypeptide sequence that is no more than 50% identical to any natural binding partner of the corresponding AB. In some embodiments, each of the MM in the multispecific activatable antibody has a polypeptide sequence that is no more than 25% identical to any natural binding partner of the corresponding AB. In some embodiments, each of the MM in the multispecific activatable antibody has a polypeptide sequence that is no more than 10% identical to any natural binding partner of the corresponding AB.

In some embodiments, the coupling of each of the MM reduces the ability of the corresponding AB to bind its target or epitope such that the dissociation constant ($K_d$) of the AB when coupled to the MM towards its corresponding target or epitope is at least 20 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 40 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 100 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 1000 times greater than the $K_d$ of the AB when not coupled to the MM towards its corresponding target or epitope.

In some embodiments, the coupling of each of the MM reduces the ability of the corresponding AB to bind its target or epitope such that the dissociation constant ($K_d$) of the AB when coupled to the MM towards its corresponding target or epitope is at least 10,000 times greater than the $K_d$ of the AB when not coupled to the MM towards its corresponding target or epitope.

In some embodiments, each of the MM is an amino acid sequence selected from a MM shown in the Examples provided herein.

In some embodiments, the protease that cleaves the first cleavable moiety (CM1) sequence is co-localized with the target of the AB1 in the multispecific activatable antibody in a tissue, and the protease cleaves the CM1 in the multispecific activatable antibody when the multispecific activatable antibody is exposed to the protease.

In some embodiments, the multispecific activatable antibody includes more than one cleavable moiety sequence, and the protease that cleaves at least one cleavable moiety sequence is co-localized with the target of at least one of the AB regions in the multispecific activatable antibody in a tissue, and the protease cleaves the CM in the multispecific activatable antibody when the multispecific activatable antibody is exposed to the protease.

In some embodiments, each CM, e.g., CM1 and at least CM2, is positioned in the multispecific activatable antibody such that in the uncleaved state, binding of the multispecific activatable antibody to a target of one of the AB regions is reduced to occur with an equilibrium dissociation constant that is at least 20-fold greater than the equilibrium dissociation constant of an unmodified AB binding to its target, and whereas in the cleaved state, the AB binds its target.

In some embodiments, each CM is positioned in the multispecific activatable antibody such that in the uncleaved state, binding of the multispecific activatable antibody to a target of one of the AB regions is reduced to occur with an equilibrium dissociation constant that is at least 40-fold greater than the equilibrium dissociation constant of an unmodified AB binding to its target, and whereas in the cleaved state, the AB binds its target.

In some embodiments, each CM is positioned in the multispecific activatable antibody such that in the uncleaved state, binding of the multispecific activatable antibody to a target of one of the AB regions is reduced to occur with an equilibrium dissociation constant that is at least 50-fold greater than the equilibrium dissociation constant of an unmodified AB binding to its target, and whereas in the cleaved state, the AB binds its target.

In some embodiments, each CM is positioned in the multispecific activatable antibody such that in the uncleaved state, binding of the multispecific activatable antibody to a target of one of the AB regions is reduced to occur with an equilibrium dissociation constant that is at least 100-fold greater than the equilibrium dissociation constant of an unmodified AB binding to its target, and whereas in the cleaved state, the AB binds its target.

In some embodiments, each CM is positioned in the multispecific activatable antibody such that in the uncleaved state, binding of the multispecific activatable antibody to a target of one of the AB regions is reduced to occur with an equilibrium dissociation constant that is at least 200-fold greater than the equilibrium dissociation constant of an unmodified AB binding to its target, and whereas in the cleaved state, the AB binds its target.

In some embodiments, each CM in the multispecific activatable antibody is a polypeptide of up to 15 amino acids in length.

In some embodiments, at least one CM in the multispecific activatable antibody includes the amino acid sequence LSGRSDNH (SEQ ID NO: 26). In some embodiments, at least one cleavable moiety is selected for use with a specific protease, for example a protease that is known to be co-localized with at least one target of the multispecific activatable antibody. For example, suitable cleavable moieties for use in the multispecific activatable antibodies of the disclosure are cleaved by at least a protease such as urokinase, legumain, and/or matriptase (also referred to herein as MT-SP1 or MTSP1). In some embodiments, a suitable cleavable moiety includes at least one of the following sequences: TGRGPSWV (SEQ ID NO: 27); SARGPSRW (SEQ ID NO: 28); TARGPSFK (SEQ ID NO: 29); LSGRSDNH (SEQ ID NO: 26); GGWHTGRN (SEQ ID NO: 30); HTGRSGAL (SEQ ID NO: 31); PLTGRSGG (SEQ ID NO: 32); AARGPAIH (SEQ ID NO: 33); RGPAFNPM (SEQ ID NO: 34); SSRGPAYL (SEQ ID NO: 35); RGPATPIM (SEQ ID NO: 36); RGPA (SEQ ID NO: 37); GGQPSGMWGW (SEQ ID NO: 38); FPRPLGITGL (SEQ ID NO: 39); VHMPLGFLGP (SEQ ID NO: 40); SPLTGRSG (SEQ ID NO: 41); SAGFSLPA (SEQ ID NO: 42); LAPLGLQRR (SEQ ID NO: 43); SGGPLGVR (SEQ ID NO: 44); and/or PLGL (SEQ ID NO: 45).

In some embodiments, each CM in the multispecific activatable antibody is a substrate for a protease selected from the group consisting of those shown in Table 3. In some embodiments, the protease is selected from the group consisting of uPA, legumain, MT-SP1, ADAM17, BMP-1, TMPRSS3, TMPRSS4, neutrophil elastase, MMP-7, MMP-9, MMP-12, MMP-13, and MMP-14. In some embodiments, the protease is a cathepsin, such as, but not limited to, cathepsin S. In some embodiments, each CM in the multispecific activatable antibody is a substrate for a protease selected from the group consisting of uPA (urokinase plasminogen activator), legumain and MT-SP1 (matriptase). In some embodiments, the protease comprises uPA. In some embodiments, the protease comprises legumain. In some embodiments, the protease comprises MT-SP1. In some embodiments, the protease comprises a matrix metalloproteinase (MMP).

In some embodiments, at least one CM in the multispecific activatable antibody is a substrate for at least two proteases. In some embodiments, each protease is selected from the group consisting of those shown in Table 3. In some embodiments, at least one CM in the multispecific activatable antibody is a substrate for at least two proteases, wherein one of the proteases is selected from the group consisting of uPA, legumain and MT-SP1 and the other protease is selected from the group consisting of those shown in Table 3. In some embodiments, at least one CM in the multispecific activatable antibody is a substrate for at least two proteases selected from the group consisting of uPA, legumain and MT-SP1.

In some embodiments, the multispecific activatable antibody includes at least a first CM (CM1) and a second CM (CM2). In some embodiments, CM1 and CM2 are part of a single cleavable linker that joins an MM to an AB. In some embodiments, CM1 is part of a cleavable linker that joins MM1 to AB1, and CM2 is part of a separate cleavable linker that joins an MM2 to AB2. In some embodiments, a multispecific activatable antibody comprises more than two CMs. In some embodiments, such a multispecific activatable antibody comprises more than two CMs and more than two MMs. In some embodiments, CM1 and CM2 are each polypeptides of no more than 15 amino acids long. In some embodiments, at least one of the first CM and the second CM is a polypeptide that functions as a substrate for a protease selected from the group consisting of those listed in Table 3. In some embodiments, at least one of the first CM and the second CM is a polypeptide that functions as a substrate for a protease selected from the group consisting of uPA, legumain, and MT-SP1. In some embodiments, the first CM is cleaved by a first cleaving agent selected from the group consisting of uPA, legumain, and MT-SP1 in a target tissue and the second CM is cleaved by a second cleaving agent in a target tissue. In some embodiments, the other protease is selected from the group consisting of those shown in Table 3. In some embodiments, the first cleaving agent and the second cleaving agent are the same protease selected from the group consisting of those listed in Table 3, and the first CM and the second CM are different substrates for the enzyme. In some embodiments, the first cleaving agent and the second cleaving agent are the same protease selected from the group consisting of uPA, legumain, and MT-SP1, and the first CM and the second CM are different substrates for the enzyme. In some embodiments, the first cleaving agent and the second cleaving agent are the same protease selected from the group listed in Table 3, and the first CM and the second CM are the same substrate. In some embodiments, the first cleaving agent and the second cleaving agent are different proteases. In some embodiments, the first cleaving agent and the second cleaving agent are different proteases selected from the group consisting of those shown in Table 3. In some embodiments, the first cleaving agent and the second cleaving agent are co-localized in the target tissue. In some embodiments, the first CM and the second CM are cleaved by at least one cleaving agent in the target tissue.

In some embodiments, the multispecific activatable antibody is exposed to and cleaved by a protease such that, in the activated or cleaved state, the activated multispecific activatable antibody includes a light chain amino acid sequence that includes at least a portion of LP2 and/or CM sequence after the protease has cleaved the CM.

In some embodiments, the multispecific activatable antibody also includes a signal peptide. In some embodiments, the signal peptide is conjugated to the multispecific activatable antibody via a spacer. In some embodiments, the spacer is conjugated to the multispecific activatable antibody in the absence of a signal peptide. In some embodiments, the spacer is joined directly to at least one of the MM of the multispecific activatable antibody.

In some embodiments, the multispecific activatable antibody in an uncleaved state comprises a spacer that is joined directly to a first MM and has the structural arrangement from N-terminus to C-terminus of spacer-MM1-CM-AB1. In some embodiments, the spacer includes at least the amino acid sequence QGQSGQ (SEQ ID NO: 46).

In some embodiments, the serum half-life of the multispecific activatable antibody is longer than that of the corresponding multispecific antibody; e.g., the pK of the multispecific activatable antibody is longer than that of the corresponding multispecific antibody. In some embodiments, the serum half-life of the multispecific activatable antibody is similar to that of the corresponding multispecific antibody. In some embodiments, the serum half-life of the multispecific activatable antibody is at least 15 days when administered to an organism. In some embodiments, the serum half-life of the multispecific activatable antibody is at least 12 days when administered to an organism. In some embodiments, the serum half-life of the multispecific activatable antibody is at least 11 days when administered to an organism. In some embodiments, the serum half-life of the multispecific activatable antibody is at least 10 days when administered to an organism. In some embodiments, the serum half-life of the multispecific activatable antibody is at least 9 days when administered to an organism. In some embodiments, the serum half-life of the multispecific activatable antibody is at least 8 days when administered to an organism. In some embodiments, the serum half-life of the multispecific activatable antibody is at least 7 days when administered to an organism. In some embodiments, the serum half-life of the multispecific activatable antibody is at least 6 days when administered to an organism. In some embodiments, the serum half-life of the multispecific activatable antibody is at least 5 days when administered to an organism. In some embodiments, the serum half-life of the multispecific activatable antibody is at least 4 days when administered to an organism. In some embodiments, the serum half-life of the multispecific activatable antibody is at least 3 days when administered to an organism. In some embodiments, the serum half-life of the multispecific activatable antibody is at least 2 days when administered to an organism. In some embodiments, the serum half-life of the multispecific activatable antibody is at least 24 hours when administered to an organism. In some embodiments, the serum half-life of the multispecific activatable antibody is at least 20 hours when administered to an organism. In some embodiments, the serum half-life of the multispecific activatable antibody is at least 18 hours when administered to an organism. In some embodiments, the serum half-life of the multispecific activatable antibody is at least 16 hours when administered to an organism. In some embodiments, the serum half-life of the multispecific activatable antibody is at least 14 hours when administered to an organism. In some embodiments, the serum half-life of the multispecific activatable antibody is at least 12 hours when administered to an organism. In some embodiments, the serum half-life of the multispecific activatable antibody is at least 10 hours when administered to an organism. In some embodiments, the serum half-life of the multispecific activatable antibody is at least 8 hours when administered to an organism. In some embodiments, the serum half-life of the multispecific activatable antibody is at least 6 hours when administered to an organism. In some embodiments, the serum half-life of the multispecific activatable antibody is at least 4 hours when administered to an organism. In some embodiments, the serum half-life of the multispecific activatable antibody is at least 3 hours when administered to an organism.

The disclosure also provides compositions and methods that include a multispecific activatable antibody that includes at least a first antibody or antibody fragment (AB1) that specifically binds a target and a second antibody or antibody fragment (AB2), where at least the first AB in the multispecific activatable antibody is coupled to a masking moiety (MM1) that decreases the ability of AB1 to bind its target. In some embodiments, each AB is coupled to a MM that decreases the ability of its corresponding AB to each target. For example, in bispecific activatable antibody embodiments, AB1 is coupled to a first masking moiety (MM1) that decreases the ability of AB1 to bind its target, and AB2 is coupled to a second masking moiety (MM2) that decreases the ability of AB2 to bind its target. In some embodiments, the multispecific activatable antibody comprises more than two AB regions; in such embodiments, AB1 is coupled to a first masking moiety (MM1) that decreases the ability of AB1 to bind its target, AB2 is coupled to a second masking moiety (MM2) that decreases the ability of AB2 to bind its target, AB3 is coupled to a third masking moiety (MM3) that decreases the ability of AB3 to bind its target, and so on for each AB in the multispecific activatable antibody.

In some embodiments, the multispecific activatable antibody further includes at least one cleavable moiety (CM) that is a substrate for a protease, where the CM links a MM to an AB. For example, in some embodiments, the multispecific activatable antibody includes at least a first antibody or antibody fragment (AB1) that specifically binds a target and a second antibody or antibody fragment (AB2), where at least the first AB in the multispecific activatable antibody is coupled via a first cleavable moiety (CM1) to a masking moiety (MM1) that decreases the ability of AB1 to bind its target. In some bispecific activatable antibody embodiments, AB1 is coupled via CM1 to MM1, and AB2 is coupled via a second cleavable moiety (CM2) to a second masking moiety (MM2) that decreases the ability of AB2 to bind its target. In some embodiments, the multispecific activatable antibody comprises more than two AB regions; in some of these embodiments, AB1 is coupled via CM1 to MM1, AB2 is coupled via CM2 to MM2, and AB3 is coupled via a third cleavable moiety (CM3) to a third masking moiety (MM3) that decreases the ability of AB3 to bind its target, and so on for each AB in the multispecific activatable antibody.

The compositions and methods provided herein enable the attachment of one or more agents to one or more cysteine residues in any of the AB regions without compromising the activity (e.g., the masking, activating or binding activity) of the multispecific activatable antibody. In some embodiments, the compositions and methods provided herein enable the attachment of one or more agents to one or more cysteine residues in any of the AB regions without reducing or otherwise disturbing one or more disulfide bonds within any of the MM. The compositions and methods provided herein produce a multispecific activatable antibody that is conjugated to one or more agents, e.g., any of a variety of therapeutic, diagnostic and/or prophylactic agents, preferably without any of the agent(s) being conjugated to any of the MM of the multispecific activatable antibody. The compositions and methods provided herein produce conjugated multispecific activatable antibodies in which each of the MM retains the ability to effectively and efficiently mask its corresponding AB of the multispecific activatable antibody in an uncleaved state. The compositions and methods provided herein produce conjugated multispecific activatable antibodies in which the activatable antibody is still activated, i.e., cleaved, in the presence of a protease that can cleave the CM.

The multispecific activatable antibodies have at least one point of conjugation for an agent, but in the methods and compositions provided herein less than all possible points of conjugation are available for conjugation to an agent. In some embodiments, the one or more points of conjugation are sulfur atoms involved in disulfide bonds. In some embodiments, the one or more points of conjugation are sulfur atoms involved in interchain disulfide bonds. In some embodiments, the one or more points of conjugation are sulfur atoms involved in interchain sulfide bonds, but not sulfur atoms involved in intrachain disulfide bonds. In some embodiments, the one or more points of conjugation are sulfur atoms of cysteine or other amino acid residues containing a sulfur atom. Such residues may occur naturally in the antibody structure or may be incorporated into the antibody by site-directed mutagenesis, chemical conversion, or mis-incorporation of non-natural amino acids.

Also provided are methods of preparing a conjugate of a multispecific activatable antibody having one or more interchain disulfide bonds in one or more of the AB and one or more intrachain disulfide bonds in the corresponding MM, and a drug reactive with free thiols is provided. The method generally includes partially reducing interchain disulfide bonds in the activatable antibody with a reducing agent, such as, for example, TCEP; and conjugating the drug reactive with free thiols to the partially reduced activatable antibody. As used herein, the term partial reduction refers to situations where a multispecific activatable antibody is contacted with a reducing agent and less than all disulfide bonds, e.g., less than all possible sites of conjugation are reduced. In some embodiments, less than 99%, 98%, 97%, 96%, 95%, 90%, 85%, 80%, 75%, 70%, 65%, 60%, 55%, 50%, 45%, 40%, 35%, 30%, 25%, 20%, 15%, 10% or less than 5% of all possible sites of conjugation are reduced.

In yet other embodiments, a method of reducing and conjugating an agent, e.g., a drug, to a multispecific activatable antibody resulting in selectivity in the placement of the agent is provided. The method generally includes partially reducing the multispecific activatable antibody with a reducing agent such that any conjugation sites in any of the masking moieties or other non-AB portion of the activatable antibody are not reduced, and conjugating the agent to interchain thiols in one or more of the AB regions of the multispecific activatable antibody. The conjugation site(s) are selected so as to allow desired placement of an agent to allow conjugation to occur at a desired site. The reducing agent is, for example, TCEP. The reduction reaction conditions such as, for example, the ratio of reducing agent to activatable antibody, the length of incubation, the temperature during the incubation, the pH of the reducing reaction solution, etc., are determined by identifying the conditions that produce a conjugated activatable antibody in which the MM retains the ability to effectively and efficiently mask the AB of the activatable antibody in an uncleaved state. The ratio of reduction agent to multispecific activatable antibody will vary depending on the activatable antibody. In some embodiments, the ratio of reducing agent to multispecific activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

In some embodiments, a method of reducing interchain disulfide bonds in one or more of the AB regions of a multispecific activatable antibody and conjugating an agent, e.g., a thiol-containing agent such as a drug, to the resulting interchain thiols to selectively locate agent(s) on the AB is provided. The method generally includes partially reducing one or more of the AB regions with a reducing agent to form at least two interchain thiols without forming all possible interchain thiols in the activatable antibody; and conjugating the agent to the interchain thiols of the partially reduced AB. For example, one or more of the AB regions of the multispecific activatable antibody is partially reduced for about 1 hour at about 37° C. at a desired ratio of reducing agent: activatable antibody. In some embodiments, the ratio of reducing agent to activatable antibody will be in a range from about 20:1 to 1:1, from about 10:1 to 1:1, from about 9:1 to 1:1, from about 8:1 to 1:1, from about 7:1 to 1:1, from about 6:1 to 1:1, from about 5:1 to 1:1, from about 4:1 to 1:1, from about 3:1 to 1:1, from about 2:1 to 1:1, from about 20:1 to 1:1.5, from about 10:1 to 1:1.5, from about 9:1 to 1:1.5, from about 8:1 to 1:1.5, from about 7:1 to 1:1.5, from about 6:1 to 1:1.5, from about 5:1 to 1:1.5, from about 4:1 to 1:1.5, from about 3:1 to 1:1.5, from about 2:1 to 1:1.5, from about 1.5:1 to 1:1.5, or from about 1:1 to 1:1.5. In some embodiments, the ratio is in a range of from about 5:1 to 1:1. In some embodiments, the ratio is in a range of from about 5:1 to 1.5:1. In some embodiments, the ratio is in a range of from about 4:1 to 1:1. In some embodiments, the ratio is in a range from about 4:1 to 1.5:1. In some embodiments, the ratio is in a range from about 8:1 to about 1:1. In some embodiments, the ratio is in a range of from about 2.5:1 to 1:1.

The thiol-containing reagent can be, for example, cysteine or N-acetyl cysteine. The reducing agent can be, for example, TCEP. In some embodiments, the reduced activatable antibody can be purified prior to conjugation, using for example, column chromatography, dialysis, or diafiltration. Alternatively, the reduced antibody is not purified after partial reduction and prior to conjugation.

The disclosure also provides partially reduced multispecific activatable antibodies in which at least one interchain disulfide bond in the multispecific activatable antibody has been reduced with a reducing agent without disturbing any intrachain disulfide bonds in the multispecific activatable antibody, wherein the multispecific activatable antibody includes at least a first antibody or an antigen binding fragment thereof (AB1) that specifically binds to a target, a first masking moiety (MM1) that inhibits the binding of the AB1 of the multispecific activatable antibody in an uncleaved state to the target, a first cleavable moiety (CM1) coupled to the AB1, wherein the CM1 is a polypeptide that functions as a substrate for a protease, and a second antibody or an antigen binding fragment thereof (AB2) that specifically binds to a second target. In some embodiments, the MM1 is coupled to the AB1 via the CM1. In some embodiments, one or more intrachain disulfide bond(s) of the multispecific activatable antibody is not disturbed by the reducing agent. In some embodiments, one or more intrachain disulfide bond(s) of the MM1 within the multispecific activatable antibody is not disturbed by the reducing agent. In some embodiments, reducing agent is TCEP.

In some embodiments, the multispecific antibodies and/or multispecific activatable antibodies described herein are used in conjunction with one or more additional agents or a combination of additional agents. Suitable additional agents include current pharmaceutical and/or surgical therapies for an intended application, such as, for example, cancer. For example, the multispecific antibodies and/or multispecific activatable antibodies can be used in conjunction with an additional chemotherapeutic or anti-neoplastic agent.

In some embodiments, the multispecific antibody and/or multispecific activatable antibody and additional agent are formulated into a single therapeutic composition, and the multispecific antibody and/or multispecific activatable antibody and additional agent are administered simultaneously. Alternatively, the multispecific antibody and/or multispecific activatable antibody and additional agent are separate from each other, e.g., each is formulated into a separate therapeutic composition, and the multispecific antibody and/or multispecific activatable antibody and the additional agent are administered simultaneously, or the multispecific antibody and/or multispecific activatable antibody and the additional agent are administered at different times during a treatment regimen. For example, the multispecific antibody and/or multispecific activatable antibody is administered prior to the administration of the additional agent, the multispecific antibody and/or multispecific activatable antibody is administered subsequent to the administration of the additional agent, or the multispecific antibody and/or multispecific activatable antibody and the additional agent are administered in an alternating fashion. As described herein, the anti-multispecific antibody and/or multispecific activatable antibody and additional agent are administered in single doses or in multiple doses.

The disclosure also provides an isolated nucleic acid molecule encoding a multispecific antibody and/or multispecific activatable antibody described herein, as well as vectors that include these isolated nucleic acid sequences. The disclosure provides methods of producing a multispecific antibody and/or multispecific activatable antibody by culturing a cell under conditions that lead to expression of the multispecific antibody and/or multispecific activatable antibody, wherein the cell comprises such a nucleic acid molecule. In some embodiments, the cell comprises such a vector.

The disclosure also provides a method of manufacturing multispecific antibodies of the disclosure and/or multispecific activatable antibodies of the disclosure by (a) culturing a cell comprising a nucleic acid construct that encodes the multispecific antibody and/or multispecific activatable antibody under conditions that lead to expression of the multispecific antibody and/or multispecific activatable, and (b) recovering the multispecific antibody and/or multispecific activatable antibody.

The present disclosure also provides methods of treating, preventing, delaying the progression of or otherwise ameliorating a symptom of one or more pathologies or alleviating a symptom associated with such pathologies, by administering a multispecific antibody and/or multispecific activatable antibody of the disclosure to a subject in which such treatment or prevention is desired. The subject to be treated is, e.g., human or other mammal. In some embodiments, the subject is a non-human mammal, such as a non-human primate, companion animal (e.g., cat, dog, horse), farm animal, work animal, or zoo animal. In some embodiments, the subject is a rodent.

The present disclosure also provides methods to induce target-dependent T-cell activation and killing of a target cell by administering a multispecific activatable antibody of the disclosure to a subject in which such induction is desired, wherein when the multispecific activatable antibody is in the cleaved state, e.g., each masking moiety in the multispecific activatable antibody is no longer attached or otherwise associated with the corresponding AB domain, target-dependent T-cell activation and killing of the target cell occurs, and when the multispecific activatable antibody is in the uncleaved state, e.g. at least one masking moiety of the multispecific activatable antibody is attached or otherwise associated with the corresponding AB domain, target-dependent T-cell activation and killing of the target cell is reduced or otherwise inhibited. Any of the multispecific activatable antibodies described herein are suitable for use in such methods. The subject to be treated is, e.g., human or other mammal. In some embodiments, the subject is a non-human mammal, such as a non-human primate, companion animal (e.g., cat, dog, horse), farm animal, work animal, or zoo animal. In some embodiments, the subject is a rodent.

A multispecific antibody and/or multispecific activatable antibody used in any of the embodiments of these methods and uses can be administered at any stage of the disease and/or any stage in which T-cell activation and killing of a target cell is desired. For example, such a multispecific antibody and/or multispecific activatable antibody can be administered to a patient suffering cancer of any stage, from early to metastatic. The terms subject and patient are used interchangeably herein. A multispecific antibody and/or multispecific activatable antibody used in any of the embodiments of these methods and uses can be used in a treatment regimen comprising neoadjuvant therapy. A multispecific antibody and/or multispecific activatable antibody used in any of the embodiments of these methods and uses can be administered either alone or in combination with one or more additional agents, including small molecule inhibitors, other antibody-based therapies, polypeptide or peptide-based therapies, nucleic acid-based therapies and/or other biologics.

The disclosure also provides methods and kits for using the multispecific antibody and/or multispecific activatable antibodies in a variety of diagnostic and/or prophylactic indications. For example, the disclosure provides methods and kits for detecting presence or absence of a cleaving agent and a target of interest in a subject or a sample by (i) contacting a subject or sample with a multispecific activatable antibody that includes at least a first masking moiety (MM1), a first cleavable moiety (CM1) that is cleaved by the cleaving agent, and at least a first antigen binding domain or fragment thereof (AB1) that specifically binds the target of interest and a second antigen binding domain or fragment thereof (AB2) that specifically binds a second target and/or a second epitope, (a) wherein the MM1 is a peptide that inhibits binding of the AB1 to the target, and wherein the MM1 does not have an amino acid sequence of a naturally occurring binding partner of the AB1 and is not a modified form of a natural binding partner of the AB1; and (b) wherein, in an uncleaved, non-activated state, the MM1 interferes with specific binding of the AB1 to the target, and in a cleaved, activated state the MM1 does not interfere or compete with specific binding of the AB1 to the target; and (ii) measuring a level of activated multispecific activatable antibody in the subject or sample, wherein a detectable level of activated multispecific activatable antibody in the subject or sample indicates that the cleaving agent and the target are present in the subject or sample and wherein no detectable level of activated multispecific activatable antibody in the subject or sample indicates that the cleaving agent, the target or both the cleaving agent and the target are absent and/or not sufficiently present in the subject or sample.

In some embodiments, the activatable multispecific activatable antibody is an activatable multispecific activatable antibody to which a therapeutic agent is conjugated. In some embodiments, the activatable multispecific activatable antibody is not conjugated to an agent. In some embodiments, the activatable multispecific activatable antibody comprises a detectable label. In some embodiments, the detectable label is positioned on the AB1. In some embodiments, measuring the level of activatable multispecific activatable antibody in the subject or sample is accomplished using a secondary reagent that specifically binds to the activated multispecific activatable antibody, wherein the reagent comprises a detectable label. In some embodiments, the secondary reagent is an antibody comprising a detectable label.

In some embodiments of these methods and kits, the activatable multispecific activatable antibody includes a detectable label. In some embodiments of these methods and kits, the detectable label includes an imaging agent, a contrasting agent, an enzyme, a fluorescent label, a chromophore, a dye, one or more metal ions, or a ligand-based label. In some embodiments of these methods and kits, the imaging agent comprises a radioisotope. In some embodiments of these methods and kits, the radioisotope is indium or technetium. In some embodiments of these methods and kits, the contrasting agent comprises iodine, gadolinium or iron oxide. In some embodiments of these methods and kits, the enzyme comprises horseradish peroxidase, alkaline phosphatase, or β-galactosidase. In some embodiments of these methods and kits, the fluorescent label comprises yellow fluorescent protein (YFP), cyan fluorescent protein (CFP), green fluorescent protein (GFP), modified red fluorescent protein (mRFP), red fluorescent protein tdimer2 (RFP tdimer2), HCRED, or a europium derivative. In some embodiments of these methods and kits, the luminescent label comprises an N-methylacrydium derivative. In some embodiments of these methods, the label comprises an Alexa Fluor® label, such as Alex Fluor® 680 or Alexa Fluor® 750. In some embodiments of these methods and kits, the ligand-based label comprises biotin, avidin, streptavidin or one or more haptens.

In some embodiments of these methods and kits, the subject is a mammal. In some embodiments of these methods and kits, the subject is a human. In some embodiments, the subject is a non-human mammal, such as a non-human primate, companion animal (e.g., cat, dog, horse), farm animal, work animal, or zoo animal. In some embodiments, the subject is a rodent.

In some embodiments of these methods, the method is an in vivo method. In some embodiments of these methods, the method is an in situ method. In some embodiments of these methods, the method is an ex vivo method. In some embodiments of these methods, the method is an in vitro method.

In some embodiments of the methods and kits, the method or kit is used to identify or otherwise refine a patient population suitable for treatment with a multispecific activatable antibody of the disclosure. For example, patients that test positive for both the target and a protease that cleaves the substrate in the first cleavable moiety (CM1) of the multispecific activatable antibody being tested in these methods are identified as suitable candidates for treatment with such a multispecific activatable antibody comprising such a CM1. Likewise, patients that test negative for both the target and the protease that cleaves the substrate in the CM1 in the multispecific activatable antibody being tested using these methods might be identified as suitable candidates for another form of therapy.

In some embodiments, a method or kit is used to identify or otherwise refine a patient population suitable for treatment with a multispecific activatable antibody and/or conjugated multispecific activatable antibody (e.g., multispecific activatable antibody to which a therapeutic agent is conjugated) of the disclosure, followed by treatment by administering that multispecific antibody and/or multispecific activatable antibody and/or conjugated multispecific activatable antibody to a subject in need thereof. For example, patients that test positive for both the target and a protease that cleaves the substrate in the first cleavable moiety (CM1) of the multispecific activatable antibody and/or conjugated multispecific activatable antibody being tested in these methods are identified as suitable candidates for treatment with a multispecific activatable antibody comprising such a CM1 and/or conjugated multispecific activatable antibody comprising such a CM1, and the patient is then administered a therapeutically effective amount of the multispecific activatable antibody and/or conjugated multispecific activatable antibody that was tested. Likewise, patients that test negative for either or both of the target and the protease that cleaves the substrate in the CM1 in the multispecific activatable antibody and/or conjugated multispecific activatable antibody being tested using these methods might be identified as suitable candidates for another form of therapy.

In some embodiments, such patients can be tested with other multispecific antibodies and/or multispecific activatable antibodies and/or conjugated multispecific activatable antibodies until a suitable multispecific activatable antibody and/or conjugated multispecific activatable antibody for treatment is identified, e.g., a multispecific activatable antibody and/or conjugated multispecific activatable antibody comprising a CM that is cleaved by the patient at the site of disease. In some embodiments, the patient is then administered a therapeutically effective amount of the multispecific activatable antibody and/or conjugated multispecific activatable antibody for which the patient tested positive.

Pharmaceutical compositions according to the disclosure can include a multispecific antibody and/or a multispecific activatable antibody of the disclosure and a carrier. These pharmaceutical compositions can be included in kits, such as, for example, diagnostic kits.

One skilled in the art will appreciate that the antibodies of the disclosure have a variety of uses. For example, the proteins of the disclosure are used as therapeutic agents for a variety of disorders. The antibodies of the disclosure are also used as reagents in diagnostic kits or as diagnostic tools, or these antibodies can be used in competition assays to generate therapeutic reagents.

BRIEF DESCRIPTION OF DRAWINGS

FIG. 1 is an illustration depicting various bispecific antibody formats (adapted from Chan and Carter, Nat. Rev. Immunol. 2010).

FIG. 19 is a series of graphs depicting primary T cell lysis of a panel of EGFR-expressing cell lines by multispecific antibody C225v5-OKT3m-H-N compared to there being no lysis of the EGFR-negative U266 cell line.

FIGS. 20A and 20B also demonstrate that such multispecific activatable antibody and multispecific antibody bind EGFR in a manner similar to that of the respective monospecific activatable antibody and monospecific antibody.

DETAILED DESCRIPTION

Figure 2A:
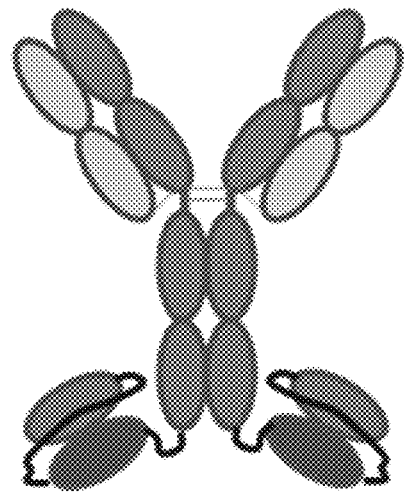
FIGS. 2A-2C are a series of illustrations depicting various multispecific antibody formats suitable for use in the compositions and methods of the disclosure. In a bispecific antibody, a scFv can be fused to the carboxyl terminus of the heavy chain (Hc) of a IgG antibody (FIG. 2A); to the carboxyl-terminus of the light chain (Lc) (FIG. 2B); or to the carboxyl terminus of both the heavy and light chains (FIG. 2C).

The present disclosure provides multispecific antibodies and/or multispecific activatable antibodies. As used herein, a multispecific antibody is an antibody that recognizes two or more different antigens or epitopes, and a multispecific activatable antibody is a multispecific antibody that includes at least one masking moiety (MM) linked to at least one antigen- or epitope-binding domain of the multispecific antibody such that coupling of the MM reduces the ability of the antigen- or epitope-binding domain to bind its target. The activatable multispecific antibodies provided herein are stable in circulation, activated at intended sites of therapy and/or diagnosis but not in normal, i.e., healthy tissue, and, when activated, exhibit binding to a target that is at least comparable to the corresponding, unmodified multispecific antibody.

Non-limiting examples of multispecific antibodies include bispecific antibodies, trispecific antibodies, tetraspecific antibodies, and other multispecific antibodies. Multispecific antibodies provided herein are also multivalent; as used herein, multivalency refers to the total number of binding sites on the antibody, regardless of whether the binding sites recognize the same or different antigens or epitopes. Non-limiting examples of multispecific activatable antibodies include bispecific activatable antibodies, trispecific activatable antibodies, tetraspecific activatable antibodies, and other multispecific activatable antibodies. Multispecific activatable antibodies provided herein are also multivalent.

In some embodiments, the multispecific antibodies or fragments thereof and/or multispecific activatable antibodies or fragments thereof are designed to engage T cells and/or other immune effector cells. Multispecific activatable antibodies or fragments thereof that engage T cells are also referred to herein as T-cell engaging multispecific antibodies or fragments thereof and/or T-cell engaging multispecific activatable antibodies or fragments thereof. Multispecific activatable antibodies or fragments thereof that engage immune effector cells are also referred to herein as immune effector cell engaging multispecific antibodies or fragments thereof and/or immune effector cell engaging multispecific activatable antibodies or fragments thereof. In some embodiments, the multispecific antibodies or fragments thereof and/or multispecific activatable antibodies or fragments thereof are designed to bind or otherwise interact with more than one target and/or more than one epitope, also referred to herein as multi-antigen targeting antibodies or fragments thereof and/or multi-antigen targeting activatable antibodies or fragments thereof.

In some embodiments, a multispecific antibody or fragment thereof includes an IgG domain and a scFv domain. In some embodiments, a multispecific antibody or fragment thereof includes an IgG variable domain and a scFv domain. In some embodiments, one antibody domain of a multispecific antibody or fragment thereof has specificity for a target antigen and another antibody domain has specificity for a T-cell surface antigen. In some embodiments, one antibody domain of a multispecific antibody or fragment thereof has specificity for a target antigen and another antibody domain has specificity for another target antigen. In some embodiments, one antibody domain of a multispecific antibody or fragment thereof has specificity for an epitope of a target antigen and another antibody domain has specificity for another epitope of the same target antigen.

Various embodiments of multispecific activatable antibodies or fragments thereof of the disclosure are shown in FIGS. 3A, and 5-9. In some embodiments, a multispecific activatable antibody or fragment thereof comprising an IgG has the IgG variable domains masked. In some embodiments, a multispecific activatable antibody or fragment thereof comprising a scFv has the scFv domains masked. In some embodiments, a multispecific activatable antibody or fragment thereof has both IgG variable domains and scFv domains, where at least one of the IgG variable domains is coupled to a masking moiety. In some embodiments, a multispecific activatable antibody or fragment thereof has both IgG variable domains and scFv domains, where at least one of the scFv domains is coupled to a masking moiety. In some embodiments, a multispecific activatable antibody or fragment thereof has both IgG variable domains and scFv domains, where at least one of the IgG variable domains is coupled to a masking moiety and at least one of the scFv domains is coupled to a masking moiety. In some embodiments, a multispecific activatable antibody or fragment thereof has both IgG variable domains and scFv domains, where each of the IgG variable domains and the scFv domains is coupled to its own masking moiety. In some embodiments, one antibody domain of a multispecific activatable antibody or fragment thereof has specificity for a target antigen and another antibody domain has specificity for a T-cell surface antigen. In some embodiments, one antibody domain of a multispecific activatable antibody or fragment thereof has specificity for a target antigen and another antibody domain has specificity for another target antigen. In some embodiments, one antibody domain of a multispecific activatable antibody or fragment thereof has specificity for an epitope of a target antigen and another antibody domain has specificity for another epitope of the same target antigen.

In some embodiments, multispecific antibodies or fragments thereof of the disclosure include at least (i) a T-cell engaging antibody or fragment thereof that includes a first antibody or antigen-binding fragment thereof (AB1) that binds a first, T-cell engaging target that is a surface antigen on a T cell and (ii) a second antibody or fragment thereof that includes a second antibody or antigen-binding fragment thereof (AB2) that binds a second target. In some embodiments, the first and second targets are the same antigen. In some embodiments, the first and second targets are different antigens. In some embodiments, the first and second targets are different epitopes on the same antigen. In some embodiments, the T-cell engaging antibody or fragment thereof is attached the N-terminus of the heavy chain of the target-specific antibody. In some embodiments, the T-cell engaging antibody or fragment thereof is attached the C-terminus of the heavy chain of the target-specific antibody. In some embodiments, the T-cell engaging antibody or fragment thereof is attached the N-terminus of the light chain of the target-specific antibody. In some embodiments, the T-cell engaging antibody or fragment thereof is attached the C-terminus of the light chain of the target-specific antibody. In some embodiments, the multispecific antibody comprises T-cell engaging antibodies or fragments thereof attached to a combination of one or more N-termini and/or one or more C-termini of the multispecific antibody. The disclosure also includes multispecific antibodies that comprise another immune effector cell engaging antibody or fragment thereof, such as one that binds a surface antigen of a natural killer (NK) cell, a mononuclear cell, such as a myeloid mononuclear cell, a macrophage, and/or other immune effector cells.

In some embodiments, the multispecific antibody or fragment thereof of the disclosure includes at least two T-cell engaging antibodies or fragments thereof that engage one or more T cell activating receptors, such as, for example, T-cell engaging scFv fragments, including but not limited to, OX40/GITR, CD 137/GITR, CD137/OX40, CD27/NKG2D, and additional combination of activating receptors, and one target-binding antibody such that the T-cell engaging scFv fragments are linked to both arms of the target binding antibody. In some embodiments, the multispecific antibody or fragment thereof of the disclosure includes two T-cell engaging antibodies or fragments thereof that engage one or more T cell inhibitory receptors, and one target-binding antibody such that the T-cell engaging scFv fragments are linked to both arms of the target binding antibody. In some embodiments, the two T-cell engaging antibody fragments bind the same T-cell engaging target. In some embodiments, the two T-cell engaging antibody fragments bind different T-cell engaging targets. In some embodiments, the two T-cell engaging antibody fragments bind different epitopes on the same T-cell engaging target.

In some embodiments, the multispecific antibody or fragment thereof of the disclosure includes at least (i) a first arm comprising an antigen-binding fragment of a T-cell engaging antibody that includes a first antibody or antigen-binding fragment thereof (AB1) that binds a first, T-cell engaging target and (ii) a second arm comprising an antigen-binding fragment of a target binding antibody that includes a second antibody or antigen-binding fragment thereof (AB2) that binds a second target. In some embodiments, the multispecific antibody or fragment thereof includes (iii) at least a third antigen-binding fragment of a target binding antibody that includes a third antibody or antigen-binding fragment thereof (AB3) that binds a third target. In some embodiments, the second and third or more targets are the same antigen. In some embodiments, the second and third or more targets are different antigens. In some embodiments, the second and third or more targets are different epitopes on the same antigen.

In some embodiments, multispecific activatable antibodies or fragments thereof of the disclosure include at least (i) a T-cell engaging antibody or fragment thereof that includes a first antibody or antigen-binding fragment thereof (AB1) that binds a first, T-cell engaging target that is a surface antigen on a T cell, where the AB1 is attached to a masking moiety (MM) such that coupling of the MM reduces the ability of the AB1 to bind the first target and (ii) a second antibody or fragment thereof that includes a second antibody or antigen-binding fragment thereof (AB2) that binds a second target. In some embodiments, the first and second targets are the same antigen. In some embodiments, the first and second targets are different antigens. In some embodiments, the first and second targets are different epitopes on the same antigen. In some embodiments, the T-cell engaging antibody or fragment thereof is attached the N-terminus of the heavy chain of the target-specific antibody. In some embodiments, the T-cell engaging antibody or fragment thereof is attached the C-terminus of the heavy chain of the target-specific antibody. In some embodiments, the T-cell engaging antibody or fragment thereof is attached the N-terminus of the light chain of the target-specific antibody. In some embodiments, the T-cell engaging antibody or fragment thereof is attached the C-terminus of the light chain of the target-specific antibody. In some embodiments, the multispecific activatable antibody comprises T-cell engaging antibodies or fragments thereof attached to a combination of one or more N-termini and/or one or more C-termini of the multispecific activatable antibody. The disclosure also includes multispecific activatable antibodies that comprise another immune effector cell engaging antibody or fragment thereof, such as one that binds a surface antigen of a natural killer (NK) cell, a mononuclear cell, such as a myeloid mononuclear cell, a macrophage, and/or other immune effector cells.

In some embodiments, the multispecific activatable antibody or fragment thereof of the disclosure includes at least (i) two T-cell engaging antibodies or antibody fragments thereof that engage one or more T cell activating receptors, such as, for example, T-cell engaging scFv fragments, including but not limited to, OX40/GITR, CD137/GITR, CD137/OX40, CD27/NKG2D, and additional combination of activating receptors, where the AB1 of one of the T-cell engaging antibody fragments is attached to a masking moiety (MM) such that coupling of the MM reduces the ability of that AB1 to bind its respective T-cell engaging target, and (ii) one target-binding antibody such that the T-cell engaging scFv fragments are linked to both arms of the target binding antibody. In some embodiments, the multispecific antibody or fragment thereof of the disclosure includes two T-cell engaging antibodies or fragments thereof that engage one or more T cell inhibitory receptors, and one target-binding antibody such that the T-cell engaging scFv fragments are linked to both arms of the target binding antibody. In some embodiments, the two T-cell engaging antibody fragments bind the same T-cell engaging target. In some embodiments, the two T-cell engaging antibody fragments bind different T-cell engaging targets. In some embodiments, the two T-cell engaging antibody fragments bind different epitopes on the same T-cell engaging target.

In some embodiments, the multispecific activatable antibody or fragment thereof of the disclosure includes at least (i) two T-cell engaging antibodies or antibody fragments thereof that engage one or more T cell activating receptors, such as, for example, T-cell engaging scFv fragments, including but not limited to, OX40/GITR, CD137/GITR, CD137/OX40, CD27/NKG2D, and additional combination of activating receptors, where each of AB1 of the T-cell engaging antibody fragments is attached to its own masking moiety (MM) such that coupling of each MM to its respective AB1 reduces the ability of that AB1 to bind its respective T-cell engaging target, and (ii) one target-binding antibody such that the T-cell engaging scFv fragments are linked to both arms of the target binding antibody. In some embodiments, the multispecific antibody or fragment thereof of the disclosure includes two T-cell engaging antibodies or fragments thereof that engage one or more T cell inhibitory receptors, and one target-binding antibody such that the T-cell engaging scFv fragments are linked to both arms of the target binding antibody. In some embodiments, the two T-cell engaging antibody fragments bind the same T-cell engaging target. In some embodiments, the two T-cell engaging antibody fragments bind different T-cell engaging targets. In some embodiments, the two T-cell engaging antibody fragments bind different epitopes on the same T-cell engaging target. In some embodiments, the T-cell engaging antibodies or fragments thereof engage one or more T cell inhibitory receptors instead of one or more T cell activating receptors.

In some embodiments, the multispecific activatable antibody or fragment thereof of the disclosure includes at least (i) a first arm comprising an antigen-binding fragment of a T-cell engaging antibody that includes a first antibody or antigen-binding fragment thereof (AB1) that binds a first, T-cell engaging target, where the AB1 is attached to a masking moiety (MM) such that coupling of the MM reduces the ability of the AB1 to bind the first target and (ii) a second arm comprising an antigen-binding fragment of a target binding antibody that includes a second antibody or antigen-binding fragment thereof (AB2) that binds a second target. In some embodiments, the first and second targets are the same antigen. In some embodiments, the first and second targets are different antigens. In some embodiments, the first and second targets are different epitopes on the same antigen. In some embodiments, the T-cell engaging antibodies or fragments thereof engage one or more T cell inhibitory receptors instead of one or more T cell activating receptors.

In some embodiments, multispecific activatable antibodies or fragments thereof of the disclosure include at least (i) a T-cell engaging antibody or fragment thereof that includes a first antibody or antigen-binding fragment thereof (AB1) that binds a first, T-cell engaging target that is a surface antigen on a T cell and (ii) a second antibody or fragment thereof that includes a second antibody or antigen-binding fragment thereof (AB2) that binds a second target, where the AB2 is attached to a masking moiety (MM) such that coupling of the MM reduces the ability of the AB2 to bind the second target. In some embodiments, the first and second targets are the same antigen. In some embodiments, the first and second targets are different antigens. In some embodiments, the first and second targets are different epitopes on the same antigen. In some embodiments, the T-cell engaging antibody or fragment thereof is attached the N-terminus of the heavy chain of the target-specific antibody. In some embodiments, the T-cell engaging antibody or fragment thereof is attached the C-terminus of the heavy chain of the target-specific antibody. In some embodiments, the T-cell engaging antibody or fragment thereof is attached the N-terminus of the light chain of the target-specific antibody. In some embodiments, the T-cell engaging antibody or fragment thereof is attached the C-terminus of the light chain of the target-specific antibody. In some embodiments, the multispecific activatable antibody comprises T-cell engaging antibodies or fragments thereof attached to a combination of one or more N-termini and/or one or more C-termini of the multispecific activatable antibody. The disclosure also includes multispecific activatable antibodies that comprise another immune effector cell engaging antibody or fragment thereof, such as one that binds a surface antigen of a natural killer (NK) cell, a mononuclear cell, such as a myeloid mononuclear cell, a macrophage, and/or other immune effector cells.

In some embodiments, the multispecific activatable antibody or fragment thereof of the disclosure includes at least (i) two T-cell engaging antibodies or antibody fragments thereof that engage one or more T cell activating receptors, such as, for example, T-cell engaging scFv fragments, including but not limited to, OX40/GITR, CD137/GITR, CD137/OX40, CD27/NKG2D, and additional combination of activating receptors and (ii) one target-binding antibody that includes a second antibody or antigen-binding fragment thereof (AB2) that binds a second target, where the AB2 is attached to a masking moiety (MM) such that coupling of the MM reduces the ability of the AB2 to bind the second target, where the T-cell engaging scFv fragments are linked to both arms of the target binding antibody. In some embodiments, the multispecific antibody or fragment thereof of the disclosure includes two T-cell engaging antibodies or fragments thereof that engage one or more T cell inhibitory receptors, and one target-binding antibody such that the T-cell engaging scFv fragments are linked to both arms of the target binding antibody. In some embodiments, the two T-cell engaging antibody fragments bind the same T-cell engaging target. In some embodiments, the two T-cell engaging antibody fragments bind different T-cell engaging targets. In some embodiments, the two T-cell engaging antibody fragments bind different epitopes on the same T-cell engaging target. In some embodiments, the T-cell engaging antibodies or fragments thereof engage one or more T cell inhibitory receptors instead of one or more T cell activating receptors.

In some embodiments, the multispecific activatable antibody or fragment thereof of the disclosure includes at least (i) a first arm comprising an antigen-binding fragment of a T-cell engaging antibody and (ii) a second arm comprising an antigen-binding fragment of a target binding antibody that includes a second antibody or antigen-binding fragment thereof (AB2) that binds a second target, where the AB2 is attached to a masking moiety (MM) such that coupling of the MM reduces the ability of the AB2 to bind the second target. In some embodiments, the first and second targets are the same antigen. In some embodiments, the first and second targets are different antigens. In some embodiments, the first and second targets are different epitopes on the same antigen. In some embodiments, the T-cell engaging antibodies or fragments thereof engage one or more T cell inhibitory receptors instead of one or more T cell activating receptors.

In some embodiments, multispecific activatable antibodies or fragments thereof of the disclosure include at least (i) a T-cell engaging antibody or fragment thereof that includes a first antibody or antigen-binding fragment thereof (AB1) that binds a first, T-cell engaging target that is a surface antigen on a T cell, where the AB1 is attached to a masking moiety (MM1) such that coupling of the MM1 reduces the ability of the AB1 to bind the first target and (ii) a second antibody or fragment thereof that includes a second antibody or antigen-binding fragment thereof (AB2) that binds a second target, where the AB2 is attached to a masking moiety (MM2) such that coupling of the MM2 reduces the ability of the AB2 to bind the second target. In some embodiments, the first and second targets are the same antigen. In some embodiments, the first and second targets are different antigens. In some embodiments, the first and second targets are different epitopes on the same antigen. In some embodiments, the T-cell engaging antibody or fragment thereof is attached the N-terminus of the heavy chain of the target-specific antibody. In some embodiments, the T-cell engaging antibody or fragment thereof is attached the C-terminus of the heavy chain of the target-specific antibody. In some embodiments, the T-cell engaging antibody or fragment thereof is attached the N-terminus of the light chain of the target-specific antibody. In some embodiments, the T-cell engaging antibody or fragment thereof is attached the C-terminus of the light chain of the target-specific antibody. In some embodiments, the multispecific activatable antibody comprises T-cell engaging antibodies or fragments thereof attached to a combination of one or more N-termini and/or one or more C-termini of the multispecific activatable antibody. The disclosure also includes multispecific activatable antibodies that comprise another immune effector cell engaging antibody or fragment thereof, such as one that binds a surface antigen of a natural killer (NK) cell, a mononuclear cell, such as a myeloid mononuclear cell, a macrophage, and/or other immune effector cells.

In some embodiments, the multispecific activatable antibody or fragment thereof of the disclosure includes at least (i) two T-cell engaging antibodies or antibody fragments thereof that engage one or more T cell activating receptors, such as, for example, T-cell engaging scFv fragments, including but not limited to, OX40/GITR, CD137/GITR, CD137/OX40, CD27/NKG2D, and additional combination of activating receptors, where the AB1 of one of the T-cell engaging antibody fragments is attached to a masking moiety (MM) such that coupling of the MM reduces the ability of that AB1 to bind its respective T-cell engaging target, and (ii) one target-binding antibody that includes a second antibody or antigen-binding fragment thereof (AB2) that binds a second target, where the AB2 is attached to a masking moiety (MM2) such that coupling of the MM2 reduces the ability of the AB2 to bind the second target, where that the T-cell engaging scFv fragments are linked to both arms of the target binding antibody. In some embodiments, the multispecific antibody or fragment thereof of the disclosure includes two T-cell engaging antibodies or fragments thereof that engage one or more T cell inhibitory receptors, and one target-binding antibody such that the T-cell engaging scFv fragments are linked to both arms of the target binding antibody. In some embodiments, the two T-cell engaging antibody fragments bind the same T-cell engaging target. In some embodiments, the two T-cell engaging antibody fragments bind different T-cell engaging targets. In some embodiments, the two T-cell engaging antibody fragments bind different epitopes on the same T-cell engaging target. In some embodiments, the T-cell engaging antibodies or fragments thereof engage one or more T cell inhibitory receptors instead of one or more T cell activating receptors.

In some embodiments, the multispecific activatable antibody or fragment thereof of the disclosure includes at least (i) two T-cell engaging antibodies or antibody fragments thereof that engage one or more T cell activating receptors, such as, for example, T-cell engaging scFv fragments, including but not limited to, OX40/GITR, CD137/GITR, CD137/OX40, CD27/NKG2D, and additional combination of activating receptors, where each of AB1 of the T-cell engaging antibody fragments is attached to its own masking moiety (MM1) such that coupling of each MM1 to its respective AB1 reduces the ability of that AB1 to bind its respective T-cell engaging target, and (ii) one target-binding antibody that includes a second antibody or antigen-binding fragment thereof (AB2) that binds a second target, where the AB2 is attached to a masking moiety (MM2) such that coupling of the MM2 reduces the ability of the AB2 to bind the second target, where the T-cell engaging scFv fragments are linked to both arms of the target binding antibody. In some embodiments, the multispecific antibody or fragment thereof of the disclosure includes two T-cell engaging antibodies or fragments thereof that engage one or more T cell inhibitory receptors, and one target-binding antibody such that the T-cell engaging scFv fragments are linked to both arms of the target binding antibody. In some embodiments, the two T-cell engaging antibody fragments bind the same T-cell engaging target. In some embodiments, the two T-cell engaging antibody fragments bind different T-cell engaging targets. In some embodiments, the two T-cell engaging antibody fragments bind different epitopes on the same T-cell engaging target. In some embodiments, the T-cell engaging antibodies or fragments thereof engage one or more T cell inhibitory receptors instead of one or more T cell activating receptors.

In some embodiments, the multispecific activatable antibody or fragment thereof of the disclosure includes at least (i) a first arm comprising an antigen-binding fragment of a T-cell engaging antibody that includes a first antibody or antigen-binding fragment thereof (AB1) that binds a first, T-cell engaging target, where the AB1 is attached to a masking moiety (MM1) such that coupling of the MM reduces the ability of the AB1 to bind the first target and (ii) a second arm comprising an antigen-binding fragment of a target binding antibody that includes a second antibody or antigen-binding fragment thereof (AB2) that binds a second target, where the AB2 is attached to a masking moiety (MM2) such that coupling of the MM reduces the ability of the AB2 to bind the second target. In some embodiments, the first and second targets are the same antigen. In some embodiments, the first and second targets are different antigens. In some embodiments, the first and second targets are different epitopes on the same antigen. In some embodiments, the T-cell engaging antibodies or fragments thereof engage one or more T cell inhibitory receptors instead of one or more T cell activating receptors.

In some embodiments, the target antigen is an antigen that is highly expressed on both normal, healthy tissue and on diseased tissue. In some embodiments, the target antigen is an antigen from Table 1 that is highly expressed on both normal, healthy tissue and on diseased tissue.

In some embodiments, the target antigen is an antigen that is highly expressed on diseased tissue, but is not highly expressed on normal, healthy tissue. In some embodiments, the target antigen is an antigen from Table 1 that is highly expressed on diseased tissue, but is not highly expressed on normal, healthy tissue. The target antigen may be expressed on normal, healthy tissue, but it is not highly or otherwise overexpressed on the normal, healthy tissue.

In some embodiments, the masking moiety (MM) is coupled to the antibody or antigen-binding fragment thereof (AB) via a cleavable moiety (CM) that functions as a substrate for a protease. Suitable proteases for use in the multispecific activatable antibodies of the disclosure are determined based on the protease expression at the intended site of treatment and/or diagnosis. In some embodiments, the protease is u-type plasminogen activator (uPA, also referred to as urokinase), legumain, and/or matriptase (also referred to as MT-SP1 or MTSP1). In some embodiments, the protease is a matrix metalloprotease (MMP).

In some embodiments, the multispecific activatable antibodies are engineered to include a masking moiety (MM) that is coupled to an antibody or antigen-binding fragment thereof (AB) via a non-cleavable linker. For example, in some embodiments, the multispecific activatable antibody is a T-cell engaging multispecific activatable antibody that includes a targeting antibody or antigen-binding fragment thereof and a T-cell engaging antibody or antigen-binding portion thereof, where the T-cell engaging antibody or antigen-binding fragment thereof includes a first antibody or antigen-binding fragment thereof (AB1) that binds a first, T-cell engaging target, where the AB1 is attached via non-cleavable linker to a masking moiety (MM1) such that coupling of the MM reduces the ability of the AB1 to bind the first target, and the targeting antibody or antigen-binding fragment thereof is not masked.

In some embodiments, the multispecific activatable antibody is a T-cell engaging multispecific activatable antibody that includes a targeting antibody or antigen-binding fragment thereof and a T-cell engaging antibody or antigen-binding portion thereof, where the T-cell engaging antibody or antigen-binding fragment thereof includes a first antibody or antigen-binding fragment thereof (AB1) that binds a first, T-cell engaging target, where the AB1 is attached via non-cleavable linker to a masking moiety (MM1) such that coupling of the MM reduces the ability of the AB1 to bind the first target, and the targeting antibody or antigen-binding fragment thereof includes a second antibody or antigen-binding fragment thereof (AB2) that binds a second target, where the AB2 is attached via a cleavable linker to a masking moiety (MM2) such that coupling of the MM reduces the ability of the AB2 to bind the second target.

The general concept of bispecific antibodies was first introduced at least 50 years ago (Nisonoff, A. and Mandy, W. J., Nature 194, 355-359 (1962), as cited in Chan, A. C. and Carter, P. J., Nature Reviews Immunol. 10, 301-316 (2010)). A variety of bispecific platforms have been described (see e.g., FIG. 1; Liu, M. A., et al., Proc. Natl. Acad. Sci. USA 82, 8648-8652 (1985); reviewed by Kroesen, B. J., et al. Adv. Drug Delivery Rev. 31, 105-129 (1998); Marvin, J. S. and Zhu, Z., Acta Pharm. Sinica 26, 649-658 (2005); Chan and Carter, Nat. Rev. Immunol. 2010; Fitzgerald and Lugovsky, MAbs. 3(3):299-309 (2011); Riethmuller, G., Cancer Immunity 12, 12-18 (2012)). The general concept for construction of bispecific antibodies is to link together protein-binding domains, usually based on multiple immunoglobulin domains, in order to construct a molecule that is capable of binding to two or more target antigens and demonstrates IgG-like physiological distribution, pharmacokinetics, and effector function. The latter may include antibody-dependent cytotoxicity (ADCC), complement-dependent cytotoxicity (CDC), T-cell recruitment (BiTEsTm) (see e.g., Baeuerle, P. A. and Reinhardt, C., Cancer Res. 69, 4941-4944 (2009), and TandAbs™ (see Cochlovius et al., Cancer Res. 60, 4336-4341 (2000)), and/or delivery of a cytotoxic payload in the form of a chemically conjugated moiety such as a microtubule inhibitor, a DNA alkylator, or other toxin, in the form of an antibody-drug conjugate (ADC). Many bispecific antibody formats are being studied, with conventional heterodimeric IgGs and BiTEsTm representing the most clinically advanced in spite of their sub-optimal production and pharmacological properties (see Chan and Carter, Nat. Rev. Immunol. 2010). Bispecific antibodies have many potential uses, based on specific features of particular formats and the target antigens chosen; not all bispecific formats are appropriate for all applications. For example, the Two-in-one Fab format (Bostrom, J., et al., Science 323, 1610-1614 (2009)) consists of a single binding domain for binding to antigens A and B in an either/or fashion; thus, this type of bispecific may engage two copies of antigen A, two copies of antigen B, or one copy of each antigen. On the other hand, the DVD format (Wu, C., et al., Nature Biotechnol. 25, 1290-1297 (2007)) provides for the engagement of two copies of antigen A in addition to two copies of antigen B. The spacing and relative orientation of each of the binding domains may also be important for engagement of multiple antigens in such a way as to confer the intended activity—for example, cross-linking receptors (Jackman, J., et al., J. Biol. Chem. 285, 20850-20859 (2010)), where engagement of one copy of each receptor is required, may necessitate a monovalent interaction with each of two distinct antigens.

A mechanistically distinct area of bispecific antibody application involves recruiting immune effector cells (such as cytotoxic T-lymphocytes, NK cells, and/or myeloid effector cells) to attack tumor cells by constructing a bispecific that engages both an antigen on the surface of a cell targeted for cytotoxicity (e.g., a tumor cell) and an antigen on the surface of a cytotoxic immune cell (e.g. a T-cell). Catumaxomab is an example of a clinically validated bispecific antibody that targets the tumor antigen EpCAM on cancer cells and recruits cytotoxic T-cells through binding to CD3 on the T-cell surface (Linke, R., Klein, A., and Seimetz, D., mAbs 2, 129-136 (2010)); however, its use has been limited and it requires intraperitoneal administration. BiTE™ antibodies are bispecific antibodies that accomplish T-cell recruitment in a different format with different pharmacological properties (Baeuerle, P. A. and Reinhardt, C., Anti-Cancer Res. 69, 4941-4944 (2009))—in particular, BiTE antibodies are comprised of two single chain variable fragments (scFvs) and have very short pharmacologic half-lives in vivo; thus they require delivery via continuous infusion. A similar format, termed TandAb™, is a tetravalent, bispecific diabody construct in which two variable domains bind to a target antigen and two variable domains bind to CD3 on the surface of T-cells (Cochlovius et al., Cancer Res. 60, 4336-4341 (2000)). This format illustrates that bivalent engagement of both the target antigen and the T-cell surface antigen can be used for T-cell engagement and antigen-directed cytotoxicity. However, the TandAb format also has a very short half-life in vivo.

A general limitation of T-cell engaging bispecific antibodies is related to the fact that T-cell cytotoxicity can be extremely potent and can be activated by relatively low levels of target antigen on the surface of cells. Therefore, even modest levels of target antigen expression, such as EGFR, on healthy tissues can lead to significant toxicity, limiting or preventing clinical therapeutic applications (Lutterbuese, R. et al., Proc. Natl. Acad. Sci. USA 107, 12605-12610 (2010)). Thus, there remains a need for effective antibody-based therapeutics that exhibit improved safety, e.g., reduced toxicity.

Multispecific activatable antibodies of the disclosure are safer than multispecific (e.g., bispecific) antibodies because multispecific activatable antibody activity is restricted to a localized disease environment. In some embodiments, a multispecific activatable antibody is an immune effector cell engaging multispecific activatable antibody. In some embodiments, a multispecific activatable antibody is a T-cell engaging multispecific activatable antibody. In some embodiments, a multispecific activatable antibody recognizes two or more targets. In some embodiments, a multispecific activatable antibody comprises an IgG-scFv format confers the long-half-life properties of an IgG. In some embodiments, such a multispecific activatable antibody is further modulated through the use of Fc mutations in the FcRn binding site (Petkova, S. B. et al., Intl. Immunol. 18, 1759-1769 (2006)); Deng, R. et al., mAbs 4, 101-109 (2012)); Olafson, T Methods Mol. Biol. 907, 537-556 (2012)). In some embodiments, such a multispecific activatable antibody includes mutations in the Fc domain, such as an N297A mutation (Lund, J. et al., Mol. Immunol. 29, 53-39 (1992)) that reduces IgG effector functions (ADCC and CDC) in order to reduce off-target toxicities.

Multispecific activatable antibodies leverage the up-regulation of protease activity widely recognized as a hallmark of multiple disease states to achieve disease-tissue-specific targeting of such therapeutics. The activatable antibody is based on the use of an IgG antibody, or fragment thereof, such as a scFv region, Fab region, single VH or VL domain that has been modified to include a masking moiety (MM), linked to the antibody through a cleavable moiety (CM), such as a protease-cleavable moiety (see, e.g., PCT International Publication Number WO 2009/025846, published Feb. 26, 2009; PCT International Publication Number WO 2010/081173, published, Jul. 15, 2010). Alternatively, a non-antibody protein domain (see e.g., PCT International Publication Number WO 2010/096838, published Aug. 26, 2010; Boersma, Y. L. et al., J. Biol. Chem. 286, 41273-41285 (2011)) may be used to achieve one or more binding specificities. A multispecific antibody, like conventional IgG, can be used as the starting point to produce a multispecific activatable antibody. Such a multispecific activatable antibody would allow the high-affinity targeting of all antigens recognized by the parental multispecific antibody, but with tissue-specificity dictated by the selectively activated cleavable linker. Depending upon the multispecific format used, the MM and CM might be placed at the N- or C-terminus of the appropriate domain.

A multispecific activatable antibody comprises at least one IgG-derived domain with specificity towards a first antigen, linked synthetically or biosynthetically to another domain (which may be derived from an IgG or other protein) with specificity for binding to a second antigen. Additional specificities may be added through linking such a multispecific activatable antibody to one or more additional domains conferring additional binding specificities for the first antigen, the second antigen, or additional antigens. In some embodiments, a multispecific activatable antibody has one or more of these domains masked by an appropriate masking moiety (MM). Each of the multispecific formats described in FIG. 1 can potentially be converted into a multispecific activatable antibody by masking one or more of the antigen binding moieties of one or more of the immunoglobulin domains. Examples of suitable multispecific activatable antibody formats are shown in FIGS. 3A, and 5-9.

The use of a scFv domain to confer specificity to a specific antigen allows for a modular construction of multispecific antibodies and multispecific activatable antibodies. The use of scFv domain(s) fused to the terminus of IgG heavy or light chains for construction of bispecific antibodies has been previously described (see e.g., Orcutt, K. D. et al., Prot. Eng. Design Select. 23, 221-228 (2010)); Dong et al., (2011)). This format ("IgG-scFv") allows a conventional IgG to be converted into a bispecific antibody wherein a first specificity is encoded in the variable domains of the IgG and a second specificity is encoded in the scFv domains attached through a flexible linker region. Variations of this format include fusing scFv domains at the N- or C-termini of the heavy or light chains; the scFvs may have the same or differing antigen-binding specificities (Spangler, J. B. et al., J. Mol. Biol. 422, 532-544 (2012)). In addition, through the use of heavy-chain heterodimers (for example, using knob-hole or similar constructs), scFvs of differing specificities may be attached to the N- or C-terminus of each heavy chain.

In some embodiments, a multispecific activatable antibody has the IgG variable domains masked. In some embodiments, a multispecific activatable antibody has the scFv domains masked. In some embodiments, a multispecific activatable antibody has both the IgG variable domains and the scFv domains masked. In some embodiments, one antibody domain of a multispecific activatable antibody has specificity for a target antigen and another antibody domain has specificity for a T-cell surface antigen. In some embodiments, one antibody domain of a multispecific activatable antibody has specificity for a target antigen and another antibody domain has specificity for another target antigen. In some embodiments, one antibody domain of a multispecific activatable antibody has specificity for an epitope of a target antigen and another antibody domain has specificity for another epitope of the target antigen.

The disclosure provides examples of multispecific activatable antibody structures which include, but are not limited to, the following: (VL-CL)$_2$:(VH-CH1-CH2-CH3-L4-VH*-L3-VL*-L2-CM-L1-MM)$_2$; (VL-CL)$_2$:(VH-CH1-CH2-CH3-L4-VL*-L3-VH*-L2-CM-L1-MM)$_2$; (MM-L1-CM-L2-VL-CL)$_2$: (VH-CH1-CH2-CH3-L4-VH*-L3-VL*)$_2$; (MM-L1-CM-L2-VL-CL)$_2$:(VH-CH1-CH2-CH3-L4-VL*-L3-VH*)$_2$; (VL-CL)$_2$:(MM-L1-CM-L2-VL*-L3-VH*-L4-VH-CH1-CH2-CH3)$_2$; (VL-CL)$_2$:(MM-L1-CM-L2-VH*-L3-VL*-L4-VH-CH1-CH2-CH3)$_2$; (MM-L1-CM-L2-VL-CL)$_2$: (VL*-L3-VH*-L4-VH-CH1-CH2-CH3)$_2$; (MM-L1-CM-L2-VL-CL)$_2$: (VH*-L3-VL*-L4-VH-CH1-CH2-CH3)$_2$; (VL-CL-L4-VH*-L3-VL*-L2-CM-L1-MM)$_2$: (VH-CH1-CH2-CH3)$_2$; (VL-CL-L4-VL*-L3-VH*-L2-CM-L1-MM)$_2$: (VH-CH1-CH2-CH3)$_2$; (MM-L1-CM-L2-VL*-L3-VH*-L4-VL-CL)$_2$:(VH-CH1-CH2-CH3)$_2$; (MM-L1-CM-L2-VH*-L3-VL*-L4-VL-CL)$_2$: (VH-CH1-CH2-CH3)$_2$; (VL-CL-L4-VH*-L3-VL*-L2-CM-L1-MM)$_2$: (MM-L1-CM-L2-VH*-L3-VH*-L4-VH-CH1-CH2-CH3)$_2$; (VL-CL-L4-VH*-L3-VL*-L2-CM-L1-MM)$_2$: (MM-L1-CM-L2-VH*-L3-VL*-L4-VH-CH1-CH2-CH3)$_2$; (VL-CL-L4-VL*-L3-VH*-L2-CM-L1-MM)$_2$: (MM-L1-CM-L2-VL*-L3-VH*-L4-VH-CH1-CH2-CH3)$_2$; (VL-CL-L4-VL*-L3-VH*-L2-CM-L1-MM)$_2$: (MM-L1-CM-L2-VH*-L3-VL*-L4-VH-CH1-CH2-CH3)$_2$; (VL-CL-L4-VH*-L3-VL*)$_2$: (MM-L1-CM-L2-VL*-L3-VH*-L4-VH-CH1-CH2-CH3)$_2$; (VL-CL-L4-VH*-L3-VL*)$_2$: (MM-L1-CM-L2-VH*-L3-VL*-L4-VH-CH1-CH2-CH3)$_2$; (VL-CL-L4-VL*-L3-VH*)$_2$: (MM-L1-CM-L2-VL*-L3-VH*-L4-VH-CH1-CH2-CH3)$_2$; (VL-CL-L4-VL*-L3-VH*)$_2$: (MM-L1-CM-L2-VH*-L3-VL*-L4-VH-CH1-CH2-CH3)2; (VL-CL-L4-VH*-L3-VL*-L2-CM-L1-MM)$_2$: (VL*-L3-VH*-L4-VH-CH1-CH2-CH3)$_2$; (VL-CL-L4-VH*-L3-VL*-L2-CM-L1-MM)$_2$: (VH*-L3-VL*-L4-VH-CH1-CH2-CH3)$_2$; (VL-CL-L4-VL*-L3-VH*-L2-CM-L1-MM)$_2$: (VL*-L3-VH*-L4-VH-CH1-CH2-CH3)$_2$; or (VL-CL-L4-VL*-L3-VH*-L2-CM-L1-MM)$_2$: (VH*-L3-VL*-L4-VH-CH1-CH2-CH3)$_2$, wherein: VL and VH represent the light and heavy variable domains of the first specificity, contained in the IgG; VL* and VH* represent the variable domains of the second specificity, contained in the scFv; L1 is a linker peptide connecting the masking moiety (MM) and the cleavable moiety (CM); L2 is a linker peptide connecting the cleavable moiety (CM), and the antibody; L3 is a linker peptide connecting the variable domains of the scFv; L4 is a linker peptide connecting the antibody of the first specificity to the antibody of the second specificity; CL is the light-chain constant domain; and CH1, CH2, CH3 are the heavy chain constant domains. The first and second specificities may be toward any antigen or epitope. Additional structures include, but are not limited to, the following: (VL-CL-L4-VH*-L3-VL*-L2-CM-L1-MM)$_2$:(VH-CH1-CH2-CH3)$_2$; (VL-CL-L4-VL*-L3-VH*-L2-CM-L1-MM)$_2$:(VH-CH1-CH2-CH3)$_2$; (MM-L1-CM-L2-VL-CL-L4-VH*-L3-VL*)$_2$: (VH-CH1-CH2-CH3)$_2$; (MM-L1-CM-L2-VL-CL-L4-VL*-L3-VH*)$_2$:(VH-CH1-CH2-CH3)$_2$; (VL-CL-L4-VH*-L3-VL*-L2-CM-L1-MM)$_2$:(VH-CH1-CH2-CH3-L4-VH*-L3-VL*-L2-CM-L1-MM)$_2$; (VL-CL-L4-VL*-L3-VH*-L2-CM-L1-MM)$_2$:(VH-CH1-CH2-CH3-L4-VL*-L3-VH*-L2-CM-L1-MM)$_2$; (MM-L1-CM-L2-VL-CL-L4-VH*-L3-VL*)$_2$: (VH-CH1-CH2-CH3)$_2$; or (MM-L1-CM-L2-VL-CL-L4-VL*-L3-VH*)$_2$: (VH-CH1-CH2-CH3)$_2$.

In some embodiments, a multispecific activatable antibody comprising an IgG has the IgG variable domains masked. In some embodiments, a multispecific activatable antibody comprising a scFv has the scFv domains masked. In some embodiments, a multispecific activatable antibody has both IgG variable domains and scFv domains, where at least one of the IgG variable domains is coupled to a masking moiety. In some embodiments, a multispecific activatable antibody has both IgG variable domains and scFv domains, where at least one of the scFv domains is coupled to a masking moiety. In some embodiments, a multispecific activatable antibody has both IgG variable domains and scFv domains, where at least one of the IgG variable domains is coupled to a masking moiety and at least one of the scFv domains is coupled to a masking moiety. In some embodiments, a multispecific activatable antibody has both IgG variable domains and scFv domains, where each of the IgG variable domains and the scFv domains is coupled to its own masking moiety. In some embodiments, one antibody domain of a multispecific activatable antibody has specificity for a target antigen and another antibody domain has specificity for a T-cell surface antigen. In some embodiments, one antibody domain of a multispecific activatable antibody has specificity for a target antigen and another antibody domain has specificity for another target antigen. In some embodiments, one antibody domain of a multispecific activatable antibody has specificity for an epitope of a target antigen and another antibody domain has specificity for another epitope of the target antigen.

In some embodiments of an immune effector cell engaging multispecific activatable antibody such as a T-cell engaging multispecific activatable antibody, one antigen is typically an antigen present on the surface of a tumor cell or other cell type associated with disease, such as, but not limited to, any target listed in Table 1, such as, but not limited to, EGFR, erbB2, EpCAM, Jagged, PD-L1, B7H3, or CD71 (transferrin receptor), and another antigen is typically a stimulatory or inhibitory antigen present on the surface of a T-cell, natural killer (NK) cell, myeloid mononuclear cell, macrophage, and/or other immune effector cell, such as, but not limited to, B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA. The antibody domain conferring specificity to the T-cell surface antigen may also be substituted by a ligand or ligand domain that binds to a T-cell receptor, a NK-cell receptor, a macrophage receptor, and/or other immune effector cell receptor, such as, but not limited to, B7-1, B7-2, B7H3, PD-L1, PD-L2, or TNFSF9. In some embodiments of a multi-antigen targeting activatable antibody, one antigen is selected from the group of targets listed in Table 1, and another antigen is selected from the group of targets listed in Table 1.

Figure 2B:
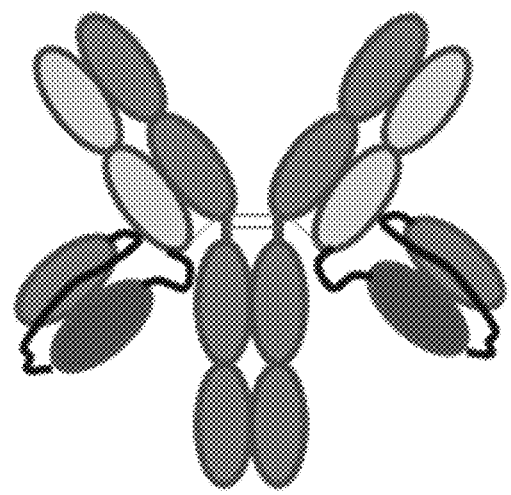
Figure 2C:
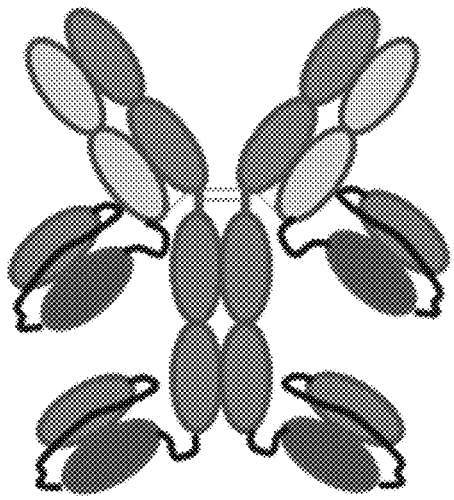
Figure 2D:
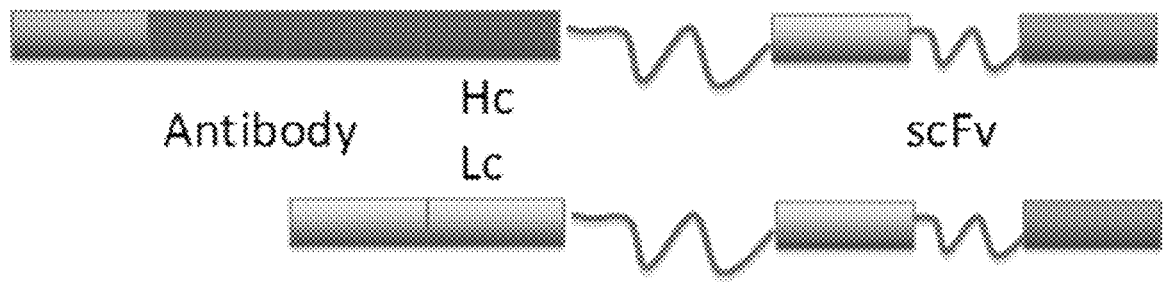
FIG. 2D is a diagram of a single genetic construct for the expression of multispecific antibody fusions.
Figure 3A:
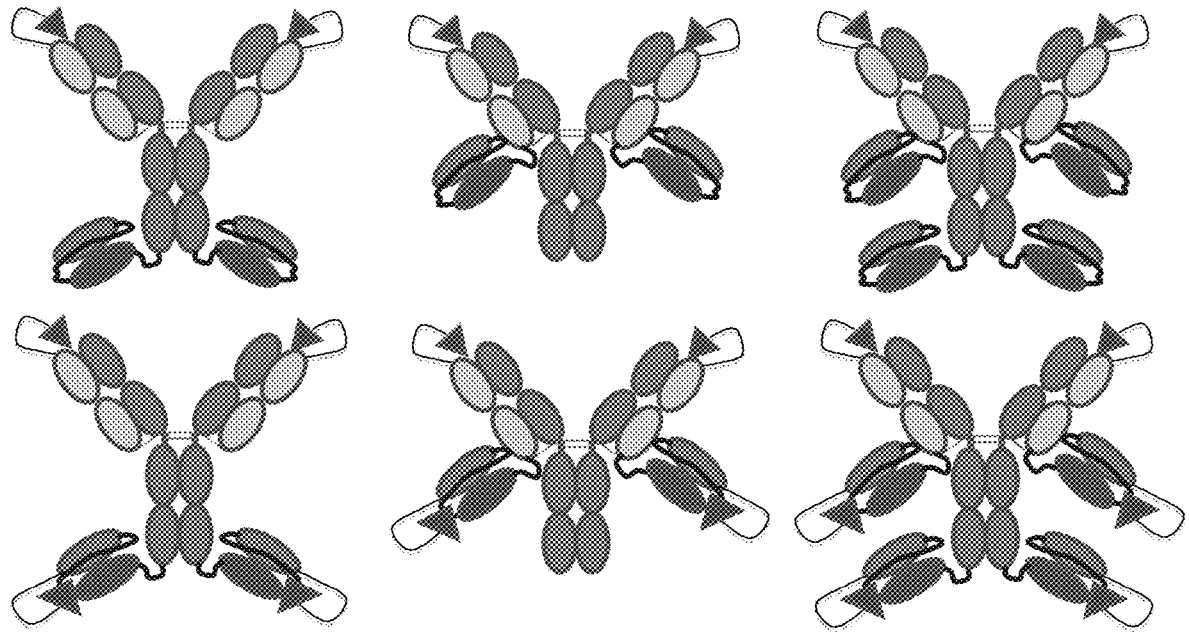
FIG. 3A is a series of illustrations depicting various multispecific activatable antibody formats suitable for use in the compositions and methods of the disclosure.
Figure 3B:
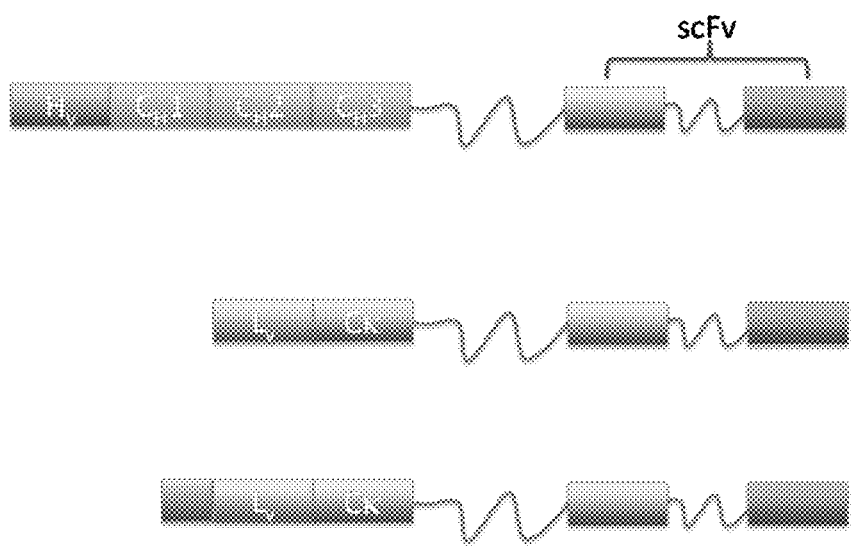
FIG. 3B is a diagram of genetic constructs for the expression of multispecific activatable antibody fusions.
Figure 4:
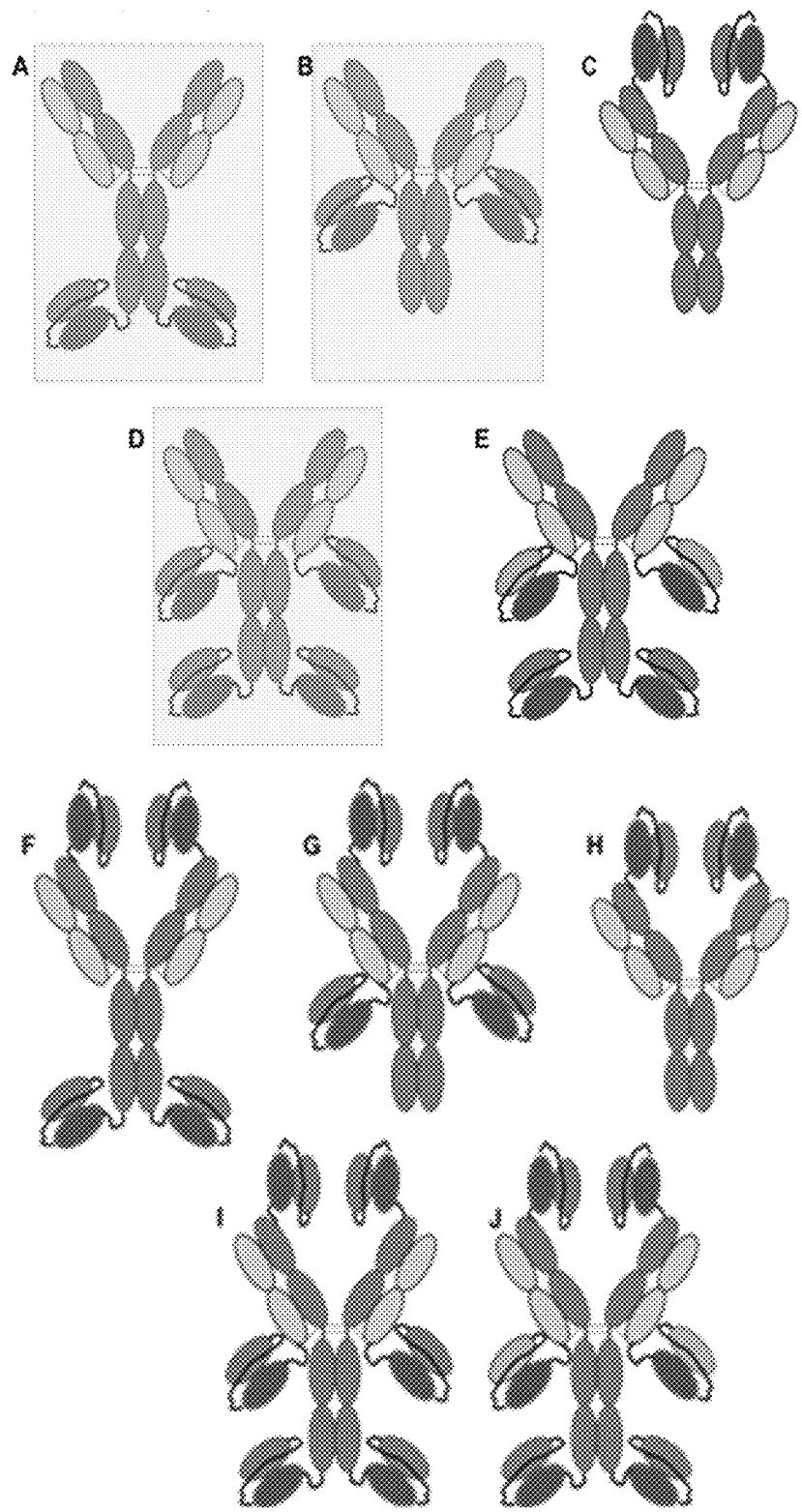
FIG. 4, Panels A-J, are a series of schematic diagrams of a selected set of the possible permutations of multispecific antibodies of the disclosure. Gray-shaded boxes cover the configurations represented in FIGS. 2A, 2B, and 2C and are included here for completeness and comparison.
Figure 5:
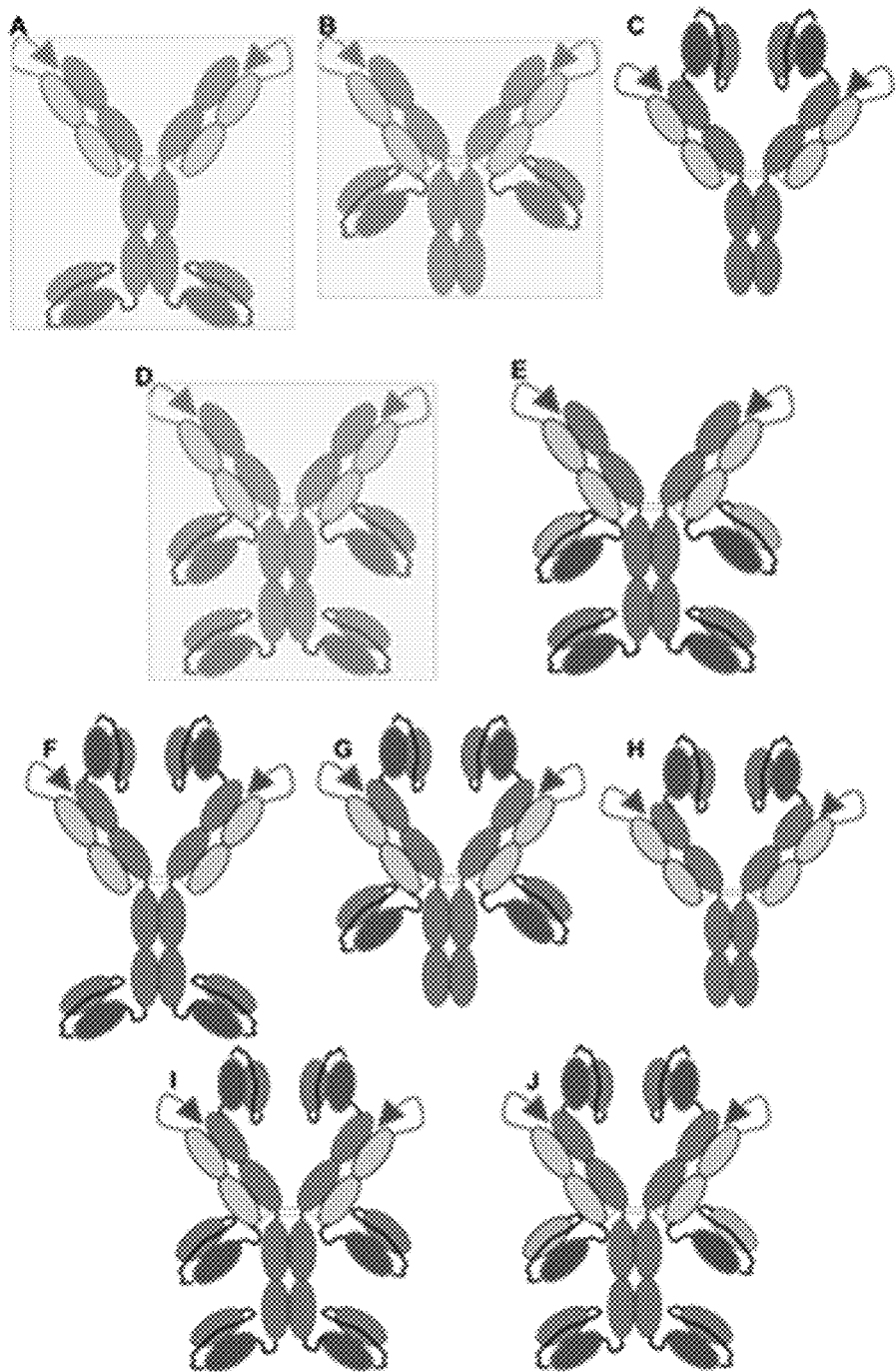
FIG. 5, Panels A-J, are a series of schematic diagrams of a selected set of the possible permutations of multispecific activatable antibodies of the disclosure. Gray-shaded boxes cover the configurations represented in FIG. 3 and are included here for completeness and comparison. In particular, this figure shows multispecific activatable antibodies in which the primary antigen binding site is masked (i.e., activatable) and the additional antigen-binding domain(s) is not masked.
Figure 6:
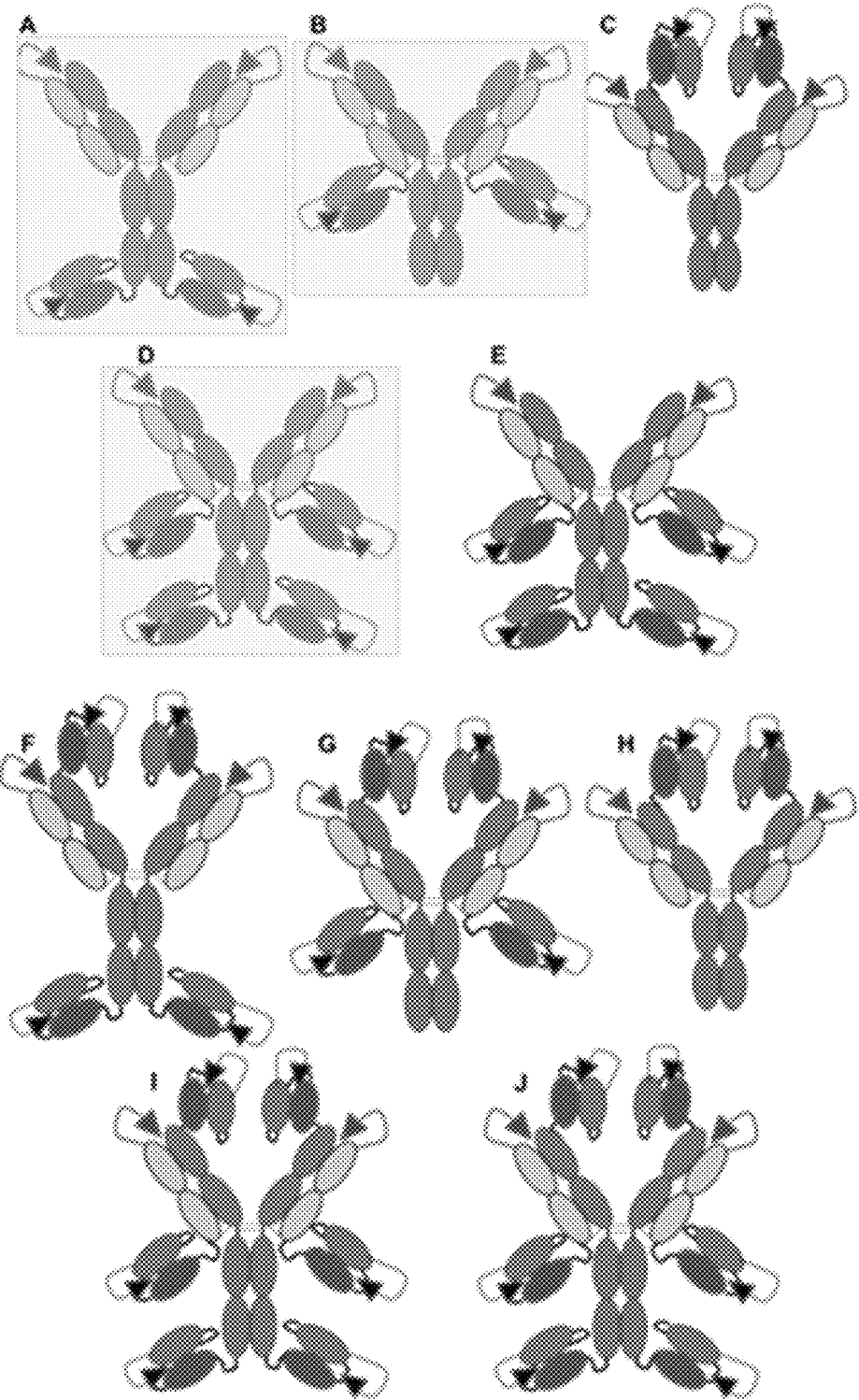
FIG. 6, Panels A-J, are a series of schematic diagrams of an array of multispecific activatable antibodies in which all antigen-binding domains are masked.
Figure 7:
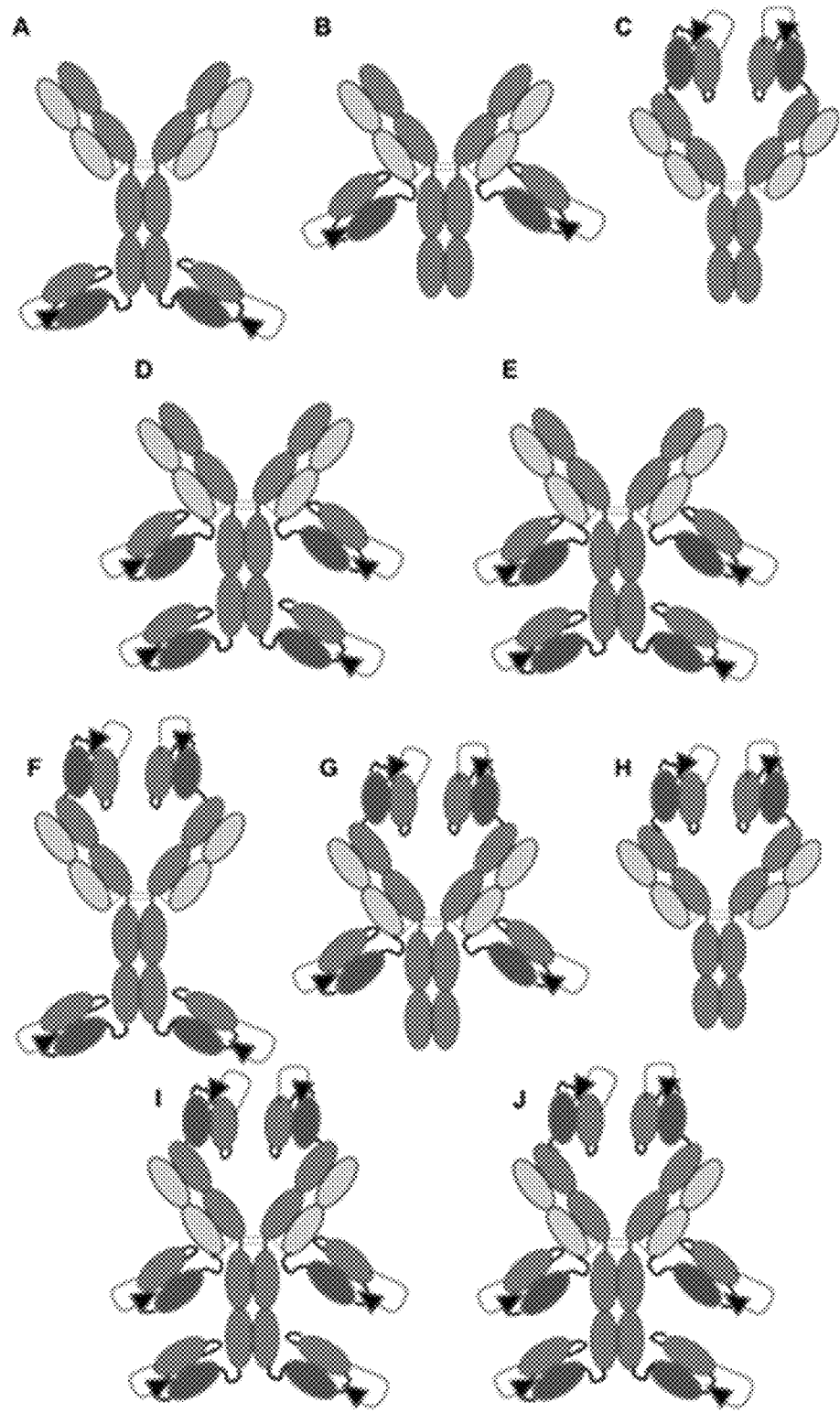
FIG. 7, Panels A-J, are a series of schematic diagrams of an array of multispecific activatable antibodies in which the secondary antigen-binding domain is masked and the additional antigen-binding domain(s) is not masked.
Figure 8:
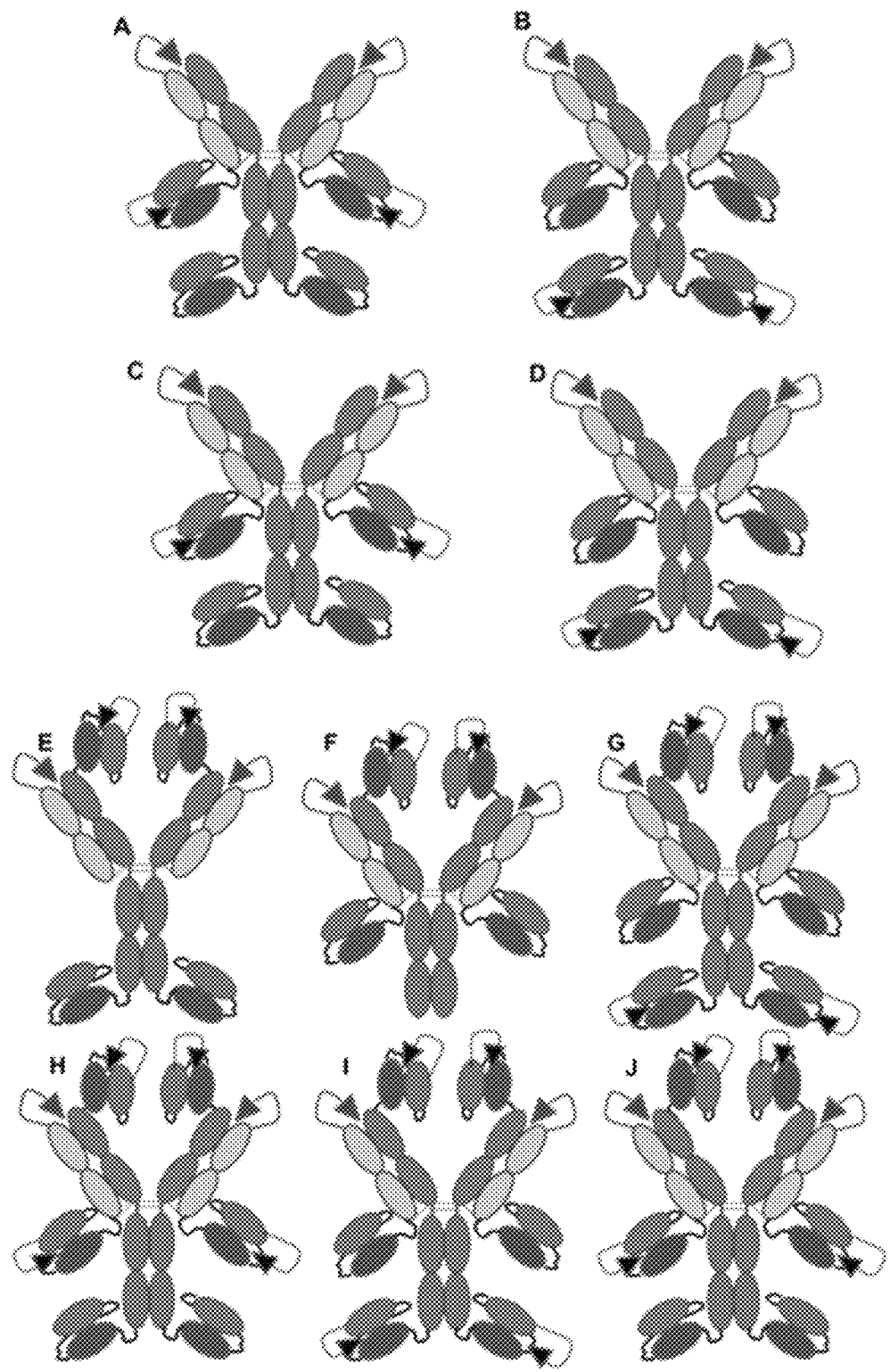
FIG. 8, Panels A-J, are a series of schematic diagrams of an array of multispecific activatable antibodies in which the majority, but not all of the antigen-binding domains are masked and at least one additional antigen-binding domain (s) is not masked.
Figure 9:
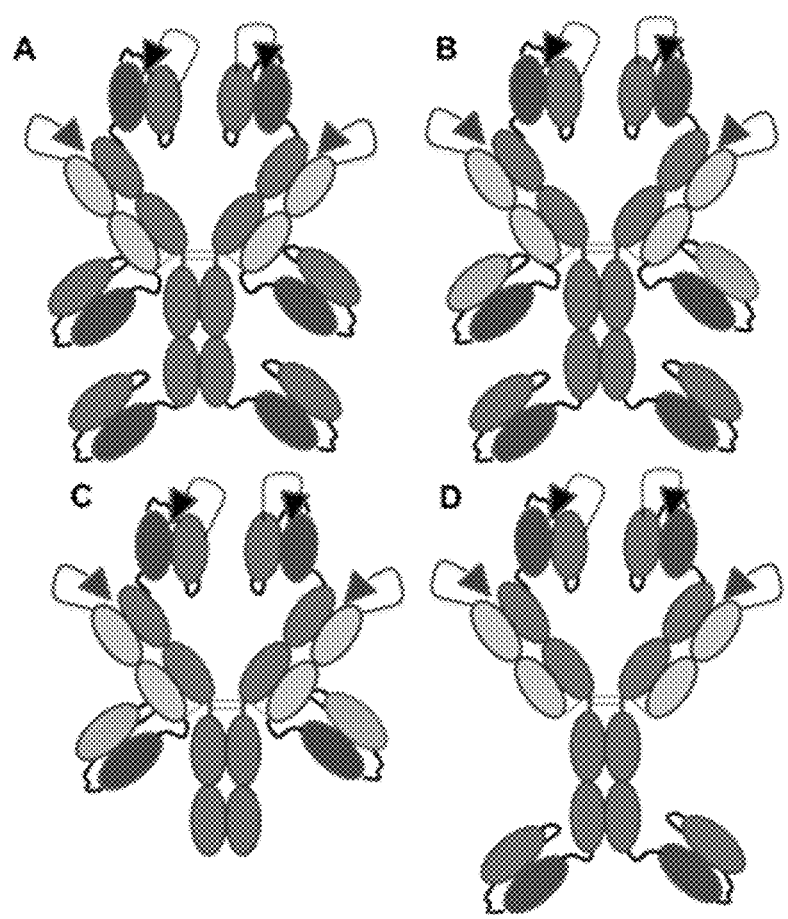
FIG. 9, Panels A-D, are a series of schematic diagrams of an array of multispecific activatable antibodies in which the primary antigen-binding domain and another antigen-binding domain are masked, and the remaining antigen-binding domain(s) is not masked.
Figure 10:
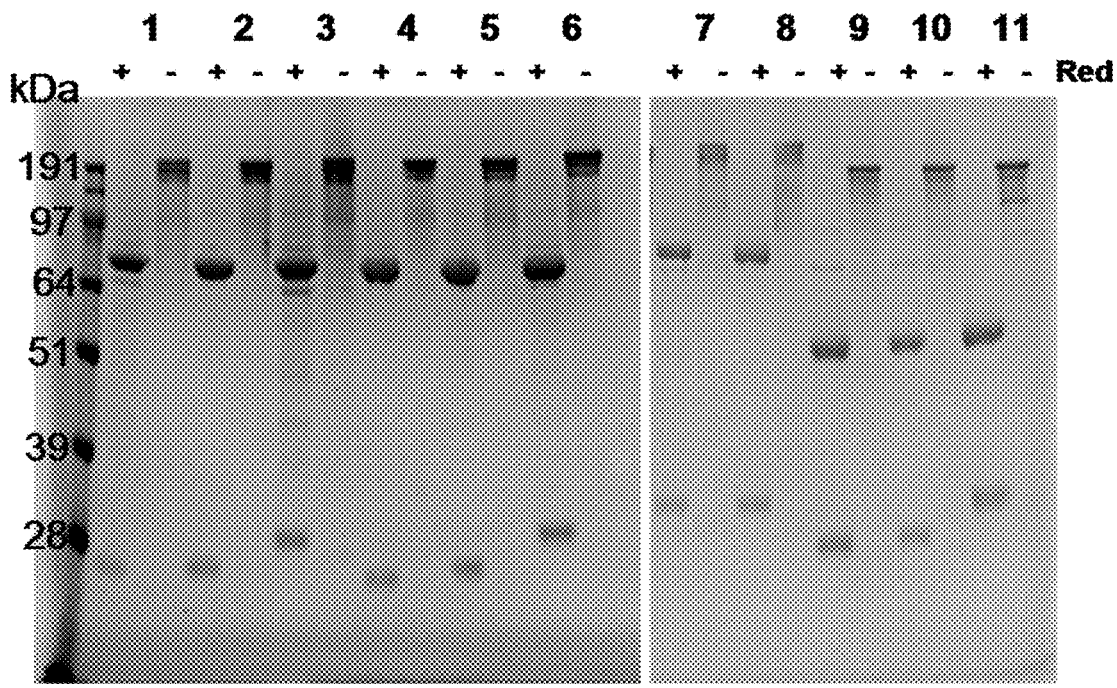
FIG. 10 is photograph depicting PAGE analysis of multispecific antibodies and multispecific activatable antibodies demonstrating the molecular weights of the scFv fused heavy chains, samples 1-8, as compared to the respective monospecific antibodies or activatable antibodies, samples 9-11.

In some embodiments, a single chain variable domain, specific for binding a T-cell surface displayed target is fused to the carboxyl terminus of a fully human IgG1 antibody (targeting antibody) that binds to a cell surface antigen. Fusion of the scFv can be to the carboxyl terminus of the heavy chain, to the carboxyl terminus of the light chain or to both chains (FIGS. 2A, 2B, and 2C). In some embodiments, a single chain variable domain, specific for binding a T-cell surface displayed target is fused to the amino terminus of a fully human IgG1 antibody (targeting antibody) that binds to a cell surface antigen. Fusion of the scFv can be to the amino terminus of the heavy chain, to the amino terminus of the light chain or to both chains. The fusions are constructed as a single genetic construct and expressed in cells in culture. The targeting antibody can be specific for binding to one or more tumor surface antigens, or any cell targeted for depletion. The scFv can be specific for the same or different antigens.

In some embodiments, the targeting antibody is an anti-EGFR antibody. In some embodiments, the targeting antibody is C225v5, which is specific for binding to EGFR. In some embodiments, the targeting antibody is C225, which is specific for binding to EGFR. In some embodiments, the targeting antibody is C225v4, which is specific for binding to EGFR. In some embodiments, the targeting antibody is C225v6, which is specific for binding to EGFR. In some embodiments, the targeting antibody is an anti-Jagged antibody. In some embodiments, the targeting antibody is 4D11, which is specific for binding to human and mouse Jagged 1 and Jagged 2. In some embodiments, the targeting antibody is 4D11v2, which is specific for binding to human and mouse Jagged 1 and Jagged 2.

In some embodiments, the targeting antibody can be in the form an activatable antibody. In some embodiments, the scFv(s) can be in the form of a Pro-scFv (see, e.g., WO 2009/025846, WO 2010/081173).

In some embodiments, the scFv is specific for binding CD3ε, e.g., OKT3. In some embodiments, the scFv is specific for binding CTLA-4 (also referred to herein as CTLA and CTLA4).

In some embodiments, the scFv is specific for binding one or more T-cells, one or more NK-cells and/or one or more macrophages. In some embodiments, the scFv is specific for binding a target selected from the group consisting of B7-H4, BTLA, CD3, CD4, CD8, CD16a, CD25, CD27, CD28, CD32, CD56, CD137, CTLA-4, GITR, HVEM, ICOS, LAG3, NKG2D, OX40, PD-1, TIGIT, TIM3, or VISTA, and combinations thereof.

Definitions

Unless otherwise defined, scientific and technical terms used in connection with the present disclosure shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" or "immunospecifically bind" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, fully human, domain antibody, single chain, Fab, and $F(ab')_2$ fragments, scFvs, and an Fab expression library.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, $IgG_3$, $IgG_4$, and others. Furthermore, in humans, the light chain may be a kappa chain or a lambda chain.

The term "monoclonal antibody" (mAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences that are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

As used herein, the term "epitope" includes any protein determinant capable of specific binding to an immunoglobulin, an scFv, or a T-cell receptor. The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide. An antibody is said to specifically bind an antigen when the dissociation constant is $\leq 1$ µM; for example, in some embodiments $\leq 100$ nM and in some embodiments $\leq 10$ nM.

As used herein, the terms "specific binding," "immunological binding," and "immunological binding properties" refer to the non-covalent interactions of the type that occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to EGFR, when the equilibrium binding constant ($K_d$) is $\leq 1$ µM, for example in some embodiments $\leq 100$ nM, in some embodiments $\leq 10$ nM, and in some embodiments $\leq 100$ pM to about 1 pM, as measured by assays such as radioligand binding assays or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide that it is not linked to in nature, or (3) does not occur in nature as part of a larger sequence. Polynucleotides in accordance with the disclosure include the nucleic acid molecules encoding the heavy chain immunoglobulin molecules shown herein, and nucleic acid molecules encoding the light chain immunoglobulin molecules shown herein.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of murine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus. Polypeptides in accordance with the disclosure comprise the heavy chain immunoglobulin molecules shown herein, and the light chain immunoglobulin molecules shown herein, as well as antibody molecules formed by combinations comprising the heavy chain immunoglobulin molecules with light chain immunoglobulin molecules, such as kappa light chain immunoglobulin molecules, and vice versa, as well as fragments and analogs thereof.

The term "naturally-occurring" as used herein as applied to an object refers to the fact that an object can be found in nature. For example, a polypeptide or polynucleotide sequence that is present in an organism (including viruses) that can be isolated from a source in nature and that has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences that are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide" as referred to herein means nucleotides of at least 10 bases in length, either ribonucleotides or deoxynucleotides or a modified form of either type of nucleotide. The term includes single and double stranded forms of DNA.

The term oligonucleotide referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length, for example in some embodiments 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotide linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-, α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' end the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and that are 5' to the 5' end of the RNA transcript are referred to as "upstream sequences", sequence regions on the DNA strand having the same sequence as the RNA and that are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, for example in some embodiments, at least 90 percent sequence identity, in some embodiments at least 95 percent sequence identity, and in some embodiments at least 99 percent sequence identity.

In some embodiments, residue positions that are not identical differ by conservative amino acid substitutions.

As discussed herein, minor variations in the amino acid sequences of antibodies or immunoglobulin molecules are contemplated as being encompassed by the present disclosure, providing that the variations in the amino acid sequence maintain at least 75%, for example in some embodiments at least 80%, 90%, 95%, and in some embodiments 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. In some embodiments, amino- and carboxy-termini of fragments or analogs occur near boundaries of functional domains. Structural and functional domains can be identified by comparison of the nucleotide and/or amino acid sequence data to public or proprietary sequence databases. Computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

In some embodiments, amino acid substitutions are those that: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354:105 (1991).

The term "polypeptide fragment" as used herein refers to a polypeptide that has an amino terminal and/or carboxy-terminal deletion and/or one or more internal deletion(s), but where the remaining amino acid sequence is identical to the corresponding positions in the naturally-occurring sequence deduced, for example, from a full length cDNA sequence. Fragments typically are at least 5, 6, 8 or 10 amino acids long, for example in some embodiments at least 14 amino acids long, in some embodiments at least 20 amino acids long, usually at least 50 amino acids long, and in some embodiments at least 70 amino acids long. The term "analog" as used herein refers to polypeptides that are comprised of a segment of at least 25 amino acids that has substantial identity to a portion of a deduced amino acid sequence and that has specific binding to EGFR, under suitable binding conditions. Typically, polypeptide analogs comprise a conservative amino acid substitution (or addition or deletion) with respect to the naturally-occurring sequence. Analogs typically are at least 20 amino acids long, for example in some embodiments at least 50 amino acids long or longer, and can often be as long as a full-length naturally-occurring polypeptide.

The term "agent" is used herein to denote a chemical compound, a mixture of chemical compounds, a biological macromolecule, or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^{3}$H, $^{14}$C, $^{15}$N, $^{35}$S, $^{90}$Y, $^{99}$Tc, $^{111}$In, $^{125}$I, $^{131}$I) fluorescent labels (e.g., a fluorophore, rhodamine, lanthanide phosphors), enzymatic labels (e.g., horseradish peroxidase, p-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present.

Generally, a substantially pure composition will comprise more than about 80 percent of all macromolecular species present in the composition, for example, in some embodiments, more than about 85%, 90%, 95%, and 99%. In some embodiments, the object species is purified to essential homogeneity (contaminant species cannot be detected in the composition by conventional detection methods) wherein the composition consists essentially of a single macromolecular species.

The term patient includes human and veterinary subjects.

Other chemistry terms herein are used according to conventional usage in the art, as exemplified by The McGraw-Hill Dictionary of Chemical Terms (Parker, S., Ed., McGraw-Hill, San Francisco (1985)).

Multispecific Antibodies and Multispecific Activatable Antibodies

Exemplary multispecific antibodies and/or multispecific activatable antibodies of the disclosure include, for example, those shown in the Examples provided herein, and variants thereof.

In some non-limiting embodiments, at least one of the AB in the multispecific antibody is a binding partner for any target listed in Table 1.

TABLE 1

| Exemplary Targets |
| --- |
| 1-92-LFA-3 |
| Alpha-4 integrin |
| Alpha-V integrin |
| alpha4beta1 integrin |
| alpha4beta7 integrin |
| AGR2 |
| Anti-Lewis-Y |
| Apelin J receptor |
| APRIL |
| B7-H4 |
| BAFF |
| BTLA |
| C5 complement |
| C-242 |
| CA9 |
| CA19-9 (Lewis a) |
| Carbonic anhydrase 9 |
| CD2 |
| CD3 |
| CD6 |
| CD9 |
| CD11a |
| CD19 |
| CD20 |
| CD22 |
| CD24 |
| CD25 |
| CD27 |
| CD28 |
| CD30 |
| CD33 |
| CD38 |
| CD40 |
| CD40L |
| CD41 |
| CD44 |
| CD44v6 |

TABLE 1-continued

| Exemplary Targets |
| --- |
| CD47 |
| CD51 |
| CD52 |
| CD56 |
| CD64 |
| CD70 |
| CD71 |
| CD74 |
| CD80 |
| CD81 |
| CD86 |
| CD95 |
| CD117 |
| CD125 |
| CD132 (IL-2RG) |
| CD133 |
| CD137 |
| CD138 |
| CD166 |
| CD172A |
| CD248 |
| CDH6 |
| CEACAM5 (CEA) |
| CEACAM6 (NCA-90) |
| CLAUDIN-3 |
| CLAUDIN-4 |
| cMet |
| Collagen |
| Cripto |
| CSFR |
| CSFR-1 |
| CTLA-4 |
| CTGF |
| CXCL10 |
| CXCL13 |
| CXCR1 |
| CXCR2 |
| CXCR4 |
| CYR61 |
| DL44 |
| DLK1 |
| DLL4 |
| DPP-4 |
| EGFR |
| EGFRviii |
| Endothelin B receptor (ETBR) |
| ENPP3 |
| EpCAM |
| EPHA2 |
| EPHB2 |
| ERBB3 |
| F protein of RSV |
| FAP |
| FGF-2 |
| FGF8 |
| FGFR1 |
| FGFR2 |
| FGFR3 |
| FGFR4 |
| Folate receptor |
| GAL3ST1 |
| G-CSF |
| G-CSFR |
| GD2 |
| GITR |
| GLUT1 |
| GLUT4 |
| GM-CSF |
| GM-CSFR |
| GP IIb/IIIa receptors |
| Gp130 |
| GPIIB/IIIA |
| GPNMB |
| GRP78 |
| HER2/neu |
| HGF |
| hGH |
| HVEM |

TABLE 1-continued

Exemplary Targets

Hyaluronidase
ICOS
IFNalpha
IFNbeta
IFNgamma
IgE
IgE Receptor (FceRI)
IGF
IGF1R
IL1B
IL1R
IL2
IL11
IL12
IL12p40
IL-12R, IL-12Rbeta1
IL13
IL13R
IL15
IL17
IL18
IL21
IL23
IL23R
IL27/IL27R (wsx1)
IL29
IL-31R
IL31/IL31R
IL2R
IL4
IL4R
IL6, IL6R
Insulin Receptor
Jagged Ligands
Jagged 1
Jagged 2
LAG-3
LIF-R
Lewis X
LIGHT
LRP4
LRRC26
MCSP
Mesothelin
MRP4
MUC1
Mucin-16 (MUC16, CA-125)
Na/K ATPase
Neutrophil elastase
NGF
Nicastrin
Notch Receptors
Notch 1
Notch 2
Notch 3
Notch 4
NOV
OSM-R
OX-40
PAR2
PDGF-AA
PDGF-BB
PDGFRalpha
PDGFRbeta
PD-1
PD-L1
PD-L2
Phosphatidyl-serine
P1GF
PSCA
PSMA
RAAG12
RAGE
SLC44A4
Sphingosine 1 Phosphate
STEAP1
STEAP2
TAG-72

TABLE 1-continued

Exemplary Targets

TAPA1
TGFbeta
TIGIT
TIM-3
TLR2
TLR4
TLR6
TLR7
TLR8
TLR9
TMEM31
TNFalpha
TNFR
TNFRS12A
TRAIL-R1
TRAIL-R2
Transferrin
Transferrin receptor
TRK-A
TRK-B
uPAR
VAP1
VCAM-1
VEGF
VEGF-A
VEGF-B
VEGF-C
VEGF-D
VEGFR1
VEGFR2
VEGFR3
VISTA
WISP-1
WISP-2
WISP-3

In some non-limiting embodiments, at least one of the AB of the multispecific antibody is or is derived from a sequence set forth in Table 7 in the Examples provided herein.

In some non-limiting embodiments, at least one of the AB of the multispecific antibody is or is derived from an antibody listed in Table 2.

TABLE 2

Exemplary sources for ABs

| Antibody Trade Name (antibody name) | Target |
| --- | --- |
| Avastin ™ (bevacizumab) | VEGF |
| Lucentis ™ (ranibizumab) | VEGF |
| Erbitux ™ (cetuximab) | EGFR |
| Vectibix ™ (panitumumab) | EGFR |
| Remicade ™ (infliximab) | TNFα |
| Humira ™ (adalimumab) | TNFα |
| Tysabri ™ (natalizumab) | Integrinα4 |
| Simulect ™ (basiliximab) | IL2R |
| Soliris ™ (eculizumab) | Complement C5 |
| Raptiva ™ (efalizumab) | CD11a |
| Bexxar ™ (tositumomab) | CD20 |
| Zevalin ™ (ibritumomab tiuxetan) | CD20 |
| Rituxan ™ (rituximab) | CD20 |
| Ocerlizumab | CD20 |
| Arzerra ™ (ofatumumab) | CD20 |
| Obinutuzumab | CD20 |
| Zenapax ™ (daclizumab) | CD25 |
| Adcetris ™ (brentuximab vedotin) | CD30 |
| Myelotarg ™ (gemtuzumab) | CD33 |
| Mylotarg ™ (gemtuzumab ozogamicin) | CD33 |
| Campath ™ (alemtuzumab) | CD52 |
| ReoPro ™ (abiciximab) | Glycoprotein receptor IIb/IIIa |
| Xolair ™ (omalizumab) | IgE |
| Herceptin ™ (trastuzumab) | Her2 |
| Kadcyla ™ (trastuzumab emtansine) | Her2 |
| Synagis ™ (palivizumab) | F protein of RSV |

TABLE 2-continued

Exemplary sources for ABs

| Antibody Trade Name (antibody name) | Target |
| --- | --- |
| (ipilimumab) | CTLA-4 |
| (tremelimumab) | CTLA-4 |
| Hu5c8 | CD40L |
| (pertuzumab) | Her2-neu |
| (ertumaxomab) | CD3/Her2-neu |
| Orencia ™ (abatacept) | CTLA-4 |
| (tanezumab) | NGF |
| (bavituximab) | Phosphatidylserine |
| (zalutumumab) | EGFR |
| (mapatumumab) | EGFR |
| (matuzumab) | EGFR |
| (nimotuzumab) | EGFR |
| ICR62 | EGFR |
| mAb 528 | EGFR |
| CH806 | EGFR |
| MDX-447 | EGFR/CD64 |
| (edrecolomab) | EpCAM |
| RAV12 | RAAG12 |
| huJ591 | PSMA |
| Enbrel ™ (etanercept) | TNF-R |
| Amevive ™ (alefacept) | 1-92-LFA-3 |
| Antril ™, Kineret ™ (ankinra) | IL-1Ra |
| GC1008 | TGFbeta |
|  | Notch, e.g., Notch 1 Jagged 1 or Jagged 2 |
| (adecatumumab) | EpCAM |
| (figitumumab) | IGF1R |
| (tocilizumab) | IL-6 receptor |
| Stelara ™ (ustekinumab) | IL-12/IL-23 |
| Prolia ™ (denosumab) | RANKL |

Also included in the disclosure are multispecific antibodies and/or multispecific activatable antibodies that bind to the same epitope as the multispecific antibodies and/or multispecific activatable antibodies described herein.

Those skilled in the art will recognize that it is possible to determine, without undue experimentation, if a multispecific antibody and/or a multispecific activatable antibody has the same or similar specificity as a multispecific antibody and/or multispecific activatable antibody of the disclosure by ascertaining whether the former prevents the latter from binding to a target. If the multispecific antibody and/or a multispecific activatable antibody being tested competes with the multispecific antibody and/or a multispecific activatable antibody of the disclosure, as shown by a decrease in binding by the multispecific antibody and/or a multispecific activatable antibody of the disclosure, then the two multispecific antibodies and/or multispecific activatable antibodies bind to the same, or a closely related, epitope.

One embodiment for determining whether a multispecific antibody and/or a multispecific activatable antibody has the same or similar specificity as a multispecific antibody and/or a multispecific activatable antibody of the disclosure is to pre-incubate the multispecific antibody and/or a multispecific activatable antibody of the disclosure with soluble target with which it is normally reactive, and then add the multispecific antibody and/or a multispecific activatable antibody being tested to determine if the multispecific antibody and/or a multispecific activatable antibody being tested is inhibited in its ability to bind the target. If the multispecific antibody and/or a multispecific activatable antibody being tested is inhibited then, in all likelihood, it has the same, or functionally equivalent, epitopic specificity as the multispecific antibody and/or a multispecific activatable antibody of the disclosure.

A multispecific antibody and/or a multispecific activatable antibody is generated, for example, using the procedures described in the Examples provided below. A multispecific antibody and/or a multispecific activatable antibody can also be generated using any of a number of art-recognized techniques for antibody production and/or purification.

Antibody fragments, such as Fv, F(ab')$_2$ and Fab, for use in a multispecific antibody and/or a multispecific activatable antibody may be prepared by cleavage of the intact protein, e.g., by protease or chemical cleavage. Alternatively, a truncated gene is designed. For example, a chimeric gene encoding a portion of the F(ab')$_2$ fragment would include DNA sequences encoding the CH1 domain and hinge region of the H chain, followed by a translational stop codon to yield the truncated molecule.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting antibody may be joined to any strong promoter, including retroviral LTRs, e.g., SV-40 early promoter, (Okayama et al. Mol. Cell. Bio. 3:280 (1983)), Rous sarcoma virus LTR (Gorman et al. P.N.A.S. 79:6777 (1982)), and moloney murine leukemia virus LTR (Grosschedl et al. Cell 41:885 (1985)). Also, as will be appreciated, native Ig promoters and the like may be used.

Further, multispecific antibodies and/or multispecific activatable antibodies can be generated through display type technologies, including, without limitation, phage display, retroviral display, ribosomal display, and other techniques, using techniques well known in the art and the resulting molecules can be subjected to additional maturation, such as affinity maturation, as such techniques are well known in the art. Wright et al. Crit, Reviews in Immunol. 12125-168 (1992), Hanes and Plückthun PNAS USA 94:4937-4942 (1997) (ribosomal display), Parmley and Smith Gene 73:305-318 (1988) (phage display), Scott, TIBS, vol. 17:241-245 (1992), Cwirla et al. PNAS USA 87:6378-6382 (1990), Russel et al. Nucl. Acids Research 21:1081-1085 (1993), Hoganboom et al. Immunol. Reviews 130:43-68 (1992), Chiswell and McCafferty TIBTECH; 10:80-8A (1992), and U.S. Pat. No. 5,733,743.

It can be desirable to modify the multispecific antibody and/or multispecific activatable antibody of the disclosure with respect to effector function, so as to enhance or reduce such function to improve the effectiveness of the antibody in treating diseases and disorders. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)). In some embodiments, Fc mutations are made to remove glycosylation sites, thereby reducing Fc function.

Multispecific Activatable Antibodies

The multispecific activatable antibodies and multispecific activatable antibody compositions provided herein contain at least a first antibody or antibody fragment thereof (collectively referred to as AB1 throughout the disclosure) that specifically binds a first target and/or a first epitope and a second antibody or antibody fragment thereof (collectively referred to as AB2 throughout the disclosure) that specifically binds a second target and/or a second epitope, wherein at least one of the AB is modified by a masking moiety (MM). In some embodiments, each AB in a multispecific activatable antibody is modified by its own masking moiety.

When at least one of the AB in a multispecific activatable antibody is modified with a MM and is in the presence of its target, specific binding of the AB to its target is reduced or inhibited, as compared to the specific binding of the AB not modified with an MM or the specific binding of the parental AB to the target.

The $K_d$ of the AB modified with a MM towards the target is at least 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM or of the parental AB towards the target. Conversely, the binding affinity of the AB modified with a MM towards the target is at least 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM or of the parental AB towards the target.

The dissociation constant ($K_d$) of the MM towards at least one the AB in the multispecific activatable antibody is generally greater than the $K_d$ of the AB towards the target. The $K_d$ of the MM towards the AB can be at least 5, 10, 25, 50, 100, 250, 500, 1,000, 2,500, 5,000, 10,000, 100,000, 1,000,000 or even 10,000,000 times greater than the $K_d$ of the AB towards the target. Conversely, the binding affinity of the MM towards the AB is generally lower than the binding affinity of the AB towards the target. The binding affinity of MM towards the AB can be at least 5, 10, 25, 50, 100, 250, 500, 1,000, 2,500, 5,000, 10,000, 100,000, 1,000,000 or even 10,000,000 times lower than the binding affinity of the AB towards the target.

When at least one of the AB in the multispecific activatable antibody is modified with a MM and is in the presence of the target, specific binding of the AB to its target is reduced or inhibited, as compared to the specific binding of the AB not modified with an MM or the specific binding of the parental AB to the target. When compared to the binding of the AB not modified with an MM or the binding of the parental AB to the target, the AB's ability to bind the target when modified with an MM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or more when measured in vivo or in an in vitro assay.

The MM inhibits the binding of at least one of the AB in the multispecific activatable antibody to its target. The MM binds the antigen binding domain of the AB and inhibits binding of the AB to its target. The MM can sterically inhibit the binding of the AB to the target. The MM can allosterically inhibit the binding of the AB to its target. In these embodiments when the AB is modified or coupled to a MM and in the presence of target, there is no binding or substantially no binding of the AB to the target, or no more than 0.001%, 0.01%, 0.1%, 1%, 2%, 3%, 4%, 5%, 6%, 7%, 8%, 9%, 10%, 15%, 20%, 25%, 30%, 35%, 40%, or 50% binding of the AB to the target, as compared to the binding of the AB not modified with an MM, the parental AB, or the AB not coupled to an MM to the target, for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

When at least one of the AB in a multispecific activatable antibody is coupled to or modified by a MM, the MM 'masks' or reduces or otherwise inhibits the specific binding of the AB to its target. When at least one of the AB in a multispecific activatable antibody is coupled to or modified by a MM, such coupling or modification can effect a structural change that reduces or inhibits the ability of the AB to specifically bind its target.

In a multispecific activatable antibody, when at least one AB is coupled to or modified with an MM, at least a portion of the multispecific activatable antibody can be represented by the following formulae (in order from an amino (N) terminal region to carboxyl (C) terminal region:

(MM)-(AB)

(AB)-(MM)

(MM)-L-(AB)

(AB)-L-(MM)

where MM is a masking moiety, the AB is an antibody or antibody fragment thereof, and the L is a linker. In many embodiments, it may be desirable to insert one or more linkers, e.g., flexible linkers, into the composition so as to provide for flexibility.

In certain embodiments, the MM is not a natural binding partner of the AB. In some embodiments, the MM contains no or substantially no homology to any natural binding partner of the AB. In other embodiments the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, 75%, or 80% identical to any natural binding partner of the AB. In some embodiments, the MM is no more than 25% identical to any natural binding partner of the AB. In some embodiments, the MM is no more than 50% identical to any natural binding partner of the AB. In some embodiments, the MM is no more than 20% identical to any natural binding partner of the AB. In some embodiments, the MM is no more than 10% identical to any natural binding partner of the AB.

In some embodiments, the multispecific activatable antibodies include an AB that is modified by an MM and also includes one or more cleavable moieties (CM). Such multispecific activatable antibodies exhibit activatable/switchable binding, to the AB's target. Multispecific activatable antibodies generally include at least one antibody or antibody fragment (AB), modified by or coupled to a masking moiety (MM) and a modifiable or cleavable moiety (CM). In some embodiments, the CM contains an amino acid sequence that serves as a substrate for a protease of interest.

The elements of the multispecific activatable antibodies are arranged so that each MM and CM are positioned such that in a cleaved (or relatively active) state and in the presence of a target, the corresponding AB binds a target, while in an uncleaved (or relatively inactive) state in the presence of the target, specific binding of the AB to its target, is reduced or inhibited. The specific binding of the AB to its target can be reduced due to the inhibition or masking of the AB's ability to specifically bind its target by the MM.

The $K_d$ of each AB modified with a MM and a CM towards the target, is at least 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB not modified with an MM and a CM or of the parental AB towards the target. Conversely, the binding affinity of each AB modified with a MM and a CM towards the target, is at least 5, 10, 20, 25, 40, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB not modified with an MM and a CM or of the parental AB towards the target.

When at least one AB is modified with a MM and a CM and is in the presence of the target but not in the presence of a modifying agent (for example a protease), specific binding of that AB to its target, is reduced or inhibited, as compared to the specific binding of the AB not modified with an MM and a CM or the parental AB to the target. When compared to the binding of the parental AB or the binding of an AB not modified with an MM and a CM to its target, the AB's ability to bind the target when modified with an MM and a CM can be reduced by at least 50%, 60%, 70%, 80%, 90%, 92%, 93%, 94%, 95%, 96%, 97%, 98%, 99% and even 100% for at least 2, 4, 6, 8, 12, 28, 24, 30, 36, 48, 60, 72, 84, or 96 hours or 5, 10, 15, 30, 45, 60, 90, 120, 150, or 180 days, or 1, 2, 3, 4, 5, 6, 7, 8, 9, 10, 11, or 12 months or longer when measured in vivo or in an in vitro assay.

As used herein, the term cleaved state refers to the condition of the multispecific activatable antibodies following modification of the CM by a protease. The term uncleaved state, as used herein, refers to the condition of the multispecific activatable antibodies in the absence of cleavage of the CM by a protease. As discussed above, the term "multispecific activatable antibodies" is used herein to refer to a multispecific activatable antibody in both its uncleaved (native) state, as well as in its cleaved state. It will be apparent to the ordinarily skilled artisan that in some embodiments, a cleaved multispecific activatable antibody may lack an MM due to cleavage of the CM by protease, resulting in release of at least the MM (e.g., where the MM is not joined to the multispecific activatable antibodies by a covalent bond (e.g., a disulfide bond between cysteine residues).

By activatable or switchable is meant that the multispecific activatable antibody exhibits a first level of binding to a target when in a inhibited, masked or uncleaved state (i.e., a first conformation), and a second level of binding to the target, in the uninhibited, unmasked and/or cleaved state (i.e., a second conformation), where the second level of target binding is greater than the first level of binding. In general, the access of target to the corresponding AB of the multispecific activatable antibody is greater in the presence of a cleaving agent capable of cleaving the CM than in the absence of such a cleaving agent. Thus, when the multispecific activatable antibody is in the uncleaved state, at least one AB is inhibited from target binding and can be masked from target binding (i.e., the first conformation is such the AB cannot bind the target), and in the cleaved state the AB is not inhibited or is unmasked to target binding.

The CM and AB of the multispecific activatable antibodies are selected so that the first AB represents a binding moiety for a first target and/or epitope, and the CM represents a substrate for a protease that is co-localized with the target at a treatment site or diagnostic site in a subject. The multispecific activatable antibodies disclosed herein find particular use where, for example, a protease capable of cleaving a site in the CM is present at relatively higher levels in target-containing tissue of a treatment site or diagnostic site than in tissue of non-treatment sites (for example in healthy tissue).

In some embodiments, multispecific activatable antibodies provide for reduced toxicity and/or adverse side effects that could otherwise result from binding of the first AB at non-treatment sites if the AB were not masked or otherwise inhibited from binding its target.

In general, a multispecific activatable antibody can be designed by selecting at first AB of interest and constructing the remainder of the activatable antibody so that, when conformationally constrained, the MM provides for masking of the AB or reduction of binding of the AB to its target. Structural design criteria can be to be taken into account to provide for this functional feature.

Multispecific activatable antibodies exhibiting a switchable phenotype of a desired dynamic range for target binding in an inhibited versus an uninhibited conformation are provided. Dynamic range generally refers to a ratio of (a) a maximum detected level of a parameter under a first set of conditions to (b) a minimum detected value of that parameter under a second set of conditions. For example, in the context of a multispecific activatable antibody, the dynamic range refers to the ratio of (a) a maximum detected level of target protein, binding to a multispecific activatable antibody in the presence of protease capable of cleaving the CM of the activatable antibodies to (b) a minimum detected level of target protein, binding to a multispecific activatable antibody in the absence of the protease. The dynamic range of a multispecific activatable antibody can be calculated as the ratio of the equilibrium dissociation constant of a multispecific activatable antibody cleaving agent (e.g., enzyme) treatment to the equilibrium dissociation constant of the activatable antibodies cleaving agent treatment. The greater the dynamic range of a multispecific activatable antibody, the better the switchable phenotype of the activatable antibody. Activatable antibodies having relatively higher dynamic range values (e.g., greater than 1) exhibit more desirable switching phenotypes such that target protein binding by the activatable antibodies occurs to a greater extent (e.g., predominantly occurs) in the presence of a cleaving agent (e.g., enzyme) capable of cleaving the CM of the activatable antibodies than in the absence of a cleaving agent.

Multispecific activatable antibodies can be provided in a variety of structural configurations. Exemplary formulae for at least a portion of a multispecific activatable antibody are provided below. It is specifically contemplated that the N- to C-terminal order of the first AB, the corresponding MM and CM may be reversed within an activatable antibody. It is also specifically contemplated that the CM and MM may overlap in amino acid sequence, e.g., such that the CM is contained within the MM.

For example, at least a portion of the multispecific activatable antibodies can be represented by the following formula (in order from an amino (N) terminal region to carboxyl (C) terminal region:

(MM)-(CM)-(AB)

(AB)-(CM)-(MM)

where MM is a masking moiety, CM is a cleavable moiety, and AB is a first antibody or fragment thereof. It should be noted that although MM and CM are indicated as distinct components in the formulae above, in all exemplary embodiments (including formulae) disclosed herein it is contemplated that the amino acid sequences of the MM and the CM could overlap, e.g., such that the CM is completely or partially contained within the MM. In addition, the formulae above provide for additional amino acid sequences that may be positioned N-terminal or C-terminal to the activatable antibodies elements.

In certain embodiments, the MM is not a natural binding partner of the AB. In some embodiments, the MM contains no or substantially no homology to any natural binding partner of the AB. In other embodiments the MM is no more than 5%, 10%, 15%, 20%, 25%, 30%, 35%, 40%, 45%, 50%, 55%, 60%, 65%, 70%, 75%, or 80% similar to any natural binding partner of the AB. In some embodiments, the MM is no more than 5%, 10%, 15%, 20%, 25%, 30%, 35%, 40%, 45%, 50%, 55%, 60%, 65%, 70%, or 80% identical to any natural binding partner of the AB. In some embodiments, the MM is no more than 50% identical to any natural binding partner of the AB. In some embodiments, the MM is no more than 25% identical to any natural binding partner of the AB. In some embodiments, the MM is no more than 20% identical to any natural binding partner of the AB. In some embodiments, the MM is no more than 10% identical to any natural binding partner of the AB.

In many embodiments it may be desirable to insert one or more linkers, e.g., flexible linkers, into the multispecific activatable antibody construct so as to provide for flexibility at one or more of the MM-CM junction, the CM-AB junction, or both. For example, the AB, MM, and/or CM may not contain a sufficient number of residues (e.g., Gly, Ser, Asp, Asn, especially Gly and Ser, particularly Gly) to provide the desired flexibility. As such, the switchable phenotype of such multispecific activatable antibody constructs may benefit from introduction of one or more amino acids to provide for a flexible linker. In addition, as described below, where the multispecific activatable antibody is provided as a conformationally constrained construct, a flexible linker can be operably inserted to facilitate formation and maintenance of a cyclic structure in the uncleaved multispecific activatable antibody.

For example, in certain embodiments a multispecific activatable antibody comprises one of the following formulae (where the formula below represent an amino acid sequence in either N- to C-terminal direction or C- to N-terminal direction):

(MM)-L1-(CM)-(AB)

(MM)-(CM)-L2-(AB)

(MM)-L1-(CM)-L2-(AB)

wherein MM, CM, and AB are as defined above; wherein L1 and L2 are each independently and optionally present or absent, are the same or different flexible linkers that include at least 1 flexible amino acid (e.g., Gly). In addition, the formulae above provide for additional amino acid sequences that may be positioned N-terminal or C-terminal to the multispecific activatable antibodies elements. Examples include, but are not limited to, targeting moieties (e.g., a ligand for a receptor of a cell present in a target tissue) and serum half-life extending moieties (e.g., polypeptides that bind serum proteins, such as immunoglobulin (e.g., IgG) or serum albumin (e.g., human serum albumin (HAS)).

In some non-limiting embodiments, at least one of the AB in the multispecific activatable antibody is a binding partner for any target listed in Table 1.

In some non-limiting embodiments, at least one of the AB in the multispecific activatable antibody comprises, is or is derived from a sequence set forth in Table 7 in the Examples provided herein.

In some non-limiting embodiments, at least one of the AB in the multispecific activatable antibody comprises, is or is derived from a sequence set forth in Example 5 in the Examples provided herein. In some non-limiting embodiments, at least one of the AB in the multispecific activatable antibody comprises, is or is derived from a sequence set forth in Table 11 in the Examples provided herein.

In some non-limiting embodiments, at least one of the AB in the multispecific activatable antibody is or is derived from an antibody listed in Table 2.

In some embodiments, the masking moiety is selected for use with a specific antibody or antibody fragment. For example, suitable masking moieties for use with antibodies that bind EGFR include MMs that include the sequence CISPRG (SEQ ID NO: 75). By way of non-limiting examples, the MM can include a sequence such as CISPRGC (SEQ ID NO: 339), CISPRGCG (SEQ ID NO: 76); CISPRGCPDGPYVMY (SEQ ID NO: 77); CISPRGCPDGPYVM (SEQ ID NO: 78), CISPRGCEPGTYVPT (SEQ ID NO: 79) and CISPRGCPGQIWHPP (SEQ ID NO: 80). Other suitable masking moieties include any of the EGFR-specific masks disclosed in PCT Publication No. WO 2010/081173, such as, by way of non-limiting example, GSHCLIPINMGAPSC (SEQ ID NO: 81); CISPRGCGGSSASQSGQGSHCLIPINMGAPSC (SEQ ID NO: 82); CNHHYFYTCGCISPRGCPG (SEQ ID NO: 83); ADHVFWGSYGCISPRGCPG (SEQ ID NO: 84); CHHVYWGHCGCISPRGCPG (SEQ ID NO: 85); CPHFTTTSCGCISPRGCPG (SEQ ID NO: 86); CNHHYHYYCGCISPRGCPG (SEQ ID NO: 87); CPHVSFGSCGCISPRGCPG (SEQ ID NO: 88); CPYYTLSYCGCISPRGCPG (SEQ ID NO: 89); CNHVYFGTCGCISPRGCPG (SEQ ID NO: 90); CNHFTLTTCGCISPRGCPG (SEQ ID NO: 91); CHHFTLTTCGCISPRGCPG (SEQ ID NO: 92); YNPCATPMCCISPRGCPG (SEQ ID NO: 93); CNHHYFYTCGCISPRGCG (SEQ ID NO: 94); CNHHY- HYYCGCISPRGCG (SEQ ID NO: 95); CNHVYFGTCG-CISPRGCG (SEQ ID NO: 96); CHHVYWGHCGCIS-PRGCG (SEQ ID NO: 97); CPHFTTTSCGCISPRGCG (SEQ ID NO: 98); CNHFTLTTCGCISPRGCG (SEQ ID NO: 99); CHHFTLTTCGCISPRGCG (SEQ ID NO: 100); CPYYTLSYCGCISPRGCG (SEQ ID NO: 101); CPHVSFGSCGCISPRGCG (SEQ ID NO: 102); ADHVFWGSYGCISPRGCG (SEQ ID NO: 103); YNP-CATPMCCISPRGCG (SEQ ID NO: 104); CHHVYWGHCGCISPRGCG (SEQ ID NO: 105); C(N/P)H(H/V/F)(Y/T)(F/W/T/L)(Y/G/T/S)(T/S/Y/H)CGCIS-PRGCG (SEQ ID NO: 106); CISPRGCGQPIPSVK (SEQ ID NO: 107); CISPRGCTQPYHVSR (SEQ ID NO: 108); and/or CISPRGCNAVSGLGS (SEQ ID NO: 109).

Suitable masking moieties for use with antibodies that bind a Jagged target, e.g., Jagged 1 and/or Jagged 2, include, by way of non-limiting example, masking moieties that include a sequence such as QGQSGQC-NIWLVGGDCRGWQG (SEQ ID NO: 338); QGQSGQGQQQWCNIWINGGDCRGWNG (SEQ ID NO: 110); PWCMQRQDFLRCPQP (SEQ ID NO: 111); QLGL-PAYMCTFECLR (SEQ ID NO: 112); CNLWVSGGDCG-GLQG (SEQ ID NO: 113); SCSLWTSGSCLPHSP (SEQ ID NO: 114); YCLQLPHYMQAMCGR (SEQ ID NO: 115); CFLYSCTDVSYWNNT (SEQ ID NO: 116); PWCMQRQDYLRCPQP (SEQ ID NO: 117); CNLWISGGDCRGLAG (SEQ ID NO: 118); CNLWVSGGDCRGVQG (SEQ ID NO: 119); CNLWVSGGDCRGLRG (SEQ ID NO: 120); CNLWISGGDCRGLPG (SEQ ID NO: 121); CNLWVSGGDCRDAPW (SEQ ID NO: 122); CNLWVSGGDCRDLLG (SEQ ID NO: 123); CNLWVSGGDCRGLQG (SEQ ID NO: 124); CNLWLHGGDCRGWQG (SEQ ID NO: 125); CNIWLVGGDCRGWQG (SEQ ID NO: 126); CTTWFCGGDCGVMRG (SEQ ID NO: 127); CNIWGPSVDCGALLG (SEQ ID NO: 128); CNIWVNGGDCRSFEG (SEQ ID NO: 129); YCLNL-PRYMQDMCWA (SEQ ID NO: 130); YCLAL-PHYMQADCAR (SEQ ID NO: 131); CFLY-SCGDVSYWGSA (SEQ ID NO: 132); CYLYSCTDSAFWNNR (SEQ ID NO: 133); CYLY-SCNDVSYWSNT (SEQ ID NO: 134); CFLYSCTDVSYW (SEQ ID NO: 135); CFLYSCTDVAYWNSA (SEQ ID NO: 136); CFLYSCTDVSYWGDT (SEQ ID NO: 137); CFLY-SCTDVSYWGNS (SEQ ID NO: 138); CFLY-SCTDVAYWNNT (SEQ ID NO: 139); CFLY-SCGDVSYWGNPGLS (SEQ ID NO: 140); CFLYSCTDVAYWSGL (SEQ ID NO: 141); CYLY-SCTDGSYWNST (SEQ ID NO: 142); CFLY-SCSDVSYWGNI (SEQ ID NO: 143); CFLYSCTDVAYW (SEQ ID NO: 144); CFLYSCTDVSYWGST (SEQ ID NO: 145); CFLYSCTDVAYWGDT (SEQ ID NO: 146); GCNIWLNGGDCRGWVDPLQG (SEQ ID NO: 147); GCNIWLVGGDCRGWIGDTNG (SEQ ID NO: 148); GCNIWLVGGDCRGWIEDSNG (SEQ ID NO: 149); GCNIWANGGDCRGWIDNIDG (SEQ ID NO: 150); GCNIWLVGGDCRGWLGEAVG (SEQ ID NO: 151); GCNIWLVGGDCRGWLEEAVG (SEQ ID NO: 152); GGPALCNIWLNGGDCRGWSG (SEQ ID NO: 153); GAPVFCNIWLNGGDCRGWMG (SEQ ID NO: 154); GQQQWCNIWINGGDCRGWNG (SEQ ID NO: 155); GKSEFCNIWLNGGDCRGWIG (SEQ ID NO: 156); GTPGGCNIWANGGDCRGWEG (SEQ ID NO: 157); GASQYCNLWINGGDCRGWRG (SEQ ID NO: 158); GCNIWLVGGDCRPWVEGG (SEQ ID NO: 159); GCNI-WAVGGDCRPFVDGG (SEQ ID NO: 160); GCNIWLNGGDCRAWVDTG (SEQ ID NO: 161); GCNI-WIVGGDCRPFINDG (SEQ ID NO: 162); GCNIWLNGGDCRPVVFGG (SEQ ID NO: 163); GCNIWLSGGDCRMFMNEG (SEQ ID NO: 164); GCNIWVNGGDCRSFVYSG (SEQ ID NO: 165); GCNIWLNGGDCRGWEASG (SEQ ID NO: 166); GCNI-WAHGGDCRGFIEPG (SEQ ID NO: 167); GCNIWLNGGDCRTFVASG (SEQ ID NO: 168); GCNI-WAHGGDCRGFIEPG (SEQ ID NO: 169); GFLENC-NIWLNGGDCRTG (SEQ ID NO: 170); GIYENC-NIWLNGGDCRMG (SEQ ID NO: 171); and/or GIPDNCNIWINGGDCRYG (SEQ ID NO: 172).

Suitable masking moieties for use with antibodies that bind an interleukin 6 target, e.g., interleukin 6 receptor (IL-6R), include, by way of non-limiting example, masking moieties that include a sequence such as QGQSGQYGSCSWNYVHIFMDC (SEQ ID NO: 174); QGQSGQGDFDIPFPAHWVPIT (SEQ ID NO: 175); QGQSGQMGVPAGCVWNYAHIFMDC (SEQ ID NO: 176); YRSCNWNYVSIFLDC (SEQ ID NO: 177); PGAF-DIPFPAHWVPNT (SEQ ID NO: 178); ESS-CVWNYVHIYMDC (SEQ ID NO: 179); YPGCKWNY-DRIFLDC (SEQ ID NO: 180); YRTCSWNYVGIFLDC (SEQ ID NO: 181); YGSCSWNYVHIFMDC (SEQ ID NO: 182); YGSCSWNYVHIFLDC (SEQ ID NO: 183); YGSCNWNYVHIFLDC (SEQ ID NO: 184); YTSCNWNYVHIFMDC (SEQ ID NO: 185); YPGCK-WNYDRIFLDC (SEQ ID NO: 186); WRSCNWNYAHI-FLDC (SEQ ID NO: 187); WSNCHWNYVHIFLDC (SEQ ID NO: 188); DRSCTWNYVRISYDC (SEQ ID NO: 189); SGSCKWDYVHIFLDC (SEQ ID NO: 190); SRSCIWNYAHIHLDC (SEQ ID NO: 191); SMSCYWQY-ERIFLDC (SEQ ID NO: 192); YRSCNWNYVSIFLDC (SEQ ID NO: 193); YGSCSWNYVHIFMDC (SEQ ID NO: 194); SGSCKWDYVHIFLDC (SEQ ID NO: 195); YKSCHWDYVHIFLDC (SEQ ID NO: 196); YGSCTWNYVHIFMEC (SEQ ID NO: 197); FSS-CNWNYVHIFLDC (SEQ ID NO: 198); WRSCNWNYA-HIFLDC (SEQ ID NO: 199); YGSCQWNYVHIFLDC (SEQ ID NO: 200); YRSCNWNYVHIFLDC (SEQ ID NO: 201); NMSCHWDYVHIFLDC (SEQ ID NO: 202); FGPCTWNYARISWDC (SEQ ID NO: 203); XXsCXWXYvhIfXdC (SEQ ID NO: 204); MGVPAGCVWNYAHIFMDC (SEQ ID NO: 205); RDTGGQCRWDYVHIFMDC (SEQ ID NO: 206); AGVPAGCTWNYVHIFMEC (SEQ ID NO: 207); VGVPNGCVWNYAHIFMEC (SEQ ID NO: 208); DGGPAGCSWNYVHIFMEC (SEQ ID NO: 209); AVGPAGCWWNYVHIFMEC (SEQ ID NO: 210); CTWNYVHIFMDCGEGEGP (SEQ ID NO: 211); GGVPEGCTWNYAHIFMEC (SEQ ID NO: 212); AEVPAGCWWNYVHIFMEC (SEQ ID NO: 213); AGVPAGCTWNYVHIFMEC (SEQ ID NO: 214); SGASGGCKWNYVHIFMDC (SEQ ID NO: 215); MGVPAGCVWNYAHIFMDC (SEQ ID NO: 216); TPGCRWNYVHIFMECEAL (SEQ ID NO: 217); VGVPNGCVWNYAHIFMEC (SEQ ID NO: 218); PGAF-DIPFPAHWVPNT (SEQ ID NO: 219); RGAC-DIPFPAHWIPNT (SEQ ID NO: 220); QGDF-DIPFPAHWVPIT (SEQ ID NO: 221); XGafDIPFPAHWvPnT (SEQ ID NO: 222); RGDGNDS-DIPFPAHWVPRT (SEQ ID NO: 223); SGVGRDR-DIPFPAHWVPRT (SEQ ID NO: 224); WAGGNDC-DIPFPAHWIPNT (SEQ ID NO: 225); WGDGMDVDIPFPAHWVPVT (SEQ ID NO: 226); AGSGNDSDIPFPAHWVPRT (SEQ ID NO: 227); ESRSG- YADIPFPAHWVPRT (SEQ ID NO: 228); and/or RECGRCGDIPFPAHWVPRT (SEQ ID NO: 173).

In some embodiments, the cleavable moiety (CM) of the multispecific activatable antibody includes an amino acid sequence that can serve as a substrate for a protease, usually an extracellular protease. The CM may be selected based on a protease that is co-localized in tissue with the desired target of at least one AB of the multispecific activatable antibody. A variety of different conditions are known in which a target of interest is co-localized with a protease, where the substrate of the protease is known in the art. In the example of cancer, the target tissue can be a cancerous tissue, particularly cancerous tissue of a solid tumor. There are reports in the literature of increased levels of proteases having known substrates in a number of cancers, e.g., solid tumors. See, e.g., La Rocca et al, (2004) British J. of Cancer 90(7): 1414-1421. Non-liming examples of disease include: all types of cancers (breast, lung, colorectal, prostate, melanomas, head and neck, pancreatic, etc.), rheumatoid arthritis, Crohn's disuse, SLE, cardiovascular damage, ischemia, etc. For example, indications would include leukemias, including T-cell acute lymphoblastic leukemia (T-ALL), lymphoblastic diseases including multiple myeloma, and solid tumors, including lung, colorectal, prostate, pancreatic and breast, including triple negative breast cancer. For example, indications include bone disease or metastasis in cancer, regardless of primary tumor origin; breast cancer, including by way of non-limiting example, ER/PR+ breast cancer, Her2+ breast cancer, triple-negative breast cancer; colorectal cancer; endometrial cancer; gastric cancer; glioblastoma; head and neck cancer, such as esophageal cancer; lung cancer, such as by way of non-limiting example, non-small cell lung cancer; multiple myeloma ovarian cancer; pancreatic cancer; prostate cancer; sarcoma, such as osteosarcoma; renal cancer, such as by way of nonlimiting example, renal cell carcinoma; and/or skin cancer, such as by way of nonlimiting example, squamous cell cancer, basal cell carcinoma, or melanoma. In some embodiments, the cancer is a squamous cell cancer. In some embodiments, the cancer is a skin squamous cell carcinoma. In some embodiments, the cancer is an esophageal squamous cell carcinoma. In some embodiments, the cancer is a head and neck squamous cell carcinoma. In some embodiments, the cancer is a lung squamous cell carcinoma.

The CM is specifically cleaved by an enzyme at a rate of about $0.001$-$1500 \times 10^4$ $M^{-1}S^{-1}$ or at least $0.001, 0.005, 0.01, 0.05, 0.1, 0.5, 1, 2.5, 5, 7.5, 10, 15, 20, 25, 50, 75, 100, 125, 150, 200, 250, 500, 750, 1000, 1250,$ or $1500 \times 10^4$ $M^{-1}S^{-1}$.

For specific cleavage by an enzyme, contact between the enzyme and CM is made. When the multispecific activatable antibody comprising at least a first AB coupled to a MM and a CM is in the presence of target and sufficient enzyme activity, the CM can be cleaved. Sufficient enzyme activity can refer to the ability of the enzyme to make contact with the CM and effect cleavage. It can readily be envisioned that an enzyme may be in the vicinity of the CM but unable to cleave because of other cellular factors or protein modification of the enzyme.

Exemplary substrates include but are not limited to substrates cleavable by one or more of the following enzymes or proteases in Table 3:

TABLE 3

| Exemplary Proteases and/or Enzymes | | |
|---|---|---|
| ADAMS, ADAMTS, e.g. ADAM8 | Cysteine proteinases, e.g., Cruzipain | Serine proteases, e.g., activated protein C |

TABLE 3-continued

| Exemplary Proteases and/or Enzymes | | |
|---|---|---|
| ADAM9 | Legumain | Cathepsin A |
| ADAM10 | Otubain-2 | Cathepsin G |
| ADAM12 | KLKs, e.g., | Chymase |
| ADAM15 | KLK4 | coagulation factor |
| ADAM17/TACE | KLK5 | proteases (e.g., FVIIa, |
| ADAMDEC1 | KLK6 | FIXa, FXa, FXIa, |
| ADAMTS1 | KLK7 | FXIIa) |
| ADAMTS4 | KLK8 | Elastase |
| ADAMTS5 | KLK10 | Granzyme B |
| Aspartate | KLK11 | Guanidinobenzoatase |
| proteases, e.g., | KLK13 | HtrA1 |
| BACE | KLK14 | Human Neutrophil |
| Renin | Metallo | Elastase |
| Aspartic | proteinases, e.g., | Lactoferrin |
| cathepsins, e.g., | Meprin | Marapsin |
| Cathepsin D | Neprilysin | NS3/4A |
| Cathepsin E | PSMA | PACE4 |
| Caspases, e.g., | BMP-1 | Plasmin |
| Caspase 1 | MMPs, e.g., | PSA |
| Caspase 2 | MMP1 | tPA |
| Caspase 3 | MMP2 | Thrombin |
| Caspase 4 | MMP3 | Tryptase |
| Caspase 5 | MMP7 | uPA |
| Caspase 6 | MMP8 | Type II |
| Caspase 7 | MMP9 | Transmembrane |
| Caspase 8 | MMP10 | Serine Proteases |
| Caspase 9 | MMP11 | (TTSPs), e.g., |
| Caspase 10 | MMP12 | DESC1 |
| Caspase 14 | MMP13 | DPP-4 |
| Cysteine | MMP14 | FAP |
| cathepsins, e.g., | MMP15 | Hepsin |
| Cathepsin B | MMP16 | Matriptase-2 |
| Cathepsin C | MMP17 | MT-SP1/Matriptase |
| Cathepsin K | MMP19 | TMPRSS2 |
| Cathepsin L | MMP20 | TMPRSS3 |
| Cathepsin S | MMP23 | TMPRSS4 |
| Cathepsin V/L2 | MMP24 | |
| Cathepsin X/Z/P | MMP26 | |
| | MMP27 | |

For example, in some embodiments, the substrate is cleavable by one or more of the following enzymes or proteases: uPA, legumain, MT-SP1, ADAM17, BMP-1, TMPRSS3, TMPRSS4, MMP-9, MMP-12, MMP-13, and/or MMP-14. In some embodiments, the protease is selected from the group of uPA, legumain, and MT-SP1. In some embodiments, the protease is a matrix metalloproteinase. In some embodiments, the protease comprises uPA. In some embodiments, the protease comprises legumain. In some embodiments, the protease comprises MT-SP1.

In some embodiments, the CM is selected for use with a specific protease. In some embodiments, the CM is a substrate for at least one protease selected from the group consisting of an ADAM 17, a BMP-1, a cysteine protease such as a cathepsin, a HtrA1, a legumain, a matriptase (MT-SP1), a matrix metalloprotease (MMP), a neutrophil elastase, a TMPRSS, such as TMPRSS3 or TMPRSS4, a thrombin, and a u-type plasminogen activator (uPA, also referred to as urokinase).

In some embodiments, the CM is a substrate for an ADAM17. In some embodiments, the CM is a substrate for a BMP-1. In some embodiments, the CM is a substrate for a cathepsin. In some embodiments, the CM is a substrate for a cysteine protease. In some embodiments, the CM is a substrate for a HtrA1. In some embodiments, the CM is a substrate for a legumain. In some embodiments, the CM is a substrate for a MT-SP1. In some embodiments, the CM is a substrate for a MMP. In some embodiments, the CM is a substrate for a neutrophil elastase. In some embodiments, the CM is a substrate for a thrombin. In some embodiments, the CM is a substrate for a TMPRSS. In some embodiments, the CM is a substrate for TMPRSS3. In some embodiments, the CM is a substrate for TMPRSS4. In some embodiments, the CM is a substrate for uPA.

In some embodiments, the cleavable moiety is selected for use with a specific protease, for example a protease that is known to be co-localized with the target of the activatable antibody. For example, suitable cleavable moieties for use in the activatable antibodies of the disclosure include the sequence TGRGPSWV (SEQ ID NO: 27); SARGPSRW (SEQ ID NO: 28); TARGPSFK (SEQ ID NO: 29); LSGRSDNH (SEQ ID NO: 26); GGWHTGRN (SEQ ID NO: 30); HTGRSGAL (SEQ ID NO: 31); PLTGRSGG (SEQ ID NO: 32); AARGPAIH (SEQ ID NO: 33); RGPAFNPM (SEQ ID NO: 34); SSRGPAYL (SEQ ID NO: 35); RGPATPIM (SEQ ID NO: 36); RGPA (SEQ ID NO: 37); GGQPSGMWGW (SEQ ID NO: 38); FPRPLGITGL (SEQ ID NO: 39); VHMPLGFLGP (SEQ ID NO: 40); SPLTGRSG (SEQ ID NO: 41); SAGFSLPA (SEQ ID NO: 42); LAPLGLQRR (SEQ ID NO: 43); SGGPLGVR (SEQ ID NO: 44); and/or PLGL (SEQ ID NO: 45).

In some embodiments, the CM is a substrate for at least one matrix metalloprotease (MMP). Examples of MMPs include MMP1; MMP2; MMP3; MMP7; MMP8; MMP9; MMP10; MMP11; MMP12; MMP13; MMP14; MMP15; MMP16; MMP17; MMP19; MMP20; MMP23; MMP24; MMP26; and MMP27. In some embodiments, the CM is a substrate for MMP9, MMP14, MMP1, MMP3, MMP13, MMP17, MMP11, and MMP19. In some embodiments, the CM is a substrate for MMP7. In some embodiments, the CM is a substrate for MMP9. In some embodiments, the CM is a substrate for MMP14. In some embodiments, the CM is a substrate for two or more MMPs. In some embodiments, the CM is a substrate for at least MMP9 and MMP14. In some embodiments, the CM comprises two or more substrates for the same MMP. In some embodiments, the CM comprises at least two or more MMP9 substrates. In some embodiments, the CM comprises at least two or more MMP14 substrates.

In some embodiments, the CM is a substrate for an MMP and includes the sequence ISSGLLSS (SEQ ID NO: 316); QNQALRMA (SEQ ID NO: 317); AQNLLGMV (SEQ ID NO: 318); STFPFGMF (SEQ ID NO: 319); PVGYTSSL (SEQ ID NO: 320); DWLYWPGI (SEQ ID NO: 321); MIAPVAYR (SEQ ID NO: 322); RPSPMWAY (SEQ ID NO: 21); WATPRPMR (SEQ ID NO: 323); FRLLDWQW (SEQ ID NO: 324); LKAAPRWA (SEQ ID NO: 325); GPSHLVLT (SEQ ID NO: 326); LPGGLSPW (SEQ ID NO: 327); MGLFSEAG (SEQ ID NO: 328); SPLPLRVP (SEQ ID NO: 329); RMHLRSLG (SEQ ID NO: 330); LAAPLGLL (SEQ ID NO: 331); AVGLLAPP (SEQ ID NO: 332); LLAPSHRA (SEQ ID NO: 333); PAGLWLDP (SEQ ID NO: 334); and/or ISSGLSS (SEQ ID NO: 335).

In some embodiments, multispecific antibodies and/or multispecific activatable antibodies of the disclosure may be made biosynthetically using recombinant DNA technology and expression in eukaryotic or prokaryotic species. For the multispecific activatable antibodies, the cDNAs encoding the masking moiety, linker sequence (that may include a cleavable moiety (CM), and antibody chain (heavy or light)) can be linked in an 5' to 3' (N- to C-terminal in the translated product) sequence to create the nucleic acid construct, which is expressed as the multispecific activatable antibody protein following a conventional antibody expression process. In some embodiments, the multispecific activatable antibody could be semi-synthetically produced by expressing a CM-antibody and then coupling the mask chemically at or near the N-terminus of the protein. In some embodiments, the multispecific activatable antibody could be produced by expressing an antibody and then coupling the mask and the CM chemically at or near the N-terminus of the protein such that the multispecific activatable antibody in the uncleaved state has the structural arrangement from N-terminus to C-terminus as follows: MM-CM-AB or AB-CM-MM.

Linkers suitable for use in compositions described herein are generally ones that provide flexibility of the modified AB or the multispecific activatable antibodies to facilitate the inhibition of the binding of at least the first AB to the target. Such linkers are generally referred to as flexible linkers. Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, 7, 8, 9, 10, 11, 12, 13, 14, 15, 16, 17, 18, 19, or 20 amino acids in length.

Exemplary flexible linkers include glycine polymers (G)n, glycine-serine polymers (including, for example, (GS)n, (GSGGS)n (SEQ ID NO: 18) and (GGGS)n (SEQ ID NO: 19), where n is an integer of at least one), glycine-alanine polymers, alanine-serine polymers, and other flexible linkers known in the art. Glycine and glycine-serine polymers are relatively unstructured, and therefore may be able to serve as a neutral tether between components. Glycine accesses significantly more phi-psi space than even alanine, and is much less restricted than residues with longer side chains (see Scheraga, Rev. Computational Chem. 11173-142 (1992)). Exemplary flexible linkers include, but are not limited to Gly-Gly-Ser-Gly (SEQ ID NO: 20), Gly-Gly-Ser-Gly-Gly (SEQ ID NO: 21), Gly-Ser-Gly-Ser-Gly (SEQ ID NO: 22), Gly-Ser-Gly-Gly-Gly (SEQ ID NO: 23), Gly-Gly-Gly-Ser-Gly (SEQ ID NO: 24), Gly-Ser-Ser-Ser-Gly (SEQ ID NO: 25), and the like. The ordinarily skilled artisan will recognize that design of an activatable antibodies can include linkers that are all or partially flexible, such that the linker can include a flexible linker as well as one or more portions that confer less flexible structure to provide for a desired multispecific activatable antibodies structure.

In addition to the elements described above, the multispecific activatable antibodies can contain additional elements such as, for example, amino acid sequence N- or C-terminal of the multispecific activatable antibodies. For example, multispecific activatable antibodies can include a targeting moiety to facilitate delivery to a cell or tissue of interest. Multispecific activatable antibodies can be conjugated to an agent, such as a therapeutic agent, an antineoplastic agent, a toxin or fragment thereof, a detectable moiety or a diagnostic agent. Examples of agents are disclosed herein.

The multispecific activatable antibodies can also include any of the conjugated agents, linkers and other components described herein in conjunction with a multispecific antibody of the disclosure, including by way of non-limiting example, any of the agents listed in Table 4 and/or any of the linkers listed in Table 5 and/or Table 6.

Conjugated Multispecific Antibodies and Conjugated Multispecific Activatable Antibodies The disclosure also pertains to immunoconjugates comprising a multispecific antibody and/or a multispecific activatable antibody conjugated to a cytotoxic agent such as a toxin (e.g., an enzymatically active toxin of bacterial, fungal, plant, or animal origin, or fragments thereof), or a radioactive isotope (i.e., a radioconjugate). Suitable cytotoxic agents include, for example, dolastatins and derivatives thereof (e.g. auristatin E, AFP, MMAD, MMAF, MMAE). For example, the cytotoxic agent is monomethyl auristatin E (MMAE). In some embodiments, the agent is monomethyl auristatin D (MMAD). In some embodiments, the agent is an agent selected from the group listed in Table 4. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *Momordica Charantia* inhibitor, curcin, crotin, *Sapaonaria Officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{64}$Cu, $^{125}$I, $^{131}$I, $^{131}$In, $^{99m}$Tc, $^{90}$Y, $^{186}$Re, and $^{89}$Zr.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Table 4 lists some of the exemplary pharmaceutical agents that may be employed in the herein described disclosure but in no way is meant to be an exhaustive list.

TABLE 4

Exemplary Pharmaceutical Agents for Conjugation

CYTOTOXIC AGENTS

Auristatins
Auristatin E
Monomethyl auristatin D (MMAD)
Monomethyl auristatin E (MMAE)
Desmethyl auristatin E (DMAE)
Auristatin F
Monomethyl auristatin F (MMAF)
Desmethyl auristatin F (DMAF)
Auristatin derivatives, e.g., amides thereof
Auristatin tyramine
Auristatin quinolone
Dolastatins
Dolastatin derivatives TABLE 4-continued Exemplary Pharmaceutical Agents for Conjugation Dolastatin 16 DmJ
Dolastatin 16 Dpv
Maytansinoids, e.g. DM-1; DM-4
Maytansinoid derivatives
Duocarmycin
Duocarmycin derivatives
Alpha-amanitin
Anthracyclines
Doxorubicin
Daunorubicin
Bryostatins
Camptothecin
Camptothecin derivatives
7-substituted Camptothecin
10,11-Difluoromethylenedioxycamptothecin
Combretastatins
Debromoaplysiatoxin
Kahalalide-F
Discodermolide
Ecteinascidins
Turbostatin
Phenstatins
Hydroxyphenstatin
Spongistatin 5
Spongistatin 7
Halistatin 1
Halistatin 2
Halistatin 3
Modified Bryostatins
Halocomstatins
Pyrrolobenzimidazoles (PBI)
Cibrostatin6
Doxaliform
Anthracyclins analogues
Cemadotin analogue (CemCH2-SH)
*Pseudomonas* toxin A (PE38) variant
*Pseudomonas* toxin A (ZZ-PE38) variant
ZJ-101
OSW-1
4-Nitrobenzyloxycarbonyl Derivatives of O6-Benzylguanine
Topoisomerase inhibitors
Hemiasterlin
Cephalotaxine
Homoharringtonine
Pyrrolobenzodiazepine dimers (PBDs)
Functionalized pyrrolobenzodiazepenes
Calicheamicins
Podophyllotoxins
Taxanes
Vinca alkaloids
ANTIVIRALS Acyclovir
Vira A
Symmetrel
ANTIFUNGALS Nystatin
ADDITIONAL ANTI-NEOPLASTICS Adriamycin
Cerubidine
Bleomycin
Alkeran
Velban
Oncovin
Fluorouracil
Methotrexate
Thiotepa
Bisantrene
Novantrone
Thioguanine
Procarabizine
Cytarabine
ANTI-BACTERIALS Aminoglycosides
Streptomycin

TABLE 4-continued

Exemplary Pharmaceutical Agents for Conjugation

Neomycin
Kanamycin
Amikacin
Gentamicin
Tobramycin
Streptomycin B
Spectinomycin
Ampicillin
Sulfanilamide
Polymyxin
Chloramphenicol

CONJUGATABLE DETECTION REAGENTS

Fluorescein and derivatives thereof
Fluorescein isothiocyanate (FITC)

RADIOPHARMACEUTICALS $^{125}$I
$^{131}$I
$^{89}$Zr
$^{111}$In
$^{123}$I
$^{131}$I
$^{99m}$Tc
$^{201}$Tl
$^{133}$Xe
$^{11}$C
$^{62}$Cu
$^{18}$F
$^{68}$Ga
$^{13}$N
$^{15}$O
$^{38}$K
$^{82}$Rb
$^{99m}$Tc (Technetium)

HEAVY METALS

Barium
Gold
Platinum

ANTI-MYCOPLASMALS

Tylosine
Spectinomycin

Those of ordinary skill in the art will recognize that a large variety of possible moieties can be coupled to the resultant multispecific antibodies and/or multispecific activatable antibodies of the disclosure. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. In some embodiments, the preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present disclosure, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238:1098 (1987).

In some embodiments, in addition to the compositions and methods provided herein, the conjugated activatable antibody can also be modified for site-specific conjugation through modified amino acid sequences inserted or otherwise included in the activatable antibody sequence. These modified amino acid sequences are designed to allow for controlled placement and/or dosage of the conjugated agent within a conjugated activatable antibody. For example, the activatable antibody can be engineered to include cysteine substitutions at positions on light and heavy chains that provide reactive thiol groups and do not negatively impact protein folding and assembly, nor alter antigen binding. In some embodiments, the activatable antibody can be engineered to include or otherwise introduce one or more non-natural amino acid residues within the activatable antibody to provide suitable sites for conjugation. In some embodiments, the activatable antibody can be engineered to include or otherwise introduce enzymatically activatable peptide sequences within the activatable antibody sequence.

Suitable linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly suitable linkers include: (i) SMPT (4-succinimidyloxycarbonyl-alpha-methyl-alpha-(2-pridyl-dithio)-toluene (Pierce Chem. Co., Cat. (21558G); (ii) SPDP (succinimidyl-6 [3-(2-pyridyldithio) propionamido]hexanoate (Pierce Chem. Co., Cat #21651G); and (iii) Sulfo-LC-SPDP (sulfosuccinimidyl 6 [3-(2-pyridyldithio)-propianamide] hexanoate (Pierce Chem. Co. Cat. #2165-G. Additional linkers include, but are not limited to, SMCC, sulfo-SMCC, SPDB, or sulfo-SPDB.

The linkers described above contain components that have different attributes, thus leading to conjugates with differing physio-chemical properties. For example, the linker SMPT contains a sterically hindered disulfide bond, and can form conjugates with increased stability. Disulfide linkages, are in general, less stable than other linkages because the disulfide linkage is cleaved in vitro, resulting in less conjugate available.

The reagent EDC (1-ethyl-3-(3-dimethylaminopropyl) carbodiimide hydrochloride is useful to create a carboxamide starting with a carboxylic acid and a primary or secondary amine. Thus, EDC may be used to link lysine residues in an antibody with a carboxylic acid in a linker or toxin, or to link aspartate or glutamate residues in an antibody with an amine in a linker or toxin. Such conjugation reactions utilizing EDC may be enhanced by addition of NHS (N-hydroxysuccinimide) or sulfo-NHS (N-hydroxy-3-oxysulfonylsuccinimide). Addition of NHS or sulfo-NHS to such conjugation reactions may enhance the rate, completeness, selectivity, and/or reproducibility of the conjugation reactions.

In some embodiments, the linkers are cleavable. In some embodiments, the linkers are non-cleavable. In some embodiments, two or more linkers are present. The two or more linkers are all the same, e.g., cleavable or non-cleavable, or the two or more linkers are different, e.g., at least one cleavable and at least one non-cleavable.

The present disclosure utilizes several methods for attaching agents to Abs of the multispecific antibodies and/or multispecific activatable antibodies: (a) attachment to the carbohydrate moieties of the AB, or (b) attachment to sulfhydryl groups of the AB, or (c) attachment to amino groups of the AB, or (d) attachment to carboxylate groups of the AB. According to the disclosure, ABs may be covalently attached to an agent through an intermediate linker having at least two reactive groups, one to react with AB and one to react with the agent. The linker, which may include any compatible organic compound, can be chosen such that the reaction with AB (or agent) does not adversely affect AB reactivity and selectivity. Furthermore, the attachment of linker to agent might not destroy the activity of the agent. Suitable linkers for reaction with oxidized antibodies or oxidized antibody fragments include those containing an amine selected from the group consisting of primary amine, secondary amine, hydrazine, hydrazide, hydroxylamine, phenylhydrazine, semicarbazide and thiosemicarbazide groups. Such reactive functional groups may exist as part of the structure of the linker, or may be introduced by suitable chemical modification of linkers not containing such groups.

According to the present disclosure, suitable linkers for attachment to reduced ABs of the multispecific antibodies and/or multispecific activatable antibodies include those having certain reactive groups capable of reaction with a sulfhydryl group of a reduced antibody or fragment. Such reactive groups include, but are not limited to: reactive haloalkyl groups (including, for example, haloacetyl groups), p-mercuribenzoate groups and groups capable of Michael-type addition reactions (including, for example, maleimides and groups of the type described by Mitra and Lawton, 1979, J. Amer. Chem. Soc. 101: 3097-3110).

According to the present disclosure, suitable linkers for attachment to neither oxidized nor reduced ABs of the multispecific antibodies and/or multispecific activatable antibodies include those having certain functional groups capable of reaction with the primary amino groups present in unmodified lysine residues in the AB. Such reactive groups include, but are not limited to, NHS carboxylic or carbonic esters, sulfo-NHS carboxylic or carbonic esters, 4-nitrophenyl carboxylic or carbonic esters, pentafluorophenyl carboxylic or carbonic esters, acyl imidazoles, isocyanates, and isothiocyanates.

According to the present disclosure, suitable linkers for attachment to neither oxidized nor reduced ABs include those having certain functional groups capable of reaction with the carboxylic acid groups present in aspartate or glutamate residues in the AB, which have been activated with suitable reagents. Suitable activating reagents include EDC, with or without added NHS or sulfo-NHS, and other dehydrating agents utilized for carboxamide formation. In these instances, the functional groups present in the suitable linkers would include primary and secondary amines, hydrazines, hydroxylamines, and hydrazides.

The agent may be attached to the linker before or after the linker is attached to the AB. In certain applications it may be desirable to first produce an AB-linker intermediate in which the linker is free of an associated agent. Depending upon the particular application, a specific agent may then be covalently attached to the linker. In other embodiments the AB is first attached to the MM, CM and associated linkers and then attached to the linker for conjugation purposes.

Branched Linkers:

In specific embodiments, branched linkers that have multiple sites for attachment of agents are utilized. For multiple site linkers, a single covalent attachment to an AB would result in an AB-linker intermediate capable of binding an agent at a number of sites. The sites may be aldehyde or sulfhydryl groups or any chemical site to which agents can be attached.

Alternatively, higher specific activity (or higher ratio of agents to AB) can be achieved by attachment of a single site linker at a plurality of sites on the AB. This plurality of sites may be introduced into the AB by either of two methods. First, one may generate multiple aldehyde groups and/or sulfhydryl groups in the same AB. Second, one may attach to an aldehyde or sulfhydryl of the AB a "branched linker" having multiple functional sites for subsequent attachment to linkers. The functional sites of the branched linker or multiple site linker may be aldehyde or sulfhydryl groups, or may be any chemical site to which linkers may be attached. Still higher specific activities may be obtained by combining these two approaches, that is, attaching multiple site linkers at several sites on the AB.

Cleavable Linkers:

Peptide linkers that are susceptible to cleavage by enzymes of the complement system, such as but not limited to urokinase, tissue plasminogen activator, trypsin, plasmin, or another enzyme having proteolytic activity may be used in one embodiment of the present disclosure. According to one method of the present disclosure, an agent is attached via a linker susceptible to cleavage by complement. The antibody is selected from a class that can activate complement. The antibody-agent conjugate, thus, activates the complement cascade and releases the agent at the target site. According to another method of the present disclosure, an agent is attached via a linker susceptible to cleavage by enzymes having a proteolytic activity such as a urokinase, a tissue plasminogen activator, plasmin, or trypsin. These cleavable linkers are useful in conjugated activatable antibodies that include an extracellular toxin, e.g., by way of non-limiting example, any of the extracellular toxins shown in Table 4.

Non-liming examples of cleavable linker sequences are provided in Table 5.

TABLE 5

| Exemplary Linker Sequences for Conjugation | |
|---|---|
| Types of Cleavable Sequences | Amino Acid Sequence |
| Plasmin cleavable sequences | |
| Pro-urokinase | PRFKIIGG (SEQ ID NO: 47) |
|  | PRFRIIGG (SEQ ID NO: 48) |
| TGFβ | SSRHRRALD (SEQ ID NO: 49) |
| Plasminogen | RKSSIIIRMRDVVL (SEQ ID NO: 50) |
| Staphylokinase | SSSFDKGKYKKGDDA (SEQ ID NO: 51) |
|  | SSSFDKGKYKRGDDA (SEQ ID NO: 52) |

TABLE 5-continued

Exemplary Linker Sequences for Conjugation

| Types of Cleavable Sequences | Amino Acid Sequence |
|---|---|
| Factor Xa cleavable sequences | |
| | IEGR (SEQ ID NO: 53) |
| | IDGR (SEQ ID NO: 54) |
| | GGSIDGR (SEQ ID NO: 55) |
| MMP cleavable sequences | |
| Gelatinase A | PLGLWA (SEQ ID NO: 56) |
| Collagenase cleavable sequences | |
| Calf skin collagen (α1(I) chain) | GPQGIAGQ (SEQ ID NO: 57) |
| Calf skin collagen (α2(I) chain) | GPQGLLGA (SEQ ID NO: 58) |
| Bovine cartilage collagen (α1(II) chain) | GIAGQ (SEQ ID NO: 59) |
| Human liver collagen (α1(III) chain) | GPLGIAGI (SEQ ID NO: 60) |
| Human α$_2$M | GPEGLRVG (SEQ ID NO: 61) |
| Human PZP | YGAGLGVV (SEQ ID NO: 62) |
| | AGLGVVER (SEQ ID NO: 63) |
| | AGLGISST (SEQ ID NO: 64) |
| Rat α$_1$M | EPQALAMS (SEQ ID NO: 65) |
| | QALAMSAI (SEQ ID NO: 66) |
| Rat α$_2$M | AAYHLVSQ (SEQ ID NO: 67) |
| | MDAFLESS (SEQ ID NO: 68) |
| Rat α$_1$I$_3$(2J) | ESLPVVAV (SEQ ID NO: 69) |
| Rat α$_1$I$_3$(27J) | SAPAVESE (SEQ ID NO: 70) |
| Human fibroblast collagenase (autolytic cleavages) | DVAQFVLT (SEQ ID NO: 71) |
| | VAQFVLTE (SEQ ID NO: 72) |
| | AQFVLTEG (SEQ ID NO: 73) |
| | PVQPIGPQ (SEQ ID NO: 74) |

In addition, agents may be attached via disulfide bonds (for example, the disulfide bonds on a cysteine molecule) to the AB. Since many tumors naturally release high levels of glutathione (a reducing agent) this can reduce the disulfide bonds with subsequent release of the agent at the site of delivery. In certain specific embodiments the reducing agent that would modify a CM would also modify the linker of the conjugated activatable antibody.

Spacers and Cleavable Elements:

In still another embodiment, it may be necessary to construct the linker in such a way as to optimize the spacing between the agent and the AB of the activatable antibody. This may be accomplished by use of a linker of the general structure:

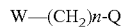

wherein
W is either —NH—CH$_2$— or —CH$_2$—;
Q is an amino acid, peptide; and
n is an integer from 0 to 20.

In still other embodiments, the linker may comprise a spacer element and a cleavable element. The spacer element serves to position the cleavable element away from the core of the AB such that the cleavable element is more accessible to the enzyme responsible for cleavage. Certain of the branched linkers described above may serve as spacer elements.

Throughout this discussion, it should be understood that the attachment of linker to agent (or of spacer element to cleavable element, or cleavable element to agent) need not be particular mode of attachment or reaction. Any reaction providing a product of suitable stability and biological compatibility is acceptable.

Serum Complement and Selection of Linkers:

According to one method of the present disclosure, when release of an agent is desired, an AB that is an antibody of a class that can activate complement is used. The resulting conjugate retains both the ability to bind antigen and activate the complement cascade. Thus, according to this embodiment of the present disclosure, an agent is joined to one end of the cleavable linker or cleavable element and the other end of the linker group is attached to a specific site on the AB. For example, if the agent has an hydroxy group or an amino group, it may be attached to the carboxy terminus of a peptide, amino acid or other suitably chosen linker via an ester or amide bond, respectively. For example, such agents may be attached to the linker peptide via a carbodimide reaction. If the agent contains functional groups that would interfere with attachment to the linker, these interfering functional groups can be blocked before attachment and deblocked once the product conjugate or intermediate is made. The opposite or amino terminus of the linker is then used either directly or after further modification for binding to an AB that is capable of activating complement.

Linkers (or spacer elements of linkers) may be of any desired length, one end of which can be covalently attached to specific sites on the AB of the activatable antibody. The other end of the linker or spacer element may be attached to an amino acid or peptide linker.

Thus when these conjugates bind to antigen in the presence of complement the amide or ester bond that attaches the agent to the linker will be cleaved, resulting in release of the agent in its active form. These conjugates, when administered to a subject, will accomplish delivery and release of the agent at the target site, and are particularly effective for the in vivo delivery of pharmaceutical agents, antibiotics, antimetabolites, antiproliferative agents and the like as presented in but not limited to those in Table 4.

Linkers for Release without Complement Activation:

In yet another application of targeted delivery, release of the agent without complement activation is desired since activation of the complement cascade will ultimately lyse the target cell. Hence, this approach is useful when delivery and release of the agent should be accomplished without killing the target cell. Such is the goal when delivery of cell mediators such as hormones, enzymes, corticosteroids, neurotransmitters, genes or enzymes to target cells is desired. These conjugates may be prepared by attaching the agent to an AB that is not capable of activating complement via a linker that is mildly susceptible to cleavage by serum proteases. When this conjugate is administered to an individual, antigen-antibody complexes will form quickly whereas cleavage of the agent will occur slowly, thus resulting in release of the compound at the target site.

Biochemical Cross Linkers:

In other embodiments, the activatable antibody may be conjugated to one or more therapeutic agents using certain biochemical cross-linkers. Cross-linking reagents form molecular bridges that tie together functional groups of two different molecules. To link two different proteins in a step-wise manner, hetero-bifunctional cross-linkers can be used that eliminate unwanted homopolymer formation.

Peptidyl linkers cleavable by lysosomal proteases are also useful, for example, Val-Cit, Val-Ala or other dipeptides. In addition, acid-labile linkers cleavable in the low-pH environment of the lysosome may be used, for example: bis-sialyl ether. Other suitable linkers include cathepsin-labile substrates, particularly those that show optimal function at an acidic pH.

Exemplary hetero-bifunctional cross-linkers are referenced in Table 6.

TABLE 6

Exemplary Hetero-Bifunctional Cross Linkers
HETERO-BIFUNCTIONAL CROSS-LINKERS

| Linker | Reactive Toward | Advantages and Applications | Spacer Arm Length after cross-linking (Angstroms) |
|---|---|---|---|
| SMPT | Primary amines Sulfhydryls | Greater stability | 11.2 Å |
| SPDP | Primary amines Sulfhydryls | Thiolation Cleavable cross-linking | 6.8 Å |
| LC-SPDP | Primary amines Sulfhydryls | Extended spacer arm | 15.6 Å |
| Sulfo-LC-SPDP | Primary amines Sulfhydryls | Extender spacer arm Water-soluble | 15.6 Å |
| SMCC | Primary amines Sulfhydryls | Stable maleimide reactive group Enzyme-antibody conjugation Hapten-carrier protein conjugation | 11.6 Å |
| Sulfo-SMCC | Primary amines Sulfhydryls | Stable maleimide reactive group Water-soluble Enzyme-antibody conjugation | 11.6 Å |
| MBS | Primary amines Sulfhydryls | Enzyme-antibody conjugation Hapten-carrier protein conjugation | 9.9 Å |
| Sulfo-MBS | Primary amines Sulfhydryls | Water-soluble | 9.9 Å |
| SIAB | Primary amines Sulfhydryls | Enzyme-antibody conjugation | 10.6 Å |
| Sulfo-SIAB | Primary amines Sulfhydryls | Water-soluble | 10.6 Å |
| SMPB | Primary amines Sulfhydryls | Extended spacer arm Enzyme-antibody conjugation | 14.5 Å |
| Sulfo-SMPB | Primary amines Sulfhydryls | Extended spacer arm Water-soluble | 14.5 Å |
| EDE/Sulfo-NHS | Primary amines Carboxyl groups | Hapten-Carrier conjugation | 0 |
| ABH | Carbohydrates Nonselective | Reacts with sugar groups | 11.9 Å |

Non-Cleavable Linkers or Direct Attachment:

In still other embodiments of the disclosure, the conjugate may be designed so that the agent is delivered to the target but not released. This may be accomplished by attaching an agent to an AB either directly or via a non-cleavable linker.

These non-cleavable linkers may include amino acids, peptides, D-amino acids or other organic compounds that may be modified to include functional groups that can subsequently be utilized in attachment to ABs by the methods described herein. A general formula for such an organic linker could be

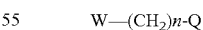

W—(CH$_2$)$n$-Q wherein
W is either —NH—CH$_2$— or —CH$_2$—;
Q is an amino acid, peptide; and
n is an integer from 0 to 20.

Non-Cleavable Conjugates:

Alternatively, a compound may be attached to ABs that do not activate complement. When using ABs that are incapable of complement activation, this attachment may be accomplished using linkers that are susceptible to cleavage by activated complement or using linkers that are not susceptible to cleavage by activated complement.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present disclosure can be conjugated to the liposomes as described in Martin et al., J. Biol. Chem., 257: 286-288 (1982) via a disulfide-interchange reaction.

Multispecific Activatable Antibodies Having Non-Binding Steric Moieties or Binding Partners for Non-Binding Steric Moieties The disclosure also provides multispecific activatable antibodies that include non-binding steric moieties (NB) or binding partners (BP) for non-binding steric moieties, where the BP recruits or otherwise attracts the NB to the multispecific activatable antibody. The multispecific activatable antibodies provided herein include, for example, a multispecific activatable antibody that includes a non-binding steric moiety (NB), a cleavable linker (CL) and at least a first antibody or antibody fragment (AB1) that binds a first target or epitope; a multispecific activatable antibody that includes a binding partner for a non-binding steric moiety (BP), a CL and an AB1; and a multispecific activatable antibody that includes a BP to which an NB has been recruited, a CL and AB1 that binds a first target or epitope. Multispecific activatable antibodies in which the NB is covalently linked to the CL and AB1 or is associated by interaction with a BP that is covalently linked to the CL and AB1 are referred to herein as "NB-containing multispecific activatable antibodies." By activatable or switchable is meant that the activatable antibody exhibits a first level of binding to a target when the activatable antibody is in an inhibited, masked or uncleaved state (i.e., a first conformation), and a second level of binding to the target when the activatable antibody is in an uninhibited, unmasked and/or cleaved state (i.e., a second conformation, i.e., activated antibody), where the second level of target binding is greater than the first level of target binding. The multispecific activatable antibody compositions can exhibit increased bioavailability and more favorable biodistribution compared to conventional antibody therapeutics.

In some embodiments, multispecific activatable antibodies provide for reduced toxicity and/or adverse side effects that could otherwise result from binding of the multispecific activatable antibody at non-treatment sites and/or non-diagnostic sites if the multispecific activatable antibody were not masked or otherwise inhibited from binding to such a site.

In one embodiment, the multispecific activatable antibody includes a non-binding steric moiety (NB); a cleavable linker (CL); and at least a first antibody or antibody fragment (AB1) that binds specifically to a first target or epitope, wherein the NB is a polypeptide that does not bind specifically to the AB1; the CL is a polypeptide that includes a substrate (S) for an enzyme; the CL is positioned such that in an uncleaved state, the NB interferes with binding of the AB1 to its target and in a cleaved state, the NB does not interfere with binding of the AB1 to its target; and the NB does not inhibit cleavage of the CL by the enzyme. As used herein and throughout, the term polypeptide refers to any polypeptide that includes at least two amino acid residues, including larger polypeptides, full-length proteins and fragments thereof, and the term polypeptide is not limited to single-chain polypeptides and can include multi-unit, e.g., multi-chain, polypeptides. In cases where the polypeptide is of a shorter length, for example, less than 50 amino acids total, the terms peptide and polypeptide are used interchangeably herein, and in cases where the polypeptide is of a longer length, for example, 50 amino acids or greater, the terms polypeptide and protein are used interchangeably herein.

In one embodiment, the multispecific activatable antibody includes a non-binding steric moiety (NB); a cleavable linker (CL); and at least a first antibody or antibody fragment (AB1) that binds specifically to a first target or epitope, wherein (i) the NB includes a polypeptide that does not bind specifically to the AB1; (ii) CL is a polypeptide of up to 50 amino acids in length that includes a substrate (S) for an enzyme; (iii) the CL is positioned such that in an uncleaved state, the NB interferes with binding of the AB1 to its target and in a cleaved state, the NB does not interfere with binding of the AB1 to its target; and (iv) the NB does not inhibit cleavage of the CL by the enzyme. For example, the CL has a length of up to 15 amino acids, a length of up to 20 amino acids, a length of up to 25 amino acids, a length of up to 30 amino acids, a length of up to 35 amino acids, a length of up to 40 amino acids, a length of up to 45 amino acids, a length of up to 50 amino acids, a length in the range of 10-50 amino acids, a length in the range of 15-50 amino acids, a length in the range of 20-50 amino acids, a length in the range of 25-50 amino acids, a length in the range of 30-50 amino acids, a length in the range of 35-50 amino acids, a length in the range of 40-50 amino acids, a length in the range of 45-50 amino acids, a length in the range of 10-40 amino acids, a length in the range of 15-40 amino acids, a length in the range of 20-40 amino acids, a length in the range of 25-40 amino acids, a length in the range of 30-40 amino acids, a length in the range of 35-40 amino acids, a length in the range of 10-30 amino acids, a length in the range of 15-30 amino acids, a length in the range of 20-30 amino acids, a length in the range of 25-30 amino acids, a length in the range of 10-20 amino acids, or a length in the range of 10-15 amino acids.

In one embodiment, the multispecific activatable antibody includes a non-binding steric moiety (NB); a cleavable linker (CL); and at least a first antibody or antibody fragment (AB1) that binds specifically to a first target or epitope, wherein (i) the NB includes a polypeptide that does not bind specifically to the AB1; (ii) the CL is a polypeptide that includes a substrate (S) for an enzyme; (iii) the CL is positioned such that in an uncleaved state, the NB interferes with binding of the AB1 to its target and in a cleaved state, the NB does not interfere with binding of the AB1 to its target; (iv) the NB does not inhibit cleavage of the CL by the enzyme; and (v) at least a portion of the multispecific activatable antibody has the structural arrangement from N-terminus to C-terminus as follows in the uncleaved state: NB-CL-AB1 or AB1-CL-NB.

In one embodiment, the multispecific activatable antibody includes a non-binding steric moiety (NB); a cleavable linker (CL); and at least a first antibody or antibody fragment (AB1) that binds specifically to a first target or epitope, wherein (i) the NB includes a polypeptide that does not bind specifically to the AB1; (ii) the CL is a polypeptide that includes a substrate (S) for an enzyme; (iii) the CL is positioned such that in an uncleaved state, the NB interferes with binding of the AB1 to its target and in a cleaved state, the NB does not interfere with binding of the AB1 to its target, and wherein the NB in the uncleaved activatable antibody reduces the ability of the AB1 to bind its target by at least 50%, for example, by at least 60%, by at least 70%, by at least 75%, by at least 80%, by at least 85%, by at least 90%, by at least 95%, by at least 96%, by at least 97%, by at least 98%, by at least 99%, by at least 100% as compared to the ability of the cleaved AB1 to bind its target; and (iv) the NB does not inhibit cleavage of the CL by the enzyme. The reduction in the ability of the AB to bind its target is determined, for example, using an assay as described herein or an in vitro target displacement assay such as, for example, the assay described in PCT Publication Nos. WO 2009/025846 and WO 2010/081173.

In one embodiment, the multispecific activatable antibody includes a binding partner (BP) for a non-binding steric moiety (NB); a cleavable linker (CL); and at least a first antibody or antibody fragment (AB1) that binds specifically to a first target and/or epitope, wherein the BP is a polypeptide that binds to the NB when exposed thereto; the NB does not bind specifically to the AB1; the CL is a polypeptide that includes a substrate (S) for an enzyme; the CL is positioned such that in an uncleaved state in the presence of the NB, the NB interferes with binding of the AB to the target and in a cleaved state, the NB does not interfere with binding of the AB to the target and the BP does not interfere with binding of the AB to the target; and the NB and the BP do not inhibit cleavage of the CL by the enzyme. In some examples of this embodiment, the BP of the activatable antibody is optionally bound to the NB. In one embodiment, the NB is recruited by the BP of the activatable antibody in vivo.

In some examples of any of these multispecific activatable antibody embodiments, the multispecific activatable antibody is formulated as a composition. In some of these embodiments, the composition also includes the NB, where the NB is co-formulated with the multispecific activatable antibody that includes the BP, the CL, and the AB. In some examples of this embodiment, the BP is selected from the group consisting of an albumin binding peptide, a fibrinogen binding peptide, a fibronectin binding peptide, a hemoglobin binding peptide, a transferrin binding peptide, an immunoglobulin domain binding peptide, and other serum protein binding peptides.

In some examples of any of these multispecific activatable antibody embodiments, the NB is a soluble, globular protein. In some examples of any of these multispecific activatable antibody embodiments, the NB is a protein that circulates in the bloodstream. In some examples of any of these multispecific activatable antibody embodiments, the NB is selected from the group consisting of albumin, fibrinogen, fibronectin, hemoglobin, transferrin, an immunoglobulin domain, and other serum proteins.

In some examples of any of these multispecific activatable antibody embodiments, the CL is a polypeptide that includes a substrate (S) for a protease. In some examples of any of these multispecific activatable antibody embodiments, the protease is co-localized with its target in a tissue, and the protease cleaves the CL in the multispecific activatable antibody when the multispecific activatable antibody is exposed to the protease. In some examples of any of these multispecific activatable antibody embodiments, the CL is a polypeptide of up to 50 amino acids in length. In some examples of any of these multispecific activatable antibody embodiments, the CL is a polypeptide that includes a substrate (S) having a length of up to 15 amino acids, e.g., 3 amino acids long, 4 amino acids long, 5 amino acids long, 6 amino acids long, 7 amino acids long, 8 amino acids long, 9 amino acids long, 10 amino acids long, 11 amino acids long, 12 amino acids long, 13 amino acids long, 14 amino acids long, or 15 amino acids long.

In some examples of any of these multispecific activatable antibody embodiments, at least a portion of the multispecific activatable antibody has the structural arrangement from N-terminus to C-terminus as follows in the uncleaved state: NB-CL-AB, AB-CL-NB, BP-CL-AB or AB-CL-BP. In embodiments where the multispecific activatable antibody includes a BP and the multispecific activatable antibody is in the presence of the corresponding NB, at least a portion of the multispecific activatable antibody has a structural arrangement from N-terminus to C-terminus as follows in the uncleaved state: NB:BP-CM-AB or AB-CM-BP:NB, where ":" represents an interaction, e.g., binding, between the NB and BP.

In some examples of any of these multispecific activatable antibody embodiments, the multispecific activatable antibody includes an antibody or antigen-binding fragment thereof that specifically binds Its target and is a monoclonal antibody, domain antibody, single chain, Fab fragment, a F(ab')$_2$ fragment, a scFv, a scab, a dAb, a single domain heavy chain antibody, and a single domain light chain antibody. In some embodiments, such an antibody or immunologically active fragment thereof that binds its target is a mouse, chimeric, humanized or fully human monoclonal antibody.

In some examples of any of these multispecific activatable antibody embodiments, the multispecific activatable antibody also includes an agent conjugated to the AB. In some embodiments, the agent is a therapeutic agent. In some embodiments, the agent is an antineoplastic agent. In some embodiments, the agent is a toxin or fragment thereof. In some embodiments, the agent is conjugated to the AB via a linker. In some embodiments, the linker is a cleavable linker. In some embodiments, the agent is an agent selected from the group listed in Table 4. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some examples of any of these multispecific activatable antibody embodiments, the multispecific activatable antibody also includes a detectable moiety. In some embodiments, the detectable moiety is a diagnostic agent.

In some examples of any of these multispecific activatable antibody embodiments, the multispecific activatable antibody also includes a spacer. In some examples of any of these multispecific activatable antibody embodiments, the multispecific activatable antibody also includes a signal peptide. In some embodiments, the signal peptide is conjugated to the multispecific activatable antibody via a spacer. In some examples of any of these multispecific activatable antibody embodiments, the spacer is joined directly to the MM of the multispecific activatable antibody.

In some embodiments, the serum half-life of the multispecific activatable antibody is longer than that of the corresponding multispecific antibody; e.g., the pK of the multispecific activatable antibody is longer than that of the corresponding multispecific antibody. In some embodiments, the serum half-life of the multispecific activatable antibody is similar to that of the corresponding multispecific antibody. In some embodiments, the serum half-life of the multispecific activatable antibody is at least 15 days when administered to an organism. In some embodiments, the serum half-life of the multispecific activatable antibody is at least 12 days when administered to an organism. In some embodiments, the serum half-life of the multispecific activatable antibody is at least 11 days when administered to an organism. In some embodiments, the serum half-life of the multispecific activatable antibody is at least 10 days when administered to an organism. In some embodiments, the serum half-life of the multispecific activatable antibody is at least 9 days when administered to an organism. In some embodiments, the serum half-life of the multispecific activatable antibody is at least 8 days when administered to an organism. In some embodiments, the serum half-life of the multispecific activatable antibody is at least 7 days when administered to an organism. In some embodiments, the serum half-life of the multispecific activatable antibody is at least 6 days when administered to an organism. In some examples of any of these multispecific activatable antibody embodiments, the serum half-life of the multispecific activatable antibody is at least 5 days when administered to an organism. In some embodiments, the serum half-life of the multispecific activatable antibody is at least 4 days when administered to an organism. In some embodiments, the serum half-life of the multispecific activatable antibody is at least 3 days when administered to an organism. In some embodiments, the serum half-life of the multispecific activatable antibody is at least 2 days when administered to an organism. In some embodiments, the serum half-life of the multispecific activatable antibody is at least 24 hours when administered to an organism. In some embodiments, the serum half-life of the multispecific activatable antibody is at least 20 hours when administered to an organism. In some embodiments, the serum half-life of the multispecific activatable antibody is at least 18 hours when administered to an organism. In some embodiments, the serum half-life of the multispecific activatable antibody is at least 16 hours when administered to an organism. In some embodiments, the serum half-life of the multispecific activatable antibody is at least 14 hours when administered to an organism. In some embodiments, the serum half-life of the multispecific activatable antibody is at least 12 hours when administered to an organism. In some embodiments, the serum half-life of the multispecific activatable antibody is at least 10 hours when administered to an organism. In some embodiments, the serum half-life of the multispecific activatable antibody is at least 8 hours when administered to an organism. In some embodiments, the serum half-life of the multispecific activatable antibody is at least 6 hours when administered to an organism. In some embodiments, the serum half-life of the multispecific activatable antibody is at least 4 hours when administered to an organism. In some embodiments, the serum half-life of the multispecific activatable antibody is at least 3 hours when administered to an organism.

The disclosure also provides an isolated nucleic acid molecule encoding any of these multispecific activatable antibodies, as well as vectors that include these isolated nucleic acid sequences. The disclosure provides methods of producing a multispecific activatable antibody by culturing a cell under conditions that lead to expression of the multispecific activatable antibody, wherein the cell comprises such a nucleic acid sequence. In some embodiments, the cell comprises such a vector.

The dissociation constant ($K_d$) of the NB-containing multispecific activatable antibody toward the target is greater than the $K_d$ of the AB towards the target when it is not associated with the NB or NB:BP. The dissociation constant ($K_d$) of the NB-containing multispecific activatable antibody toward the target is greater than the $K_d$ of the parental AB towards the target. For example, the $K_d$ of the NB-containing multispecific activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times greater than the $K_d$ of the AB when it is not associated with the NB or NB:BP or the $K_d$ of the parental AB towards the target. Conversely, the binding affinity of the NB-containing multispecific activatable antibody towards the target is lower than the binding affinity of the AB when it is not associated with the NB or NB:BP or lower than the binding affinity of the parental AB towards the target. For example, the binding affinity of the NB-containing multispecific activatable antibody toward the target is at least 5, 10, 25, 50, 100, 250, 500, 1,000, 2,500, 5,000, 10,000, 50,000, 100,000, 500,000, 1,000,000, 5,000,000, 10,000,000, 50,000,000 or greater, or between 5-10, 10-100, 10-1,000, 10-10,000, 10-100,000, 10-1,000,000, 10-10,000,000, 100-1,000, 100-10,000, 100-100,000, 100-1,000,000, 100-10,000,000, 1,000-10,000, 1,000-100,000, 1,000-1,000,000, 1000-10,000,000, 10,000-100,000, 10,000-1,000,000, 10,000-10,000,000, 100,000-1,000,000, or 100,000-10,000,000 times lower than the binding affinity of the AB when it is not associated with the NB or NB:BP or lower than the binding affinity of the parental AB towards the target.

When the NB-containing multispecific activatable antibody is in the presence of Its target, specific binding of the AB to its target is reduced or inhibited, as compared to the specific binding of the AB when it is not associated with the NB or NB:BP. When the NB-containing multispecific activatable antibody is in the presence of its target, specific binding of the AB to Its target is reduced or inhibited, as compared to the specific binding of the parental AB to Its target. When compared to the binding of the AB not associated with an NB or NB:BP or the binding of the parental AB to Its target, the ability of the NB-containing multispecific activatable antibody to bind Its target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

When the NB-containing multispecific activatable antibody is in the presence of Its target but not in the presence of a modifying agent (for example a protease or other enzyme), specific binding of the AB to Its target is reduced or inhibited, as compared to the specific binding of the AB when it is not associated with the NB or NB:BP. When the NB-containing multispecific activatable antibody is in the presence of Its target but not in the presence of a modifying agent (for example a protease, other enzyme, reduction agent, or light), specific binding of the AB to Its target is reduced or inhibited, as compared to the specific binding of the parental AB to Its target. When compared to the binding of the AB not associated with an NB or NB:BP or the binding of the parental AB to Its target, the ability of the NB-containing multispecific activatable antibody to bind Its target is reduced, for example, by at least 50%, 60%, 70%, 80%, 90%, 92%, 93%, 94%, 95%, 96%, 97%, 98%, 99%, or even 100% for at least 2, 4, 6, 8, 12, 28, 24, 30, 36, 48, 60, 72, 84, or 96 hours, or 5, 10, 15, 30, 45, 60, 90, 120, 150, or 180 days, or 1, 2, 3, 4, 5, 6, 7, 8, 9, 10, 11, or 12 months or longer when measured in vitro and/or in vivo.

In some examples of any of these multispecific activatable antibody embodiments, the multispecific activatable antibody includes an agent conjugated to the AB to produce a multispecific activatable antibody conjugate. In some embodiments of the multispecific activatable antibody conjugate, the agent is a therapeutic agent. In some embodiments, the agent is a diagnostic agent. In some embodiments, the agent is a detectable marker. In some embodiments of the multispecific activatable antibody conjugate, the agent is an antineoplastic agent. In some embodiments of the multispecific activatable antibody conjugate, the agent is a toxin or fragment thereof. In some embodiments of the multispecific activatable antibody conjugate, the agent is conjugated to the AB via a linker. In some embodiments of the multispecific activatable antibody conjugate, the linker is a cleavable linker. In some embodiments, the agent is an agent selected from the group listed in Table 4. In some embodiments, the agent is a dolastatin. In some embodiments, the agent is an auristatin or derivative thereof. In some embodiments, the agent is auristatin E or a derivative thereof. In some embodiments, the agent is monomethyl auristatin E (MMAE). In some embodiments, the agent is monomethyl auristatin D (MMAD). In some embodiments, the agent is a maytansinoid or maytansinoid derivative. In some embodiments, the agent is DM1 or DM4. In some embodiments, the agent is a duocarmycin or derivative thereof. In some embodiments, the agent is a calicheamicin or derivative thereof. In some embodiments, the agent is a pyrrolobenzodiazepine.

In some examples of any of these multispecific activatable antibody embodiments, the multispecific activatable antibodies are dual-target binding multispecific activatable antibodies. Such dual target binding multispecific activatable antibodies contain two Abs that may bind the same or different targets. In specific embodiments, dual-targeting multispecific activatable antibodies contain bispecific antibodies or antibody fragments.

Dual target binding multispecific activatable antibodies are designed so as to have a CL cleavable by a cleaving agent that is co-localized in a target tissue with one or both of the targets capable of binding to the ABs of the multispecific activatable antibodies. Dual target binding multispecific activatable antibodies with more than one AB to the same or different targets can be designed so as to have more than one CL, wherein the first CL is cleavable by a cleaving agent in a first target tissue and wherein the second CL is cleavable by a cleaving agent in a second target tissue, with one or more of the targets binding to the ABs of the multispecific activatable antibodies. In one embodiment, the first and second target tissues are spatially separated, for example, at different sites in the organism. In one embodiment, the first and second target tissues are the same tissue temporally separated, for example the same tissue at two different points in time, for example the first time point is when the tissue is an early stage tumor, and the second time point is when the tissue is a late stage tumor.

The disclosure also provides nucleic acid molecules encoding the multispecific activatable antibodies described herein. The disclosure also provides vectors that include these nucleic acids. The multispecific activatable antibodies described herein are produced by culturing a cell under conditions that lead to expression of the multispecific activatable antibody, wherein the cell includes these nucleic acid molecules or vectors.

The disclosure also provides methods of manufacturing multispecific activatable antibodies. In one embodiment, the method includes the steps of (a) culturing a cell that includes a nucleic acid construct that encodes the multispecific activatable antibody under conditions that lead to expression of the multispecific activatable antibody, wherein the multispecific activatable antibody includes (i) a non-binding steric moiety (NB); (ii) a cleavable linker (CL); and (iii) an antibody or an antigen binding fragment thereof (AB) that specifically binds a target, wherein (1) the NB does not bind specifically to the AB; (2) the CL is a polypeptide that includes a substrate (S) for an enzyme; (3) the CL is positioned such that in an uncleaved state, the NB interferes with binding of the AB to the target and in a cleaved state, the NB does not interfere with binding of the AB to the target; and (4) the NB does not inhibit cleavage of the CL by the enzyme; and (b) recovering the multispecific activatable antibody.

In another embodiment, the method includes the steps of (a) culturing a cell that includes a nucleic acid construct that encodes the multispecific activatable antibody under conditions that lead to expression of the multispecific activatable antibody, wherein the multispecific activatable antibody includes (i) a binding partner (BP) for a non-binding steric moiety (NB); (ii) a cleavable linker (CL); and (iii) an antibody or an antigen binding fragment thereof (AB) that specifically binds a target, wherein (1) the NB does not bind specifically to the AB; (2) the CL is a polypeptide that includes a substrate (S) for an enzyme; (3) the CL is positioned such that in an uncleaved state in the presence of the NB, the NB interferes with binding of the AB to the target and in a cleaved state, the NB does not interfere with binding of the AB to the target and the BP does not interfere with binding of the AB to the target; and (4) the NB and the BP do not inhibit cleavage of the CL by the enzyme; and (b) recovering the multispecific activatable antibody. In some examples of this embodiment, the BP of the multispecific activatable antibody is bound to the NB.

Use of Multispecific Antibodies and Multispecific Activatable Antibodies

It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In one embodiment, a multispecific antibody and/or a multispecific activatable antibody of the disclosure may be used as therapeutic agents. Such agents will generally be employed to diagnose, prognose, monitor, treat, alleviate, and/or prevent a disease or pathology in a subject. A therapeutic regimen is carried out by identifying a subject, e.g., a human patient or other mammal suffering from (or at risk of developing) a disorder using standard methods. A multispecific antibody and/or a multispecific activatable antibody preparation, for example in some embodiments, one having high specificity and high affinity for its two or more target antigens, is administered to the subject and will generally have an effect due to its binding with the targets. Administration of the multispecific antibody and/or a multispecific activatable antibody may abrogate or inhibit or interfere with the signaling function of one or more of the targets. Administration of the multispecific antibody and/or a multispecific activatable antibody may abrogate or inhibit or interfere with the binding of one or more of the targets with an endogenous ligand to which it naturally binds.

Generally, alleviation or treatment of a disease or disorder involves the lessening of one or more symptoms or medical problems associated with the disease or disorder. For example, in the case of cancer, the therapeutically effective amount of the drug can accomplish one or a combination of the following: reduce the number of cancer cells; reduce the tumor size; inhibit (i.e., to decrease to some extent and/or stop) cancer cell infiltration into peripheral organs; inhibit tumor metastasis; inhibit, to some extent, tumor growth; and/or relieve to some extent one or more of the symptoms associated with the cancer. In some embodiments, a composition of this disclosure can be used to prevent the onset or reoccurrence of the disease or disorder in a subject, e.g., a human or other mammal, such as a non-human primate, companion animal (e.g., cat, dog, horse), farm animal, work animal, or zoo animal. The terms subject and patient are used interchangeably herein.

A therapeutically effective amount of a multispecific antibody and/or a multispecific activatable antibody of the disclosure relates generally to the amount needed to achieve a therapeutic objective. As noted above, this may be a binding interaction between the multispecific antibody and/or a multispecific activatable antibody and its target antigens that, in certain cases, interferes with the functioning of the targets. The amount required to be administered will furthermore depend on the binding affinity of the multispecific antibody and/or a multispecific activatable antibody for its specific antigen, and will also depend on the rate at which an administered multispecific antibody and/or a multispecific activatable antibody is depleted from the free volume other subject to which it is administered. Common ranges for therapeutically effective dosing of a multispecific antibody and/or antibody fragment and/or a multispecific activatable antibody of the disclosure may be, by way of nonlimiting example, from about 0.1 mg/kg body weight to about 50 mg/kg body weight. Common dosing frequencies may range, for example, from twice daily to once a week.

Efficaciousness of treatment is determined in association with any known method for diagnosing or treating the particular disorder. Methods for the screening of multispecific antibodies and/or multispecific activatable antibodies that possess the desired specificity include, but are not limited to, enzyme linked immunosorbent assay (ELISA) and other immunologically mediated techniques known within the art.

In another embodiment, a multispecific antibody and/or a multispecific activatable antibody directed two or more targets are used in methods known within the art relating to the localization and/or quantitation of the targets (e.g., for use in measuring levels of one or more of the targets within appropriate physiological samples, for use in diagnostic methods, for use in imaging the protein, and the like). In a given embodiment, a multispecific antibody and/or a multispecific activatable antibody directed two or more targets, or a derivative, fragment, analog or homolog thereof, that contain the antibody derived antigen binding domain, are utilized as pharmacologically active compounds (referred to hereinafter as "Therapeutics").

In another embodiment, a multispecific antibody and/or a multispecific activatable antibody directed two or more targets is used to isolate one or more of the targets by standard techniques, such as immunoaffinity, chromatography or immunoprecipitation. A multispecific antibody and/or a multispecific activatable antibody directed two or more targets (or a fragment thereof) are used diagnostically to monitor protein levels in tissue as part of a clinical testing procedure, e.g., to determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

In yet another embodiment, a multispecific antibody and/or a multispecific activatable antibody directed two or more targets can be used as an agent for detecting the presence of one or more of the targets (or a fragment thereof) in a sample. In some embodiments, the antibody contains a detectable label. Antibodies are polyclonal, or in some embodiments, monoclonal. An intact antibody, or a fragment thereof (e.g., $F_{ab}$, scFv, or $F_{(ab)2}$, is used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of an antibody with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the disclosure can be used to detect a protein in a biological sample in vitro as well as in vivo. For example, in vitro techniques for detection of an analyte protein include enzyme linked immunosorbent assays (ELISAs), Western blots, immunoprecipitations, and immunofluorescence. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

The multispecific antibodies and/or multispecific activatable antibodies of the disclosure are also useful in a variety of diagnostic and prophylactic formulations. In one embodiment, a multispecific antibody and/or multispecific activatable antibody is administered to patients that are at risk of developing one or more of the aforementioned disorders. A patient's or organ's predisposition to one or more of the disorders can be determined using genotypic, serological or biochemical markers.

In another embodiment of the disclosure, a multispecific antibody and/or multispecific activatable antibody is administered to human individuals diagnosed with a clinical indication associated with one or more of the aforementioned disorders. Upon diagnosis, a multispecific antibody and/or multispecific activatable antibody is administered to mitigate or reverse the effects of the clinical indication.

Multispecific antibodies and/or multispecific activatable antibodies are also useful in the detection of one or more targets in patient samples and accordingly are useful as diagnostics. For example, the multispecific antibodies and/or multispecific activatable antibodies of the disclosure are used in in vitro assays, e.g., ELISA, to detect one or more target levels in a patient sample.

In one embodiment, a multispecific antibody and/or multispecific activatable antibody is immobilized on a solid support (e.g., the well(s) of a microtiter plate). The immobilized antibody and/or activatable antibody serves as a capture antibody for any target(s) that may be present in a test sample. Prior to contacting the immobilized multispecific antibody and/or immobilized multispecific activatable antibody with a patient sample, the solid support is rinsed and treated with a blocking agent such as milk protein or albumin to prevent nonspecific adsorption of the analyte.

Subsequently the wells are treated with a test sample suspected of containing the antigen, or with a solution containing a standard amount of the antigen. Such a sample is, e.g., a serum sample from a subject suspected of having levels of circulating antigen considered to be diagnostic of a pathology. After rinsing away the test sample or standard, the solid support is treated with a second antibody that is detectably labeled. The labeled second antibody serves as a detecting antibody. The level of detectable label is measured, and the concentration of target antigen(s) in the test sample is determined by comparison with a standard curve developed from the standard samples.

It will be appreciated that based on the results obtained using the multispecific antibody and/or multispecific activatable antibody in an in vitro diagnostic assay, it is possible to stage a disease in a subject based on expression levels of the target antigen(s). For a given disease, samples of blood are taken from subjects diagnosed as being at various stages in the progression of the disease, and/or at various points in the therapeutic treatment of the disease. Using a population of samples that provides statistically significant results for each stage of progression or therapy, a range of concentrations of the antigen that may be considered characteristic of each stage is designated.

Multispecific antibodies and/or multispecific activatable antibodies can also be used in diagnostic and/or imaging methods. In some embodiments, such methods are in vitro methods. In some embodiments, such methods are in vivo methods. In some embodiments, such methods are in situ methods. In some embodiments, such methods are ex vivo methods. For example, multispecific antibodies and/or multispecific activatable antibodies having an enzymatically cleavable CM can be used to detect the presence or absence of an enzyme that is capable of cleaving the CM. Such multispecific antibodies and/or multispecific activatable antibodies can be used in diagnostics, which can include in vivo detection (e.g., qualitative or quantitative) of enzyme activity (or, in some embodiments, an environment of increased reduction potential such as that which can provide for reduction of a disulfide bond) through measured accumulation of multispecific activated antibodies (i.e., antibodies resulting from cleavage of a multispecific activatable antibody) in a given cell or tissue of a given host organism. Such accumulation of activated multispecific antibodies indicates not only that the tissue expresses enzymatic activity (or an increased reduction potential depending on the nature of the CM) but also that the tissue expresses at least one target to which the activated antibody binds.

For example, the CM can be selected to be a protease substrate for a protease found at the site of a tumor, at the site of a viral or bacterial infection at a biologically confined site (e.g., such as in an abscess, in an organ, and the like), and the like. At least one of the AB can be one that binds a target antigen. Using methods familiar to one skilled in the art, a detectable label (e.g., a fluorescent label or radioactive label or radiotracer) can be conjugated to an AB or other region of a multispecific antibody and/or multispecific activatable antibody. Suitable detectable labels are discussed in the context of the above screening methods and additional specific examples are provided below. Using at least one AB specific to a protein or peptide of the disease state, along with a protease whose activity is elevated in the disease tissue of interest, activatable antibodies will exhibit an increased rate of binding to disease tissue relative to tissues where the CM specific enzyme is not present at a detectable level or is present at a lower level than in disease tissue or is inactive (e.g., in zymogen form or in complex with an inhibitor). Since small proteins and peptides are rapidly cleared from the blood by the renal filtration system, and because the enzyme specific for the CM is not present at a detectable level (or is present at lower levels in non-disease tissues or is present in inactive conformation), accumulation of activated multispecific antibodies in the disease tissue is enhanced relative to non-disease tissues.

In another example, activatable multispecific antibodies can be used to detect the presence or absence of a cleaving agent in a sample. For example, where the multispecific activatable antibodies contain a CM susceptible to cleavage by an enzyme, the multispecific activatable antibodies can be used to detect (either qualitatively or quantitatively) the presence of an enzyme in the sample. In another example, where the multispecific activatable antibodies contain a CM susceptible to cleavage by reducing agent, the multispecific activatable antibodies can be used to detect (either qualitatively or quantitatively) the presence of reducing conditions in a sample. To facilitate analysis in these methods, the multispecific activatable antibodies can be detectably labeled, and can be bound to a support (e.g., a solid support, such as a slide or bead). The detectable label can be positioned on a portion of the activatable antibody that is not released following cleavage, for example, the detectable label can be a quenched fluorescent label or other label that is not detectable until cleavage has occurred. The assay can be conducted by, for example, contacting the immobilized, detectably labeled multispecific activatable antibodies with a sample suspected of containing an enzyme and/or reducing agent for a time sufficient for cleavage to occur, then washing to remove excess sample and contaminants. The presence or absence of the cleaving agent (e.g., enzyme or reducing agent) in the sample is then assessed by a change in detectable signal of the multispecific activatable antibodies prior to contacting with the sample e.g., the presence of and/or an increase in detectable signal due to cleavage of the multispecific activatable antibody by the cleaving agent in the sample.

Such detection methods can be adapted to also provide for detection of the presence or absence of a target that is capable of binding at least one AB of the multispecific activatable antibodies when cleaved. Thus, the assays can be adapted to assess the presence or absence of a cleaving agent and the presence or absence of a target of interest. The presence or absence of the cleaving agent can be detected by the presence of and/or an increase in detectable label of the multispecific activatable antibodies as described above, and the presence or absence of the target can be detected by detection of a target-AB complex e.g., by use of a detectably labeled anti-target antibody.

Multispecific activatable antibodies are also useful in in situ imaging for the validation of activatable antibody activation, e.g., by protease cleavage, and binding to a particular target. In situ imaging is a technique that enables localization of proteolytic activity and target in biological samples such as cell cultures or tissue sections. Using this technique, it is possible to confirm both binding to a given target and proteolytic activity based on the presence of a detectable label (e.g., a fluorescent label).

These techniques are useful with any frozen cells or tissue derived from a disease site (e.g. tumor tissue) or healthy tissues. These techniques are also useful with fresh cell or tissue samples.

In these techniques, an activatable antibody is labeled with a detectable label. The detectable label may be a fluorescent dye, (e.g. a fluorophore, Fluorescein Isothiocyanate (FITC), Rhodamine Isothiocyanate (TRITC), an Alexa Fluor® label), a near infrared (NIR) dye (e.g., Qdot® nanocrystals), a colloidal metal, a hapten, a radioactive marker, biotin and an amplification reagent such as streptavidin, or an enzyme (e.g. horseradish peroxidase or alkaline phosphatase).

Detection of the label in a sample that has been incubated with the labeled, multispecific activatable antibody indicates that the sample contains the target and contains a protease that is specific for the CM of the multispecific activatable antibody. In some embodiments, the presence of the protease can be confirmed using broad spectrum protease inhibitors such as those described herein, and/or by using an agent that is specific for the protease, for example, an antibody such as A11, which is specific for the protease matriptase (MT-SP1) and inhibits the proteolytic activity of MT-SP1; see e.g., International Publication Number WO 2010/129609, published 11 Nov. 2010. The same approach of using broad spectrum protease inhibitors such as those described herein, and/or by using a more selective inhibitory agent can be used to identify a protease or class of proteases specific for the CM of the activatable antibody. In some embodiments, the presence of the target can be confirmed using an agent that is specific for the target or the detectable label can be competed with unlabeled target. In some embodiments, unlabeled activatable antibody could be used, with detection by a labeled secondary antibody or more complex detection system.

Similar techniques are also useful for in vivo imaging where detection of the fluorescent signal in a subject, e.g., a mammal, including a human, indicates that the disease site contains the target and contains a protease that is specific for the CM of the multispecific activatable antibody.

These techniques are also useful in kits and/or as reagents for the detection, identification or characterization of protease activity in a variety of cells, tissues, and organisms based on the protease-specific CM in the multispecific activatable antibody.

Therapeutic Administration and Formulations of Multispecific Antibodies and/or Multispecific Activatable Antibodies It will be appreciated that administration of therapeutic entities in accordance with the disclosure will be administered with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences (15th ed, Mack Publishing Company, Easton, Pa. (1975)), particularly Chapter 87 by Blaug, Seymour, therein. These formulations include, for example, powders, pastes, ointments, jellies, waxes, oils, lipids, lipid (cationic or anionic) containing vesicles (such as Lipofectin™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. Any of the foregoing mixtures may be appropriate in treatments and therapies in accordance with the present disclosure, provided that the active ingredient in the formulation is not inactivated by the formulation and the formulation is physiologically compatible and tolerable with the route of administration. See also Baldrick P. "Pharmaceutical excipient development: the need for preclinical guidance." Regul. Toxicol Pharmacol. 32(2):210-8 (2000), Wang W. "Lyophilization and development of solid protein pharmaceuticals." Int. J. Pharm. 203(1-2):1-60 (2000), Charman W N "Lipids, lipophilic drugs, and oral drug delivery-some emerging concepts." J Pharm Sci. 89(8):967-78 (2000), Powell et al. "Compendium of excipients for parenteral formulations" PDA J Pharm Sci Technol. 52:238-311 (1998) and the citations therein for additional information related to formulations, excipients and carriers well known to pharmaceutical chemists.

In some embodiments, the multispecific antibodies, the multispecific activatable antibodies and/or the conjugated multispecific activatable antibody compositions are administered in conjunction with one or more additional agents, or a combination of additional agents. Suitable additional agents include current pharmaceutical and/or surgical therapies for an intended application. For example, the multispecific antibodies, the multispecific activatable antibodies and/or the conjugated multispecific activatable antibody compositions can be used in conjunction with an additional chemotherapeutic or anti-neoplastic agent. For example, the multispecific antibodies, the multispecific activatable antibodies and/or the conjugated multispecific activatable antibody compositions and additional agent are formulated into a single therapeutic composition, and the multispecific antibodies, the multispecific activatable antibodies and/or the conjugated multispecific activatable antibody compositions and additional agent are administered simultaneously. Alternatively, the multispecific antibodies, the multispecific activatable antibodies and/or the conjugated multispecific activatable antibody compositions and additional agent are separate from each other, e.g., each is formulated into a separate therapeutic composition, and the multispecific antibodies, the multispecific activatable antibodies and/or the conjugated multispecific activatable antibody compositions and the additional agent are administered simultaneously, or the multispecific antibodies, the multispecific activatable antibodies and/or the conjugated multispecific activatable antibody compositions and the additional agent are administered at different times during a treatment regimen. For example, the multispecific antibodies, the multispecific activatable antibodies and/or the conjugated multispecific activatable antibody compositions is administered prior to the administration of the additional agent, the multispecific antibodies, the multispecific activatable antibodies and/or the conjugated multispecific activatable antibody compositions is administered subsequent to the administration of the additional agent, or the multispecific antibodies, the multispecific activatable antibodies and/or the conjugated multispecific activatable antibody compositions and the additional agent are administered in an alternating fashion. As described herein, the multispecific antibodies, the multispecific activatable antibodies and/or the conjugated multispecific activatable antibody compositions and additional agent are administered in single doses or in multiple doses.

In some embodiments, the additional agent is coupled or otherwise attached to the multispecific antibodies, the multispecific activatable antibodies and/or the conjugated multispecific activatable antibody compositions.

Suitable additional agents are selected according to the purpose of the intended application (i.e., killing, prevention of cell proliferation, hormone therapy or gene therapy). Such agents may include but is not limited to, for example, pharmaceutical agents, toxins, fragments of toxins, alkylating agents, enzymes, antibiotics, antimetabolites, antiproliferative agents, hormones, neurotransmitters, DNA, RNA, siRNA, oligonucleotides, antisense RNA, aptamers, diagnostics, radioopaque dyes, radioactive isotopes, fluorogenic compounds, magnetic labels, nanoparticles, marker compounds, lectins, compounds that alter cell membrane permeability, photochemical compounds, small molecules, liposomes, micelles, gene therapy vectors, viral vectors, and the like. Finally, combinations of agents or combinations of different classes of agents may be used.

The multispecific antibodies, the multispecific activatable antibodies and/or the conjugated multispecific activatable antibody compositions of the disclosure (also referred to herein as "active compounds"), and derivatives, fragments, analogs and homologs thereof, can be incorporated into pharmaceutical compositions suitable for administration. Principles and considerations involved in preparing such compositions, as well as guidance in the choice of components are provided, for example, in Remington's Pharmaceutical Sciences: The Science And Practice Of Pharmacy 19th ed. (Alfonso R. Gennaro, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Such compositions typically comprise the multispecific antibody and/or the multispecific activatable antibody and a pharmaceutically acceptable carrier. Where a multispecific antibody and/or a multispecific activatable antibody includes a fragment of the AB domain, the smallest fragment of the AB that specifically binds to the binding domain of the target protein can be used. For example, based upon the variable-region sequences of an antibody, peptide molecules can be designed that retain the ability of the AB to bind the target protein sequence. Such peptides can be synthesized chemically and/or produced by recombinant DNA technology. (See, e.g., Marasco et al., Proc. Natl. Acad. Sci. USA, 90: 7889-7893 (1993)).

As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Suitable examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated.

The formulations to be used for in vivo administration must be sterile. This is readily accomplished by filtration through sterile filtration membranes.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be suitable to include isotonic agents, for example, sugars, polyalcohols such as manitol, sorbitol, sodium chloride in the composition. Prolonged absorption of the injectable compositions can be brought about by including in the composition an agent that delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as sustained/controlled release formulations, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

For example, the active ingredients can be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

The materials can also be obtained commercially from Alza Corporation and Nova Pharmaceuticals, Inc. Liposomal suspensions (including liposomes targeted to infected cells with monoclonal antibodies to viral antigens) and can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The pharmaceutical compositions can be included in a container, pack, or dispenser together with instructions for administration.

The formulation can also contain more than one active compound as necessary for the particular indication being treated, for example, those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

In one embodiment, the active compounds are administered in combination therapy, i.e., combined with other agents, e.g., therapeutic agents, that are useful for treating pathological conditions or disorders, such as autoimmune disorders and inflammatory diseases. The term "in combination" in this context means that the agents are given substantially contemporaneously, either simultaneously or sequentially. If given sequentially, at the onset of administration of the second compound, the first of the two compounds is still detectable at effective concentrations at the site of treatment.

For example, the combination therapy can include one or more antibodies of the disclosure coformulated with, and/or coadministered with, one or more additional therapeutic agents, e.g., one or more cytokine and growth factor inhibitors, immunosuppressants, anti-inflammatory agents, metabolic inhibitors, enzyme inhibitors, and/or cytotoxic or cytostatic agents, as described in more detail below. Furthermore, one or more antibodies described herein may be used in combination with two or more of the therapeutic agents described herein. Such combination therapies may advantageously utilize lower dosages of the administered therapeutic agents, thus avoiding possible toxicities or complications associated with the various monotherapies.

In other embodiments, one or more antibodies of the disclosure can be coformulated with, and/or coadministered with, one or more anti-inflammatory drugs, immunosuppressants, or metabolic or enzymatic inhibitors. Nonlimiting examples of the drugs or inhibitors that can be used in combination with the antibodies described herein, include, but are not limited to, one or more of: nonsteroidal anti-inflammatory drug(s) (NSAIDs), e.g., ibuprofen, tenidap, naproxen, meloxicam, piroxicam, diclofenac, and indomethacin; sulfasalazine; corticosteroids such. as prednisolone; cytokine suppressive anti-inflammatory drug(s) (CSAIDs); inhibitors of nucleotide biosynthesis, e.g., inhibitors of purine biosynthesis, folate antagonists (e.g., methotrexate (N-[4-[[(2,4-diamino-6-pteridinyl)methyl]methylamino]benzoyl]-L-glutamic acid); and inhibitors of pyrimidine biosynthesis, e.g., dihydroorotate dehydrogenase (DHODH) inhibitors. Suitable therapeutic agents for use in combination with the antibodies of the disclosure include NSAIDs, CSAIDs, (DHODH) inhibitors (e.g., leflunomide), and folate antagonists (e.g., methotrexate).

Examples of additional inhibitors include one or more of: corticosteroids (oral, inhaled and local injection); immunosuppressants, e.g., cyclosporin, tacrolimus (FK-506); and mTOR inhibitors, e.g., sirolimus (rapamycin-RAPAMUNE™ or rapamycin derivatives, e.g., soluble rapamycin derivatives (e.g., ester rapamycin derivatives, e.g., CCI-779); agents that interfere with signaling by proinflammatory cytokines such as TNFα or IL-1 (e.g. IRAK, NIK, IKK, p38 or MAP kinase inhibitors); COX2 inhibitors, e.g., celecoxib, rofecoxib, and variants thereof; phosphodiesterase inhibitors, e.g., R973401 (phosphodiesterase Type IV inhibitor); phospholipase inhibitors, e.g., inhibitors of cytosolic phospholipase 2 (cPLA2) (e.g., trifluoromethyl ketone analogs); inhibitors of vascular endothelial cell growth factor or growth factor receptor, e.g., VEGF inhibitor and/or VEGF-R inhibitor; and inhibitors of angiogenesis. Suitable therapeutic agents for use in combination with the antibodies of the disclosure are immunosuppressants, e.g., cyclosporin, tacrolimus (FK-506); mTOR inhibitors, e.g., sirolimus (rapamycin) or rapamycin derivatives, e.g., soluble rapamycin derivatives (e.g., ester rapamycin derivatives, e.g., CCI-779); COX2 inhibitors, e.g., celecoxib and variants thereof; and phospholipase inhibitors, e.g., inhibitors of cytosolic phospholipase 2 (cPLA2), e.g., trifluoromethyl ketone analogs.

Additional examples of therapeutic agents that can be combined with an antibody of the disclosure include one or more of: 6-mercaptopurines (6-MP); azathioprine sulphasalazine; mesalazine; olsalazine; chloroquine/hydroxychloroquine (PLAQUENIL®); pencillamine; aurothiornalate (intramuscular and oral); azathioprine; coichicine; beta-2 adrenoreceptor agonists (salbutamol, terbutaline, salmeteral); xanthines (theophylline, arninophylline); cromoglycate; nedocromil; ketotifen; ipratropium and oxitropium; mycophenolate mofetil; adenosine agonists; antithrombotic agents; complement inhibitors; and adrenergic agents.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

The following sequences shown in Table 7 include sequences that were used throughout the Examples provided herein:

TABLE 7

Exemplary Sequences

Anti-human CTLA-4 scFv Antibody:
(SEQ ID NO: 229)
GGAGGTGGATCTGGAGGTGGCGGTTCAGGCTCTGGCGGAGGCTCAGGTGGTGGAGGATCAGGCG

GAGGTGAAATTGTGTTGACACAGTCTCCAGGCACCCTGTCTTTGTCTCCAGGGGAAAGAGCCAC

CCTCTCCTGCAGGGCCAGTCAGAGTGTTAGCAGCAGCTACTTAGCCTGGTACCAGCAGAAACCT

TABLE 7-continued

Exemplary Sequences

GGCCAGGCTCCCAGGCTCCTCATCTATGGTGCATCCAGCAGGGCCACTGGCATCCCAGACAGGT

TCAGTGGCAGTGGGTCTGGGACAGACTTCACTCTCACCATCAGCAGACTGGAGCCTGAAGATTT

TGCAGTGTATTACTGTCAGCAGTATGGTAGCTCACCGCTCACTTTCGGCGGAGGGACCAAGGTG

GAAATCAAACGTTCCGGAGGGTCGACCATAACTTCGTATAATGTATACTATACGAAGTTATCCT

CGAGCGGTACCCAGGTGCAGCTGGTGCAGACTGGGGGAGGCGTGGTCCAGCCTGGGAGGTCCCT

GAGACTCTCCTGTGCAGCCTCTGGATCCACCTTTAGCAGCTATGCCATGAGCTGGGTCCGCCAG

GCTCCAGGGAAGGGGCTGGAGTGGGTCTCAGCTATTAGTGGTAGTGGTGGTAGCACATACTACG

CAGACTCCGTGAAGGGCCGGTTCACCATCTCCAGAGACAATTCCAAGAACACGCTGTATCTGCA

AATGAACAGCCTGAGAGCCGAGGACACGGCCGTATATTACTGTGCGACAAACTCCCTTTACTGG

TACTTCGATCTCTGGGGCCGTGGCACCCTGGTCACTGTCTCTTCAGCTAGC (SEQ ID NO: 230)
GGGSGGGGSGSGGGSGGGGSGGGEIVLTQSPGTLSLSPGERATLSCRASQSVSSSYLAWYQQKP
GQAPRLLIYGASSRATGIPDRFSGSGSGTDFTLTISRLEPEDFAVYYCQQYGSSPLTFGGGTKV
EIKRSGGSTITSYNVYYTKLSSSGTQVQLVQTGGGVVQPGRSLRLSCAASGSTFSSYAMSWVRQ
APGKGLEWVSAISGSGGSTYYADSVKGRFTISRDNSKNTLYLQMNSLRAEDTAVYYCATNSLYW
YFDLWGRGTLVTVSSAS

Anti-human CD3 epsilon OKT3 scFv Antibody:

(SEQ ID NO: 231)
GGAGGTGGATCTGGAGGTGGCGGTTCAGGCTCTGGCGGAGGCTCAGGTGGTGGAGGATCAGGCG

GAGGTCAGGTTCAGCTGCAGCAGAGCGGTGCAGAACTGGCACGTCCGGGTGCAAGCGTTAAAAT

GAGCTGTAAAGCAAGCGGTTATACCTTTACCCGTTATACCATGCATTGGGTTAAACAGCGTCCG

GGTCAGGGTCTGGAATGGATTGGTTATATCAATCCGAGCCGTGGTTATACCAACTACAACCAGA

AATTCAAAGATAAAGCAACCCTGACCACCGATAAAAGCAGCAGCACCGCCTATATGCAGCTGAG

CAGCCTGACCTCAGAGGATAGCGCAGTTTATTACTGTGCACGCTATTATGATGATCACTATTGC

CTGGATTATTGGGGTCAGGGCACCACCCTGACCGTTAGCAGCGGTGGTGGTGGTAGTGGTGGCG

GTGGTTCAGGCGGTGGCGGTAGCCAGATTGTTCTGACCCAGAGTCCGGCAATTATGAGCGCAAG

TCCGGGTGAAAAAGTTACCATGACCTGTAGCGCCAGCAGCAGCGTTAGCTATATGAATTGGTAT

CAGCAGAAAGCGGCACCAGCCCGAAACGTTGGATTTATGATACCAGCAAACTGGCAAGCGGTG

TTCCGGCACATTTTCGTGGTAGCGGTAGCGGCACCTCATATAGCCTGACCATTAGCGGTATGGA

AGCAGAAGATGCAGCAACCTATTATTGTCAGCAGTGGTCAAGCAATCCGTTTACCTTTGGTAGT

GGCACCAAACTGGAAATTAATCGT (SEQ ID NO: 232)
GGGSGGGGSGSGGGSGGGGSGGGQVQLQQSGAELARPGASVKMSCKASGYTFTRYTMHWVKQRP
GQGLEWIGYINPSRGYTNYNQKFKDKATLTTDKSSSTAYMQLSSLTSEDSAVYYCARYYDDHYC
LDYWGQGTTLTVSSGGGGSGGGGSGGGGSQIVLTQSPAIMSASPGEKVTMTCSASSSVSYMNWY
QQKSGTSPKRWIYDTSKLASGVPAHFRGSGSGTSYSLTISGMEAEDAATYYCQQWSSNPFTFGS
GTKLEINR

Anti-human Jagged 4D11v2 Antibody: Heavy Chain (SEQ ID NO: 233)
gaggtgcacctgttggagtctggggggaggcttggtacagcctggggggtccctgagactctcct gtgcagcctctggattcacctttagcagctatgccatgagctgggtccgccaggctccagggaa ggggctggagtgggtgtcaagtattgacccggaaggtcggcagacatattacgcagactccgtg TABLE 7-continued Exemplary Sequences aagggccggttcaccatctccagagacaattccaagaacacgctgtatctgcaaatgaacagcc tgagagccgaggacacggccgtatattactgtgcgaaagacatcggcggcaggtcggcctttga ctactggggccagggaaccctggtcaccgtctcctcagctagcaccaagggcccatcggtcttc cccctggcaccctcctccaagagcacctctgggggcacagcggccctgggctgcctggtcaagg actacttccccgaaccggtgacggtgtcgtggaactcaggcgccctgaccagcggcgtgcacac cttcccggctgtcctacagtcctcaggactctactccctcagcagcgtggtgaccgtgccctcc agcagcttgggcacccagacctacatctgcaacgtgaatcacaagcccagcaacaccaaggtgg acaagaaagttgagcccaaatcttgtgacaaaactcacacatgcccaccgtgcccagcacctga actcctggggggaccgtcagtcttcctcttccccccaaaacccaaggacaccctcatgatctcc cggacccctgaggtcacatgcgtggtggtggacgtgagccacgaagaccctgaggtcaagttca actggtacgtggacggcgtggaggtgcataatgccaagacaaagccgcgggaggagcagtacaa cagcacgtaccgtgtggtcagcgtcctcaccgtcctgcaccaggactggctgaatggcaaggag tacaagtgcaaggtctccaacaaagcccctcccagcccccatcgagaaaaccatctccaaagcca aagggcagccccgagaaccacaggtgtacaccctgcccccatcccgggaggagatgaccaagaa ccaggtcagcctgacctgcctggtcaaaggcttctatcccagcgacatcgccgtggagtgggag agcaatgggcagccggagaacaactacaagaccacgcctcccgtgctggactccgacggctcct tcttcctctacagcaagctcaccgtggacaagagcaggtggcagcaggggaacgtcttctcatg ctccgtgatgcatgaggctctgcacaaccactacacgcagaagagcctctccctgtctccgggt aaa (SEQ ID NO: 234)
EVHLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSSASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEALHNHYTQKSLSLSPG

K

Anti-human Jagged 4D11v2 Antibody: Light Chain (SEQ ID NO: 235)
Gacatccagatgacccagtctccatcctccctgtctgcatctgtaggagacagagtcaccatca cttgccgggcaagtcagagcattagcagctatttaaattggtatcagcagaaaccagggaaagc ccctaagctcctgatctatgcggcatccagtttgcaaagtggggtcccatcaaggttcagtggc agtggatctgggacagatttcactctcaccatcagcagtctgcaacctgaagattttgcaactt actactgtcaacagacggttgtggcgcctccgttattcggccaagggaccaaggtggaaatcaa acgtacggtggctgcaccatctgtcttcatcttcccgccatctgatgagcagttgaaatctgga actgcctctgttgtgtgcctgctgaataacttctatcccagagaggccaaagtacagtggaagg tggataacgccctccaatcgggtaactcccaggagagtgtcacagagcaggacagcaaggacag cacctacagcctcagcagcaccctgacgctgancaaagcagactacgagaaacacaaagtctac gcctgcgaagtcacccatcagggcctgagctcgcccgtcacaaagagcttcaacaggggagagt gt TABLE 7-continued Exemplary Sequences (SEQ ID NO: 236)
DIQMTQSPSSLSASVGDRVTITCRASQSISSYLNWYQQKPGKAPKLLIYAASSLQSGVPSRFSG

SGSGTDFTLTISSLQPEDFATYYCQQTVVAPPLFGQGTKVEIKRTVAAPSVFIFPPSDEQLKSG

TASVVCLLNNFYPREAKVQWKVDNALQSGNSQESVTEQDSKDSTYSLSSTLTLXKADYEKHKVY

ACEVTHQGLSSPVTKSFNRGEC

Anti-human Jagged 4D11 Antibody: Heavy Chain (SEQ ID NO: 237)
gaggtgcagctgttggagtctgggggaggcttggtacagcctggggggtccctgagactctcct gtgcagcctctggattcacctttagcagctatgccatgagctgggtccgccaggctccagggaa ggggctggagtgggtgtcaagtattgacccggaaggtcggcagacatattacgcagactccgtg aagggccggttcaccatctccagagacaattccaagaacacgctgtatctgcaaatgaacagcc tgagagccgaggacacggccgtatattactgtgcgaaagacatcggcggcaggtcggcctttga ctactggggccagggaaccctggtcaccgtctcctcagctagcaccaagggcccatcggtcttc cccctggcaccctcctccaagagcacctctgggggcacagcggccctgggctgcctggtcaagg actacttccccgaaccggtgacggtgtcgtggaactcaggcgccctgaccagcggcgtgcacac cttcccggctgtcctacagtcctcaggactctactccctcagcagcgtggtgaccgtgccctcc agcagcttgggcacccagacctacatctgcaacgtgaatcacaagcccagcaacaccaaggtgg acaagaaagttgagcccaaatcttgtgacaaaactcacacatgcccaccgtgcccagcacctga actcctggggggaccgtcagtcttcctcttccccccaaaacccaaggacaccctcatgatctcc cggacccctgaggtcacatgcgtggtggtggacgtgagccacgaagaccctgaggtcaagttca actggtacgtggacggcgtggaggtgcataatgccaagacaaagccgcgggaggagcagtacaa cagcacgtaccgtgtggtcagcgtcctcaccgtcctgcaccaggactggctgaatgcaaggag tacaagtgcaaggtctccaacaaagccctcccagcccccatcgagaaaaccatctccaaagcca aagggcagccccgagaaccacaggtgtacaccctgcccccatcccgggaggagatgaccaagaa ccaggtcagcctgacctgcctggtcaaaggcttctatcccagcgacatcgccgtggagtgggag agcaatgggcagccggagaacaactacaagaccacgcctcccgtgctggactccgacggctcct tcttcctctacagcaagctcaccgtggacaagagcaggtggcagcaggggaacgtcttctcatg ctccgtgatgcatgaggctctgcacaaccactacacgcagaagagcctctccctgtctccgggt aaa (SEQ ID NO: 238)
EVQLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSSASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEALHNHYTQKSLSLSPG

K

Anti-Jagged Activatable Antibody 5342-1204-4D11v2: Light Chain (SEQ ID NO: 239)
caaggccagtctggccagtgcaatatttggctcgtaggtggtgattgcaggggctggcagggg gctcgagcggtggcagcggtggctctggtggtctgagcggccgttccgataatcatggcggcgg

TABLE 7-continued

Exemplary Sequences ttctgacatccagatgacccagtctccatcctccctgtctgcatctgtaggagacagagtcacc
atcacttgccgggcaagtcagagcattagcagctatttaaattggtatcagcagaaaccaggga
aagcccctaagctcctgatctatgcggcatccagtttgcaaagtggggtcccatcaaggttcag
tggcagtggatctgggacagatttcactctcaccatcagcagtctgcaacctgaagattttgca
acttactactgtcaacagacggttgtggcgcctccgttattcggccaagggaccaaggtggaaa
tcaaacgtacggtggctgcaccatctgtcttcatcttcccgccatctgatgagcagttgaaatc
tggaactgcctctgttgtgtgcctgctgaataacttctatcccagagaggccaaagtacagtgg
aaggtggataacgcccctccaatcgggtaactcccaggagagtgtcacagagcaggacagcaagg
acagcacctacagcctcagcagcaccctgacgctgagcaaagcagactacgagaaacacaaagt
ctacgcctgcgaagtcacccatcagggcctgagctcgcccgtcacaaagagcttcaacagggga
gagtgt (SEQ ID NO: 240)
QGQSGQCNIWLVGGDCRGWQGGSSGGSGGSGGLSGRSDNHGGGSDIQMTQSPSSLSASVGDRVT
ITCRASQSISSYLNWYQQKPGKAPKLLIYAASSLQSGVPSRFSGSGSGTDFTLTISSLQPEDFA
TYYCQQTVVAPPLFGQGTKVEIKRTVAAPSVFIFPPSDEQLKSGTASVVCLLNNFYPREAKVQW
KVDNALQSGNSQESVTEQDSKDSTYSLSSTLTLXKADYEKHKVYACEVTHQGLSSPVTKSFNRG
EC Anti-Jagged 4D11v2 - anti-CD3 OKT3 Multispecific Antibody:
Heavy Chain
(SEQ ID NO: 241)
GAGGTGCACCTGTTGGAGTCTGGGGGAGGCTTGGTACAGCCTGGGGGGTCCCTGAGACTCTCCT
GTGCAGCCTCTGGATTCACCTTTAGCAGCTATGCCATGAGCTGGGTCCGCCAGGCTCCAGGGAA
GGGGCTGGAGTGGGTGTCAAGTATTGACCCGGAAGGTCGGCAGACATATTACGCAGACTCCGTG
AAGGGCCGGTTCACCATCTCCAGAGACAATTCCAAGAACACGCTGTATCTGCAAATGAACAGCC
TGAGAGCCGAGGACACGGCCGTATATTACTGTGCGAAAGACATCGGCGGCAGGTCGGCCTTTGA
CTACTGGGGCCAGGGAACCCTGGTCACCGTCTCCTCAGCTAGCACCAAGGGCCCATCGGTCTTC
CCCCTGGCACCCTCCTCCAAGAGCACCTCTGGGGGCACAGCGGCCCTGGGCTGCCTGGTCAAGG
ACTACTTCCCCGAACCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGGTGACCGTGCCCTCC
AGCAGCTTGGGCACCCAGACCTACATCTGCAACGTGAATCACAAGCCCAGCAACACCAAGGTGG
ACAAGAAAGTTGAGCCCAAATCTTGTGACAAAACTCACACATGCCCACCGTGCCCAGCACCTGA
ACTCCTGGGGGGACCGTCAGTCTTCCTCTTCCCCCCAAAACCCAAGGACACCCTCATGATCTCC
CGGACCCCTGAGGTCACATGCGTGGTGGTGGACGTGAGCCACGAAGACCCTGAGGTCAAGTTCA
ACTGGTACGTGGACGGCGTGGAGGTGCATAATGCCAAGACAAAGCCGCGGGAGGAGCAGTACAA
CAGCACGTACCGTGTGGTCAGCGTCCTCACCGTCCTGCACCAGGACTGGCTGAATGGCAAGGAG
TACAAGTGCAAGGTCTCCAACAAAGCCCTCCCAGCCCCCATCGAGAAAACCATCTCCAAAGCCA
AAGGGCAGCCCCGAGAACCACAGGTGTACACCCTGCCCCCATCCCGGGAGGAGATGACCAAGAA
CCAGGTCAGCCTGACCTGCCTGGTCAAAGGCTTCTATCCCAGCGACATCGCCGTGGAGTGGGAG
AGCAATGGGCAGCCGGAGAACAACTACAAGACCACGCCTCCCGTGCTGGACTCCGACGGCTCCT
TCTTCCTCTACAGCAAGCTCACCGTGGACAAGAGCAGGTGGCAGCAGGGGAACGTCTTCTCATG
CTCCGTGATGCATGAGGCTCTGCACAACCACTACACGCAGAAGAGCCTCTCCCTGTCTCCGGGT TABLE 7-continued Exemplary Sequences

AAAGGAGGTGGATCTGGAGGTGGCGGTTCAGGCTCTGGCGGAGGCTCAGGTGGTGGAGGATCAG

GCGGAGGTCAGGTTCAGCTGCAGCAGAGCGGTGCAGAACTGGCACGTCCGGGTGCAAGCGTTAA

AATGAGCTGTAAAGCAAGCGGTTATACCTTTACCCGTTATACCATGCATTGGGTTAAACAGCGT

CCGGGTCAGGGTCTGGAATGGATTGGTTATATCAATCCGAGCCGTGGTTATACCAACTACAACC

AGAAATTCAAAGATAAAGCAACCCTGACCACCGATAAAAGCAGCAGCACCGCCTATATGCAGCT

GAGCAGCCTGACCTCAGAGGATAGCGCAGTTTATTACTGTGCACGCTATTATGATGATCACTAT

TGCCTGGATTATTGGGGTCAGGGCACCACCCTGACCGTTAGCAGCGGTGGTGGTGGTAGTGGTG

GCGGTGGTTCAGGCGGTGGCGGTAGCCAGATTGTTCTGACCCAGAGTCCGGCAATTATGAGCGC

AAGTCCGGGTGAAAAAGTTACCATGACCTGTAGCGCCAGCAGCAGCGTTAGCTATATGAATTGG

TATCAGCAGAAAAGCGGCACCAGCCCGAAACGTTGGATTTATGATACCAGCAAACTGGCAAGCG

GTGTTCCGGCACATTTTCGTGGTAGCGGTAGCGGCACCTCATATAGCCTGACCATTAGCGGTAT

GGAAGCAGAAGATGCAGCAACCTATTATTGTCAGCAGTGGTCAAGCAATCCGTTTACCTTTGGT

AGTGGCACCAAACTGGAAATTAATCGT (SEQ ID NO: 242)
EVHLLESGGGLVQPGGSLRLSCAASGFTFSSYAMSWVRQAPGKGLEWVSSIDPEGRQTYYADSV

KGRFTISRDNSKNTLYLQMNSLRAEDTAVYYCAKDIGGRSAFDYWGQGTLVTVSSASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSREEMTKNQVSLTCLVKGFYPSDIAVEWE

SNGQPENNYKTTPPVLDSDGSFFLYSKLTVDKSRWQQGNVFSCSVMHEALHNHYTQKSLSLSPG

KGGGSGGGGSGSGGGSGGGGSGGGQVQLQQSGAELARPGASVKMSCKASGYTFTRYTMHWVKQR

PGQGLEWIGYINPSRGYTNYNQKFKDKATLTTDKSSSTAYMQLSSLTSEDSAVYYCARYYDDHY

CLDYWGQGTTLTVSSGGGGSGGGGSGGGGSQIVLTQSPAIMSASPGEKVTMTCSASSSVSYMNW

YQQKSGTSPKRWIYDTSKLASGVPAHFRGSGSGTSYSLTISGMEAEDAATYYCQQWSSNPFTFG

SGTKLEINR

Anti-Jagged 4D11v2 - anti-CD3 OKT3 Multispecific Antibody:
Light Chain (SEQ ID NO: 243)
GACATCCAGATGACCCAGTCTCCATCCTCCCTGTCTGCATCTGTAGGAGACAGAGTCACCATCA

CTTGCCGGGCAAGTCAGAGCATTAGCAGCTATTTAAATTGGTATCAGCAGAAACCAGGGAAAGC

CCCTAAGCTCCTGATCTATGCGGCATCCAGTTTGCAAAGTGGGGTCCCATCAAGGTTCAGTGGC

AGTGGATCTGGGACAGATTTCACTCTCACCATCAGCAGTCTGCAACCTGAAGATTTTGCAACTT

ACTACTGTCAACAGACGGTTGTGGCGCCTCCGTTATTCGGCCAAGGGACCAAGGTGGAAATCAA

ACGTACGGTGGCTGCACCATCTGTCTTCATCTTCCCGCCATCTGATGAGCAGTTGAAATCTGGA

ACTGCCTCTGTTGTGTGCCTGCTGAATAACTTCTATCCCAGAGAGGCCAAAGTACAGTGGAAGG

TGGATAACGCCCTCCAATCGGGTAACTCCCAGGAGAGTGTCACAGAGCAGGACAGCAAGGACAG

CACCTACAGCCTCAGCAGCACCCTGACGCTGANCAAAGCAGACTACGAGAAACACAAAGTCTAC

GCCTGCGAAGTCACCCATCAGGGCCTGAGCTCGCCCGTCACAAAGAGCTTCAACAGGGGAGAGT

GTGGAGGTGGATCTGGAGGTGGCGGTTCAGGCTCTGGCGGAGGCTCAGGTGGTGGAGGATCAGG

CGGAGGTCAGGTTCAGCTGCAGCAGAGCGGTGCAGAACTGGCACGTCCGGGTGCAAGCGTTAAA

TABLE 7-continued

Exemplary Sequences

ATGAGCTGTAAAGCAAGCGGTTATACCTTTACCCGTTATACCATGCATTGGGTTAAACAGCGTC

CGGGTCAGGGTCTGGAATGGATTGGTTATATCAATCCGAGCCGTGGTTATACCAACTACAACCA

GAAATTCAAAGATAAAGCAACCCTGACCACCGATAAAAGCAGCAGCACCGCCTATATGCAGCTG

AGCAGCCTGACCTCAGAGGATAGCGCAGTTTATTACTGTGCACGCTATTATGATGATCACTATT

GCCTGGATTATTGGGGTCAGGGCACCACCCTGACCGTTAGCAGCGGTGGTGGTGGTAGTGGTGG

CGGTGGTTCAGGCGGTGGCGGTAGCCAGATTGTTCTGACCCAGAGTCCGGCAATTATGAGCGCA

AGTCCGGGTGAAAAAGTTACCATGACCTGTAGCGCCAGCAGCAGCGTTAGCTATATGAATTGGT

ATCAGCAGAAAAGCGGCACCAGCCCGAAACGTTGGATTTATGATACCAGCAAACTGGCAAGCGG

TGTTCCGGCACATTTTCGTGGTAGCGGTAGCGGCACCTCATATAGCCTGACCATTAGCGGTATG

GAAGCAGAAGATGCAGCAACCTATTATTGTCAGCAGTGGTCAAGCAATCCGTTTACCTTTGGTA

GTGGCACCAAACTGGAAATTAATCGT (SEQ ID NO: 244)
DIQMTQSPSSLSASVGDRVTITCRASQSISSYLNWYQQKPGKAPKLLIYAASSLQSGVPSRFSG

SGSGTDFTLTISSLQPEDFATYYCQQTVVAPPLFGQGTKVEIKRTVAAPSVFIFPPSDEQLKSG

TASVVCLLNNFYPREAKVQWKVDNALQSGNSQESVTEQDSKDSTYSLSSTLTLXKADYEKHKVY

ACEVTHQGLSSPVTKSFNRGECGGGSGGGGSGSGGGSGGGGSGGGQVQLQQSGAELARPGASVK

MSCKASGYTFTRYTMHWVKQRPGQGLEWIGYINPSRGYTNYNQKFKDKATLTTDKSSSTAYMQL

SSLTSEDSAVYYCARYYDDHYCLDYWGQGTTLTVSSGGGGSGGGGSGGGGSQIVLTQSPAIMSA

SPGEKVTMTCSASSSVSYMNWYQQKSGTSPKRWIYDTSKLASGVPAHFRGSGSGTSYSLTISGM

EAEDAATYYCQQWSSNPFTFGSGTKLEINR

Anti-Jagged-anti-CD3 Multispecific Activatable Antibody 5342-
1204-4D11v2-CD3 OKT3: Light Chain (SEQ ID NO: 245)
CAAGGCCAGTCTGGCCAGTGCAATATTTGGCTCGTAGGTGGTGATTGCAGGGGCTGGCAGGGGG

GCTCGAGCGGTGGCAGCGGTGGCTCTGGTGGTCTGAGCGGCCGTTCCGATAATCATGGCGGCGG

TTCTGACATCCAGATGACCCAGTCTCCATCCTCCCTGTCTGCATCTGTAGGAGACAGAGTCACC

ATCACTTGCCGGGCAAGTCAGAGCATTAGCAGCTATTTAAATTGGTATCAGCAGAAACCAGGGA

AAGCCCCTAAGCTCCTGATCTATGCGGCATCCAGTTTGCAAAGTGGGGTCCCATCAAGGTTCAG

TGGCAGTGGATCTGGGACAGATTTCACTCTCACCATCAGCAGTCTGCAACCTGAAGATTTTGCA

ACTTACTACTGTCAACAGACGGTTGTGGCGCCTCCGTTATTCGGCCAAGGGACCAAGGTGGAAA

TCAAACGTACGGTGGCTGCACCATCTGTCTTCATCTTCCCGCCATCTGATGAGCAGTTGAAATC

TGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGG

ACAGCACCTACAGCCTCAGCAGCACCCTGACGCTGANCAAAGCAGACTACGAGAAACACAAAGT

CTACGCCTGCGAAGTCACCCATCAGGGCCTGAGCTCGCCCGTCACAAAGAGCTTCAACAGGGGA

GAGTGTGGAGGTGGATCTGGAGGTGGCGGTTCAGGCTCTGGCGGAGGCTCAGGTGGTGGAGGAT

CAGGCGGAGGTCAGGTTCAGCTGCAGCAGAGCGGTGCAGAACTGGCACGTCCGGGTGCAAGCGT

TAAAATGAGCTGTAAAGCAAGCGGTTATACCTTTACCCGTTATACCATGCATTGGGTTAAACAG

CGTCCGGGTCAGGGTCTGGAATGGATTGGTTATATCAATCCGAGCCGTGGTTATACCAACTACA

ACCAGAAATTCAAAGATAAAGCAACCCTGACCACCGATAAAAGCAGCAGCACCGCCTATATGCA

GCTGAGCAGCCTGACCTCAGAGGATAGCGCAGTTTATTACTGTGCACGCTATTATGATGATCAC

TABLE 7-continued

Exemplary Sequences

TATTGCCTGGATTATTGGGGTCAGGGCACCACCCTGACCGTTAGCAGCGGTGGTGGTGGTAGTG

GTGGCGGTGGTTCAGGCGGTGGCGGTAGCCAGATTGTTCTGACCCAGAGTCCGGCAATTATGAG

CGCAAGTCCGGGTGAAAAAGTTACCATGACCTGTAGCGCCAGCAGCAGCGTTAGCTATATGAAT

TGGTATCAGCAGAAAAGCGGCACCAGCCCGAAACGTTGGATTTATGATACCAGCAAACTGGCAA

GCGGTGTTCCGGCACATTTTCGTGGTAGCGGTAGCGGCACCTCATATAGCCTGACCATTAGCGG

TATGGAAGCAGAAGATGCAGCAACCTATTATTGTCAGCAGTGGTCAAGCAATCCGTTTACCTTT

GGTAGTGGCACCAAACTGGAAATTAATCGT (SEQ ID NO: 246)
QGQSGQCNIWLVGGDCRGWQGGSSGGSGGSGGLSGRSDNHGGGSDIQMTQSPSSLSASVGDRVT

ITCRASQSISSYLNWYQQKPGKAPKLLIYAASSLQSGVPSRFSGSGSGTDFTLTISSLQPEDFA

TYYCQQTVVAPPLFGQGTKVEIKRTVAAPSVFIFPPSDEQLKSGTASVVCLLNNFYPREAKVQW

KVDNALQSGNSQESVTEQDSKDSTYSLSSTLTLXKADYEKHKVYACEVTHQGLSSPVTKSFNRG

ECGGGSGGGGSGSGGGSGGGGSGGGGQVQLQQSGAELARPGASVKMSCKASGYTFTRYTMHWVKQ

RPGQGLEWIGYINPSRGYTNYNQKFKDKATLTTDKSSSTAYMQLSSLTSEDSAVYYCARYYDDH

YCLDYWGQGTTLTVSSGGGGSGGGGSGGGGSQIVLTQSPAIMSASPGEKVTMTCSASSSVSYMN

WYQQKSGTSPKRWIYDTSKLASGVPAHFRGSGSGTSYSLTISGMEAEDAATYYCQQWSSNPFTF

GSGTKLEINR

Anti-Jagged 4D11v2-anti-CTLA-4 Multispecific Antibody: Heavy
Chain (SEQ ID NO: 247)
GAGGTGCACCTGTTGGAGTCTGGGGGAGGCTTGGTACAGCCTGGGGGGTCCCTGAGACTCTCCT

GTGCAGCCTCTGGATTCACCTTTAGCAGCTATGCCATGAGCTGGGTCCGCCAGGCTCCAGGGAA

GGGGCTGGAGTGGGTGTCAAGTATTGACCCGGAAGGTCGGCAGACATATTACGCAGACTCCGTG

AAGGGCCGGTTCACCATCTCCAGAGACAATTCCAAGAACACGCTGTATCTGCAAATGAACAGCC

TGAGAGCCGAGGACACGGCCGTATATTACTGTGCGAAAGACATCGGCGGCAGGTCGGCCTTTGA

CTACTGGGGCCAGGGAACCCTGGTCACCGTCTCCTCAGCTAGCACCAAGGGCCCATCGGTCTTC

CCCCTGGCACCCTCCTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACCAGCGGCGTGCACAC

CTTCCCGGCTGTCCTACAGTCCTCAGGACTCTACTCCCTCAGCAGCGTGGTGACCGTGCCCTCC

AGCAGCTTGGGCACCCAGACCTACATCTGCAACGTGAATCACAAGCCCAGCAACACCAAGGTGG

ACAAGAAAGTTGAGCCCAAATCTTGTGACAAAACTCACACATGCCCACCGTGCCCAGCACCTGA

ACTCCTGGGGGGACCGTCAGTCTTCCTCTTCCCCCCAAAACCCAAGGACACCCTCATGATCTCC

CGGACCCCTGAGGTCACATGCGTGGTGGTGGACGTGAGCCACGAAGACCCTGAGGTCAAGTTCA

ACTGGTACGTGGACGGCGTGGAGGTGCATAATGCCAAGACAAAGCCGCGGGAGGAGCAGTACAA

CAGCACGTACCGTGTGGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAACCATCTCCAAAGCCA

AAGGGCAGCCCCGAGAACCACAGGTGTACACCCTGCCCCCATCCCGGGAGGAGATGACCAAGAA

CCAGGTCAGCCTGACCTGCCTGGTCAAAGGCTTCTATCCCAGCGACATCGCCGTGGAGTGGGAG

AGCAATGGGCAGCCGGAGAACAACTACAAGACCACGCCTCCCGTGCTGGACTCCGACGGCTCCT

TCTTCCTCTACAGCAAGCTCACCGTGGACAAGAGCAGGTGGCAGCAGGGGAACGTCTTCTCATG

CTCCGTGATGCATGAGGCTCTGCACAACCACTACACGCAGAAGAGCCTCTCCCTGTCTCCGGGT

TABLE 7-continued

Exemplary Sequences

AAAGGAGGTGGATCTGGAGGTGGCGGTTCAGGCTCTGGCGGAGGCTCAGGTGGTGGAGGATCAG

GCGGAGGTGAAATTGTGTTGACACAGTCTCCAGGCACCCTGTCTTTGTCTCCAGGGGAAAGAGC

CACCCTCTCCTGCAGGGCCAGTCAGAGTGTTAGCAGCAGCTACTTAGCCTGGTACCAGCAGAAA

CCTGGCCAGGCTCCCAGGCTCCTCATCTATGGTGCATCCAGCAGGGCCACTGGCATCCCAGACA

GGTTCAGTGGCAGTGGGTCTGGGACAGACTTCACTCTCACCATCAGCAGACTGGAGCCTGAAGA

TTTTGCAGTGTATTACTGTCAGCAGTATGGTAGCTCACCGCTCACTTTCGGCGGAGGGACCAAG

GTGGAAATCAAACGTTCCGGAGGGTCGACCATAACTTCGTATAATGTATACTATACGAAGTTAT

CCTCGAGCGGTACCCAGGTGCAGCTGGTGCAGACTGGGGGAGGCGTGGTCCAGCCTGGGAGGTC

CCTGAGACTCTCCTGTGCAGCCTCTGGATCCACCTTTAGCAGCTATGCCATGAGCTGGGTCCGC

CAGGCTCCAGGGAAGGGGCTGGAGTGGGTCTCAGCTATTAGTGGTAGTGGTGGTAGCACATACT

ACGCAGACTCCGTGAAGGGCCGGTTCACCATCTCCAGAGACAATTCCAAGAACACGCTGTATCT

GCAAATGAACAGCCTGAGAGCCGAGGACACGGCCGTATATTACTGTGCGACAAACTCCCTTTAC

TGGTACTTCGATCTCTGGGGCCGTGGCACCCTGGTCACTGTCTCTTCAGC (SEQ ID NO: 248)
EVHLLESGGGLVQPGGSLRLSCAASGFTFSSYAMSWVRQAPGKGLEWVSSIDPEGRQTYYADSV
KGRFTISRDNSKNTLYLQMNSLRAEDTAVYYCAKDIGGRSAFDYWGQGTLVTVSSASTKGPSVF
PLAPSSKSTSGGTAALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLGGPSVFLFPPKPKDTLMIS
RTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSREEMTKNQVSLTCLVKGFYPSDIAVEWE
SNGQPENNYKTTPPVLDSDGSFFLYSKLTVDKSRWQQGNVFSCSVMHEALHNHYTQKSLSLSPG
KGGGSGGGGSGSGGGSGGGGSGGGEIVLTQSPGTLSLSPGERATLSCRASQSVSSSYLAWYQQK
PGQAPRLLIYGASSRATGIPDRFSGSGSGTDFTLTISRLEPEDFAVYYCQQYGSSPLTFGGGTK
VEIKRSGGSTITSYNVYYTKLSSSGTQVQLVQTGGGVVQPGRSLRLSCAASGSTFSSYAMSWVR
QAPGKGLEWVSAISGSGGSTYYADSVKGRFTISRDNSKNTLYLQMNSLRAEDTAVYYCATNSLY
WYFDLWGRGTLVTVSSAS

Anti-Jagged 4D11v2-anti-CTLA-4 Multispecific Antibody: Light
Chain (SEQ ID NO: 249)
GACATCCAGATGACCCAGTCTCCATCCTCCCTGTCTGCATCTGTAGGAGACAGAGTCACCATCA

CTTGCCGGGCAAGTCAGAGCATTAGCAGCTATTTAAATTGGTATCAGCAGAAACCAGGGAAAGC

CCCTAAGCTCCTGATCTATGCGGCATCCAGTTTGCAAAGTGGGGTCCCATCAAGGTTCAGTGGC

AGTGGATCTGGGACAGATTTCACTCTCACCATCAGCAGTCTGCAACCTGAAGATTTTGCAACTT

ACTACTGTCAACAGACGGTTGTGGCGCCTCCGTTATTCGGCCAAGGGACCAAGGTGGAAATCAA

ACGTACGGTGGCTGCACCATCTGTCTTCATCTTCCCGCCATCTGATGAGCAGTTGAAATCTGGA

ACTGCCTCTGTTGTGTGCCTGCTGAATAACTTCTATCCCAGAGAGGCCAAAGTACAGTGGAAGG

TGGATAACGCCCTCCAATCGGGTAACTCCCAGGAGAGTGTCACAGAGCAGGACAGCAAGGACAG

CACCTACAGCCTCAGCAGCACCCTGACGCTGANCAAAGCAGACTACGAGAAACACAAAGTCTAC

GCCTGCGAAGTCACCCATCAGGGCCTGAGCTCGCCCGTCACAAAGAGCTTCAACAGGGGAGAGT

GTGGAGGTGGATCTGGAGGTGGCGGTTCAGGCTCTGGCGGAGGCTCAGGTGGTGGAGGATCAGG

CGGAGGTGAAATTGTGTTGACACAGTCTCCAGGCACCCTGTCTTTGTCTCCAGGGGAAAGAGCC

TABLE 7-continued

Exemplary Sequences

ACCCTCTCCTGCAGGGCCAGTCAGAGTGTTAGCAGCAGCTACTTAGCCTGGTACCAGCAGAAAC

CTGGCCAGGCTCCCAGGCTCCTCATCTATGGTGCATCCAGCAGGGCCACTGGCATCCCAGACAG

GTTCAGTGGCAGTGGGTCTGGGACAGACTTCACTCTCACCATCAGCAGACTGGAGCCTGAAGAT

TTTGCAGTGTATTACTGTCAGCAGTATGGTAGCTCACCGCTCACTTTCGGCGGAGGGACCAAGG

TGGAAATCAAACGTTCCGGAGGGTCGACCATAACTTCGTATAATGTATACTATACGAAGTTATC

CTCGAGCGGTACCCAGGTGCAGCTGGTGCAGACTGGGGGAGGCGTGGTCCAGCCTGGGAGGTCC

CTGAGACTCTCCTGTGCAGCCTCTGGATCCACCTTTAGCAGCTATGCCATGAGCTGGGTCCGCC

AGGCTCCAGGGAAGGGGCTGGAGTGGGTCTCAGCTATTAGTGGTAGTGGTGGTAGCACATACTA

CGCAGACTCCGTGAAGGGCCGGTTCACCATCTCCAGAGACAATTCCAAGAACACGCTGTATCTG

CAAATGAACAGCCTGAGAGCCGAGGACACGGCCGTATATTACTGTGCGACAAACTCCCTTTACT

GGTACTTCGATCTCTGGGGCCGTGGCACCCTGGTCACTGTCTCTTCAGCTAGC (SEQ ID NO: 250)
DIQMTQSPSSLSASVGDRVTITCRASQSISSYLNWYQQKPGKAPKLLIYAASSLQSGVPSRFSG

SGSGTDFTLTISSLQPEDFATYYCQQTVVAPPLFGQGTKVEIKRTVAAPSVFIFPPSDEQLKSG

TASVVCLLNNFYPREAKVQWKVDNALQSGNSQESVTEQDSKDSTYSLSSTLTLXKADYEKHKVY

ACEVTHQGLSSPVTKSFNRGECGGGSGGGGSGSGGGSGGGGSGGGEIVLTQSPGTLSLSPGERA

TLSCRASQSVSSSYLAWYQQKPGQAPRLLIYGASSRATGIPDRFSGSGSGTDFTLTISRLEPED

FAVYYCQQYGSSPLTFGGGTKVEIKRSGGSTITSYNVYYTKLSSSGTQVQLVQTGGGVVQPGRS

LRLSCAASGSTFSSYAMSWVRQAPGKGLEWVSAISGSGGSTYYADSVKGRFTISRDNSKNTLYL

QMNSLRAEDTAVYYCATNSLYWYFDLWGRGTLVTVSSAS

Anti-Jagged-anti-CTLA-4 Multispecific Activatable Antibody
5342-1204-4D11v2-CTLA-4: Light Chain (SEQ ID NO: 251)
CAAGGCCAGTCTGGCCAGTGCAATATTTGGCTCGTAGGTGGTGATTGCAGGGGCTGGCAGGGGG

GCTCGAGCGGTGGCAGCGGTGGCTCTGGTGGTCTGAGCGGCCGTTCCGATAATCATGGCGGCGG

TTCTGACATCCAGATGACCCAGTCTCCATCCTCCCTGTCTGCATCTGTAGGAGACAGAGTCACC

ATCACTTGCCGGGCAAGTCAGAGCATTAGCAGCTATTTAAATTGGTATCAGCAGAAACCAGGGA

AAGCCCCTAAGCTCCTGATCTATGCGGCATCCAGTTTGCAAAGTGGGGTCCCATCAAGGTTCAG

TGGCAGTGGATCTGGGACAGATTTCACTCTCACCATCAGCAGTCTGCAACCTGAAGATTTTGCA

ACTTACTACTGTCAACAGACGGTTGTGGCGCCTCCGTTATTCGGCCAAGGGACCAAGGTGGAAA

TCAAACGTACGGTGGCTGCACCATCTGTCTTCATCTTCCCGCCATCTGATGAGCAGTTGAAATC

TGGAACTGCCTCTGTTGTGTGCCTGCTGAATAACTTCTATCCCAGAGAGGCCAAAGTACAGTGG

AAGGTGGATAACGCCCTCCAATCGGGTAACTCCCAGGAGAGTGTCACAGAGCAGGACAGCAAGG

ACAGCACCTACAGCCTCAGCAGCACCCTGACGCTGANCAAAGCAGACTACGAGAAACACAAAGT

CTACGCCTGCGAAGTCACCCATCAGGGCCTGAGCTCGCCCGTCACAAAGAGCTTCAACAGGGGA

GAGTGTGGAGGTGGATCTGGAGGTGGCGGTTCAGGCTCTGGCGGAGGCTCAGGTGGTGGAGGAT

CAGGCGGAGGTGAAATTGTGTTGACACAGTCTCCAGGCACCCTGTCTTTGTCTCCAGGGGAAAG

AGCCACCCTCTCCTGCAGGGCCAGTCAGAGTGTTAGCAGCAGCTACTTAGCCTGGTACCAGCAG

AAACCTGGCCAGGCTCCCAGGCTCCTCATCTATGGTGCATCCAGCAGGGCCACTGGCATCCCAG

ACAGGTTCAGTGGCAGTGGGTCTGGGACAGACTTCACTCTCACCATCAGCAGACTGGAGCCTGA

AGATTTTGCAGTGTATTACTGTCAGCAGTATGGTAGCTCACCGCTCACTTTCGGCGGAGGGACC

TABLE 7-continued

Exemplary Sequences

AAGGTGGAAATCAAACGTTCCGGAGGGTCGACCATAACTTCGTATAATGTATACTATACGAAGT
TATCCTCGAGCGGTACCCAGGTGCAGCTGGTGCAGACTGGGGGAGGCGTGGTCCAGCCTGGGAG
GTCCCTGAGACTCTCCTGTGCAGCCTCTGGATCCACCTTTAGCAGCTATGCCATGAGCTGGGTC
CGCCAGGCTCCAGGGAAGGGGCTGGAGTGGGTCTCAGCTATTAGTGGTAGTGGTGGTAGCACAT
ACTACGCAGACTCCGTGAAGGGCCGGTTCACCATCTCCAGAGACAATTCCAAGAACACGCTGTA
TCTGCAAATGAACAGCCTGAGAGCCGAGGACACGGCCGTATATTACTGTGCGACAAACTCCCTT
TACTGGTACTTCGATCTCTGGGGCCGTGGCACCCTGGTCACTGTCTCTTCAGCTAGC (SEQ ID NO: 252)
QGQSGQCNIWLVGGDCRGWQGSSGGSGGSGGLSGRSDNHGGGSDIQMTQSPSSLSASVGDRVT
ITCRASQSISSYLNWYQQKPGKAPKLLIYAASSLQSGVPSRFSGSGSGTDFTLTISSLQPEDFA
TYYCQQTVVAPPLFGQGTKVEIKRTVAAPSVFIFPPSDEQLKSGTASVVCLLNNFYPREAKVQW
KVDNALQSGNSQESVTEQDSKDSTYSLSSTLTLXKADYEKHKVYACEVTHQGLSSPVTKSFNRG
ECGGGSGGGGSGSGGGSGGGGSGGGEIVLTQSPGTLSLSPGERATLSCRASQSVSSSYLAWYQQ
KPGQAPRLLIYGASSRATGIPDRFSGSGSGTDFTLTISRLEPEDFAVYYCQQYGSSPLTFGGGT
KVEIKRSGGSTITSYNVYYTKLSSSGTQVQLVQTGGGVVQPGRSLRLSCAASGSTFSSYAMSWV
RQAPGKGLEWVSAISGSGGSTYYADSVKGRFTISRDNSKNTLYLQMNSLRAEDTAVYYCATNSL
YWYFDLWGRGTLVTVSSAS

Anti-EGFR C225v5 Antibody: Heavy Chain (SEQ ID NO: 253)
caggtgcagctgaaacagagcggcccgggcctggtgcagccgagccagagcctgagcattacct
gcaccgtgagcggctttagcctgaccaactatggcgtgcattgggtgcgccagagcccgggcaa
aggcctggaatggctgggcgtgatttggagcggcggcaacaccgattataacacccccgtttac
cagccgcctgagcattaacaaagataacagcaaaagccaggtgttttttaaaatgaacagcctgc
aaagccaggataccgcgatttattattgcgcgcgcgcgctgacctattatgattatgaatttgc
gtattggggccagggcacccctggtgaccgtgagcgcggctagcaccaagggcccatcggtcttc
cccctggcaccctcctccaagagcacctctgggggcacagcggccctgggctgcctggtcaagg
actacttccccgaaccggtgacggtgtcgtggaactcaggcgccctgaccagcggcgtgcacac
cttcccggctgtcctacagtcctcaggactctactccctcagcagcgtggtgaccgtgccctcc
agcagcttgggcacccagacctacatctgcaacgtgaatcacaagcccagcaacaccaaggtgg
acaagaaagttgagcccaaatcttgtgacaaaactcacacatgcccaccgtgcccagcacctga
actcctggggggaccgtcagtcttcctcttccccccaaaacccaaggacaccctcatgatctcc
cggacccctgaggtcacatgcgtggtggtggacgtgagccacgaagaccctgaggtcaagttca
actggtacgtggacggcgtggaggtgcataatgccaagacaaagccgcgggaggagcagtacaa
cagcacgtaccgtgtggtcagcgtcctcaccgtcctgcaccaggactggctgaatggcaaggag
tacaagtgcaaggtctccaacaaagccctcccagcccccatcgagaaaaccatctccaaagcca
aagggcagccccgagaaccacaggtgtacaccctgcccccatcccgggatgaactgaccaagaa
ccaggtcagcctgacctgcctggtcaaaggcttctatcccagcgacatcgccgtggagtgggag
agcaatgggcagccggagaacaactacaagaccacgcctcccgtgctggactccgacggctcct
tcttcctctacagcaagctcaccgtggacaagagcaggtggcagcaggggaacgtcttctcatg TABLE 7-continued Exemplary Sequences ctccgtgatgcatgaggctctgcacaaccactacacgcagaagagcctctccctgtctccgggt aaatga (SEQ ID NO: 254)
QVQLKQSGPGLVQPSQSLSITCTVSGFSLTNYGVHWVRQSPGKGLEWLGVIWSGGNTDYNTPFT

SRLSINKDNSKSQVFFKMNSLQSQDTAIYYCARALTYYDYEFAYWGQGTLVTVSAASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEALHNHYTQKSLSLSPG

K

Anti-EGFR C225v5 Antibody: Light Chain (SEQ ID NO: 255)
CAGATCTTGCTGACCCAGAGCCCGGTGATTCTGAGCGTGAGCCCGGGCGAACGTGTGAGCTTTA

GCTGCCGCGCGAGCCAGAGCATTGGCACCAACATTCATTGGTATCAGCAGCGCACCAACGGCAG

CCCGCGCCTGCTGATTAAATATGCGAGCGAAAGCATTAGCGGCATTCCGAGCCGCTTTAGCGGC

AGCGGCAGCGGCACCGATTTTACCCTGAGCATTAACAGCGTGGAAAGCGAAGATATTGCGGATT

ATTATTGCCAGCAGAACAACAACTGGCCGACCACCTTTGGCGCGGGCACCAAACTGGAACTGAA

ACGTACGGTGGCTGCACCATCTGTCTTCATCTTCCCGCCATCTGATGAGCAGTTGAAATCTGGA

ACTGCCTCTGTTGTGTGCCTGCTGAATAACTTCTATCCCAGAGAGGCCAAAGTACAGTGGAAGG

TGGATAACGCCCTCCAATCGGGTAACTCCCAGGAGAGTGTCACAGAGCAGGACAGCAAGGACAG

CACCTACAGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGGGGAGAGT

GT (SEQ ID NO: 256)
QILLTQSPVILSVSPGERVSFSCRASQSIGTNIHWYQQRTNGSPRLLIKYASESISGIPSRFSG

SGSGTDFTLSINSVESEDIADYYCQQNNNWPTTFGAGTKLELKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGEC

Anti-EGFR C225v5 Antibody: Heavy Chain (SEQ ID NO: 257)
caggtgcagctgaaacagagcggcccgggcctggtgcagccgagccagagcctgagcattacct gcaccgtgagcggctttagcctgaccaactatggcgtgcattgggtgcgccagagcccgggcaa aggcctggaatggctgggcgtgatttggagcggcggcaacaccgattataacacccgtttacc agccgcctgagcattaacaaagataacagcaaaagccaggtgttttttaaaatgaacagcctgc aaagcaacgataccgcgatttattattgcgcgcgcgcgctgacctattatgattatgaatttgc gtattggggccagggcaccctggtgaccgtgagcgcggctagcaccaagggcccatcggtcttc cccctggcaccctcctccaagagcacctctgggggcacagcggccctgggctgcctggtcaagg actacttccccgaaccggtgacggtgtcgtggaactcaggcgccctgaccagcggcgtgcacac cttcccggctgtcctacagtcctcaggactctactccctcagcagcgtggtgaccgtgccctcc agcagcttgggcacccagacctacatctgcaacgtgaatcacaagcccagcaacaccaaggtgg acaagcgcgttgagcccaaatcttgtgacaaaactcacacatgcccaccgtgcccagcacctga TABLE 7-continued Exemplary Sequences actcctgggggaccgtcagtcttcctcttcccccaaaacccaaggacaccctcatgatctcc cggacccctgaggtcacatgcgtggtggtggacgtgagccacgaagaccctgaggtcaagttca actggtacgtggacggcgtggaggtgcataatgccaagacaaagccgcgggaggagcagtacaa cagcacgtaccgtgtggtcagcgtcctcaccgtcctgcaccaggactggctgaatggcaaggag tacaagtgcaaggtctccaacaaagcccctcccagcccccatcgagaaaaccatctccaaagcca aagggcagccccgagaaccacaggtgtacaccctgcccccatcccgggatgaactgaccaagaa ccaggtcagcctgacctgcctggtcaaaggcttctatcccagcgacatcgccgtggagtgggag agcaatgggcagccggagaacaactacaagaccacgcctcccgtgctggactccgacggctcct tcttcctctacagcaagctcaccgtggacaagagcaggtggcagcaggggaacgtcttctcatg ctccgtgatgcatgaggctctgcacaaccactacacgcagaagagcctctccctgtctccgggt aaa (SEQ ID NO: 258)
QVQLKQSGPGLVQPSQSLSITCTVSGFSLTNYGVHWVRQSPGKGLEWLGVIWSGGNTDYNTPFT
SRLSINKDNSKSQVFFKMNSLQSNDTAIYYCARALTYYDYEFAYWGQGTLVTVSAASTKGPSVF
PLAPSSKSTSGGTAALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLGGPSVFLFPPKPKDTLMIS
RTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLSLSPG
K Anti-EGFR C225v5 Antibody: Light Chain (SEQ ID NO: 259)
Ggcggtacccagatcttgctgacccagagcccggtgattctgagcgtgagcccgggcgaacgtg
tgagctttagctgccgcgcgagccagagcattggcaccaacattcattggtatcagcagcgcac
caacggcagcccgcgcctgctgattaaatatgcgagcgaaagcattagcggcattccgagccgc
tttagcggcagcggcagcggcaccgattttaccctgagcattaacagcgtggaaagcgaagata
ttgcggattattattgccagcagaacaacaactggccgaccacctttggcgcgggcaccaaact
ggaactgaaacgtacggtggctgcaccatctgtcttcatcttcccgccatctgatgagcagttg
aaatctggaactgcctctgttgtgtgcctgctgaataacttctatcccagagaggccaaagtac
agtggaaggtggataacgcccctccaatcgggtaactcccaggagagtgtcacagagcaggacag
caaggacagcacctacagcctcagcagcaccctgacgctgagcaaagcagactacgagaaacac
aaagtctacgcctgcgaagtcacccatcagggcctgagctcgcccgtcacaaagagcttcaaca
ggggagcg (SEQ ID NO: 260)
DILLTQSPVILSVSPGERVSFSCRASQSIGTNIHWYQQRTNGSPRLLIKYASESISGIPSRFSG
SGSGTDFTLSINSVESEDIADYYCQQNNNWPTTFGAGTKLELKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGEC Anti-EGFR C225v4 Antibody: Heavy Chain (SEQ ID NO: 261)
caggtgcagctgaaacagagcggcccgggcctggtgcagccgagccagagcctgagcattacct
gcaccgtgagcggctttagcctgaccaactatggcgtgcattgggtgcgccagagcccgggcaa TABLE 7-continued Exemplary Sequences aggcctggaatggctgggcgtgatttggagcggcggcaacaccgattataacaccccgtttacc
agccgcctgagcattaacaaagataacagcaaaagccaggtgttttttaaaatgaacagcctgc
aaagcaacgataccgcgatttattattgcgcgcgcgcgctgacctattatgattatgaatttgc
gtattggggccagggcaccctggtgaccgtgagcgcggctagcaccaagggcccatcggtcttc
cccctggcaccctcctccaagagcacctctgggggcacagcggccctgggctgcctggtcaagg
actacttccccgaaccggtgacggtgtcgtggaactcaggcgccctgaccagcggcgtgcacac
cttcccggctgtcctacagtcctcaggactctactccctcagcagcgtggtgaccgtgccctcc
agcagcttgggcacccagacctacatctgcaacgtgaatcacaagcccagcaacaccaaggtgg
acaagaaagttgagcccaaatcttgtgacaaaactcacacatgcccaccgtgcccagcacctga
actcctggggggaccgtcagtcttcctcttccccccaaaacccaaggacaccctcatgatctcc
cggacccctgaggtcacatgcgtggtggtggacgtgagccacgaagaccctgaggtcaagttca
actggtacgtggacggcgtggaggtgcataatgccaagacaaagccgcgggaggagcagtacaa
cagcacgtaccgtgtggtcagcgtcctcaccgtcctgcaccaggactggctgaatggcaaggag
tacaagtgcaaggtctccaacaaagccctcccagcccccatcgagaaaaccatctccaaagcca
aagggcagccccgagaaccacaggtgtacaccctgcccccatcccgggatgaactgaccaagaa
ccaggtcagcctgacctgcctggtcaaaggcttctatcccagcgacatcgccgtggagtgggag
agcaatgggcagccggagaacaactacaagaccacgcctcccgtgctggactccgacggctcct
tcttcctctacagcaagctcaccgtggacaagagcaggtggcagcaggggaacgtcttctcatg
ctccgtgatgcatgaggctctgcacaaccactacacgcagaagagcctctccctgtctccgggt
aaatga (SEQ ID NO: 262)
QVQLKQSGPGLVQPSQSLSITCTVSGFSLTNYGVHWVRQSPGKGLEWLGVIWSGGNTDYNTPFT
SRLSINKDNSKSQVFFKMNSLQSNDTAIYYCARALTYYDYEFAYWGQGTLVTVSAASTKGPSVF
PLAPSSKSTSGGTAALGCLVKDYFPEPVTVSWNSGALTSGVHTFPAVLQSSGLYSLSSVVTVPS
SSLGTQTYICNVNHKPSNTKVDKKVEPKSCDKTHTCPPCPAPELLGGPSVFLFPPKPKDTLMIS
RTPEVTCVVVDVSHEDPEVKFNWYVDGVEVHNAKTKPREEQYNSTYRVVSVLTVLHQDWLNGKE
YKCKVSNKALPAPIEKTISKAKGQPREPQVYTLPPSRDELTKNQVSLTCLVKGFYPSDIAVEWE
SNGQPENNYKTTPPVLDSDGSFFLYSKLTVDKSRWQQGNVFSCSVMHEALHNHYTQKSLSLSPG
K Anti-EGFR C225v4 Antibody: Light Chain (SEQ ID NO: 263)
Cagatcttgctgacccagagcccggtgattctgagcgtgagcccgggcgaacgtgtgagcttta
gctgccgcgcgagccagagcattggcaccaacattcattggtatcagcagcgcaccaacggcag
cccgcgcctgctgattaaatatgcgagcgaaagcattagcggcattccgagccgctttagcggc
agcggcagcggcaccgattttaccctgagcattaacagcgtggaaagcgaagatattgcggatt
attattgccagcagaacaacaactggccgaccacctttggcgcgggcaccaaactggaactgaa
acgtacggtggctgcaccatctgtcttcatcttcccgccatctgatgagcagttgaaatctgga
actgcctctgttgtgtgcctgctgaataacttctatcccagagaggccaaagtacagtggaagg
tggataacgccctccaatcgggtaactcccaggagagtgtcacagagcaggacagcaaggacag
cacctacagcctcagcagcaccctgacgctgagcaaagcagactacgagaaacacaaagtctac TABLE 7-continued Exemplary Sequences gcctgcgaagtcacccatcagggcctgagctcgcccgtcacaaagagcttcaacaggggagagt gttag (SEQ ID NO: 264)
QILLTQSPVILSVSPGERVSFSCRASQSIGTNIHWYQQRTNGSPRLLIKYASESISGIPSRFSG

SGSGTDFTLSINSVESEDIADYYCQQNNNWPTTFGAGTKLELKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGEC

Anti-EGFR C225v6 Antibody: Heavy Chain (SEQ ID NO: 265)
caggtgcagctgaaacagagcggcccgggcctggtgcagccgagccagagcctgagcattacct gcaccgtgagcggctttagcctgaccaactatggcgtgcattgggtgcgccagagcccgggcaa aggcctggaatggctgggcgtgatttggagcggcggcaacaccgattataacaccccgtttacc agccgcctgagcattaacaaagataacagcaaaagccaggtgttttttaaaatgaacagcctgc aaagccaggataccgcgatttattattgcgcgcgcgcgctgacctattatgattatgaatttgc gtattggggccagggcacccggtgaccgtgagcgcggctagcaccaagggcccatcggtcttc cccctggcaccctcctccaagagcacctctgggggcacagcggccctgggctgcctggtcaagg actacttccccgaaccggtgacggtgtcgtggaactcaggcgccctgaccagcggcgtgcacac cttcccggctgtcctacagtcctcaggactctactccctcagcagcgtggtgaccgtgccctcc agcagcttgggcacccagacctacatctgcaacgtgaatcacaagcccagcaacaccaaggtgg acaagaaagttgagcccaaatcttgtgacaaaactcacacatgcccaccgtgcccagcacctga actcctggggggaccgtcagtcttcctcttccccccaaaacccaaggacaccctcatgatctcc cggacccctgaggtcacatgcgtggtggtggacgtgagccacgaagaccctgaggtcaagttca actggtacgtggacggcgtggaggtgcataatgccaagacaaagccgcgggaggagcagtacgc cagcacgtaccgtgtggtcagcgtcctcaccgtcctgcaccaggactggctgaatggcaaggag tacaagtgcaaggtctccaacaaagccctcccagcccccatcgagaaaaccatctccaaagcca aagggcagccccgagaaccacaggtgtacaccctgcccccatcccgggatgaactgaccaagaa ccaggtcagcctgacctgcctggtcaaaggcttctatcccagcgacatcgccgtggagtgggag agcaatgggcagccggagaacaactacaagaccacgcctcccgtgctggactccgacggctcct tcttcctctacagcaagctcaccgtggacaagagcaggtggcagcaggggaacgtcttctcatg ctccgtgatgcatgaggctctgcacaaccactacacgcagaagagcctctccctgtctccgggt aaatga (SEQ ID NO: 266)
QVQLKQSGPGLVQPSQSLSITCTVSGFSLTNYGVHWVRQSPGKGLEWLGVIWSGGNTDYNTPFT

SRLSINKDNSKSQVFFKMNSLQSQDTAIYYCARALTYYDYEFAYWGQGTLVTVSAASTKGPSVF

PLAPSSKSTSGGTAALGCLVKDYFPEPVTVSWNSGALTSGVHTFPAVLQSSGLYSLSSVVTVPS

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYASTYRVVSVLTVLHQDWLNGKE

YKCKVSNKALPAPIEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEALHNHYTQKSLSLSPG

K

TABLE 7-continued

Exemplary Sequences

Anti-EGFR C225v6 Antibody: Light Chain (SEQ ID NO: 267)
Cagatcttgctgacccagagcccggtgattctgagcgtgagcccgggcgaacgtgtgagctttagctgccgcgcgagccagagcattggcaccaacattcattggtatcagcagcgcaccaacggcagcccgcgcctgctgattaaatatgcgagcgaaagcattagcggcattccgagccgctttagcggcagcggcagcggcaccgattttacccctgagcattaacagcgtggaaagcgaagatattgcggattattattgccagcagaacaacaactggccgaccacctttggcgcgggcaccaaactggaactgaaacgtacggtggctgcaccatctgtcttcatcttcccgccatctgatgagcagttgaaatctggaactgcctctgttgtgtgcctgctgaataacttctatcccagagaggccaaagtacagtggaaggtggataacgccctccaatcgggtaactcccaggagagtgtcacagagcaggacagcaaggacagcacctacagcctcagcagcaccctgacgctgagcaaagcagactacgagaaacacaaagtctacgcctgcgaagtcacccatcagggcctgagctcgcccgtcacaaagagcttcaacaggggagagtgttag (SEQ ID NO: 268)
QILLTQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC Anti-EGFR Activatable Antibody 3954-1204-C225v5: Light Chain:
[Spacer (SEQ ID NO: 283)][Mask (SEQ ID NO: 284)][Linker 1 (SEQ ID NO: 285)][1204 Substrate (SEQ ID NO: 286)][Linker 2 (SEQ ID NO: 287)][C225v5 light chain (SEQ ID NO: 255)]

(SEQ ID NO: 269)
[caaggccagtctggccag][tgcatctcacctcgtggttgtccggacggcccatacgtcatgtacggctcgagcggtggcagcggtggctctggtggatccggt][ctgagcggccgttccgataatcat][*ggcagtagcggtacc*][cagatcttgctgacccagagcccggtgattctgagcgtgagcccgggcgaacgtgtgagctttagctgccgcgcgagccagagcattggcaccaacattcattggtatcagcagcgcaccaacggcagcccgcgcctgctgattaaatatgcgagcgaaagcattagcggcattccgagccgctttagcggcagcggcagcggcaccgattttacccctgagcattaacagcgtggaaagcgaagatattgcggattattattgccagcagaacaacaactggccgaccacctttggcgcgggcaccaaactggaactgaaacgtacggtggctgcaccatctgtcttcatcttcccgccatctgatgagcagttgaaatctggaactgcctctgttgtgtgcctgctgaataacttctatcccagagaggccaaagtacagtggaaggtggataacgccctccaatcgggtaactcccaggagagtgtcacagagcaggacagcaaggacagcacctacagcctcagcagcaccctgacgctgagcaaagcagactacgagaaacacaaagtctacgcctgcgaagtcacccatcagggcctgagctcgcccgtcacaaagagcttcaacaggggagagtgttag]

[Spacer (SEQ ID NO: 46)][Mask (SEQ ID NO: 77)][Linker 1 (SEQ ID NO: 288)][1204 Substrate (SEQ ID NO: 26)][Linker 2 (SEQ ID NO: 289)][C225v5 (SEQ ID NO: 256)]

(SEQ ID NO: 270)
[QGQSGQ][CISPRGCPDGPYVMY][*GSSGGSGGSGGSG*][LSGRSDNH][*GSSGT*][QILLIQSPVILSVSPGERVSFSCRASQSIGTNIHWYQQRTNGSPRLLIKYASESISGIPSRFSGSGSGTDFTLSINSVESEDIADYYCQQNNNWPTTFGAGTKLELKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC*]

TABLE 7-continued

Exemplary Sequences

Anti-EGFR C225v5 - Anti-CD3 OKT3 Multispecific Antibody: Heavy
Chain (SEQ ID NO: 271)
CAGGTGCAGCTGAAACAGAGCGGCCCGGGCCTGGTGCAGCCGAGCCAGAGCCTGAGCATTACCT

GCACCGTGAGCGGCTTTAGCCTGACCAACTATGGCGTGCATTGGGTGCGCCAGAGCCCGGGCAA

AGGCCTGGAATGGCTGGGCGTGATTTGGAGCGGCGGCAACACCGATTATAACACCCCGTTTACC

AGCCGCCTGAGCATTAACAAAGATAACAGCAAAAGCCAGGTGTTTTTTAAAATGAACAGCCTGC

AAAGCCAGGATACCGCGATTTATTATTGCGCGCGCGCGCTGACCTATTATGATTATGAATTTGC

GTATTGGGGCCAGGGCACCCTGGTGACCGTGAGCGCGGCTAGCACCAAGGGCCCATCGGTCTTC

CCCCTGGCACCCTCCTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACCAGCGGCGTGCACAC

CTTCCCGGCTGTCCTACAGTCCTCAGGACTCTACTCCCTCAGCAGCGTGGTGACCGTGCCCTCC

AGCAGCTTGGGCACCCAGACCTACATCTGCAACGTGAATCACAAGCCCAGCAACACCAAGGTGG

ACAAGAAAGTTGAGCCCAAATCTTGTGACAAAACTCACACATGCCCACCGTGCCCAGCACCTGA

ACTCCTGGGGGGACCGTCAGTCTTCCTCTTCCCCCCAAAACCCAAGGACACCCTCATGATCTCC

CGGACCCCTGAGGTCACATGCGTGGTGGTGGACGTGAGCCACGAAGACCCTGAGGTCAAGTTCA

ACTGGTACGTGGACGGCGTGGAGGTGCATAATGCCAAGACAAAGCCGCGGGAGGAGCAGTACAA

CAGCACGTACCGTGTGGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAACCATCTCCAAAGCCA

AAGGGCAGCCCCGAGAACCACAGGTGTACACCCTGCCCCCATCCCGGGATGAACTGACCAAGAA

CCAGGTCAGCCTGACCTGCCTGGTCAAAGGCTTCTATCCCAGCGACATCGCCGTGGAGTGGGAG

AGCAATGGGCAGCCGGAGAACAACTACAAGACCACGCCTCCCGTGCTGGACTCCGACGGCTCCT

TCTTCCTCTACAGCAAGCTCACCGTGGACAAGAGCAGGTGGCAGCAGGGGAACGTCTTCTCATG

CTCCGTGATGCATGAGGCTCTGCACAACCACTACACGCAGAAGAGCCTCTCCCTGTCTCCGGGT

AAAGGAGGTGGATCTGGAGGTGGCGGTTCAGGCTCTGGCGGAGGCTCAGGTGGTGGAGGATCAG

GCGGAGGTCAGGTTCAGCTGCAGCAGAGCGGTGCAGAACTGGCACGTCCGGGTGCAAGCGTTAA

AATGAGCTGTAAAGCAAGCGGTTATACCTTTACCCGTTATACCATGCATTGGGTTAAACAGCGT

CCGGGTCAGGGTCTGGAATGGATTGGTTATATCAATCCGAGCCGTGGTTATACCAACTACAACC

AGAAATTCAAAGATAAAGCAACCCTGACCACCGATAAAAGCAGCAGCACCGCCTATATGCAGCT

GAGCAGCCTGACCTCAGAGGATAGCGCAGTTTATTACTGTGCACGCTATTATGATGATCACTAT

TGCCTGGATTATTGGGGTCAGGGCACCACCCTGACCGTTAGCAGCGGTGGTGGTGGTAGTGGTG

GCGGTGGTTCAGGCGGTGGCGGTAGCCAGATTGTTCTGACCCAGAGTCCGGCAATTATGAGCGC

AAGTCCGGGTGAAAAAGTTACCATGACCTGTAGCGCCAGCAGCAGCGTTAGCTATATGAATTGG

TATCAGCAGAAAGCGGCACCAGCCCGAAACGTTGGATTTATGATACCAGCAAACTGGCAAGCG

GTGTTCCGGCACATTTTCGTGGTAGCGGTAGCGGCACCTCATATAGCCTGACCATTAGCGGTAT

GGAAGCAGAAGATGCAGCAACCTATTATTGTCAGCAGTGGTCAAGCAATCCGTTTACCTTTGGT

AGTGGCACCAAACTGGAAATTAATCGT (SEQ ID NO: 272)
QVQLKQSGPGLVQPSQSLSITCTVSGFSLTNYGVHWVRQSPGKGLEWLGVIWSGGNTDYNTPFT

SRLSINKDNSKSQVFFKMNSLQSQDTAIYYCARALTYYDYEFAYWGQGTLVTVSAASTKGPSVF

PLAPSSKSTSGGTAALGCLVKDYFPEPVTVSWNSGALTSGVHTFPAVLQSSGLYSLSSVVTVPS

TABLE 7-continued

Exemplary Sequences

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEALHNHYTQKSLSLSPG

KGGGSGGGGSGSGGGSGGGGSGGGQVQLQQSGAELARPGASVKMSCKASGYTFTRYTMHWVKQR

PGQGLEWIGYINPSRGYTNYNQKFKDKATLTTDKSSSTAYMQLSSLTSEDSAVYYCARYYDDHY

CLDYWGQGTTLTVSSGGGGSGGGGSGGGGSQIVLTQSPAIMSASPGEKVTMTCSASSSVSYMNW

YQQKSGTSPKRWIYDTSKLASGVPAHFRGSGSGTSYSLTISGMEAEDAATYYCQQWSSNPFTFG

SGTKLEINR

Anti-EGFR C225v5 - Anti-CD3 OKT3 Multispecific Antibody: Light
Chain (SEQ ID NO: 273)
CAGATCTTGCTGACCCAGAGCCCGGTGATTCTGAGCGTGAGCCCGGGCGAACGTGTGAGCTTTA

GCTGCCGCGCGAGCCAGAGCATTGGCACCAACATTCATTGGTATCAGCAGCGCACCAACGGCAG

CCCGCGCCTGCTGATTAAATATGCGAGCGAAAGCATTAGCGGCATTCCGAGCCGCTTTAGCGGC

AGCGGCAGCGGCACCGATTTTACCCTGAGCATTAACAGCGTGGAAAGCGAAGATATTGCGGATT

ATTATTGCCAGCAGAACAACAACTGGCCGACCACCTTTGGCGCGGGCACCAAACTGGAACTGAA

ACGTACGGTGGCTGCACCATCTGTCTTCATCTTCCCGCCATCTGATGAGCAGTTGAAATCTGGA

ACTGCCTCTGTTGTGTGCCTGCTGAATAACTTCTATCCCAGAGAGGCCAAAGTACAGTGGAAGG

TGGATAACGCCCTCCAATCGGGTAACTCCCAGGAGAGTGTCACAGAGCAGGACAGCAAGGACAG

CACCTACAGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGGGGAGAGT

GTGGAGGTGGATCTGGAGGTGGCGGTTCAGGCTCTGGCGGAGGCTCAGGTGGTGGAGGATCAGG

CGGAGGTCAGGTTCAGCTGCAGCAGAGCGGTGCAGAACTGGCACGTCCGGGTGCAAGCGTTAAA

ATGAGCTGTAAAGCAAGCGGTTATACCTTTACCCGTTATACCATGCATTGGGTTAAACAGCGTC

CGGGTCAGGGTCTGGAATGGATTGGTTATATCAATCCGAGCCGTGGTTATACCAACTACAACCA

GAAATTCAAAGATAAAGCAACCCTGACCACCGATAAAAGCAGCAGCACCGCCTATATGCAGCTG

AGCAGCCTGACCTCAGAGGATAGCGCAGTTTATTACTGTGCACGCTATTATGATGATCACTATT

GCCTGGATTATTGGGGTCAGGGCACCACCCTGACCGTTAGCAGCGGTGGTGGTGGTAGTGGTGG

CGGTGGTTCAGGCGGTGGCGGTAGCCAGATTGTTCTGACCCAGAGTCCGGCAATTATGAGCGCA

AGTCCGGGTGAAAAAGTTACCATGACCTGTAGCGCCAGCAGCAGCGTTAGCTATATGAATTGGT

ATCAGCAGAAAAGCGGCACCAGCCCGAAACGTTGGATTTATGATACCAGCAAACTGGCAAGCGG

TGTTCCGGCACATTTTCGTGGTAGCGGTAGCGGCACCTCATATAGCCTGACCATTAGCGGTATG

GAAGCAGAAGATGCAGCAACCTATTATTGTCAGCAGTGGTCAAGCAATCCGTTTACCTTTGGTA

GTGGCACCAAACTGGAAATTAATCGT (SEQ ID NO: 274)
QILLTQSPVILSVSPGERVSFSCRASQSIGTNIHWYQQRTNGSPRLLIKYASESISGIPSRFSG

SGSGTDFTLSINSVESEDIADYYCQQNNNWPTTFGAGTKLELKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGECGGGSGGGGSGSGGGSGGGGSGGGQVQLQQSGAELARPGASVK

MSCKASGYTFTRYTMHWVKQRPGQGLEWIGYINPSRGYTNYNQKFKDKATLTTDKSSSTAYMQL

TABLE 7-continued

Exemplary Sequences

SSLTSEDSAVYYCARYYDDHYCLDYWGQGTTLTVSSGGGGSGGGGSGGGGSQIVLTQSPAIMSA

SPGEKVTMTCSASSSVSYMNWYQQKSGTSPKRWIYDTSKLASGVPAHFRGSGSGTSYSLTISGM

EAEDAATYYCQQWSSNPFTFGSGTKLEINR

Anti-EGFR - anti-CD3 Multispecific Activatable Antibody 3954-
1204-C225v5-0K13: Light Chain (SEQ ID NO: 275)
CAAGGCCAGTCTGGCCAGTGCATCTCACCTCGTGGTTGTCCGGACGGCCCATACGTCATGTACG

GCTCGAGCGGTGGCAGCGGTGGCTCTGGTGGATCCGGTCTGAGCGGCCGTTCCGATAATCATGG

CAGTAGCGGTACCCAGATCTTGCTGACCCAGAGCCCGGTGATTCTGAGCGTGAGCCCGGGCGAA

CGTGTGAGCTTTAGCTGCCGCGCGAGCCAGAGCATTGGCACCAACATTCATTGGTATCAGCAGC

GCACCAACGGCAGCCCGCGCCTGCTGATTAAATATGCGAGCGAAAGCATTAGCGGCATTCCGAG

CCGCTTTAGCGGCAGCGGCAGCGGCACCGATTTTACCCTGAGCATTAACAGCGTGGAAAGCGAA

GATATTGCGGATTATTATTGCCAGCAGAACAACAACTGGCCGACCACCTTTGGCGCGGGCACCA

AACTGGAACTGAAACGTACGGTGGCTGCACCATCTGTCTTCATCTTCCCGCCATCTGATGAGCA

GTTGAAATCTGGAACTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAGTGTCACAGAGCAGG

ACAGCAAGGACAGCACCTACAGCCTCAGCAGCACCCTGACGCTGAGCAAAGCAGACTACGAGAA

ACACAAAGTCTACGCCTGCGAAGTCACCCATCAGGGCCTGAGCTCGCCCGTCACAAAGAGCTTC

AACAGGGGAGAGTGTGGAGGTGGATCTGGAGGTGGCGGTTCAGGCTCTGGCGGAGGCTCAGGTG

GTGGAGGATCAGGCGGAGGTCAGGTTCAGCTGCAGCAGAGCGGTGCAGAACTGGCACGTCCGGG

TGCAAGCGTTAAAATGAGCTGTAAAGCAAGCGGTTATACCTTTACCCGTTATACCATGCATTGG

GTTAAACAGCGTCCGGGTCAGGGTCTGGAATGGATTGGTTATATCAATCCGAGCCGTGGTTATA

CCAACTACAACCAGAAATTCAAAGATAAAGCAACCCTGACCACCGATAAAAGCAGCAGCACCGC

CTATATGCAGCTGAGCAGCCTGACCTCAGAGGATAGCGCAGTTTATTACTGTGCACGCTATTAT

GATGATCACTATTGCCTGGATTATTGGGGTCAGGGCACCACCCTGACCGTTAGCAGCGGTGGTG

GTGGTAGTGGTGGCGGTGGTTCAGGCGGTGGCGGTAGCCAGATTGTTCTGACCCAGAGTCCGGC

AATTATGAGCGCAAGTCCGGGTGAAAAAGTTACCATGACCTGTAGCGCCAGCAGCAGCGTTAGC

TATATGAATTGGTATCAGCAGAAAAGCGGCACCAGCCCGAAACGTTGGATTTATGATACCAGCA

AACTGGCAAGCGGTGTTCCGGCACATTTTCGTGGTAGCGGTAGCGGCACCTCATATAGCCTGAC

CATTAGCGGTATGGAAGCAGAAGATGCAGCAACCTATTATTGTCAGCAGTGGTCAAGCAATCCG

TTTACCTTTGGTAGTGGCACCAAACTGGAAATTAATCGT (SEQ ID NO: 276)
QGQSGQCISPRGCPDGPYVMYGSSGGSGGSGGSGLSGRSDNHGSSGTQILLTQSPVILSVSPGE

RVSFSCRASQSIGTNIHWYQQRTNGSPRLLIKYASESISGIPSRFSGSGSGTDFTLSINSVESE

DIADYYCQQNNNWPTTFGAGTKLELKRTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSF

NRGECGGGSGGGGSGSGGGSGGGGSGGGQVQLQQSGAELARPGASVKMSCKASGYTFTRYTMHW

VKQRPGQGLEWIGYINPSRGYTNYNQKFKDKATLTTDKSSSTAYMQLSSLTSEDSAVYYCARYY

DDHYCLDYWGQGTTLTVSSGGGGSGGGGSGGGGSQIVLTQSPAIMSASPGEKVTMTCSASSSVS

YMNWYQQKSGTSPKRWIYDTSKLASGVPAHFRGSGSGTSYSLTISGMEAEDAATYYCQQWSSNP

FTFGSGTKLEINR

TABLE 7-continued

Exemplary Sequences

Anti-EGFR C225v5-Anti-CTLA-4 Multispecific Antibody: Heavy Chain
(SEQ ID NO: 277)
CAGGTGCAGCTGAAACAGAGCGGCCCGGGCCTGGTGCAGCCGAGCCAGAGCCTGAGCATTACCT

GCACCGTGAGCGGCTTTAGCCTGACCAACTATGGCGTGCATTGGGTGCGCCAGAGCCCGGGCAA

AGGCCTGGAATGGCTGGGCGTGATTTGGAGCGGCGGCAACACCGATTATAACACCCCGTTTACC

AGCCGCCTGAGCATTAACAAAGATAACAGCAAAAGCCAGGTGTTTTTTAAAATGAACAGCCTGC

AAAGCCAGGATACCGCGATTTATTATTGCGCGCGCGCGCTGACCTATTATGATTATGAATTTGC

GTATTGGGGCCAGGGCACCCTGGTGACCGTGAGCGCGGCTAGCACCAAGGGCCCATCGGTCTTC

CCCCTGGCACCCTCCTCCAAGAGCACCTCTGGGGGCACAGCGGCCCTGGGCTGCCTGGTCAAGG

ACTACTTCCCCGAACCGGTGACGGTGTCGTGGAACTCAGGCGCCCTGACCAGCGGCGTGCACAC

CTTCCCGGCTGTCCTACAGTCCTCAGGACTCTACTCCCTCAGCAGCGTGGTGACCGTGCCCTCC

AGCAGCTTGGGCACCCAGACCTACATCTGCAACGTGAATCACAAGCCCAGCAACACCAAGGTGG

ACAAGAAAGTTGAGCCCAAATCTTGTGACAAAACTCACACATGCCCACCGTGCCCAGCACCTGA

ACTCCTGGGGGGACCGTCAGTCTTCCTCTTCCCCCCAAAACCCAAGGACACCCTCATGATCTCC

CGGACCCCTGAGGTCACATGCGTGGTGGTGGACGTGAGCCACGAAGACCCTGAGGTCAAGTTCA

ACTGGTACGTGGACGGCGTGGAGGTGCATAATGCCAAGACAAAGCCGCGGGAGGAGCAGTACAA

CAGCACGTACCGTGTGGTCAGCGTCCTCACCGTCCTGCACCAGGACTGGCTGAATGGCAAGGAG

TACAAGTGCAAGGTCTCCAACAAAGCCCTCCCAGCCCCCATCGAGAAAACCATCTCCAAAGCCA

AAGGGCAGCCCCGAGAACCACAGGTGTACACCCTGCCCCCATCCCGGGATGAACTGACCAAGAA

CCAGGTCAGCCTGACCTGCCTGGTCAAAGGCTTCTATCCCAGCGACATCGCCGTGGAGTGGGAG

AGCAATGGGCAGCCGGAGAACAACTACAAGACCACGCCTCCCGTGCTGGACTCCGACGGCTCCT

TCTTCCTCTACAGCAAGCTCACCGTGGACAAGAGCAGGTGGCAGCAGGGGAACGTCTTCTCATG

CTCCGTGATGCATGAGGCTCTGCACAACCACTACACGCAGAAGAGCCTCTCCCTGTCTCCGGGT

AAAGGAGGTGGATCTGGAGGTGGCGGTTCAGGCTCTGGCGGAGGCTCAGGTGGTGGAGGATCAG

GCGGAGGTGAAATTGTGTTGACACAGTCTCCAGGCACCCTGTCTTTGTCTCCAGGGGAAAGAGC

CACCCTCTCCTGCAGGGCCAGTCAGAGTGTTAGCAGCAGCTACTTAGCCTGGTACCAGCAGAAA

CCTGGCCAGGCTCCCAGGCTCCTCATCTATGGTGCATCCAGCAGGGCCACTGGCATCCCAGACA

GGTTCAGTGGCAGTGGGTCTGGGACAGACTTCACTCTCACCATCAGCAGACTGGAGCCTGAAGA

TTTTGCAGTGTATTACTGTCAGCAGTATGGTAGCTCACCGCTCACTTTCGGCGGAGGGACCAAG

GTGGAAATCAAACGTTCCGGAGGGTCGACCATAACTTCGTATAATGTATACTATACGAAGTTAT

CCTCGAGCGGTACCCAGGTGCAGCTGGTGCAGACTGGGGGAGGCGTGGTCCAGCCTGGGAGGTC

CCTGAGACTCTCCTGTGCAGCCTCTGGATCCACCTTTAGCAGCTATGCCATGAGCTGGGTCCGC

CAGGCTCCAGGGAAGGGGCTGGAGTGGGTCTCAGCTATTAGTGGTAGTGGTGGTAGCACATACT

ACGCAGACTCCGTGAAGGGCCGGTTCACCATCTCCAGAGACAATTCCAAGAACACGCTGTATCT

GCAAATGAACAGCCTGAGAGCCGAGGACACGGCCGTATATTACTGTGCGACAAACTCCCTTTAC

TGGTACTTCGATCTCTGGGGCCGTGGCACCCTGGTCACTGTCTCTTCAGCTAGC (SEQ ID NO: 278)
QVQLKQSGPGLVQPSQSLSITCTVSGFSLTNYGVHWVRQSPGKGLEWLGVIWSGGNTDYNTPFT

SRLSINKDNSKSQVFFKMNSLQSQDTAIYYCARALTYYDYEFAYWGQGTLVTVSAASTKGPSVF

PLAPSSKSTSGGTAALGCLVKDYFPEPVTVSWNSGALTSGVHTFPAVLQSSGLYSLSSVVTVPS

TABLE 7-continued

Exemplary Sequences

SSLGTQTYICNVNHKPSNTKVDKKVEPKSCDKTHTCPPCPAPELLGGPSVFLFPPKPKDTLMIS

RTPEVTCVVVDVSHEDPEVKFNWYVDGVEVHNAKTKPREEQYNSTYRVVSVLTVLHQDWLNGKE

YKCKVSNKALPAPIEKTISKAKGQPREPQVYTLPPSRDELTKNQVSLTCLVKGFYPSDIAVEWE

SNGQPENNYKTTPPVLDSDGSFFLYSKLTVDKSRWQQGNVFSCSVMHEALHNHYTQKSLSLSPG

KGGGSGGGGSGSGGGSGGGGSGGGEIVLTQSPGTLSLSPGERATLSCRASQSVSSSYLAWYQQK

PGQAPRLLIYGASSRATGIPDRFSGSGSGTDFTLTISRLEPEDFAVYYCQQYGSSPLTFGGGTK

VEIKRSGGSTITSYNVYYTKLSSSGTQVQLVQTGGGVVQPGRSLRLSCAASGSTFSSYAMSWVR

QAPGKGLEWVSAISGSGGSTYYADSVKGRFTISRDNSKNTLYLQMNSLRAEDTAVYYCATNSLY

WYFDLWGRGTLVTVSSAS

Anti-EGFR C225v5-Anti-CTLA-4 Multispecific Antibody: Light Chain
(SEQ ID NO: 279)
CAGATCTTGCTGACCCAGAGCCCGGTGATTCTGAGCGTGAGCCCGGGCGAACGTGTGAGCTTTA

GCTGCCGCGCGAGCCAGAGCATTGGCACCAACATTCATTGGTATCAGCAGCGCACCAACGGCAG

CCCGCGCCTGCTGATTAAATATGCGAGCGAAAGCATTAGCGGCATTCCGAGCCGCTTTAGCGGC

AGCGGCAGCGGCACCGATTTTACCCTGAGCATTAACAGCGTGGAAAGCGAAGATATTGCGGATT

ATTATTGCCAGCAGAACAACAACTGGCCGACCACCTTTGGCGCGGGCACCAAACTGGAACTGAA

ACGTACGGTGGCTGCACCATCTGTCTTCATCTTCCCGCCATCTGATGAGCAGTTGAAATCTGGA

ACTGCCTCTGTTGTGTGCCTGCTGAATAACTTCTATCCCAGAGAGGCCAAAGTACAGTGGAAGG

TGGATAACGCCCTCCAATCGGGTAACTCCCAGGAGAGTGTCACAGAGCAGGACAGCAAGGACAG

CACCTACAGCCTCAGCAGCACCCTGACGCTGAGCAAAGCAGACTACGAGAAACACAAAGTCTAC

GCCTGCGAAGTCACCCATCAGGGCCTGAGCTCGCCCGTCACAAAGAGCTTCAACAGGGGAGAGT

GTGGAGGTGGATCTGGAGGTGGCGGTTCAGGCTCTGGCGGAGGCTCAGGTGGTGGAGGATCAGG

CGGAGGTGAAATTGTGTTGACACAGTCTCCAGGCACCCTGTCTTTGTCTCCAGGGGAAAGAGCC

ACCCTCTCCTGCAGGGCCAGTCAGAGTGTTAGCAGCAGCTACTTAGCCTGGTACCAGCAGAAAC

CTGGCCAGGCTCCCAGGCTCCTCATCTATGGTGCATCCAGCAGGGCCACTGGCATCCCAGACAG

GTTCAGTGGCAGTGGGTCTGGGACAGACTTCACTCTCACCATCAGCAGACTGGAGCCTGAAGAT

TTTGCAGTGTATTACTGTCAGCAGTATGGTAGCTCACCGCTCACTTTCGGCGGAGGGACCAAGG

TGGAAATCAAACGTTCCGGAGGGTCGACCATAACTTCGTATAATGTATACTATACGAAGTTATC

CTCGAGCGGTACCCAGGTGCAGCTGGTGCAGACTGGGGGAGGCGTGGTCCAGCCTGGGAGGTCC

CTGAGACTCTCCTGTGCAGCCTCTGGATCCACCTTTAGCAGCTATGCCATGAGCTGGGTCCGCC

AGGCTCCAGGGAAGGGGCTGGAGTGGGTCTCAGCTATTAGTGGTAGTGGTGGTAGCACATACTA

CGCAGACTCCGTGAAGGGCCGGTTCACCATCTCCAGAGACAATTCCAAGAACACGCTGTATCTG

CAAATGAACAGCCTGAGAGCCGAGGACACGGCCGTATATTACTGTGCGACAAACTCCCTTTACT

GGTACTTCGATCTCTGGGGCCGTGGCACCCTGGTCACTGTCTCTTCAGCTAGC (SEQ ID NO: 280)
QILLTQSPVILSVSPGERVSFSCRASQSIGTNIHWYQQRTNGSPRLLIKYASESISGIPSRFSG

SGSGTDFTLSINSVESEDIADYYCQQNNNWPTTFGAGTKLELKRTVAAPSVFIFPPSDEQLKSG

TASVVCLLNNFYPREAKVQWKVDNALQSGNSQESVTEQDSKDSTYSLSSTLTLSKADYEKHKVY

ACEVTHQGLSSPVTKSFNRGECGGGSGGGGSGSGGGSGGGGSGGGEIVLTQSPGTLSLSPGERA

TLSCRASQSVSSSYLAWYQQKPGQAPRLLIYGASSRATGIPDRFSGSGSGTDFTLTISRLEPED

FAVYYCQQYGSSPLTFGGGTKVEIKRSGGSTITSYNVYYTKLSSSGTQVQLVQTGGGVVQPGRS

TABLE 7-continued

Exemplary Sequences

LRLSCAASGSTFSSYAMSWVRQAPGKGLEWVSAISGSGGSTYYADSVKGRFTISRDNSKNTLYL

QMNSLRAEDTAVYYCATNSLYWYFDLWGRGTLVTVSSAS

Anti-EGFR - Anti-CTLA-4 Multispecific Activatable Antibody 3954-
1204-C225v5-CTLA-4: Light Chain (SEQ ID NO: 281)
CAAGGCCAGTCTGGCCAGTGCATCTCACCTCGTGGTTGTCCGGACGGCCCATACGTCATGTACG

GCTCGAGCGGTGGCAGCGGTGGCTCTGGTGGATCCGGTCTGAGCGGCCGTTCCGATAATCATGG

CAGTAGCGGTACCCAGATCTTGCTGACCCAGAGCCCGGTGATTCTGAGCGTGAGCCCGGGCGAA

CGTGTGAGCTTTAGCTGCCGCGCGAGCCAGAGCATTGGCACCAACATTCATTGGTATCAGCAGC

GCACCAACGGCAGCCCGCGCCTGCTGATTAAATATGCGAGCGAAAGCATTAGCGGCATTCCGAG

CCGCTTTAGCGGCAGCGGCAGCGGCACCGATTTTACCCTGAGCATTAACAGCGTGGAAAGCGAA

GATATTGCGGATTATTATTGCCAGCAGAACAACAACTGGCCGACCACCTTTGGCGCGGGCACCA

AACTGGAACTGAAACGTACGGTGGCTGCACCATCTGTCTTCATCTTCCCGCCATCTGATGAGCA

GTTGAAATCTGGAACTGCCTCTGTTGTGTGCCTGCTGAATAACTTCTATCCCAGAGAGGCCAAA

GTACAGTGGAAGGTGGATAACGCCCTCCAATCGGGTAACTCCCAGGAGAGTGTCACAGAGCAGG

ACAGCAAGGACAGCACCTACAGCCTCAGCAGCACCCTGACGCTGAGCAAAGCAGACTACGAGAA

ACACAAAGTCTACGCCTGCGAAGTCACCCATCAGGGCCTGAGCTCGCCCGTCACAAAGAGCTTC

AACAGGGGAGAGTGTGGAGGTGGATCTGGAGGTGGCGGTTCAGGCTCTGGCGGAGGCTCAGGTG

GTGGAGGATCAGGCGGAGGTGAAATTGTGTTGACACAGTCTCCAGGCACCCTGTCTTTGTCTCC

AGGGGAAAGAGCCACCCTCTCCTGCAGGGCCAGTCAGAGTGTTAGCAGCAGCTACTTAGCCTGG

TACCAGCAGAAACCTGGCCAGGCTCCCAGGCTCCTCATCTATGGTGCATCCAGCAGGGCCACTG

GCATCCCAGACAGGTTCAGTGGCAGTGGGTCTGGGACAGACTTCACTCTCACCATCAGCAGACT

GGAGCCTGAAGATTTTGCAGTGTATTACTGTCAGCAGTATGGTAGCTCACCGCTCACTTTCGGC

GGAGGGACCAAGGTGGAAATCAAACGTTCCGGAGGGTCGACCATAACTTCGTATAATGTATACT

ATACGAAGTTATCCTCGAGCGGTACCCAGGTGCAGCTGGTGCAGACTGGGGGAGGCGTGGTCCA

GCCTGGGAGGTCCCTGAGACTCTCCTGTGCAGCCTCTGGATCCACCTTTAGCAGCTATGCCATG

AGCTGGGTCCGCCAGGCTCCAGGGAAGGGGCTGGAGTGGGTCTCAGCTATTAGTGGTAGTGGTG

GTAGCACATACTACGCAGACTCCGTGAAGGGCCGGTTCACCATCTCCAGAGACAATTCCAAGAA

CACGCTGTATCTGCAAATGAACAGCCTGAGAGCCGAGGACACGGCCGTATATTACTGTGCGACA

AACTCCCTTTACTGGTACTTCGATCTCTGGGGCCGTGGCACCCTGGTCACTGTCTCTTCAGCTA

GC (SEQ ID NO: 282)
QGQSGQCISPRGCPDGPYVMYGSSGGSGGSGGSGLSGRSDNHGSSGTQILLTQSPVILSVSPGE

RVSFSCRASQSIGTNIHWYQQRTNGSPRLLIKYASESISGIPSRFSGSGSGTDFTLSINSVESE

DIADYYCQQNNNWPTTFGAGTKLELKRTVAAPSVFIFPPSDEQLKSGTASVVCLLNNFYPREAK

VQWKVDNALQSGNSQESVTEQDSKDSTYSLSSTLTLSKADYEKHKVYACEVTHQGLSSPVTKSF

NRGECGGGSGGGGSGSGGGSGGGGSGGGEIVLTQSPGTLSLSPGERATLSCRASQSVSSSYLAW

YQQKPGQAPRLLIYGASSRATGIPDRFSGSGSGTDFTLTISRLEPEDFAVYYCQQYGSSPLTFG

GGTKVEIKRSGGSTITSYNVYYTKLSSSGTQVQLVQTGGGVVQPGRSLRLSCAASGSTFSSYAM

TABLE 7-continued

Exemplary Sequences

SWVRQAPGKGLEWVSAISGSGGSTYYADSVKGRFTISRDNSKNTLYLQMNSLRAEDTAVYYCAT

NSLYWYFDLWGRGTLVTVSSAS

Example 1

Preparation of Multispecific Antibodies

This Example demonstrates the construction, expression and purification of anti-Jagged-CD3, anti-Jagged-CTLA-4, anti-EGFR-CD3 and anti-EGFR-CTLA-4 multispecific antibodies.

Vectors were used to express the anti-Jagged (4D11v2) heavy chain, the 5342-1204-4D11v2 light chain, the anti-EGFR C225v5 heavy chain, and the 3954-1204-C225v5 light chain sequences shown above. Such vectors are described in co-pending applications PCT/US2013/038540, filed Apr. 26, 2013 (entitled "Activatable Antibodies That Bind Epidermal Growth Factor Receptor And Methods Of Use Thereof") and PCT/US2013/047109, filed Jun. 21, 2013 (entitled "Anti-Jagged Antibodies, Activatable Anti-Jagged Antibodies and Methods of Use Thereof"), the contents of each of which are hereby incorporated by reference in their entirety.

Vectors were digested with restriction enzymes NheI and NotI and the vector fragment isolated by gel electrophoresis. Inserts were prepared as follows. Human IgG CH2CH3 fragment was amplified in reaction 1, from Pop Hygro 4D11v2 using primer HCForNhe (Table 8, SEQ ID NO: 3) and primer HCRevOL (Table 8, SEQ ID NO: 4), CTLA-4 scFv was amplified in reaction 2, from CTLA-4 scFv cDNA (SEQ ID NO: 229) using primer CTRevNot (Table 8, SEQ ID NO: 1) and primer CTForOL (Table 8, SEQ ID NO: 2), OKT3 scFv was amplified in reaction 3, from OKT3 scFv cDNA (SEQ ID NO: 231) using primer OKRevNot (Table 8, SEQ ID NO: 5) and primer CTForOL (Table 8, SEQ ID NO: 2). Human IgG, CH2CH3/CTLA-4 scFv fusions were prepared by combining 10% of reaction 1, 10% of reaction 2, and amplifying with primers, HCForNhe and CTRevNot.

TABLE 8

Primer sequences

| Primer | Nucleic acid sequence | SEQ ID NO |
|---|---|---|
| CTRevNot | TCGAGCGGCCGCTCAACTAGCTGAAGAGA CAGTG | SEQ ID NO: 1 |
| CTForOL | GCCCTCTAGACTCGATCTAGCTAGCTGAA GAGACAGTGACCAGG | SEQ ID NO: 2 |
| HCForNhe | CTCAGCTAGCACCAGGGCCCATCGGTC | SEQ ID NO: 3 |
| HCRevOL | CTTTACCCGGAGACAGGGAGAGGCTCTTC TGC | SEQ ID NO: 4 |
| OKRevNot | CTCGAGCGGCCGCTCAACGATTAATTTCC AGTTTG | SEQ ID NO: 5 |

Following amplification, the resulting DNA was digested with restriction enzymes NheI and NotI and the CH2CH3/CTLA-4 scFv fusion DNA isolated by gel electrophoresis.

Human IgG, CH2CH3/OKT3 scFv fusions were prepared by combining 10% of reaction 1, 10% of reaction 3, and amplifying with primers, HCForNhe and CTRevNot. Following amplification, the resulting DNA was digested with restriction enzymes NheI and NotI and the CH2CH3/CTLA-4 scFv fusion DNA isolated by gel electrophoresis.

To insert the CH2CH3/scFv fragments into expression vectors, the following combinations shown in Table 9 were ligated overnight with T4 DNA Ligase (Invitrogen Inc., Carlsbad, Calif.). Following ligation, the DNA was transformed into E. coli strain MC 106 and selected for ampicillin resistance. DNA sequencing identified clones containing DNA inserts encoding the correct multispecific antibodies or multispecific activatable antibodies, and DNA was prepared for mammalian cell transfection.

TABLE 9

Ligation reactions

| | |
|---|---|
| 1 µl Nhe/NotI digested anti-Jagged (4D11v2) heavy chain | 10 µl Nhe/NotI digested human IgG, CH2CH3/CTLA scFv fusion DNA |
| 1 µl Nhe/NotI digested anti-Jagged (4D11v2) heavy chain | 10 µl Nhe/NotI digested human IgG, CH2CH3/OKT3 scFv fusion DNA |
| 1 µl Nhe/NotI digested 5342-1204-4D11v2 heavy chain | 10 µl Nhe/NotI digested human IgG, CH2CH3/CTLA scFv fusion DNA |
| 1 µl Nhe/NotI digested 5342-1204-4D11v2 heavy chain | 10 µl Nhe/NotI digested human IgG, CH2CH3/OKT3 scFv fusion DNA |
| 1 µl Nhe/NotI digested anti-EGFR (C225v5) heavy chain | 10 µl Nhe/NotI digested human IgG, CH2CH3/CTLA scFv fusion DNA |
| 1 µl Nhe/NotI digested anti-EGFR (C225v5) heavy chain | 10 µl Nhe/NotI digested human IgG, CH2CH3/OKT3 scFv fusion DNA |
| 1 µl Nhe/NotI digested 3954-1204-C225v5 | 10 µl Nhe/NotI digested human IgG, CH2CH3/CTLA scFv fusion DNA |
| 1 µl Nhe/NotI digested 3954-1204-C225v5 | 10 µl Nhe/NotI digested human IgG, CH2CH3/OKT3 scFv fusion DNA |

Example 2

Production of Multispecific Antibodies and Multispecific Activatable Antibodies Fully human IgGs were expressed from transiently transfected HEK-293 cells. Co-transfection with distinct heavy chain and light chain expression vectors, shown in Table 10 enabled the expression of multispecific activatable antibodies.

TABLE 10

| Transfection number | Light chain vector | Heavy chain vector |
|---|---|---|
| 1 | anti-EGFR C225v5 LC | C225v5-OKT3 HC |
| 2 | 3954-1204-C225v5 LC | C225v5-OKT3 HC |
| 3 | C225v5 LC | C225v5-CTLA HC |
| 4 | 3954-1204-C225v5 LC | C225v5-CTLA HC |
| 5 | anti-Jagged 4D11v2 LC | 4D11v2-OKT3 HC |
| 6 | 5342-1204-4D11v2 LC | 4D11v2-OKT3 HC |
| 7 | 4D11v2 LC | 4D11v2-CTLA HC |
| 8 | 5342-1204-4D11v2 LC | 4D11v2-CTLA HC |

Multispecific antibodies and multispecific activatable antibodies expressed in HEK-293 cells were purified by Protein A chromatography.

Figure 11:
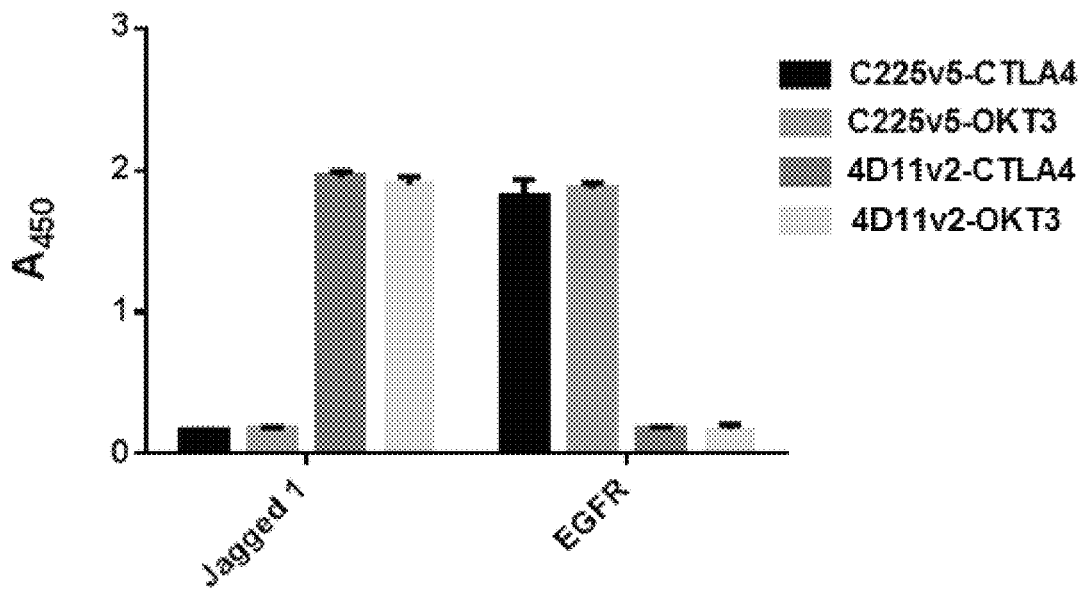
FIG. 11 is a graph depicting the ability of multispecific antibodies to bind specifically to their cognate antigens.

Binding Assays:

As shown in FIG. 11, ELISA-binding experiments revealed that anti-Jagged-CTLA-4 and anti-Jagged-OKT3 multispecific antibodies and multispecific activatable antibodies bound human Jagged 1, and anti-EGFR-CTLA-4 and anti-EGFR-OKT3 multispecific antibodies and multispecific activatable antibodies specifically bound human EGFR.

Human Jagged 1-Fc (R&D Systems; Cat #1277-JG-050) and human EGFR (R&D Systems, Cat #344-ER-050) were adsorbed to different wells of a 96-well ELISA plate. Purified anti-Jagged-CTLA and anti-Jagged-OKT3, anti-EGFR-CTLA or anti-EGFR-OKT3 antibodies were applied to the plate and allowed to bind. Bound antibody was visualized with an anti-human IgG-HRP conjugate (Fab specific, Sigma, St Louis, Mo.; Cat #A0293-1ML) and developed with the chromogenic substrate TMB.

Figure 12A:
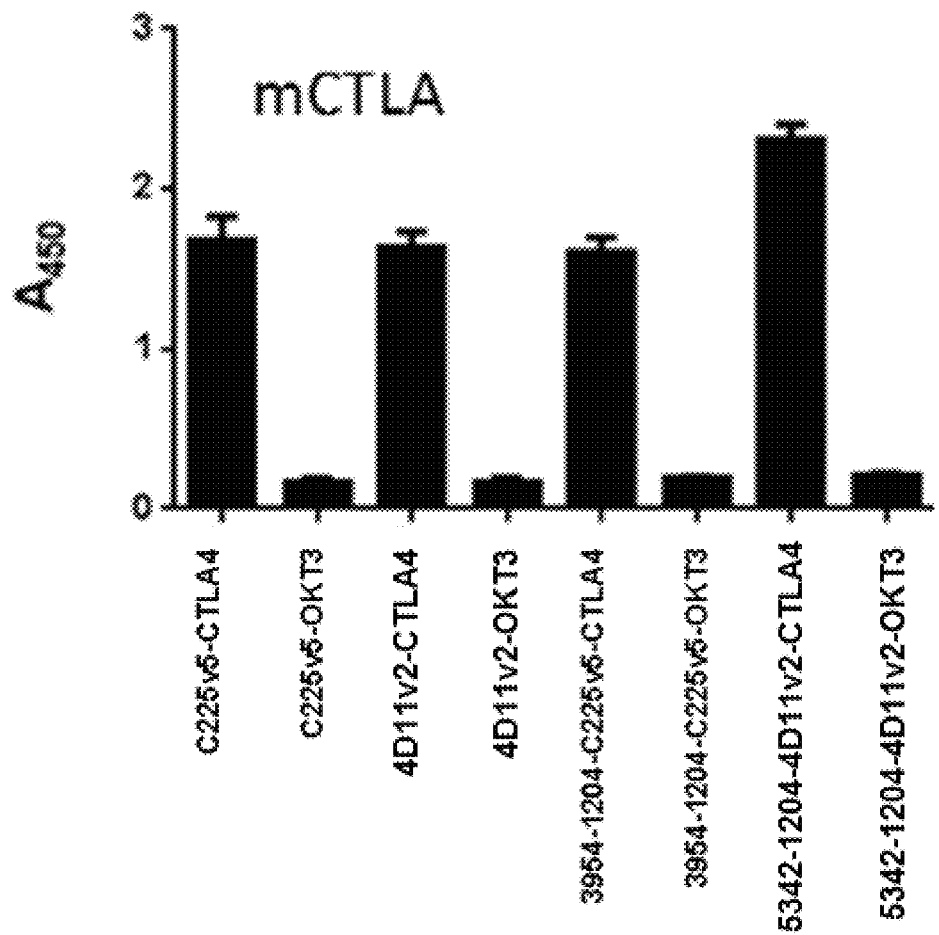
FIG. 12A-12B are a series of graphs depicting the ability of multispecific antibodies and multispecific activatable antibodies that include anti-human CTLA-4 scFvs to bind specifically to (A) mouse and (B) human CTLA-4.
Figure 12B:
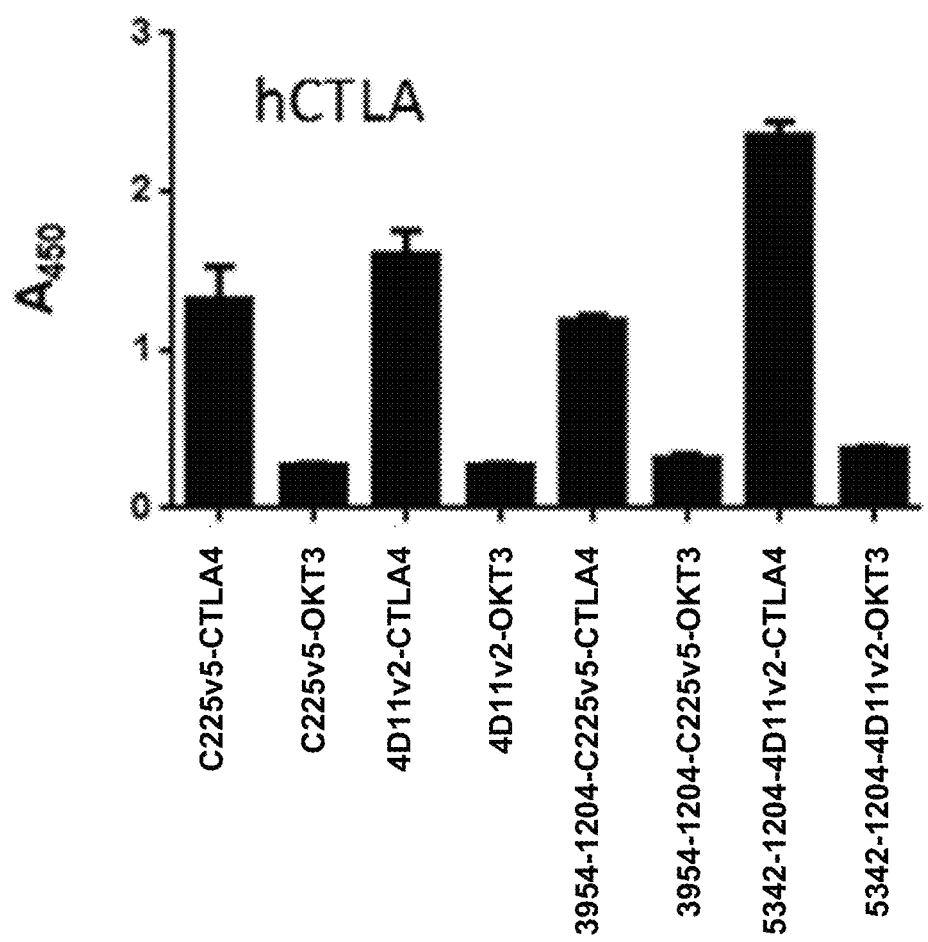

As shown in FIGS. 12A and 12B, ELISA-binding experiments revealed that anti-Jagged-CTLA-4 and anti-EGFR-CTLA-4 specifically bind both human and mouse CTLA-4 (the anti-human CTLA-4 antibody crossreacts with both mouse and human CTLA-4): Either human CTLA-4 (R&D Systems; Cat #325-CT-200/CF) or mouse CTLA-4 (R&D Systems, Cat #434-CT-200/CF) were adsorbed to the wells of separate 96-well ELISA plates. Purified anti-Jagged 4D11v2-CTLA-4, anti-Jagged activatable antibody 5342-1204-4D11v2-CTLA-4, anti-EGFR C225v5-CTLA-4 or activatable antibody 3954-1204-C225v5-CTLA-4 were applied to the plate and allowed to bind. Bound antibody was visualized with an anti-human IgG-HRP conjugate (Fab specific, Sigma, St Louis, Mo.; Cat #A0293-1ML) and developed with the chromogenic substrate TMB. Specificity of binding was demonstrated by the inability of antibody-OKT3 fusions, specific for human CD3ε, to bind.

Example 3

OKT3 Binding to CD3ε

Figure 13:
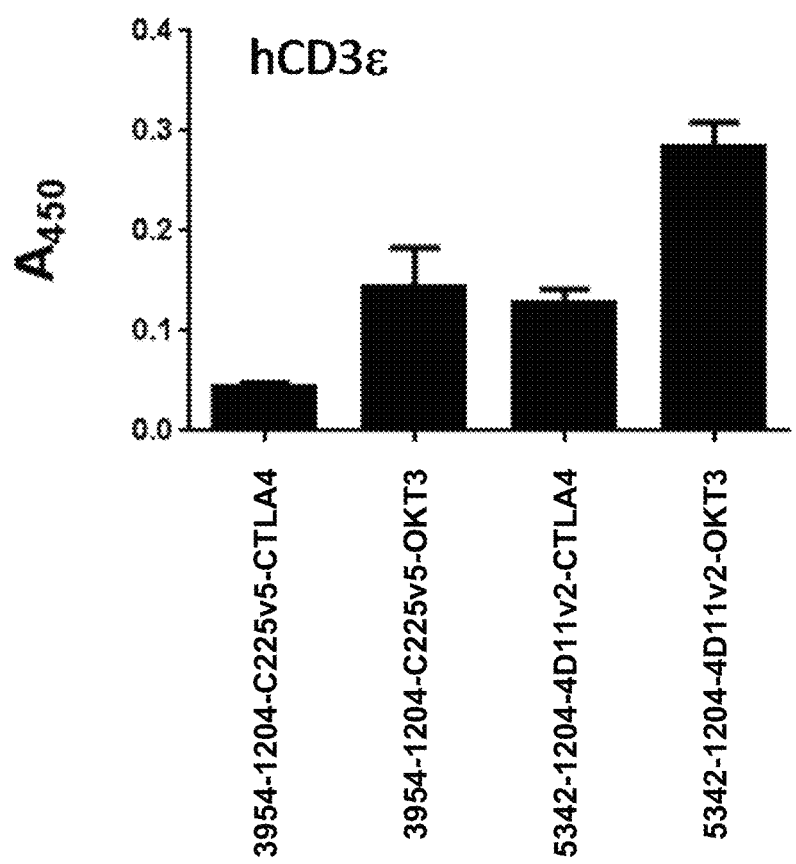
FIG. 13 is a graph depicting the ability of the OKT3-containing multispecific activatable antibodies referred to herein as anti-EGFR multispecific activatable antibody 3954-1204-C225v5-OKT3 and anti-Jagged multispecific activatable antibody 5342-1204-4D11v2-OKT3 to specifically bind human CD3ε in ELISA binding experiments.

As shown in FIG. 13, ELISA-binding experiments revealed that anti-EGFR multispecific activatable antibody 3954-1204-C225v5-OKT3 and anti-Jagged multispecific activatable antibody 5342-1204-4D11v2-OKT3 specifically bind human CD3ε. Human CD3ε(NovoProtein, Cat #C578) was adsorbed to the wells of a 96-well ELISA plate. Purified anti-EGFR multispecific activatable antibody 3954-1204-C225v5-CTLA-4, anti-EGFR multispecific activatable antibody 3954-1204-C225v5-OKT3, anti-Jagged multispecific activatable antibody 5342-1204-4D11v2-CTLA-4, or anti-Jagged multispecific activatable antibody 5342-1204-4D11v2-OKT3 was applied to the plate and allowed to bind. Bound antibody was visualized with an anti-human IgG-HRP conjugate (Fab specific, Sigma, St Louis, Mo.; Cat #A0293-1ML) and developed with the chromogenic substrate TMB.

Example 4

Protease Activation of Multispecific Activatable Antibodies

Activation

Multispecific antibodies and multispecific activatable antibodies were diluted in PBS to a final concentration of 0.8 mg/ml. Recombinant human uPA (R&D Systems, Catalog 1310-SE) was added to a final concentration of 700 nM and incubated at 37° C. for ~20 h. Digest aliquots were removed and prepared for SDS-PAGE analysis as described below, and diluted to 100 nM in PBS; 0.05% Tween20 and 10 mg/mL bovine serum albumin for analysis in binding ELISA assays.

Figure 14:
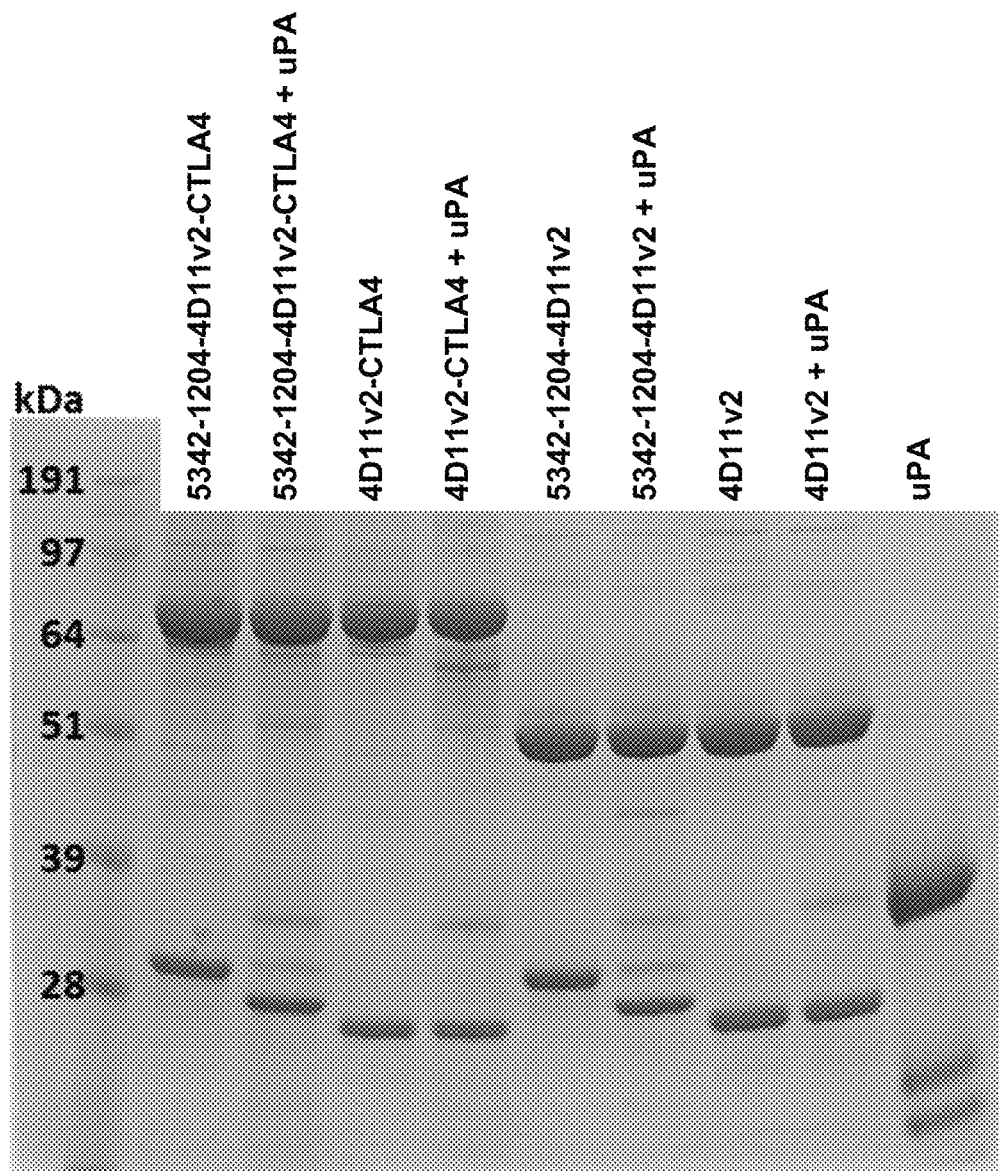
FIG. 14 is a series of photographs depicting PAGE analysis of uPA digests demonstrating activation of multispecific activatable antibodies without cleavage of heavy chain scFv fusions.
Figure 15A:
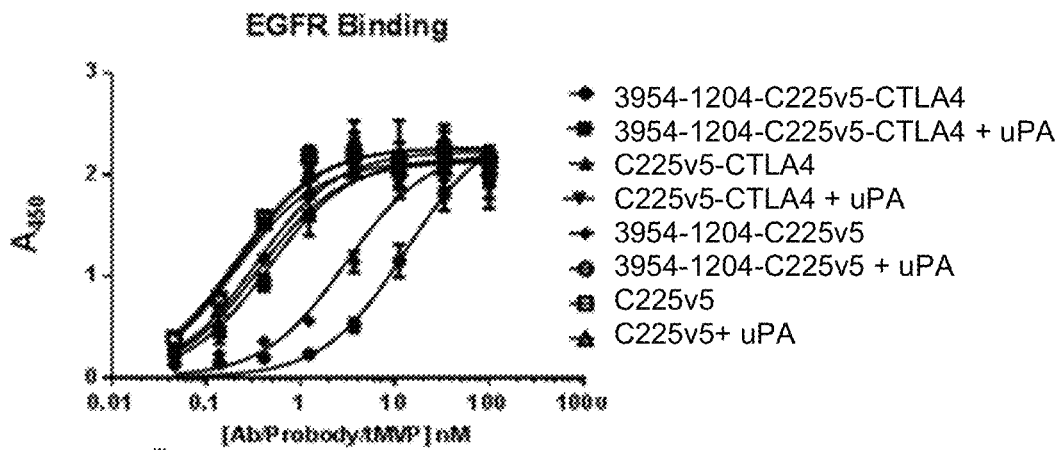
FIG. 15 is a series of graphs depicting the ability of activated multispecific activatable antibodies to bind various targets.
Figure 15B:
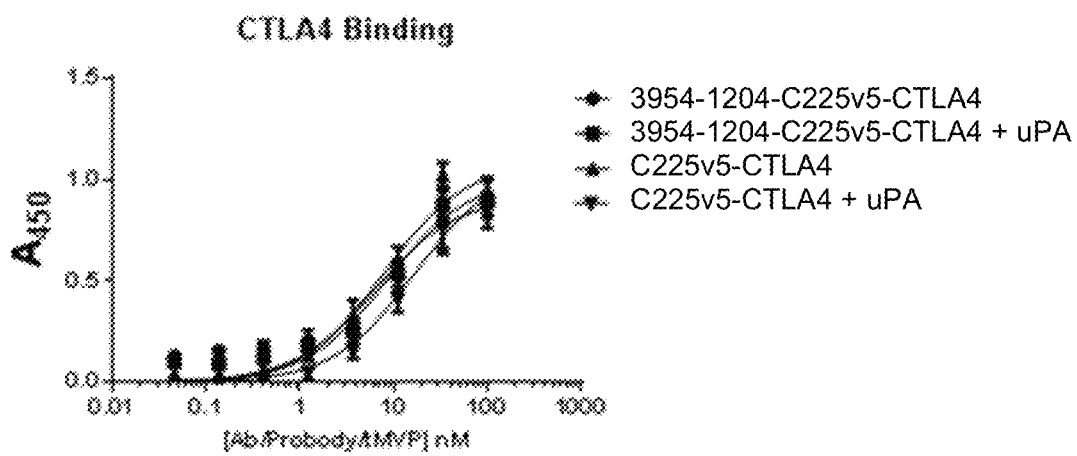
Figure 15C:
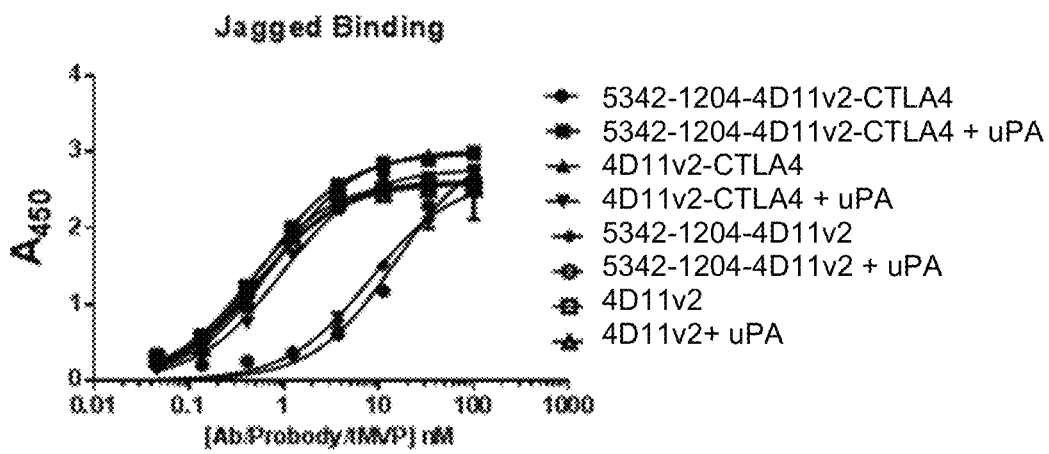
Figure 15D:
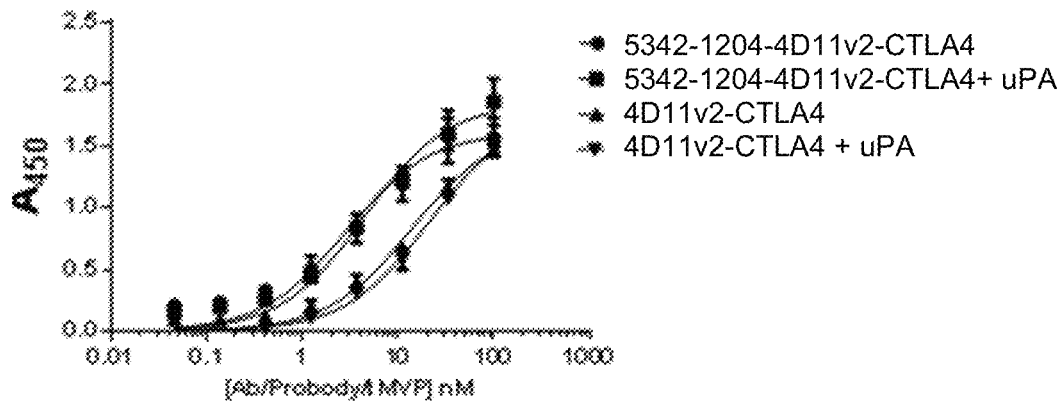

For PAGE, the samples were denatured at 70° C. for 10 min in 1×LDS sample buffer and TCEP was added to a final concentration of 40 mM before electrophoresis. Six μg of antibody was loaded onto a NuPAGE 10% Bis-Tris gel (Invitrogen) and proteins were separated by size using the MOPS electrophoresis buffer. Following electrophoresis the gel was stain with Coomassie blue and the results are shown in FIG. 14. The change in mobility of anti-EGFR activatable antibody 3954-1204-C225v5, anti-EGFR multispecific activatable antibody 3954-1204-C225v5-CTLA-4, anti-Jagged activatable antibody 5342-1204-4D11v2, and anti-Jagged multispecific activatable antibody 5342-1204-4D11v2-CTLA-4 light chains, in the presence of uPA, demonstrate proteolytic activation of the multispecific activatable antibodies. The lack of any change in the mobility of the heavy chain fusions demonstrates the resistance to protease cleavage.

Binding Assays

Panel A in FIG. 15 shows that anti-EGFR multispecific activatable antibody 3954-1204-C225v5-CTLA-4 bound to EGFR, by ELISA, with lower affinity (Kd=12.8 nM) as compared to C225v5 (3 nM) or to C225v5-CTLA-4 (0.33 nM). However, once activated by uPA, anti-EGFR multispecific activatable antibody 3954-1204-C225v5-CTLA-4 bound to EGFR with similar affinity (0.45 nM) as compared to C225v5 (0.21 nM) and C225v5-CTLA4 (0.33 nM). Importantly uPA did not cleave the anti-CTLA4 scFv fused to the carboxyl terminus of the heavy chain: As illustrated in panel B of FIG. 15, uPA treatment had no effect of binding to human CTLA4.

Similarly, anti-Jagged multispecific activatable antibody 5342-1204-4D11v2-CTLA-4 bound to human Jagged 1, by ELISA, with lower affinity (15 nM) as compared to 4D11v2 (0.44 nM) or 4D11v2-CTLA4 (0.77 nM). Once activated, anti-Jagged multispecific activatable antibody 5342-1204-4D11v2-CTLA-4 bound to human Jagged 1 with similar affinity as 4D11v2 (0.54 nM) and 4D11v2-CTLA4 (0.92 nM) (FIG. 15, panel C). uPA treatment had no effect on CTLA4 binding (FIG. 15, panel D). ELISA binding measurements were performed as follows. Human Jagged 1-Fc (R&D Systems; Cat #1277-JG-050), human EGFR (R&D Systems, Cat #344-ER-050) or human CTLA4 (R&D Systems; Cat #325-CT-200/CF) were adsorbed onto wells of a 96-well ELISA plate. Three-fold dilutions, starting at 100 nM, of untreated and uPA treated antibodies, multispecific antibodies or multispecific activatable antibodies were applied to the plate and allowed to associate with plate-bound antigen for 1 hour. Following binding, the bound antibody was visualized with an anti-human IgG-HRP conjugate (Fab specific, Sigma, St Louis, Mo.; Cat #A0293-1ML) and developed with the chromogenic substrate TMB.

Example 5

Additional Multispecific Antibody and Multispecific Activatable Antibody Sequences This Example provides the sequences of additional multispecific antibodies and multispecific activatable antibodies.

Antibody OKT3m scFv

AMINO ACID SEQUENCE
(SEQ ID NO: 306)
QVQLQQSGAELARPGASVKMSCKASGYTFTRYTMHWVKQRPGQGLE
WIGYINPSRGYTNYNQKFKDKATLTTDKSSSTAYMQLSSLTSEDSA
VYYCARYYDDHYSLDYWGQGTTLTVSSGGGGSGGGGSGGGGSQIVL
TQSPAIMSASPGEKVTMTCSASSSVSYMNWYQQKSGTSPKRWIYDT
SKLASGVPAHFRGSGSGTSYSLTISGMEAEDAATYYCQQWSSNPFT
FGSGTKLEINR

NUCLEOTIDE SEQUENCE
(SEQ ID NO: 307)
CAGGTTCAGCTGCAGCAGAGCGGTGCAGAACTGGCACGTCCGGGTG
CAAGCGTTAAAATGAGCTGTAAAGCAAGCGGTTATACCTTTACCCG
TTATACCATGCATTGGGTTAAACAGCGTCCGGGTCAGGGTCTGGAA
TGGATTGGTTATATCAATCCGAGCCGTGGTTATACCAACTACAACC
AGAAATTCAAAGATAAAGCAACCCTGACCACCGATAAAAGCAGCAG
CACCGCCTATATGCAGCTGAGCAGCCTGACCTCAGAGGATAGCGCA
GTTTATTACTGTGCACGCTATTATGATGATCACTATAGCCTGGATT
ATTGGGGTCAGGGCACCACCCTGACCGTTAGCAGCGGTGGTGGTGG
TAGTGGTGGCGGTGGTTCAGGCGGTGGCGGTAGCCAGATTGTTCTG
ACCCAGAGTCCGGCAATTATGAGCGCAAGTCCGGGTGAAAAAGTTA
CCATGACCTGTAGCGCCAGCAGCAGCGTTAGCTATATGAATTGGTA
TCAGCAGAAAAGCGGCACCAGCCCGAAACGTTGGATTTATGATACC
AGCAAACTGGCAAGCGGTGTTCCGGCACATTTTCGTGGTAGCGGTA
GCGGCACCTCATATAGCCTGACCATTAGCGGTATGGAAGCAGAAGA
TGCAGCAACCTATTATTGTCAGCAGTGGTCAAGCAATCCGTTTACC
TTTGGTAGTGGCACCAAACTGGAAATTAATCGT

Antibody OKT3m scFv Lv

AMINO ACID SEQUENCE
(SEQ ID NO: 308)
QIVLTQSPAIMSASPGEKVTMTCSASSSVSYMNWYQQKSGTSPKRW
IYDTSKLASGVPAHFRGSGSGTSYSLTISGMEAEDAATYYCQQWSS
NPFTFGSGTKLEINR

NUCLEOTIDE SEQUENCE
(SEQ ID NO: 309)
CAGATTGTTCTGACCCAGAGTCCGGCAATTATGAGCGCAAGTCCGG
GTGAAAAAGTTACCATGACCTGTAGCGCCAGCAGCAGCGTTAGCTA
TATGAATTGGTATCAGCAGAAAAGCGGCACCAGCCCGAAACGTTGG
ATTTATGATACCAGCAAACTGGCAAGCGGTGTTCCGGCACATTTTC
GTGGTAGCGGTAGCGGCACCTCATATAGCCTGACCATTAGCGGTAT
GGAAGCAGAAGATGCAGCAACCTATTATTGTCAGCAGTGGTCAAGC
AATCCGTTTACCTTTGGTAGTGGCACCAAACTGGAAATTAATCGT

Antibody OKT3m scFv Hv

AMINO ACID SEQUENCE
(SEQ ID NO: 310)
QVQLQQSGAELARPGASVKMSCKASGYTFTRYTMHWVKQRPGQGLE
WIGYINPSRGYTNYNQKFKDKATLTTDKSSSTAYMQLSSLTSEDSA
VYYCARYYDDHYSLDYWGQGTTLTVSS

NUCLEOTIDE SEQUENCE
(SEQ ID NO: 311)
CAGGTTCAGCTGCAGCAGAGCGGTGCAGAACTGGCACGTCCGGGTG
CAAGCGTTAAAATGAGCTGTAAAGCAAGCGGTTATACCTTTACCCG
TTATACCATGCATTGGGTTAAACAGCGTCCGGGTCAGGGTCTGGAA
TGGATTGGTTATATCAATCCGAGCCGTGGTTATACCAACTACAACC
AGAAATTCAAAGATAAAGCAACCCTGACCACCGATAAAAGCAGCAG
CACCGCCTATATGCAGCTGAGCAGCCTGACCTCAGAGGATAGCGCA
GTTTATTACTGTGCACGCTATTATGATGATCACTATAGCCTGGATT
ATTGGGGTCAGGGCACCACCCTGACCGTTAGCAGC

Antibody OKT3m scFv w/long linker to allow attachment to the C-terminus of either the heavy chain (HC) or light chain (LC) of an antibody or activatable antibody to produce a multispecific antibody or activatable antibody, respectively AMINO ACID SEQUENCE
(SEQ ID NO: 290)
GGGSGGGGSGSGGGSGGGGSGGGQVQLQQSGAELARPGASVKMSCK
ASGYTFTRYTMHWVKQRPGQGLEWIGYINPSRGYTNYNQKFKDKAT
LTTDKSSSTAYMQLSSLTSEDSAVYYCARYYDDHYSLDYWGQGTTL
TVSSGGGGSGGGGSGGGGSQIVLTQSPAIMSASPGEKVTMTCSASS
SVSYMNWYQQKSGTSPKRWIYDTSKLASGVPAHFRGSGSGTSYSLT
ISGMEAEDAATYYCQQWSSNPFTFGSGTKLEINR*

NUCLEOTIDE SEQUENCE
(SEQ ID NO: 291)
GGAGGTGGATCTGGAGGTGGCGGTTCAGGCTCTGGCGGAGGCTCAG
GTGGTGGAGGATCAGGCGGAGGTCAGGTTCAGCTGCAGCAGAGCGG
TGCAGAACTGGCACGTCCGGGTGCAAGCGTTAAAATGAGCTGTAAA
GCAAGCGGTTATACCTTTACCCGTTATACCATGCATTGGGTTAAAC
AGCGTCCGGGTCAGGGTCTGGAATGGATTGGTTATATCAATCCGAG
CCGTGGTTATACCAACTACAACCAGAAATTCAAAGATAAAGCAACC
CTGACCACCGATAAAAGCAGCAGCACCGCCTATATGCAGCTGAGCA
GCCTGACCTCAGAGGATAGCGCAGTTTATTACTGTGCACGCTATTA
TGATGATCACTATAGCCTGGATTATTGGGGTCAGGGCACCACCCTG
ACCGTTAGCAGCGGTGGTGGTGGTAGTGGTGGCGGTGGTTCAGGCG
GTGGCGGTAGCCAGATTGTTCTGACCCAGAGTCCGGCAATTATGAG
CGCAAGTCCGGGTGAAAAAGTTACCATGACCTGTAGCGCCAGCAGC
AGCGTTAGCTATATGAATTGGTATCAGCAGAAAAGCGGCACCAGCC
CGAAACGTTGGATTTATGATACCAGCAAACTGGCAAGCGGTGTTCC
GGCACATTTTCGTGGTAGCGGTAGCGGCACCTCATATAGCCTGACC

```
ATTAGCGGTATGGAAGCAGAAGATGCAGCAACCTATTATTGTCAGC

AGTGGTCAAGCAATCCGTTTACCTTTGGTAGTGGCACCAAACTGGA

AATTAATCGTTGA
```

Antibody OKT3m scFv with/short linker to allow attachment to the N-terminus of the HC of an antibody or activatable antibody to produce a multispecific antibody or activatable antibody respectively

```
AMINO ACID SEQUENCE
                                     (SEQ ID NO: 292)
QVQLQQSGAELARPGASVKMSCKASGYTFTRYTMHWVKQRPGQGLE

WIGYINPSRGYTNYNQKFKDKATLTTDKSSSTAYMQLSSLTSEDSA

VYYCARYYDDHYSLDYWGQGTTLTVSSGGGGSGGGGSGGGGSQIVL

TQSPAIMSASPGEKVTMTCSASSSVSYMNWYQQKSGTSPKRWIYDT

SKLASGVPAHFRGSGSGTSYSLTISGMEAEDAATYYCQQWSSNPFT

FGSGTKLEINRGGGS

NUCLEOTIDE SEQUENCE
                                     (SEQ ID NO: 293)
CAGGTTCAGCTGCAGCAGAGCGGTGCAGAACTGGCACGTCCGGGTG

CAAGCGTTAAAATGAGCTGTAAAGCAAGCGGTTATACCTTTACCCG

TTATACCATGCATTGGGTTAAACAGCGTCCGGGTCAGGGTCTGGAA

TGGATTGGTTATATCAATCCGAGCCGTGGTTATACCAACTACAACC

AGAAATTCAAAGATAAAGCAACCCTGACCACCGATAAAAGCAGCAG

CACCGCCTATATGCAGCTGAGCAGCCTGACCTCAGAGGATAGCGCA

GTTTATTACTGTGCACGCTATTATGATGATCACTATAGCCTGGATT

ATTGGGGTCAGGGCACCACCCTGACCGTTAGCAGCGGTGGTGGTGG

TAGTGGTGGCGGTGGTTCAGGCGGTGGCGGTAGCCAGATTGTTCTG

ACCCAGAGTCCGGCAATTATGAGCGCAAGTCCGGGTGAAAAAGTTA

CCATGACCTGTAGCGCCAGCAGCAGCGTTAGCTATATGAATTGGTA

TCAGCAGAAAAGCGGCACCAGCCCGAAACGTTGGATTTATGATACC

AGCAAACTGGCAAGCGGTGTTCCGGCACATTTTCGTGGTAGCGGTA

GCGGCACCTCATATAGCCTGACCATTAGCGGTATGGAAGCAGAAGA

TGCAGCAACCTATTATTGTCAGCAGTGGTCAAGCAATCCGTTTACC

TTTGGTAGTGGCACCAAACTGGAAATTAATCGTGGAGGTGGTGGAT

CC
```

Multispecific antibody C225v5-OKT3m-H-N heavy chain (antibody OKT3m attached to the N-terminus of antibody C225v5 HC)

```
AMINO ACID SEQUENCE
                                     (SEQ ID NO: 294)
QVQLQQSGAELARPGASVKMSCKASGYTFTRYTMHWVKQRPGQGLE

WIGYINPSRGYTNYNQKFKDKATLTTDKSSSTAYMQLSSLTSEDSA

VYYCARYYDDHYSLDYWGQGTTLTVSSGGGGSGGGGSGGGGSQIVL

TQSPAIMSASPGEKVTMTCSASSSVSYMNWYQQKSGTSPKRWIYDT

SKLASGVPAHFRGSGSGTSYSLTISGMEAEDAATYYCQQWSSNPFT

FGSGTKLEINRGGGGSQVQLKQSGPGLVQPSQSLSITCTVSGFSLT

NYGVHWVRQSPGKGLEWLGVIWSGGNTDYNTPFTSRLSINKDNSKS

QVFFKMNSLQSQDTAIYYCARALTYYDYEFAYWGQGTLVTVSAAST

KGPSVFPLAPSSKSTSGGTAALGCLVKDYFPEPVTVSWNSGALTSG

VHTFPAVLQSSGLYSLSSVVTVPSSSLGTQTYICNVNHKPSNTKVD

KKVEPKSCDKTHTCPPCPAPELLGGPSVFLFPPKPKDTLMISRTPE

VTCVVVDVSHEDPEVKFNWYVDGVEVHNAKTKPREEQYNSTYRVVS

VLTVLHQDWLNGKEYKCKVSNKALPAPIEKTISKAKGQPREPQVYT

LPPSREEMTKNQVSLTCLVKGFYPSDIAVEWESNGQPENNYKTTPP

VLDSDGSFFLYSKLTVDKSRWQQGNVFSCSVMHEALHNHYTQKSLS

LSPGK*

NUCLEOTIDE SEQUENCE
                                     (SEQ ID NO: 295)
CAGGTTCAGCTGCAGCAGAGCGGTGCAGAACTGGCACGTCCGGGTG

CAAGCGTTAAAATGAGCTGTAAAGCAAGCGGTTATACCTTTACCCG

TTATACCATGCATTGGGTTAAACAGCGTCCGGGTCAGGGTCTGGAA

TGGATTGGTTATATCAATCCGAGCCGTGGTTATACCAACTACAACC

AGAAATTCAAAGATAAAGCAACCCTGACCACCGATAAAAGCAGCAG

CACCGCCTATATGCAGCTGAGCAGCCTGACCTCAGAGGATAGCGCA

GTTTATTACTGTGCACGCTATTATGATGATCACTATAGCCTGGATT

ATTGGGGTCAGGGCACCACCCTGACCGTTAGCAGCGGTGGTGGTGG

TAGTGGTGGCGGTGGTTCAGGCGGTGGCGGTAGCCAGATTGTTCTG

ACCCAGAGTCCGGCAATTATGAGCGCAAGTCCGGGTGAAAAAGTTA

CCATGACCTGTAGCGCCAGCAGCAGCGTTAGCTATATGAATTGGTA

TCAGCAGAAAAGCGGCACCAGCCCGAAACGTTGGATTTATGATACC

AGCAAACTGGCAAGCGGTGTTCCGGCACATTTTCGTGGTAGCGGTA

GCGGCACCTCATATAGCCTGACCATTAGCGGTATGGAAGCAGAAGA

TGCAGCAACCTATTATTGTCAGCAGTGGTCAAGCAATCCGTTTACC

TTTGGTAGTGGCACCAAACTGGAAATTAATCGTGGAGGTGGTGGAT

CCCAGGTGCAGCTGAAACAGAGCGGCCCGGGCCTGGTGCAGCCGAG

CCAGAGCCTGAGCATTACCTGCACCGTGAGCGGCTTTAGCCTGACC

AACTATGGCGTGCATTGGGTGCGCCAGAGCCCGGGCAAGGCCTGG

AATGGCTGGGCGTGATTTGGAGCGGCGGCAACACCGATTATAACAC

CCCGTTTACCAGCCGCCTGAGCATTAACAAAGATAACAGCAAAAGC

CAGGTGTTTTTTAAAATGAACAGCCTGCAAAGCCAGGATACCGCGA

TTTATTATTGCGCGCGCGCTGACCTATTATGATTATGAATTTGC

GTATTGGGGCCAGGGCACCCTGGTGACCGTGAGCGCGGCTAGCACC

AAGGGCCCATCGGTCTTCCCCCTGGCACCCTCCTCCAAGAGCACCT

CTGGGGGCACAGCGGCCCTGGGCTGCCTGGTCAAGGACTACTTCCC

CGAACCGGTGACGGTGTCGTGGAACTCAGGCGCCCTGACCAGCGGC

GTGCACACCTTCCCGGCTGTCCTACAGTCCTCAGGACTCTACTCCC
```

```
TCAGCAGCGTGGTGACCGTGCCCTCCAGCAGCTTGGGCACCCAGAC
CTACATCTGCAACGTGAATCACAAGCCCAGCAACACCAAGGTGGAC
AAGAAAGTTGAGCCCAAATCTTGTGACAAAACTCACACATGCCCAC
CGTGCCCAGCACCTGAACTCCTGGGGGACCGTCAGTCTTCCTCTT
CCCCCCAAAACCCAAGGACACCCTCATGATCTCCCGGACCCCTGAG
GTCACATGCGTGGTGGTGGACGTGAGCCACGAAGACCCTGAGGTCA
AGTTCAACTGGTACGTGGACGGCGTGGAGGTGCATAATGCCAAGAC
AAAGCCGCGGGAGGAGCAGTACAACAGCACGTACCGTGTGGTCAGC
GTCCTCACCGTCCTGCACCAGGACTGGCTGAATGGCAAGGAGTACA
AGTGCAAGGTCTCCAACAAAGCCCTCCCAGCCCCCATCGAGAAAAC
CATCTCCAAAGCCAAAGGGCAGCCCCGAGAACCACAGGTGTACACC
CTGCCCCCATCCCGGGAGGAGATGACCAAGAACCAGGTCAGCCTGA
CCTGCCTGGTCAAAGGCTTCTATCCCAGCGACATCGCCGTGGAGTG
GGAGAGCAATGGGCAGCCGGAGAACAACTACAAGACCACGCCTCCC
GTGCTGGACTCCGACGGCTCCTTCTTCCTCTACAGCAAGCTCACCG
TGGACAAGAGCAGGTGGCAGCAGGGGAACGTCTTCTCATGCTCCGT
GATGCATGAGGCTCTGCACAACCACTACACGCAGAAGAGCCTCTCC
CTGTCTCCGGGTAAATGA
```

Multispecific antibody C225v5-OKT3m-H-C heavy chain (antibody OKT3m attached to the C-terminus of antibody C225v5 HC)

```
AMINO ACID SEQUENCE
                                        (SEQ ID NO: 296)
QVQLKQSGPGLVQPSQSLSITCTVSGFSLTNYGVHWVRQSPGKGLE
WLGVIWSGGNTDYNTPFTSRLSINKDNSKSQVFFKMNSLQSQDTAI
YYCARALTYYDYEFAYWGQGTLVTVSAASTKGPSVFPLAPSSKSTS
GGTAALGCLVKDYFPEPVTVSWNSGALTSGVHTFPAVLQSSGLYSL
SSVVTVPSSSLGTQTYICNVNHKPSNTKVDKKVEPKSCDKTHTCPP
CPAPELLGGPSVFLFPPKPKDTLMISRTPEVTCVVVDVSHEDPEVK
FNWYVDGVEVHNAKTKPREEQYNSTYRVVSVLTVLHQDWLNGKEYK
CKVSNKALPAPIEKTISKAKGQPREPQVYTLPPSREEMTKNQVSLT
CLVKGFYPSDIAVEWESNGQPENNYKTTPPVLDSDGSFFLYSKLTV
DKSRWQQGNVFSCSVMHEALHNHYTQKSLSLSPGKGGGSGGGGSGS
GGGSGGGGSGGGQVQLQQSGAELARPGASVKMSCKASGYTFTRYTM
HWVKQRPGQGLEWIGYINPSRGYTNYNQKFKDKATLTTDKSSSTAY
MQLSSLTSEDSAVYYCARYYDDHYSLDYWGQGTTLTVSSGGGGSGG
GGSGGGGSQIVLTQSPAIMSASPGEKVTMTCSASSSVSYMNWYQQK
SGTSPKRWIYDTSKLASGVPAHFRGSGSGTSYSLTISGMEAEDAAT
YYCQQWSSNPFTFGSGTKLEINR*
NUCLEOTIDE SEQUENCE
                                        (SEQ ID NO: 297)
CAGGTGCAGCTGAAACAGAGCGGCCCGGGCCTGGTGCAGCCGAGCC
AGAGCCTGAGCATTACCTGCACCGTGAGCGGCTTTAGCCTGACCAA
CTATGGCGTGCATTGGGTGCGCCAGAGCCCGGGCAAAGGCCTGGAA
TGGCTGGGCGTGATTTGGAGCGGCGGCAACACCGATTATAACACCC
CGTTTACCAGCCGCCTGAGCATTAACAAAGATAACAGCAAAAGCCA
GGTGTTTTTTAAAATGAACAGCCTGCAAAGCCAGGATACCGCGATT
TATTATTGCGCGCGCGCGCTGACCTATTATGATTATGAATTTGCGT
ATTGGGGCCAGGGCACCCTGGTGACCGTGAGCGCGGCTAGCACCAA
GGGCCCATCGGTCTTCCCCCTGGCACCCTCCTCCAAGAGCACCTCT
GGGGGCACAGCGGCCCTGGGCTGCCTGGTCAAGGACTACTTCCCCG
AACCGGTGACGGTGTCGTGGAACTCAGGCGCCCTGACCAGCGGCGT
GCACACCTTCCCGGCTGTCCTACAGTCCTCAGGACTCTACTCCCTC
AGCAGCGTGGTGACCGTGCCCTCCAGCAGCTTGGGCACCCAGACCT
ACATCTGCAACGTGAATCACAAGCCCAGCAACACCAAGGTGGACAA
GAAAGTTGAGCCCAAATCTTGTGACAAAACTCACACATGCCCACCG
TGCCCAGCACCTGAACTCCTGGGGGACCGTCAGTCTTCCTCTTCC
CCCCAAAACCCAAGGACACCCTCATGATCTCCCGGACCCCTGAGGT
CACATGCGTGGTGGTGGACGTGAGCCACGAAGACCCTGAGGTCAAG
TTCAACTGGTACGTGGACGGCGTGGAGGTGCATAATGCCAAGACAA
AGCCGCGGGAGGAGCAGTACAACAGCACGTACCGTGTGGTCAGCGT
CCTCACCGTCCTGCACCAGGACTGGCTGAATGGCAAGGAGTACAAG
TGCAAGGTCTCCAACAAAGCCCTCCCAGCCCCCATCGAGAAACCA
TCTCCAAAGCCAAAGGGCAGCCCCGAGAACCACAGGTGTACACCCT
GCCCCCATCCCGGGAGGAGATGACCAAGAACCAGGTCAGCCTGACC
TGCCTGGTCAAAGGCTTCTATCCCAGCGACATCGCCGTGGAGTGGG
AGAGCAATGGGCAGCCGGAGAACAACTACAAGACCACGCCTCCCGT
GCTGGACTCCGACGGCTCCTTCTTCCTCTACAGCAAGCTCACCGTG
GACAAGAGCAGGTGGCAGCAGGGGAACGTCTTCTCATGCTCCGTGA
TGCATGAGGCTCTGCACAACCACTACACGCAGAAGAGCCTCTCCCT
GTCTCCGGGTAAAGGAGGTGGATCTGGAGGTGGCGGTTCAGGCTCT
GGCGGAGGCTCAGGTGGTGGAGGATCAGGCGGAGGTCAGGTTCAGC
TGCAGCAGAGCGGTGCAGAACTGGCACGTCCGGGTGCAAGCGTTAA
AATGAGCTGTAAAGCAAGCGGTTATACCTTTACCCGTTATACCATG
CATTGGGTTAAACAGCGTCCGGGTCAGGGTCTGGAATGGATTGGTT
ATATCAATCCGAGCCGTGGTTATACCAACTACAACCAGAAATTCAA
AGATAAAGCAACCCTGACCACCGATAAAAGCAGCAGCACCGCCTAT
ATGCAGCTGAGCAGCCTGACCTCAGAGGATAGCGCAGTTTATTACT
GTGCACGCTATTATGATGATCACTATAGCCTGGATTATTGGGGTCA
GGGCACCACCCTGACCGTTAGCAGCGGTGGTGGTGGTAGTGGTGGC
GGTGGTTCAGGCGGTGGCGGTAGCCAGATTGTTCTGACCCAGAGTC
CGGCAATTATGAGCGCAAGTCCGGGTGAAAAAGTTACCATGACCTG
TAGCGCCAGCAGCAGCGTTAGCTATATGAATTGGTATCAGCAGAAA
```

```
AGCGGCACCAGCCCGAAACGTTGGATTTATGATACCAGCAAACTGG

CAAGCGGTGTTCCGGCACATTTTCGTGGTAGCGGTAGCGGCACCTC

ATATAGCCTGACCATTAGCGGTATGGAAGCAGAAGATGCAGCAACC

TATTATTGTCAGCAGTGGTCAAGCAATCCGTTTACCTTTGGTAGTG

GCACCAAACTGGAAATTAATCGTTGA
```

Multispecific antibody C225v5-OKT3m-L-C light chain (antibody OKT3m attached to the C-terminus of antibody C225v5 LC)

```
AMINO ACID SEQUENCE
                                    (SEQ ID NO: 298)
DILLTQSPVILSVSPGERVSFSCRASQSIGTNIHWYQQRTNGSPRL

LIKYASESISGIPSRFSGSGSGTDFTLSINSVESEDIADYYCQQNN

NWPTTFGAGTKLELKRTVAAPSVFIFPPSDEQLKSGTASVVCLLNN

FYPREAKVQWKVDNALQSGNSQESVTEQDSKDSTYSLSSTLTLSKA

DYEKHKVYACEVTHQGLSSPVTKSFNRGECGGGSGGGGSGSGGGSG

GGGSGGGQVQLQQSGAELARPGASVKMSCKASGYTFTRYTMHWVKQ

RPGQGLEWIGYINPSRGYTNYNQKFKDKATLTTDKSSSTAYMQLSS

LTSEDSAVYYCARYYDDHYSLDYWGQTTLTVSSGGGGSGGGGSGG

GGSQIVLTQSPAIMSASPGEKVTMTCSASSSVSYMNWYQQKSGTSP

KRWIYDTSKLASGVPAHFRGSGSGTSYSLTISGMEAEDAATYYCQQ

WSSNPFTFGSGTKLEINR*

NUCLEOTIDE SEQUENCE
                                    (SEQ ID NO: 299)
GACATCTTGCTGACCCAGAGCCCGGTGATTCTGAGCGTGAGCCCGG

GCGAACGTGTGAGCTTTAGCTGCCGCGCGAGCCAGAGCATTGGCAC

CAACATTCATTGGTATCAGCAGCGCACCAACGGCAGCCCGCGCCTG

CTGATTAAATATGCGAGCGAAAGCATTAGCGGCATTCCGAGCCGCT

TTAGCGGCAGCGGCAGCGGCACCGATTTTACCCTGAGCATTAACAG

CGTGGAAAGCGAAGATATTGCGGATTATTATTGCCAGCAGAACAAC

AACTGGCCGACCACCTTTGGCGCGGGCACCAAACTGGAACTGAAAC

GTACGGTGGCTGCACCATCTGTCTTCATCTTCCCGCCATCTGATGA

GCAGTTGAAATCTGGAACTGCCTCTGTTGTGTGCCTGCTGAATAAC

TTCTATCCCAGAGAGGCCAAAGTACAGTGGAAGGTGGATAACGCCC

TCCAATCGGGTAACTCCCAGGAGAGTGTCACAGAGCAGGACAGCAA

GGACAGCACCTACAGCCTCAGCAGCACCCTGACGCTGAGCAAAGCA

GACTACGAGAAACACAAAGTCTACGCCTGCGAAGTCACCCATCAGG

GCCTGAGCTCGCCCGTCACAAAGAGCTTCAACAGGGGAGAGTGTGG

AGGTGGATCTGGAGGTGGCGGTTCAGGCTCTGGCGGAGGCTCAGGT

GGTGGAGGATCAGGCGGAGGTCAGGTTCAGCTGCAGCAGAGCGGTG

CAGAACTGGCACGTCCGGGTGCAAGCGTTAAAATGAGCTGTAAAGC

AAGCGGTTATACCTTTACCCGTTATACCATGCATTGGGTTAAACAG

CGTCCGGGTCAGGGTCTGGAATGGATTGGTTATATCAATCCGAGCC

GTGGTTATACCAACTACAACCAGAAATTCAAAGATAAAGCAACCCT
```

```
GACCACCGATAAAAGCAGCAGCACCGCCTATATGCAGCTGAGCAGC

CTGACCCTCAGAGGATAGCGCAGTTTATTACTGTGCACGCTATTATG

ATGATCACTATAGCCTGGATTATTGGGGTCAGGGCACCACCCTGAC

CGTTAGCAGCGGTGGTGGTGGTAGTGGTGGCGGTGGTTCAGGCGGT

GGCGGTAGCCAGATTGTTCTGACCCAGAGTCCGGCAATTATGAGCG

CAAGTCCGGGTGAAAAAGTTACCATGACCTGTAGCGCCAGCAGCAG

CGTTAGCTATATGAATTGGTATCAGCAGAAAAGCGGCACCAGCCCG

AAACGTTGGATTTATGATACCAGCAAACTGGCAAGCGGTGTTCCGG

CACATTTTCGTGGTAGCGGTAGCGGCACCTCATATAGCCTGACCAT

TAGCGGTATGGAAGCAGAAGATGCAGCAACCTATTATTGTCAGCAG

TGGTCAAGCAATCCGTTTACCTTTGGTAGTGGCACCAAACTGGAAA

TTAATCGTTAG
```

Multispecific antibody C225v5(N297Q)-OKT3m-H-N heavy chain

```
AMINO ACID SEQUENCE
                                    (SEQ ID NO: 300)
QVQLQQSGAELARPGASVKMSCKASGYTFTRYTMHWVKQRPGQGLE

WIGYINPSRGYTNYNQKFKDKATLTTDKSSSTAYMQLSSLTSEDSA

VYYCARYYDDHYSLDYWGQGTTLTVSSGGGGSGGGGSGGGGSQIVL

TQSPAIMSASPGEKVTMTCSASSSVSYMNWYQQKSGTSPKRWIYDT

SKLASGVPAHFRGSGSGTSYSLTISGMEAEDAATYYCQQWSSNPFT

FGSGTKLEINRGGGGSQVQLKQSGPGLVQPSQSLSITCTVSGFSLT

NYGVHWVRQSPGKGLEWLGVIWSGGNTDYNTPFTSRLSINKDNSKS

QVFFKMNSLQSQDTAIYYCARALTYYDYEFAYWGQGTLVTVSAAST

KGPSVFPLAPSSKSTSGGTAALGCLVKDYFPEPVTVSWNSGALTSG

VHTFPAVLQSSGLYSLSSVVTVPSSSLGTQTYICNVNHKPSNTKVD

KKVEPKSCDKTHTCPPCPAPELLGGPSVFLFPPKPKDTLMISRTPE

VTCVVVDVSHEDPEVKFNWYVDGVEVHNAKTKPREEQYQSTYRVVS

VLTVLHQDWLNGKEYKCKVSNKALPAPIEKTISKAKGQPREPQVYT

LPPSREEMTKNQVSLTCLVKGFYPSDIAVEWESNGQPENNYKTTPP

VLDSDGSFFLYSKLTVDKSRWQQGNVFSCSVMHEALHNHYTQKSLS

LSPGK*

NUCLEOTIDE SEQUENCE
                                    (SEQ ID NO: 301)
CAGGTTCAGCTGCAGCAGAGCGGTGCAGAACTGGCACGTCCGGGTG

CAAGCGTTAAAATGAGCTGTAAAGCAAGCGGTTATACCTTTACCCG

TTATACCATGCATTGGGTTAAACAGCGTCCGGGTCAGGGTCTGGAA

TGGATTGGTTATATCAATCCGAGCCGTGGTTATACCAACTACAACC

AGAAATTCAAAGATAAAGCAACCCTGACCACCGATAAAAGCAGCAG

CACCGCCTATATGCAGCTGAGCAGCCTGACCTCAGAGGATAGCGCA

GTTTATTACTGTGCACGCTATTATGATGATCACTATAGCCTGGATT

ATTGGGGTCAGGGCACCACCCTGACCGTTAGCAGCGGTGGTGGTGG
```

```
TAGTGGTGGCGGTGGTTCAGGCGGTGGCGGTAGCCAGATTGTTCTG
ACCCAGAGTCCGGCAATTATGAGCGCAAGTCCGGGTGAAAAAGTTA
CCATGACCTGTAGCGCCAGCAGCAGCGTTAGCTATATGAATTGGTA
TCAGCAGAAAAGCGGCACCAGCCCGAAAGTTGGATTTATGATACC
AGCAAACTGGCAAGCGGTGTTCCGGCACATTTTCGTGGTAGCGGTA
GCGGCACCTCATATAGCCTGACCATTAGCGGTATGGAAGCAGAAGA
TGCAGCAACCTATTATTGTCAGCAGTGGTCAAGCAATCCGTTTACC
TTTGGTAGTGGCACCAAACTGGAAATTAATCGTGGAGGTGGTGGAT
CCCAGGTGCAGCTGAAACAGAGCGGCCCGGGCCTGGTGCAGCCGAG
CCAGAGCCTGAGCATTACCTGCACCGTGAGCGGCTTTAGCCTGACC
AACTATGGCGTGCATTGGGTGCGCCAGAGCCCGGGCAAAGGCCTGG
AATGGCTGGGCGTGATTTGGAGCGGCGGCAACACCGATTATAACAC
CCCGTTTACCAGCCGCCTGAGCATTAACAAAGATAACAGCAAAAGC
CAGGTGTTTTTTAAAATGAACAGCCTGCAAAGCCAGGATACCGCGA
TTTATTATTGCGCGCGCGCGCTGACCTATTATGATTATGAATTTGC
GTATTGGGGCCAGGGCACCCTGGTGACCGTGAGCGCGGCTAGCACC
AAGGGCCCATCGGTCTTCCCCCTGGCACCCTCCTCCAAGAGCACCT
CTGGGGGCACAGCGGCCCTGGGCTGCCTGGTCAAGGACTACTTCCC
CGAACCGGTGACGGTGTCGTGGAACTCAGGCGCCCTGACCAGCGGC
GTGCACACCTTCCCGGCTGTCCTACAGTCCTCAGGACTCTACTCCC
TCAGCAGCGTGGTGACCGTGCCCTCCAGCAGCTTGGGCACCCAGAC
CTACATCTGCAACGTGAATCACAAGCCCAGCAACACCAAGGTGGAC
AAGAAAGTTGAGCCCAAATCTTGTGACAAAACTCACACATGCCCAC
CGTGCCCAGCACCTGAACTCCTGGGGGGACCGTCAGTCTTCCTCTT
CCCCCCAAAACCCAAGGACACCCTCATGATCTCCCGGACCCCTGAG
GTCACATGCGTGGTGGTGGACGTGAGCCACGAAGACCCTGAGGTCA
AGTTCAACTGGTACGTGGACGGCGTGGAGGTGCATAATGCCAAGAC
AAAGCCGCGGGAGGAGCAGTACCAGAGCACGTACCGTGTGGTCAGC
GTCCTCACCGTCCTGCACCAGGACTGGCTGAATGGCAAGGAGTACA
AGTGCAAGGTCTCCAACAAAGCCCTCCCAGCCCCCATCGAGAAAAC
CATCTCCAAAGCCAAAGGGCAGCCCCGAGAACCACAGGTGTACACC
CTGCCCCCATCCCGGGAGGAGATGACCAAGAACCAGGTCAGCCTGA
CCTGCCTGGTCAAAGGCTTCTATCCCAGCGACATCGCCGTGGAGTG
GGAGAGCAATGGGCAGCCGGAGAACAACTACAAGACCACGCCTCCC
GTGCTGGACTCCGACGGCTCCTTCTTCCTCTACAGCAAGCTCACCG
TGGACAAGAGCAGGTGGCAGCAGGGGAACGTCTTCTCATGCTCCGT
GATGCATGAGGCTCTGCACAACCACTACACGCAGAAGAGCCTCTCC
CTGTCTCCGGGTAAATGA
```

Multispecific antibody C225v5(N297Q)-OKT3m-H-C heavy chain

AMINO ACID SEQUENCE
(SEQ ID NO: 302)
QVQLKQSGPGLVQPSQSLSITCTVSGFSLTNYGVHWVRQSPGKGLE
WLGVIWSGGNTDYNTPFTSRLSINKDNSKSQVFFKMNSLQSQDTAI
YYCARALTYYDYEFAYWGQGTLVTVSAASTKGPSVFPLAPSSKSTS
GGTAALGCLVKDYFPEPVTVSWNSGALTSGVHTFPAVLQSSGLYSL
SSVVTVPSSSLGTQTYICNVNHKPSNTKVDKKVEPKSCDKTHTCPP
CPAPELLGGPSVFLFPPKPKDTLMISRTPEVTCVVVDVSHEDPEVK
FNWYVDGVEVHNAKTKPREEQYQSTYRVVSVLTVLHQDWLNGKEYK
CKVSNKALPAPIEKTISKAKGQPREPQVYTLPPSREEMTKNQVSLT
CLVKGFYPSDIAVEWESNGQPENNYKTTPPVLDSDGSFFLYSKLTV
DKSRWQQGNVFSCSVMHEALHNHYTQKSLSLSPGKGGGSGGGGSGS
GGGSGGGGSGGGQVQLQQSGAELARPGASVKMSCKASGYTFTRYTM
HWVKQRPGQGLEWIGYINPSRGYTNYNQKFKDKATLTTDKSSSTAY
MQLSSLTSEDSAVYYCARYYDDHYSLDYWGQGTTLTVSSGGGGSGG
GGSGGGGSQIVLTQSPAIMSASPGEKVTMTCSASSSVSYMNWYQQK
SGTSPKRWIYDTSKLASGVPAHFRGSGSGTSYSLTISGMEAEDAAT
YYCQQWSSNPFTFGSGTKLEINR*

NUCLEOTIDE SEQUENCE
(SEQ ID NO: 303)
CAGGTGCAGCTGAAACAGAGCGGCCCGGGCCTGGTGCAGCCGAGCC
AGAGCCTGAGCATTACCTGCACCGTGAGCGGCTTTAGCCTGACCAA
CTATGGCGTGCATTGGGTGCGCCAGAGCCCGGGCAAAGGCCTGGAA
TGGCTGGGCGTGATTTGGAGCGGCGGCAACACCGATTATAACACCC
CGTTTACCAGCCGCCTGAGCATTAACAAAGATAACAGCAAAAGCCA
GGTGTTTTTTAAAATGAACAGCCTGCAAAGCCAGGATACCGCGATT
TATTATTGCGCGCGCGCGCTGACCTATTATGATTATGAATTTGCGT
ATTGGGGCCAGGGCACCCTGGTGACCGTGAGCGCGGCTAGCACCAA
GGGCCCATCGGTCTTCCCCCTGGCACCCTCCTCCAAGAGCACCTCT
GGGGGCACAGCGGCCCTGGGCTGCCTGGTCAAGGACTACTTCCCCG
AACCGGTGACGGTGTCGTGGAACTCAGGCGCCCTGACCAGCGGCGT
GCACACCTTCCCGGCTGTCCTACAGTCCTCAGGACTCTACTCCCTC
AGCAGCGTGGTGACCGTGCCCTCCAGCAGCTTGGGCACCCAGACCT
ACATCTGCAACGTGAATCACAAGCCCAGCAACACCAAGGTGGACAA
GAAAGTTGAGCCCAAATCTTGTGACAAAACTCACACATGCCCACCG
TGCCCAGCACCTGAACTCCTGGGGGGACCGTCAGTCTTCCTCTTCC
CCCCAAAACCCAAGGACACCCTCATGATCTCCCGGACCCCTGAGGT
CACATGCGTGGTGGTGGACGTGAGCCACGAAGACCCTGAGGTCAAG
TTCAACTGGTACGTGGACGGCGTGGAGGTGCATAATGCCAAGACAA
AGCCGCGGGAGGAGCAGTACCAGAGCACGTACCGTGTGGTCAGCGT
CCTCACCGTCCTGCACCAGGACTGGCTGAATGGCAAGGAGTACAAG

```
TGCAAGGTCTCCAACAAAGCCCTCCCAGCCCCCATCGAGAAAACCA
TCTCCAAAGCCAAAGGGCAGCCCCGAGAACCACAGGTGTACACCCT
GCCCCCATCCCGGGAGGAGATGACCAAGAACCAGGTCAGCCTGACC
TGCCTGGTCAAAGGCTTCTATCCCAGCGACATCGCCGTGGAGTGGG
AGAGCAATGGGCAGCCGGAGAACAACTACAAGACCACGCCTCCCGT
GCTGGACTCCGACGGCTCCTTCTTCCTCTACAGCAAGCTCACCGTG
GACAAGAGCAGGTGGCAGCAGGGGAACGTCTTCTCATGCTCCGTGA
TGCATGAGGCTCTGCACAACCACTACACGCAGAAGAGCCTCTCCCT
GTCTCCGGGTAAAGGAGGTGGATCTGGAGGTGGCGGTTCAGGCTCT
GGCGGAGGCTCAGGTGGTGGAGGATCAGGCGGAGGTCAGGTTCAGC
TGCAGCAGAGCGGTGCAGAACTGGCACGTCCGGGTGCAAGCGTTAA
AATGAGCTGTAAAGCAAGCGGTTATACCTTTACCCGTTATACCATG
CATTGGGTTAAACAGCGTCCGGGTCAGGGTCTGGAATGGATTGGTT
ATATCAATCCGAGCCGTGGTTATACCAACTACAACCAGAAATTCAA
AGATAAAGCAACCCTGACCACCGATAAAAGCAGCAGCACCGCCTAT
ATGCAGCTGAGCAGCCTGACCTCAGAGGATAGCGCAGTTTATTACT
GTGCACGCTATTATGATGATCACTATAGCCTGGATTATTGGGGTCA
GGGCACCACCCTGACCGTTAGCAGCGGTGGTGGTGGTAGTGGTGGC
GGTGGTTCAGGCGGTGGCGGTAGCCAGATTGTTCTGACCCAGAGTC
CGGCAATTATGAGCGCAAGTCCGGGTGAAAAAGTTACCATGACCTG
TAGCGCCAGCAGCAGCGTTAGCTATATGAATTGGTATCAGCAGAAA
AGCGGCACCAGCCCGAAACGTTGGATTTATGATACCAGCAAACTGG
CAAGCGGTGTTCCGGCACATTTTCGTGGTAGCGGTAGCGGCACCTC
ATATAGCCTGACCATTAGCGGTATGGAAGCAGAAGATGCAGCAACC
TATTATTGTCAGCAGTGGTCAAGCAATCCGTTTACCTTTGGTAGTG
GCACCAAACTGGAAATTAATCGTTGA
```

Multispecific antibody C225v5(N297Q)-OKT3m-L-C light chain

```
AMINO ACID SEQUENCE
                                    (SEQ ID NO: 298)
DILLTQSPVILSVSPGERVSFSCRASQSIGTNIHWYQQRTNGSPRL

LIKYASESISGIPSRFSGSGSGTDFTLSINSVESEDIADYYCQQNN

NWPTTFGAGTKLELKRTVAAPSVFIFPPSDEQLKSGTASVVCLLNN

FYPREAKVQWKVDNALQSGNSQESVTEQDSKDSTYSLSSTLTLSKA

DYEKHKVYACEVTHQGLSSPVTKSFNRGECGGGSGGGGSGSGGGSG

GGGSGGGQVQLQQSGAELARPGASVKMSCKASGYTFTRYTMHWVKQ

RPGQGLEWIGYINPSRGYTNYNQKFKDKATLTTDKSSSTAYMQLSS

LTSEDSAVYYCARYYDDHYSLDYWGQTTLTVSSGGGGSGGGGSGG

GGSQIVLTQSPAIMSASPGEKVTMTCSASSSVSYMNWYQQKSGTSP

KRWIYDTSKLASGVPAHFRGSGSGTSYSLTISGMEAEDAATYYCQQ

WSSNPFTFGSGTKLEINR*
```

```
NUCLEOTIDE SEQUENCE
                                    (SEQ ID NO: 299)
GACATCTTGCTGACCCAGAGCCCGGTGATTCTGAGCGTGAGCCCGG

GCGAACGTGTGAGCTTTAGCTGCCGCGCGAGCCAGAGCATTGGCAC

CAACATTCATTGGTATCAGCAGCGCACCAACGGCAGCCCGCGCCTG

CTGATTAAATATGCGAGCGAAAGCATTAGCGGCATTCCGAGCCGCT

TTAGCGGCAGCGGCAGCGGCACCGATTTTACCCTGAGCATTAACAG

CGTGGAAAGCGAAGATATTGCGGATTATTATTGCCAGCAGAACAAC

AACTGGCCGACCACCTTTGGCGCGGGCACCAAACTGGAACTGAAAC

GTACGGTGGCTGCACCATCTGTCTTCATCTTCCCGCCATCTGATGA

GCAGTTGAAATCTGGAACTGCCTCTGTTGTGTGCCTGCTGAATAAC

TTCTATCCCAGAGAGGCCAAAGTACAGTGGAAGGTGGATAACGCCC

TCCAATCGGGTAACTCCCAGGAGAGTGTCACAGAGCAGGACAGCAA

GGACAGCACCTACAGCCTCAGCAGCACCCTGACGCTGAGCAAAGCA

GACTACGAGAAACACAAAGTCTACGCCTGCGAAGTCACCCATCAGG

GCCTGAGCTCGCCCGTCACAAAGAGCTTCAACAGGGGAGAGTGTGG

AGGTGGATCTGGAGGTGGCGGTTCAGGCTCTGGCGGAGGCTCAGGT

GGTGGAGGATCAGGCGGAGGTCAGGTTCAGCTGCAGCAGAGCGGTG

CAGAACTGGCACGTCCGGGTGCAAGCGTTAAAATGAGCTGTAAAGC

AAGCGGTTATACCTTTACCCGTTATACCATGCATTGGGTTAAACAG

CGTCCGGGTCAGGGTCTGGAATGGATTGGTTATATCAATCCGAGCC

GTGGTTATACCAACTACAACCAGAAATTCAAAGATAAAGCAACCCT

GACCACCGATAAAAGCAGCAGCACCGCCTATATGCAGCTGAGCAGC

CTGACCTCAGAGGATAGCGCAGTTTATTACTGTGCACGCTATTATG

ATGATCACTATAGCCTGGATTATTGGGGTCAGGGCACCACCCTGAC

CGTTAGCAGCGGTGGTGGTGGTAGTGGTGGCGGTGGTTCAGGCGGT

GGCGGTAGCCAGATTGTTCTGACCCAGAGTCCGGCAATTATGAGCG

CAAGTCCGGGTGAAAAAGTTACCATGACCTGTAGCGCCAGCAGCAG

CGTTAGCTATATGAATTGGTATCAGCAGAAAAGCGGCACCAGCCCG

AAACGTTGGATTTATGATACCAGCAAACTGGCAAGCGGTGTTCCGG

CACATTTTCGTGGTAGCGGTAGCGGCACCTCATATAGCCTGACCAT

TAGCGGTATGGAAGCAGAAGATGCAGCAACCTATTATTGTCAGCAG

TGGTCAAGCAATCCGTTTACCTTTGGTAGTGGCACCAAACTGGAAA

TTAATCGTTAG
```

Antibody C225v5(N297Q) heavy chain

```
AMINO ACID SEQUENCE
                                    (SEQ ID NO: 336)
QVQLKQSGPGLVQPSQSLSITCTVSGFSLTNYGVHWVRQSPGKGLE

WLGVIWSGGNTDYNTPFTSRLSINKDNSKSQVFFKMNSLQSDTAI

YYCARALTYYDYEFAYWGQGTLVTVSAASTKGPSVFPLAPSSKSTS

GGTAALGCLVKDYFPEPVTVSWNSGALTSGVHTFPAVLQSSGLYSL
```

-continued

SSVVTVPSSSLGTQTYICNVNHKPSNTKVDKKVEPKSCDKTHTCPP

CPAPELLGGPSVFLFPPKPKDTLMISRTPEVTCVVVDVSHEDPEVK

FNWYVDGVEVHNAKTKPREEQYQSTYRVVSVLTVLHQDWLNGKEYK

CKVSNKALPAPIEKTISKAKGQPREPQVYTLPPSREEMTKNQVSLT

CLVKGFYPSDIAVEWESNGQPENNYKTTPPVLDSDGSFFLYSKLTV

DKSRWQQGNVFSCSVMHEALHNHYTQKSLSLSPGK*

NUCLEOTIDE SEQUENCE
(SEQ ID NO: 337)
CAGGTGCAGCTGAAACAGAGCGGCCCGGGCCTGGTGCAGCCGAGCC

AGAGCCTGAGCATTACCTGCACCGTGAGCGGCTTTAGCCTGACCAA

CTATGGCGTGCATTGGGTGCGCCAGAGCCCGGGCAAAGGCCTGGAA

TGGCTGGGCGTGATTTGGAGCGGCGGCAACACCGATTATAACACCC

CGTTTACCAGCCGCCTGAGCATTAACAAAGATAACAGCAAAAGCCA

GGTGTTTTTTAAAATGAACAGCCTGCAAAGCCAGGATACCGCGATT

TATTATTGCGCGCGCGCGCTGACCTATTATGATTATGAATTTGCGT

ATTGGGGCCAGGGCACCCTGGTGACCGTGAGCGCGGCTAGCACCAA

GGGCCCATCGGTCTTCCCCCTGGCACCCTCCTCCAAGAGCACCTCT

GGGGGCACAGCGGCCCTGGGCTGCCTGGTCAAGGACTACTTCCCCG

AACCGGTGACGGTGTCGTGGAACTCAGGCGCCCTGACCAGCGGCGT

GCACACCTTCCCGGCTGTCCTACAGTCCTCAGGACTCTACTCCCTC

AGCAGCGTGGTGACCGTGCCCTCCAGCAGCTTGGGCACCCAGACCT

ACATCTGCAACGTGAATCACAAGCCCAGCAACACCAAGGTGGACAA

GAAAGTTGAGCCCAAATCTTGTGACAAAACTCACACATGCCCACCG

TGCCCAGCACCTGAACTCCTGGGGGGACCGTCAGTCTTCCTCTTCC

CCCCAAAACCCAAGGACACCCTCATGATCTCCCGGACCCCTGAGGT

CACATGCGTGGTGGTGGACGTGAGCCACGAAGACCCTGAGGTCAAG

TTCAACTGGTACGTGGACGGCGTGGAGGTGCATAATGCCAAGACAA

AGCCGCGGGAGGAGCAGTACCAGAGCACGTACCGTGTGGTCAGCGT

CCTCACCGTCCTGCACCAGGACTGGCTGAATGGCAAGGAGTACAAG

TGCAAGGTCTCCAACAAAGCCCTCCCAGCCCCCATCGAGAAAACCA

TCTCCAAAGCCAAAGGGCAGCCCCGAGAACCACAGGTGTACACCCT

GCCCCCATCCCGGGAGGAGATGACCAAGAACCAGGTCAGCCTGACC

TGCCTGGTCAAAGGCTTCTATCCCAGCGACATCGCCGTGGAGTGGG

AGAGCAATGGGCAGCCGGAGAACAACTACAAGACCACGCCTCCCGT

GCTGGACTCCGACGGCTCCTTCTTCCTCTACAGCAAGCTCACCGTG

GACAAGAGCAGGTGGCAGCAGGGGAACGTCTTCTCATGCTCCGTGA

TGCATGAGGCTCTGCACAACCACTACACGCAGAAGAGCCTCTCCCT

GTCTCCGGGTAAATGA

Activatable antibody 3954-1204-C225v5 light chain

AMINO ACID SEQUENCE
(SEQ ID NO: 304)
QGQSGQCISPRGCPDGPYVMYGSSGGSGGSGGSGLSGRSDNHGSSG

-continued

TQILLTQSPVILSVSPGERVSFSCRASQSIGTNIHWYQQRTNGSPR

LLIKYASESISGIPSRFSGSGSGTDFTLSINSVESEDIADYYCQQN

NNWPTTFGAGTKLELKRTVAAPSVFIFPPSDEQLKSGTASVVCLLN

NFYPREAKVQWKVDNALQSGNSQESVTEQDSKDSTYSLSSTLTLSK

ADYEKHKVYACEVTHQGLSSPVTKSFNRGEC*

NUCLEOTIDE SEQUENCE
(SEQ ID NO: 305)
CAAGGCCAGTCTGGCCAGTGCATCTCACCTCGTGGTTGTCCGGACG

GCCCATACGTCATGTACGGCTCGAGCGGTGGCAGCGGTGGCTCTGG

TGGATCCGGTCTGAGCGGCCGTTCCGATAATCATGGCAGTAGCGGT

ACCCAGATCTTGCTGACCCAGAGCCCGGTGATTCTGAGCGTGAGCC

CGGGCGAACGTGTGAGCTTTAGCTGCCGCGCGAGCCAGAGCATTGG

CACCAACATTCATTGGTATCAGCAGCGCACCAACGGCAGCCCGCGC

CTGCTGATTAAATATGCGAGCGAAAGCATTAGCGGCATTCCGAGCC

GCTTTAGCGGCAGCGGCAGCGGCACCGATTTTACCCTGAGCATTAA

CAGCGTGGAAAGCGAAGATATTGCGGATTATTATTGCCAGCAGAAC

AACAACTGGCCGACCACCTTTGGCGCGGGCACCAAACTGGAACTGA

AACGTACGGTGGCTGCACCATCTGTCTTCATCTTCCCGCCATCTGA

TGAGCAGTTGAAATCTGGAACTGCCTCTGTTGTGTGCCTGCTGAAT

AACTTCTATCCCAGAGAGGCCAAAGTACAGTGGAAGGTGGATAACG

CCCTCCAATCGGGTAACTCCCAGGAGAGTGTCACAGAGCAGGACAG

CAAGGACAGCACCTACAGCCTCAGCAGCACCCTGACGCTGAGCAAA

GCAGACTACGAGAAACACAAAGTCTACGCCTGCGAAGTCACCCATC

AGGGCCTGAGCTCGCCCGTCACAAAGAGCTTCAACAGGGGAGAGTG

TGGAGGTGGATCTGGAGGTGGCGGTTCAGGCTCTGGCGGAGGCTCA

GGTGGTGGAGGATCAGGCGGAGGTCAGGTTCAGCTGCAGCAGAGCG

GTGCAGAACTGGCACGTCCGGGTGCAAGCGTTAAAATGAGCTGTAA

AGCAAGCGGTTATACCTTTACCCGTTATACCATGCATTGGGTTAAA

CAGCGTCCGGGTCAGGGTCTGGAATGGATTGGTTATATCAATCCGA

GCCGTGGTTATACCAACTACAACCAGAAATTCAAAGATAAAGCAAC

CCTGACCACCGATAAAAGCAGCAGCACCGCCTATATGCAGCTGAGC

AGCCTGACCTCAGAGGATAGCGCAGTTTATTACTGTGCACGCTATT

ATGATGATCACTATAGCCTGGATTATTGGGGTCAGGGCACCACCCT

GACCGTTAGCAGCGGTGGTGGTGGTAGTGGTGGCGGTGGTTCAGGC

GGTGGCGGTAGCCAGATTGTTCTGACCCAGAGTCCGGCAATTATGA

GCGCAAGTCCGGGTGAAAAAGTTACCATGACCTGTAGCGCCAGCAG

CAGCGTTAGCTATATGAATTGGTATCAGCAGAAAAGCGGCACCAGC

CCGAAACGTTGGATTTATGATACCAGCAAACTGGCAAGCGGTGTTC

CGGCACATTTTCGTGGTAGCGGTAGCGGCACCTCATATAGCCTGAC

CATTAGCGGTATGGAAGCAGAAGATGCAGCAACCTATTATTGTCAG

-continued

```
CAGTGGTCAAGCAATCCGTTTACCTTTGGTAGTGGCACCAAACTGG

AAATTAATCGTTAG
```

Multispecific activatable antibody 3954-1204-C225v5-OKT3m-H-N, which comprises light chain 3954-1204-C225 plasmid and heavy chain C225v5-OKT3m-H-N plasmid.

```
Antibody C225v5 light chain
AMINO ACID SEQUENCE
                              (SEQ ID NO: 314)
DILLTQSPVILSVSPGERVSFSCRASQSIGTNIHWYQQRTNGSPRL

LIKYASESISGIPSRFSGSGSGTDFTLSINSVESEDIADYYCQQNN

NWPTTFGAGTKLELKRTVAAPSVFIFPPSDEQLKSGTASVVCLLNN

FYPREAKVQWKVDNALQSGNSQESVTEQDSKDSTYSLSSTLTLSKA

DYEKHKVYACEVTHQGLSSPVTKSFNRGEC*

NUCLEOTIDE SEQUENCE
                              (SEQ ID NO: 315)
GACATCTTGCTGACCCAGAGCCCGGTGATTCTGAGCGTGAGCCCGG

GCGAACGTGTGAGCTTTAGCTGCCGCGCGAGCCAGAGCATTGGCAC

CAACATTCATTGGTATCAGCAGCGCACCAACGGCAGCCCGCGCCTG

CTGATTAAATATGCGAGCGAAAGCATTAGCGGCATTCCGAGCCGCT

TTAGCGGCAGCGGCAGCGGCACCGATTTTACCCTGAGCATTAACAG

CGTGGAAAGCGAAGATATTGCGGATTATTATTGCCAGCAGAACAAC

AACTGGCCGACCACCTTTGGCGCGGGCACCAAACTGGAACTGAAAC

GTACGGTGGCTGCACCATCTGTCTTCATCTTCCCGCCATCTGATGA

GCAGTTGAAATCTGGAACTGCCTCTGTTGTGTGCCTGCTGAATAAC

TTCTATCCCAGAGAGGCCAAAGTACAGTGGAAGGTGGATAACGCCC

TCCAATCGGGTAACTCCCAGGAGAGTGTCACAGAGCAGGACAGCAA

GGACAGCACCTACAGCCTCAGCAGCACCCTGACGCTGAGCAAAGCA

GACTACGAGAAACACAAAGTCTACGCCTGCGAAGTCACCCATCAGG

GCCTGAGCTCGCCCGTCACAAAGAGCTTCAACAGGGGAGAGTGTGG

AGGTGGATCTGGAGGTGGCGGTTCAGGCTCTGGCGGAGGCTCAGGT

GGTGGAGGATCAGGCGGAGGTCAGGTTCAGCTGCAGCAGAGCGGTG

CAGAACTGGCACGTCCGGGTGCAAGCGTTAAAATGAGCTGTAAAGC

AAGCGGTTATACCTTTACCCGTTATACCATGCATTGGGTTAAACAG

CGTCCGGGTCAGGGTCTGGAATGGATTGGTTATATCAATCCGAGCC

GTGGTTATACCAACTACAACCAGAAATTCAAAGATAAAGCAACCCT

GACCACCGATAAAGCAGCAGCACCGCCTATATGCAGCTGAGCAGC

CTGACCTCAGAGGATAGCGCAGTTTATTACTGTGCACGCTATTATG

ATGATCACTATAGCCTGGATTATTGGGGTCAGGGCACCACCCTGAC

CGTTAGCAGCGGTGGTGGTGGTAGTGGTGGCGGTGGTTCAGGCGGT

GGCGGTAGCCAGATTGTTCTGACCCAGAGTCCGGCAATTATGAGCG

CAAGTCCGGGTGAAAAAGTTACCATGACCTGTAGCGCCAGCAGCAG

CGTTAGCTATATGAATTGGTATCAGCAGAAAAGCGGCACCAGCCCG

AAACGTTGGATTTATGATACCAGCAAACTGGCAAGCGGTGTTCCGG

CACATTTTCGTGGTAGCGGTAGCGGCACCTCATATAGCCTGACCAT

TAGCGGTATGGAAGCAGAAGATGCAGCAACCTATTATTGTCAGCAG

TGGTCAAGCAATCCGTTTACCTTTGGTAGTGGCACCAAACTGGAAA

TTAATCGTTAG
```

Table 11 shows examples of pairing of heavy chain (HC) and light chain (LC) sequences to make a multispecific antibody or multispecific activatable antibody of the disclosure. As used herein when referring to light chains, antibody light chains comprising C225v5 are also referred to as light chains comprising C225.

TABLE 11

Multispecific antibodies and multispecific activatable antibodies of the disclosure

| Protein name | Plasmid(nucleotide) pairs for transfection |
|---|---|
| C225v5-OKT3m-H-N | HC C225v5-OKT3m-H-N<br>LC C225 |
| C225v5-OKT3m-H-C | HC C225v5-OKT3m-H-C<br>LC C225 |
| C225v5-OKT3m-L-C | HC C225v5<br>LC C225-OKT3m-L-C |
| 3954-1204-C225v5-OKT3m-H-N | HC C225v5-OKT3m-H-N<br>LC C225-3954-1204 |
| 3954-1204-C225v5-OKT3m-H-C | HC C225v5-OKT3m-H-C<br>LC C225-3954-1204 |
| C225v5-N297Q-OKT3m-H-N | HC C225v5-N297Q-OKT3m-H-N<br>LC C225 |
| C225v5-N297Q-OKT3m-H-C | HC C225v5-N297Q-OKT3m-H-C<br>LC C225 |
| C225v5-N297Q-OKT3m-L-C | HC C225v5-N297Q<br>LC C225-OKT3m-L-C |
| 3954-1204-C225v5-N297Q-OKT3m-H-N | HC C225v5-N297Q-OKT3m-H-N<br>LC C225-3954-1204 |
| 3954-1204-C225v5-N297Q-OKT3m-H-C | HC C225v5-N297Q-OKT3m-H-C<br>LC C225-3954-1204 |
| 3954-1204-G225v5-N297Q-OKT3m-L-C | HC C225v5-N297Q<br>LC C225-3954-1204-OKT3m-L-C | vS refers to version 5 of C225

Example 6

Binding of Multispecific Antibodies to CD3ε on Jurkat T Cells

This Example demonstrates the ability of multispecific antibodies of the disclosure to bind to T cells.

Three formats of multispecific antibodies were tested: (1) C225v5-OKT3m-H-N, a multispecific antibody in which an OKT3m scFv (which binds CD3ε (also referred to herein as CD3e and CD3) on T cells) was attached to the N-terminus of the heavy chain of anti-EGFR antibody C225v5; (2) C225v5-OKT3m-H-C, a multispecific antibody in which an OKT3m scFv was attached to the C-terminus of the heavy chain of anti-EGFR antibody C225v5; and (3) C225v5-OKT3m-L-C, a multispecific antibody in which an OKT3m scFv was attached to the C-terminus of the light chain of anti-EGFR antibody C225v5. The amino acid sequences of these multispecific antibodies are provided herein, as are the amino acid sequences of the C225v5 and OKT3 antibodies. Also tested was an isotype control, namely human IgG$_1$ isotype control, Enzo, Catalog ALX-804-133-C100.

To determine if the three multispecific antibody formats could bind to CD3ε-positive Jurkat T cells (also referred to herein as Jurkat cells and Jurkats), a flow cytometry-based binding assay was performed. Jurkat T cells (Clone E6-1, ATCC, TIB-152) were cultured in RPMI-1640 with GlutaMAX™ (Life Technologies, Catalog 72400-120), 10% Heat Inactivated-Fetal Bovine Serum (HI-FBS, Life Technologies, Catalog 10438-026), 100 U/ml penicillin, and 100 μg/ml streptomycin (Life Technologies, Catalog 15140-122) (also referred to herein as complete media) according to ATCC guidelines. Cells were harvested by centrifugation (200×g, 4° C., 5 min) and re-suspended in PBS with 2% HI-FBS (FACS Buffer). About 250,000 Jurkat cells per well were transferred to a 96-well U-bottom plate, harvested, and re-suspended in 50 microliters (also referred to herein as μL or ul) of the antibodies being tested. The starting concentration of the antibodies was 100 nM for the multispecific antibodies and 166.7 nM for the isotype control, followed by 5-fold serial dilutions for a total of 8 concentrations for each antibody.

The cells and antibodies were incubated at 4° C. with shaking for about 1 hour, harvested, and washed 3 times with 200 μL FACS Buffer. The resultant Jurkat cells were resuspended in 50 μl of AlexaFluor® 647 conjugated anti-human IgG (H+L) (Jackson ImmunoResearch, Catalog 709-606-149) and incubated at 4° C. with shaking for about 30 min. The resultant Jurkat cells were harvested, washed 3 times with 200 μL FACS Buffer, and resuspended in a final volume of 150 μL of FACS Buffer with 2.5 μg/ml 7-AAD (BD Pharmigen, Catalog 559925). Samples were analyzed on a BD Accuri C6 flow cytometer (BD Biosciences), and the median fluorescence intensity (MFI) of viable cells was calculated using FlowJo V10 (Treestar). 7-AAD staining showed that a forward side scatter gate was sufficient to identify viable cells. $EC_{50}$ values were calculated in GraphPad Prism 6 by curve fitting the data to log(agonist) vs. response (three parameters).

Figure 16A:
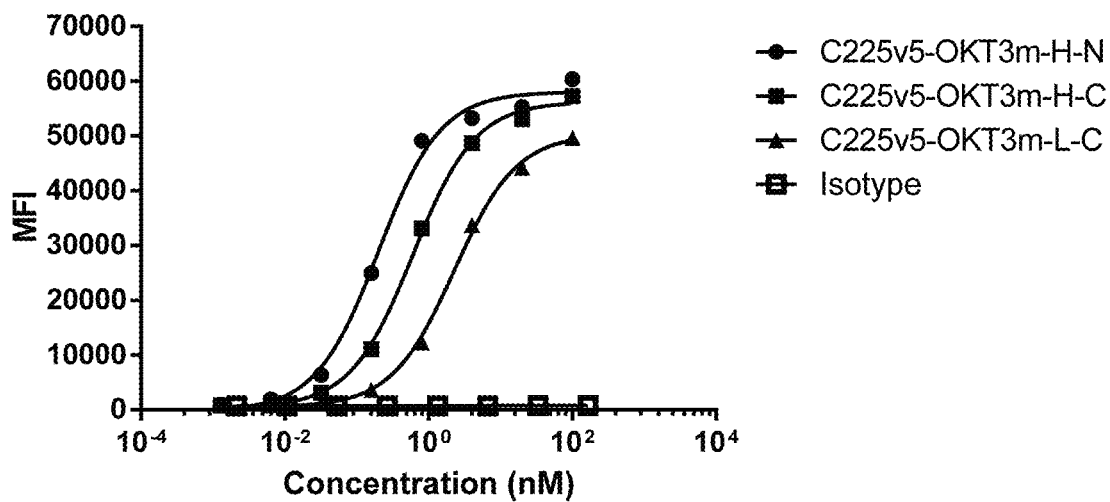
FIG. 16A is a graph depicting binding of multispecific antibodies of the disclosure to CD3ε-positive Jurkat T cells.

FIG. 16A demonstrates that all three multispecific antibody formats bound Jurkat T cells with $EC_{50}$ values ranging from single-digit nM to sub-nM.

Example 7

Multispecific Antibodies Bind to CD3ε-Expressing T Cells and Recombinant Human EGFR This Example demonstrates the ability of multispecific antibodies of the disclosure to bind to both (also referred to herein as co-bind) T cells and target antigen-containing cells.

To determine if multispecific antibody C225v5-OKT3m-H-N, C225v5-OKT3m-H-C, or C225v5-OKT3m-L-C could bind CD3ε-positive Jurkat T cells and EGFR, a flow cytometry-based co-binding assay was performed. Jurkat cells were pre-treated with a saturating concentration of each of the multispecific antibodies followed by titration with biotinylated EGFR and detection with Streptavidin, R-Phycoerythrin Conjugate (SAPE). Also tested was an isotype control, namely human $IgG_1$ isotype control, Enzo, Catalog ALX-804-133-C100.

Jurkat cells were cultured and harvested as described herein. About 500,000 Jurkat cells per well were transferred to a U-bottom plate, harvested, and re-suspended in 50 μL of 40 nM multispecific antibody or 67 nM isotype antibody. Cells were incubated at 4° C. with shaking for about 1 hour, harvested, and washed 3 times with 200 μL FACS Buffer. The resultant Jurkat cells (binding a multispecific antibody of the disclosure) were resuspended in 50 μl biotinylated recombinant human EGFR protein (Abcam, Catalog ab168702) starting at about 290 nM followed by 5-fold serial dilutions for a total of 8 concentrations. Cells were incubated at 4° C. with shaking for about 1 hour, harvested, and washed 3 times with 200 μL FACS Buffer. The resultant Jurkat cells were resuspended in 50 μl 10 μg/ml Streptavidin, R-Phycoerythrin Conjugate (Life Technologies, 5866) and incubated at 4° C. with shaking for about 1 hour. Cells were harvested, washed once with 200 μL FACS Buffer, and re-suspended in 150 μL FACS Buffer. Samples were analyzed on a BD Accuri C6 and MFI calculated as described herein. $EC_{50}$ values were calculated in GraphPad Prism 6 as described herein.

Figure 16B:
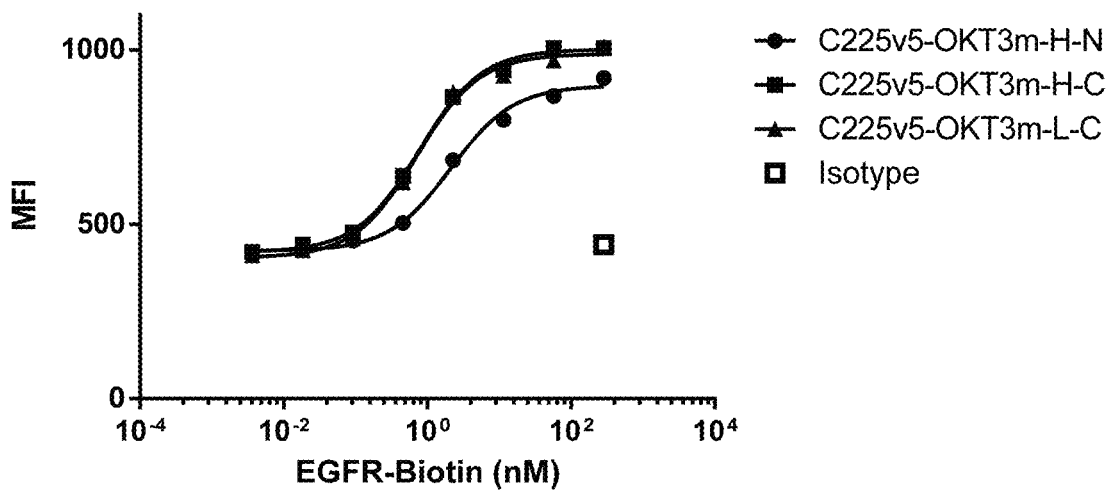
FIG. 16B is a graph depicting co-binding of multispecific antibodies of the disclosure to CD3ε-positive Jurkat T cells and EGFR.

FIG. 16B demonstrates that all three multispecific antibody formats exhibited concentration-dependent binding of EGFR that required concomitant binding to CD3ε on T cells. $EC_{50}$ values ranged from sub-nM to single digit nM.

Example 8

Target-Dependent Activation of T Cells by Multispecific Antibodies

This Example demonstrates the ability of multispecific antibodies of the disclosure to activate T cells in a target-dependent manner.

To determine if co-engagement of Jurkat T cells and EGFR-positive target cells by multispecific antibody C225v5-OKT3m-H-N, C225v5-OKT3m-H-C, or C225v5-OKT3m-L-C could induce activation of Jurkat cells, a flow cytometry-based assay was employed. Jurkat cells and CFSE-labeled target cells were co-cultured for about 15 h and T cell activation assessed by staining for surface expression of the early T cell activation marker, CD69.

EGFR-positive SW480 cells, also referred to as SW480 cells, (ATCC, Catalog CCL-228) and EGFR-negative U266 cells, also referred to as U266 cells, (ATCC, Catalog TIB-196) were each cultured in RPMI-1640 with GlutaMAX™, 10% HI-FBS, 100 U/ml penicillin, and 100 μg/ml streptomycin (referred to as complete media) according to ATCC guidelines. These target cells were harvested, washed once with PBS, and re-suspended in PBS at $2\times10^6$ cells/ml. A 5 mM CFSE stock (Life Technologies, CellTrace™ CFSE Cell Proliferation Kit, Catalog C34554) was prepared in DMSO and then diluted to 30 nM in PBS. The PBS/CFSE working stock was used immediately. Equal volumes of the target cells and CFSE stock were combined for a final CFSE concentration of 15 nM and final cell density of $1\times10^6$ cells/ml. Cells were incubated for 15 min at 37° C. Labeling was quenched by adding an equal volume of HI-FBS. The incubated target cells were harvested, washed once with complete media, and re-suspended in complete media at $5\times10^5$ cells/ml. 50 μL of cell suspension per well was added to a 96-well flat bottom plate for a total of 25,000 target cells per well.

Jurkat T cells were cultured as described herein. The Jurkat cells were harvested, re-suspended in complete media at $1\times10^6$ cells/ml, and 50 μL of cell suspension per well were added to the flat bottom plate containing target cells for a total of about 50,000 Jurkat cells per well. The ratio of effector T cells to target cells was 2:1.

Three times-concentrated antibody stocks were prepared in complete media. The highest concentrations used were 1.2 nM for each of the multispecific antibody formats and 1.5 nM for OKT3 (BioLegend, Catalog 317304), C225v5 (the amino acid sequence of which is provided herein), and isotype control antibodies. Five-fold serial dilutions were prepared in complete media for a total of 8 concentrations for each antibody. Fifty µL of antibody per well were added to the flat bottom plate containing the T cells and target cells, diluting all stocks 3-fold for a starting concentration of either 400 pM for each of the multispecific antibody formats or 500 pM for each of the OKT3, C225v5, and isotype antibodies.

After about 15 h, cells were transferred to a U-bottom plate and harvested. To maximize recovery, the cell culture plate was washed with 150 µL FACS Buffer, and the wash was transferred to the U-bottom plate. Cells were harvested, re-suspended in 50 µL anti-CD69 PE conjugated antibody (BD Biosciences, Catalog 555531, used at the manufacturer's recommended concentration), and stained for 1 h at 4° C. with shaking Cells were washed once with 200 µL FACS Buffer and then re-suspended in a final volume of 150 pt. Single color controls were used to set compensation on the BD Accuri C6. 10,000 cells were collected in a forward side scatter, CFSE-negative gate and MFI calculated using FlowJo. $EC_{50}$ values were calculated in GraphPad Prism 6 as described herein.

Figure 17:
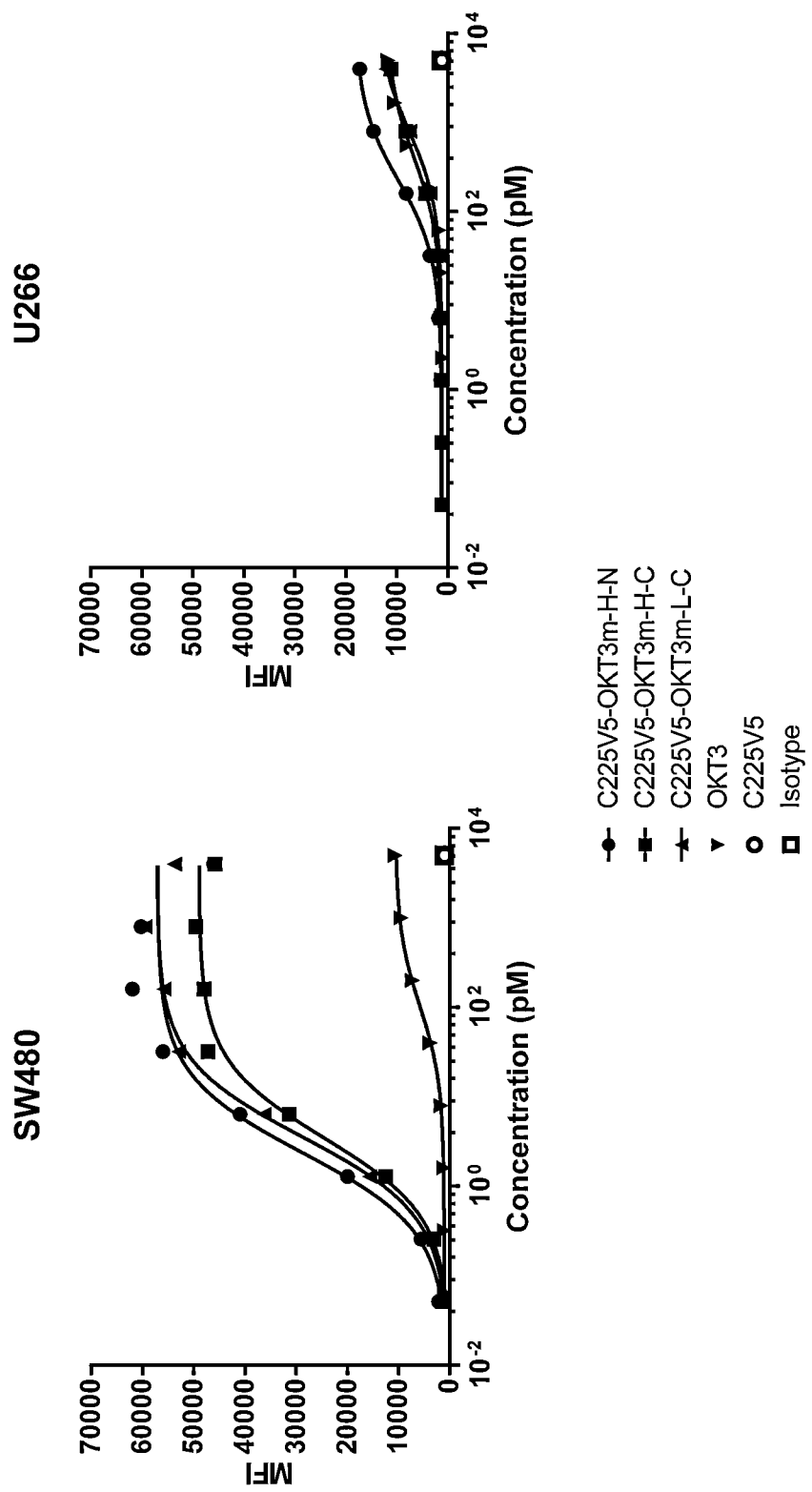
FIG. 17 is a series of graphs depicting EGFR-dependent activation of Jurkat T cells by multispecific antibodies of the disclosure.

FIG. 17 demonstrates that the most potent CD69 activation, evident beginning at sub-pM concentrations, depended on each multispecific antibody format being co-cultured in the presence of both Jurkat T cells and EGFR-positive SW480 cells. In contrast, T cell activation induced by co-culturing with EGFR-negative U266 cells was significantly less efficient, exhibiting sub-nM $EC_{50}$ values and a 75% reduction in maximal CD69 induction relative to activation induced by EGFR-positive cells. The EGFR-independent activation of the multispecific antibodies, as seen when U266 cells were used, was similar to that of OKT3 antibody, and negligible CD69 staining was observed with C225v5 and isotype control antibodies.

Example 9

Target-Dependent Activation of Primary CD8+ T Cells by Multispecific Antibodies

This Example demonstrates the ability of multispecific antibodies of the disclosure to activate primary CD8 positive (CD8') T cells.

To determine if multispecific antibody C225v5-OKT3m-H-N, C225v5-OKT3m-H-C, or C225v5-OKT3m-L-C could mediate EGFR-dependent activation of primary human CD8+ T cells, a flow cytometry based assay was performed. CD8+ T cells derived from human peripheral blood mononuclear cells (PBMCs) and DDAO-SE labeled target cells were co-cultured overnight, and activation was assessed by staining for the early activation marker, CD69.

EGFR-positive SW480 cells were cultured and labeled as described herein with the following exceptions: (1) SW480 target cells were labeled with CellTrace™ FarRed DDAO-SE (Life Technologies, Catalog C34553) and (2) complete media was supplemented with 25 U/ml IL-2 (R&D Systems, Catalog 202-IL-050/CF). Fifty µL of target cell suspension (at $5 \times 10^5$ cells/ml) per well were added to a 96-well, flat bottom plate for a total of 25,000 targets cells per well.

Fresh normal peripheral blood CD8+ Cytotoxic T cells (AllCells, Catalog PB009-3) were obtained from AllCells (Alameda, Calif.), harvested by centrifugation (200×g, RT, 15 min), and re-suspended in complete media supplemented with 25 U/ml IL-2 at $1.5 \times 10^6$ cells/ml. Fifty µL of cell suspension per well were added to the flat bottom plate containing target cells for a total of about 75,000 CD8+ cytotoxic T cells per well and a 3:1 ratio of T cells to target cells.

Three times-concentrated antibody stocks were prepared in complete media supplemented with 25 U/ml IL-2. The highest concentration was 600 pM followed by 5-fold serial dilutions for a total of eight concentrations for each antibody. Fifty µL of antibody per well were added to the flat bottom plate containing CD8+ cells and target cells, diluting all stocks 3-fold for a starting concentration of 200 pM.

After an overnight incubation, the flat bottom plate was centrifuged and 100 µL of supernatant was removed for the luminescent cytotoxicity assay described herein. The remaining supernatant was transferred to a U-bottom plate, and the cells in the flat bottom plate were detached with 0.25% trypsin (Life Technologies, Catalog 25200-056). Trypsin activity was quenched by adding 3 volumes of FACS Buffer, and the cell suspension was transferred to the U-bottom plate. After harvesting, the cells were resuspended in 50 µL of either an anti-CD69 PE/Anti-CD8 FITC cocktail (anti-CD8 FITC, BD Biosciences, Catalog 561948), FITC isotype control (BD BioSciences, Catalog 340755), or PE isotype control (BD BioSciences, Catalog 340761). All antibodies were used at the manufacturer's recommended concentrations. Cells were stained for 1 h at 4° C. with shaking, harvested and re-suspended in a final volume of 150 µL FACS Buffer with 2.5 µg/ml 7-AAD. Single color controls were used to set compensation on a BD Accuri C6, and a fixed volume of cell suspension was collected. Gating on CD8+ cells was sufficient to distinguish between target cells and viable T cells. Activation was quantified as the percentage of T cells with expression of CD69 above the PE isotype control.

Figure 18A:
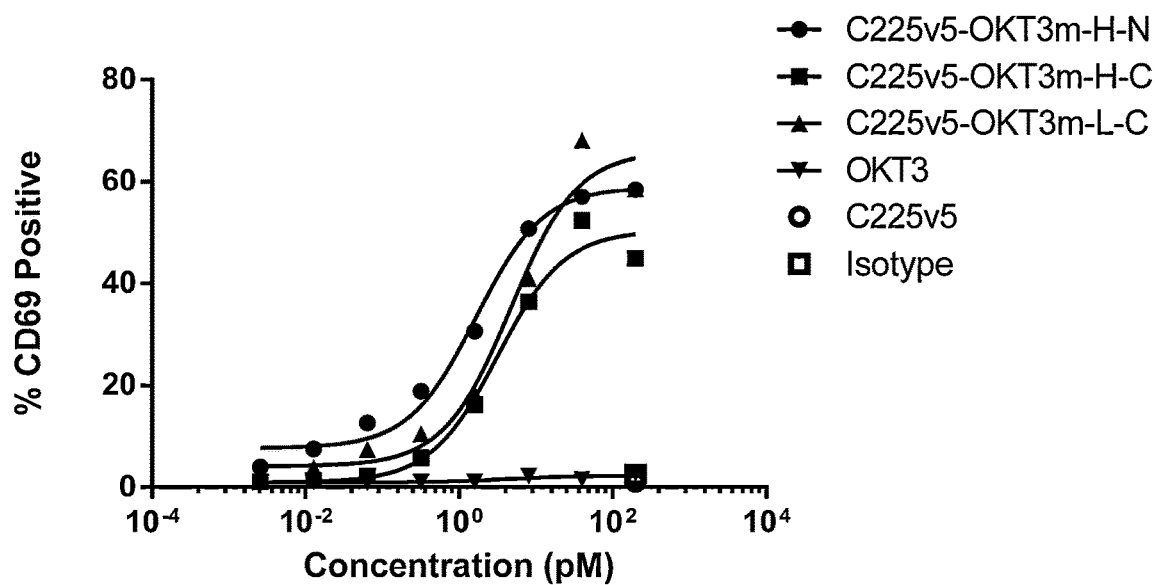
FIG. 18A is a graph depicting EGFR-dependent activation of primary $CD8^+$ T cells by multispecific antibodies of the disclosure.

FIG. 18A demonstrates that all three multispecific antibody formats demonstrated concentration-dependent activation of primary CD8+ T cells with single digit pM $EC_{50}$ values. Treatment with OKT3, C225v5, or human IgG1 isotype control (Enzo) antibodies resulted in negligible CD69 induction.

Example 10

Target-Dependent Killing of Target Cells by Multispecific Antibodies

This Example demonstrates the ability of multispecific antibodies of the disclosure to induce T cell-directed, target-dependent cell lysis.

To determine if multispecific antibody C225v5-OKT3m-H-N, C225v5-OKT3m-H-C, or C225v5-OKT3m-L-C was capable of inducing T cell-directed, target-dependent cell lysis, SW480 cells were co-cultured with CD8+ T-cells at a 3:1 effector-to-target cell ratio as described herein. After an overnight incubation, 100 µL of the supernatant was assayed in white wall 96-well plates (Greiner Bio One Catalog 655098) for distinct protease activity associated with cytotoxicity following manufacturer's protocol (CytoTox-Glo™ Cytotoxicity Assay, Catalog G9292, Promega), which uses a luminogenic peptide substrate to measure activity of proteases released by cells that have lost membrane integrity and have subsequently undergone cytolysis. Multispecific antibody-dependent cytotoxicity of target cells was expressed in luminescence after background subtraction of untreated values and plotted in Prism with curve fitting analysis log(agonist) vs. response (three parameters).

Figure 18B:
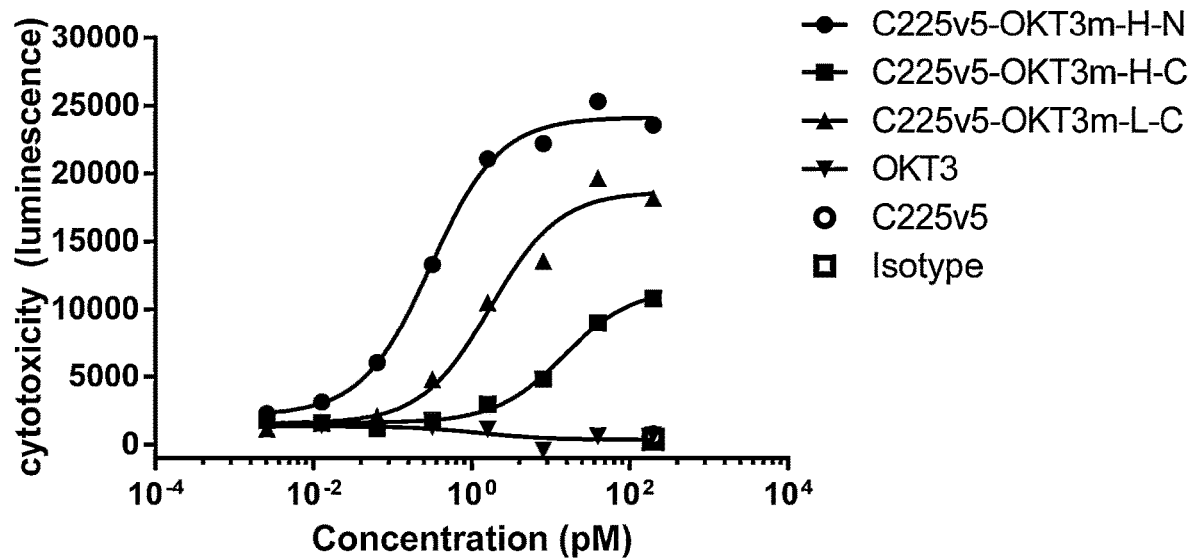
FIG. 18B is a graph depicting EGFR-dependent killing of target cells by multispecific antibodies of the disclosure.

FIG. 18B demonstrates that all three multispecific antibody formats induced T-cell-mediated killing of SW480 cells. As expected, OKT3 antibody alone exhibited no detectible killing of SW480 cells, suggesting a requirement

Example 11

Target-Dependent T-Cell Activation and Killing of Target Cells by Multispecific Antibodies This Example demonstrates the ability of multispecific antibodies of the disclosure to induce T cell-directed, target-dependent activation of $CD8^+$ T cells and killing of target cells.

To determine if the observed T-cell activation was dependent on EGFR expression by the target cell, CFSE-labeled EGFR-positive SW480 cells or EGFR-negative U266 cells were co-cultured with human $CD8^+$ T cells in the presence of multispecific antibody C225v5-OKT3m-H-N or OKT3, each in a 5-fold dilution series starting at 200 pM as described above. CFSE labeling of the target cells (30 nM) was used to distinguish the target cells from the T cells using a method described herein. Frozen normal peripheral blood $CD8^+$ Cytotoxic T cells (AllCells, Catalog PB009-3F) were thawed as specified by the manufacturer. After an overnight incubation, the T-cells (CFSE negative cells) were assayed for surface expression of the early activation marker, CD69 as described herein. Briefly, cells were removed from the assay plate, adherent cells were lifted using trypsin (Life Technologies), and cells were washed once with FACS Buffer. Cells were stained for 1 hour with anti-CD69-PE (BD Bioscience). Cells were washed and analyzed on the BD Accuri C6 for cell surface CD69 expression. MFI values were calculated as described herein. Results were expressed as the percentage of T cells with expression of CD69 above isotype control using FCS Express analysis software and plotted in Prism with curve fitting analysis log(agonist) vs. response (three parameters).

Figure 18C:
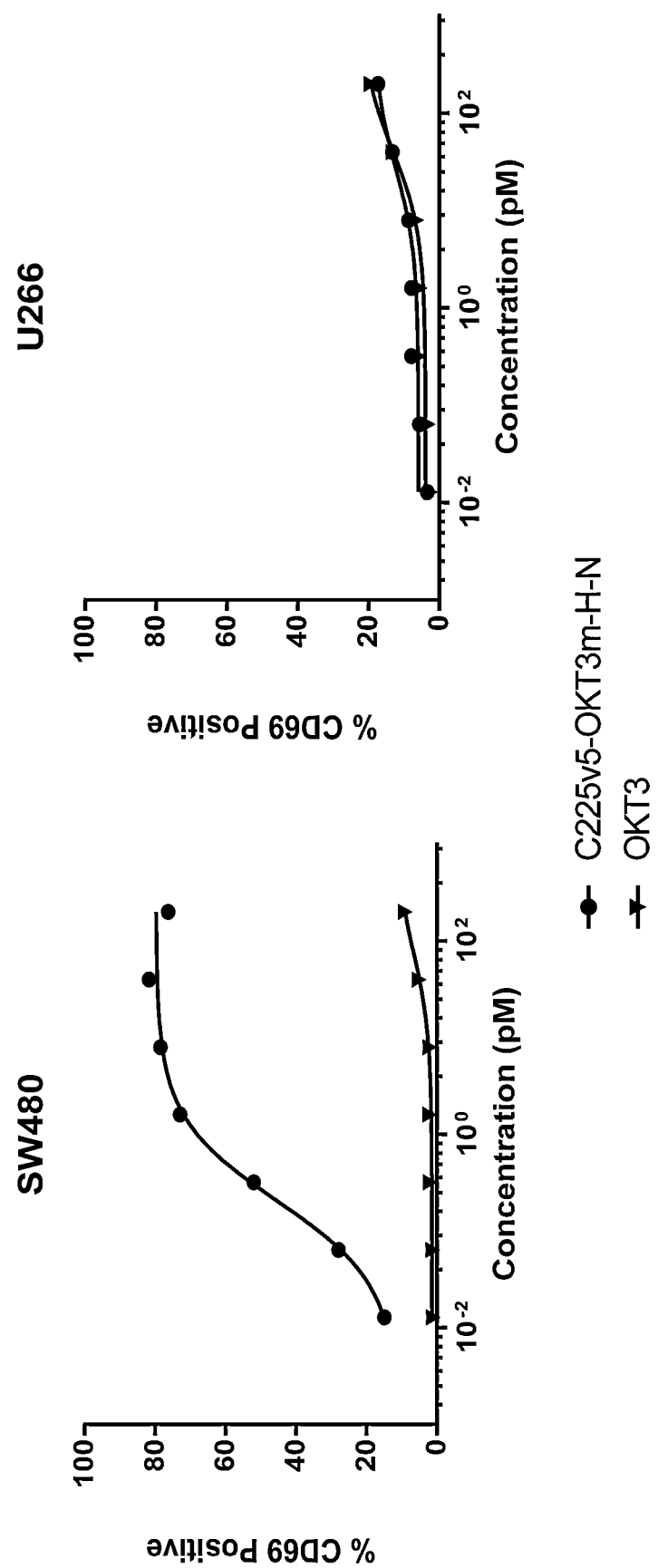
FIG. 18C is a series of graphs depicting CD69 activation of primary T cells by multispecific antibody C225v5-OKT3m-H-N in EGFR-expressing SW480 cells compared to minimal activation in EGFR-negative U266 cells.

As shown in FIG. 18C, multispecific antibody C225v5-OKT3m-H-N demonstrated potent T-cell activation at sub-pM concentrations in the presence of SW480 cells and only minimal T-cell activation by U266 cells, even at concentrations that were greater than 3 logs higher than concentrations used with SW480 cells. The OKT3 antibody exhibited minimal T-cell activation. These results demonstrated that effective T-cell activation is dependent on target cell expression of EGFR.

To determine the dependence of EGFR expression for target cell killing, 100 µl of supernatant of the T cell co-culture with SW480 or U266 cells was measured for protease activity associated with cytotoxicity (CytoTox-Glo, Promega). Results were expressed in luminescence without background subtraction to show the U266 response and plotted in Prism with curve fitting analysis log(agonist) vs. response (three parameters).

Figure 18D:
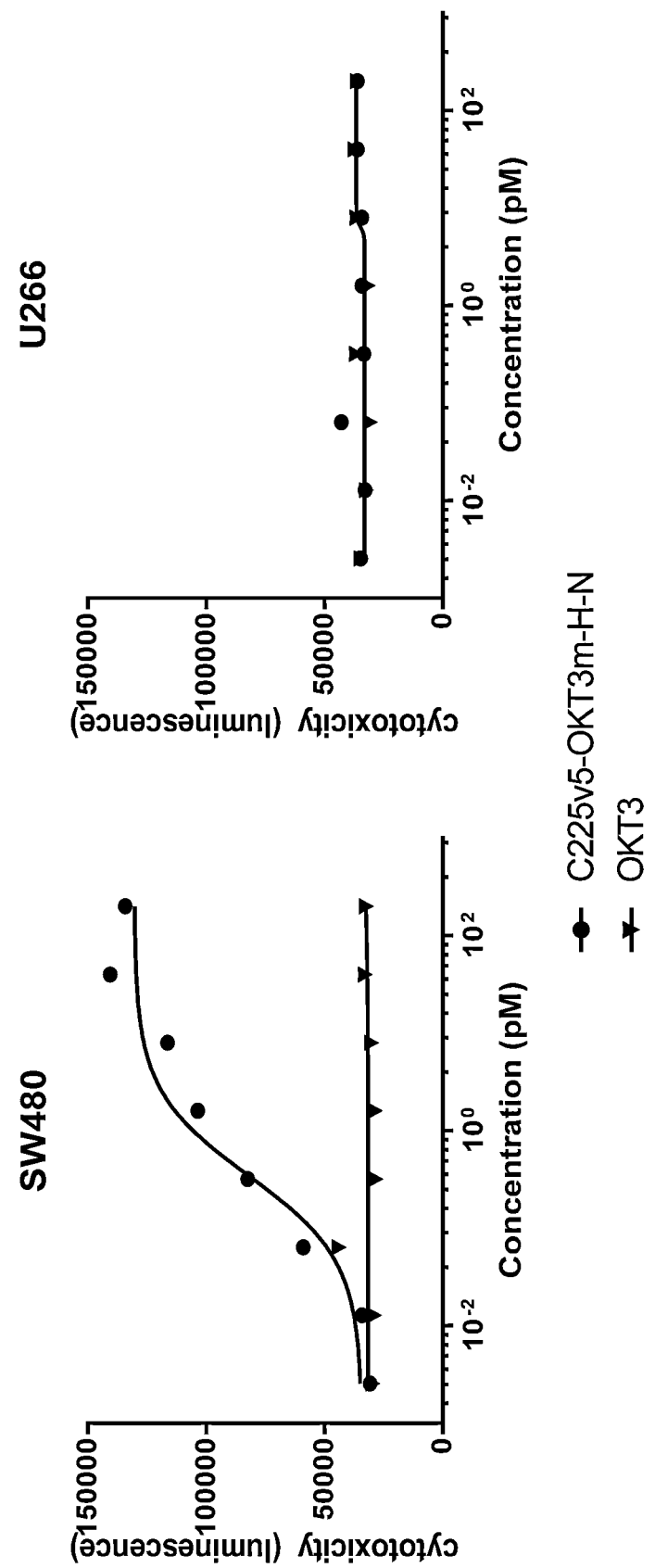
FIG. 18D is a series of graphs depicting EGFR-dependent killing of target cells by multispecific antibody C225v5-OKT3m-H-N in EGFR-expressing SW480 cells compared to negligible killing in EGFR-negative U266 cells.

FIG. 18D illustrates that multispecific antibody C225v5-OKT3m-H-N elicits cytotoxicity of EGFR-expressing SW480 cells at sub-pM concentrations while no discernable killing of EGFR-negative U266 cells is detected. OKT3 antibody also exhibited no discernable killing of either SW480 or U266 cells.

Example 12

Ability of Multispecific Antibodies to Engage T Cells to Kill a Panel of EGFR-Expressing Cell Lines This Example demonstrates the ability of multispecific antibodies of the disclosure to engage T cells to kill a panel of EGFR-expressing cell lines.

To determine if multispecific antibody C225v5-OKT3m-H-N was able to induce cytotoxicity of additional EGFR-expressing cell lines, human $CD8^+$ T cells were co-cultured in RPMI-1640, 2% human serum in white wall 96 well plates with the following EGFR-expressing cell lines at a 5:1 effector-to-target ratio (with the exception of the U266 cells, which were used at a 3:1 ratio cultured in 96-well flat bottom plates) and a titration of multispecific antibody C225v5-OKT3m-H-N: HEK-293, HCT-15, HCT 116, Hs 766T, HT-29, NCI-H2405, SW480, SK-OV-3, and an EGFR negative cell line, U266 (all cell lines from ATCC). Anti-EGFR antibody C225v5 (at 200 pM) was used as a negative control. After an overnight incubation, the luminogenic peptide substrate of the CytoTox-Glo™ Cytotoxicity Assay (Promega) was added directly to the plates (150 µl of supernatant) to measure released protease activity, with the exception of the U266 samples, where 100 µl of the U266 supernatant was used to assay for protease activity. Results were expressed in luminescence after background subtraction of untreated values and plotted in Prism with curve fitting analysis log(agonist) vs. response (three parameters).

FIG. 19 demonstrates that all EGFR-expressing cell lines treated with multispecific antibody C225v5-OKT3m-H-N in the presence of $CD8^+$ T cells exhibited dose-dependent cytotoxicity. In contrast, EGFR-negative U266 cells remained unaffected by multispecific antibody C225v5-OKT3m-H-N. None of the cell lines treated with anti-EGFR antibody C225v5 at 200 pM exhibited any evidence of cytotoxicity, regardless of their EGFR expression.

Example 13

Attenuation of EGFR Binding by Multispecific Activatable Antibodies

This Example demonstrates that EGFR binding by a multispecific activatable antibody of the disclosure is attenuated compared to EGFR binding by a multispecific antibody of the disclosure. This Example also demonstrates that EGFR binding of the multispecific activatable antibody, which includes a protease cleavable moiety, is restored upon cleavage of the multispecific activatable antibody by such protease.

Multispecific activatable antibody 3954-1204-C225v5-OKT3m-H-N, activated multispecific activatable antibody 3954-1204-C225v5-OKT3m-H-N, and multispecific antibody C225v5-OKT3m-H-N were tested for their abilities to bind to EGFR-expressing SW480 cells.

Activation of the multispecific activatable antibody was conducted as follows: 825 µg of multispecific activatable antibody 3954-1204-C225v5-OKT3m-H-N in PBS was cleaved by the addition of active site-titrated matriptase (also referred to herein as MT-SP1 and MTSP1; available from R&D Systems, Catalog 3946-SE-010) to a final concentration of 100 nM. The digest was incubated at 37° C. overnight, and cleavage was confirmed by removing an aliquot for capillary electrophoresis analysis (GX-II Capillary Electrophoresis, Perkin Elmer). Protease and the cleaved masking moiety were removed by Protein A purification. Briefly, the digested sample was diluted to 2 ml with PBS and loaded onto equilibrated MabSelect SuRe™ beads (GE Healthcare Life Sciences, Product 11-0026-01 AD). Beads were washed with 5 column volumes (CV) of 1×PBS, followed by 5 CV of 5×PBS supplemented with 5% isopropyl alcohol (IPA), and finally with 5 CV of 1×PBS. Antibody was eluted with 10 CV of 0.1 M Glycine, pH 3.0, and fractions were neutralized with 1 M Tris, pH 8.0, pooled, concentrated and buffer exchanged into PBS.

SW480 cells, which express EGFR, were lifted with cell dissociation buffer (Sigma, Catalog C5789), washed, and incubated for 1 hour with a 5-fold dilution of 1000 nM of multispecific activatable antibody 3954-1204-C225v5-OKT3m-H-N, activated multispecific activatable antibody 3954-1204-C225v5-OKT3m-H-N, multispecific antibody C225v5-OKT3m-H-N, activatable antibody 3954-1204-C225v5, or antibody C225v5 in FACS Buffer on ice. Cells were washed 3 times with FACS Buffer and incubated with 1:400 of a secondary antibody, namely anti-human FcGamma specific AF488 (Jackson ImmunoResearch Catalog 109-546-098) in FACS Buffer on ice. Cells were washed 3 times with FACS Buffer, and the MFI of AF488 was read on the BD Accuri (BD Biosciences) flow cytometer. The MFI of a sample comprising only the secondary antibody control was subtracted from the experimental MFI and plotted in Prism with curve fitting analysis log(agonist) vs. response (three parameters).

Figure 20A:
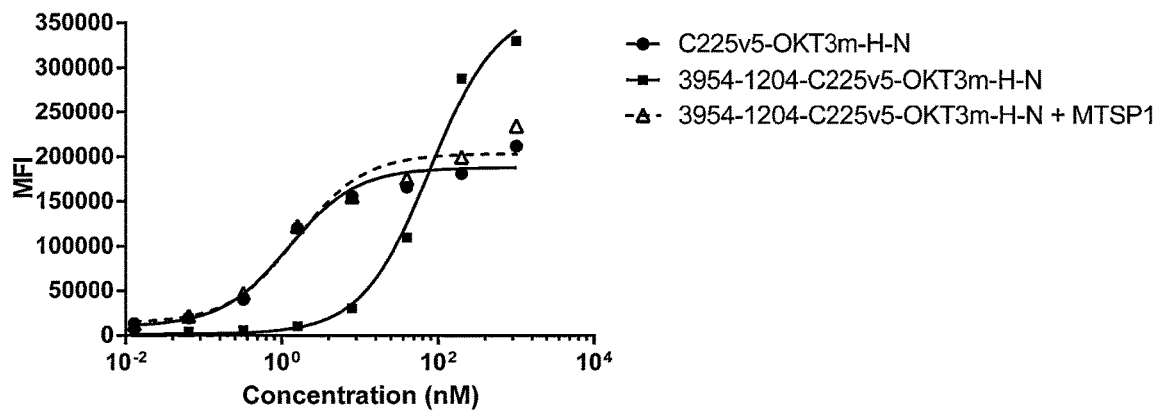
FIG. 20A and FIG. 20B are a series of graphs depicting decreased binding of multispecific activatable antibody 3954-1204-C225v5-OKT3m-H-N to EGFR-expressing cells compared to EGFR binding by multispecific antibody C225v5-OKT3m-H-N. Furthermore, FIGS. 20A and 20B demonstrate that protease activation of multispecific activatable antibody 3954-1204-C225v5-OKT3m-H-N by matriptase (also referred to herein as MTSP1 or MT-SP1) restores EGFR binding to a level equivalent to that exhibited by multispecific antibody C225v5-OKT3m-H-N.
Figure 20B:
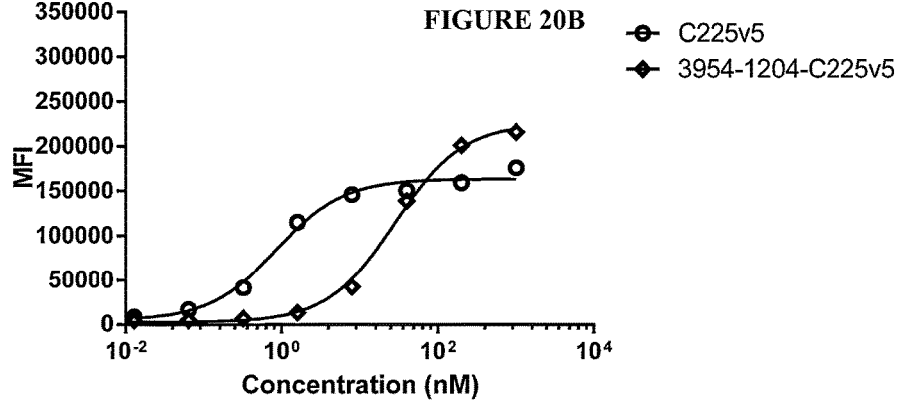

FIG. 20A demonstrates that EGFR binding by multispecific activatable antibody 3954-1204-C225v5-OKT3m-H-N was attenuated compared EGFR binding by multispecific antibody C225v5-OKT3m-H-N, but EGFR binding of the multispecific activatable antibody was fully restored upon protease cleavage of the multispecific activatable antibody by matriptase. FIG. 20B shows that EGFR binding by antibody C225v5 and by activatable antibody 3954-1204-C225v5 were comparable to EGFR binding by multispecific antibody C225v5-OKT3m-H-N and multispecific activatable antibody 3954-1204-C225v5-OKT3m-H-N, respectively, demonstrating that the anti-CD3ε moiety present in the multispecific format did not alter the EGFR binding profile of either the multispecific antibody or multispecific activatable antibody.

Example 14

Ability of Multispecific Activatable Antibodies to Bind to CD3+ T Cells

This Example demonstrates that a multispecific activatable antibody, an activated multispecific activatable antibody, and a multispecific antibody, all of the embodiments, are each able to bind to CD3+ T cells.

To determine if CD3ε binding had been affected by masking of the EGFR binding site of an anti-EGFR multispecific activatable antibody, a Jurkat T-cell binding assay was performed as described herein with multispecific activatable antibody 3954-1204-C225v5-OKT3m-H-N, activated multispecific activatable antibody 3954-1204-C225v5-OKT3m-H-N, and multispecific antibody C225v5-OKT3m-H-N. Jurkat cells were incubated with a 5-fold dilution of 1000 nM of multispecific activatable antibody 3954-1204-C225v5-OKT3m-H-N, matriptase-activated multispecific activatable antibody 3954-1204-C225v5-OKT3m-H-N, or multispecific antibody C225v5-OKT3m-H-N in FACS Buffer for 1 hour at 4° C. Cells were washed 3 times and incubated with a secondary antibody, namely 1:400 of anti-human FcGamma specific AF488 (Jackson ImmunoResearch). Cells were washed 3 times, and the MFI of AF488 was read on the BD Accuri (BD Biosciences) flow cytometer. The MFI of a sample comprising only the secondary antibody control was subtracted from the experimental MFI and plotted in Prism with curve fitting analysis log(agonist) vs. response (three parameters).

Figure 21A:
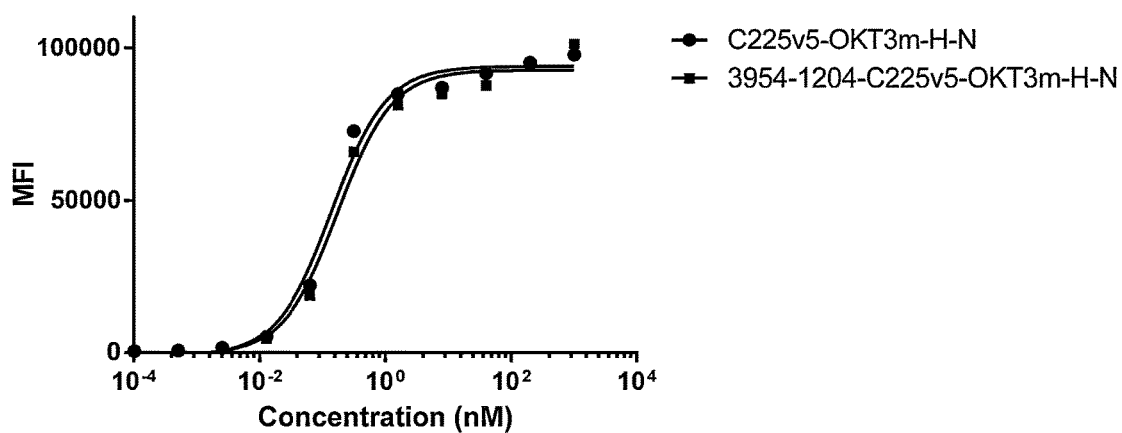
FIG. 21A and FIG. 21B are a series of graphs depicting binding of multispecific activatable antibody 3954-1204-C225v5-OKT3m-H-N, activated multispecific activatable antibody 3954-1204-C225v5-OKT3m-H-N, and multispecific antibody C225v5-OKT3m-H-N to CD3ε-positive Jurkat T cells.
Figure 21B:
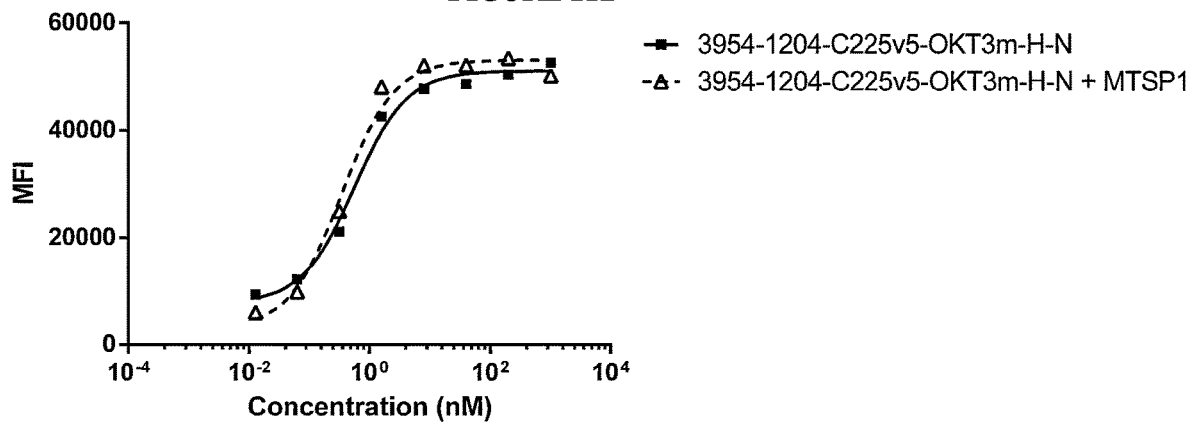

FIG. 21A demonstrates that multispecific activatable antibody 3954-1204-C225v5-OKT3m-H-N and multispecific antibody C225v5-OKT3m-H-N exhibit equivalent binding to Jurkat T cells. FIG. 21B demonstrates that multispecific activatable antibody 3954-1204-C225v5-OKT3m-H-N and activated multispecific activatable antibody 3954-1204-C225v5-OKT3m-H-N exhibit equivalent binding to Jurkat T cells. These results indicate that masking of the EGFR binding moiety of the multispecific activatable antibody does not affect the ability of the multispecific activatable antibody to engage T cells.

Example 15

Target-Dependent T-Cell Activation by Multispecific Activatable Antibodies

This Example demonstrates that target-dependent T-cell activation by a multispecific activatable antibody of the disclosure is attenuated compared to activation exhibited by a multispecific antibody of the disclosure. This Example also demonstrates that target-dependent T-cell activation by the multispecific activatable antibody, which includes a protease cleavable moiety, is restored upon cleavage of the multispecific activatable antibody by such protease.

To determine if masking of the EGFR binding site of an anti-EGFR multispecific activatable antibody attenuates target-dependent T-cell activation and to determine if protease activation of the multispecific activatable antibody restores activation, a Jurkat activation assay was performed, as described herein, testing multispecific activatable antibody 3954-1204-C225v5-OKT3m-H-N, activated multispecific activatable antibody 3954-1204-C225v5-OKT3m-H-N, multispecific antibody C225v5-OKT3m-H-N, anti-EGFR antibody C225v5, and a Synagis (Medimmune) isotype control as described herein.

Figure 22:
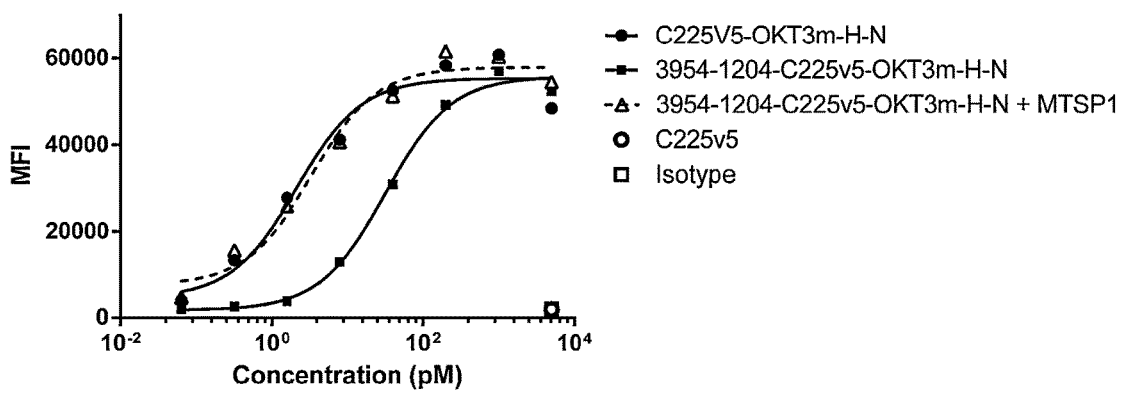
FIG. 22 is a graph depicting decreased EGFR-dependent activation of Jurkat T cells by multispecific activatable antibody 3954-1204-C225v5-OKT3m-H-N compared to activation by multispecific antibody C225v5-OKT3m-H-N. Furthermore, the figure demonstrates that protease activation of multispecific activatable antibody 3954-1204-C225v5-OKT3m-H-N by matriptase restores EGFR-dependent activation to a level equivalent to that exhibited by multispecific antibody C225v5-OKT3m-H-N.

FIG. 22 demonstrates that EGFR-dependent activation, as determined by CD69 induction of Jurkat T cells co-cultured with EGFR-expressing SW480 cells, by multispecific activatable antibody 3954-1204-C225v5-OKT3m-H-N was attenuated compared to EGFR-dependent activation exhibited by multispecific antibody C225v5-OKT3m-H-N. The figure also indicates that EGFR-dependent activation by the multispecific activatable antibody was fully restored upon protease cleavage of the multispecific activatable antibody by matriptase. Neither anti-EGFR C225v5 nor the isotype control antibody exhibited activation of T-cells.

Example 16

Target-Dependent T-Cell Activation and Killing of Target Cells by Multispecific Activatable Antibodies This Example demonstrates that target-dependent T-cell activation and killing of target cells by a multispecific activatable antibody of the disclosure is attenuated compared to activation exhibited by a multispecific antibody of the disclosure. This Example also demonstrates that target-dependent T-cell activation and killing of target cells by the multispecific activatable antibody, which includes a protease cleavable moiety, is restored upon cleavage of the multispecific activatable antibody by such protease.

To determine if masking of the EGFR binding site of an anti-EGFR multispecific activatable antibody attenuates target-dependent activation and to determine if protease activation of the multispecific activatable antibody restores activation, a Jurkat activation assay was performed, as described herein, testing multispecific activatable antibody 3954-1204-C225v5-OKT3m-H-N, activated multispecific activatable antibody 3954-1204-C225v5-OKT3m-H-N, multispecific antibody C225v5-OKT3m-H-N, anti-CD3ε antibody OKT3, anti-EGFR antibody C225v5, and an isotype control as described herein.

To determine the impact of masking the EGFR binding site of an anti-EGFR multispecific activatable antibody on cytotoxicity and the ability of protease activation to restore cytotoxic activity of the activated multispecific activatable antibody, EGFR-expressing SW480 cells were co-cultured with T-cells at a 5:1 effector-to-target cell ratio with a 5-fold dilution series, starting at 200 pM, of multispecific activatable antibody 3954-1204-C225v5-OKT3m-H-N, activated multispecific activatable antibody 3954-1204-C225v5-OKT3m-H-N, or multispecific antibody C225v5-OKT3m-H-N. 200 pM of OKT3, C225v5, and isotype control Synagis (Medimmune) IgG1 antibodies were used as controls. After an overnight incubation, 100 µL of the supernatant was assayed for in white wall 96-well plates distinct protease activity associated with cytotoxicity (CytoTox-Glo, Promega). Results were expressed in luminescence after background subtraction of untreated values and plotted in Prism with curve fitting analysis log(agonist) vs. response (three parameters).

Figure 23A:
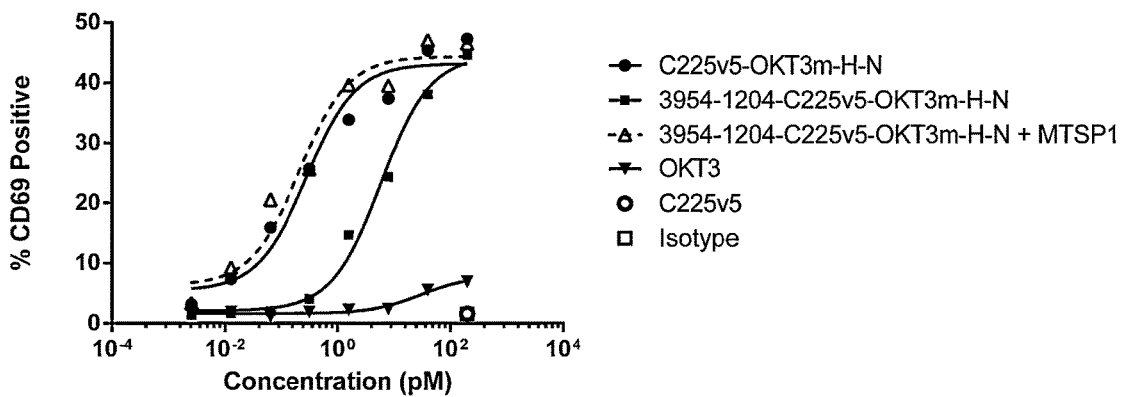
FIG. 23A is a graph depicting decreased EGFR-dependent activation of primary CD8+ T cells by multispecific activatable antibody 3954-1204-C225v5-OKT3m-H-N compared to activation by multispecific antibody C225v5-OKT3m-H-N. Furthermore, the figure demonstrates that protease activation of multispecific activatable antibody 3954-1204-C225v5-OKT3m-H-N by matriptase restores EGFR-dependent activation to a level equivalent to that exhibited by multispecific antibody C225v5-OKT3m-H-N.

FIG. 23A demonstrates that EGFR-dependent activation, as determined by CD69 induction of primary T cells co-cultured with EGFR-expressing SW480 cells, by multispecific activatable antibody 3954-1204-C225v5-OKT3m-H-N was attenuated compared to EGFR-dependent activation exhibited by multispecific antibody C225v5-OKT3m-H-N. The figure also indicates that EGFR-dependent activation by the multispecific activatable antibody was fully restored upon protease cleavage of the multispecific activatable antibody by matriptase. OKT3, anti-EGFR C225v5, and Synagis IgGlisotype control antibodies exhibited negligible activation of T-cells.

Figure 23B:
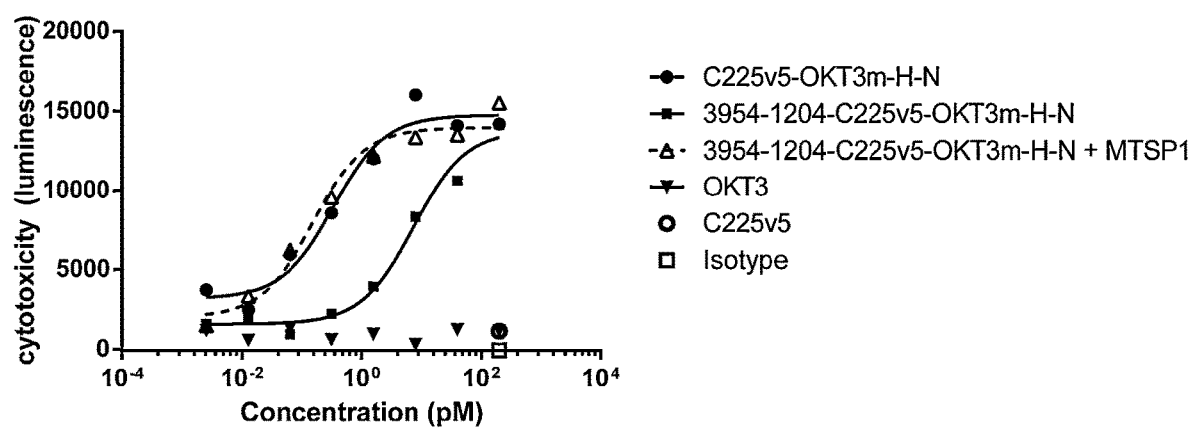
FIG. 23B is a graph depicting decreased EGFR-dependent killing of target cells by multispecific activatable antibody 3954-1204-C225v5-OKT3m-H-N compared to killing by multispecific antibody C225v5-OKT3m-H-N. Furthermore, the figure demonstrates that protease activation of multispecific activatable antibody 3954-1204-C225v5-OKT3m-H-N by matriptase restores EGFR-dependent target cell killing to a level equivalent to that exhibited by multispecific antibody C225v5-OKT3m-H-N.

FIG. 23B demonstrates that EGFR-dependent lysis of SW480 cells by multispecific activatable antibody 3954-1204-C225v5-OKT3m-H-N was attenuated compared to EGFR-dependent cytotoxicity exhibited by multispecific antibody C225v5-OKT3m-H-N. The figure also indicates that EGFR-dependent cytotoxicity by the multispecific activatable antibody was fully restored upon protease cleavage of the multispecific activatable antibody by matriptase. C225v5 and OKT3 and Synagis IgG1 isotype control antibodies exhibited negligible cytotoxicity.

Other Embodiments

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A bispecific antibody, wherein said bispecific antibody comprises the following structure:
   a. a full length IgG antibody (AB1) that specifically binds to a first antigen wherein AB1 comprises two antibody heavy chains and two antibody light chains; and wherein the AB1 is linked to:
      i. two first masking moiety peptides (MM1s) that are each no more than 40 amino acids in length and have an amino acid sequence that is no more than 50% identical to the amino acid sequence of the first antigen; and
      ii. two cleavable moiety peptides (CM1s), each CM1 being a substrate for a first protease;
      wherein each MM1 is linked in an N- to C-terminal direction to a CM1, to form two MM1-CM1 peptides; and
      wherein the carboxyl terminus of each MM1-CM1 peptide is linked to the amino terminus of a corresponding AB1 light chain; and
   b. two scFvs (each an AB2) that each specifically binds to a second antigen, wherein each AB2 comprises an antibody light chain variable domain and an antibody heavy chain variable domain; and wherein each AB2 is linked to:
      i. a second masking moiety peptide (MM2) that is no more than 40 amino acids in length and has an amino acid sequence that is no more than 50% identical to the amino acid sequence of the second antigen; and
      ii. a second cleavable moiety (CM2) peptide that is a substrate for a second protease;
      wherein MM2 is linked in an N- to C-terminal direction to CM2 to form an MM2-CM2 peptide;
      wherein the carboxyl terminus of the MM2-CM2 peptide is linked to the amino terminus of the AB2,
   wherein the carboxyl terminus of each AB2 is linked to the amino terminus of a corresponding heavy chain of AB1, and
   wherein the dissociation constant (Kd) of each AB1 linked to MM1 towards the first antigen and AB2 linked to MM2 towards the second antigen is at least 5 times greater than the Kd of AB1 towards the first antigen and AB2 towards the second antigen when AB1 and AB2 are not linked to MM1 and MM2, respectively.

2. The bispecific antibody of claim 1, wherein each MM1-CM1 peptide comprises a linking peptide between the MM1 and the CM1.

3. The bispecific antibody of claim 1, comprising a linking peptide between each CM1 and the corresponding AB1 light chain.

4. The bispecific antibody of claim 1, wherein each MM1-CM1 peptide comprises a first linking peptide between the MM1 and the CM1 and wherein the bispecific antibody further comprises a second linking peptide between each CM1 and the corresponding AB1 light chain.

5. The bispecific antibody of claim 4, wherein the first linking peptide and the second linking peptide are not identical to each other.

6. The bispecific antibody of claim 4, wherein each of the first linking peptide and the second linking peptide is about 1 to 20 amino acids in length.

7. The bispecific antibody of claim 1, wherein each CM1 is no more than 15 amino acids in length.

8. The bispecific antibody of claim 1, wherein each CM2 is no more than 15 amino acids in length.

9. The bispecific antibody of claim 1, wherein the first protease and the second protease are the same protease.

10. The bispecific antibody of claim 9, wherein the CM1s and the CM2s are different substrates for the same protease.

11. The bispecific antibody of claim 1, wherein the first protease and the second protease are different proteases.

12. The bispecific antibody of claim 1, comprising a therapeutic agent, an antineoplastic agent, a toxin or fragment thereof, a detectable moiety or a diagnostic agent linked to at least one of AB1 and AB2.

13. The bispecific antibody of claim 12, wherein the therapeutic agent, the antineoplastic agent, the toxin or fragment thereof, the detectable moiety or the diagnostic agent is conjugated to at least one of AB1 and AB2 via a linker.

14. The bispecific antibody of claim 1, wherein AB2 is an immune effector cell engaging scFv.

15. The bispecific antibody of claim 1, wherein AB2 is a leukocyte engaging scFv.

16. The bispecific antibody of claim 1, wherein AB2 is a T-cell engaging scFv.

17. The bispecific antibody of claim 1, wherein AB2 is a NK-cell engaging scFv.

18. The bispecific antibody of claim 1, wherein AB2 is a macrophage engaging scFv.

19. The bispecific antibody of claim 1, wherein AB2 is a mononuclear cell engaging scFv.

20. The bispecific antibody of claim 1, wherein AB2 is an anti-CD3 epsilon scFv.

21. The bispecific antibody of claim 20, wherein the anti-CD3 epsilon scFv is derived from OKT3.

22. The bispecific antibody of claim 1, wherein AB1 is an anti-EGFR antibody.

23. The bispecific antibody of claim 1, wherein AB1 is an anti-Jagged antibody.

24. The bispecific antibody of claim 1, wherein AB1 is an anti-Jagged antibody or an anti-EGFR antibody and wherein AB2 is an anti-CD3 epsilon scFv or an anti-CTLA-4 scFv.

25. The bispecific antibody of claim 1, wherein AB1 is an anti-EGFR antibody and wherein AB2 is an anti-CD3 epsilon scFv.

26. The bispecific antibody of claim 1, wherein AB1 is an anti-Jagged antibody and wherein AB2 is an anti-CD3 epsilon scFv.

27. The bispecific antibody of claim 1, wherein the bispecific antibody comprises an amino acid sequence as set forth in SEQ ID NOs: 234, 236, 238, 240, 254, 256, 258, 260, 262, 264, 266, 268, or 270; or an amino acid sequence encoded by a nucleic acid sequence as set forth in SEQ ID NOs: 233, 235, 237, 239, 253, 255, 257, 259, 261, 263, 265, 267, or 269.

28. The bispecific antibody of claim 1, wherein the bispecific antibody comprises an amino acid sequence as set forth in SEQ ID NOs: 254, 256, or 336.

29. The bispecific antibody of claim 1 wherein the first antigen and the second antigen are different.

30. The bispecific antibody of claim 1, wherein AB2 is an anti-CTLA4 scFv.

31. The bispecific antibody of claim 1, wherein each MM2-CM2 peptide comprises a linking peptide between the MM2 and the CM2.

32. The bispecific antibody of claim 1, comprising a linking peptide between each CM2 and the amino terminus of the AB2.

33. The bispecific antibody of claim 1, wherein each MM2-CM2 peptide comprises a first linking peptide between the MM2 and the CM2 and wherein the bispecific antibody further comprises a second linking peptide between each CM2 and the amino terminus of the AB2.

34. The bispecific antibody of claim 33, wherein the first linking peptide and the second linking peptide are not identical to each other.

35. The bispecific antibody of claim 33, wherein each of the first linking peptide and the second linking peptide is about 1 to 20 amino acids in length.

36. The bispecific antibody of claim 1, wherein MM1 or MM2 comprises an amino acid sequence as set forth in SEQ ID NOs: 75-228, 338, or 339.

37. The bispecific antibody of claim 1, wherein the MM1s reduce or inhibit binding of AB1 to the first antigen when the CM1s are in an uncleaved state; and the MM2s reduce or inhibit binding of AB2 to the second antigen when the CM2s are in the uncleaved state.

38. The bispecific antibody of claim 37, wherein the MM1s do not interfere or compete with specific binding of the AB1 to the first antigen when the CM1s are in a cleaved state; and the MM2s do not interfere or compete with specific binding of the AB2 to the second antigen when the CM2s are in the cleaved state.

39. A bispecific antibody wherein the bispecific antibody comprises a sequence as set forth in SEQ ID NOs: 292, 294, or 300.

40. An isolated nucleic acid molecule encoding the bispecific antibody of claim 1.

41. A vector comprising the isolated nucleic acid molecule of claim 40.

42. A method of producing a bispecific antibody by culturing a cell under conditions that lead to expression of the bispecific antibody, wherein the cell comprises the nucleic acid molecule of claim 40, and recovering the bispecific antibody.

43. An isolated nucleic acid molecule encoding the bispecific antibody of claim 39.

44. A vector comprising the isolated nucleic acid molecule of claim 43.

45. A method of manufacturing the bispecific antibody of claim 28, the method comprising:

(a) culturing a cell comprising a nucleic acid construct that encodes the bispecific antibody under conditions that lead to expression of the bispecific antibody, wherein the bispecific antibody comprises the structure of the bispecific antibody of claim 28; and (b) recovering the bispecific antibody.

* * * * *